US008486418B2

(12) United States Patent
Bublot et al.

(10) Patent No.: US 8,486,418 B2
(45) Date of Patent: Jul. 16, 2013

(54) RECOMBINANT AVIAN PARAMYXOVIRUS VACCINE AND METHOD FOR MAKING AND USING THEREOF

(75) Inventors: Michel Bublot, Chaponost (FR); Teshome Mebatsion, Watkinsville, GA (US); Joyce Pritchard, Gainesville, GA (US); Egburt Mundt, Watkinsville, GA (US)

(73) Assignees: Merial Limited, Duluth, GA (US); University of Georgia Research Foundation, Inc., Athens, GA (US)

( * ) Notice: Subject to any disclaimer, the term of this patent is extended or adjusted under 35 U.S.C. 154(b) by 108 days.

(21) Appl. No.: 12/860,589

(22) Filed: Aug. 20, 2010

(65) Prior Publication Data

US 2011/0081374 A1 Apr. 7, 2011

Related U.S. Application Data

(60) Provisional application No. 61/235,912, filed on Aug. 21, 2009.

(51) Int. Cl.

| | |
|---|---|
| ***A61K 39/155*** | (2006.01) |
| ***A61K 39/295*** | (2006.01) |
| ***C12N 7/00*** | (2006.01) |
| ***C12N 7/01*** | (2006.01) |
| ***C12N 7/02*** | (2006.01) |
| ***C12N 15/45*** | (2006.01) |
| ***C12N 15/861*** | (2006.01) |

(52) U.S. Cl.
USPC .................. 424/199.1; 424/211.1; 435/235.1; 435/320.1; 435/236; 435/472; 536/23.72

(58) Field of Classification Search
None
See application file for complete search history.

(56) References Cited

U.S. PATENT DOCUMENTS 6,719,979 B2 4/2004 Peeters et al. .............. 424/214.1

FOREIGN PATENT DOCUMENTS

| | | |
|---|---|---|
| WO | WO02/36617 | 5/2002 |
| WO | WO2007/104782 | 9/2007 |
| WO | WO2009/101149 | 8/2009 |

OTHER PUBLICATIONS

Nakaya et al (Journal of Virology 75:11868-11873, 2001).*
Ge et al (Journal of Virology 81:150-158, 2007).*
Paldurai et al (Virus Research 142:144-153, 2009, available online Feb. 13, 2009).*
Alexander (Rev. sci. tech. Off. int Epiz 19:443-462, 2000).*
Lipkind et al (Archives of Virology 89:89-111, 1986).*
Vigil et al ( Molecular Therapy 16:1883-1890, 2008).*
Janke et al (Gene Therapy 14:1639-1649, 2007).*
Thorner et al (Journal of Virology 80:12009-12016, 2006).*
Dharmapuri et al (Expert Opinion on Biological Therapy 9:1279-1287, 2009).*
Genbank FJ215863 (Jul. 22, 2009).*
Brun et al "Antigen delivery systems for veterinary vaccine development, Viral-vector based delivery systems." Vaccine 26:6508-6528, 2008.*
Genbank FJ619036 (Jun. 1, 2009).*
Paldural, A, et al., "complete Genome Sequences of Avian Paramyxovirus Type 8 Strains goos/Delaware/1053/76 and pintail/Wakuya/2-/78", Virus Research 142, 144-153 (2009).
Peeters BPH, et al., "Generatiaon of a recombinant chimeric Newcastle disease virus vaccine that allows serological differentiation between vaccinated and infected animals", vaccine, vol. 19, pp. 1616-1627 (Jan. 1, 2001).
Zou, et al., 2005. Complete Genome Sequence and Biological Characterizations of a Novel Goose Paramyxovirus-SF02 Isolated in China. Virus Genes 30:13-21.
Alexander, 2003. Newcastle Disease, other Paramyxoviruses, and Pneumovirus Avian Paramyxoviruses 2-9, p. 63-99. In Y. M. Saif (ed.), Diseases of poultry, 11th ed. Iowa State Press, Ames, Iowa.
Alexander, 1983, Characterization of viruses which represent further distinct serotypes (PMV-8 and PMV-9) of avian paramyxoviruses. Arch Virol 78:29-36.
Alexander, et al., 1979. Properties of a newly isolated, serologically distinct avian paramyxovirus. Arch Virol 60:105-13.
Andreal, et al., 1984. Isolation of avian paramyxovirus 2 and 3 from turkeys in Brittany. Vet Rec 114:570-1.
Bankowski, et al., 1960. Isolation of an Unidentified Agent from the Respiratory Tract of Chickens. Science 132:292-293.
Bankowski, et al., 1981, Effect of paramyxovirus yucaipa on fertility, hatchability, and poult yield of turkeys. Avian Dis 25:517-20.
Bradshaw, et al., 1979. The Epidemiology of Yucaipa Virus in Relationship to the Acute Respiratory Disease Syndrome in Turkeys. Avian Diseases 23:539-542.
Capua, et al., 2004. Isolation of an avian paramyxovirus type 9 from migratory waterfowl in Italy. Vet Rec 155:156.
Chambers, et al., 1988. Protection of chickens from lethal influenza infection by vaccineexpressed hemagglutinin. Virology 167:414-421.
Darteil, RM. et al., (1995). Herpesvirus of turkey recombinant viruses expressing infectious bursal disease virus (IBDV) VP2 immunogen induce protection against an IBDV virulent challenge in chickens. Virology 211,481-490.
De Leeuw, et al., 1999. Complete nucleotide sequence of Newcastle disease virus: evidence for the existence of a new genus within the subfamily Paramyxovirinae. J Gen Virol 80:131-136.
Fleury, et al., 1979. Isolation of twenty-three Yucaipa-like viruses from 616 wild birds in Senegal, West Africa. Avian Dis 23:742-4.
Gao, et al., (2006). Protection of mice and poultry from lethal H5N1 avian influenza virus through adenovirus-based immunization. J Virol 80:1959-1964.
Ge, et al., (2007) Newcastle disease virus-based live attenuated vaccine completely protects chickens and mice from lethal challenge of homologous and heterologous H5N1 avian influenza viruses. Journal of Virology, 81(1), 150-158.

(Continued)

*Primary Examiner* — Mary E Mosher
(74) *Attorney, Agent, or Firm* — Judy Jarecki-Black; Ruoying Chen; Merial Limited

(57) ABSTRACT

The present invention encompasses engineered APMV compositions or vaccines. The vaccine or composition may be a recombinant APMV composition or vaccine. The present invention encompasses methods for modifying the genome of APMV to produce recombinant APMV; modified APMV prepared by such methods; DNA and protein sequences; and methods for infecting cells and host animals with such recombinant APMV.

32 Claims, 54 Drawing Sheets

OTHER PUBLICATIONS

Goodman, et al., 1988. Isolation of avian paramyxovirus-2 from domestic and wild birds in Costa Rica. Avian Dis 32:713-7.
Gough, et al., 1984. Avian paramyxovirus type 4 isolated from a ringed teal (*Calonetta leucophrys*). Vet Rec 115:653.
Hoelscher, et al., (2008). A broadly protective vaccine against globally dispersed clade 1 and clade 2 H5N1 influenza viruses. J Infect Dis. 197:1185-1188.
Huang, et al., (2004) A recombinant Newcastle Disease Virus (NDV) expressing VP2 protein of Infectious Bursal Disease Virus (IBDV) protects against NDV and IBDV. Journal of Virology, 78,10054-10063.
Hunt, et al., (1988). Retrovirus-expressed hemagglutinin protects against lethal influenza virus infections. J Virol 62:3014-3019.
Krishnamurthy, et al., 1998. Nucleotide sequences of the trailer, nucleocapsid protein gene and intergenic regions of Newcastle disease virus strain Beaudette C and completion of the entire genome sequence. J Gen Virol 79:2419-2424.
Krishnamurthy, S., et al., (2000) Recovery of a virulent strain of Newcastle disease virus from cloned cDNA: expression of a foreign gene results in growth retardation and attenuation. Virology, 278,168-182.
Zhang, et al., 2006. Isolation, identification, and comparison of four isolates of avian paramyxovirus serotype 2 in China. Avian Dis 50:386-90.
Lang, GA, et al., 1975. The occurrence of Paramyxovirus yucaipa in Canadian poultry. Can Vet J 16:233-7.
Lipkind, et al., 1982. Isolation of yucaipa-like avian paramyxovirus from a wild mallard duck (*Anas platyrhinchos*) wintering in Israel. Vet Rec 110:15-6.
Maldonado, et al., (1995) Serological survey for avian paramyxoviruses from wildfowl in aquatic habitats in Andalusia. Journal of Wildlife Diseases, 31(1), 66-69.
Mayo, et al., 2002. A summary of taxonomic changes recently approved by ICTV. Arch Virol 147:1655-63.
Nayak B, et al., (2008). Molecular characterization and complete genome sequence of avian paramyxovirus type 4 prototype strain duck/Hong Kong/D3/75. Virol J. 20;5:124.
Park, et al., (2006) Engineered viral vaccine constructs with dual specificity: Avian influenza and Newcastle disease. Proceedings of the National Academy of Sciences, 103(21), 8203-8208.
Peeters, et al., (1999) Rescue of Newcastle disease virus from cloned cDNA: evidence that cleavability of the fusion protein is a major determinant for virulence. Journal of Virology, 73(6), 5001-5009.
Redmann, et al., 1991. [Isolation of a paramyxovirus-3 from turkeys with respiratory tract disease in Germany]. Dtsch Tierarztl Wochenschr 98:138-41.
Römer-Oberdörfer, et al., (1999) Generation of recombinant lentogenic Newcastle disease virus from cDNA. Journal of General Virology, 80, 2987-2995.
Rosenberger, et al., (1974) Isolation of Newcastle disease and type-A influenza viruses from migratory waterfowl in the Atlantic flyway. Avian Diseases, 18(4), 610-613.
Saif, et al., 1997. Natural and Experimental Infection of Turkeys with Avian Paramyxovirus-7. Avian Diseases 41:326-329.
Schultz-Cherry, et al., (2000). Influenza virus (A/HK/156/97) hemagglutinin expressed by an alphavirus replicon system protects chickens against lethal infection with Hong Kong-origin H5N1 viruses. Virology 278:55-59.
Shihmanter, et al., 1998. Avian paramyxoviruses serotype 3 isolated from captive birds in Israel: clinical signs, pathology, and antigenic characterization. Avian Dis 42:418-22.
Shihmanter, et al., 1998. Isolation of avian serotype 3 paramyxoviruses from imported caged birds in Israel. Avian Dis 42:829-31.
Shortridge, et al., 1980. Isolation and properties of viruses from poultry in Hong Kong which represent a new (sixth) distinct group of avian paramyxoviruses. J Gen Virol 49:255-262.
Stallknecht, et al., (1991) Avian paramyxoviruses from migrating and resident ducks in coastal Louisiana. Journal of Wildlive Diseases. 27:123-128.
Zhang, et al., 2007. Serological survey on prevalence of antibodies to avian paramyxovirus serotype 2 in China. Avian Dis 51:137-9.
Tang M, et al., 2002. Recombinant adenovirus encoding the HA gene from swine H3N2 influenza virus partially protects mice from challenge with heterologous virus: A/HK/I/68 (H3N2). Arch Virol 147:2125-2141.
Taylor, et al., (1998). Protective Immunity Against Avian Influenza Induced by a Fowlpox Virus Recombinant. Vaccine 6:504-508.
Toro, et al., (2007). Protective avian influenza in ovo vaccination with non-replicating human adenovirus vector. Vaccine 25:2886-2891.
Tumova, et al., 1979. A hitherto unreported paramyxovirus of turkeys. Res Vet Sci 27:135-40.
Tumova, et al., 1989. Further evidence of the circulation of PMV-4 and influenza viruses with N2-1957 enzyme in the migratory waterfowls. Acta Virol 33:573-6.
Veits, et al., (2006) Newcastle disease virus expressing H5 hemagglutinin gene protects chickens against Newcastle disease and avian influenza. Proceedings of the National Academy of Sciences, 103(21), 8197-8202.
Veits, et al., (2003). Deletion of the non-essential UL0 gene of infectious laryngotracheitis (ILT) virus leads to attenuation in chickens, and UL0 mutants expressing influenza virus haemagglutinin (H7) protect against ILT and fowl plague. J Gen Virol 84:3343-3352.
Webster, et al., 1976. Ortho- and paramyxoviruses from migrating feral ducks: characterization of a new group of influenza A viruses. J Gen Virol 32:217-25.
Yamane, et al., 1982. Characterization of avian paramyxoviruses isolated from feral ducks in northern Japan: the presence of three distinct viruses in nature. Microbiol Immunol 26:557-68.

* cited by examiner

Figure 1

| Day of Necropsy | Organ | Control | APMV-2 | APMV-4 | APMV-6 |
|---|---|---|---|---|---|
| 2 | Trachea | 0/5 | 0/5 | **2/5** | 0/5 |
| | Lung | 0/5 | 0/5 | **1/5** | **2/5** |
| | Gut | 0/5 | 0/5 | 0/5 | 0/5 |
| | Pancreas | 0/5 | 0/5 | **1/5** | **2/5** |
| 4 | Trachea | 0/5 | **2/5** | 0/5 | **1/5** |
| | Lung | 0/5 | **2/5** | 0/5 | **1/5** |
| | Gut | 0/5 | 0/5 | 0/5 | 0/5 |
| | Pancreas | 0/5 | 0/5 | 0/5 | **1/5** |
| 7 | Trachea | 0/5 | 0/5 | 0/5 | 0/5 |
| | Lung | 0/5 | 0/5 | 0/5 | **2/5** |
| | Gut | 0/5 | **1/5** | 0/5 | 0/5 |
| | Pancreas | 0/5 | 0/5 | 0/5 | **1/5** |
| 14 | Trachea | 0/5 | 0/5 | 0/5 | 0/5 |
| | Lung | 0/5 | 0/5 | 0/5 | 0/5 |
| | Gut | 0/5 | 0/5 | 0/5 | 0/5 |
| | Pancreas | 0/5 | 0/5 | 0/5 | 0/5 |
| 28 | Trachea | 0/5 | 0/5 | 0/5 | 0/5 |
| | Lung | 0/5 | 0/5 | 0/5 | 0/5 |
| | Gut | 0/5 | 0/5 | 0/5 | 0/5 |
| | Pancreas | 0/5 | **2/5** | **1/5** | **1/5** |

Figure 2

| Day of Necropsy | Organ | Control | APMV serotype 2 | 4 | 6 |
|---|---|---|---|---|---|
| 2 | **Trachea** – catarrhal Tracheitis | + | + | + | + |
| | **Gut** – mild enteritis | - | + | + | + |
| 4 | **Trachea** – focal ulceration of the respiratory epithelium, mild tracheitis | - | + | + | + |
| | **Lung** – focal BALT hyperplasia | - | - | + | - |
| | **Pancreas** – multifocal lymphocytic pancreatitis | - | - | + | + |
| 7 | **Trachea** – focal tracheal attenuation | - | + | - | - |
| | **Lung** – mild BALT hyperplasia | - | - | + | + |
| | **Gut** – cystic enteropathy, focal enteritis | - | - | - | + |
| | **Pancreas** – lymphocytic infiltrates in the pancreas | - | - | - | + |
| 14 | **Trachea** – tracheal attenuation, catarrhal tracheitis | - | + | + | + |
| | **Lung** – mild interstitial pneumonia, BALT hyperplasia | - | - | + | + |
| | **Gut** – GALT hyperplasia | - | - | + | + |
| 28 | **Lung** – lymphocytic bronchitis | - | + | + | + |
| | **Gut** – GALT hyperplasia | - | + | + | + |
| | **Pancreas** – lymphocytic pancreatitis | - | + | + | + |

Figure 4
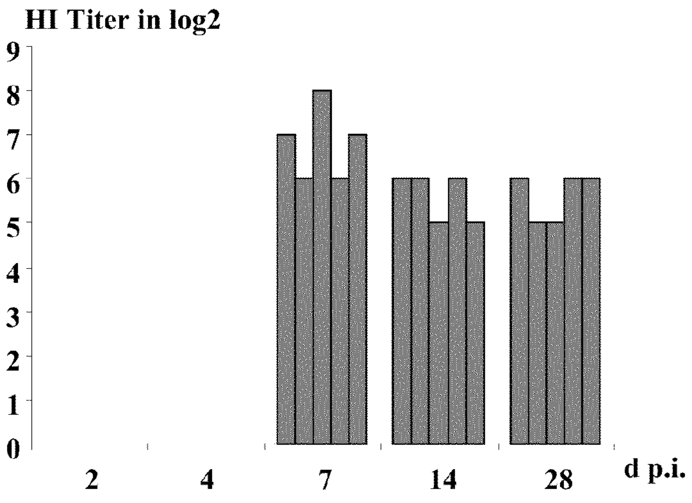
APMV-8 in chickens
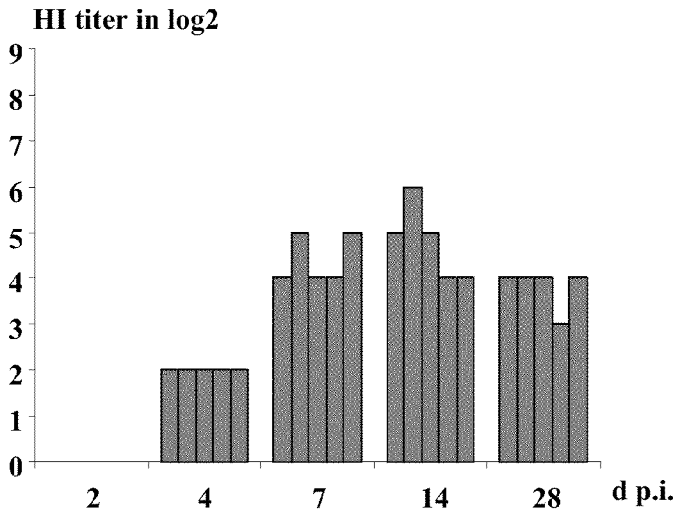
APMV-8 in ducks

Figure 7

| Day p.i. | Organ | Chicken | | Ducks | |
|---|---|---|---|---|---|
| | | Control | APMV-8 | Control | APMV-8 |
| | | Virus isolation [a] | | RT-PCR | |
| 2 | Trachea | 0/5[b] | 5/5 | 0/5 | 5/5 |
| | Lung | 0/5 | 3/5 | 0/5 | 3/5 |
| | Gut | 0/5 | 2/5 | 0/5 | 2/5 |
| | Pancreas | 0/5 | 0/5 | 0/5 | 0/5 |
| 4 | Trachea | 0/5 | 5/5 | 0/5 | 5/5 |
| | Lung | 0/5 | 1/5 | 0/5 | 1/5 |
| | Gut | 0/5 | 1/5 | 0/5 | 1/5 |
| | Pancreas | 0/5 | 1/5 | 0/5 | 1/5 |
| 7 | Trachea | 0/5 | 0/5 | 0/5 | 0/5 |
| | Lung | 0/5 | 0/5 | 0/5 | 0/5 |
| | Gut | 0/5 | 0/5 | 0/5 | 0/5 |
| | Pancreas | 0/5 | 2/5 | 0/5 | 2/5 |
| 14 | Trachea | 0/5 | 0/5 | 0/5 | 0/5 |
| | Lung | 0/5 | 0/5 | 0/5 | 0/5 |
| | Gut | 0/5 | 0/5 | 0/5 | 0/5 |
| | Pancreas | 0/5 | 0/5 | 0/5 | 0/5 |
| 28 | Trachea | 0/5 | 0/5 | 0/5 | 0/5 |
| | Lung | 0/5 | 0/5 | 0/5 | 0/5 |
| | Gut | 0/5 | 1/5 | 0/5 | 1/5 |
| | Pancreas | 0/5 | 0/5 | 0/5 | 0/5 |

[a] Method used for the detection of virus

[b] Number of tissue samples tested positive/total number tested

Figure 8

| Day p.i | Organ | Chicken | | Duck | |
|---|---|---|---|---|---|
| | | Control | APMV-8 | Control | APMV-8 |
| 2 | **Trachea** – catarrhal tracheitis | 0/5 [a] | 5/5 | 0/5 | 3/5 |
| | **Lung**- interstitial pneumonia | 0/5 | 0/5 | 0/5 | 1/5 |
| | **Gut** – mild enteritis | 0/5 | 0/5 | 0/5 | 1/5 |
| 4 | **Trachea** - regeneration of respiratory epithelium, minimal tracheitis | 0/5 | 1/5 | 0/5 | 5/5 |
| | **Pancreas** - mild multifocal lymphocytic pancreatitis | 0/5 | 1/5 | 0/5 | 0/5 |
| 7 | **Trachea** – catarrhal tracheitis | 0/5 | 5/5 | 0/5 | 2/5 |
| | **Lung** - moderate to severe BALT | 0/5 | 4/5 | 0/5 | 0/5 |
| | **Pancreas** – multifocal lymphocytic pancreatitis | 0/5 | 3/5 | 0/5 | 1/5 |
| 14 | **Trachea** - catarrhal tracheitis | 0/5 | 5/5 | 0/5 | 4/5 |
| | **Pancreas** – lymphocytic pancreatitis | 0/5 | 2/5 | 0/5 | 1/5 |
| 28 | **Trachea** – catarrhal tracheitis | 0/5 | 5/5 | 0/5 | 4/5 |
| | **Lung** – BALT hyperplasia | 0/5 | 2/5 | 0/5 | 2/5 |
| | **Gut** – mild enteritis | 0/5 | 3/5 | 0/5 | 0/5 |

[a] number of tissues showing the histopathological changes/total number analyzed

Figure 11A

| SEQ ID NO: | type | Gene name |
|---|---|---|
| 1 | DNA | APMV-8 genomic DNA |
| 2 | DNA | APMV-8 Nucleoprotein (NP) DNA |
| 3 | Protein | APMV-8 Nucleoprotein (NP) protein |
| 4 | DNA | APMV-8 phosphoprotein (P) DNA |
| 5 | Protein | APMV-8 phosphoprotein (P) protein |
| 6 | DNA | APMV-8 Matrixprotein (M) DNA |
| 7 | Protein | APMV-8 Matrixprotein (M) protein |
| 8 | DNA | APMV-8 Fusionprotein (F) DNA |
| 9 | Protein | APMV-8 Fusionprotein (F) protein |
| 10 | DNA | APMV-8 Hemagglutinin/neuraminidase (HN) DNA |
| 11 | Protein | APMV-8 Hemagglutinin/neuraminidase (HN) protein |
| 12 | DNA | APMV-8 Polymerase (L) DNA |
| 13 | Protein | APMV-8 Polymerase (L) protein 1 |
| 14 | Protein | APMV-8 Polymerase (L) protein 2 |
| 15 | DNA | APMV-1 genomic DNA (AF077761) |
| 16 | DNA | APMV-2 genomic DNA (EU338414) |
| 17 | DNA | APMV-3 genomic DNA (EU403085) |
| 18 | DNA | APMV-4 genomic DNA (FJ177514) |
| 19 | DNA | APMV-6 genomic DNA (EU622637) |
| 20 | DNA | APMV-7 genomic DNA Genbank No. FJ231524 |
| 21 | oligo | APMV-PolyT (sense) |
| 22 | Oligo | 8NPf1 (sense) |
| 23 | oligo | 8NPr (antisense) |
| 24 | oligo | NP gene start sequence |
| 25 | oligo | P gene start sequence |
| 26 | oligo | M gene start sequence |
| 27 | oligo | F gene start sequence |
| 28 | oligo | HN gene start sequence |
| 29 | oligo | L gene start sequence |
| 30 | oligo | NP gene end sequence |
| 31 | oligo | P gene end sequence |
| 32 | oligo | M gene end sequence |
| 33 | oligo | F gene end sequence |
| 34 | oligo | HN gene end sequence |
| 35 | oligo | L gene (1) end sequence |
| 36 | oligo | L gene (2) end sequence |
| 37 | DNA | APMV-8 genomic DNA Genbank No. FJ215863.1 |
| 38 | DNA | APMV-8 genomic DNA Genbank No. FJ215864.1 |
| 39 | DNA | APMV-8 genomic DNA Genbank No. FJ619036 |
| 40 | DNA | APMV-9 genomic DNA Genbank No. EU910942 |
| 41 | Oligo | NP-FP-pc3 primer |

Figure 11B

| | | |
|---|---|---|
| 42 | Oligo | NP-RP-pc3 primer |
| 43 | Oligo | P-FP-pc3 primer |
| 44 | Oligo | P-RP-pc3 primer |
| 45 | Oligo | L-FP-pc3 primer |
| 46 | Oligo | L-RP-pc3 primer |
| 47 | DNA | 5'-FLG of APMV-8 genome |
| 48 | DNA | 3'-FLG of APMV-8 genome |
| 49 | DNA | Codon-optimized T7 polymerase (no EcoRI or NotI site) |
| 50 | oligo | EGFP-FP primer |
| 51 | oligo | EGFP-RP primer |
| 52 | DNA | APMV8 minigenome |
| 53 | DNA | NP gene of APMV-8 (FJ215863.1) Genbank FJ215863 |
| 54 | Protein | NP protein of APMV-8 (FJ215863.1) Genbank ACO48297 |
| 55 | DNA | P gene of APMV-8 (FJ215863.1) Genbank FJ215863 |
| 56 | Protein | P protein of APMV-8 (FJ215863.1) Genbank ACO48298 |
| 57 | DNA | M gene of APMV-8 (FJ215863.1) Genbank FJ215863 |
| 58 | Protein | M protein of APMV-8 (FJ215863.1) Genbank ACO48299 |
| 59 | DNA | F gene of APMV-8 (FJ215863.1) Genbank FJ215863 |
| 60 | Protein | F protein of APMV-8 (FJ215863.1) Genbank ACO48300 |
| 61 | DNA | HN gene of APMV-8 (FJ215863.1) Genbank FJ215863 |
| 62 | Protein | HN protein of APMV-8 (FJ215863.1) Genbank ACO48301 |
| 63 | DNA | L gene of APMV-8 (FJ215863.1) Genbank FJ215863 |
| 64 | Protein | L protein of APMV-8 (FJ215863.1) Genbank ACO48302 |
| 65 | DNA | NP gene of APMV-8 (FJ215864.1) Genbank FJ215864 |
| 66 | Protein | NP protein of APMV-8 (FJ215864.1) Genbank ACO48303 |
| 67 | DNA | P gene of APMV-8 (FJ215864.1) Genbank FJ215864 |
| 68 | Protein | P protein of APMV-8 (FJ215864.1) Genbank ACO48304 |
| 69 | DNA | M gene of APMV-8 (FJ215864.1) Genbank FJ215864 |
| 70 | Protein | M protein of APMV-8 (FJ215864.1) Genbank ACO48305 |
| 71 | DNA | F gene of APMV-8 (FJ215864.1) Genbank FJ215864 |
| 72 | Protein | F protein of APMV-8 (FJ215864.1) Genbank ACO48306 |
| 73 | DNA | HN gene of APMV-8 (FJ215864.1) Genbank FJ215864 |
| 74 | Protein | HN protein of APMV-8 (FJ215864.1) Genbank ACO48307 |
| 75 | DNA | L gene of APMV-8 (FJ215864.1) Genbank FJ215864 |
| 76 | Protein | L protein of APMV-8 (FJ215864.1) Genbank ACO48308 |
| 77 | DNA | NP gene of APMV-8 (FJ619036) Genbank FJ619036 |
| 78 | Protein | NP protein of APMV-8 (FJ619036) Genbank ACN88139 |
| 79 | DNA | P gene of APMV-8 (FJ619036) Genbank FJ619036 |
| 80 | Protein | P protein of APMV-8 (FJ619036) Genbank ACN88140 |
| 81 | DNA | M gene of APMV-8 (FJ619036) Genbank FJ619036 |
| 82 | Protein | M protein of APMV-8 (FJ619036) Genbank ACN88143 |
| 83 | DNA | F gene of APMV-8 (FJ619036) Genbank FJ619036 |
| 84 | Protein | F protein of APMV-8 (FJ619036) Genbank ACN88144 |

Figure 11C

| | | |
|---|---|---|
| 85 | DNA | HN gene of APMV-8 (FJ619036) Genbank FJ619036 |
| 86 | Protein | HN protein of APMV-8 (FJ619036) Genbank ACN88145 |
| 87 | DNA | L gene of APMV-8 (FJ619036) Genbank FJ619036 |
| 88 | Protein | L protein of APMV-8 (FJ619036) Genbank ACN88146 |

Figure 12A

SEQ ID NO:1 full length genome sequence of APMV-8

```
15342 BP    DNA  (antigenome, 5' to 3')
BASE COUNT      4850 A   3168 C   3159 G   4165 T
ORIGIN
       1 ACCAAACAAG GAATGCAAGA CCAACGGGAA CTTTAAATAA AACAATCGAA TTATTGGCGG
      61 CGAAGCAAGT GGATCTCGAG CTCGAGGCCG AAACCCTGAA TTTCACTGGA GGTTTTGAAT
     121 AGGTCGCTAT AGGACTCAAT ATGTCATCTG TGTTCAATGA GTATCAGGCG CTTCAAGAAC
     181 AACTTGTGAA GCCGGCTGTC AGGAGACCTG ATGTTGCCTC AACGGGTTTA CTCAGAGCGG
     241 AAATACCTGT CTGTGTTACA TTATCTCAAG ACCCCGGTGA GAGATGGAGC CTTGCTTGCT
     301 TGAATATTAG ATGGCTTGCG AGTGATTCAT CAACCACACC AATGAAGCAA GGAGCAATAT
     361 TGTCACTGCT GAGTCTACAT TCAGACAATA TGCGAGCTCA CGCAACATTA GCAGCAAGGT
     421 CTGCAGATGC TTCACTCACC ATACTTGAGG TAGATGAAGT AGATATTAGC AACTCACTAA
     481 TCAAATTCAA CGCCAGAAGT GGTGTATCTG ACAAACGCTC AAATCAATTG CTTGCAATTG
     541 CGGATGACAT CCCCAAAAGT TGCAGTAATG GGCATCCATT TCTTGACACA GACATTGAGA
     601 CCAGAGACCC GCTCGATCTA TCAGAGACTA TAGATCGCCT GCAGGGTATT GCAGCTCAGA
     661 TATGGGTGTC AGCCATAAAG AGCATGACAG CGCCTGACAC CGCATCAGAG TCAGAAAGTA
     721 AGAGGCTGGC CAAATATCAA CAACAAGGCC GACTGGTTAA GCAAGTACTC TTGCATTCTG
     781 TAGTCAGGAC AGAATTTATG AGAGTTATTC GGGGCAGCTT GGTACTGCGC CAGTTTATGG
     841 TTAGCGAGTG CAAGAGGGCT TCAGCCATGG GCGGAGACAC ATCTAGGTAC TATGCTATGG
     901 TGGGTGACAT CAGTCTTTAC ATCAAGAATG CAGGATTGAC TGCATTTTTC CTCACCCTGA
     961 AGTTCGGAGT TGGTACCCAG TATCCAACCT TAGCAATGAG TGTTTTCTCC AGTGACCTTA
    1021 AAAGGCTTGC TGCACTCATC AGGCTATACA AAACCAAGGG AGACAATGCA CCATACATGG
    1081 CATTCCTGGA GGACTCCGAT ATGGGAAATT TTGCTCCAGC AAATTATAGC ACAATGTACT
    1141 CTTATGCCAT GGGCATTGGG ACAATTCTGG AAGCATCTGT ATCTCGATAC CAGTATGCCA
    1201 GAGACTTTAC CAGTGAGAAT TATTTCCGTC TTGGAGTTGA GACAGCCCAA AGCCAGCAGG
    1261 GAGCATTTGA CGAGAGAACA GCCCGAGAAA TGGGCTTGAC TGAGGAATCA AAACAGCAGG
    1321 TTAGATCACT GCTAATGTCA GTAGACATGG GTCCCAGTTC AATTCATGAG CCATCTCGCC
    1381 CTGCATTTAT CAGTCAAGAA GAAAATAGGC AGCCTGCCCA GAACTTGTCA GATACTCAGG
    1441 GTCAGACCAA GCCAGTCCCG AAGCAGCCCG CACCAAGGGC CGACTCAGAT GACATTGATC
    1501 CATACGAGAA CGGGCTAGAA TGGTAATTCA ACCACCCCGA CACATCCACC TATACACCAA
    1561 TTCCGTGACA TATTAACCCA ATCAAACATT TCATAAACTA TAGTAGTCAT TGATTTAAGA
    1621 AAAAATTGGG GGCGACCTCA ATTGTGAAAC ATACCAGATC CGTCCACAAC ACCACTCAAC
    1681 AACCCACACA CAATGGATTT CGCCAATGAT GAAGAAATTG CAGAACTTTT GAATCTCAGC
    1741 ACCAATGTAA TCAAGGAGAT TCAGAAATCC GAACTCAAGC CTCCCCAAAC CACCGGACGA
    1801 CCACCTGTCA GTCAAGGGAA CACAAGAAAT CTAACTGATC TATGGGAAAA GGAGACTGCA
    1861 AGTCAGACCA AGACACCGGC CCAATCTACA CAAACCACAC AAGTTCAGTC TGATGAAAAT
    1921 GAGGAGGGAG AAATCAAGTC CGAGTCAACT GATGGCCACA TCAGAGGAAC TGTTAATCAA
    1981 TCAGAGCAAG TCCCAGAACA AAACCAGAGC AGATCTTCAC CAGGTGATGA TCTCGACAGA
    2041 GCTCTCAACA AGCTTGAAGG GAGAATCAAT TTAATCAGCT CAATGGACAA AGAAATTAAA
    2101 AAGGGCCCTC GCATCCAGAA TCTCCCTGGG TCCCAGGCGG CAACTCAACA GGCGACCCAC
    2161 CCATTGGCAG GGGACACCCC GAACATGCAA GCACAGACAA AAGCCCTGGC GAAGCCACAT
    2221 CAAGAGGCAA TCAATCCTGG CAACCAGGAC ACAGGAGAGA GTATTCATTT ACCACCTTCC
    2281 ATGGCACCAC CAGAGTCATT AGTTGGTGCA ATCCGCAATG CACCCCAATT CGTGCCAGAC
    2341 CAATCTATGA CGAATGTAGA TGCGGGGAGT GTCCAACTAC ATGCATCATG TGCAGAGATG
    2401 ATAAGTAGAA TGTTTGTAGA AGTTATATCC AAGCTTGATA AACTCGAGTC GAGACTGAAT
    2461 GATATAGCAA AAGTTGTGAA CACTACCCCC CTTATTAGGA ATGATATTAA CCAACTTAAG
    2521 GCCACAACCG CACTGATGTC TAACCAAATT GCCTCCATAC AAATTCTTGA CCCAGGGAAT
    2581 GCAGGGGTGA GGTCCCTCTC TGAAATGAAA TCTGTGACGA AGAAAGCTGC TGTTGTAATT
    2641 GCAGGGTTTG GAGACGACCC AACTCAAATT ATTGAAGAAG GCATTATGGC CAAAGATGCT
    2701 CTTGGAAAAC CTGTGCCTCC AACATCTGTT ATCTCAGCCA AAGCTCAGAC TTCTTCCGGT
    2761 GTGAGTAAGG GTGAAATAGA AGGATTGATT GCATTGGTGG AAACATTAGT TGACAATGAC
    2821 AAGAAGGCAG CAAAACTGAT TAAAATGATT GATCAAGTTA AATCCCATGC CGATTACGCC
    2881 CGAGTCAAGC AGGCAATATA TAATGCGTAA TACTGTAACT ACACAAACAA TCAATACTGC
    2941 TGTCGGTTGC ACCCACCTCA GCAAATCAAT AATCTTTTAG AATTTATTGA TTAAGAAAAA
    3001 ATTGACTACT ATAAGAAAAG AACACCAAGT TGGGGGCGAA GACACGATTG ACCACAGTCG
```

Figure 12B

```
3061 CTATCTGTAA GGCTCCTCAC CAAAAATGGC ATATACAACA TTGAAACTGT GGGTGGATGA
3121 GGGTGACATG TCGTCTTCGC TCCTATCATT CCCGTTGGTA CTAAAAGAGA CAGACAGAGG
3181 CACAAAGGAG CTTCAACCAC AGGTAAGGGT AGATTCAATT GGCGATGTGC AGAACGCCAA
3241 AGAGTCCTCG ATATTCGTGA CTCTATATGG TTTCATCCAA GCAATTAAGG AGAGTTCAGA
3301 TCGATCGAAA TTCTTCCATC CAAAAGATGA CTTCAAACCT GAGACAGTCA CTGCAGGACT
3361 GGTAGTGGTA GGTGCGATCC GAATGATGGC TGATGTTAAT ACCATCTCTA ATGACGCACT
3421 AGCGCTGGAG ATCACTGTTA AGAAATCTGC AACTTCTCAA GAGAAAATGA CGGTGATGTT
3481 CCACAATAGC CCCCCTTCAT TGAGAACTGC AATAACTATC CGAGCAGGAG GTTTCATCTC
3541 GAATGCAGAC GAGAATATAA AATGTGCCAG CAAATTGACT GCAGGAGTGC AGTACATATT
3601 CCGCCCAATG TTTGTTTCAA TCACTAAATT ACACAATGGC AAACTATATA GGGTGCCCAA
3661 AAGCATCCAC AGCATCTCAT CCACTCTACT GTATAGTGTG ATGTTGGAGG TAGGATTCAA
3721 AGTGGATATT GGGAAGGATC ATCCCCAGGC AAAGATGCTG AAGAAGGTCA CAATCGGCGA
3781 TGCAGACACA TACTGGGGGT TTGCATGGTT CCACCTGTGC AATTTCAAAA AGACATCCTC
3841 TAAGGGAAAG CCAAGAACGC TAGACGAACT AAAGACAAAA GTCAAAAAAT TGGGGTTGAA
3901 ATTGGAGTTA CATGACCTGT GGGGTCCGAC TATTGTGGTC CAAATCACTG GCAAGAGCAG
3961 CAAATATGCT CAAGGATTTT TTTCCTCCAA TGGTACTTGT TGTCTCCCAA TCAGCAGATC
4021 TGCACCAGAG CTTGGGAAGC TTCTGTGGTC TTGTTCAGCA ACTATAGGTG ACGCAACAGT
4081 TGTTATCCAA TCAAGCGAGA AAGGGGAACT CCTAAGGTCT GATGACCTCG AGATACGAGG
4141 TGCTGTGGCC TCCAAGAAAG GTAGACTGGG CTCATTTCAC CCCTTCAAAA AATGATGCAG
4201 GACATAGTAC AGAGAATTAG AGAGCCATTA GATGTGCGCA AAAAACATAA TCTGCGATGA
4261 ACTGCCCAGA CTCCACTTTA ATCTAGGTTG CAGGGAAATA GTACACGACA TGCGAAATAC
4321 TATCACGGTC ACCAGCAATC AATAAAGCTG ATCAATCACT ATATTAGGAA TCAAATAGGA
4381 TAACAATTAT TAATCCAATT TCCTAATTAT AAAAAATTGC TTTAAAGGTT ATTGACGAGT
4441 CGGGGGCGAA ATCTTGCCAC TTAGTCTGCA GTCAATCTTA GAATCTACAT ATTGAACTAT
4501 GGGTCAAATA TCAGTATATC TAATTAATAG CGTGCTATTA TTGCTGGTAT ATCCTGTGAA
4561 TTCGATTGAC AATACACTCA TTGCCCCAAT CGGAGTTGCC AGCGCAAATG AATGGCAGCT
4621 TGCTGCATAT ACAACATCAC TTTCAGGGAC AATTGCCGTG CGATTCCTAC CTGTGCTCCC
4681 GGATAATATG ACTACCTGTC TTAAAGAAAC AATCACTACA TACAATAATA CTGTCAACAA
4741 CATCTTAGGC CCACTCAAAT CCAATCTGGA TGCACTGCTC TCATCTGAGA CTTATCCCCA
4801 GACAAGATTA ATTGGGGCAG TTATAGGTTC AATTGCTCTC GGTGTTGCAA CATCGGCTCA
4861 AATCACTGCT GCAGTTGCTC TCAAGCAAGC GCAAGACAAT GCAAGGAACA TACTAGCACT
4921 CAAAGAAGCA CTGTCCAAAA CCAATGAGGC GGTCAAGGAG CTTAGTAGTG GGTTACAACA
4981 AACAGCTATT GCACTTGGTA AGATACAGAG TTTTGTGAAT GAGGAAATTC TGCCATCTAT
5041 CAACCAACTG AGCTGCGAGG TGACAGCCAA TAAACTTGGG GTGTATTTAT CTCTGTATCT
5101 CACAGAACTG ACCACCATAT TCGGTGCACA GCTGACCAAC CCTGCATTGA CTTCATTATC
5161 ATATCAAGCA CTGTACAACC TGTGTGGTGG CAACATGGCA ATGCTTACTC AGAAGATTGG
5221 AATTAAACAG CAAGACGTTA ATTCGCTATA TGAAGCCGGA CTAATCACAG GACAAGTCAT
5281 TGGTTATGAC TCTCATTACC AGCTGCTGGT CATCCAGGTC AATTATCCAA GCATTTCTGA
5341 GGTCACTGGT GTACGTGCGA CAGAATTAGT CACTGTTAGT GTAACAACAG ACAAGGGTGA
5401 AGGGAAAGCA ATTGTACCCC AATTTGTAGC TGAAAGTCGG GTGACTATTG AAGAGCTTGA
5461 TGTCGCATCT TGTAAATTCA GCAGCACGAC CCTATATTGC AGGCAGGTCA ACACAAGGGC
5521 ACTTCCCCCG CTAGTAGCTA GCTGTCTTCG AGGTAACTAT GATGATTGTC AATATACCAC
5581 AGAGATTGGA GCATTATCAT CCCGGTATAT AACACTAGAT GGGGGGGTCT TAGTTAATTG
5641 CAAGTCAATT GTTTGTAGGT GCCTTAATCC AAGTAAGATC ATCTCTCAAA ATACAAACGC
5701 TGCAGTAACA TATGTTGATG CCACAATCTG CAAAACAATT CAATTGGATG ATATACAACT
5761 CCAGCTGGAA GGGTCACTAT CATCAGTTTA TGCAAGAAAC ATCTCAATTG AGATCAGTCA
5821 GGTGACCACA TCCGGGTCTT TAGATATCAG CAGTGAGATA GGAAACATCA ATAATACGGT
5881 GAATCGTGTG GAGGATTTAA TTCACCAATC AGAGGAATGG CTGGCAAAGG TTAACCCACA
5941 CATTGTTAAT AATACAACAC TAATTGTACT CTGTGTGTTA AGTGCGCTTG CTGTGATCTG
6001 GCTGGCAGTA TTAACGGCTA TTATAATATA CTTGAGAACA AAGTTGAAGA CTATATCGGC
6061 ATTAGCTGTA ACCAATACAA TACAGTCTAA CCCCTATGTT AACCAAACGA AACATGAATC
6121 TAAGTTTTGA TCATTCAAGC CAAAACAGAG GATCTAGGCT CAGGTTAATA ATAGTTCAAT
6181 CAATATTTGA TTTATTAGGT TTTTTTCACT AATTATTAAT ATACTCGTGA TTAGATGATA
6241 ACGTTAAAAG TCTTAGATAT TTTAATAAAAA ATGTAACCTG GGGGCGACCC ATTTATAGGT
6301 GAGTATATAT TAGGAAGTCC TTATATTGCA CTGTGATTTC AAACAATTAT ATTACCTCAT
6361 ATCTACCTTG TCTAAAGACA TCATGAGTAA CATTGCATCC AGTTTAGAAA ACATTGTAGA
6421 GCAGGATAGT CGAAAAACAA CTTGGAGGGC CATCTTTAGA TGGTCCGTTC TTCTTATTAC
6481 AACAGGATGC TTAGCCTTAT CCATTGTTAG CATAGTTCAA ATTGGAAATT TGAAAATTCC
```

Figure 12C

```
6541 TTCTGTAGGG GATCTGGCTG ATGAAGTGGT GACACCCTTG AAAACCACTC TGTCAGATAC
6601 ACTCAGGAAT CCAATTAACC AGATAAATGA TATATTTAGG ATTGTTGCCC TTGATATTCC
6661 ATTGCAAGTG ACCAGTATCC AAAAAGACCT TGCAAGTCAA TTTAACATGT TGATAGATAG
6721 TTTAAATGCT ATCAAATTAG GCAACGGGAC CAACCTTATC ATACCTACAT CAGACAAGGA
6781 GTATGCAGGA GGAATTGGAA ACCCTGTATT TACTGTCGAT GCTGGAGGTT CTATAGGATT
6841 CAAACAGTTT AGCTTAATAG AACATCCGAG CTTTATTGCT GGACCTACAA CGACCCGAGG
6901 CTGTACAAGA ATACCCACTT TTCACATGTC AGAAAGTCAT TGGTGCTACT CACACAACAT
6961 CATCGCTGCT GGCTGTCAAG ATGCCAGTGC ATCCAGTATG TATATCTCAA TGGGAGTTCT
7021 CCATGTGTCC TCATCTGGCA CTCCCATTTT TCTTACTACT GCAAGTGAGC TGATAGACGA
7081 TGGAGTTAAC CGTAAGTCAT GCAGCATTGT AGCAACCCAA TTTGGCTGTG ACATTTTGTG
7141 CAGTATTGTC ACAGAGAAGG AGGGAGATGA TTACTGGTCT GATACTCCGA CTCCAATGCG
7201 CCACGGCCGT TTTTCATTCA ATGGTAGTTT TGTAGAAGCC GAACTACCAG TGTCCAGTAT
7261 GTTCTCATCA TTCTCTGCCA ACTACCCTGC TGTGGGATCA GGCGAAATTG TAAAAGATAG
7321 AATATTATTC CCAATTTACG GAGGTATAAA GCAGACTTCA CCAGAGTTTA CCGAATTAGT
7381 GAAATACGGA CTCTTTGTAT CAACACCTAC AACTGTGTGC CAGAGTAGCT GGACTTATGA
7441 CCAGGTAAAA GCTGCGTATA GGCCAGATTA CATATCAGGC CGGTTCTGGG CACAAGTGAT
7501 ACTCAGCTGC GCTCTTGATG CAGTCGACTT ATCAAGTTGT ATTGTAAAGA TTATGAATAG
7561 CAGCACAGTG ATGATGGCAG CGGAAGGAAG GATAATGAAG ATAGGGATTG ATTACTTTTA
7621 CTATCAGCGG TCATCTTCTT GGTGGCCATT GGCATTTGTC ACAAAACTAG ACCCGCAAGA
7681 GTTGGCAGAC ACAAACTCAA TATGGCTGAC CAATTCCATA CCAATCCCGC AATCAAAGTT
7741 CCCTCGGCCT TCATATTCAG AAAATTATTG CACAAAGCCA GCAGTTTGCC CTGCTACTTG
7801 TGTCACTGGT GTGTACTCTG ATATTTGGCC CCTGACCTCA TCTTCATCAC TCCCGAGCAT
7861 AATTTGGATC GGCCAGTACC TTGATGCTCC TGTTGGAAGG ACTTATCCTA GATTTGGAAT
7921 TGCAAATCAG TCACACTGGT ACCTCCAAGA AGATATTCTA CCCACTTCCA CCGCAAGTGC
7981 GTATTCAACC ACTACATGTT TTAAGAATAC TGCCAGGAAT AGAGTGTTCT GCGTCACCAT
8041 TGCCGAATTT GCAGATGGGT TGTTTGGAGA GTACAGGATA ACACCTCAGT TGTACGAATT
8101 AGTGAGAAAT AATTGAATAA CAATAATTTT GGGACTCATT TTGTCGCAAA GTGAAATTGT
8161 CATCTTTAAA AATAATCAAT TCGATGATTT TTATTGAACA TGATTAAGCA ATCATGTGGG
8221 AAATTTATTA TCTCATAAAT TCTAATAGTT GTAAATGATG AATTAAGAAA AAATGGAGGG
8281 CGACCTCTAC ACAAACATGG ATATAAAACA AGTTGACCTG ATAATACAAC CCGAGGTTCA
8341 TCTCGATTCA CCCATCATAT TGAATAAACT GGCACTATTA TGGCGCTTGA GTGGTTTACC
8401 CATGCCTGCA GACCTACGAC AAAAATCCGT AGTGATGCAC ATCCCGGACC ACATCTTAGA
8461 AAAATCAGAA TATCGGATCA AGCACCGTCT AGGGAAAATC AAGAGTGACA TAACACATTA
8521 CTGTCAGTAT TTTAATATTA ATTTGGCAAA TATTGATCCG ATAACCCACC CCAAAAGTTT
8581 GTATTGGTTA TCCAGACTAA CAATAGCTAG TGCTGGAACT TTTAGGCATA TGAAAGATAG
8641 AATCTTGTGT ACAGTTGGCT CTGAATTTGG ACACAAAATT CAAGATTTAT TTTCACTGCT
8701 GAGCCATAAA CTAGTAGGTA ACGGGGATTT ATTTAATCAA AGTCTCTCAG GTACACGTTT
8761 GACTGCAAGT CCGTTATCCC CTTTATGCAA TCAATTTGTC TCTGACATCA AGTCTGCAGT
8821 CACGACACCC TGGTCAGAAG CTCGTTGGTC TTGGCTTCAT ATCAAACAAA CAATGAGATA
8881 TCTGATAAAA CAATCACGCA CTACAAATTC GGCTCATTTA ACAGAAATCA TAAAAGAAGA
8941 ATGGGGTTTA GTAGGTATTA CTCCAGATCT TGTCATTCTT TTTGACAGAG TCAATAATAG
9001 TCTGACTGCA TTAACATTTG AGATGGTTCT AATGTATTCA GATGTATTAG AATCCCGTGA
9061 CAATATTGTG TTAGTGGGGC GACTATCTAC CTTTCTACAG CCAGTAGTTA GTAGACTGGA
9121 GGTGTTGTTT GATCTAGTAG ATTCATTGGC AAAAATCTTA GGTGACACAA TATATGAGAT
9181 TATTGCAGTG TTAGAGAGCT TGTCTTATGG GTCAGTTCAA CTACATGATG CAAGTCACTC
9241 TCATGCAGGG TCTTTTTTTT CATTTAACAT GAATGAACTT GATAACACAC TATCAAAGAG
9301 GGTAGATCCG AAACACAAGA ACACTATAAT GAGCATTATA AGACAATGCT TTTCTAATCT
9361 AGATGTTGAT CAAGCTGCAG AGATGCTATG CCTGATGAGA TTATTCGGAC ACCCAATGTT
9421 AACTGCACCG GATGCAGCAG CCAAAGTGAG GAAAGCAATG TGTGCTCCAA AACTTGTTGA
9481 ACACGACACC ATCTTGCAGA CATTATCTTT CTTCAAGGGG ATAATTATAA ATGGGTACAG
9541 AAGATCACAC TCTGGCCTGT GGCCCAATGT AGAGCCGTCT TCAATTTATG ATGATGATCT
9601 CAGACAGCTG TACTTAGAGT CAGCAGAGAT TTCCCATCAT TTTATGCTTA AAAACTACAA
9661 GAGTTTAAGC ATGATAGAAT TCAAGAAGAG CATAGACTAC GATCTTCATG ATGACCTAAG
9721 TACTTTCTTA AAGGATAGAG CAATTTGCCG GCCGAAATCC CAGTGGGATG TCATATTTCG
9781 TAAGTCTTTA CGCAGATCTC ATACGCAGTC CCAGTATCTG GACGAAATTA AGAGCAACCG
9841 ATTGCTAATT GATTTTCTTG ATTCTGCTGA ATTTGACCCT GGAAAAGAAT TTGCATATGT
9901 AACCACAATG GATTATTTGC ACGATAATGA ATTTTGTGCT TCATATTCTC TAAAGGAAAA
9961 GGAGATCAAA ACTACTGGGA GGATATTTGC AAAAATGACA CGCAATATGA GAAGTTGCCA
```

Figure 12D

```
10021 AGTAATACTT GAATCTTTGT TATCAAAGCA TATATGCAAG TTCTTCAAAG AGAATGGCGT
10081 TTCGATGGAG CAATTGTCAT TGACCAAGAG TCTACTTGCA ATGTCTCAAC TCTCACCAAA
10141 AGTCTCGACT TTGCAGGACA CTGCATCACG TCATGTAGGT AACTCAAAAT CTCAGATTGC
10201 AACCAGCAAC CCATCTCGGC ATCACTCGAC ACCCAATCAG ATGTCACTCT CAAATCGAAA
10261 AACGGTTGTA GCAACTTTCT TAACAACTGA CTTGGAAAAA TACTGCCTGC AGTGGCGATA
10321 TTCAACTATT AAATTGTTTG CACAAGCTCT AAATCAACTC TTTGGGATTG ATCACGGATT
10381 TGAATGGATA CATTTAAGAC TTATGAACAG CACCTTATTT GTTGGCGATC CTTACTCGCC
10441 TCCTGAAGAT CCAACACTAG AAGATATAGA TAAAGCACCA AATGATGATA TCTTCATAGT
10501 TTCTCCAAGG GGAGGCATAG AGGGTTTATG TCAGAAAATG TGGACCATGA TATCAATTAG
10561 TGCTATACAC TGTGTAGCAG AGAAAATTGG TGCACGAGTG GCAGCAATGG TGCAGGGTGA
10621 TAATCAAGTA ATAGCTATCA CCAAAGAATT ATTCAGAGGA GAGAAAGCTT GTGATGTCAG
10681 AGATGAGTTA GACGAGCTTG GTCAAGTGTT TTTTGATGAG TTCAAGAGAC ACAATTATGC
10741 AATTGGACAC AATCTTAAGC TAAATGAGAC AATACAAAGC CAATCCTTTT TTGTATATTC
10801 CAAACGAATA TTCTTTGAAG GGCGATTGCT TAGTCAAGTC CTCAAAAAATG CTGCCAAGTT
10861 ATGTATGGTT GCTGACCATC TAGGTGAAAA CACTGTATCT TCCTGTAGCA ACCTGAGCTC
10921 GACAATTGCC CGCTTAGTGG AAAATGGGTT TGAGAAGGAC ACTGCTTTTG TGTTGAACCT
10981 AGTCTACATC ATGACTCAGA TTCTTTTTGA TGAGCATTAC TCGATTGTAT GCGATCACCA
11041 TAGTGTCAAA AGCTTGATTG GATCAAAAAA CCATCGGAAT TTATTGTATT CATCTCTAAT
11101 ACCAGGTCAG CTCGGCGGTT TCAACTTCCT CAATATAAGT CGGTTGTTCA CTAGGAATAT
11161 AGGTGACCCA GTAACATGTA GTCTGTCTGA TCTCAAATGC TTCATAGCCG CAGGTCTCCT
11221 TCCACCCTAT GTCCTAAAAA ATGTGGTTCT GCGTGAGCCT GGTCCTGGGA CATGGTTGAC
11281 GTTGTGCTCT GATCCTTACA CCCTTAACAT ACCATACACA CAGCTTCCAA CCACATATCT
11341 CAAAAAGCAC ACCCAGCGAT CATTGCTTTC ACGTGCAGTA AATCCTTTAT TAGCCGGTGT
11401 ACAAGTGCCA AATCAGCATG AGGAAGAAGA GATGTTGGCT CGCTTTCTCC TTGATCGTGA
11461 ATATGTGATG CCCCGCGTTG CTCATGTAAT ACTAGAATCA TCAGTCCTTG GCAAACGGAA
11521 ACAAATCCAA GGCTTAATTG ATACAACTCC AACCATCATT AGAACATCTC TAGTTAATCT
11581 GCCAGTGTCT AGAAAGAAAT GCGAAAAAAT AATCAATTAC TCTCTCAATT ATATTGCTGA
11641 GTGTCATGAC TCCTTACTTA GCCAGGTCTG CTTCAGTGAT AATAAGGAAT ACTTGTGGTC
11701 AACCTCCTTA ATATCAGTTG AGACCTGTAG TGTGACAATT GCGGACTATC TGAGAGCTGT
11761 CAGCTGGTCT AATATATTAG GGGGAAGAAA CATATCCGGG GTGACTACAC CTGATACTAT
11821 TGAATTAATT CAAGGTTGTT TAATAGGTGA AAATTCTAGT TGTACTCTTT GTGAATCGCA
11881 TGATGACGCA TTCACGTGGA TGCACTTGCC TGGCCCACTT TACATCCCTG AACCATCAGT
11941 TACTAACTCT AAAATGCGTG TGCCATATCT GGGTTCAAAA ACAGAGGAGC GGAAAACAGC
12001 CTCAATGGCA GCAATAAAAG GAATGTCACA TCACCTGCGT GCAGTCTTAA GAGGCACATC
12061 CGTATTTATT TGGGCATTTG GGGATACAGA TATCAATTGG GATAATGCAT TGCAGATTGC
12121 CCAATCACGG TGTAACATCA CATTGGATCA AATGAGATTA CTTACACCAA TTCCTAGCAG
12181 TTCAAATATT CAACATAGAC TCGATGACGG AATCAGCACG CAGAAATTTA CTCCTGCAAG
12241 CCTTGCTCGA ATCACATCCT TCGTTCACAT CTGTAATGAC AGCCAGAGGT TAGAGAAGGA
12301 TGGCTCATCT GTCGACTCAA ACTTGATTTA CCAGCAAATT ATGTTACTTG GACTCAGCAT
12361 CTTTGAAACA ATGTACTCAA TGGACCAAAA GTGGGTATTC AATAACCATA CCTTGCATTT
12421 GCACACTGGA CACTCCTGTT GTCCAAGGGA ACTAGACATA AGTTTGGTGA ACCCGCCGAG
12481 ACATCAGACC CCGGAGCTGA CTAGCACAAC AACCAACCCG TTCCTATATG ATCAGCTCCC
12541 ATTAAATCAA GAAAACTTGA CAACACTTGA GATTAAGACA TTTAAATTCA ATGAGCTCAA
12601 CATTGATGGT TTAGATTTTG GTGAAGGAAT ACAATTATTG AGTCGTTGTA CTGCAAGATT
12661 AATGGCAGAA TGTATTCTAG AGGAGGGAAT AGGCTCGTCA GTTAAAAATG AAGCAATTGT
12721 CAATTTTGAT AATTCAGTCA ATTGGATTTC AGAGTGCCTA ATGTGTGATA TTCGCTCACT
12781 TTGTGTTAAT TTAGGTCAAG AGATACTATG TAGCCTGGCA TACCAAATGT ATTACTTGCG
12841 AATCAGGGGT AGACGGGCCA TTCTTAATTA CTTGGACACA ACTTTGCAAA GGATCCCTGT
12901 GATACAATTA GCCAACATTG CACTCACCAT TTCGCACCCT GAGATATTTC GCAGAATTGT
12961 CAACACCGGG ATCCATAACC AGATTAAGGG CCCATATGTG GCAACAACGG ATTTCATAGC
13021 TGCAAGTAGA GATATCATAT TATCAGGTGC AAGGGAGTAT CTATCTTATT TAAGCAGTGG
13081 GCAGGAAGAC TGTTACACAT TCTTCAACTG TCAAGATGGG GATCTTACTC CAAAAATGGA
13141 ACAGTATCTT GCAAGGAGGG CATGCCTTTT AACATTATTG TATAATACTG GGCACCAGAT
13201 CCCCGTTATC CGATCACTGA CGCCAATAGA GAAGTGCAAG GTGCTCACAG AATACAATCA
13261 ACAAATTGAG TACGCAGATC AAGAGTTTAG CTCTGTACTA AAAGTGGTCA ATGCACTACT
13321 ACAAAATCCT AAGATAGATG CATTAGTTTC AAATCTCTAC TTCACCACCA GACGTGTTCT
13381 ATCAAACCTC AGATCATGTG ATAAGGCTAG ATCATATATT GAATATTTGT ACACTGAGGA
13441 CTTCGGAGAG AAAGAGGATA CAGTACAATA TGACATCATG ACAACAAACG ATATCATACT
```

Figure 12E

```
13501 TACTCATGGT CTATTCACAC AGATCGAAAT ATCTTATCAA GGGAATAGTC TCCATAAGTT
13561 CCTTACTCCG GATAACGCGC CTGGATCTTT GATCCCATTC TCTATTTCAC CAAATTCACT
13621 TGCATGTGAC CCTCTTCATC ACTTGCTCAA GTCGGTCGGT ACATCAAGCA CAAGTTGGTA
13681 CAAGTATGCA ATCGCCTATG CAGTGTCTGA AAAGAGGTCA GCTCGATTAG GAGGGAGCTT
13741 GTACATTGGT GAAGGGAGCG GAAGTGTGAT GACTTTACTC GAGTATCTTG AGCCATCTGT
13801 TGACATATTT TACAATTCAC TCTTCTCAAA TGGTATGAAC CCACCACAAC GAAATTATGG
13861 GCTTATGCCA CTACAATTTG TGAATTCGGT GGTTTATAAG AACTTAACGG CTAAATCAGA
13921 ATGTAAGCTA GGGTTTGTCC AGCAATTTAA ACCGTTGTGG AGAGACATAG ACATTGAGAC
13981 TAATGTTACA GATCCATCAT TTATCAATTT TGCATTGAAT GAAATCCCAA TGCAATCATT
14041 AAAACGAGTA AATTGTGATG TGGAATTTGA CCGTGGTATG CCGATTGAAC GGGTTATTCA
14101 GGGTTACACC CATATCTTAC TTGTTGCCAC TTACGGATTA CAGCAAGATT CAATACTGTG
14161 GGTGAAGGTA TATAGGACAT CTGAAAAAGT ATTTCAATTC TTACTGAGTG CCATGATCAT
14221 GATCTTTGGT TATGTAAAAA TCCACAGGAA TGGTTATATG TCGACAAAGG ATGAAGAGTA
14281 CATATTGATG TCTGACTGCA AGGAACCTGT AAACTATACA GCTGTCCCTA ACATTCTTAC
14341 ACGTGTAAGT GATTTAGTGT CGAAGAATCT GAGTCTTATC CATCCAGAAG ACCTCAGAAA
14401 AGTAAGGTGT GAAACAGATT CCCTGAATTT GAAGTGCAAT CATATTTATG AGAAAATAAT
14461 TGCCAGAAAA ATTCCATTAC AGGTATCATC AACTGACTCT TTGCTCCTCC AATTAGGCGG
14521 TGTTATCAAC TCGGTGGGCT CAACTGATCC TAGAGAGGTT GCAACATTAT CTTCTATTGA
14581 GTGTATGGAC TATGTTGTCT CATCAATTGA TTTGGCTATA TTGGAGGCAA ATATTGTAAT
14641 CTCAGAGAGT GCTGGTCTTG ACCTCGCTTT AATGTTAGGC CCATTCAACT TAAATAAGCT
14701 TAAGAAAATT GACACAATCC TTAAGTCAAG CACCTATCAG CTAATCCCGT ACTGGTTGCG
14761 CTATGAGTAC TCTATTAATC CGAGATCTTT GTCATTTCTA ATCACTAAAT TACAACAATG
14821 CCGAATTTCA TGGTCAGATA TGATCACGAT TTCTGAATTT CGTAAGAAAT CCAAGCGGCC
14881 TATATTTATC AAACGAGTAA TAGGGAATCA ACAGCTAAAA TCATTCTTTA ATGAAAGCTC
14941 AAGTATTGTT TTGACTCGGG CTGAAGTTAA AGTCTGTATA AAGTTCCTCG GTGCAATCAT
15001 CAAGTTGAAA TAATTTCTGC GATTTTAAAG GGGTGTAATG TTCTAATTTG CACTTGAAGT
15061 AATATAGCTT GTAATCATTC GCTAGGGGAT AGGATAATTT CTCTAACCTC TGAATCTATA
15121 TTCCTAGAGT ATAACAAATA TATACATAAT AAAAATGATT TTAAGAAAAA ATCCGACACT
15181 CAAAGAAAAT TGGTGCCTGT AATATTCTTC TTGCCAAATG ATTGTGAAGT GTCTAGCCTA
15241 ACTTAAAACA ATCGTATTCG ATAGGGAAGA ATGATATATA AAATAACTAA TAAAAAATTG
15301 TATTAGTAAA AATTACCGTA TTTCCTGTAT TCCATTTCTG GT
```

Figure 12F

SEQ ID NO:2 DNA sequence encoding APMV-8 Nucleoprotein (NP)

| | | |
|---|---|---|
| 1 | ATG TCA TCT GTG TTC AAT GAG TAT CAG GCG CTT CAA GAA CAA CTT GTG | 48 |
| 49 | AAG CCG GCT GTC AGG AGA CCT GAT GTT GCC TCA ACG GGT TTA CTC AGA | 96 |
| 97 | GCG GAA ATA CCT GTC TGT GTT ACA TTA TCT CAA GAC CCC GGT GAG AGA | 144 |
| 145 | TGG AGC CTT GCT TGC TTG AAT ATT AGA TGG CTT GCG AGT GAT TCA TCA | 192 |
| 193 | ACC ACA CCA ATG AAG CAA GGA GCA ATA TTG TCA CTG CTG AGT CTA CAT | 240 |
| 241 | TCA GAC AAT ATG CGA GCT CAC GCA ACA TTA GCA GCA AGG TCT GCA GAT | 288 |
| 289 | GCT TCA CTC ACC ATA CTT GAG GTA GAT GAA GTA GAT ATT AGC AAC TCA | 336 |
| 337 | CTA ATC AAA TTC AAC GCC AGA AGT GGT GTA TCT GAC AAA CGC TCA AAT | 384 |
| 385 | CAA TTG CTT GCA ATT GCG GAT GAC ATC CCC AAA AGT TGC AGT AAT GGG | 432 |
| 433 | CAT CCA TTT CTT GAC ACA GAC ATT GAG ACC AGA GAC CCG CTC GAT CTA | 480 |
| 481 | TCA GAG ACT ATA GAT CGC CTG CAG GGT ATT GCA GCT CAG ATA TGG GTG | 528 |
| 529 | TCA GCC ATA AAG AGC ATG ACA GCG CCT GAC ACC GCA TCA GAG TCA GAA | 576 |
| 577 | AGT AAG AGG CTG GCC AAA TAT CAA CAA CAA GGC CGA CTG GTT AAG CAA | 624 |
| 625 | GTA CTC TTG CAT TCT GTA GTC AGG ACA GAA TTT ATG AGA GTT ATT CGG | 672 |
| 673 | GGC AGC TTG GTA CTG CGC CAG TTT ATG GTT AGC GAG TGC AAG AGG GCT | 720 |
| 721 | TCA GCC ATG GGC GGA GAC ACA TCT AGG TAC TAT GCT ATG GTG GGT GAC | 768 |
| 769 | ATC AGT CTT TAC ATC AAG AAT GCA GGA TTG ACT GCA TTT TTC CTC ACC | 816 |
| 817 | CTG AAG TTC GGA GTT GGT ACC CAG TAT CCA ACC TTA GCA ATG AGT GTT | 864 |
| 865 | TTC TCC AGT GAC CTT AAA AGG CTT GCT GCA CTC ATC AGG CTA TAC AAA | 912 |
| 913 | ACC AAG GGA GAC AAT GCA CCA TAC ATG GCA TTC CTG GAG GAC TCC GAT | 960 |
| 961 | ATG GGA AAT TTT GCT CCA GCA AAT TAT AGC ACA ATG TAC TCT TAT GCC | 1008 |
| 1009 | ATG GGC ATT GGG ACA ATT CTG GAA GCA TCT GTA TCT CGA TAC CAG TAT | 1056 |
| 1057 | GCC AGA GAC TTT ACC AGT GAG AAT TAT TTC CGT CTT GGA GTT GAG ACA | 1104 |
| 1105 | GCC CAA AGC CAG CAG GGA GCA TTT GAC GAG AGA ACA GCC CGA GAA ATG | 1152 |
| 1153 | GGC TTG ACT GAG GAA TCA AAA CAG CAG GTT AGA TCA CTG CTA ATG TCA | 1200 |
| 1201 | GTA GAC ATG GGT CCC AGT TCA ATT CAT GAG CCA TCT CGC CCT GCA TTT | 1248 |
| 1249 | ATC AGT CAA GAA GAA AAT AGG CAG CCT GCC CAG AAC TTG TCA GAT ACT | 1296 |
| 1297 | CAG GGT CAG ACC AAG CCA GTC CCG AAG CAG CCC GCA CCA AGG GCC GAC | 1344 |
| 1345 | TCA GAT GAC ATT GAT CCA TAC GAG AAC GGG CTA GAA TGG TAA | 1386 |

SEQ ID NO:3 Protein sequence of APMV-8 Nucleoprotein (NP)

| | | |
|---|---|---|
| 1 | MSSVFNEYQALQEQLVKPAVRRPDVASTGLLRAEIPVCVTLSQDPGER | 48 |
| 49 | WSLACLNIRWLASDSSTTPMKQGAILSLLSLHSDNMRAHATLAARSAD | 96 |
| 97 | ASLTILEVDEVDISNSLIKFNARSGVSDKRSNQLLAIADDIPKSCSNG | 144 |
| 145 | HPFLDTDIETRDPLDLSETIDRLQGIAAQIWVSAIKSMTAPDTASESE | 192 |
| 193 | SKRLAKYQQQGRLVKQVLLHSVVRTEFMRVIRGSLVLRQFMVSECKRA | 240 |
| 241 | SAMGGDTSRYYAMVGDISLYIKNAGLTAFFLTLKFGVGTQYPTLAMSV | 288 |
| 289 | FSSDLKRLAALIRLYKTKGDNAPYMAFLEDSDMGNFAPANYSTMYSYA | 336 |
| 337 | MGIGTILEASVSRYQYARDFTSENYFRLGVETAQSQQGAFDERTAREM | 384 |
| 385 | GLTEESKQQVRSLLMSVDMGPSSIHEPSRPAFISQEENRQPAQNLSDT | 432 |
| 433 | QGQTKPVPKQPAPRADSDDIDPYENGLEW* | 462 |

Figure 13

SEQ ID NO:4 DNA sequence encoding APMV-8 Phosphoprotein (P)

```
   1  ATG GAT TTC GCC AAT GAT GAA GAA ATT GCA GAA CTT TTG AAT CTC AGC    48
  49  ACC AAT GTA ATC AAG GAG ATT CAG AAA TCC GAA CTC AAG CCT CCC CAA    96
  97  ACC ACC GGA CGA CCA CCT GTC AGT CAA GGG AAC ACA AGA AAT CTA ACT   144
 145  GAT CTA TGG GAA AAG GAG ACT GCA AGT CAG ACC AAG ACA CCG GCC CAA   192
 193  TCT ACA CAA ACC ACA CAA GTT CAG TCT GAT GAA AAT GAG GAG GGA GAA   240
 241  ATC AAG TCC GAG TCA ACT GAT GGC CAC ATC AGA GGA ACT GTT AAT CAA   288
 289  TCA GAG CAA GTC CCA GAA CAA AAC CAG AGC AGA TCT TCA CCA GGT GAT   336
 337  GAT CTC GAC AGA GCT CTC AAC AAG CTT GAA GGG AGA ATC AAT TTA ATC   384
 385  AGC TCA ATG GAC AAA GAA ATT AAA AAG GGC CCT CGC ATC CAG AAT CTC   432
 433  CCT GGG TCC CAG GCG GCA ACT CAA CAG GCG ACC CAC CCA TTG GCA GGG   480
 481  GAC ACC CCG AAC ATG CAA GCA CAG ACA AAA GCC CTG GCG AAG CCA CAT   528
 529  CAA GAG GCA ATC AAT CCT GGC AAC CAG GAC ACA GGA GAG AGT ATT CAT   576
 577  TTA CCA CCT TCC ATG GCA CCA CCA GAG TCA TTA GTT GGT GCA ATC CGC   624
 625  AAT GCA CCC CAA TTC GTG CCA GAC CAA TCT ATG ACG AAT GTA GAT GCG   672
 673  GGG AGT GTC CAA CTA CAT GCA TCA TGT GCA GAG ATG ATA AGT AGA ATG   720
 721  TTT GTA GAA GTT ATA TCC AAG CTT GAT AAA CTC GAG TCG AGA CTG AAT   768
 769  GAT ATA GCA AAA GTT GTG AAC ACT ACC CCC CTT ATT AGG AAT GAT ATT   816
 817  AAC CAA CTT AAG GCC ACA ACC GCA CTG ATG TCT AAC CAA ATT GCC TCC   864
 865  ATA CAA ATT CTT GAC CCA GGG AAT GCA GGG GTG AGG TCC CTC TCT GAA   912
 913  ATG AAA TCT GTG ACG AAG AAA GCT GCT GTT GTA ATT GCA GGG TTT GGA   960
 961  GAC GAC CCA ACT CAA ATT ATT GAA GAA GGC ATT ATG GCC AAA GAT GCT  1008
1009  CTT GGA AAA CCT GTG CCT CCA ACA TCT GTT ATC TCA GCC AAA GCT CAG  1056
1057  ACT TCT TCC GGT GTG AGT AAG GGT GAA ATA GAA GGA TTG ATT GCA TTG  1104
1105  GTG GAA ACA TTA GTT GAC AAT GAC AAG AAG GCA GCA AAA CTG ATT AAA  1152
1153  ATG ATT GAT CAA GTT AAA TCC CAT GCC GAT TAC GCC CGA GTC AAG CAG  1200
1201  GCA ATA TAT AAT GCG TAA                                          1218
```

SEQ ID NO:5 Protein sequence of APMV-8 PhosphoProtein (P)

```
1      MDFANDEEIAELLNLSTNVIKEIQKSELKPPQTTGRPPVSQGNTRNLT      48
49     DLWEKETASQTKTPAQSTQTTQVQSDENEEGEIKSESTDGHIRGTVNQ      96
97     SEQVPEQNQSRSSPGDDLDRALNKLEGRINLISSMDKEIKKGPRIQNL      144
145    PGSQAATQQATHPLAGDTPNMQAQTKALAKPHQEAINPGNQDTGESIH      192
193    LPPSMAPPESLVGAIRNAPQFVPDQSMTNVDAGSVQLHASCAEMISRM      240
241    FVEVISKLDKLESRLNDIAKVVNTTPLIRNDINQLKATTALMSNQIAS      288
289    IQILDPGNAGVRSLSEMKSVTKKAAVVIAGFGDDPTQIIEEGIMAKDA      336
337    LGKPVPPTSVISAKAQTSSGVSKGEIEGLIALVETLVDNDKKAAKLIK      384
385    MIDQVKSHADYARVKQAIYNA*                                406
```

Figure 14

SEQ ID NO:6 DNA sequence encoding APMV-8 Matrixprotein (M)

```
   1  ATG GCA TAT ACA ACA TTG AAA CTG TGG GTG GAT GAG GGT GAC ATG TCG     48
  49  TCT TCG CTC CTA TCA TTC CCG TTG GTA CTA AAA GAG ACA GAC AGA GGC     96
  97  ACA AAG GAG CTT CAA CCA CAG GTA AGG GTA GAT TCA ATT GGC GAT GTG    144
 145  CAG AAC GCC AAA GAG TCC TCG ATA TTC GTG ACT CTA TAT GGT TTC ATC    192
 193  CAA GCA ATT AAG GAG AGT TCA GAT CGA TCG AAA TTC TTC CAT CCA AAA    240
 241  GAT GAC TTC AAA CCT GAG ACA GTC ACT GCA GGA CTG GTA GTG GTA GGT    288
 289  GCG ATC CGA ATG ATG GCT GAT GTT AAT ACC ATC TCT AAT GAC GCA CTA    336
 337  GCG CTG GAG ATC ACT GTT AAG AAA TCT GCA ACT TCT CAA GAG AAA ATG    384
 385  ACG GTG ATG TTC CAC AAT AGC CCC CCT TCA TTG AGA ACT GCA ATA ACT    432
 433  ATC CGA GCA GGA GGT TTC ATC TCG AAT GCA GAC GAG AAT ATA AAA TGT    480
 481  GCC AGC AAA TTG ACT GCA GGA GTG CAG TAC ATA TTC CGC CCA ATG TTT    528
 529  GTT TCA ATC ACT AAA TTA CAC AAT GGC AAA CTA TAT AGG GTG CCC AAA    576
 577  AGC ATC CAC AGC ATC TCA TCC ACT CTA CTG TAT AGT GTG ATG TTG GAG    624
 625  GTA GGA TTC AAA GTG GAT ATT GGG AAG GAT CAT CCC CAG GCA AAG ATG    672
 673  CTG AAG AAG GTC ACA ATC GGC GAT GCA GAC ACA TAC TGG GGG TTT GCA    720
 721  TGG TTC CAC CTG TGC AAT TTC AAA AAG ACA TCC TCT AAG GGA AAG CCA    768
 769  AGA ACG CTA GAC GAA CTA AAG ACA AAA GTC AAA AAT ATG GGG TTG AAA    816
 817  TTG GAG TTA CAT GAC CTG TGG GGT CCG ACT ATT GTG GTC CAA ATC ACT    864
 865  GGC AAG AGC AGC AAA TAT GCT CAA GGA TTT TTT TCC TCC AAT GGT ACT    912
 913  TGT TGT CTC CCA ATC AGC AGA TCT GCA CCA GAG CTT GGG AAG CTT CTG    960
 961  TGG TCT TGT TCA GCA ACT ATA GGT GAC GCA ACA GTT GTT ATC CAA TCA   1008
1009  AGC GAG AAA GGG GAA CTC CTA AGG TCT GAT GAC CTC GAG ATA CGA GGT   1056
1057  GCT GTG GCC TCC AAG AAA GGT AGA CTG GGC TCA TTT CAC CCC TTC AAA   1104
1105  AAA TGA                                                           1110
```

SEQ ID NO:7 Protein sequence of APMV-8 Matrixprotein (M)

```
1      MAYTTLKLWVDEGDMSSSLLSFPLVLKETDRGTKELQPQVRVDSIGDV      48
49     QNAKESSIFVTLYGFIQAIKESSDRSKFFHPKDDFKPETVTAGLVVVG      96
97     AIRMMADVNTISNDALALEITVKKSATSQEKMTVMFHNSPPSLRTAIT      144
145    IRAGGFISNADENIKCASKLTAGVQYIFRPMFVSITKLHNGKLYRVPK      192
193    SIHSISSTLLYSVMLEVGFKVDIGKDHPQAKMLKKVTIGDADTYWGFA      240
241    WFHLCNFKKTSSKGKPRTLDELKTKVKNMGLKLELHDLWGPTIVVQIT      288
289    GKSSKYAQGFFSSNGTCCLPISRSAPELGKLLWSCSATIGDATVVIQS      336
337    SEKGELLRSDDLEIRGAVASKKGRLGSFHPFKK*                    370
```

Figure 15

SEQ ID NO:8 DNA sequence encoding APMV-8 Fusionprotein (F)

```
   1 ATG GGT CAA ATA TCA GTA TAT CTA ATT AAT AGC GTG CTA TTA TTG CTG   48
  49 GTA TAT CCT GTG AAT TCG ATT GAC AAT ACA CTC ATT GCC CCA ATC GGA   96
  97 GTT GCC AGC GCA AAT GAA TGG CAG CTT GCT GCA TAT ACA ACA TCA CTT  144
 145 TCA GGG ACA ATT GCC GTG CGA TTC CTA CCT GTG CTC CCG GAT AAT ATG  192
 193 ACT ACC TGT CTT AAA GAA ACA ATC ACT ACA TAC AAT AAT ACT GTC AAC  240
 241 AAC ATC TTA GGC CCA CTC AAA TCC AAT CTG GAT GCA CTG CTC TCA TCT  288
 289 GAG ACT TAT CCC CAG ACA AGA TTA ATT GGG GCA GTT ATA GGT TCA ATT  336
 337 GCT CTC GGT GTT GCA ACA TCG GCT CAA ATC ACT GCT GCA GTT GCT CTC  384
 385 AAG CAA GCG CAA GAC AAT GCA AGG AAC ATA CTA GCA CTC AAA GAA GCA  432
 433 CTG TCC AAA ACC AAT GAG GCG GTC AAG GAG CTT AGT AGT GGG TTA CAA  480
 481 CAA ACA GCT ATT GCA CTT GGT AAG ATA CAG AGT TTT GTG AAT GAG GAA  528
 529 ATT CTG CCA TCT ATC AAC CAA CTG AGC TGC GAG GTG ACA GCC AAT AAA  576
 577 CTT GGG GTG TAT TTA TCT CTG TAT CTC ACA GAA CTG ACC ACC ATA TTC  624
 625 GGT GCA CAG CTG ACC AAC CCT GCA TTG ACT TCA TTA TCA TAT CAA GCA  672
 673 CTG TAC AAC CTG TGT GGT GGC AAC ATG GCA ATG CTT ACT CAG AAG ATT  720
 721 GGA ATT AAA CAG CAA GAC GTT AAT TCG CTA TAT GAA GCC GGA CTA ATC  768
 769 ACA GGA CAA GTC ATT GGT TAT GAC TCT CAT TAC CAG CTG CTG GTC ATC  816
 817 CAG GTC AAT TAT CCA AGC ATT TCT GAG GTC ACT GGT GTA CGT GCG ACA  864
 865 GAA TTA GTC ACT GTT AGT GTA ACA ACA GAC AAG GGT GAA GGG AAA GCA  912
 913 ATT GTA CCC CAA TTT GTA GCT GAA AGT CGG GTG ACT ATT GAA GAG CTT  960
 961 GAT GTC GCA TCT TGT AAA TTC AGC AGC ACG ACC CTA TAT TGC AGG CAG 1008
1009 GTC AAC ACA AGG GCA CTT CCC CCG CTA GTA GCT AGC TGT CTT CGA GGT 1056
1057 AAC TAT GAT GAT TGT CAA TAT ACC ACA GAG ATT GGA GCA TTA TCA TCC 1104
1105 CGG TAT ATA ACA CTA GAT GGG GGG GTC TTA GTT AAT TGC AAG TCA ATT 1152
1153 GTT TGT AGG TGC CTT AAT CCA AGT AAG ATC ATC TCT CAA AAT ACA AAC 1200
1201 GCT GCA GTA ACA TAT GTT GAT GCC ACA ATC TGC AAA ACA ATT CAA TTG 1248
1249 GAT GAT ATA CAA CTC CAG CTG GAA GGG TCA CTA TCA TCA GTT TAT GCA 1296
1297 AGA AAC ATC TCA ATT GAG ATC AGT CAG GTG ACC ACA TCC GGG TCT TTA 1344
1345 GAT ATC AGC AGT GAG ATA GGA AAC ATC AAT AAT ACG GTG AAT CGT GTG 1392
1393 GAG GAT TTA ATT CAC CAA TCA GAG GAA TGG CTG GCA AAG GTT AAC CCA 1440
1441 CAC ATT GTT AAT AAT ACA ACA CTA ATT GTA CTC TGT GTG TTA AGT GCG 1488
1489 CTT GCT GTG ATC TGG CTG GCA GTA TTA ACG GCT ATT ATA ATA TAC TTG 1536
1537 AGA ACA AAG TTG AAG ACT ATA TCG GCA TTA GCT GTA ACC AAT ACA ATA 1584
1585 CAG TCT AAC CCC TAT GTT AAC CAA ACG AAA CAT GAA TCT AAG TTT TGA 1632
```

SEQ ID NO:9 Protein sequence of APMV-8 Fusionprotein (F)

```
1    MGQISVYLINSVLLLLVYPVNSIDNTLIAPIGVASANEWQLAAYTTSL  48
49   SGTIAVRFLPVLPDNMTTCLKETITTYNNTVNNILGPLKSNLDALLSS  96
97   ETYPQTRLIGAVIGSIALGVATSAQITAAVALKQAQDNARNILALKEA  144
145  LSKTNEAVKELSSGLQQTAIALGKIQSFVNEEILPSINQLSCEVTANK  192
193  LGVYLSLYLTELTTIFGAQLTNPALTSLSYQALYNLCGGNMAMLTQKI  240
241  GIKQQDVNSLYEAGLITGQVIGYDSHYQLLVIQVNYPSISEVTGVRAT  288
289  ELVTVSVTTDKGEGKAIVPQFVAESRVTIEELDVASCKFSSTTLYCRQ  336
337  VNTRALPPLVASCLRGNYDDCQYTTEIGALSSRYITLDGGVLVNCKSI  384
385  VCRCLNPSKIISQNTNAAVTYVDATICKTIQLDDIQLQLEGSLSSVYA  432
433  RNISIEISQVTTSGSLDISSEIGNINNTVNRVEDLIHQSEEWLAKVNP  480
481  HIVNNTTLIVLCVLSALAVIWLAVLTAIIIYLRTKLKTISALAVTNTI  528
529  QSNPYVNQTKHESKF*                                  544
```

Figure 16

SEQ ID NO:10 DNA sequence encoding APMV-8 Hemagglutinin/neuraminidase (HN)

```
   1  ATG AGT AAC ATT GCA TCC AGT TTA GAA AAC ATT GTA GAG CAG GAT AGT    48
  49  CGA AAA ACA ACT TGG AGG GCC ATC TTT AGA TGG TCC GTT CTT CTT ATT    96
  97  ACA ACA GGA TGC TTA GCC TTA TCC ATT GTT AGC ATA GTT CAA ATT GGA   144
 145  AAT TTG AAA ATT CCT TCT GTA GGG GAT CTG GCT GAT GAA GTG GTG ACA   192
 193  CCC TTG AAA ACC ACT CTG TCA GAT ACA CTC AGG AAT CCA ATT AAC CAG   240
 241  ATA AAT GAT ATA TTT AGG ATT GTT GCC CTT GAT ATT CCA TTG CAA GTG   288
 289  ACC AGT ATC CAA AAA GAC CTT GCA AGT CAA TTT AAC ATG TTG ATA GAT   336
 337  AGT TTA AAT GCT ATC AAA TTA GGC AAC GGG ACC AAC CTT ATC ATA CCT   384
 385  ACA TCA GAC AAG GAG TAT GCA GGA GGA ATT GGA AAC CCT GTA TTT ACT   432
 433  GTC GAT GCT GGA GGT TCT ATA GGA TTC AAA CAG TTT AGC TTA ATA GAA   480
 481  CAT CCG AGC TTT ATT GCT GGA CCT ACA ACG ACC CGA GGC TGT ACA AGA   528
 529  ATA CCC ACT TTT CAC ATG TCA GAA AGT CAT TGG TGC TAC TCA CAC AAC   576
 577  ATC ATC GCT GCT GGC TGT CAA GAT GCC AGT GCA TCC AGT ATG TAT ATC   624
 625  TCA ATG GGA GTT CTC CAT GTG TCC TCA TCT GGC ACT CCC ATT TTT CTT   672
 673  ACT ACT GCA AGT GAG CTG ATA GAC GAT GGA GTT AAC CGT AAG TCA TGC   720
 721  AGC ATT GTA GCA ACC CAA TTT GGC TGT GAC ATT TTG TGC AGT ATT GTC   768
 769  ACA GAG AAG GAG GGA GAT GAT TAC TGG TCT GAT ACT CCG ACT CCA ATG   816
 817  CGC CAC GGC CGT TTT TCA TTC AAT GGT AGT TTT GTA GAA GCC GAA CTA   864
 865  CCA GTG TCC AGT ATG TTC TCA TCA TTC TCT GCC AAC TAC CCT GCT GTG   912
 913  GGA TCA GGC GAA ATT GTA AAA GAT AGA ATA TTA TTC CCA ATT TAC GGA   960
 961  GGT ATA AAG CAG ACT TCA CCA GAG TTT ACC GAA TTA GTG AAA TAC GGA  1008
1009  CTC TTT GTA TCA ACA CCT ACA ACT GTG TGC CAG AGT AGC TGG ACT TAT  1056
1057  GAC CAG GTA AAA GCT GCG TAT AGG CCA GAT TAC ATA TCA GGC CGG TTC  1104
1105  TGG GCA CAA GTG ATA CTC AGC TGC GCT CTT GAT GCA GTC GAC TTA TCA  1152
1153  AGT TGT ATT GTA AAG ATT ATG AAT AGC AGC ACA GTG ATG ATG GCA GCG  1200
1201  GAA GGA AGG ATA ATG AAG ATA GGG ATT GAT TAC TTT TAC TAT CAG CGG  1248
1249  TCA TCT TCT TGG TGG CCA TTG GCA TTT GTC ACA AAA CTA GAC CCG CAA  1296
1297  GAG TTG GCA GAC ACA AAC TCA ATA TGG CTG ACC AAT TCC ATA CCA ATC  1344
1345  CCG CAA TCA AAG TTC CCT CGG CCT TCA TAT TCA GAA AAT TAT TGC ACA  1392
1393  AAG CCA GCA GTT TGC CCT GCT ACT TGT GTC ACT GGT GTG TAC TCT GAT  1440
1441  ATT TGG CCC CTG ACC TCA TCT TCA TCA CTC CCG AGC ATA ATT TGG ATC  1488
1489  GGC CAG TAC CTT GAT GCT CCT GTT GGA AGG ACT TAT CCT AGA TTT GGA  1536
1537  ATT GCA AAT CAG TCA CAC TGG TAC CTC CAA GAA GAT ATT CTA CCC ACT  1584
1585  TCC ACC GCA AGT GCG TAT TCA ACC ACT ACA TGT TTT AAG AAT ACT GCC  1632
1633  AGG AAT AGA GTG TTC TGC GTC ACC ATT GCC GAA TTT GCA GAT GGG TTG  1680
1681  TTT GGA GAG TAC AGG ATA ACA CCT CAG TTG TAC GAA TTA GTG AGA AAT  1728
1729  AAT TGA                                                          1734
```

SEQ ID NO:11 Protein sequence of APMV-8 Hemagglutinin/neuraminidase (HN)

```
1     MSNIASSLENIVEQDSRKTTWRAIFRWSVLLITTGCLALSIVSIVQIG    48
49    NLKIPSVGDLADEVVTPLKTTLSDTLRNPINQINDIFRIVALDIPLQV    96
97    TSIQKDLASQFNMLIDSLNAIKLGNGTNLIIPTSDKEYAGGIGNPVFT    144
145   VDAGGSIGFKQFSLIEHPSFIAGPTTTRGCTRIPTFHMSESHWCYSHN    192
193   IIAAGCQDASASSMYISMGVLHVSSSGTPIFLTTASELIDDGVNRKSC    240
241   SIVATQFGCDILCSIVTEKEGDDYWSDTPTPMRHGRFSFNGSFVEAEL    288
289   PVSSMFSSFSANYPAVGSGEIVKDRILFPIYGGIKQTSPEFTELVKYG    336
337   LFVSTPTTVCQSSWTYDQVKAAYRPDYISGRFWAQVILSCALDAVDLS    384
385   SCIVKIMNSSTVMMAAEGRIMKIGIDYFYYQRSSSWWPLAFVTKLDPQ    432
433   ELADTNSIWLTNSIPIPQSKFPRPSYSENYCTKPAVCPATCVTGVYSD    480
481   IWPLTSSSSLPSIIWIGQYLDAPVGRTYPRFGIANQSHWYLQEDILPT    528
529   STASAYSTTTCFKNTARNRVFCVTIAEFADGLFGEYRITPQLYELVRN    576
577   N*                                                  578
```

Figure 17A

SEQ ID NO:12 DNA sequence encoding APMV-8 Polymerase (L)

| | | |
|---|---|---|
| 1 | **ATG** GAG GGC GAC CTC TAC ACA AAC **ATG** GAT ATA AAA CAA GTT GAC CTG | 48 |
| 49 | ATA ATA CAA CCC GAG GTT CAT CTC GAT TCA CCC ATC ATA TTG AAT AAA | 96 |
| 97 | CTG GCA CTA TTA TGG CGC TTG AGT GGT TTA CCC ATG CCT GCA GAC CTA | 144 |
| 145 | CGA CAA AAA TCC GTA GTG ATG CAC ATC CCG GAC CAC ATC TTA GAA AAA | 192 |
| 193 | TCA GAA TAT CGG ATC AAG CAC CGT CTA GGG AAA ATC AAG AGT GAC ATA | 240 |
| 241 | ACA CAT TAC TGT CAG TAT TTT AAT ATT AAT TTG GCA AAT ATT GAT CCG | 288 |
| 289 | ATA ACC CAC CCC AAA AGT TTG TAT TGG TTA TCC AGA CTA ACA ATA GCT | 336 |
| 337 | AGT GCT GGA ACT TTT AGG CAT ATG AAA GAT AGA ATC TTG TGT ACA GTT | 384 |
| 385 | GGC TCT GAA TTT GGA CAC AAA ATT CAA GAT TTA TTT TCA CTG CTG AGC | 432 |
| 433 | CAT AAA CTA GTA GGT AAC GGG GAT TTA TTT AAT CAA AGT CTC TCA GGT | 480 |
| 481 | ACA CGT TTG ACT GCA AGT CCG TTA TCC CCT TTA TGC AAT CAA TTT GTC | 528 |
| 529 | TCT GAC ATC AAG TCT GCA GTC ACG ACA CCC TGG TCA GAA GCT CGT TGG | 576 |
| 577 | TCT TGG CTT CAT ATC AAA CAA ACA ATG AGA TAT CTG ATA AAA CAA TCA | 624 |
| 625 | CGC ACT ACA AAT TCG GCT CAT TTA ACA GAA ATC ATA AAA GAA GAA TGG | 672 |
| 673 | GGT TTA GTA GGT ATT ACT CCA GAT CTT GTC ATT CTT TTT GAC AGA GTC | 720 |
| 721 | AAT AAT AGT CTG ACT GCA TTA ACA TTT GAG ATG GTT CTA ATG TAT TCA | 768 |
| 769 | GAT GTA TTA GAA TCC CGT GAC AAT ATT GTG TTA GTG GGG CGA CTA TCT | 816 |
| 817 | ACC TTT CTA CAG CCA GTA GTT AGT AGA CTG GAG GTG TTG TTT GAT CTA | 864 |
| 865 | GTA GAT TCA TTG GCA AAA ATC TTA GGT GAC ACA ATA TAT GAG ATT ATT | 912 |
| 913 | GCA GTG TTA GAG AGC TTG TCT TAT GGG TCA GTT CAA CTA CAT GAT GCA | 960 |
| 961 | AGT CAC TCT CAT GCA GGG TCT TTT TTT TCA TTT AAC ATG AAT GAA CTT | 1008 |
| 1009 | GAT AAC ACA CTA TCA AAG AGG GTA GAT CCG AAA CAC AAG AAC ACT ATA | 1056 |
| 1057 | ATG AGC ATT ATA AGA CAA TGC TTT TCT AAT CTA GAT GTT GAT CAA GCT | 1104 |
| 1105 | GCA GAG ATG CTA TGC CTG ATG AGA TTA TTC GGA CAC CCA ATG TTA ACT | 1152 |
| 1153 | GCA CCG GAT GCA GCA GCC AAA GTG AGG AAA GCA ATG TGT GCT CCA AAA | 1200 |
| 1201 | CTT GTT GAA CAC GAC ACC ATC TTG CAG ACA TTA TCT TTC TTC AAG GGG | 1248 |
| 1249 | ATA ATT ATA AAT GGG TAC AGA AGA TCA CAC TCT GGC CTG TGG CCC AAT | 1296 |
| 1297 | GTA GAG CCG TCT TCA ATT TAT GAT GAT GAT CTC AGA CAG CTG TAC TTA | 1344 |
| 1345 | GAG TCA GCA GAG ATT TCC CAT CAT TTT ATG CTT AAA AAC TAC AAG AGT | 1392 |
| 1393 | TTA AGC ATG ATA GAA TTC AAG AAG AGC ATA GAC TAC GAT CTT CAT GAT | 1440 |
| 1441 | GAC CTA AGT ACT TTC TTA AAG GAT AGA GCA ATT TGC CGG CCG AAA TCC | 1488 |
| 1489 | CAG TGG GAT GTC ATA TTT CGT AAG TCT TTA CGC AGA TCT CAT ACG CAG | 1536 |
| 1537 | TCC CAG TAT CTG GAC GAA ATT AAG AGC AAC CGA TTG CTA ATT GAT TTT | 1584 |
| 1585 | CTT GAT TCT GCT GAA TTT GAC CCT GGA AAA GAA TTT GCA TAT GTA ACC | 1632 |
| 1633 | ACA ATG GAT TAT TTG CAC GAT AAT GAA TTT TGT GCT TCA TAT TCT CTA | 1680 |
| 1681 | AAG GAA AAG GAG ATC AAA ACT ACT GGG AGG ATA TTT GCA AAA ATG ACA | 1728 |
| 1729 | CGC AAT ATG AGA AGT TGC CAA GTA ATA CTT GAA TCT TTG TTA TCA AAG | 1776 |
| 1777 | CAT ATA TGC AAG TTC TTC AAA GAG AAT GGC GTT TCG ATG GAG CAA TTG | 1824 |
| 1825 | TCA TTG ACC AAG AGT CTA CTT GCA ATG TCT CAA CTC TCA CCA AAA GTC | 1872 |
| 1873 | TCG ACT TTG CAG GAC ACT GCA TCA CGT CAT GTA GGT AAC TCA AAA TCT | 1920 |
| 1921 | CAG ATT GCA ACC AGC AAC CCA TCT CGG CAT CAC TCG ACA CCC AAT CAG | 1968 |
| 1969 | ATG TCA CTC TCA AAT CGA AAA ACG GTT GTA GCA ACT TTC TTA ACA ACT | 2016 |
| 2017 | GAC TTG GAA AAA TAC TGC CTG CAG TGG CGA TAT TCA ACT ATT AAA TTG | 2064 |
| 2065 | TTT GCA CAA GCT CTA AAT CAA CTC TTT GGG ATT GAT CAC GGA TTT GAA | 2112 |
| 2113 | TGG ATA CAT TTA AGA CTT ATG AAC AGC ACC TTA TTT GTT GGC GAT CCT | 2160 |
| 2161 | TAC TCG CCT CCT GAA GAT CCA ACA CTA GAA GAT ATA GAT AAA GCA CCA | 2208 |
| 2209 | AAT GAT GAT ATC TTC ATA GTT TCT CCA AGG GGA GGC ATA GAG GGT TTA | 2256 |
| 2257 | TGT CAG AAA ATG TGG ACC ATG ATA TCA ATT AGT GCT ATA CAC TGT GTA | 2304 |
| 2305 | GCA GAG AAA ATT GGT GCA CGA GTG GCA GCA ATG GTG CAG GGT GAT AAT | 2352 |
| 2353 | CAA GTA ATA GCT ATC ACC AAA GAA TTA TTC AGA GGA GAG AAA GCT TGT | 2400 |
| 2401 | GAT GTC AGA GAT GAG TTA GAC GAG CTT GGT CAA GTG TTT TTT GAT GAG | 2448 |
| 2449 | TTC AAG AGA CAC AAT TAT GCA ATT GGA CAC AAT CTT AAG CTA AAT GAG | 2496 |
| 2497 | ACA ATA CAA AGC CAA TCC TTT TTT GTA TAT TCC AAA CGA ATA TTC TTT | 2544 |
| 2545 | GAA GGG CGA TTG CTT AGT CAA GTC CTC AAA AAT GCT GCC AAG TTA TGT | 2592 |
| 2593 | ATG GTT GCT GAC CAT CTA GGT GAA AAC ACT GTA TCT TCC TGT AGC AAC | 2640 |

Figure 17B

```
2641 CTG AGC TCG ACA ATT GCC CGC TTA GTG GAA AAT GGG TTT GAG AAG GAC 2688
2689 ACT GCT TTT GTG TTG AAC CTA GTC TAC ATC ATG ACT CAG ATT CTT TTT 2736
2737 GAT GAG CAT TAC TCG ATT GTA TGC GAT CAC CAT AGT GTC AAA AGC TTG 2784
2785 ATT GGA TCA AAA AAC CAT CGG AAT TTA TTG TAT TCA TCT CTA ATA CCA 2832
2833 GGT CAG CTC GGC GGT TTC AAC TTC CTC AAT ATA AGT CGG TTG TTC ACT 2880
2881 AGG AAT ATA GGT GAC CCA GTA ACA TGT AGT CTG TCT GAT CTC AAA TGC 2928
2929 TTC ATA GCC GCA GGT CTC CTT CCA CCC TAT GTC CTA AAA AAT GTG GTT 2976
2977 CTG CGT GAG CCT GGT CCT GGG ACA TGG TTG ACG TTG TGC TCT GAT CCT 3024
3025 TAC ACC CTT AAC ATA CCA TAC ACA CAG CTT CCA ACC ACA TAT CTC AAA 3072
3073 AAG CAC ACC CAG CGA TCA TTG CTT TCA CGT GCA GTA AAT CCT TTA TTA 3120
3121 GCC GGT GTA CAA GTG CCA AAT CAG CAT GAG GAA GAA GAG ATG TTG GCT 3168
3169 CGC TTT CTC CTT GAT CGT GAA TAT GTG ATG CCC CGC GTT GCT CAT GTA 3216
3217 ATA CTA GAA TCA TCA GTC CTT GGC AAA CGG AAA CAA ATC CAA GGC TTA 3264
3265 ATT GAT ACA ACT CCA ACC ATC ATT AGA ACA TCT CTA GTT AAT CTG CCA 3312
3313 GTG TCT AGA AAG AAA TGC GAA AAA ATA ATC AAT TAC TCT CTC AAT TAT 3360
3361 ATT GCT GAG TGT CAT GAC TCC TTA CTT AGC CAG GTC TGC TTC AGT GAT 3408
3409 AAT AAG GAA TAC TTG TGG TCA ACC TCC TTA ATA TCA GTT GAG ACC TGT 3456
3457 AGT GTG ACA ATT GCG GAC TAT CTG AGA GCT GTC AGC TGG TCT AAT ATA 3504
3505 TTA GGG GGA AGA AAC ATA TCC GGG GTG ACT ACA CCT GAT ACT ATT GAA 3552
3553 TTA ATT CAA GGT TGT TTA ATA GGT GAA AAT TCT AGT TGT ACT CTT TGT 3600
3601 GAA TCG CAT GAT GAC GCA TTC ACG TGG ATG CAC TTG CCT GGC CCA CTT 3648
3649 TAC ATC CCT GAA CCA TCA GTT ACT AAC TCT AAA ATG CGT GTG CCA TAT 3696
3697 CTG GGT TCA AAA ACA GAG GAG CGG AAA ACA GCC TCA ATG GCA GCA ATA 3744
3745 AAA GGA ATG TCA CAT CAC CTG CGT GCA GTC TTA AGA GGC ACA TCC GTA 3792
3793 TTT ATT TGG GCA TTT GGG GAT ACA GAT ATC AAT TGG GAT AAT GCA TTG 3840
3841 CAG ATT GCC CAA TCA CGG TGT AAC ATC ACA TTG GAT CAA ATG AGA TTA 3888
3889 CTT ACA CCA ATT CCT AGC AGT TCA AAT ATT CAA CAT AGA CTC GAT GAC 3936
3937 GGA ATC AGC ACG CAG AAA TTT ACT CCT GCA AGC CTT GCT CGA ATC ACA 3984
3985 TCC TTC GTT CAC ATC TGT AAT GAC AGC CAG AGG TTA GAG AAG GAT GGC 4032
4033 TCA TCT GTC GAC TCA AAC TTG ATT TAC CAG CAA ATT ATG TTA CTT GGA 4080
4081 CTC AGC ATC TTT GAA ACA ATG TAC TCA ATG GAC CAA AAG TGG GTA TTC 4128
4129 AAT AAC CAT ACC TTG CAT TTG CAC ACT GGA CAC TCC TGT TGT CCA AGG 4176
4177 GAA CTA GAC ATA AGT TTG GTG AAC CCG CCG AGA CAT CAG ACC CCG GAG 4224
4225 CTG ACT AGC ACA ACA ACC AAC CCG TTC CTA TAT GAT CAG CTC CCA TTA 4272
4273 AAT CAA GAA AAC TTG ACA ACA CTT GAG ATT AAG ACA TTT AAA TTC AAT 4320
4321 GAG CTC AAC ATT GAT GGT TTA GAT TTT GGT GAA GGA ATA CAA TTA TTG 4368
4369 AGT CGT TGT ACT GCA AGA TTA ATG GCA GAA TGT ATT CTA GAG GAG GGA 4416
4417 ATA GGC TCG TCA GTT AAA AAT GAA GCA ATT GTC AAT TTT GAT AAT TCA 4464
4465 GTC AAT TGG ATT TCA GAG TGC CTA ATG TGT GAT ATT CGC TCA CTT TGT 4512
4513 GTT AAT TTA GGT CAA GAG ATA CTA TGT AGC CTG GCA TAC CAA ATG TAT 4560
4561 TAC TTG CGA ATC AGG GGT AGA CGG GCC ATT CTT AAT TAC TTG GAC ACA 4608
4609 ACT TTG CAA AGG ATC CCT GTG ATA CAA TTA GCC AAC ATT GCA CTC ACC 4656
4657 ATT TCG CAC CCT GAG ATA TTT CGC AGA ATT GTC AAC ACC GGG ATC CAT 4704
4705 AAC CAG ATT AAG GGC CCA TAT GTG GCA ACA ACG GAT TTC ATA GCT GCA 4752
4753 AGT AGA GAT ATC ATA TTA TCA GGT GCA AGG GAG TAT CTA TCT TAT TTA 4800
4801 AGC AGT GGG CAG GAA GAC TGT TAC ACA TTC TTC AAC TGT CAA GAT GGG 4848
4849 GAT CTT ACT CCA AAA ATG GAA CAG TAT CTT GCA AGG AGG GCA TGC CTT 4896
4897 TTA ACA TTA TTG TAT AAT ACT GGG CAC CAG ATC CCC GTT ATC CGA TCA 4944
4945 CTG ACG CCA ATA GAG AAG TGC AAG GTG CTC ACA GAA TAC AAT CAA CAA 4992
4993 ATT GAG TAC GCA GAT CAA GAG TTT AGC TCT GTA CTA AAA GTG GTC AAT 5040
5041 GCA CTA CTA CAA AAT CCT AAG ATA GAT GCA TTA GTT TCA AAT CTC TAC 5088
5089 TTC ACC ACC AGA CGT GTT CTA TCA AAC CTC AGA TCA TGT GAT AAG GCT 5136
5137 AGA TCA TAT ATT GAA TAT TTG TAC ACT GAG GAC TTC GGA GAG AAA GAG 5184
5185 GAT ACA GTA CAA TAT GAC ATC ATG ACA ACA AAC GAT ATC ATA CTT ACT 5232
5233 CAT GGT CTA TTC ACA CAG ATC GAA ATA TCT TAT CAA GGG AAT AGT CTC 5280
5281 CAT AAG TTC CTT ACT CCG GAT AAC GCG CCT GGA TCT TTG ATC CCA TTC 5328
```

Figure 17C

```
5329  TCT ATT TCA CCA AAT TCA CTT GCA TGT GAC CCT CTT CAT CAC TTG CTC  5376
5377  AAG TCG GTC GGT ACA TCA AGC ACA AGT TGG TAC AAG TAT GCA ATC GCC  5424
5425  TAT GCA GTG TCT GAA AAG AGG TCA GCT CGA TTA GGA GGG AGC TTG TAC  5472
5473  ATT GGT GAA GGG AGC GGA AGT GTG ATG ACT TTA CTC GAG TAT CTT GAG  5520
5521  CCA TCT GTT GAC ATA TTT TAC AAT TCA CTC TTC TCA AAT GGT ATG AAC  5568
5569  CCA CCA CAA CGA AAT TAT GGG CTT ATG CCA CTA CAA TTT GTG AAT TCG  5616
5617  GTG GTT TAT AAG AAC TTA ACG GCT AAA TCA GAA TGT AAG CTA GGG TTT  5664
5665  GTC CAG CAA TTT AAA CCG TTG TGG AGA GAC ATA GAC ATT GAG ACT AAT  5712
5713  GTT ACA GAT CCA TCA TTT ATC AAT TTT GCA TTG AAT GAA ATC CCA ATG  5760
5761  CAA TCA TTA AAA CGA GTA AAT TGT GAT GTG GAA TTT GAC CGT GGT ATG  5808
5809  CCG ATT GAA CGG GTT ATT CAG GGT TAC ACC CAT ATC TTA CTT GTT GCC  5856
5857  ACT TAC GGA TTA CAG CAA GAT TCA ATA CTG TGG GTG AAG GTA TAT AGG  5904
5905  ACA TCT GAA AAA GTA TTT CAA TTC TTA CTG AGT GCC ATG ATC ATG ATC  5952
5953  TTT GGT TAT GTA AAA ATC CAC AGG AAT GGT TAT ATG TCG ACA AAG GAT  6000
6001  GAA GAG TAC ATA TTG ATG TCT GAC TGC AAG GAA CCT GTA AAC TAT ACA  6048
6049  GCT GTC CCT AAC ATT CTT ACA CGT GTA AGT GAT TTA GTG TCG AAG AAT  6096
6097  CTG AGT CTT ATC CAT CCA GAA GAC CTC AGA AAA GTA AGG TGT GAA ACA  6144
6145  GAT TCC CTG AAT TTG AAG TGC AAT CAT ATT TAT GAG AAA ATA ATT GCC  6192
6193  AGA AAA ATT CCA TTA CAG GTA TCA TCA ACT GAC TCT TTG CTC CTC CAA  6240
6241  TTA GGC GGT GTT ATC AAC TCG GTG GGC TCA ACT GAT CCT AGA GAG GTT  6288
6289  GCA ACA TTA TCT TCT ATT GAG TGT ATG GAC TAT GTT GTC TCA TCA ATT  6336
6337  GAT TTG GCT ATA TTG GAG GCA AAT ATT GTA ATC TCA GAG AGT GCT GGT  6384
6385  CTT GAC CTC GCT TTA ATG TTA GGC CCA TTC AAC TTA AAT AAG CTT AAG  6432
6433  AAA ATT GAC ACA ATC CTT AAG TCA AGC ACC TAT CAG CTA ATC CCG TAC  6480
6481  TGG TTG CGC TAT GAG TAC TCT ATT AAT CCG AGA TCT TTG TCA TTT CTA  6528
6529  ATC ACT AAA TTA CAA CAA TGC CGA ATT TCA TGG TCA GAT ATG ATC ACG  6576
6577  ATT TCT GAA TTT CGT AAG AAA TCC AAG CGG CCT ATA TTT ATC AAA CGA  6624
6625  GTA ATA GGG AAT CAA CAG CTA AAA TCA TTC TTT AAT GAA AGC TCA AGT  6672
6673  ATT GTT TTG ACT CGG GCT GAA GTT AAA GTC TGT ATA AAG TTC CTC GGT  6720
6721  GCA ATC ATC AAG TTG AAA TAA                                      6741
```

There are two ATG codons (bold and underline) that could be the start codon for APMV 8 Polymerase (L).

Figure 17D

SEQ ID NO:13 Protein sequence (1) of APMV-8 Polymerase (L)

| | | |
|---|---|---|
| 1 | **M**EGDLYTN**M**DIKQVDLIIQPEVHLDSPIILNKLALLWRLSGLPMPADL | 48 |
| 49 | RQKSVVMHIPDHILEKSEYRIKHRLGKIKSDITHYCQYFNINLANIDP | 96 |
| 97 | ITHPKSLYWLSRLTIASAGTFRHMKDRILCTVGSEFGHKIQDLFSLLS | 144 |
| 145 | HKLVGNGDLFNQSLSGTRLTASPLSPLCNQFVSDIKSAVTTPWSEARW | 192 |
| 193 | SWLHIKQTMRYLIKQSRTTNSAHLTEIIKEEWGLVGITPDLVILFDRV | 240 |
| 241 | NNSLTALTFEMVLMYSDVLESRDNIVLVGRLSTFLQPVVSRLEVLFDL | 288 |
| 289 | VDSLAKILGDTIYEIIAVLESLSYGSVQLHDASHSHAGSFFSFNMNEL | 336 |
| 337 | DNTLSKRVDPKHKNTIMSIIRQCFSNLDVDQAAEMLCLMRLFGHPMLT | 384 |
| 385 | APDAAAKVRKAMCAPKLVEHDTILQTLSFFKGIIINGYRRSHSGLWPN | 432 |
| 433 | VEPSSIYDDDLRQLYLESAEISHHFMLKNYKSLSMIEFKKSIDYDLHD | 480 |
| 481 | DLSTFLKDRAICRPKSQWDVIFRKSLRRSHTQSQYLDEIKSNRLLIDF | 528 |
| 529 | LDSAEFDPGKEFAYVTTMDYLHDNEFCASYSLKEKEIKTTGRIFAKMT | 576 |
| 577 | RNMRSCQVILESLLSKHICKFFKENGVSMEQLSLTKSLLAMSQLSPKV | 624 |
| 625 | STLQDTASRHVGNSKSQIATSNPSRHHSTPNQMSLSNRKTVVATFLTT | 672 |
| 673 | DLEKYCLQWRYSTIKLFAQALNQLFGIDHGFEWIHLRLMNSTLFVGDP | 720 |
| 721 | YSPPEDPTLEDIDKAPNDDIFIVSPRGGIEGLCQKMWTMISISAIHCV | 768 |
| 769 | AEKIGARVAAMVQGDNQVIAITKELFRGEKACDVRDELDELGQVFFDE | 816 |
| 817 | FKRHNYAIGHNLKLNETIQSQSFFVYSKRIFFEGRLLSQVLKNAAKLC | 864 |
| 865 | MVADHLGENTVSSCSNLSSTIARLVENGFEKDTAFVLNLVYIMTQILF | 912 |
| 913 | DEHYSIVCDHHSVKSLIGSKNHRNLLYSSLIPGQLGGFNFLNISRLFT | 960 |
| 961 | RNIGDPVTCSLSDLKCFIAAGLLPPYVLKNVVLREPGPGTWLTLCSDP | 1008 |
| 1009 | YTLNIPYTQLPTTYLKKHTQRSLLSRAVNPLLAGVQVPNQHEEEEMLA | 1056 |
| 1057 | RFLLDREYVMPRVAHVILESSVLGKRKQIQGLIDTTPTIIRTSLVNLP | 1104 |
| 1105 | VSRKKCEKIINYSLNYIAECHDSLLSQVCFSDNKEYLWSTSLISVETC | 1152 |
| 1153 | SVTIADYLRAVSWSNILGGRNISGVTTPDTIELIQGCLIGENSSCTLC | 1200 |
| 1201 | ESHDDAFTWMHLPGPLYIPEPSVTNSKMRVPYLGSKTEERKTASMAAI | 1248 |
| 1249 | KGMSHHLRAVLRGTSVFIWAFGDTDINWDNALQIAQSRCNITLDQMRL | 1296 |
| 1297 | LTPIPSSSNIQHRLDDGISTQKFTPASLARITSFVHICNDSQRLEKDG | 1344 |
| 1345 | SSVDSNLIYQQIMLLGLSIFETMYSMDQKWVFNNHTLHLHTGHSCCPR | 1392 |
| 1393 | ELDISLVNPPRHQTPELTSTTTNPFLYDQLPLNQENLTTLEIKTFKFN | 1440 |
| 1441 | ELNIDGLDFGEGIQLLSRCTARLMAECILEEGIGSSVKNEAIVNFDNS | 1488 |
| 1489 | VNWISECLMCDIRSLCVNLGQEILCSLAYQMYYLRIRGRRAILNYLDT | 1536 |
| 1537 | TLQRIPVIQLANIALTISHPEIFRRIVNTGIHNQIKGPYVATTDFIAA | 1584 |
| 1585 | SRDIILSGAREYLSYLSSGQEDCYTFFNCQDGDLTPKMEQYLARRACL | 1632 |
| 1633 | LTLLYNTGHQIPVIRSLTPIEKCKVLTEYNQQIEYADQEFSSVLKVVN | 1680 |
| 1681 | ALLQNPKIDALVSNLYFTTRRVLSNLRSCDKARSYIEYLYTEDFGEKE | 1728 |
| 1729 | DTVQYDIMTTNDIILTHGLFTQIEISYQGNSLHKFLTPDNAPGSLIPF | 1776 |
| 1777 | SISPNSLACDPLHHLLKSVGTSSTSWYKYAIAYAVSEKRSARLGGSLY | 1824 |
| 1825 | IGEGSGSVMTLLEYLEPSVDIFYNSLFSNGMNPPQRNYGLMPLQFVNS | 1872 |
| 1873 | VVYKNLTAKSECKLGFVQQFKPLWRDIDIETNVTDPSFINFALNEIPM | 1920 |
| 1921 | QSLKRVNCDVEFDRGMPIERVIQGYTHILLVATYGLQQDSILWVKVYR | 1968 |
| 1969 | TSEKVFQFLLSAMIMIFGYVKIHRNGYMSTKDEEYILMSDCKEPVNYT | 2016 |
| 2017 | AVPNILTRVSDLVSKNLSLIHPEDLRKVRCETDSLNLKCNHIYEKIIA | 2064 |
| 2065 | RKIPLQVSSTDSLLLQLGGVINSVGSTDPREVATLSSIECMDYVVSSI | 2112 |
| 2113 | DLAILEANIVISESAGLDLALMLGPFNLNKLKKIDTILKSSTYQLIPY | 2160 |
| 2161 | WLRYEYSINPRSLSFLITKLQQCRISWSDMITISEFRKKSKRPIFIKR | 2208 |
| 2209 | VIGNQQLKSFFNESSSIVLTRAEVKVCIKFLGAIIKLK* | 2247 |

Figure 18

SEQ ID NO:14 Protein sequence (2) of APMV-8 Polymerase (L)

```
   1 MDIKQVDLII QPEVHLDSPI ILNKLALLWR LSGLPMPADL RQKSVVMHIP
  51 DHILEKSEYR IKHRLGKIKS DITHYCQYFN INLANIDPIT HPKSLYWLSR
 101 LTIASAGTFR HMKDRILCTV GSEFGHKIQD LFSLLSHKLV GNGDLFNQSL
 151 SGTRLTASPL SPLCNQFVSD IKSAVTTPWS EARWSWLHIK QTMRYLIKQS
 201 RTTNSAHLTE IIKEEWGLVG ITPDLVILFD RVNNSLTALT FEMVLMYSDV
 251 LESRDNIVLV GRLSTFLQPV VSRLEVLFDL VDSLAKILGD TIYEIIAVLE
 301 SLSYGSVQLH DASHSHAGSF FSFNMNELDN TLSKRVDPKH KNTIMSIIRQ
 351 CFSNLDVDQA AEMLCLMRLF GHPMLTAPDA AAKVRKAMCA PKLVEHDTIL
 401 QTLSFFKGII INGYRRSHSG LWPNVEPSSI YDDDLRQLYL ESAEISHHFM
 451 LKNYKSLSMI EFKKSIDYDL HDDLSTFLKD RAICRPKSQW DVIFRKSLRR
 501 SHTQSQYLDE IKSNRLLIDF LDSAEFDPGK EFAYVTTMDY LHDNEFCASY
 551 SLKEKEIKTT GRIFAKMTRN MRSCQVILES LLSKHICKFF KENGVSMEQL
 601 SLTKSLLAMS QLSPKVSTLQ DTASRHVGNS KSQIATSNPS RHHSTPNQMS
 651 LSNRKTVVAT FLTTDLEKYC LQWRYSTIKL FAQALNQLFG IDHGFEWIHL
 701 RLMNSTLFVG DPYSPPEDPT LEDIDKAPND DIFIVSPRGG IEGLCQKMWT
 751 MISISAIHCV AEKIGARVAA MVQGDNQVIA ITKELFRGEK ACDVRDELDE
 801 LGQVFFDEFK RHNYAIGHNL KLNETIQSQS FFVYSKRIFF EGRLLSQVLK
 851 NAAKLCMVAD HLGENTVSSC SNLSSTIARL VENGFEKDTA FVLNLVYIMT
 901 QILFDEHYSI VCDHHSVKSL IGSKNHRNLL YSSLIPGQLG GFNFLNISRL
 951 FTRNIGDPVT CSLSDLKCFI AAGLLPPYVL KNVVLREPGP GTWLTLCSDP
1001 YTLNIPYTQL PTTYLKKHTQ RSLLSRAVNP LLAGVQVPNQ HEEEEMLARF
1051 LLDREYVMPR VAHVILESSV LGKRKQIQGL IDTTPTIIRT SLVNLPVSRK
1101 KCEKIINYSL NYIAECHDSL LSQVCFSDNK EYLWSTSLIS VETCSVTIAD
1151 YLRAVSWSNI LGGRNISGVT TPDTIELIQG CLIGENSSCT LCESHDDAFT
1201 WMHLPGPLYI PEPSVTNSKM RVPYLGSKTE ERKTASMAAI KGMSHHLRAV
1251 LRGTSVFIWA FGDTDINWDN ALQIAQSRCN ITLDQMRLLT PIPSSSNIQH
1301 RLDDGISTQK FTPASLARIT SFVHICNDSQ RLEKDGSSVD SNLIYQQIML
1351 LGLSIFETMY SMDQKWVFNN HTLHLHTGHS CCPRELDISL VNPPRHQTPE
1401 LTSTTTNPFL YDQLPLNQEN LTTLEIKTFK FNELNIDGLD FGEGIQLLSR
1451 CTARLMAECI LEEGIGSSVK NEAIVNFDNS VNWISECLMC DIRSLCVNLG
1501 QEILCSLAYQ MYYLRIRGRR AILNYLDTTL QRIPVIQLAN IALTISHPEI
1551 FRRIVNTGIH NQIKGPYVAT TDFIAASRDI ILSGAREYLS YLSSGQEDCY
1601 TFFNCQDGDL TPKMEQYLAR RACLLTLLYN TGHQIPVIRS LTPIEKCKVL
1651 TEYNQQIEYA DQEFSSVLKV VNALLQNPKI DALVSNLYFT TRRVLSNLRS
1701 CDKARSYIEY LYTEDFGEKE DTVQYDIMTT NDIILTHGLF TQIEISYQGN
1751 SLHKFLTPDN APGSLIPFSI SPNSLACDPL HHLLKSVGTS STSWYKYAIA
1801 YAVSEKRSAR LGGSLYIGEG SGSVMTLLEY LEPSVDIFYN SLFSNGMNPP
1851 QRNYGLMPLQ FVNSVVYKNL TAKSECKLGF VQQFKPLWRD IDIETNVTDP
1901 SFINFALNEI PMQSLKRVNC DVEFDRGMPI ERVIQGYTHI LLVATYGLQQ
1951 DSILWVKVYR TSEKVFQFLL SAMIMIFGYV KIHRNGYMST KDEEYILMSD
2001 CKEPVNYTAV PNILTRVSDL VSKNLSLIHP EDLRKVRCET DSLNLKCNHI
2051 YEKIIARKIP LQVSSTDSLL LQLGGVINSV GSTDPREVAT LSSIECMDYV
2101 VSSIDLAILE ANIVISESAG LDLALMLGPF NLNKLKKIDT ILKSSTYQLI
2151 PYWLRYEYSI NPRSLSFLIT KLQQCRISWS DMITISEFRK KSKRPIFIKR
2201 VIGNQQLKSF FNESSSIVLT RAEVKVCIKF LGAIIKLK
```

Commercial broiler 2 weeks after APMV-8 vaccination

Commercial broiler 4 weeks after APMV-8 vaccination

HI titer

■ NDV
▨ APMV-8 threshold

No of animals

Group 2-2: controls

Group 2-1: APMV-8 vaccinated 2 weeks

Group 1-2: APMV-8 vaccinated 1 day old

Group 1-1: APMV-8 vaccinated 1 day old boosted 2 weeks

Study 1, *in ovo* vaccinated at day 18 p.h. = post hatch
w = weeks p.h. = post hatch
w = weeks

Study 3: *in ovo* vaccinated at day 18

Figure 25A

5'-part, full length genome (5'-FLG) SEQ ID NO:47:

ggGCGGCCGCGTTGACATTGATTATTGACTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACCCCCGCCCATTGACGTCAAT
AATGACGTATGTTCCCATAGTAACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGCCCCATTGACGCAAA
TGGGCGGTAGGCGTGTACGGTGGGAGGTCTATATAAGCAGAGCTCCCGGGtgttaagcgtctgatgagtccgtgaggac
gaaactataggaaaggaattcctatagtcACCAAACAAGGAATGCAAGACCAACGGGAACTTTAAATAAAACAATCGAA
TTATTGGGGGCGAAGCAAGTGGATCTCGAGCTCGAGGCCGAAACCCTGAATTTCACTGGAGGTTTTGAATAGGTCGCTA
TAGGACTCAATATGTCATCTGTGTTCAATGAGTATCAGGCGCTTCAAGAACAACTTGTGAAGCCGGCTGTCAGGAGACC
TGATGTTGCCTCAACGGGTTTACTCAGAGCGGAAATACCTGTCTGTGTTACATTATCTCAAGACCCCGGTGAGAGATGG
AGCCTTGCTTGCTTGAATATTAGATGGCTTGCGAGTGATTCATCAACCACACCAATGAAGCAAGGAGCAATATTGTCAC
TGCTGAGTCTACATTCAGACAATATGCGAGCTCACGCAACATTAGCAGCAAGGTCTGCAGATGCTTCACTCACCATACT
TGAGGTAGATGAAGTAGATATTAGCAACTCACTAATCAAATTCAACGCCAGAAGTGGTGTATCTGACAAACGCTCAAAT
CAATTGCTTGCAATTGCGGATGACATCCCCAAAAGTTGCAGTAATGGGCATCCATTTCTTGACACAGACATTGAGACCA
GAGACCCGCTCGATCTATCAGAGACTATAGATCGCCTGCAGGGTATTGCAGCTCAGATATGGGTGTCAGCCATAAAGAG
CATGACAGCGCCTGACACCGCATCAGAGTCAGAAAGTAAGAGGCTGGCCAAATATCAACAACAAGGCCGACTGGTTAAG
CAAGTACTCTTGCATTCTGTAGTCAGGACAGAATTTATGAGAGTTATTCGGGGCAGCTTGGTACTGCGCCAGTTTATGG
TTAGCGAGTGCAAGAGGGCTTCAGCCATGGGCGGAGACACATCTAGGTACTATGCTATGGTGGGTGACATCAGTCTTTA
CATCAAGAATGCAGGATTGACTGCATTTTTCCTCACCCTGAAGTTCGGAGTTGGTACCCAGTATCCAACCTTAGCAATG
AGTGTTTTCTCCAGTGACCTTAAAAGGCTTGCTGCACTCATCAGGCTATACAAAACCAAGGGAGACAATGCACCATACA
TGGCATTCCTGGAGGACTCCGATATGGGAAATTTTGCTCCAGCAAATTATAGCACAATGTACTCTTATGCCATGGGCAT
TGGGACAATTCTGGAAGCATCTGTATCTCGATACCAGTATGCCAGAGACTTTACCAGTGAGAATTATTTCCGTCTTGGA
GTTGAGACAGCCCAAAGCCAGCAGGGAGCATTTGACGAGAGAACAGCCCGAGAAATGGGCTTGACTGAGGAATCAAAAC
AGCAGGTTAGATCACTGCTAATGTCAGTAGACATGGGTCCCAGTTCAATTCATGAGCCATCTCGCCCTGCATTTATCAG
TCAAGAAGAAAATAGGCAGCCTGCCCAGAACTTGTCAGATACTCAGGGTCAGACCAAGCCAGTCCCGAAGCAGCCCGCA
CCAAGGGCCGACTCAGATGACATTGATCCATACGAGAACGGGCTAGAATGGTAATTCAACCACCCCGACACATCCACCT
ATACACCAATTCCGTGACATATTAACCCAATCAAACATTTCATAAACTATAGTAGTCATTGATTTAAGAAAAAATTGGG
GGCGACCTCAATTGTGAAACATACCAGATCCGTCCACAACACCACTCAACAACCCACACACAATGGATTTCGCCAATGA
TGAAGAAATTGCAGAACTTTTGAATCTCAGCACCAATGTAATCAAGGAGATTCAGAAATCCGAACTCAAGCCTCCCCAA
ACCACCGGACGACCACCTGTCAGTCAAGGGAACACAAGAAATCTAACTGATCTATGGGAAAAGGAGACTGCAAGTCAGA
CCAAGACACCGGCCCAATCTACACAAACCACACAAGTTCAGTCTGATGAAAATGAGGAGGGAGAAATCAAGTCCGAGTC
AACTGATGGCCACATCAGAGGAACTGTTAATCAATCAGAGCAAGTCCCAGAACAAAACCAGAGCAGATCTTCACCAGGT
GATGATCTCGACAGAGCTCTCAACAAGCTTGAAGGGAGAATCAATTTAATCAGCTCAATGGACAAAGAAATTAAAAAGG
GCCCTCGCATCCAGAATCTCCCTGGGTCCCAGGCGGCAACTCAACAGGCGACCCACCCATTGGCAGGGGACACCCCGAA
CATGCAAGCACAGACAAAAGCCCTGGCGAAGCCACATCAAGAGGCAATCAATCCTGGCAACCAGGACACAGGAGAGAGT
ATTCATTTACCACCTTCCATGGCACCACCAGAGTCATTAGTTGGTGCAATCCGCAATGCACCCCAATTCGTGCCAGACC
AATCTATGACGAATGTAGATGCGGGGAGTGTCCAACTACATGCATCATGTGCAGAGATGATAAGTAGAATGTTTGTAGA
AGTTATATCCAAGCTTGATAAACTCGAGTCGAGACTGAATGATATAGCAAAAGTTGTGAACACTACCCCCCTTATTAGG
AATGATATTAACCAACTTAAGGCCACAACCGCACTGATGTCTAACCAAATTGCCTCCATACAAATTCTTGACCCAGGGA
ATGCAGGGGTGAGGTCCCTCTCTGAAATGAAATCTGTGACGAAGAAAGCTGCTGTTGTAATTGCAGGGTTTGGAGACGA
CCCAACTCAAATTATTGAAGAAGGCATTATGGCCAAAGATGCTCTTGGAAAACCTGTGCCTCCAACATCTGTTATCTCA
GCCAAAGCTCAGACTTCTTCCGGTGTGAGTAAGGGTGAAATAGAAGGATTGATTGCATTGGTGGAAACATTAGTTGACA
ATGACAAGAAGGCAGCAAAACTGATTAAAATGATTGATCAAGTTAAATCCCATGCCGATTACGCCCGAGTCAAGCAGGC
AATATATAATGCGTAATACTGTAACTACACAAACAATCAATACTGCTGTCGGTTGCACCCACCTCAGCAAATCAATAAT
CTTTTAGAATTTATTGATTAAGAAAAAATTGACTACTATAAGAAAAGAACACCAAGTTGGGGGCGAAGACACGATTGAC
CACAGTCGCTATCTGTAAGGCTCCTCACCAAAAATGGCATATACAACATTGAAACTGTGGGTGGATGAGGGTGACATGT
CGTCTTCGCTCCTATCATTCCCGTTGGTACTAAAAGAGACAGACAGAGGCACAAAGGAGCTTCAACCACAGGTAAGGGT
AGATTCAATTGGCGATGTGCAGAACGCCAAAGAGTCCTCGATATTCGTGACTCTATATGGTTTCATCCAAGCAATTAAG
GAGAGTTCAGATCGATCGAAATTCTTCCATCCAAAAGATGACTTCAAACCTGAGACAGTCACTGCAGGACTGGTAGTGG
TAGGTGCGATCCGAATGATGGCTGATGTTAATACCATCTCTAATGACGCACTAGCGCTGGAGATCACTGTTAAGAAATC
TGCAACTTCTCAAGAGAAAATGACGGTGATGTTCCACAATAGCCCCCTTCATTGAGAACTGCAATAACTATCCGAGCA
GGAGGTTTCATCTCGAATGCAGACGAGAATATAAAATGTGCCAGCAAATTGACTGCAGGAGTGCAGTACATATTCCGCC
CAATGTTTGTTTCAATCACTAAATTACACAATGGCAAACTATATAGGGTGCCCAAAAGCATCCACAGCATCTCATCCAC
TCTACTGTATAGTGTGATGTTGGAGGTAGGATTCAAAGTGGATATTGGGAAGGATCATCCCCAGGCAAAGATGCTGAAG

Figure 25B

AAGGTCACAATCGGCGATGCAGACACATACTGGGGGTTTGCATGGTTCCACCTGTGCAATTTCAAAAAGACATCCTCTA
AGGGAAAGCCAAGAACGCTAGACGAACTAAAGACAAAAGTCAAAAATATGGGGTTGAAATTGGAGTTACATGACCTGTG
GGGTCCGACTATTGTGGTCCAAATCACTGGCAAGAGCAGCAAATATGCTCAAGGATTTTTTTCCTCCAATGGTACTTGT
TGTCTCCCAATCAGCAGATCTGCACCAGAGCTTGGGAAGCTTCTGTGGTCTTGTTCAGCAACTATAGGTGACGCAACAG
TTGTTATCCAATCAAGCGAGAAAGGGGAACTCCTAAGGTCTGATGACCTCGAGATACGAGGTGCTGTGGCCTCCAAGAA
AGGTAGACTGGGCTCATTTCACCCCTTCAAAAAATGATGCAGGACATAGTACAGAGAATTAGAGAGCCATTAGATGTGC
GCAAAAAACATAATCTGCGATGAACTGCCCAGACTCCACTTTAATCTAGGTTGCAGGGAAATAGTACACGACATGCGAA
ATACTATCACGGTCACCAGCAATCAATAAAGCTGATCAATCACTATATTAGGAATCAAATAGGATAACAATTATTAATC
CAATTTCCTAATTATAAAAAATTGCTTTAAAGGTTATTGACGAGTCGGGGGCGAAATCTTGCCACTTAGTCTGCAGTCA
ATCTTAGAATCTACATATTGAACTATGGGTCAAATATCAGTATATCTAATTAATAGCGTGCTATTATTGCTGGTATATC
CTGTGAATTCGATTGACAATACACTCATTGCCCCAATCGGAGTTGCCAGCGCAAATGAATGGCAGCTTGCTGCATATAC
AACATCACTTTCAGGGACAATTGCCGTGCGATTCCTACCTGTGCTCCCGGATAATATGACTACCTGTCTTAAAGAAACA
ATCACTACATACAATAATACTGTCAACAACATCTTAGGCCCACTCAAATCCAATCTGGATGCACTGCTCTCATCTGAGA
CTTATCCCCAGACAAGATTAATTGGGGCAGTTATAGGTTCAATTGCTCTCGGTGTTGCAACATCGGCTCAAATCACTGC
TGCAGTTGCTCTCAAGCAAGCGCAAGACAATGCAAGGAACATACTAGCACTCAAAGAAGCACTGTCCAAAACCAATGAG
GCGGTCAAGGAGCTTAGTAGTGGGTTACAACAAACAGCTATTGCACTTGGTAAGATACAGAGTTTTGTGAATGAGGAAA
TTCTGCCATCTATCAACCAACTGAGCTGCGAGGTGACAGCCAATAAACTTGGGGTGTATTTATCTCTGTATCTCACAGA
ACTGACCACCATATTCGGTGCACAGCTGACCAACCCTGCATTGACTTCATTATCATATCAAGCACTGTACAACCTGTGT
GGTGGCAACATGGCAATGCTTACTCAGAAGATTGGAATTAAACAGCAAGACGTTAATTCGCTATATGAAGCCGGACTAA
TCACAGGACAAGTCATTGGTTATGACTCTCATTACCAGCTGCTGGTCATCCAGGTCAATTATCCAAGCATTTCTGAGGT
CACTGGTGTACGTGCGACAGAATTAGTCACTGTTAGTGTAACAACAGACAAGGGTGAAGGGAAAGCAATTGTACCCCAA
TTTGTAGCTGAAAGTCGGGTGACTATTGAAGAGCTTGATGTCGCATCTTGTAAATTCAGCAGCACGACCCTATATTGCA
GGCAGGTCAACACAAGGGCACTTCCCCCGCTAGTAGCTAGCTGTCTTCGAGGTAACTATGATGCCGCGG

Restriction enzyme cleavage sites: upper case letter, bold and underlined
Human cytomegalovirus immediate early promoter: upper case letter, bold, italics
Hammerhead ribozyme sequence: lower case
Open reading frame for the viral proteins: upper case letter, bold
Non-coding sequences: upper case letter Not I: GCGGCCGC
Bmt I: GCTAGC
Sac II: CCGCGG

3'-part, full length genome (3'-FLG) SEQ ID NO:48:

GCGGCCGCCAGGTCAACACAAGGGCACTTCCCCCGCTAGTAGCTAGCTGTCTTCGAGGTAACTATGATGATTGTCAATA
TACCACAGAGATTGGAGCATTATCATCCCGGTATATAACACTAGATGGGGGGGTCTTAGTTAATTGCAAGTCAATTGTT
TGTAGGTGCCTTAATCCAAGTAAGATCATCTCTCAAAATACAAACGCTGCAGTAACATATGTTGATGCCACAATCTGCA
AAACAATTCAATTGGATGATATACAACTCCAGCTGGAAGGGTCACTATCATCAGTTTATGCAAGAAACATCTCAATTGA
GATCAGTCAGGTGACCACATCCGGGTCTTTAGATATCAGCAGTGAGATAGGAAACATCAATAATACGGTGAATCGTGTG
GAGGATTTAATTCACCAATCAGAGGAATGGCTGGCAAAGGTTAACCCACACATTGTTAATAATACAACACTAATTGTAC
TCTGTGTGTTAAGTGCGCTTGCTGTGATCTGGCTGGCAGTATTAACGGCTATTATAATATACTTGAGAACAAAGTTGAA
GACTATATCGGCATTAGCTGTAACCAATACAATACAGTCTAACCCCTATGTTAACCAAACGAAACATGAATCTAAGTTT
TGATCATTCAAGCCAAAACAGAGGATCTAGGCTCAGGTTAATAATAGTTCAATCAATATTTGATTTATTAGGTTTTTTT
CACTAATTATTAATATACTCGTGATTAGATGATAACGTTAAAAGTCTTAGATATTTAATAAAAAATGTAACCTGGGGGC
GACCCATTTATAGGTGAGTATATATTAGGAAGTCCTTATATTGCACTGTGATTTCAAACAATTATATTACCTCATATCT
ACCTTGTCTAAAGACATCATGAGTAACATTGCATCCAGTTTAGAAAACATTGTAGAGCAGGATAGTCGAAAAACAACTT
GGAGGGCCATCTTTAGATGGTCCGTTCTTCTTATTACAACAGGATGCTTAGCCTTATCCATTGTTAGCATAGTTCAAAT
TGGAAATTTGAAAATTCCTTCTGTAGGGGATCTGGCTGATGAAGTGGTGACACCCTTGAAAACCACTCTGTCAGATACA
CTCAGGAATCCAATTAACCAGATAAATGATATATTTAGGATTGTTGCCCTTGATATTCCATTGCAAGTGACCAGTATCC
AAAAAGACCTTGCAAGTCAATTTAACATGTTGATAGATAGTTTAAATGCTATCAAATTAGGCAACGGGACCAACCTTAT
CATACCTACATCAGACAAGGAGTATGCAGGAGGAATTGGAAACCCTGTATTTACTGTCGATGCTGGAGGTTCTATAGGA
TTCAAACAGTTTAGCTTAATAGAACATCCGAGCTTTATTGCTGGACCTACAACGACCCGAGGCTGTACAAGAATACCCA
CTTTTCACATGTCAGAAAGTCATTGGTGCTACTCACACAACATCATCGCTGCTGGCTGTCAAGATGCCAGTGCATCCAG
TATGTATATCTCAATGGGAGTTCTCCATGTGTCCTCATCTGGCACTCCCATTTTTCTTACTACTGCAAGTGAGCTGATA
GACGATGGAGTTAACCGTAAGTCATGCAGCATTGTAGCAACCCAATTTGGCTGTGACATTTTGTGCAGTATTGTCACAG

Figure 25C

AGAAGGAGGGAGATGATTACTGGTCTGATACTCCGACTCCAATGCGCCACGGCCGTTTTTCATTCAATGGTAGTTTTGT
AGAAGCCGAACTACCAGTGTCCAGTATGTTCTCATCATTCTCTGCCAACTACCCTGCTGTGGGATCAGGCGAAATTGTA
AAAGATAGAATATTATTCCCAATTTACGGAGGTATAAAGCAGACTTCACCAGAGTTTACCGAATTAGTGAAATACGGAC
TCTTTGTATCAACACCTACAACTGTGTGCCAGAGTAGCTGGACTTATGACCAGGTAAAAGCTGCGTATAGGCCAGATTA
CATATCAGGCCGGTTCTGGGCACAAGTGATACTCAGCTGCGCTCTTGATGCAGTCGACTTATCAAGTTGTATTGTAAAG
ATTATGAATAGCAGCACAGTGATGATGGCAGCGGAAGGAAGGATAATGAAGATAGGGATTGATTACTTTTACTATCAGC
GGTCATCTTCTTGGTGGCCATTGGCATTTGTCACAAAACTAGACCCGCAAGAGTTGGCAGACACAAACTCAATATGGCT
GACCAATTCCATACCAATCCCGCAATCAAAGTTCCCTCGGCCTTCATATTCAGAAAATTATTGCACAAAGCCAGCAGTT
TGCCCTGCTACTTGTGTCACTGGTGTGTACTCTGATATTTGGCCCCTGACCTCATCTTCATCACTCCCGAGCATAATTT
GGATCGGCCAGTACCTTGATGCTCCTGTTGGAAGGACTTATCCTAGATTTGGAATTGCAAATCAGTCACACTGGTACCT
CCAAGAAGATATTCTACCCACTTCCACCGCAAGTGCGTATTCAACCACTACATGTTTTAAGAATACTGCCAGGAATAGA
GTGTTCTGCGTCACCATTGCCGAATTTGCAGATGGGTTGTTTGGAGAGTACAGGATAACACCTCAGTTGTACGAATTAG
TGAGAAATAATTGAATAACAATAATTTTGGGACTCATTTTGTCGCAAAGTGAAATTGTCATCTTTAAAAATAATCAATT
CGATGATTTTTATTGAACATGATTAAGCAATCATGTGGGAAATTTATTATCTCATAAATTCTAATAGTTGTAAATGATG
AATTAAGAAAAAATGGAGGGCGACCTCTACACAAACATGGATATAAAACAAGTTGACCTGATAATACAACCCGAGGTTC
ATCTCGATTCACCCATCATATTGAATAAACTGGCACTATTATGGCGCTTGAGTGGTTTACCCATGCCTGCAGACCTACG
ACAAAAATCCGTAGTGATGCACATCCCGGACCACATCTTAGAAAAATCAGAATATCGGATCAAGCACCGTCTAGGGAAA
ATCAAGAGTGACATAACACATTACTGTCAGTATTTTAATATTAATTTGGCAAATATTGATCCGATAACCCACCCCAAAA
GTTTGTATTGGTTATCCAGACTAACAATAGCTAGTGCTGGAACTTTTAGGCATATGAAAGATAGAATCTTGTGTACAGT
TGGCTCTGAATTTGGACACAAAATTCAAGATTTATTTTCACTGCTGAGCCATAAACTAGTAGGTAACGGGGATTTATTT
AATCAAAGTCTCTCAGGTACACGTTTGACTGCAAGTCCGTTATCCCCTTTATGCAATCAATTTGTCTCTGACATCAAGT
CTGCAGTCACGACACCCTGGTCAGAAGCTCGTTGGTCTTGGCTTCATATCAAACAAACAATGAGATATCTGATAAAACA
ATCACGCACTACAAATTCGGCTCATTTAACAGAAATCATAAAAGAAGAATGGGGTTTAGTAGGTATTACTCCAGATCTT
GTCATTCTTTTTGACAGAGTCAATAATAGTCTGACTGCATTAACATTTGAGATGGTTCTAATGTATTCAGATGTATTAG
AATCCCGTGACAATATTGTGTTAGTGGGGCGACTATCTACCTTTCTACAGCCAGTAGTTAGTAGACTGGAGGTGTTGTT
TGATCTAGTAGATTCATTGGCAAAAATCTTAGGTGACACAATATATGAGATTATTGCAGTGTTAGAGAGCTTGTCTTAT
GGGTCAGTTCAACTACATGATGCAAGTCACTCTCATGCAGGGTCTTTTTTTTCATTTAACATGAATGAACTTGATAACA
CACTATCAAAGAGGGTAGATCCGAAACACAAGAACACTATAATGAGCATTATAAGACAATGCTTTTCTAATCTAGATGT
TGATCAAGCTGCAGAGATGCTATGCCTGATGAGATTATTCGGACACCCAATGTTAACTGCACCGGATGCAGCAGCCAAA
GTGAGGAAAGCAATGTGTGCTCCAAAACTTGTTGAACACGACACCATCTTGCAGACATTATCTTTCTTCAAGGGGATAA
TTATAAATGGGTACAGAAGATCACACTCTGGCCTGTGGCCCAATGTAGAGCCGTCTTCAATTTATGATGATGATCTCAG
ACAGCTGTACTTAGAGTCAGCAGAGATTTCCCATCATTTTATGCTTAAAAACTACAAGAGTTTAAGCATGATAGAATTC
AAGAAGAGCATAGACTACGATCTTCATGATGACCTAAGTACTTTCTTAAAGGATAGAGCAATTTGCCGGCCGAAATCCC
AGTGGGATGTCATATTTCGTAAGTCTTTACGCAGATCTCATACGCAGTCCCAGTATCTGGACGAAATTAAGAGCAACCG
ATTGCTAATTGATTTTCTTGATTCTGCTGAATTTGACCCTGGAAAAGAATTTGCATATGTAACCACAATGGATTATTTG
CACGATAATGAATTTTGTGCTTCATATTCTCTAAAGGAAAAGGAGATCAAAACTACTGGGAGGATATTTGCAAAAATGA
CACGCAATATGAGAAGTTGCCAAGTAATACTTGAATCTTTGTTATCAAAGCATATATGCAAGTTCTTCAAAGAGAATGG
CGTTTCGATGGAGCAATTGTCATTGACCAAGAGTCTACTTGCAATGTCTCAACTCTCACCAAAAGTCTCGACTTTGCAG
GACACTGCATCACGTCATGTAGGTAACTCAAAATCTCAGATTGCAACCAGCAACCCATCTCGGCATCACTCGACACCCA
ATCAGATGTCACTCTCAAATCGAAAAACGGTTGTAGCAACTTTCTTAACAACTGACTTGGAAAAATACTGCCTGCAGTG
GCGATATTCAACTATTAAATTGTTTGCACAAGCTCTAAATCAACTCTTTGGGATTGATCACGGATTTGAATGGATACAT
TTAAGACTTATGAACAGCACCTTATTTGTTGGCGATCCTTACTCGCCTCCTGAAGATCCAACACTAGAAGATATAGATA
AAGCACCAAATGATGATATCTTCATAGTTTCTCCAAGGGGAGGCATAGAGGGTTTATGTCAGAAAATGTGGACCATGAT
ATCAATTAGTGCTATACACTGTGTAGCAGAGAAAATTGGTGCACGAGTGGCAGCAATGGTGCAGGGTGATAATCAAGTA
ATAGCTATCACCAAAGAATTATTCAGAGGAGAGAAAGCTTGTGATGTCAGAGATGAGTTAGACGAGCTTGGTCAAGTGT
TTTTTGATGAGTTCAAGAGACACAATTATGCAATTGGACACAATCTTAAGCTAAATGAGACAATACAAAGCCAATCCTT
TTTTGTATATTCCAAACGAATATTCTTTGAAGGGCGATTGCTTAGTCAAGTCCTCAAAAATGCTGCCAAGTTATGTATG
GTTGCTGACCATCTAGGTGAAAACACTGTATCTTCCTGTAGCAACCTGAGCTCGACAATTGCCCGCTTAGTGGAAAATG
GGTTTGAGAAGGACACTGCTTTTGTGTTGAACCTAGTCTACATCATGACTCAGATTCTTTTTGATGAGCATTACTCGAT
TGTATGCGATCACCATAGTGTCAAAAGCTTGATTGGATCAAAAAACCATCGGAATTTATTGTATTCATCTCTAATACCA
GGTCAGCTCGGCGGTTTCAACTTCCTCAATATAAGTCGGTTGTTCACTAGGAATATAGGTGACCCAGTAACATGTAGTC
TGTCTGATCTCAAATGCTTCATAGCCGCAGGTCTCCTTCCACCCTATGTCCTAAAAAATGTGGTTCTGCGTGAGCCTGG
TCCTGGGACATGGTTGACGTTGTGCTCTGATCCTTACACCCTTAACATACCATACACACAGCTTCCAACCACATATCTC
AAAAAGCACACCCAGCGATCATTGCTTTCACGTGCAGTAAATCCTTTATTAGCCGGTGTACAAGTGCCAAATCAGCATG
AGGAAGAAGAGATGTTGGCTCGCTTTCTCCTTGATCGTGAATATGTGATGCCCCGCGTTGCTCATGTAATACTAGAATC
ATCAGTCCTTGGCAAACGGAAACAAATCCAAGGCTTAATTGATACAACTCCAACCATCATTAGAACATCTCTAGTTAAT
CTGCCAGTGTCTAGAAAGAAATGCGAAAAAATAATCAATTACTCTCTCAATTATATTGCTGAGTGTCATGACTCCTTAC
TTAGCCAGGTCTGCTTCAGTGATAATAAGGAATACTTGTGGTCAACCTCCTTAATATCAGTTGAGACCTGTAGTGTGAC
AATTGCGGACTATCTGAGAGCTGTCAGCTGGTCTAATATATTAGGGGGAAGAAACATATCCGGGTGACTACACCTGAT

Figure 25D

ACTATTGAATTAATTCAAGGTTGTTTAATAGGTGAAAATTCTAGTTGTACTCTTTGTGAATCGCATGATGACGCATTCA
CGTGGATGCACTTGCCTGGCCCACTTTACATCCCTGAACCATCAGTTACTAACTCTAAAATGCGTGTGCCATATCTGGG
TTCAAAAACAGAGGAGCGGAAAACAGCCTCAATGGCAGCAATAAAAGGAATGTCACATCACCTGCGTGCAGTCTTAAGA
GGCACATCCGTATTTATTTGGGCATTTGGGGATACAGATATCAATTGGGATAATGCATTGCAGATTGCCCAATCACGGT
GTAACATCACATTGGATCAAATGAGATTACTTACACCAATTCCTAGCAGTTCAAATATTCAACATAGACTCGATGACGG
AATCAGCACGCAGAAATTTACTCCTGCAAGCCTTGCTCGAATCACATCCTTCGTTCACATCTGTAATGACAGCCAGAGG
TTAGAGAAGGATGGCTCATCTGTCGACTCAAACTTGATTTACCAGCAAATTATGTTACTTGGACTCAGCATCTTTGAAA
CAATGTACTCAATGGACCAAAAGTGGGTATTCAATAACCATACCTTGCATTTGCACACTGGACACTCCTGTTGTCCAAG
GGAACTAGACATAAGTTTGGTGAACCCGCCGAGACATCAGACCCCGGAGCTGACTAGCACAACAACCAACCCGTTCCTA
TATGATCAGCTCCCATTAAATCAAGAAAACTTGACAACACTTGAGATTAAGACATTTAAATTCAATGAGCTCAACATTG
ATGGTTTAGATTTTGGTGAAGGAATACAATTATTGAGTCGTTGTACTGCAAGATTAATGGCAGAATGTATTCTAGAGGA
GGGAATAGGCTCGTCAGTTAAAAATGAAGCAATTGTCAATTTTGATAATTCAGTCAATTGGATTTCAGAGTGCCTAATG
TGTGATATTCGCTCACTTTGTGTTAATTTAGGTCAAGAGATACTATGTAGCCTGGCATACCAAATGTATTACTTGCGAA
TCAGGGGTAGACGGGCCATTCTTAATTACTTGGACACAACTTTGCAAAGGATCCCTGTGATACAATTAGCCAACATTGC
ACTCACCATTTCGCACCCTGAGATATTTCGCAGAATTGTCAACACCGGGATCCATAACCAGATTAAGGGCCCATATGTG
GCAACAACGGATTTCATAGCTGCAAGTAGAGATATCATATTATCAGGTGCAAGGGAGTATCTATCTTATTTAAGCAGTG
GGCAGGAAGACTGTTACACATTCTTCAACTGTCAAGATGGGGATCTTACTCCAAAAATGGAACAGTATCTTGCAAGGAG
GGCATGCCTTTTAACATTATTGTATAATACTGGGCACCAGATCCCCGTTATCCGATCACTGACGCCAATAGAGAAGTGC
AAGGTGCTCACAGAATACAATCAACAAATTGAGTACGCAGATCAAGAGTTTAGCTCTGTACTAAAAGTGGTCAATGCAC
TACTACAAAATCCTAAGATAGATGCATTAGTTTCAAATCTCTACTTCACCACCAGACGTGTTCTATCAAACCTCAGATC
ATGTGATAAGGCTAGATCATATATTGAATATTTGTACACTGAGGACTTCGGAGAGAAAGAGGATACAGTACAATATGAC
ATCATGACAACAAACGATATCATACTTACTCATGGTCTATTCACACAGATCGAAATATCTTATCAAGGGAATAGTCTCC
ATAAGTTCCTTACTCCGGATAACGCGCCTGGATCTTTGATCCCATTCTCTATTTCACCAAATTCACTTGCATGTGACCC
TCTTCATCACTTGCTCAAGTCGGTCGGTACATCAAGCACAAGTTGGTACAAGTATGCAATCGCCTATGCAGTGTCTGAA
AAGAGGTCAGCTCGATTAGGAGGGAGCTTGTACATTGGTGAAGGGAGCGGAAGTGTGATGACTTTACTCGAGTATCTTG
AGCCATCTGTTGACATATTTTACAATTCACTCTTCTCAAATGGTATGAACCCACCACAACGAAATTATGGGCTTATGCC
ACTACAATTTGTGAATTCGGTGGTTTATAAGAACTTAACGGCTAAATCAGAATGTAAGCTAGGGTTTGTCCAGCAATTT
AAACCGTTGTGGAGAGACATAGACATTGAGACTAATGTTACAGATCCATCATTTATCAATTTTGCATTGAATGAAATCC
CAATGCAATCATTAAAACGAGTAAATTGTGATGTGGAATTTGACCGTGGTATGCCGATTGAACGGGTTATTCAGGGTTA
CACCCATATCTTACTTGTTGCCACTTACGGATTACAGCAAGATTCAATACTGTGGGTGAAGGTATATAGGACATCTGAA
AAAGTATTTCAATTCTTACTGAGTGCCATGATCATGATCTTTGGTTATGTAAAAATCCACAGGAATGGTTATATGTCGA
CAAAGGATGAAGAGTACATATTGATGTCTGACTGCAAGGAACCTGTAAACTATACAGCTGTCCCTAACATTCTTACACG
TGTAAGTGATTTAGTGTCGAAGAATCTGAGTCTTATCCATCCAGAAGACCTCAGAAAAGTAAGGTGTGAAACAGATTCC
CTGAATTTGAAGTGCAATCATATTTATGAGAAAATAATTGCCAGAAAAATTCCATTACAGGTATCATCAACTGACTCTT
TGCTCCTCCAATTAGGCGGTGTTATCAACTCGGTGGGCTCAACTGATCCTAGAGAGGTTGCAACATTATCTTCTATTGA
GTGTATGGACTATGTTGTCTCATCAATTGATTTGGCTATATTGGAGGCAAATATTGTAATCTCAGAGAGTGCTGGTCTT
GACCTCGCTTTAATGTTAGGCCCATTCAACTTAAATAAGCTTAAGAAAATTGACACAATCCTTAAGTCAAGCACCTATC
AGCTAATCCCGTACTGGTTGCGCTATGAGTACTCTATTAATCCGAGATCTTTGTCATTTCTAATCACTAAATTACAACA
ATGCCGAATTTCATGGTCAGATATGATCACGATTTCTGAATTTCGTAAGAAATCCAAGCGGCCTATATTTATCAAACGA
GTAATAGGGAATCAACAGCTAAAATCATTCTTTAATGAAAGCTCAAGTATTGTTTTGACTCGGGCTGAAGTTAAAGTCT
GTATAAAGTTCCTCGGTGCAATCATCAAGTTGAAATAATTTCTGCGATTTTAAAGGGGTGTAATGTTCTAATTTGCACT
TGAAGTAATATAGCTTGTAATCATTCGCTAGGGGATAGGATAATTTCTCTAACCTCTGAATCTATATTCCTAGAGTATA
ACAAATATATACATAATAAAAATGATTTTAAGAAAAAATCCGACACTCAAAGAAAATTGGTGCCTGTAATATTCTTCTT
GCCAAATGATTGTGAAGTGTCTAGCCTAACTTAAAACAATCGTATTCGATAGGGAAGAATGATATATAAAATAACTAAT
AAAAAATTGTATTAGTAAAAATTACCGTATTTCCTGTATTCCATTTCTGGTgggtcggcatggcatctccacctcctcg
cggtccgacctgggcatccgaaggaggacgcacgtccactcggatggctaagggagggcgctagagctcgctgatcagc
ctcgactgtgccttctagttgccagccatctgttgtttgcccctcccccgtgccttccttgaccctggaaggtgccact
cccactgtcctttcctaataaaatgaggaaattgcatcgcattgtctgagtaggtgtcattctattctggggggtgggg
tggggcaggacagcaagggggaggattgggaagacaatagcaggcatgctggggatgcggtgggctctatgCCGCGG

Restriction enzyme cleavage sites: upper case letter, bold and underlined
Human cytomegalovirus immediate early promoter: upper case letter, bold, italics
Hepatitis delta ribozyme sequence: lower case
Open reading frame for the viral proteins: upper case letter, bold typed
Non-coding sequences: upper case letter
Bovine growth hormone poly A sequence: lower case letter, underlined Not I: GCGGCCGC
Bmt I: GCTAGC
Sac II: CCGCGG

Plasmid encoding the proteins which are part of the riboprotein complex of APMV-8

| Eco RI | | Not I | |
|---|---|---|---|
| HCMV-ie | ATG | TAA | BGH-poly-A |

pcDNA-NP

| Eco RI | | Not I | |
|---|---|---|---|
| HCMV-ie | ATG | TAA | BGH-poly-A |

pcDNA-P

| Kpn I | | Not I | |
|---|---|---|---|
| HCMV-ie | ATG | TAA | BGH-poly-A |

pcDNA-L

Plasmid encoding the T7 polymerase

| Eco RI | | Not I | |
|---|---|---|---|
| HCMV-ie | ATG | TAA | BGH-poly-A |

pcDNA3-T7

Figure 27

Plasmid containing a minigenome for APMV-8

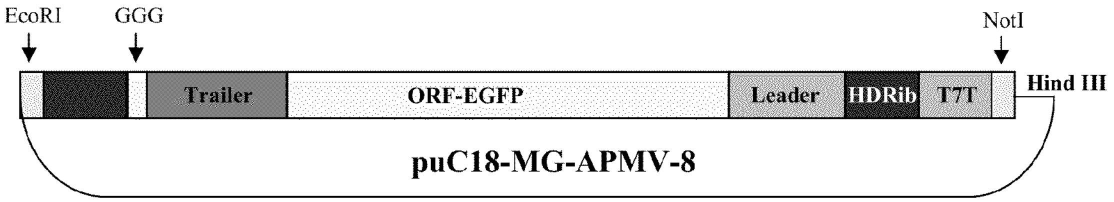

| | |
|---|---|
| **T7Pro:** | **T7 promoter** |
| **GGG:** | **base triplet consisting of three G** |
| **Trailer:** | **complete sequence of the trailer sequence of the APMV-8 virus** |
| **Leader:** | **complete sequence of the leader sequence of the APMV-8 virus** |
| **ORF-EGFP:** | **open reading frame of the enhanced green fluorescent protein** |
| **HDRib:** | **hepatitis delta ribozyme sequence** |
| **T7T:** | **T7 terminator** |

Restriction enzyme cleavage sites: EcoRI, NotI, HindIII

Plasmid encoding the EGFP under the control of the SITE promoter

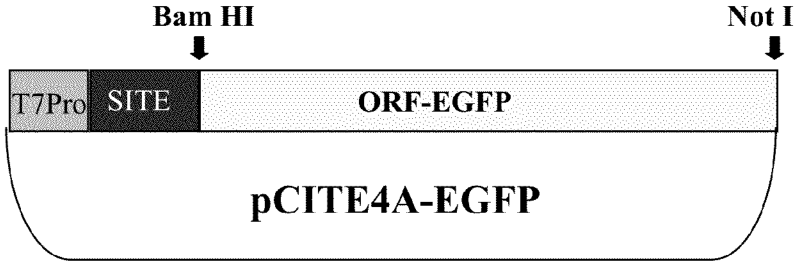

| | |
|---|---|
| **T7Pro:** | **T7 promoter** |
| **Site:** | **internal ribosome entry site** |
| **ORF-EGFP:** | **open reading frame of the enhanced green fluorescent protein** |

Restriction enzyme cleavage sites: BamHI, NotI

Figure 28

Plasmid containing the full length sequence of APMV-8

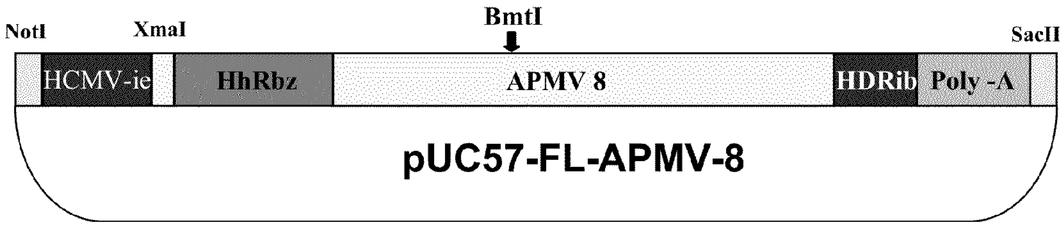

| | |
|---|---|
| **HCMV-ie:** | **human cytomegalovirus immediate early promoter** |
| **AMPV 8:** | **full length sequence of APMV 8 in antigenomic orientation** |
| **HhRbz:** | **hammerhead ribozyme sequence** |
| **HDRib:** | **hepatitis delta ribozyme sequence** |
| **Poly A:** | **bovine growth hormone polyadenylation signal sequence** |

Restriction enzyme cleavage sites: Not I, XmaI, BmtI, SacII

Figure 29

Construction of the minigenome (SEQ ID NO:52)

Eco RI

*GAATTC*TAATACGACTCACTATAGGGaccagaaatggaatacaggaaatacggtaatttttactaatacaatttttattagttat<br>
tttatatatcattcttccctatcgaatacgattgttttaagttaggctagacacttcacaatcatttggcaagaagaatattacag<br>
gcaccaattttctttgagtgtcggatttttcttaaaatcattttattatgtatatatttgttatactctaggaatatagattca<br>
gaggttagagaaattatcctatcccctagcgaatgattacaagctatattacttcaagtgcaaattagaacattacacccctttaa<br>
aatcgcagaaaTTACAAGCTATATTACTTCAAGTGCAAATTAGAACATTACACCCCTTTAAAATCGCAGAAATTACTTGTACAGCT<br>
CGTCCATGCCGAGAGTGATCCCGGCGGCGGTCACGAACTCCAGCAGGACCATGTGATCGCGCTTCTCGTTGGGGTCTTTGCTCAGG<br>
GCGGACTGGGTGCTCAGGTAGTGGTTGTCGGGCAGCAGCACGGGGCCGTCGCCGATGGGGGTGTTCTGCTGGTAGTGGTCGGCGAG<br>
CTGCACGCTGCCGTCCTCGATGTTGTGGCGGATCTTGAAGTTCACCTTGATGCCGTTCTTCTGCTTGTCGGCCATGATATAGACGT<br>
TGTGGCTGTTGTAGTTGTACTCCAGCTTGTGCCCCAGGATGTTGCCGTCCTCCTTGAAGTCGATGCCCTTCAGCTCGATGCGGTTC<br>
ACCAGGGTGTCGCCCTCGAACTTCACCTCGGCGCGGGTCTTGTAGTTGCCGTCGTCCTTGAAGAAGATGGTGCGCTCCTGGACGTA<br>
GCCTTCGGGCATGGCGGACTTGAAGAAGTCGTGCTGCTTCATGTGGTCGGGGTAGCGGCTGAAGCACTGCACGCCGTAGGTCAGGG<br>
TGGTCACGAGGGTGGGCCAGGGCACGGGCAGCTTGCCGGTGGTGCAGATGAACTTCAGGGTCAGCTTGCCGTAGGTGGCATCGCCC<br>
TCGCCCTCGCCGGACACGCTGAACTTGTGGCCGTTTACGTCGCCGTCCAGCTCGACCAGGATGGGCACCACCCCGGTGAACAGCTC<br>
CTCGCCCTTGCTCACCATattgagtcctatagcgacctattcaaaacctccagtgaaattcagggtttcggcctcgagctcgagat<br>
ccacttgcttcgcccccaataattcgattgttttatttaaagttcccgttggtcttgcattccttgtttggtgggtcggcatggca<br>
tctccacctcctcgcggtccgacctgggcatccgaaggaggacgcacgtccactcggatggctaagggagggcgTAGCATAACCCC<br>
TTGGGGCCTCTAAACGGGTCTTGAGGGGTTTTTG*GCGGCCGC*

Not I

Restriction enzymes: italics and underlined<br>
T7 polymerase promoter: upper case letter, bold and underlined<br>
Additional three G nucleotides: upper case letter and underlined<br>
Trailer sequence with genomic sequence: lower case letter<br>
Sequence of the open reading frame of the enhanced green fluorescent protein in antisense orientation: upper case letter, bold<br>
Leader sequence with genomic sequence: lower case letter and underlined<br>
Hepatitis delta ribozyme sequence: lower case letter, underlined, and bold<br>
T7 terminator sequence: upper case letter

Figure 30

NP protein alignment

```
                               1                                                50
 SEQ ID NO:3  (NP)     (1)    MSSVFNEYQALQEQLVKPAVRRPDVASTGLLRAEIPVCVTLSQDPGERWS
SEQ ID NO:54  (NP)     (1)    MSSVFNEYQALQEQLVKPAVRRPDVASTGLLRAEIPVCVTLSQDPGERWS
SEQ ID NO:66  (NP)     (1)    MSSVFNEYQALQEQLVKPAVRRPDVASTGLLRAEIPVCVTLSQDPGERWS
SEQ ID NO:78  (NP)     (1)    MSSVFNEYQALQEQLVKPAVRRPDVASTGLLRAEIPVCVTLSQDPGERWS
                               51                                              100
 SEQ ID NO:3  (NP)    (51)    LACLNIRWLASDSSTTPMKQGAILSLLSLHSDNMRAHATLAARSADASLT
SEQ ID NO:54  (NP)    (51)    LACLNIRWLVSDSSTTPMKQGAILSLLSLHSDNMRAHATLAARSADASLT
SEQ ID NO:66  (NP)    (51)    LACLNIRWLVSDSSTTPMKQGAILSLLSLHSDNMRAHATLAARSADASLT
SEQ ID NO:78  (NP)    (51)    LACLNIRWLVSDSSTTPMKQGAILSLLSLHSDNMRAHATLAARSADASLT
                               101                                             150
 SEQ ID NO:3  (NP)   (101)    ILEVDEVDISNSLIKFNARSGVSDKRSNQLLAIADDIPKSCSNGHPFLDT
SEQ ID NO:54  (NP)   (101)    ILEVDEVDIGNSLIKFNARSGVSDKRSNQLLAIADDIPKSCSNGHPFLDT
SEQ ID NO:66  (NP)   (101)    ILEVDEVDIGNSLIKFNARSGVSDKRSNQLLAIADDIPKSCSNGHPFLDT
SEQ ID NO:78  (NP)   (101)    ILEVDEVDIGNSLIKFNARSGVSDKRSNQLLAIADDIPKSCSNGHPFLDT
                               151                                             200
 SEQ ID NO:3  (NP)   (151)    DIETRDPLDLSETIDRLQGIAAQIWVSAIKSMTAPDTASESESKRLAKYQ
SEQ ID NO:54  (NP)   (151)    DIETRDPLDLSETIDRLQGIAAQIWVSAIKSMTAPDTASESESKRLAKYQ
SEQ ID NO:66  (NP)   (151)    DIETRDPLDLSETIDRLQGIAAQIWVSAIKSMTAPDTASESESKRLAKYQ
SEQ ID NO:78  (NP)   (151)    DIETRDPLDLSETIDRLQGIAAQIWVSAIKSMTAPDTASESESKRLAKYQ
                               201                                             250
 SEQ ID NO:3  (NP)   (201)    QQGRLVKQVLLHSVVRTEFMRVIRGSLVLRQFMVSECKRASAMGGDTSRY
SEQ ID NO:54  (NP)   (201)    QQGRLVKQVLLHSVVRTEFMRVIRGSLVLRQFMVSECKRASAMGGDTSRY
SEQ ID NO:66  (NP)   (201)    QQGRLVKQVLLHSVVRTEFMRVIRGSLVLRQFMVSECKRASAMGGDTSRY
SEQ ID NO:78  (NP)   (201)    QQGRLVKQVLLHSVVRTEFMRVIRGSLVLRQFMVSECKRASAMGGDTSRY
                               251                                             300
 SEQ ID NO:3  (NP)   (251)    YAMVGDISLYIKNAGLTAFFLTLKFGVGTQYPTLAMSVFSSDLKRLAALI
SEQ ID NO:54  (NP)   (251)    YAMVGDISLYIKNAGLTAFFLTLKFGVGTQYPTLAMSVFSSDLKRLAALI
SEQ ID NO:66  (NP)   (251)    YAMVGDISLYIKNAGLTAFFLTLKFGVGTQYPTLAMSVFSSDLKRLAALI
SEQ ID NO:78  (NP)   (251)    YAMVGDISLYIKNAGLTAFFLTLKFGVGTQYPTLAMSVFSSDLKRLAALI
                               301                                             350
 SEQ ID NO:3  (NP)   (301)    RLYKTKGDNAPYMAFLEDSDMGNFAPANYSTMYSYAMGIGTILEASVSRY
SEQ ID NO:54  (NP)   (301)    RLYKTKGDNAPYMAFLEDSDMGNFAPANYSTMYSYAMGIGTILEASVSRY
SEQ ID NO:66  (NP)   (301)    RLYKTKGDNAPYMAFLEDSDMGNFAPANYSTMYSYAMGIGTILEASVSRY
SEQ ID NO:78  (NP)   (301)    RLYKTKGDNAPYMAFLEDSDMGNFAPANYSTMYSYAMGIGTILEASVSRY
                               351                                             400
 SEQ ID NO:3  (NP)   (351)    QYARDFTSENYFRLGVETAQSQQGAFDERTAREMGLTEESKQQVRSLLMS
SEQ ID NO:54  (NP)   (351)    QYARDFTSENYFRLGVETAQSQQGAFDERTAREMGLTEESKQQVRSLLMS
SEQ ID NO:66  (NP)   (351)    QYARDFTSENYFRLGVETAQSQQGAFDERTAREMGLTEESKQQVRSLLMS
SEQ ID NO:78  (NP)   (351)    QYARDFTSENYFRLGVETAQSQQGAFDERTAREMGLTEESKQQVRSLLMS
                               401                                             450
 SEQ ID NO:3  (NP)   (401)    VDMGPSSIHEPSRPAFISQEENRQPAQNLSDTQGQTKPVPKQPAPRADSD
SEQ ID NO:54  (NP)   (401)    VDMGPSSVHEPSRPAFISQEENRQPAQNSSDTQGQTKPVPKQPAPRADSD
SEQ ID NO:66  (NP)   (401)    VDMGPSSVREPSRPAFISQEENRQPAQNSSDTQGQTKPVPNQPAPRADPD
SEQ ID NO:78  (NP)   (401)    VDMGPSSVREPSRPAFISQEENRQPAQNSSDTQGQTKPVPNQPAPRADPD
                               451        462
 SEQ ID NO:3  (NP)   (451)    DIDPYENGLEW-
SEQ ID NO:54  (NP)   (451)    DIDPYENGLEW-
SEQ ID NO:66  (NP)   (451)    DIDPYENGLEW-
SEQ ID NO:78  (NP)   (451)    DIDPYENGLEW-
```

Protein sequence identity:

SEQ ID NO:3 v. SEQ ID NO:54: 99% sequence identity
SEQ ID NO:3 v. SEQ ID NO:66: 98% sequence identity
SEQ ID NO:3 v. SEQ ID NO:78: 98% sequence identity DNA sequence identity:

SEQ ID NO:2 v. SEQ ID NO:53: 99% sequence identity
SEQ ID NO:2 v. SEQ ID NO:65: 97% sequence identity
SEQ ID NO:2 v. SEQ ID NO:77: 97% sequence identity

Figure 31

P protein alignment

```
                              1                                                50
SEQ ID NO:5  (P)      (1)  MDFANDEEIAELLNLSTNVIKEIQKSELKPPQTTGRPPVSQGNTRNLTDL
SEQ ID NO:56 (P)      (1)  MDFANDEEIAELLNLSTNVIKEIQKSELKPPQTTGRPPVSQGNTRNLTDL
SEQ ID NO:68 (P)      (1)  MDFANDEEIAELLNLSTTVIKEIQKSELKPPQTTGRPPVSQGNTRNLTDL
SEQ ID NO:80 (P)      (1)  MDFANDEEIAELLNLSTTVIKEIQKSELKPPQTTGRPPVSQGNTRNLTDL
                              51                                              100
SEQ ID NO:5  (P)     (51)  WEKETASQTKTPAQSTQTTQVQSDENEEGEIKSESTDGHIRGTVNQSEQV
SEQ ID NO:56 (P)     (51)  WEKETASQTKTPAQSPQTTQVQSDENEEGEIKSESIDGHIRGTVNQSEQV
SEQ ID NO:68 (P)     (51)  WEKETASQNKTSAQSPQTTQVQSDGNEEEEIKSESIDGHISGTVNQLEQV
SEQ ID NO:80 (P)     (51)  WEKETASQNKTSAQSPQTTQVQSDGNEEEEIKSESIDGHISGTVNQLEQV
                              101                                             150
SEQ ID NO:5  (P)    (101)  PEQNQSRSSPGDDLDRALNKLEGRINLISSMDKEIKKGPRIQNLPGSQAA
SEQ ID NO:56 (P)    (101)  PEQNQSRSSPGDDLDRALNKLEGRINSISSMDKEIKKGPRIQNLPGSQAA
SEQ ID NO:68 (P)    (101)  PEQNQSRSSPGDDLDRALNKLEGRINSISSMDKEIKKGPRIQNLPGSQAA
SEQ ID NO:80 (P)    (101)  PEQNQSRSSPGDDLDRALNKLEGRINSISSMDKEIKKGPRIQNLPGSQAA
                              151                                             200
SEQ ID NO:5  (P)    (151)  TQQATHPLAGDTPNMQAQTKALAKPHQEAINPGNQDTGESIHLPPSMAPP
SEQ ID NO:56 (P)    (151)  TQQATHPLAGDTPNMQAQTKALAKPHQEAINPGNQDTGESIHLPPSMAPP
SEQ ID NO:68 (P)    (151)  TQQATHPLAGDTPNMQARTKPLTKPHQEAINPGNQDTGENIHLPPSMAPP
SEQ ID NO:80 (P)    (151)  TQQATHPLAGDTPNMQARTKPLTKPHQEAINPGNQDTGENIHLPPSMAPP
                              201                                             250
SEQ ID NO:5  (P)    (201)  ESLVGAIRNAPQFVPDQSMTNVDAGSVQLHASCAEMISRMFVEVISKLDK
SEQ ID NO:56 (P)    (201)  ESLVGAIRNAPQFVPDQSMTNVDAGSVQLHASCAEMISRMFVEVISKLDK
SEQ ID NO:68 (P)    (201)  ESLVGAIRNVPQFVPDQSMTNVDAGSVQLHASCAEMISRMFVEVISKLDK
SEQ ID NO:80 (P)    (201)  ESLVGAIRNVPQFVPDQSMTNVDAGSVQLHASCAEMISRMLVEVISKLDK
                              251                                             300
SEQ ID NO:5  (P)    (251)  LESRLNDIAKVVNTTPLIRNDINQLKATTALMSNQIASIQILDPGNAGVR
SEQ ID NO:56 (P)    (251)  LESRLNDIAKVVNTTPLIRNDINQLKATTALMSNQIASIQILDPGNAGVR
SEQ ID NO:68 (P)    (251)  LESRLNDIAKVVNTTPLIRNDINQLKATTALMSNQIASIQILDPGNAGVR
SEQ ID NO:80 (P)    (251)  LESRLNDIAKVVNTTPLIRNDINQLKATTALMSNQIASIQILDPGNAGVR
                              301                                             350
SEQ ID NO:5  (P)    (301)  SLSEMKSVTKKAAVVIAGFGDDPTQIIEEGIMAKDALGKPVPPTSVISAK
SEQ ID NO:56 (P)    (301)  SLSEMKSVTKKAAVVIAGFGDDPTQIIEEGIMAKDALGKPVPPTSVISAK
SEQ ID NO:68 (P)    (301)  SLSEMRSVTKKAAVVIAGFGDDPTQIIEEGIMAKDALGKPVPPTSVIAAK
SEQ ID NO:80 (P)    (301)  SLSEMRSVTKKAAVVIAGFGDDPTQIIEEGIMAKDALGKPVPPTSVIAAK
                              351                                             400
SEQ ID NO:5  (P)    (351)  AQTSSGVSKGEIEGLIALVETLVDNDKKAAKLIKMIDQVKSHADYARVKQ
SEQ ID NO:56 (P)    (351)  AQTSSGVSKGEIEGLIALVETLVDNDKKAAKLIKMIDQVKSHADYARVKQ
SEQ ID NO:68 (P)    (351)  AQTSSGVSKGEIEGLIALVETLVDNDKKAAKLIKMIDQVKSHADYARVKQ
SEQ ID NO:80 (P)    (351)  AQTSSGVSKGEIEGLIALVETLVDNDKKAAKLIKMIDQVKSHADYARVKQ
                              401
SEQ ID NO:5  (P)    (401)  AIYNA-
SEQ ID NO:56 (P)    (401)  AIYNA-
SEQ ID NO:68 (P)    (401)  AIYNA-
SEQ ID NO:80 (P)    (401)  AIYNA-
```

Protein sequence identity:

SEQ ID NO:5 v. SEQ ID NO:56: 99% sequence identity
SEQ ID NO:5 v. SEQ ID NO:68: 96% sequence identity
SEQ ID NO:5 v. SEQ ID NO:80: 95% sequence identity DNA sequence identity:

SEQ ID NO:4 v. SEQ ID NO:55: 99% sequence identity
SEQ ID NO:4 v. SEQ ID NO:67: 96% sequence identity
SEQ ID NO:4 v. SEQ ID NO:79: 96% sequence identity

Figure 32

M protein alignment

```
                           1                                                50
SEQ ID NO:58 (M)     (1)  MAYTTLKLWVDEGDMSSSLLSFPLVLKETDRGTKELQPQVRVDSIGDVQN
 SEQ ID NO:7 (M)     (1)  MAYTTLKLWVDEGDMSSSLLSFPLVLKETDRGTKELQPQVRVDSIGDVQN
SEQ ID NO:70 (M)     (1)  MAYTTLKLWVDEGDMSSSLLSFPLVLKETDRGTKKLQPQVRVDSIGDVQN
SEQ ID NO:82 (M)     (1)  MAYTTLKLWVDEGDMSSSLLSFPLVLKETDRGTKKLQPQVRVDSIGDVQN
                           51                                              100
SEQ ID NO:58 (M)    (51)  AKESSIFVTLYGFIQAIKESTDRSKFFHPKDDFKPETVTAGLVVVGAIRM
 SEQ ID NO:7 (M)    (51)  AKESSIFVTLYGFIQAIKESSDRSKFFHPKDDFKPETVTAGLVVVGAIRM
SEQ ID NO:70 (M)    (51)  AKESSIFVTLYGFIQAIKENSDRSKFFHPKDDFKPETVTAGLVVVGAIRM
SEQ ID NO:82 (M)    (51)  AKESSIFVTLYGFIQAIKENSDRSKFFHPKDDFKPETVTAGLVVVGAIRM
                           101                                             150
SEQ ID NO:58 (M)   (101)  MADVNTISNDALALEITVKKSATSQEKMTVMFHNSPPSLRTAITIRAGGF
 SEQ ID NO:7 (M)   (101)  MADVNTISNDALALEITVKKSATSQEKMTVMFHNSPPSLRTAITIRAGGF
SEQ ID NO:70 (M)   (101)  MADVNTISNDALALEITVKKSATSQEKMTVMFHNSPPSLRTAITIRAGGF
SEQ ID NO:82 (M)   (101)  MADVNTISNDALALEITVKKSATSQEKMTVMFHNSPPSLRTAITIRAGGF
                           151                                             200
SEQ ID NO:58 (M)   (151)  ISNADENIKCASKLTAGVQYIFRPMFVSITKLHNGKLYRVPKSIHSISST
 SEQ ID NO:7 (M)   (151)  ISNADENIKCASKLTAGVQYIFRPMFVSITKLHNGKLYRVPKSIHSISST
SEQ ID NO:70 (M)   (151)  ISNADENIKCASKLTAGVQYIFRPMFVSITKLHNGKLYRVPKSIHSISST
SEQ ID NO:82 (M)   (151)  ISNADENIKCASKLTAGVQYIFRPMFVSITKLHNGKLYRVPKSIHSISST
                           201                                             250
SEQ ID NO:58 (M)   (201)  LLYSVMLEVGFKVDIGKDHPQAKMLKKVTIGDADTYWGFAWFHLCNFKKT
 SEQ ID NO:7 (M)   (201)  LLYSVMLEVGFKVDIGKDHPQAKMLKKVTIGDADTYWGFAWFHLCNFKKT
SEQ ID NO:70 (M)   (201)  LLYSVMLEVGFKVDIGKDHPQAKMLKRVTIGDADTYWGFAWFHLCNFKKT
SEQ ID NO:82 (M)   (201)  LLYSVMLEVGFKVDIGKDHPQAKMLKRVTIGDADTYWGFAWFHLCNFKKT
                           251                                             300
SEQ ID NO:58 (M)   (251)  SSKGKPRTLDELKTKVKNMGLKLELHDLWGPTIVVQITGKSSKYAQGFFS
 SEQ ID NO:7 (M)   (251)  SSKGKPRTLDELKTKVKNMGLKLELHDLWGPTIVVQITGKSSKYAQGFFS
SEQ ID NO:70 (M)   (251)  SSKGKPRTLDELKTKVKNMGLKLELHDLWGPTIVVQITGKSSKYAQGFFS
SEQ ID NO:82 (M)   (251)  SSKGKPRTLDELRTKVKNMGLKLELHDLWGPTIVVQITGKSSKYAQGFFS
                           301                                             350
SEQ ID NO:58 (M)   (301)  SNGTCCLPISRSAPGLGKLLWSCSATIGDATVVIQSSEKGELLRSDDLEI
 SEQ ID NO:7 (M)   (301)  SNGTCCLPISRSAPELGKLLWSCSATIGDATVVIQSSEKGELLRSDDLEI
SEQ ID NO:70 (M)   (301)  SNGTCCLPISRSAPELGKLLWSCSATIGDATVVIQSSEKGELLRSDDLEI
SEQ ID NO:82 (M)   (301)  SNGTCCLPISRSAPELGKLLWSCSATIGDATVVIQSSEKGELLRSDDLEI
                           351               370
SEQ ID NO:58 (M)   (351)  RGAVASKKGRLSSFHPFKK-
 SEQ ID NO:7 (M)   (351)  RGAVASKKGRLGSFHPFKK-
SEQ ID NO:70 (M)   (351)  RGAVASKKGRLSSFHPFKK-
SEQ ID NO:82 (M)   (351)  RGAVASKKGRLSSFHPFKK-
```

Protein sequence identity:

SEQ ID NO:7 v. SEQ ID NO:58: 99% sequence identity
SEQ ID NO:7 v. SEQ ID NO:70: 98% sequence identity
SEQ ID NO:7 v. SEQ ID NO:82: 98% sequence identity DNA sequence identity:

SEQ ID NO:6 v. SEQ ID NO:57: 99% sequence identity
SEQ ID NO:6 v. SEQ ID NO:69: 97% sequence identity
SEQ ID NO:6 v. SEQ ID NO:81: 97% sequence identity

Figure 33

F protein alignment

```
                              1                                                50
SEQ ID NO:60 (F)      (1)   MGQISVYLINSVLLLLVYPVNSIDNTLIAPIGVASANEWQLAAYTTSLSG
SEQ ID NO:72 (F)      (1)   MGKISIYLINSVLLLLVYPVNSIDNTLVAPIGVASANEWQLAAYTTSLSG
SEQ ID NO:84 (F)      (1)   MGKISIYLINSVLLLLVYPVNSIDNTLVAPIGVASANEWQLAAYTTSLSG
 SEQ ID NO:9 (F)      (1)   MGQISVYLINSVLLLLVYPVNSIDNTLIAPIGVASANEWQLAAYTTSLSG
                              51                                              100
SEQ ID NO:60 (F)     (51)   TIAVRFLPVLPDNMTTCLRETITTYNNTVNNILGPLKSNLDALLSSETYP
SEQ ID NO:72 (F)     (51)   TIAVRFLPVLPDNMTTCLRETITTYNNTVNNILGPLKSNLDALLSSETYP
SEQ ID NO:84 (F)     (51)   TIAVRFLPVLPDNMTTCLRETITTYNNTVNNILGPLKSNLDALLSSETYP
 SEQ ID NO:9 (F)     (51)   TIAVRFLPVLPDNMTTCLKETITTYNNTVNNILGPLKSNLDALLSSETYP
                              101                                             150
SEQ ID NO:60 (F)    (101)   QTRLIGAVIGSIALGVATSAQITAAVALKQAQDNARNILALKEALSKTNE
SEQ ID NO:72 (F)    (101)   QTRLIGAVIGSIALGVATSAQITAAVALKQAQDNARNILALKEALSKTNE
SEQ ID NO:84 (F)    (101)   QTRLIGAVIGSIALGVATSAQITAAVALKQAQDNARNILALKEALSKTNE
 SEQ ID NO:9 (F)    (101)   QTRLIGAVIGSIALGVATSAQITAAVALKQAQDNARNILALKEALSKTNE
                              151                                             200
SEQ ID NO:60 (F)    (151)   AVKELSSGLQQTAIALGKIQSFVNEEILPSINQLSCEVTANKLGVYLSLY
SEQ ID NO:72 (F)    (151)   AVKELSSGLQQTAIALGKIQSFVNEEILPSINQLSCEVTANKLGVYLSLY
SEQ ID NO:84 (F)    (151)   AVKELSSGLQQTAIALGKIQSFVNEEILPSINQLSCEVTANKLGVYLSLY
 SEQ ID NO:9 (F)    (151)   AVKELSSGLQQTAIALGKIQSFVNEEILPSINQLSCEVTANKLGVYLSLY
                              201                                             250
SEQ ID NO:60 (F)    (201)   LTELTTIFGAQLTNPALTSLSYQALYNLCGGNMAMLTQKIGIKQQDVNSL
SEQ ID NO:72 (F)    (201)   LTELTTIFGAQLTNPALTSLSYQALYNLCGGNMAMLTQKIGIKQQDVNSL
SEQ ID NO:84 (F)    (201)   LTELTTIFGAQLTNPALTSLSYQALYNLCGGNMAMLTQKIGIKQQDVNSL
 SEQ ID NO:9 (F)    (201)   LTELTTIFGAQLTNPALTSLSYQALYNLCGGNMAMLTQKIGIKQQDVNSL
                              251                                             300
SEQ ID NO:60 (F)    (251)   YEAGLITGQVIGYDSQYQLLVIQVNYPSISEVTGVRATELVTVSVTTDKG
SEQ ID NO:72 (F)    (251)   YEAGLITGQVIGYDSQYQLLVIQVNYPSISEVTGVRATELVTVSVTTDKG
SEQ ID NO:84 (F)    (251)   YEAGLITGQVIGYDSQYQLLVIQVNYPSISEVTGVRATELVTVSVTTDKG
 SEQ ID NO:9 (F)    (251)   YEAGLITGQVIGYDSHYQLLVIQVNYPSISEVTGVRATELVTVSVTTDKG
                              301                                             350
SEQ ID NO:60 (F)    (301)   EGKAIVPQFVAESRVTIEELDVASCKFSSTTLYCRQVNTRALPPLVASCL
SEQ ID NO:72 (F)    (301)   EGKAIVPQFVAESRVTIEELDVASCKFSSTTLYCRQVNTRALPPLVASCL
SEQ ID NO:84 (F)    (301)   EGKAIVPQFVAESRVTIEELDVASCKFSSTTLYCRQVNTRALPPLVASCL
 SEQ ID NO:9 (F)    (301)   EGKAIVPQFVAESRVTIEELDVASCKFSSTTLYCRQVNTRALPPLVASCL
                              351                                             400
SEQ ID NO:60 (F)    (351)   RGNYDDCQYTTEIGALSSRYITLDGGVLVNCKSIVCRCLNPSKIISQNTN
SEQ ID NO:72 (F)    (351)   RGNYDDCQYTTEIGALSSRYITLDGGVLVNCKSIVCRCLNPSKIISQNTN
SEQ ID NO:84 (F)    (351)   RGNYDDCQYTTEIGALSSRYITLDGGVLVNCKSIVCRCLNPSKIISQNTN
 SEQ ID NO:9 (F)    (351)   RGNYDDCQYTTEIGALSSRYITLDGGVLVNCKSIVCRCLNPSKIISQNTN
                              401                                             450
SEQ ID NO:60 (F)    (401)   AAVTYVDATICKTIQLDDIQLQLEGSLSSVYARNISIEISQVTTSGSLDI
SEQ ID NO:72 (F)    (401)   AAVTYVDATICKTIQLDDIQLQLEGSLSSVYARNISIEISQVTTSGSLDI
SEQ ID NO:84 (F)    (401)   AAVTYVDATICKTIQLDDIQLQLEGSLSSVYARNISIEISQVTTSGSLDI
 SEQ ID NO:9 (F)    (401)   AAVTYVDATICKTIQLDDIQLQLEGSLSSVYARNISIEISQVTTSGSLDI
                              451                                             500
SEQ ID NO:60 (F)    (451)   SSEIGNINNTVNRVEDLIHQSEEWLAKVNPHIVNNTTLIVLCVLSALAVI
SEQ ID NO:72 (F)    (451)   SSEIGNINNTVNRVEDLIHQSEEWLAKVNPHIVNNTTLIVLCVLSALAVI
SEQ ID NO:84 (F)    (451)   SSEIGNINNTVNRVEDLIHQSEEWLAKVNPHIVNNTTLIVLCVLSALAVI
 SEQ ID NO:9 (F)    (451)   SSEIGNINNTVNRVEDLIHQSEEWLAKVNPHIVNNTTLIVLCVLSALAVI
                              501                                       544
SEQ ID NO:60 (F)    (501)   WLAVLTAIIIYLRTKLKTISALAVTNTIQSNPYVNQTKRESKF-
SEQ ID NO:72 (F)    (501)   WLAVLTAIIIYLRTKLKTISALAVTNTIQSNPYVNQTKRESKF-
SEQ ID NO:84 (F)    (501)   WLAVLTAIIIYLRTKLKTISALAVTNTIQSNPYVNQTKRESKF-
 SEQ ID NO:9 (F)    (501)   WLAVLTAIIIYLRTKLKTISALAVTNTIQSNPYVNQTKHESKF-
```

Protein sequence identity:

SEQ ID NO:9 v. SEQ ID NO:60: 99% sequence identity
SEQ ID NO:9 v. SEQ ID NO:72: 98% sequence identity
SEQ ID NO:9 v. SEQ ID NO:84: 98% sequence identity DNA sequence identity:

SEQ ID NO:8 v. SEQ ID NO:59: 99% sequence identity
SEQ ID NO:8 v. SEQ ID NO:71: 97% sequence identity
SEQ ID NO:8 v. SEQ ID NO:83: 97% sequence identity

Figure 34A

HN protein alignment

```
                             1                                                50
SEQ ID NO:11 (HN)      (1)  MSNIASSLENIVEQDSRKTTWRAIFRWSVLLITTGCLALSIVSIVQIGNL
SEQ ID NO:62 (HN)      (1)  MSNIASSLENIVEQDSRKTTWRAIFRWSVLLITTGCLALSIISIVQIGNL
SEQ ID NO:74 (HN)      (1)  MSNIASSLENIVEQDSRKTTWRAIFRWSVLLITTGCLALSIVSIVQIGNL
SEQ ID NO:86 (HN)      (1)  MSNIASSLENIVEQDSRKTTWRAIFRWSVLLITTGCLALSIVSIVQIGNL
                             51                                              100
SEQ ID NO:11 (HN)     (51)  KIPSVGDLADEVVTPLKTTLSDTLRNPINQINDIFRIVALDIPLQVTSIQ
SEQ ID NO:62 (HN)     (51)  KIPSVGDLADEVVTPLKTTLSDTLRNPINQINDIFRIVALDIPLQVTNIQ
SEQ ID NO:74 (HN)     (51)  KIPSVGDLADEVVTPLKTTLSDTLRNPINQINDIFRIVALDIPLQVTSIQ
SEQ ID NO:86 (HN)     (51)  KIPSVGDLADEVVTPLKTTLSDTLRNPINQINDIFRIVALDIPLQVTSIQ
                             101                                             150
SEQ ID NO:11 (HN)    (101)  KDLASQFNMLIDSLNAIKLGNGTNLIIPTSDKEYAGGIGNPVFTVDAGGS
SEQ ID NO:62 (HN)    (101)  KDLASQFNMLIDSLNAIKLGNGTNLIIPTSDKEYAGGIGNPVFTVDAGGS
SEQ ID NO:74 (HN)    (101)  KDLASQFSMLIDSLNAIKLGNGTNLIIPTSDKEYAGGIGNPVFTVDAGGS
SEQ ID NO:86 (HN)    (101)  KDLASQFSMLIDSLNAIKLGNGTNLIIPTSDKEYAGGIGNPVFTVDAGGS
                             151                                             200
SEQ ID NO:11 (HN)    (151)  IGFKQFSLIEHPSFIAGPTTTRGCTRIPTFHMSESHWCYSHNIIAAGCQD
SEQ ID NO:62 (HN)    (151)  IGFKQFSLIEHPSFIAGPTTTRGCTRIPTFHMSESHWCYSHNIIAAGCQD
SEQ ID NO:74 (HN)    (151)  IGFKQFSLIEHPSFIAGPTTTRGCTRIPTFHMSESHWCYSHNIIAAGCQD
SEQ ID NO:86 (HN)    (151)  IGFKQFSLIEHPSFIAGPTTTRGCTRIPTFHMSESHWCYSHNIIAAGCQD
                             201                                             250
SEQ ID NO:11 (HN)    (201)  ASASSMYISMGVLHVSSSGTPIFLTTASELIDDGVNRKSCSIVATQFGCD
SEQ ID NO:62 (HN)    (201)  ASASSMYISMGVLHVSSSGTPIFLTTASELIDDGVNRKSCSIVATRFGCD
SEQ ID NO:74 (HN)    (201)  ASASSMYISMGVLHVSSSGTPIFLTTASELIDDGVNRKSCSIVATQFGCD
SEQ ID NO:86 (HN)    (201)  ASASSMYISMGVLHVSSSGTPIFLTTASELIDDGVNRKSCSIVATQFGCD
                             251                                             300
SEQ ID NO:11 (HN)    (251)  ILCSIVTEKEGDDYWSDTPTPMRHGRFSFNGSFVEAELPVSSMFSSFSAN
SEQ ID NO:62 (HN)    (251)  ILCSIVTEKEGDDYWSDTPTPMRHGRFSFNGSFVEAELPVSSMFSSFSAN
SEQ ID NO:74 (HN)    (251)  ILCSIVIEKEGDDYWSDTPTPMRHGRFSFNGSFVETELPVSSMFSSFSAN
SEQ ID NO:86 (HN)    (251)  ILCSIVIEKEGDDYWSDTPTPMRHGRFSFNGSFVETELPVSSMFSSFSAN
                             301                                             350
SEQ ID NO:11 (HN)    (301)  YPAVGSGEIVKDRILFPIYGGIKQTSPEFTELVKYGLFVSTPTTVCQSSW
SEQ ID NO:62 (HN)    (301)  YPAVGSGEIVKDRILFPIYGGIKQTSPEFTELVKYGLFVSTPTTVCQSSW
SEQ ID NO:74 (HN)    (301)  YPAVGSGEIVKDRILFPIYGGIKQTSPEFTELVKYGLFVSTPTTVCQSSW
SEQ ID NO:86 (HN)    (301)  YPAVGSGEIVKDRILFPIYGGIKQTSPEFTELVKYGLFVSTPTTVCQSSW
                             351                                             400
SEQ ID NO:11 (HN)    (351)  TYDQVKAAYRPDYISGRFWAQVILSCALDAVDLSSCIVKIMNSSTVMMAA
SEQ ID NO:62 (HN)    (351)  TYDQVKAAYRPDYISGRFWAQVILSCALDAVDLSSCIVKIMNSSTVMMAA
SEQ ID NO:74 (HN)    (351)  TYDQVKAAYRPDYISGRFWAQVILSCALDAVDLSSCIVKIMNSSTVMMAA
SEQ ID NO:86 (HN)    (351)  TYDQVKAAYRPDYISGRFWAQVILSCALDAVDLSSCIVKIMNSSTVMMAA
                             401                                             450
SEQ ID NO:11 (HN)    (401)  EGRIMKIGIDYFYYQRSSSWWPLAFVTKLDPQELADTNSIWLTNSIPIPQ
SEQ ID NO:62 (HN)    (401)  EGRIMKIGIDYFYYQRSSSWWPLAFVTKLDPQELADTNSIWLTNSIPIPQ
SEQ ID NO:74 (HN)    (401)  EGRIIKIGIDYFYYQRSSSWWPLAFVTKLDPQELADTNSIWLTNSIPIPQ
SEQ ID NO:86 (HN)    (401)  EGRIIKIGIDYFYYQRSSSWWPLAFVTKLDPQELADTNSIWLTNSIPIPQ
                             451                                             500
SEQ ID NO:11 (HN)    (451)  SKFPRPSYSENYCTKPAVCPATCVTGVYSDIWPLTSSSSLPSIIWIGQYL
SEQ ID NO:62 (HN)    (451)  SKFPRPSYSENYCTKPAVCPATCVTGVYSDIWPLTSSSSLPSIIWIGQYL
SEQ ID NO:74 (HN)    (451)  SKFPRPSYSENYCTKPAVCPATCVTGVYSDIWPLTSSSSLPSIIWIGQYL
SEQ ID NO:86 (HN)    (451)  SKFPRPSYSENYCTKPAVCPATCVTGVYSDIWPLTSSSSLPSIIWIGQYL
                             501                                             550
SEQ ID NO:11 (HN)    (501)  DAPVGRTYPRFGIANQSHWYLQEDILPTSTASAYSTTTCFKNTARNRVFC
SEQ ID NO:62 (HN)    (501)  DAPVRRTYPRFGIANQSHWYLQEDILPTSTASAYSTTTCFKNTARNRVFC
SEQ ID NO:74 (HN)    (501)  DAPVGRTYPRFGIANQSHWYLQEDILPTSTASAYSTTTCFKNTARNRVFC
SEQ ID NO:86 (HN)    (501)  DAPVGRTYPRFGIANQSHWYLQEDILPTSTASAYSTTTCFKNTARNRVFC
                             551                        578
SEQ ID NO:11 (HN)    (551)  VTIAEFADGLFGEYRITPQLYELVRNN-
SEQ ID NO:62 (HN)    (551)  VTIAEFADGLFGEYRITPQLYELVRNN-
SEQ ID NO:74 (HN)    (551)  VTIAEFADGLFGEYRITPQLYELVRNN-
SEQ ID NO:86 (HN)    (551)  VTIAEFADGLFGEYRITPQLYELVRNN-
```

Figure 34B

Protein sequence identity:

SEQ ID NO:11 v. SEQ ID NO:62: 99% sequence identity
SEQ ID NO:11 v. SEQ ID NO:74: 99% sequence identity
SEQ ID NO:11 v. SEQ ID NO:86: 99% sequence identity DNA sequence identity:

SEQ ID NO:10 v. SEQ ID NO:61: 99% sequence identity
SEQ ID NO:10 v. SEQ ID NO:73: 97% sequence identity
SEQ ID NO:10 v. SEQ ID NO:85: 97% sequence identity

Figure 35A

L protein alignment

```
                              1                                                50
SEQ ID NO:13 (L1)      (1)   MEGDLYTNMDIKQVDLIIQPEVHLDSPIILNKLALLWRLSGLPMPADLRQ
SEQ ID NO:14 (L2)      (1)   --------MDIKQVDLIIQPEVHLDSPIILNKLALLWRLSGLPMPADLRQ
 SEQ ID NO:64 (L)      (1)   --------MDIKQVDLIIQPEVHLDSPIILNKLALLWRLSGLPMPADLRQ
 SEQ ID NO:76 (L)      (1)   --------MDVKQVDLIIQPEVHLDSPIILNKLALLWRLSGLPMPADLRQ
 SEQ ID NO:88 (L)      (1)   --------MDVKQVDLIIQPEVHLDSPIILNKLALLWRLSGLPMPADLRQ
                              51                                              100
SEQ ID NO:13 (L1)     (51)   KSVVMHIPDHILEKSEYRIKHRLGKIKSDITHYCQYFNINLANIDPITHP
SEQ ID NO:14 (L2)     (43)   KSVVMHIPDHILEKSEYRIKHRLGKIKSDITHYCQYFNINLANIDPITHP
 SEQ ID NO:64 (L)     (43)   KSVVMHIPDHILEKSEYRIKHRLGKIKSDITHYCQYFNINLANLDPITHP
 SEQ ID NO:76 (L)     (43)   KSVVMHIPDHILEKSEYRIKHRLGKIKSDIAHYCQYFNINLANLDPITHP
 SEQ ID NO:88 (L)     (43)   KSVVMHIPDHILEKSEYRIKHRLGKIKSDIAHYCQYFNINLANLDPITHP
                              101                                             150
SEQ ID NO:13 (L1)    (101)   KSLYWLSRLTIASAGTFRHMKDRILCTVGSEFGHKIQDLFSLLSHKLVGN
SEQ ID NO:14 (L2)     (93)   KSLYWLSRLTIASAGTFRHMKDRILCTVGSEFGHKIQDLFSLLSHKLVGN
 SEQ ID NO:64 (L)     (93)   KSLYWLSRLTIASAGTFRHMKDRILCTVGSEFGHKIQDLFSLLSHKLVGN
 SEQ ID NO:76 (L)     (93)   KSLYWLSRLTIASAGTFRHMKDRILCTVGSEFGHKIQDLFSLLSHKLVGN
 SEQ ID NO:88 (L)     (93)   KSLYWLSRLTIASAGTFRHMKDRILCTVGSEFGHKIQDLFSLLSHKLVGN
                              151                                             200
SEQ ID NO:13 (L1)    (151)   GDLFNQSLSGTRLTASPLSPLCNQFVSDIKSAVTTPWSEARWSWLHIKQT
SEQ ID NO:14 (L2)    (143)   GDLFNQSLSGTRLTASPLSPLCNQFVSDIKSAVTTPWSEARWSWLHIKQT
 SEQ ID NO:64 (L)    (143)   GDLFNQSLSGTRLTASPLSPLCDQFVSDIKSAVTTPWSEARWSWLHIKQT
 SEQ ID NO:76 (L)    (143)   GDLFNQSLSGTRLTASPLSPLCNQFVSDIKSAVTTPWSEARWSWLHIKQT
 SEQ ID NO:88 (L)    (143)   GDLFNQSLSGTRLTASPLSPLCNQFVSDIKSAVTTPWSEARWSWLHIKQT
                              201                                             250
SEQ ID NO:13 (L1)    (201)   MRYLIKQSRTTNSAHLTEIIKEEWGLVGITPDLVILFDRVNNSLTALTFE
SEQ ID NO:14 (L2)    (193)   MRYLIKQSRTTNSAHLTEIIKEEWGLVGITPDLVILFDRVNNSLTALTFE
 SEQ ID NO:64 (L)    (193)   MRYLIKQSCTTNSAHLTEIIKEEWGLVGITPDLVILFDRVNNSLTALTFE
 SEQ ID NO:76 (L)    (193)   MRYLIKQSRTTNSAHLTEIIKEEWGLVGITPDLVILFDRVNNSLTALTFE
 SEQ ID NO:88 (L)    (193)   MRYLIKQSRTTNSAHLTEIIKEEWGLVGITPDLVILFDRVNNSLTALTFE
                              251                                             300
SEQ ID NO:13 (L1)    (251)   MVLMYSDVLESRDNIVLVGRLSTFLQPVVSRLEVLFDLVDSLAKILGDTI
SEQ ID NO:14 (L2)    (243)   MVLMYSDVLESRDNIVLVGRLSTFLQPVVSRLEVLFDLVDSLAKILGDTI
 SEQ ID NO:64 (L)    (243)   MVLMYSDVLESRDNIVLVGRLSTFLQPVVSRLEVLFDLVDSLAKILGDTI
 SEQ ID NO:76 (L)    (243)   MVLMYSDVLESRDNIVLVGRLSTFLQPVVSRLEVLFDLVDSLAKTLGDTI
 SEQ ID NO:88 (L)    (243)   MVLMYSDVLESRDNIVLVGRLSTFLQPVVSRLEVLFDLVDSLAKTLGDTI
                              301                                             350
SEQ ID NO:13 (L1)    (301)   YEIIAVLESLSYGSVQLHDASHSHAGSFFSFNMNELDNTLSKRVDPKHKN
SEQ ID NO:14 (L2)    (293)   YEIIAVLESLSYGSVQLHDASHSHAGSFFSFNMNELDNTLSKRVDPKHKN
 SEQ ID NO:64 (L)    (293)   YEIIAVLESLSYGSVQLHDASHSHAGSFFSFNMNELDNTLSKRVDPKHKN
 SEQ ID NO:76 (L)    (293)   YEIIAVLESLSYGSVQLHDASHSHAGSFFSFNMNELDNTLSKRVDPKHKN
 SEQ ID NO:88 (L)    (293)   YEIIAVLESLSYGSVQLHDASHSHAGSFFSFNMNELDNTLSKRVDPKHKN
                              351                                             400
SEQ ID NO:13 (L1)    (351)   TIMSIIRQCFSNLDVDQAAEMLCLMRLFGHPMLTAPDAAAKVRKAMCAPK
SEQ ID NO:14 (L2)    (343)   TIMSIIRQCFSNLDVDQAAEMLCLMRLFGHPMLTAPDAAAKVRKAMCAPK
 SEQ ID NO:64 (L)    (343)   TIMSIIRQCFSNLDVDQAAEMLCLMRLFGHPMLTAPDAAAKVRKAMCAPK
 SEQ ID NO:76 (L)    (343)   TIMSIIRQCFSNLDVDQAAEMLCLMRLFGHPMLTAPDAAAKVRKAMCAPK
 SEQ ID NO:88 (L)    (343)   TIMSIIRQCFSNLDVDQAAEMLCLMRLFGHPMLTAPDAAAKVRKAMCAPK
                              401                                             450
SEQ ID NO:13 (L1)    (401)   LVEHDTILQTLSFFKGIIINGYRRSHSGLWPNVEPSSIYDDDLRQLYLES
SEQ ID NO:14 (L2)    (393)   LVEHDTILQTLSFFKGIIINGYRRSHSGLWPNVEPSSIYDDDLRQLYLES
 SEQ ID NO:64 (L)    (393)   LVEHDTILQTLSFFKGIIINGYRRSHSGLWPNVEPSSIYDDDLRQLYLES
 SEQ ID NO:76 (L)    (393)   LVEHDTILQTLSFFKGIIINGYRRSHSGLWPNVEPSSIYDDDLRQLYLES
 SEQ ID NO:88 (L)    (393)   LVEHDTILQTLSFFKGIIINGYRRSHSGLWPNVEPSSIYDDDLRQLYLES
                              451                                             500
SEQ ID NO:13 (L1)    (451)   AEISHHFMLKNYKSLSMIEFKKSIDYDLHDDLSTFLKDRAICRPKSQWDV
SEQ ID NO:14 (L2)    (443)   AEISHHFMLKNYKSLSMIEFKKSIDYDLHDDLSTFLKDRAICRPKSQWDV
 SEQ ID NO:64 (L)    (443)   AEISHHFMLKNYKSLSMIEFKKSIDYDLHDDLSTFLKDRAICRPKSQWDV
 SEQ ID NO:76 (L)    (443)   AEISHHFMLKNYKSLSMIEFKKSIDYDLHDDLSTFLKDRAICRPKSQWDV
 SEQ ID NO:88 (L)    (443)   AEISHHFMLKNYKSLSMIEFKKSIDYDLHDDLSTFLKDRAICRPKSQWDV
```

Figure 35B

| | | |
|---|---|---|
| | | 501 550 |
| SEQ ID NO:13 (L1) | (501) | IFRKSLRRSHTQSQYLDEIKSNRLLIDFLDSAEFDPGKEFAYVTTMDYLH |
| SEQ ID NO:14 (L2) | (493) | IFRKSLRRSHTQSQYLDEIKSNRLLIDFLDSAEFDPGKEFAYVTTMDYLH |
| SEQ ID NO:64 (L) | (493) | IFRKSLRRSHTQSQYLDEIKSNRLLIDFLDSAEFDPEKEFAYVTTMDYLH |
| SEQ ID NO:76 (L) | (493) | IFRKSLRRSHTRSQYMDEIKSNRLLIDFLDSADFDPEKEFAYVTTMDYLH |
| SEQ ID NO:88 (L) | (493) | IFRKSLRRSHTRSQYMDEIKSNRLLIDFLDSADFDPEKEFAYVTTMDYLH |
| | | 551 600 |
| SEQ ID NO:13 (L1) | (551) | DNEFCASYSLKEKEIKTTGRIFAKMTRNMRSCQVILESLLSKHICKFFKE |
| SEQ ID NO:14 (L2) | (543) | DNEFCASYSLKEKEIKTTGRIFAKMTRNMRSCQVILESLLSKHICKFFKE |
| SEQ ID NO:64 (L) | (543) | DNEFCASYSLKEKEIKTTGRIFAKMTRNMRSCQVILESLLSKHICKFFKE |
| SEQ ID NO:76 (L) | (543) | DNEFCASYSLKEKEIKTTGRIFAKMTRNMRSCQVILESLLSKHICKFFKE |
| SEQ ID NO:88 (L) | (543) | DNEFCASYSLKEKEIKTTGRIFAKMTRNMRSCQVILESLLSKHICKFFKE |
| | | 601 650 |
| SEQ ID NO:13 (L1) | (601) | NGVSMEQLSLTKSLLAMSQLSPKVSTLQDTASRHVGNSKSQIATSNPSRH |
| SEQ ID NO:14 (L2) | (593) | NGVSMEQLSLTKSLLAMSQLSPKVSTLQDTASRHVGNSKSQIATSNPSRH |
| SEQ ID NO:64 (L) | (593) | NGVSMEQLSLTKSLLAMSQLSPKVSTLQDTASRHVGNSKSQIATSNPSRH |
| SEQ ID NO:76 (L) | (593) | NGVSMEQLSLTKSLLAMSQLSPKVSTLQDTASRHVGNSKSQIATSNPSRH |
| SEQ ID NO:88 (L) | (593) | NGVSMEQLSLTKSLLAMSQLSPKVSTLQDTASRHVGNSKSQIATSNPSRH |
| | | 651 700 |
| SEQ ID NO:13 (L1) | (651) | HSTPNQMSLSNRKTVVATFLTTDLEKYCLQWRYSTIKLFAQALNQLFGID |
| SEQ ID NO:14 (L2) | (643) | HSTPNQMSLSNRKTVVATFLTTDLEKYCLQWRYSTIKLFAQALNQLFGID |
| SEQ ID NO:64 (L) | (643) | HSTANQMSLSNRKTVVATFLTTDLEKYCLQWRYSTIKLFAQALNQLFGID |
| SEQ ID NO:76 (L) | (643) | HSTTNQMSLSNRKTVVATFLTTDLEKYCLQWRYSTIKLFAQALNQLFGID |
| SEQ ID NO:88 (L) | (643) | HSTTNQMSLSNRKTVVATFLTTDLEKYCLQWRYSTIKLFAQALNQLFGID |
| | | 701 750 |
| SEQ ID NO:13 (L1) | (701) | HGFEWIHLRLMNSTLFVGDPYSPPEDPTLEDIDKAPNDDIFIVSPRGGIE |
| SEQ ID NO:14 (L2) | (693) | HGFEWIHLRLMNSTLFVGDPYSPPEDPTLEDIDKAPNDDIFIVSPRGGIE |
| SEQ ID NO:64 (L) | (693) | HGFEWIHLRLMNSTLFVGDPYSPPEDPTLEDIDKAPNDDIFIVSPRGGIE |
| SEQ ID NO:76 (L) | (693) | HGFEWIHLRLMNSTLFVGDPYSPPEDPTLEDIDKAPNDDIFIVSPRGGIE |
| SEQ ID NO:88 (L) | (693) | HGFEWIHLRLMNSTLFVGDPYSPPEDPTLEDIDKAPNDDIFIVSPRGGIE |
| | | 751 800 |
| SEQ ID NO:13 (L1) | (751) | GLCQKMWTMISISAIHCVAEKIGARVAAMVQGDNQVIAITKELFRGEKAC |
| SEQ ID NO:14 (L2) | (743) | GLCQKMWTMISISAIHCVAEKIGARVAAMVQGDNQVIAITKELFRGEKAC |
| SEQ ID NO:64 (L) | (743) | GLCQKMWTMISISAIHCVAEKIGARVAAMVQGDNQVIAITKELFRGEKAC |
| SEQ ID NO:76 (L) | (743) | GLCQKMWTMISISAIHCVAEKIGARVAAMVQGDNQVIAITKELFRGEKAC |
| SEQ ID NO:88 (L) | (743) | GLCQKMWTMISISAIHCVAEKIGARVAAMVQGDNQVIAITKELFRGEKAC |
| | | 801 850 |
| SEQ ID NO:13 (L1) | (801) | DVRDELDELGQVFFDEFKRHNYAIGHNLKLNETIQSQSFFVYSKRIFFEG |
| SEQ ID NO:14 (L2) | (793) | DVRDELDELGQVFFDEFKRHNYAIGHNLKLNETIQSQSFFVYSKRIFFEG |
| SEQ ID NO:64 (L) | (793) | DVRDELDELGQVFFDEFKRHNYAIGHNLKLNETIQSQSFFVYSKRIFFEG |
| SEQ ID NO:76 (L) | (793) | DVRDELDELGQVFFDEFKRHNYAIGHNLKLNETIQSQSFFVYSKRIFFEG |
| SEQ ID NO:88 (L) | (793) | DVRDELDELGQVFFDEFKRHNYAIGHNLKLNETIQSQSFFVYSKRIFFEG |
| | | 851 900 |
| SEQ ID NO:13 (L1) | (851) | RLLSQVLKNAAKLCMVADHLGENTVSSCSNLSSTIARLVENGFEKDTAFV |
| SEQ ID NO:14 (L2) | (843) | RLLSQVLKNAAKLCMVADHLGENTVSSCSNLSSTIARLVENGFEKDTAFV |
| SEQ ID NO:64 (L) | (843) | RLLSQVLKNAAKLCMVADHLGENTVSSCSNLSSTIARLVENGFEKDTAFV |
| SEQ ID NO:76 (L) | (843) | RLLSQVLKNAAKLCMVADHLGENTVSSCSNLSSTIARLVENGFEKDTAFV |
| SEQ ID NO:88 (L) | (843) | RLLSQVLKNAAKLCMVADHLGENTVSSCSNLSSTIARLVENGFEKDTAFV |
| | | 901 950 |
| SEQ ID NO:13 (L1) | (901) | LNLVYIMTQILFDEHYSIVCDHHSVKSLIGSKNHRNLLYSSLIPGQLGGF |
| SEQ ID NO:14 (L2) | (893) | LNLVYIMTQILFDEHYSIVCDHHSVKSLIGSKNHRNLLYSSLIPGQLGGF |
| SEQ ID NO:64 (L) | (893) | LNLVYIMTQILFDEHYSIVCDHHSVKSLIGSKNHRNLLYSSLIPGQLGGF |
| SEQ ID NO:76 (L) | (893) | LNLVYIMTQILFDEHYSIVCDHNSVKSLIGSKNYRNLLYSSLIPGQLGGF |
| SEQ ID NO:88 (L) | (893) | LNLVYIMTQILFDEHYSIVCDHNSVKSLIGSKNYRNLLYSSLIPGQLGGF |
| | | 951 1000 |
| SEQ ID NO:13 (L1) | (951) | NFLNISRLFTRNIGDPVTCSLSDLKCFIAAGLLPPYVLKNVVLREPGPGT |
| SEQ ID NO:14 (L2) | (943) | NFLNISRLFTRNIGDPVTCSLSDLKCFIAAGLLPPYVLKNVVLREPGPGT |
| SEQ ID NO:64 (L) | (943) | NFLNISRLFTRNIGDPVTCSLSDLKCFIAAGLLPPYVLKNVVLREPGPGT |
| SEQ ID NO:76 (L) | (943) | NFLNISRLFTRNIGDPVTCSLSDLKCFIAAGLLPPYVLKNVVLREPGPGT |
| SEQ ID NO:88 (L) | (943) | NFLNISRLFTRNIGDPVTCSLSDLKCFIAAGLLPPYVLKNVVLREPGPGT |
| | | 1001 1050 |
| SEQ ID NO:13 (L1) | (1001) | WLTLCSDPYTLNIPYTQLPTTYLKKHTQRSLLSRAVNPLLAGVQVPNQHE |
| SEQ ID NO:14 (L2) | (993) | WLTLCSDPYTLNIPYTQLPTTYLKKHTQRSLLSRAVNPLLAGVQVPNQHE |
| SEQ ID NO:64 (L) | (993) | WLTLCSDPYTLNIPYTQLPTTYLKKHTQRSLLSRAVNPLLAGVQVPNQHE |
| SEQ ID NO:76 (L) | (993) | WLTLCSDPYTLNIPYTQLPTTYLKKHTQRSLLSRAVNPLLAGVQVPNQHE |
| SEQ ID NO:88 (L) | (993) | WLTLCSDPYTLNIPYTQLPTTYLKKHTQRSLLSRAVNPLLAGVQVPNQHE |

Figure 35C

| | | |
|---|---|---|
| | | 1051 1100 |
| SEQ ID NO:13 (L1) | (1051) | EEEMLARFLLDREYVMPRVAHVILESSVLGKRKQIQGLIDTTPTIIRTSL |
| SEQ ID NO:14 (L2) | (1043) | EEEMLARFLLDREYVMPRVAHVILESSVLGKRKQIQGLIDTTPTIIRTSL |
| SEQ ID NO:64 (L) | (1043) | EEEVLARFLLDREYVMPRVAHVILETSVLGKRKQIQGLIDTTPTIIRTSL |
| SEQ ID NO:76 (L) | (1043) | EEEMLARFLLDREYVMPRVAHVILETSVLGKRKQIQGLIDTTPTIIRTSL |
| SEQ ID NO:88 (L) | (1043) | EEEMLARFLLDREYVMPRVAHVTLETSVLGKRKQIQGLIDTTPTIIRTSL |
| | | 1101 1150 |
| SEQ ID NO:13 (L1) | (1101) | VNLPVSRKKCEKIINYSLNYIAECHDSLLSQVCFSDNKEYLWSTSLISVE |
| SEQ ID NO:14 (L2) | (1093) | VNLPVSRKKCEKIINYSLNYIAECHDSLLSQVCFSDNKEYLWSTSLISVE |
| SEQ ID NO:64 (L) | (1093) | VNLPVSRKKCEKIINYSLNYIAECHDSLLSQVCFSDNKEYLWSTSLISVE |
| SEQ ID NO:76 (L) | (1093) | VNLPVSRKKCEKIINYSLNYIAECHDSLLSQICFSDNKEYLWSTSLISVE |
| SEQ ID NO:88 (L) | (1093) | VNLPVSRKKCEKIINYSLNYIAECHDSLLSQICFSDNKEYLWSTSLISVE |
| | | 1151 1200 |
| SEQ ID NO:13 (L1) | (1151) | TCSVTIADYLRAVSWSNILGGRNISGVTTPDTIELIQGCLIGENSSCTLC |
| SEQ ID NO:14 (L2) | (1143) | TCSVTIADYLRAVSWSNILGGRNISGVTTPDTIELIQGCLIGENSSCTLC |
| SEQ ID NO:64 (L) | (1143) | TCSVTIADYLRAVSWSNILGGRNISGVTTPDTIELIQGCLIGENSSCTLC |
| SEQ ID NO:76 (L) | (1143) | TCSVTIADYLRAVSWSNILGGRNISGVTTPDTIELIQGCLIGENSSCTLC |
| SEQ ID NO:88 (L) | (1143) | TCSVTIADYLRAVSWSNILGGRSISGVTTPDTIELIQGCLIGENSSCTLC |
| | | 1201 1250 |
| SEQ ID NO:13 (L1) | (1201) | ESHDDAFTWMHLPGPLYIPEPSVTNSKMRVPYLGSKTEERKTASMAAIKG |
| SEQ ID NO:14 (L2) | (1193) | ESHDDAFTWMHLPGPLYIPEPSVTNSKMRVPYLGSKTEERKTASMAAIKG |
| SEQ ID NO:64 (L) | (1193) | ESHDDAFTWMHLPGPLYIPEPSVTNSKMRVPYLGSKTEERKTASMAAIKG |
| SEQ ID NO:76 (L) | (1193) | ESHDDAFTWMHLPGPLYIPEPSVTNSKMRVPYLGSKTEERKTASMAAIKG |
| SEQ ID NO:88 (L) | (1193) | ESHDDAFTWMHLPGPLYIPEPSVTNSKMRVPYLGSKTEERKTASMAAIKG |
| | | 1251 1300 |
| SEQ ID NO:13 (L1) | (1251) | MSHHLRAVLRGTSVFIWAFGDTDINWDNALQIAQSRCNITLDQMRLLTPI |
| SEQ ID NO:14 (L2) | (1243) | MSHHLRAVLRGTSVFIWAFGDTDINWDNALQIAQSRCNITLDQMRLLTPI |
| SEQ ID NO:64 (L) | (1243) | MSHHLRAVLRGTSVFIWAFGDTDINWDNALQIAQSRCNITLDQMRLLTPI |
| SEQ ID NO:76 (L) | (1243) | MSHHLRAVLRGTSVFIWAFGDTDINWDNALQIAQSRCNITLDQMRLLTPI |
| SEQ ID NO:88 (L) | (1243) | MSHHLRAVLRGTSVFIWASGDTDINWDNALQIAQSRCNITLDQMRLLTPI |
| | | 1301 1350 |
| SEQ ID NO:13 (L1) | (1301) | PSSSNIQHRLDDGISTQKFTPASLARITSFVHICNDSQRLEKDGSSVDSN |
| SEQ ID NO:14 (L2) | (1293) | PSSSNIQHRLDDGISTQKFTPASLARITSFVHICNDSQRLEKDGSSVDSN |
| SEQ ID NO:64 (L) | (1293) | PSSSNIQHRLDDGISTQKFTPASLARITSFVHICNDSQRLEKDGSSVDSN |
| SEQ ID NO:76 (L) | (1293) | PSSSNIQHRLDDGISTQKFTPASLARITSFVHICNDSQRLEKDGSSVDSN |
| SEQ ID NO:88 (L) | (1293) | PSSSNIQRRLDDGISTQKFTPASLARITSSVHICNDSQRLEKDGSSVDSN |
| | | 1351 1400 |
| SEQ ID NO:13 (L1) | (1351) | LIYQQIMLLGLSIFETMYSMDQKWVFNNHTLHLHTGHSCCPRELDISLVN |
| SEQ ID NO:14 (L2) | (1343) | LIYQQIMLLGLSIFETMYSMDQKWVFNNHTLHLHTGHSCCPRELDISLVN |
| SEQ ID NO:64 (L) | (1343) | LIYQQIMLLGLSIFETMYSMDQKWVFNNHTLHLHTGHSCCPRELDISLVN |
| SEQ ID NO:76 (L) | (1343) | LIYQQIMLLGLSIFETMYSMDQKWVFNNHTLHLHTGHSCCPRELDISLVN |
| SEQ ID NO:88 (L) | (1343) | LIYQQIMLLGLSIFETMYSMDQKWVFNNHTLHLHTGHSCCPRELDISLVN |
| | | 1401 1450 |
| SEQ ID NO:13 (L1) | (1401) | PPRHQTPELTSTTTNPFLYDQLPLNQENLTTLEIKTFKFNELNIDGLDFG |
| SEQ ID NO:14 (L2) | (1393) | PPRHQTPELTSTTTNPFLYDQLPLNQENLTTLEIKTFKFNELNIDGLDFG |
| SEQ ID NO:64 (L) | (1393) | PPRHQTPELTSTTTNPFLYDQLPLNQENLTTLEIKTFKFNELNIDGLDFG |
| SEQ ID NO:76 (L) | (1393) | PPRHQTPELTSTTTNPFLYDQLPLNQDNLTTLEIKTFKFNELNIDGLDFG |
| SEQ ID NO:88 (L) | (1393) | PPRHQTPELTSTTTNPFLYDQLPLNQDNLTTLEIKTFKFNELNIDGLDFG |
| | | 1451 1500 |
| SEQ ID NO:13 (L1) | (1451) | EGIQLLSRCTARLMAECILEEGIGSSVKNEAIVNFDNSVNWISECLMCDI |
| SEQ ID NO:14 (L2) | (1443) | EGIQLLSRCTARLMAECILEEGIGSSVKNEAIVNFDNSVNWISECLMCDI |
| SEQ ID NO:64 (L) | (1443) | EGIQLLSRCTARLMAECILEEGIGSSVKNEAIVNFDNSVNWISECLMCDI |
| SEQ ID NO:76 (L) | (1443) | EGIQLLSRCTARLMAECILEEGIGSSVKNEAIVNFDNSVNWISECLMCDI |
| SEQ ID NO:88 (L) | (1443) | EGIQLLSRCTARLMAECILEEGIGSSVKNEAIVNFDNSVNWISECLMCDI |
| | | 1501 1550 |
| SEQ ID NO:13 (L1) | (1501) | RSLCVNLGQEILCSLAYQMYYLRIRGRRAILNYLDTTLQRIPVIQLANIA |
| SEQ ID NO:14 (L2) | (1493) | RSLCVNLGQEILCSLAYQMYYLRIRGRRAILNYLDTTLQRIPVIQLANIA |
| SEQ ID NO:64 (L) | (1493) | RSLCVNLGQEILCSLAYQMYYLRIRGRRAILNYLDTTLQRIPVIQLANIA |
| SEQ ID NO:76 (L) | (1493) | RSLCVNLGQEILCSLAYQMYYLRIRGRRAILNYLDTTLQRIPVIQLANIA |
| SEQ ID NO:88 (L) | (1493) | RSLCVNLGQEILCSLAYQMYYLRIRGRRAILNYLDTTLQRIPVIQLANIA |
| | | 1551 1600 |
| SEQ ID NO:13 (L1) | (1551) | LTISHPEIFRRIVNTGIHNQIKGPYVATTDFIAASRDIILSGAREYLSYL |
| SEQ ID NO:14 (L2) | (1543) | LTISHPEIFRRIVNTGIHNQIKGPYVATTDFIAASRDIILSGAREYLSYL |
| SEQ ID NO:64 (L) | (1543) | LTISHPEIFRRIVNTGIHNQIKGPYVATTDFIAASRDIILSGAREYLSYL |
| SEQ ID NO:76 (L) | (1543) | LTISHPEIFRRIVNTGIHNQIKGPYVATTDFIAASRDIILSGAREYLSYL |
| SEQ ID NO:88 (L) | (1543) | LTISHPEIFRRIVNTGIHNQIKGPYVATTDFIAASRDIILSGAREYLSYL |

Figure 35D

| | | |
|---|---|---|
| | | 1601 1650 |
| SEQ ID NO:13 (L1) | (1601) | SSGQEDCYTFFNCQDGDLTPKMEQYLARRACLLTLLYNTGHQIPVIRSLT |
| SEQ ID NO:14 (L2) | (1593) | SSGQEDCYTFFNCQDGDLTPKMEQYLARRACLLTLLYNTGHQIPVIRSLT |
| SEQ ID NO:64 (L) | (1593) | SSGQEDCYTFFNCQDGDLTPKMEQYLARRACLLTLLYNTGHQIPVIRSLT |
| SEQ ID NO:76 (L) | (1593) | SSGQEDCYTFFNCQDGDLTPKMEQYLARRACLLTLLYNTGHQIPIIRSLT |
| SEQ ID NO:88 (L) | (1593) | SSGQEDCYTFFNCQDGDLTPKMEQYLARRACLLTLLYNTGHQIPIIRSLT |
| | | 1651 1700 |
| SEQ ID NO:13 (L1) | (1651) | PIEKCKVLTEYNQQIEYADQEFSSVLKVVNALLQNPKIDALVSNLYFTTR |
| SEQ ID NO:14 (L2) | (1643) | PIEKCKVLTEYNQQIEYADQEFSSVLKVVNALLQNPKIDALVSNLYFTTR |
| SEQ ID NO:64 (L) | (1643) | PIEKCKVLTEYNQQIEYADQEFSSVLKVVNALLQNPKIDALVSNLYFTTR |
| SEQ ID NO:76 (L) | (1643) | PIEKCKVLTEYNQQIEYADQEFSSVLKVVNALLQNPNIDALVSNLYFTTR |
| SEQ ID NO:88 (L) | (1643) | PIEKCKVLTEYNQQIEYADQEFSSVLKVVNALLQNPNIDALVSNLYFTTR |
| | | 1701 1750 |
| SEQ ID NO:13 (L1) | (1701) | RVLSNLRSCDKARSYIEYLYTEDFGEKEDTVQYDIMTTNDIILTEGLFTQ |
| SEQ ID NO:14 (L2) | (1693) | RVLSNLRSCDKARSYIEYLYTEDFGEKEDTVQYDIMTTNDIILTEGLFTQ |
| SEQ ID NO:64 (L) | (1693) | RVLSNLRSCDKARSYIEYLYTEDFGEKEDTVQYDIMTTNDIILTEGLFTQ |
| SEQ ID NO:76 (L) | (1693) | RVLSNLRSCDKAISYIEYLYTEDFGEKEDTVQYDIMTTNDIILTEGLFTQ |
| SEQ ID NO:88 (L) | (1693) | RVLSNLRSCDKAISYIEYLYTEDFGEKEDTVQYDIMTTNDIILTEGLFTQ |
| | | 1751 1800 |
| SEQ ID NO:13 (L1) | (1751) | IEISYQGNSLHKFLTPDNAPGSLIPFSISPNSLACDPLHHLLKSVGTSST |
| SEQ ID NO:14 (L2) | (1743) | IEISYQGNSLHKFLTPDNAPGSLIPFSISPNSLACDPLHHLLKSVGTSST |
| SEQ ID NO:64 (L) | (1743) | IEISYQGNSLHKFLTPDNAPGSLIPFSISPNSLACDPLHHLLKSVGTSST |
| SEQ ID NO:76 (L) | (1743) | IEISYQGSSLHKFLTPDNAPGSLIPFSISPNSLACDPLHHLLKSVGTSST |
| SEQ ID NO:88 (L) | (1743) | IEISYQGSSLHKFLTPDNAPGSLIPFSISPNSLACDPLHHLLKSVGTSST |
| | | 1801 1850 |
| SEQ ID NO:13 (L1) | (1801) | SWYKYAIAYAVSEKRSARLGGSLYIGEGSGSVMTLLEYLEPSVDIFYNSL |
| SEQ ID NO:14 (L2) | (1793) | SWYKYAIAYAVSEKRSARLGGSLYIGEGSGSVMTLLEYLEPSVDIFYNSL |
| SEQ ID NO:64 (L) | (1793) | SWYKYAIAYAVSEKRSARLGGSLYIGEGSGSVMTLLEYLEPSVDIFYNSL |
| SEQ ID NO:76 (L) | (1793) | SWYKYAIAYAVSEKRSARLGGSLYIGEGSGSVMTLLEYLEPSVDIFYNSL |
| SEQ ID NO:88 (L) | (1793) | SWYKYAIAYAVSEKRSARLGGSLYIGEGSGSVMTLLEYLEPSVDIFYNSL |
| | | 1851 1900 |
| SEQ ID NO:13 (L1) | (1851) | FSNGMNPPQRNYGLMPLQFVNSVVYKNLTAKSECKLGFVQQFKPLWRDID |
| SEQ ID NO:14 (L2) | (1843) | FSNGMNPPQRNYGLMPLQFVNSVVYKNLTAKSECKLGFVQQFKPLWRDID |
| SEQ ID NO:64 (L) | (1843) | FSNGMNPPQRNYGLMPLQFVNSVVYKNLTAKSECKLGFVQQFKPLWRDID |
| SEQ ID NO:76 (L) | (1843) | FSNGMNPPQRNYGLMPLQFVNSVVYKNLTAKSECKLGFVQQFKPLWRDID |
| SEQ ID NO:88 (L) | (1843) | FSNGMNPPQRNYGLMPLQFVNSVVYKNLTAKSECKLGFVQQFKPLWRDID |
| | | 1901 1950 |
| SEQ ID NO:13 (L1) | (1901) | IETNVTDPSFINFALNEIPMQSLKRVNCDVEFDRGMPIERVIQGYTHILL |
| SEQ ID NO:14 (L2) | (1893) | IETNVTDPSFINFALNEIPMQSLKRVNCDVEFDRGMPIERVIQGYTHILL |
| SEQ ID NO:64 (L) | (1893) | IETNVTDPSFVNFALNEIPMQSLKRVNCDVEFDRGMPIERVIQGYTHILL |
| SEQ ID NO:76 (L) | (1893) | IETNVTDPSFVNFALNEIPMQSLKRVNCDVEFDRGMPIERVIQGYTHILL |
| SEQ ID NO:88 (L) | (1893) | IETNVTDPSFVNFALNEIPMQSLKRVNCDVEFDRGMPIERVIQGYTHILL |
| | | 1951 2000 |
| SEQ ID NO:13 (L1) | (1951) | VATYGLQQDSILWVKVYRTSEKVFQFLLSAMIMIFGYVKIHRNGYMSTKD |
| SEQ ID NO:14 (L2) | (1943) | VATYGLQQDSILWVKVYRTSEKVFQFLLSAMIMIFGYVKIHRNGYMSTKD |
| SEQ ID NO:64 (L) | (1943) | VATYGLQQDSILWVKVYRTSEKVFQFLLSAMIMIFGYVKIHRNGYMSTKD |
| SEQ ID NO:76 (L) | (1943) | VATYGLQQDSILWVKVYRTSEKVFQFLLSAMIMIFGYVKIHRNGYMSAKD |
| SEQ ID NO:88 (L) | (1943) | VATYGLQQDSILWVKVYRTSEKVFQFLLSAMIMIFGYVKIHRNGYMSAKD |
| | | 2001 2050 |
| SEQ ID NO:13 (L1) | (2001) | EEYILMSDCKEPVNYTAVPNILTRVSDLVSKNLSLIHPEDLRKVRCETDS |
| SEQ ID NO:14 (L2) | (1993) | EEYILMSDCKEPVNYTAVPNILTRVSDLVSKNLSLIHPEDLRKVRCETDS |
| SEQ ID NO:64 (L) | (1993) | EEYILMSDCKEPVNYTAVPNILTRVSDLVSKNLSLIHPEDLRKVRCETDS |
| SEQ ID NO:76 (L) | (1993) | EEYILMSDCKEPVNYTAVPNILTRVSDLVSKNLSLIHPEDLRKVRCETDS |
| SEQ ID NO:88 (L) | (1993) | EEYILMSDCKEPVNYTAVPNILTRVSDLVSKNLSLIHPEDLRKVRCETDS |
| | | 2051 2100 |
| SEQ ID NO:13 (L1) | (2051) | LNLKCNHIYEKIIARKIPLQVSSTDSLLLQLGGVINSVGSTDPREVATLS |
| SEQ ID NO:14 (L2) | (2043) | LNLKCNHIYEKIIARKIPLQVSSTDSLLLQLGGVINSVGSTDPREVATLS |
| SEQ ID NO:64 (L) | (2043) | LNLKCNHIYEKIIARKIPLQVSSTDSLLLQLGGVINSVGSTDPREVATLS |
| SEQ ID NO:76 (L) | (2043) | LNLKCNHIYEKIIARKIPLQVSSTDSLLLQLGGVINSVGSTDPREVATLS |
| SEQ ID NO:88 (L) | (2043) | LNLKCNHIYEKIIARKIPLQVSSTDSLLLQLGGVINSVGSTDPREVATLS |
| | | 2101 2150 |
| SEQ ID NO:13 (L1) | (2101) | SIECMDYVVSSIDLAILEANIVISESAGLDLALMLGPFNLNKLKKIDTIL |
| SEQ ID NO:14 (L2) | (2093) | SIECMDYVVSSIDLAILEANIVISESAGLDLALMLGPFNLNKLKKIDTIL |
| SEQ ID NO:64 (L) | (2093) | SIECMDYVVSSIDLAILEANIVISESAGLDLALMLGPFNLNKLKKIDTIL |
| SEQ ID NO:76 (L) | (2093) | SIECMDYVVSSIDLAILEANIVISESAGLDLALMLGPFNLNKLKKIDTIL |
| SEQ ID NO:88 (L) | (2093) | SIECMDYVVSSIDLAILEANIVISESADLDLALMLGPFNLNKLKKIDTIL |

Figure 35E

| | | |
|---|---|---|
| | | 2151 2200 |
| SEQ ID NO:13 (L1) | (2151) | KSSTYQLIPYWLRYEYSINPRSLSFLITKLQQCRISWSDMITISEFRKKS |
| SEQ ID NO:14 (L2) | (2143) | KSSTYQLIPYWLRYEYSINPRSLSFLITKLQQCRISWSDMITISEFRKKS |
| SEQ ID NO:64 (L) | (2143) | KSSTYQLIPYWLRYEYSINPRSLSFLITKLQQCRISWSDMITISEFRKKS |
| SEQ ID NO:76 (L) | (2143) | KSSTYQLIPYWLRYEYSINPRSLSFLITKLQQCRISWSDMITISEFCKKS |
| SEQ ID NO:88 (L) | (2143) | KSSTYQLIPYWLRYEYSINPRSLSFLITKLQQCRISWSDMITISEFCKKS |
| | | 2201 2247 |
| SEQ ID NO:13 (L1) | (2201) | KRPIFIKRVIGNQQLKSFFNESSSIVLTRAEVKVCIKFLGAIIKLK- |
| SEQ ID NO:14 (L2) | (2193) | KRPIFIKRVIGNQQLKSFFNESSSIVLTRAEVKVCIKFLGAIIKLK- |
| SEQ ID NO:64 (L) | (2193) | KRPIFIKRVIGNQQLKSFFNESSSIVLTRAEVKVCIKFLGAIIKLK- |
| SEQ ID NO:76 (L) | (2193) | KRPIFIKRVIGNQQLKSFFNESSSIVLTRAEVKVCIKFLGAIIKLK- |
| SEQ ID NO:88 (L) | (2193) | KRPIFIKRVIGNQRLKSFFNESSSIVLTRAEVKVCIKFLGAIIKLK- |

Protein sequence identity:

SEQ ID NO:14 v. SEQ ID NO:64: 99% sequence identity
SEQ ID NO:14 v. SEQ ID NO:76: 99% sequence identity
SEQ ID NO:14 v. SEQ ID NO:88: 98% sequence identity DNA sequence identity:

SEQ ID NO:12 v. SEQ ID NO:63: 99% sequence identity
SEQ ID NO:12 v. SEQ ID NO:75: 97% sequence identity
SEQ ID NO:12 v. SEQ ID NO:87: 97% sequence identity

```
                        SEQUENCE LISTING

<160> NUMBER OF SEQ ID NOS: 88

<210> SEQ ID NO 1
<211> LENGTH: 15342
<212> TYPE: DNA
<213> ORGANISM: artificial sequence
<220> FEATURE:
<223> OTHER INFORMATION: APMV8 genome sequence

<400> SEQUENCE: 1

accaaacaag gaatgcaaga ccaacgggaa ctttaaataa aacaatcgaa ttattggggg      60

cgaagcaagt ggatctcgag ctcgaggccg aaaccctgaa tttcactgga ggttttgaat     120

aggtcgctat aggactcaat atgtcatctg tgttcaatga gtatcaggcg cttcaagaac     180

aacttgtgaa gccggctgtc aggagacctg atgttgcctc aacgggttta ctcagagcgg     240

aaatacctgt ctgtgttaca ttatctcaag accccggtga gagatggagc cttgcttgct     300
```

```
tgaatattag atggcttgcg agtgattcat caaccacacc aatgaagcaa ggagcaatat    360
tgtcactgct gagtctacat tcagacaata tgcgagctca cgcaacatta gcagcaaggt    420
ctgcagatgc ttcactcacc atacttgagg tagatgaagt agatattagc aactcactaa    480
tcaaattcaa cgccagaagt ggtgtatctg acaaacgctc aaatcaattg cttgcaattg    540
cggatgacat ccccaaaagt tgcagtaatg ggcatccatt tcttgacaca gacattgaga    600
ccagagaccc gctcgatcta tcagagacta tagatcgcct gcagggtatt gcagctcaga    660
tatgggtgtc agccataaag agcatgacag cgcctgacac cgcatcagag tcagaaagta    720
agaggctggc caaatatcaa caacaaggcc gactggttaa gcaagtactc ttgcattctg    780
tagtcaggac agaatttatg agagttattc ggggcagctt ggtactgcgc cagtttatgg    840
ttagcgagtg caagagggct tcagccatgg gcggagacac atctaggtac tatgctatgg    900
tgggtgacat cagtctttac atcaagaatg caggattgac tgcatttttc ctcaccctga    960
agttcggagt tggtacccag tatccaacct tagcaatgag tgttttctcc agtgacctta   1020
aaaggcttgc tgcactcatc aggctataca aaaccaaggg agacaatgca ccatacatgg   1080
cattcctgga ggactccgat atgggaaatt ttgctccagc aaattatagc acaatgtact   1140
cttatgccat gggcattggg acaattctgg aagcatctgt atctcgatac cagtatgcca   1200
gagactttac cagtgagaat tatttccgtc ttggagttga gacagcccaa agccagcagg   1260
gagcatttga cgagagaaca gcccgagaaa tgggcttgac tgaggaatca aaacagcagg   1320
ttagatcact gctaatgtca gtagacatgg gtcccagttc aattcatgag ccatctcgcc   1380
ctgcatttat cagtcaagaa gaaaataggc agcctgccca gaacttgtca gatactcagg   1440
gtcagaccaa gccagtcccg aagcagcccg caccaagggc cgactcagat gacattgatc   1500
catacgagaa cgggctagaa tggtaattca accaccccga cacatccacc tatacaccaa   1560
ttccgtgaca tattaaccca atcaaacatt tcataaacta tagtagtcat tgatttaaga   1620
aaaaattggg ggcgacctca attgtgaaac ataccagatc cgtccacaac accactcaac   1680
aacccacaca caatggattt cgccaatgat gaagaaattg cagaactttt gaatctcagc   1740
accaatgtaa tcaaggagat tcagaaatcc gaactcaagc ctccccaaac caccggacga   1800
ccacctgtca gtcaagggaa cacaagaaat ctaactgatc tatgggaaaa ggagactgca   1860
agtcagacca agacaccggc ccaatctaca caaaccacac aagttcagtc tgatgaaaat   1920
gaggagggag aaatcaagtc cgagtcaact gatggccaca tcagaggaac tgttaatcaa   1980
tcagagcaag tcccagaaca aaaccagagc agatcttcac caggtgatga tctcgacaga   2040
gctctcaaca agcttgaagg gagaatcaat ttaatcagct caatggacaa agaaattaaa   2100
aagggccctc gcatccagaa tctccctggg tcccaggcgg caactcaaca ggcgacccac   2160
ccattggcag gggacacccc gaacatgcaa gcacagacaa aagccctggc gaagccacat   2220
caagaggcaa tcaatcctgg caaccaggac acaggagaga gtattcattt accaccttcc   2280
atggcaccac cagagtcatt agttggtgca atccgcaatg caccccaatt cgtgccagac   2340
caatctatga cgaatgtaga tgcggggagt gtccaactac atgcatcatg tgcagagatg   2400
ataagtagaa tgtttgtaga agttatatcc aagcttgata aactcgagtc gagactgaat   2460
gatatagcaa aagttgtgaa cactaccccc cttattagga atgatattaa ccaacttaag   2520
gccacaaccg cactgatgtc taaccaaatt gcctccatac aaattcttga cccagggaat   2580
gcaggggtga ggtccctctc tgaaatgaaa tctgtgacga agaaagctgc tgttgtaatt   2640
gcagggtttg gagacgaccc aactcaaatt attgaagaag gcattatggc caaagatgct   2700
```

```
cttggaaaac ctgtgcctcc aacatctgtt atctcagcca aagctcagac ttcttccggt   2760
gtgagtaagg gtgaaataga aggattgatt gcattggtgg aaacattagt tgacaatgac   2820
aagaaggcag caaaactgat taaaatgatt gatcaagtta aatcccatgc cgattacgcc   2880
cgagtcaagc aggcaatata taatgcgtaa tactgtaact acacaaacaa tcaatactgc   2940
tgtcggttgc acccacctca gcaaatcaat aatcttttag aatttattga ttaagaaaaa   3000
attgactact ataagaaaag aacaccaagt tgggggcgaa gacacgattg accacagtcg   3060
ctatctgtaa ggctcctcac caaaaatggc atatacaaca ttgaaactgt gggtggatga   3120
gggtgacatg tcgtcttcgc tcctatcatt cccgttggta ctaaaagaga cagacagagg   3180
cacaaaggag cttcaaccac aggtaagggt agattcaatt ggcgatgtgc agaacgccaa   3240
agagtcctcg atattcgtga ctctatatgg tttcatccaa gcaattaagg agagttcaga   3300
tcgatcgaaa ttcttccatc caaaagatga cttcaaacct gagacagtca ctgcaggact   3360
ggtagtggta ggtgcgatcc gaatgatggc tgatgttaat accatctcta atgacgcact   3420
agcgctggag atcactgtta agaaatctgc aacttctcaa gagaaaatga cggtgatgtt   3480
ccacaatagc cccccttcat tgagaactgc aataactatc cgagcaggag gtttcatctc   3540
gaatgcagac gagaatataa aatgtgccag caaattgact gcaggagtgc agtacatatt   3600
ccgcccaatg tttgtttcaa tcactaaatt acacaatggc aaactatata gggtgcccaa   3660
aagcatccac agcatctcat ccactctact gtatagtgtg atgttggagg taggattcaa   3720
agtggatatt gggaaggatc atccccaggc aaagatgctg aagaaggtca caatcggcga   3780
tgcagacaca tactgggggt ttgcatggtt ccacctgtgc aatttcaaaa agacatcctc   3840
taagggaaag ccaagaacgc tagacgaact aaagacaaaa gtcaaaaata tggggttgaa   3900
attggagtta catgacctgt ggggtccgac tattgtggtc caaatcactg gcaagagcag   3960
caaatatgct caaggatttt tttcctccaa tggtacttgt tgtctcccaa tcagcagatc   4020
tgcaccagag cttgggaagc ttctgtggtc ttgttcagca actataggtg acgcaacagt   4080
tgttatccaa tcaagcgaga aaggggaact cctaaggtct gatgacctcg agatacgagg   4140
tgctgtggcc tccaagaaag gtagactggg ctcatttcac cccttcaaaa aatgatgcag   4200
gacatagtac agagaattag agagccatta gatgtgcgca aaaaacataa tctgcgatga   4260
actgcccaga ctccacttta atctaggttg cagggaaata gtacacgaca tgcgaaatac   4320
tatcacggtc accagcaatc aataaagctg atcaatcact atattaggaa tcaaatagga   4380
taacaattat taatccaatt tcctaattat aaaaaattgc tttaaaggtt attgacgagt   4440
cgggggcgaa atcttgccac ttagtctgca gtcaatctta gaatctacat attgaactat   4500
gggtcaaata tcagtatatc taattaatag cgtgctatta ttgctggtat atcctgtgaa   4560
ttcgattgac aatacactca ttgccccaat cggagttgcc agcgcaaatg aatggcagct   4620
tgctgcatat acaacatcac tttcagggac aattgccgtg cgattcctac ctgtgctccc   4680
ggataatatg actacctgtc ttaaagaaac aatcactaca tacaataata ctgtcaacaa   4740
catcttaggc ccactcaaat ccaatctgga tgcactgctc tcatctgaga cttatcccca   4800
gacaagatta attggggcag ttataggttc aattgctctc ggtgttgcaa catcggctca   4860
aatcactgct gcagttgctc tcaagcaagc gcaagacaat gcaaggaaca tactagcact   4920
caaagaagca ctgtccaaaa ccaatgaggc ggtcaaggag cttagtagtg ggttacaaca   4980
aacagctatt gcacttggta agatacagag ttttgtgaat gaggaaattc tgccatctat   5040
caaccaactg agctgcgagg tgacagccaa taaacttggg gtgtatttat ctctgtatct   5100
```

```
cacagaactg accaccatat tcggtgcaca gctgaccaac cctgcattga cttcattatc   5160
atatcaagca ctgtacaacc tgtgtggtgg caacatggca atgcttactc agaagattgg   5220
aattaaacag caagacgtta attcgctata tgaagccgga ctaatcacag gacaagtcat   5280
tggttatgac tctcattacc agctgctggt catccaggtc aattatccaa gcatttctga   5340
ggtcactggt gtacgtgcga cagaattagt cactgttagt gtaacaacag acaagggtga   5400
agggaaagca attgtacccc aatttgtagc tgaaagtcgg gtgactattg aagagcttga   5460
tgtcgcatct tgtaaattca gcagcacgac cctatattgc aggcaggtca acacaagggc   5520
acttcccccg ctagtagcta gctgtcttcg aggtaactat gatgattgtc aatataccac   5580
agagattgga gcattatcat cccggtatat aacactagat ggggggggtct tagttaattg   5640
caagtcaatt gtttgtaggt gccttaatcc aagtaagatc atctctcaaa atacaaacgc   5700
tgcagtaaca tatgttgatg ccacaatctg caaaacaatt caattggatg atatacaact   5760
ccagctggaa gggtcactat catcagttta tgcaagaaac atctcaattg agatcagtca   5820
ggtgaccaca tccgggtctt tagatatcag cagtgagata ggaaacatca ataatacggt   5880
gaatcgtgtg gaggatttaa ttcaccaatc agaggaatgg ctggcaaagg ttaacccaca   5940
cattgttaat aatacaacac taattgtact ctgtgtgtta agtgcgcttg ctgtgatctg   6000
gctggcagta ttaacggcta ttataatata cttgagaaca aagttgaaga ctatatcggc   6060
attagctgta accaatacaa tacagtctaa cccctatgtt aaccaaacga aacatgaatc   6120
taagttttga tcattcaagc caaaacagag gatctaggct caggttaata atagttcaat   6180
caatatttga tttattaggt ttttttcact aattattaat atactcgtga ttagatgata   6240
acgttaaaag tcttagatat ttaataaaaa atgtaacctg ggggcgaccc atttataggt   6300
gagtatatat taggaagtcc ttatattgca ctgtgatttc aaacaattat attacctcat   6360
atctaccttg tctaaagaca tcatgagtaa cattgcatcc agtttagaaa acattgtaga   6420
gcaggatagt cgaaaaacaa cttggagggc catctttaga tggtccgttc ttcttattac   6480
aacaggatgc ttagccttat ccattgttag catagttcaa attggaaatt tgaaaattcc   6540
ttctgtaggg gatctggctg atgaagtggt gacacccttg aaaaccactc tgtcagatac   6600
actcaggaat ccaattaacc agataaatga tatatttagg attgttgccc ttgatattcc   6660
attgcaagtg accagtatcc aaaaagacct tgcaagtcaa tttaacatgt tgatagatag   6720
tttaaatgct atcaaattag gcaacgggac caaccttatc atacctacat cagacaagga   6780
gtatgcagga ggaattggaa accctgtatt tactgtcgat gctggaggtt ctataggatt   6840
caaacagttt agcttaatag aacatccgag ctttattgct ggacctacaa cgacccgagg   6900
ctgtacaaga atacccactt ttcacatgtc agaaagtcat tggtgctact cacacaacat   6960
catcgctgct ggctgtcaag atgccagtgc atccagtatg tatatctcaa tgggagttct   7020
ccatgtgtcc tcatctggca ctcccatttt tcttactact gcaagtgagc tgatagacga   7080
tggagttaac cgtaagtcat gcagcattgt agcaacccaa tttggctgtg acattttgtg   7140
cagtattgtc acagagaagg agggagatga ttactggtct gatactccga ctccaatgcg   7200
ccacggccgt tttcattcca atggtagttt tgtagaagcc gaactaccag tgtccagtat   7260
gttctcatca ttctctgcca actaccctgc tgtgggatca ggcgaaattg taaaagatag   7320
aatattattc ccaatttacg gaggtataaa gcagacttca ccagagttta ccgaattagt   7380
gaaatacgga ctctttgtat caacacctac aactgtgtgc cagagtagct ggacttatga   7440
ccaggtaaaa gctgcgtata ggccagatta catatcaggc cggttctggg cacaagtgat   7500
```

-continued actcagctgc gctcttgatg cagtcgactt atcaagttgt attgtaaaga ttatgaatag 7560
cagcacagtg atgatggcag cggaaggaag gataatgaag atagggattg attactttta 7620
ctatcagcgg tcatcttctt ggtggccatt ggcatttgtc acaaaactag acccgcaaga 7680
gttggcagac acaaactcaa tatggctgac caattccata ccaatcccgc aatcaaagtt 7740
ccctcggcct tcatattcag aaaattattg cacaaagcca gcagtttgcc ctgctacttg 7800
tgtcactggt gtgtactctg atatttggcc cctgacctca tcttcatcac tcccgagcat 7860
aatttggatc ggccagtacc ttgatgctcc tgttggaagg acttatccta gatttggaat 7920
tgcaaatcag tcacactggt acctccaaga agatattcta cccacttcca ccgcaagtgc 7980
gtattcaacc actacatgtt ttaagaatac tgccaggaat agagtgttct gcgtcaccat 8040
tgccgaattt gcagatgggt tgtttggaga gtacaggata acacctcagt tgtacgaatt 8100
agtgagaaat aattgaataa caataatttt gggactcatt ttgtcgcaaa gtgaaattgt 8160
catctttaaa aataatcaat tcgatgattt ttattgaaca tgattaagca atcatgtggg 8220
aaatttatta tctcataaat tctaatagtt gtaaatgatg aattaagaaa aaatggaggg 8280
cgacctctac acaaacatgg atataaaaca agttgacctg ataatacaac ccgaggttca 8340
tctcgattca cccatcatat tgaataaact ggcactatta tggcgcttga gtggtttacc 8400
catgcctgca gacctacgac aaaaatccgt agtgatgcac atcccggacc acatcttaga 8460
aaaatcagaa tatcggatca agcaccgtct agggaaaatc aagagtgaca taacacatta 8520
ctgtcagtat tttaatatta atttggcaaa tattgatccg ataacccacc ccaaaagttt 8580
gtattggtta tccagactaa caatagctag tgctggaact tttaggcata tgaaagatag 8640
aatcttgtgt acagttggct ctgaatttgg acacaaaatt caagatttat tttcactgct 8700
gagccataaa ctagtaggta acggggattt atttaatcaa agtctctcag gtacacgttt 8760
gactgcaagt ccgttatccc ctttatgcaa tcaatttgtc tctgacatca agtctgcagt 8820
cacgacaccc tggtcagaag ctcgttggtc ttggcttcat atcaaacaaa caatgagata 8880
tctgataaaa caatcacgca ctacaaattc ggctcattta acagaaatca taaaagaaga 8940
atggggttta gtaggtatta ctccagatct tgtcattctt tttgacagag tcaataatag 9000
tctgactgca ttaacatttg agatggttct aatgtattca gatgtattag aatcccgtga 9060
caatattgtg ttagtggggc gactatctac ctttctacag ccagtagtta gtagactgga 9120
ggtgttgttt gatctagtag attcattggc aaaaatctta ggtgacacaa tatatgagat 9180
tattgcagtg ttagagagct tgtcttatgg gtcagttcaa ctacatgatg caagtcactc 9240
tcatgcaggg tcttttttt catttaacat gaatgaactt gataacacac tatcaaagag 9300
ggtagatccg aaacacaaga acactataat gagcattata agacaatgct tttctaatct 9360
agatgttgat caagctgcag agatgctatg cctgatgaga ttattcggac acccaatgtt 9420
aactgcaccg gatgcagcag ccaaagtgag gaaagcaatg tgtgctccaa aacttgttga 9480
acacgacacc atcttgcaga cattatcttt cttcaagggg ataattataa atgggtacag 9540
aagatcacac tctggcctgt ggcccaatgt agagccgtct tcaatttatg atgatgatct 9600
cagacagctg tacttagagt cagcagagat ttcccatcat tttatgctta aaaactacaa 9660
gagtttaagc atgatagaat tcaagaagag catagactac gatcttcatg atgacctaag 9720
tactttctta aaggatagag caatttgccg gccgaaatcc cagtgggatg tcatatttcg 9780
taagtcttta cgcagatctc atacgcagtc ccagtatctg gacgaaatta agagcaaccg 9840
attgctaatt gattttcttg attctgctga atttgaccct ggaaaagaat ttgcatatgt 9900

-continued aaccacaatg gattatttgc acgataatga attttgtgct tcatattctc taaaggaaaa 9960
ggagatcaaa actactggga ggatatttgc aaaaatgaca cgcaatatga gaagttgcca 10020
agtaatactt gaatctttgt tatcaaagca tatatgcaag ttcttcaaag agaatggcgt 10080
ttcgatggag caattgtcat tgaccaagag tctacttgca atgtctcaac tctcaccaaa 10140
agtctcgact ttgcaggaca ctgcatcacg tcatgtaggt aactcaaaat ctcagattgc 10200
aaccagcaac ccatctcggc atcactcgac acccaatcag atgtcactct caaatcgaaa 10260
aacggttgta gcaactttct taacaactga cttggaaaaa tactgcctgc agtggcgata 10320
ttcaactatt aaattgtttg cacaagctct aaatcaactc tttgggattg atcacggatt 10380
tgaatggata catttaagac ttatgaacag caccttattt gttggcgatc cttactcgcc 10440
tcctgaagat ccaacactag aagatataga taaagcacca aatgatgata tcttcatagt 10500
ttctccaagg ggaggcatag agggtttatg tcagaaaatg tggaccatga tatcaattag 10560
tgctatacac tgtgtagcag agaaaattgg tgcacgagtg gcagcaatgg tgcagggtga 10620
taatcaagta atagctatca ccaaagaatt attcagagga gagaaagctt gtgatgtcag 10680
agatgagtta gacgagcttg gtcaagtgtt ttttgatgag ttcaagagac acaattatgc 10740
aattggacac aatcttaagc taaatgagac aatacaaagc caatcctttt ttgtatattc 10800
caaacgaata ttctttgaag ggcgattgct tagtcaagtc ctcaaaaatg ctgccaagtt 10860
atgtatggtt gctgaccatc taggtgaaaa cactgtatct tcctgtagca acctgagctc 10920
gacaattgcc cgcttagtgg aaaatgggtt tgagaaggac actgcttttg tgttgaacct 10980
agtctacatc atgactcaga ttctttttga tgagcattac tcgattgtat gcgatcacca 11040
tagtgtcaaa agcttgattg gatcaaaaaa ccatcggaat ttattgtatt catctctaat 11100
accaggtcag ctcggcggtt tcaacttcct caatataagt cggttgttca ctaggaatat 11160
aggtgaccca gtaacatgta gtctgtctga tctcaaatgc ttcatagccg caggtctcct 11220
tccaccctat gtcctaaaaa atgtggttct gcgtgagcct ggtcctggga catggttgac 11280
gttgtgctct gatccttaca cccttaacat accatacaca cagcttccaa ccacatatct 11340
caaaaagcac acccagcgat cattgctttc acgtgcagta aatcctttat tagccggtgt 11400
acaagtgcca aatcagcatg aggaagaaga gatgttggct cgctttctcc ttgatcgtga 11460
atatgtgatg ccccgcgttg ctcatgtaat actagaatca tcagtccttg gcaaacggaa 11520
acaaatccaa ggcttaattg atacaactcc aaccatcatt agaacatctc tagttaatct 11580
gccagtgtct agaaagaaat gcgaaaaaat aatcaattac tctctcaatt atattgctga 11640
gtgtcatgac tccttactta gccaggtctg cttcagtgat aataaggaat acttgtggtc 11700
aacctcctta atatcagttg agacctgtag tgtgacaatt gcggactatc tgagagctgt 11760
cagctggtct aatatattag ggggaagaaa catatccggg gtgactacac ctgatactat 11820
tgaattaatt caaggttgtt taataggtga aaattctagt tgtactcttt gtgaatcgca 11880
tgatgacgca ttcacgtgga tgcacttgcc tggcccactt tacatccctg aaccatcagt 11940
tactaactct aaaatgcgtg tgccatatct gggttcaaaa acagaggagc ggaaaacagc 12000
ctcaatggca gcaataaaag gaatgtcaca tcacctgcgt gcagtcttaa gaggcacatc 12060
cgtatttatt tgggcatttg gggatacaga tatcaattgg gataatgcat tgcagattgc 12120
ccaatcacgg tgtaacatca cattggatca aatgagatta cttacaccaa ttcctagcag 12180
ttcaaatatt caacatagac tcgatgacgg aatcagcacg cagaaattta ctcctgcaag 12240
ccttgctcga atcacatcct tcgttcacat ctgtaatgac agccagaggt tagagaagga 12300

```
tggctcatct gtcgactcaa acttgattta ccagcaaatt atgttacttg gactcagcat  12360
ctttgaaaca atgtactcaa tggaccaaaa gtgggtattc aataaccata ccttgcattt  12420
gcacactgga cactcctgtt gtccaaggga actagacata agtttggtga acccgccgag  12480
acatcagacc ccggagctga ctagcacaac aaccaacccg ttcctatatg atcagctccc  12540
attaaatcaa gaaaacttga caacacttga gattaagaca tttaaattca atgagctcaa  12600
cattgatggt ttagattttg gtgaaggaat acaattattg agtcgttgta ctgcaagatt  12660
aatggcagaa tgtattctag aggagggaat aggctcgtca gttaaaaatg aagcaattgt  12720
caattttgat aattcagtca attggatttc agagtgccta atgtgtgata ttcgctcact  12780
ttgtgttaat ttaggtcaag agatactatg tagcctggca taccaaatgt attacttgcg  12840
aatcaggggt agacgggcca ttcttaatta cttggacaca actttgcaaa ggatccctgt  12900
gatacaatta gccaacattg cactcaccat ttcgcaccct gagatatttc gcagaattgt  12960
caacaccggg atccataacc agattaaggg cccatatgtg gcaacaacgg atttcatagc  13020
tgcaagtaga gatatcatat tatcaggtgc aagggagtat ctatcttatt taagcagtgg  13080
gcaggaagac tgttacacat tcttcaactg tcaagatggg gatcttactc caaaaatgga  13140
acagtatctt gcaaggaggg catgcctttt aacattattg tataatactg ggcaccagat  13200
ccccgttatc cgatcactga cgccaataga gaagtgcaag gtgctcacag aatacaatca  13260
acaaattgag tacgcagatc aagagtttag ctctgtacta aaagtggtca atgcactact  13320
acaaaatcct aagatagatg cattagtttc aaatctctac ttcaccacca gacgtgttct  13380
atcaaacctc agatcatgtg ataaggctag atcatatatt gaatatttgt acactgagga  13440
cttcggagag aaagaggata cagtacaata tgacatcatg acaacaaacg atatcatact  13500
tactcatggt ctattcacac agatcgaaat atcttatcaa gggaatagtc tccataagtt  13560
ccttactccg gataacgcgc ctggatcttt gatcccattc tctatttcac caaattcact  13620
tgcatgtgac cctcttcatc acttgctcaa gtcggtcggt acatcaagca caagttggta  13680
caagtatgca atcgcctatg cagtgtctga aaagaggtca gctcgattag gagggagctt  13740
gtacattggt gaagggagcg gaagtgtgat gactttactc gagtatcttg agccatctgt  13800
tgacatattt tacaattcac tcttctcaaa tggtatgaac ccaccacaac gaaattatgg  13860
gcttatgcca ctacaatttg tgaattcggt ggtttataag aacttaacgg ctaaatcaga  13920
atgtaagcta gggtttgtcc agcaatttaa accgttgtgg agagacatag acattgagac  13980
taatgttaca gatccatcat ttatcaattt tgcattgaat gaaatcccaa tgcaatcatt  14040
aaaacgagta aattgtgatg tggaatttga ccgtggtatg ccgattgaac gggttattca  14100
gggttacacc catatcttac ttgttgccac ttacggatta cagcaagatt caatactgtg  14160
ggtgaaggta tataggacat ctgaaaaagt atttcaattc ttactgagtg ccatgatcat  14220
gatctttggt tatgtaaaaa tccacaggaa tggttatatg tcgacaaagg atgaagagta  14280
catattgatg tctgactgca aggaacctgt aaactataca gctgtcccta acattcttac  14340
acgtgtaagt gatttagtgt cgaagaatct gagtcttatc catccagaag acctcagaaa  14400
agtaaggtgt gaaacagatt ccctgaattt gaagtgcaat catatttatg agaaaataat  14460
tgccagaaaa attccattac aggtatcatc aactgactct ttgctcctcc aattaggcgg  14520
tgttatcaac tcggtgggct caactgatcc tagagaggtt gcaacattat cttctattga  14580
gtgtatggac tatgttgtct catcaattga tttggctata ttggaggcaa atattgtaat  14640
ctcagagagt gctggtcttg acctcgcttt aatgttaggc ccattcaact taaataagct  14700
```

-continued taagaaaatt gacacaatcc ttaagtcaag cacctatcag ctaatcccgt actggttgcg 14760
ctatgagtac tctattaatc cgagatcttt gtcatttcta atcactaaat tacaacaatg 14820
ccgaatttca tggtcagata tgatcacgat ttctgaattt cgtaagaaat ccaagcggcc 14880
tatatttatc aaacgagtaa tagggaatca acagctaaaa tcattcttta atgaaagctc 14940
aagtattgtt ttgactcggg ctgaagttaa agtctgtata aagttcctcg gtgcaatcat 15000
caagttgaaa taatttctgc gattttaaag gggtgtaatg ttctaatttg cacttgaagt 15060
aatatagctt gtaatcattc gctaggggat aggataattt ctctaacctc tgaatctata 15120
ttcctagagt ataacaaata tatacataat aaaaatgatt ttaagaaaaa atccgacact 15180
caaagaaaat tggtgcctgt aatattcttc ttgccaaatg attgtgaagt gtctagccta 15240
acttaaaaca atcgtattcg atagggaaga atgatatata aaataactaa taaaaaattg 15300
tattagtaaa aattaccgta tttcctgtat tccatttctg gt 15342

<210> SEQ ID NO 2
<211> LENGTH: 1386
<212> TYPE: DNA
<213> ORGANISM: artificial sequence
<220> FEATURE:
<223> OTHER INFORMATION: APMV8 NP gene

<400> SEQUENCE: 2
atgtcatctg tgttcaatga gtatcaggcg cttcaagaac aacttgtgaa gccggctgtc 60
aggagacctg atgttgcctc aacgggttta ctcagagcgg aaatacctgt ctgtgttaca 120
ttatctcaag accccggtga gagatggagc cttgcttgct tgaatattag atggcttgcg 180
agtgattcat caaccacacc aatgaagcaa ggagcaatat tgtcactgct gagtctacat 240
tcagacaata tgcgagctca cgcaacatta gcagcaaggt ctgcagatgc ttcactcacc 300
atacttgagg tagatgaagt agatattagc aactcactaa tcaaattcaa cgccagaagt 360
ggtgtatctg acaaacgctc aaatcaattg cttgcaattg cggatgacat ccccaaaagt 420
tgcagtaatg ggcatccatt tcttgacaca gacattgaga ccagagaccc gctcgatcta 480
tcagagacta tagatcgcct gcagggtatt gcagctcaga tatgggtgtc agccataaag 540
agcatgacag cgcctgacac cgcatcagag tcagaaagta agaggctggc caaatatcaa 600
caacaaggcc gactggttaa gcaagtactc ttgcattctg tagtcaggac agaatttatg 660
agagttattc ggggcagctt ggtactgcgc cagtttatgg ttagcgagtg caagagggct 720
tcagccatgg gcggagacac atctaggtac tatgctatgg tgggtgacat cagtctttac 780
atcaagaatg caggattgac tgcatttttc ctcaccctga agttcggagt tggtacccag 840
tatccaacct tagcaatgag tgttttctcc agtgacctta aaaggcttgc tgcactcatc 900
aggctataca aaaccaaggg agacaatgca ccatacatgg cattcctgga ggactccgat 960
atgggaaatt ttgctccagc aaattatagc acaatgtact cttatgccat gggcattggg 1020
acaattctgg aagcatctgt atctcgatac cagtatgcca gagactttac cagtgagaat 1080
tatttccgtc ttggagttga gacagcccaa agccagcagg gagcatttga cgagagaaca 1140
gcccgagaaa tgggcttgac tgaggaatca aaacagcagg ttagatcact gctaatgtca 1200
gtagacatgg gtcccagttc aattcatgag ccatctcgcc ctgcatttat cagtcaagaa 1260
gaaaataggc agcctgccca gaacttgtca gatactcagg gtcagaccaa gccagtcccg 1320
aagcagcccg caccaagggc cgactcagat gacattgatc catacgagaa cgggctagaa 1380
tggtaa 1386

-continued

```
<210> SEQ ID NO 3
<211> LENGTH: 461
<212> TYPE: PRT
<213> ORGANISM: artificial sequence
<220> FEATURE:
<223> OTHER INFORMATION: APMV8 NP protein

<400> SEQUENCE: 3

Met Ser Ser Val Phe Asn Glu Tyr Gln Ala Leu Gln Glu Gln Leu Val
1               5                   10                  15

Lys Pro Ala Val Arg Arg Pro Asp Val Ala Ser Thr Gly Leu Leu Arg
            20                  25                  30

Ala Glu Ile Pro Val Cys Val Thr Leu Ser Gln Asp Pro Gly Glu Arg
        35                  40                  45

Trp Ser Leu Ala Cys Leu Asn Ile Arg Trp Leu Ala Ser Asp Ser Ser
    50                  55                  60

Thr Thr Pro Met Lys Gln Gly Ala Ile Leu Ser Leu Leu Ser Leu His
65                  70                  75                  80

Ser Asp Asn Met Arg Ala His Ala Thr Leu Ala Ala Arg Ser Ala Asp
                85                  90                  95

Ala Ser Leu Thr Ile Leu Glu Val Asp Glu Val Asp Ile Ser Asn Ser
            100                 105                 110

Leu Ile Lys Phe Asn Ala Arg Ser Gly Val Ser Asp Lys Arg Ser Asn
        115                 120                 125

Gln Leu Leu Ala Ile Ala Asp Asp Ile Pro Lys Ser Cys Ser Asn Gly
    130                 135                 140

His Pro Phe Leu Asp Thr Asp Ile Glu Thr Arg Asp Pro Leu Asp Leu
145                 150                 155                 160

Ser Glu Thr Ile Asp Arg Leu Gln Gly Ile Ala Ala Gln Ile Trp Val
                165                 170                 175

Ser Ala Ile Lys Ser Met Thr Ala Pro Asp Thr Ala Ser Glu Ser Glu
            180                 185                 190

Ser Lys Arg Leu Ala Lys Tyr Gln Gln Gln Gly Arg Leu Val Lys Gln
        195                 200                 205

Val Leu Leu His Ser Val Val Arg Thr Glu Phe Met Arg Val Ile Arg
    210                 215                 220

Gly Ser Leu Val Leu Arg Gln Phe Met Val Ser Glu Cys Lys Arg Ala
225                 230                 235                 240

Ser Ala Met Gly Gly Asp Thr Ser Arg Tyr Tyr Ala Met Val Gly Asp
                245                 250                 255

Ile Ser Leu Tyr Ile Lys Asn Ala Gly Leu Thr Ala Phe Phe Leu Thr
            260                 265                 270

Leu Lys Phe Gly Val Gly Thr Gln Tyr Pro Thr Leu Ala Met Ser Val
        275                 280                 285

Phe Ser Ser Asp Leu Lys Arg Leu Ala Ala Leu Ile Arg Leu Tyr Lys
    290                 295                 300

Thr Lys Gly Asp Asn Ala Pro Tyr Met Ala Phe Leu Glu Asp Ser Asp
305                 310                 315                 320

Met Gly Asn Phe Ala Pro Ala Asn Tyr Ser Thr Met Tyr Ser Tyr Ala
                325                 330                 335

Met Gly Ile Gly Thr Ile Leu Glu Ala Ser Val Ser Arg Tyr Gln Tyr
            340                 345                 350

Ala Arg Asp Phe Thr Ser Glu Asn Tyr Phe Arg Leu Gly Val Glu Thr
        355                 360                 365
```

```
Ala Gln Ser Gln Gln Gly Ala Phe Asp Glu Arg Thr Ala Arg Glu Met
    370                 375                 380

Gly Leu Thr Glu Glu Ser Lys Gln Gln Val Arg Ser Leu Leu Met Ser
385                 390                 395                 400

Val Asp Met Gly Pro Ser Ser Ile His Glu Pro Ser Arg Pro Ala Phe
                405                 410                 415

Ile Ser Gln Glu Glu Asn Arg Gln Pro Ala Gln Asn Leu Ser Asp Thr
            420                 425                 430

Gln Gly Gln Thr Lys Pro Val Pro Lys Gln Pro Ala Pro Arg Ala Asp
        435                 440                 445

Ser Asp Asp Ile Asp Pro Tyr Glu Asn Gly Leu Glu Trp
    450                 455                 460


<210> SEQ ID NO 4
<211> LENGTH: 1218
<212> TYPE: DNA
<213> ORGANISM: artificial sequence
<220> FEATURE:
<223> OTHER INFORMATION: APMV8 P gene

<400> SEQUENCE: 4

atggatttcg ccaatgatga agaaattgca gaacttttga atctcagcac caatgtaatc     60

aaggagattc agaaatccga actcaagcct ccccaaacca ccggacgacc acctgtcagt    120

caagggaaca caagaaatct aactgatcta tgggaaaagg agactgcaag tcagaccaag    180

acaccggccc aatctacaca aaccacacaa gttcagtctg atgaaaatga ggagggagaa    240

atcaagtccg agtcaactga tggccacatc agaggaactg ttaatcaatc agagcaagtc    300

ccagaacaaa accagagcag atcttcacca ggtgatgatc tcgacagagc tctcaacaag    360

cttgaaggga gaatcaattt aatcagctca atggacaaag aaattaaaaa gggccctcgc    420

atccagaatc tccctgggtc ccaggcggca actcaacagg cgacccaccc attggcaggg    480

gacaccccga acatgcaagc acagacaaaa gccctggcga agccacatca agaggcaatc    540

aatcctggca accaggacac aggagagagt attcatttac caccttccat ggcaccacca    600

gagtcattag ttggtgcaat ccgcaatgca ccccaattcg tgccagacca atctatgacg    660

aatgtagatg cggggagtgt ccaactacat gcatcatgtg cagagatgat aagtagaatg    720

tttgtagaag ttatatccaa gcttgataaa ctcgagtcga gactgaatga tatagcaaaa    780

gttgtgaaca ctaccccccct tattaggaat gatattaacc aacttaaggc cacaaccgca    840

ctgatgtcta accaaattgc ctccatacaa attcttgacc cagggaatgc aggggtgagg    900

tccctctctg aaatgaaatc tgtgacgaag aaagctgctg ttgtaattgc agggtttgga    960

gacgacccaa ctcaaattat tgaagaaggc attatggcca aagatgctct tggaaaacct   1020

gtgcctccaa catctgttat ctcagccaaa gctcagactt cttccggtgt gagtaagggt   1080

gaaatagaag gattgattgc attggtggaa acattagttg acaatgacaa gaaggcagca   1140

aaactgatta aaatgattga tcaagttaaa tcccatgccg attacgcccg agtcaagcag   1200

gcaatatata atgcgtaa                                                 1218


<210> SEQ ID NO 5
<211> LENGTH: 405
<212> TYPE: PRT
<213> ORGANISM: artificial sequence
<220> FEATURE:
<223> OTHER INFORMATION: APMV8 P protein

<400> SEQUENCE: 5
```

-continued

```
Met Asp Phe Ala Asn Asp Glu Glu Ile Ala Glu Leu Leu Asn Leu Ser
1               5                   10                  15

Thr Asn Val Ile Lys Glu Ile Gln Lys Ser Glu Leu Lys Pro Pro Gln
            20                  25                  30

Thr Thr Gly Arg Pro Pro Val Ser Gln Gly Asn Thr Arg Asn Leu Thr
        35                  40                  45

Asp Leu Trp Glu Lys Glu Thr Ala Ser Gln Thr Lys Thr Pro Ala Gln
    50                  55                  60

Ser Thr Gln Thr Thr Gln Val Gln Ser Asp Glu Asn Glu Glu Gly Glu
65                  70                  75                  80

Ile Lys Ser Glu Ser Thr Asp Gly His Ile Arg Gly Thr Val Asn Gln
                85                  90                  95

Ser Glu Gln Val Pro Glu Gln Asn Gln Ser Arg Ser Ser Pro Gly Asp
            100                 105                 110

Asp Leu Asp Arg Ala Leu Asn Lys Leu Glu Gly Arg Ile Asn Leu Ile
        115                 120                 125

Ser Ser Met Asp Lys Glu Ile Lys Lys Gly Pro Arg Ile Gln Asn Leu
    130                 135                 140

Pro Gly Ser Gln Ala Ala Thr Gln Gln Ala Thr His Pro Leu Ala Gly
145                 150                 155                 160

Asp Thr Pro Asn Met Gln Ala Gln Thr Lys Ala Leu Ala Lys Pro His
                165                 170                 175

Gln Glu Ala Ile Asn Pro Gly Asn Gln Asp Thr Gly Glu Ser Ile His
            180                 185                 190

Leu Pro Pro Ser Met Ala Pro Pro Glu Ser Leu Val Gly Ala Ile Arg
        195                 200                 205

Asn Ala Pro Gln Phe Val Pro Asp Gln Ser Met Thr Asn Val Asp Ala
    210                 215                 220

Gly Ser Val Gln Leu His Ala Ser Cys Ala Glu Met Ile Ser Arg Met
225                 230                 235                 240

Phe Val Glu Val Ile Ser Lys Leu Asp Lys Leu Glu Ser Arg Leu Asn
                245                 250                 255

Asp Ile Ala Lys Val Val Asn Thr Thr Pro Leu Ile Arg Asn Asp Ile
            260                 265                 270

Asn Gln Leu Lys Ala Thr Thr Ala Leu Met Ser Asn Gln Ile Ala Ser
        275                 280                 285

Ile Gln Ile Leu Asp Pro Gly Asn Ala Gly Val Arg Ser Leu Ser Glu
    290                 295                 300

Met Lys Ser Val Thr Lys Lys Ala Ala Val Val Ile Ala Gly Phe Gly
305                 310                 315                 320

Asp Asp Pro Thr Gln Ile Ile Glu Glu Gly Ile Met Ala Lys Asp Ala
                325                 330                 335

Leu Gly Lys Pro Val Pro Pro Thr Ser Val Ile Ser Ala Lys Ala Gln
            340                 345                 350

Thr Ser Ser Gly Val Ser Lys Gly Glu Ile Glu Gly Leu Ile Ala Leu
        355                 360                 365

Val Glu Thr Leu Val Asp Asn Asp Lys Lys Ala Ala Lys Leu Ile Lys
    370                 375                 380

Met Ile Asp Gln Val Lys Ser His Ala Asp Tyr Ala Arg Val Lys Gln
385                 390                 395                 400

Ala Ile Tyr Asn Ala
                405
```

<210> SEQ ID NO 6

<211> LENGTH: 1110
<212> TYPE: DNA
<213> ORGANISM: artificial sequence
<220> FEATURE:
<223> OTHER INFORMATION: APMV8 M gene

<400> SEQUENCE: 6

```
atggcatata caacattgaa actgtgggtg gatgagggtg acatgtcgtc ttcgctccta      60

tcattcccgt tggtactaaa agagacagac agaggcacaa aggagcttca accacaggta     120

agggtagatt caattggcga tgtgcagaac gccaaagagt cctcgatatt cgtgactcta     180

tatggtttca tccaagcaat taaggagagt tcagatcgat cgaaattctt ccatccaaaa     240

gatgacttca aacctgagac agtcactgca ggactggtag tggtaggtgc gatccgaatg     300

atggctgatg ttaataccat ctctaatgac gcactagcgc tggagatcac tgttaagaaa     360

tctgcaactt ctcaagagaa aatgacggtg atgttccaca atagcccccc ttcattgaga     420

actgcaataa ctatccgagc aggaggtttc atctcgaatg cagacgagaa tataaaatgt     480

gccagcaaat tgactgcagg agtgcagtac atattccgcc caatgtttgt ttcaatcact     540

aaattacaca atggcaaact atatagggtg cccaaaagca tccacagcat ctcatccact     600

ctactgtata gtgtgatgtt ggaggtagga ttcaaagtgg atattgggaa ggatcatccc     660

caggcaaaga tgctgaagaa ggtcacaatc ggcgatgcag acacatactg ggggtttgca     720

tggttccacc tgtgcaattt caaaaagaca tcctctaagg gaaagccaag aacgctagac     780

gaactaaaga caaaagtcaa aaatatgggg ttgaaattgg agttacatga cctgtggggt     840

ccgactattg tggtccaaat cactggcaag agcagcaaat atgctcaagg attttttcc      900

tccaatggta cttgttgtct cccaatcagc agatctgcac cagagcttgg gaagcttctg     960

tggtcttgtt cagcaactat aggtgacgca acagttgtta tccaatcaag cgagaaaggg    1020

gaactcctaa ggtctgatga cctcgagata cgaggtgctg tggcctccaa gaaaggtaga    1080

ctgggctcat ttcacccctt caaaaaatga                                     1110
```

<210> SEQ ID NO 7
<211> LENGTH: 369
<212> TYPE: PRT
<213> ORGANISM: artificial sequence
<220> FEATURE:
<223> OTHER INFORMATION: APMV8 M protein

<400> SEQUENCE: 7

```
Met Ala Tyr Thr Thr Leu Lys Leu Trp Val Asp Glu Gly Asp Met Ser
1               5                   10                  15

Ser Ser Leu Leu Ser Phe Pro Leu Val Leu Lys Glu Thr Asp Arg Gly
            20                  25                  30

Thr Lys Glu Leu Gln Pro Gln Val Arg Val Asp Ser Ile Gly Asp Val
        35                  40                  45

Gln Asn Ala Lys Glu Ser Ser Ile Phe Val Thr Leu Tyr Gly Phe Ile
    50                  55                  60

Gln Ala Ile Lys Glu Ser Ser Asp Arg Ser Lys Phe Phe His Pro Lys
65                  70                  75                  80

Asp Asp Phe Lys Pro Glu Thr Val Thr Ala Gly Leu Val Val Val Gly
                85                  90                  95

Ala Ile Arg Met Met Ala Asp Val Asn Thr Ile Ser Asn Asp Ala Leu
            100                 105                 110

Ala Leu Glu Ile Thr Val Lys Lys Ser Ala Thr Ser Gln Glu Lys Met
        115                 120                 125
```

-continued

```
Thr Val Met Phe His Asn Ser Pro Pro Ser Leu Arg Thr Ala Ile Thr
    130                 135                 140

Ile Arg Ala Gly Gly Phe Ile Ser Asn Ala Asp Glu Asn Ile Lys Cys
145                 150                 155                 160

Ala Ser Lys Leu Thr Ala Gly Val Gln Tyr Ile Phe Arg Pro Met Phe
                165                 170                 175

Val Ser Ile Thr Lys Leu His Asn Gly Lys Leu Tyr Arg Val Pro Lys
            180                 185                 190

Ser Ile His Ser Ile Ser Ser Thr Leu Leu Tyr Ser Val Met Leu Glu
        195                 200                 205

Val Gly Phe Lys Val Asp Ile Gly Lys Asp His Pro Gln Ala Lys Met
    210                 215                 220

Leu Lys Lys Val Thr Ile Gly Asp Ala Asp Thr Tyr Trp Gly Phe Ala
225                 230                 235                 240

Trp Phe His Leu Cys Asn Phe Lys Lys Thr Ser Ser Lys Gly Lys Pro
                245                 250                 255

Arg Thr Leu Asp Glu Leu Lys Thr Lys Val Lys Asn Met Gly Leu Lys
            260                 265                 270

Leu Glu Leu His Asp Leu Trp Gly Pro Thr Ile Val Val Gln Ile Thr
        275                 280                 285

Gly Lys Ser Ser Lys Tyr Ala Gln Gly Phe Phe Ser Ser Asn Gly Thr
    290                 295                 300

Cys Cys Leu Pro Ile Ser Arg Ser Ala Pro Glu Leu Gly Lys Leu Leu
305                 310                 315                 320

Trp Ser Cys Ser Ala Thr Ile Gly Asp Ala Thr Val Val Ile Gln Ser
                325                 330                 335

Ser Glu Lys Gly Glu Leu Leu Arg Ser Asp Asp Leu Glu Ile Arg Gly
            340                 345                 350

Ala Val Ala Ser Lys Lys Gly Arg Leu Gly Ser Phe His Pro Phe Lys
        355                 360                 365

Lys
```

<210> SEQ ID NO 8
<211> LENGTH: 1632
<212> TYPE: DNA
<213> ORGANISM: artificial sequence
<220> FEATURE:
<223> OTHER INFORMATION: APMV8 F gene

<400> SEQUENCE: 8

```
atgggtcaaa tatcagtata tctaattaat agcgtgctat tattgctggt atatcctgtg     60

aattcgattg acaatacact cattgcccca atcggagttg ccagcgcaaa tgaatggcag    120

cttgctgcat atacaacatc actttcaggg acaattgccg tgcgattcct acctgtgctc    180

ccggataata tgactacctg tcttaaagaa acaatcacta catacaataa tactgtcaac    240

aacatcttag gcccactcaa atccaatctg gatgcactgc tctcatctga gacttatccc    300

cagacaagat taattggggc agttataggt tcaattgctc tcggtgttgc aacatcggct    360

caaatcactg ctgcagttgc tctcaagcaa gcgcaagaca atgcaaggaa catactagca    420

ctcaaagaag cactgtccaa aaccaatgag gcggtcaagg agcttagtag tgggttacaa    480

caaacagcta ttgcacttgg taagatacag agttttgtga atgaggaaat tctgccatct    540

atcaaccaac tgagctgcga ggtgacagcc aataaacttg ggtgtatttt atctctgtat    600

ctcacagaac tgaccaccat attcggtgca cagctgacca accctgcatt gacttcatta    660

tcatatcaag cactgtacaa cctgtgtggt ggcaacatgg caatgcttac tcagaagatt    720
```

```
ggaattaaac agcaagacgt taattcgcta tatgaagccg gactaatcac aggacaagtc    780
attggttatg actctcatta ccagctgctg gtcatccagg tcaattatcc aagcatttct    840
gaggtcactg gtgtacgtgc gacagaatta gtcactgtta gtgtaacaac agacaagggt    900
gaagggaaag caattgtacc ccaatttgta gctgaaagtc gggtgactat tgaagagctt    960
gatgtcgcat cttgtaaatt cagcagcacg accctatatt gcaggcaggt caacacaagg   1020
gcacttcccc cgctagtagc tagctgtctt cgaggtaact atgatgattg tcaatatacc   1080
acagagattg gagcattatc atcccggtat ataacactag atgggggggt cttagttaat   1140
tgcaagtcaa ttgtttgtag gtgccttaat ccaagtaaga tcatctctca aaatacaaac   1200
gctgcagtaa catatgttga tgccacaatc tgcaaaacaa ttcaattgga tgatatacaa   1260
ctccagctgg aagggtcact atcatcagtt tatgcaagaa acatctcaat tgagatcagt   1320
caggtgacca catccgggtc tttagatatc agcagtgaga taggaaacat caataatacg   1380
gtgaatcgtg tggaggattt aattcaccaa tcagaggaat ggctggcaaa ggttaaccca   1440
cacattgtta ataatacaac actaattgta ctctgtgtgt taagtgcgct tgctgtgatc   1500
tggctggcag tattaacggc tattataata tacttgagaa caaagttgaa gactatatcg   1560
gcattagctg taaccaatac aatacagtct aacccctatg ttaaccaaac gaaacatgaa   1620
tctaagtttt ga                                                       1632
```

<210> SEQ ID NO 9
<211> LENGTH: 543
<212> TYPE: PRT
<213> ORGANISM: artificial sequence
<220> FEATURE:
<223> OTHER INFORMATION: APMV8 F protein

<400> SEQUENCE: 9

```
Met Gly Gln Ile Ser Val Tyr Leu Ile Asn Ser Val Leu Leu Leu Leu
1               5                   10                  15

Val Tyr Pro Val Asn Ser Ile Asp Asn Thr Leu Ile Ala Pro Ile Gly
            20                  25                  30

Val Ala Ser Ala Asn Glu Trp Gln Leu Ala Ala Tyr Thr Thr Ser Leu
        35                  40                  45

Ser Gly Thr Ile Ala Val Arg Phe Leu Pro Val Leu Pro Asp Asn Met
    50                  55                  60

Thr Thr Cys Leu Lys Glu Thr Ile Thr Thr Tyr Asn Asn Thr Val Asn
65                  70                  75                  80

Asn Ile Leu Gly Pro Leu Lys Ser Asn Leu Asp Ala Leu Leu Ser Ser
                85                  90                  95

Glu Thr Tyr Pro Gln Thr Arg Leu Ile Gly Ala Val Ile Gly Ser Ile
            100                 105                 110

Ala Leu Gly Val Ala Thr Ser Ala Gln Ile Thr Ala Ala Val Ala Leu
        115                 120                 125

Lys Gln Ala Gln Asp Asn Ala Arg Asn Ile Leu Ala Leu Lys Glu Ala
    130                 135                 140

Leu Ser Lys Thr Asn Glu Ala Val Lys Glu Leu Ser Ser Gly Leu Gln
145                 150                 155                 160

Gln Thr Ala Ile Ala Leu Gly Lys Ile Gln Ser Phe Val Asn Glu Glu
                165                 170                 175

Ile Leu Pro Ser Ile Asn Gln Leu Ser Cys Glu Val Thr Ala Asn Lys
            180                 185                 190

Leu Gly Val Tyr Leu Ser Leu Tyr Leu Thr Glu Leu Thr Thr Ile Phe
```

-continued

```
        195                 200                 205

Gly Ala Gln Leu Thr Asn Pro Ala Leu Thr Ser Leu Ser Tyr Gln Ala
    210                 215                 220

Leu Tyr Asn Leu Cys Gly Gly Asn Met Ala Met Leu Thr Gln Lys Ile
225                 230                 235                 240

Gly Ile Lys Gln Gln Asp Val Asn Ser Leu Tyr Glu Ala Gly Leu Ile
                245                 250                 255

Thr Gly Gln Val Ile Gly Tyr Asp Ser His Tyr Gln Leu Leu Val Ile
            260                 265                 270

Gln Val Asn Tyr Pro Ser Ile Ser Glu Val Thr Gly Val Arg Ala Thr
        275                 280                 285

Glu Leu Val Thr Val Ser Val Thr Thr Asp Lys Gly Glu Gly Lys Ala
    290                 295                 300

Ile Val Pro Gln Phe Val Ala Glu Ser Arg Val Thr Ile Glu Glu Leu
305                 310                 315                 320

Asp Val Ala Ser Cys Lys Phe Ser Ser Thr Thr Leu Tyr Cys Arg Gln
                325                 330                 335

Val Asn Thr Arg Ala Leu Pro Pro Leu Val Ala Ser Cys Leu Arg Gly
            340                 345                 350

Asn Tyr Asp Asp Cys Gln Tyr Thr Thr Glu Ile Gly Ala Leu Ser Ser
        355                 360                 365

Arg Tyr Ile Thr Leu Asp Gly Gly Val Leu Val Asn Cys Lys Ser Ile
    370                 375                 380

Val Cys Arg Cys Leu Asn Pro Ser Lys Ile Ile Ser Gln Asn Thr Asn
385                 390                 395                 400

Ala Ala Val Thr Tyr Val Asp Ala Thr Ile Cys Lys Thr Ile Gln Leu
                405                 410                 415

Asp Asp Ile Gln Leu Gln Leu Glu Gly Ser Leu Ser Ser Val Tyr Ala
            420                 425                 430

Arg Asn Ile Ser Ile Glu Ile Ser Gln Val Thr Thr Ser Gly Ser Leu
        435                 440                 445

Asp Ile Ser Ser Glu Ile Gly Asn Ile Asn Asn Thr Val Asn Arg Val
    450                 455                 460

Glu Asp Leu Ile His Gln Ser Glu Glu Trp Leu Ala Lys Val Asn Pro
465                 470                 475                 480

His Ile Val Asn Asn Thr Thr Leu Ile Val Leu Cys Val Leu Ser Ala
                485                 490                 495

Leu Ala Val Ile Trp Leu Ala Val Leu Thr Ala Ile Ile Ile Tyr Leu
            500                 505                 510

Arg Thr Lys Leu Lys Thr Ile Ser Ala Leu Ala Val Thr Asn Thr Ile
        515                 520                 525

Gln Ser Asn Pro Tyr Val Asn Gln Thr Lys His Glu Ser Lys Phe
    530                 535                 540
```

<210> SEQ ID NO 10
<211> LENGTH: 1734
<212> TYPE: DNA
<213> ORGANISM: artificial sequence
<220> FEATURE:
<223> OTHER INFORMATION: APMV8 HN gene

<400> SEQUENCE: 10

```
atgagtaaca ttgcatccag tttagaaaac attgtagagc aggatagtcg aaaaacaact      60

tggagggcca tctttagatg gtccgttctt cttattacaa caggatgctt agccttatcc     120

attgttagca tagttcaaat tggaaatttg aaaattcctt ctgtagggga tctggctgat     180
```

-continued

```
gaagtggtga cacccttgaa aaccactctg tcagatacac tcaggaatcc aattaaccag    240

ataaatgata tatttaggat tgttgccctt gatattccat tgcaagtgac cagtatccaa    300

aaagaccttg caagtcaatt taacatgttg atagatagtt taaatgctat caaattaggc    360

aacgggacca accttatcat acctacatca gacaaggagt atgcaggagg aattggaaac    420

cctgtattta ctgtcgatgc tggaggttct ataggattca aacagtttag cttaatagaa    480

catccgagct ttattgctgg acctacaacg acccgaggct gtacaagaat acccactttt    540

cacatgtcag aaagtcattg gtgctactca cacaacatca tcgctgctgg ctgtcaagat    600

gccagtgcat ccagtatgta tatctcaatg ggagttctcc atgtgtcctc atctggcact    660

cccatttttc ttactactgc aagtgagctg atagacgatg gagttaaccg taagtcatgc    720

agcattgtag caacccaatt tggctgtgac attttgtgca gtattgtcac agagaaggag    780

ggagatgatt actggtctga tactccgact ccaatgcgcc acggccgttt ttcattcaat    840

ggtagttttg tagaagccga actaccagtg tccagtatgt tctcatcatt ctctgccaac    900

taccctgctg tgggatcagg cgaaattgta aaagatagaa tattattccc aatttacgga    960

ggtataaagc agacttcacc agagtttacc gaattagtga aatacggact ctttgtatca   1020

acacctacaa ctgtgtgcca gagtagctgg acttatgacc aggtaaaagc tgcgtatagg   1080

ccagattaca tatcaggccg gttctgggca caagtgatac tcagctgcgc tcttgatgca   1140

gtcgacttat caagttgtat tgtaaagatt atgaatagca gcacagtgat gatggcagcg   1200

gaaggaagga taatgaagat agggattgat tacttttact atcagcggtc atcttcttgg   1260

tggccattgg catttgtcac aaaactagac ccgcaagagt tggcagacac aaactcaata   1320

tggctgacca attccatacc aatcccgcaa tcaaagttcc ctcggccttc atattcagaa   1380

aattattgca caaagccagc agtttgccct gctacttgtg tcactggtgt gtactctgat   1440

atttggcccc tgacctcatc ttcatcactc ccgagcataa tttggatcgg ccagtacctt   1500

gatgctcctg ttggaaggac ttatcctaga tttggaattg caaatcagtc acactggtac   1560

ctccaagaag atattctacc cacttccacc gcaagtgcgt attcaaccac tacatgtttt   1620

aagaatactg ccaggaatag agtgttctgc gtcaccattg ccgaatttgc agatgggttg   1680

tttggagagt acaggataac acctcagttg tacgaattag tgagaaataa ttga         1734
```

<210> SEQ ID NO 11
<211> LENGTH: 577
<212> TYPE: PRT
<213> ORGANISM: artificial sequence
<220> FEATURE:
<223> OTHER INFORMATION: APMV8 HN protein

<400> SEQUENCE: 11

```
Met Ser Asn Ile Ala Ser Ser Leu Glu Asn Ile Val Glu Gln Asp Ser
1               5                   10                  15

Arg Lys Thr Thr Trp Arg Ala Ile Phe Arg Trp Ser Val Leu Leu Ile
            20                  25                  30

Thr Thr Gly Cys Leu Ala Leu Ser Ile Val Ser Ile Val Gln Ile Gly
        35                  40                  45

Asn Leu Lys Ile Pro Ser Val Gly Asp Leu Ala Asp Glu Val Val Thr
    50                  55                  60

Pro Leu Lys Thr Thr Leu Ser Asp Thr Leu Arg Asn Pro Ile Asn Gln
65                  70                  75                  80

Ile Asn Asp Ile Phe Arg Ile Val Ala Leu Asp Ile Pro Leu Gln Val
                85                  90                  95
```

-continued

```
Thr Ser Ile Gln Lys Asp Leu Ala Ser Gln Phe Asn Met Leu Ile Asp
            100                 105                 110

Ser Leu Asn Ala Ile Lys Leu Gly Asn Gly Thr Asn Leu Ile Ile Pro
        115                 120                 125

Thr Ser Asp Lys Glu Tyr Ala Gly Gly Ile Gly Asn Pro Val Phe Thr
    130                 135                 140

Val Asp Ala Gly Gly Ser Ile Gly Phe Lys Gln Phe Ser Leu Ile Glu
145                 150                 155                 160

His Pro Ser Phe Ile Ala Gly Pro Thr Thr Thr Arg Gly Cys Thr Arg
                165                 170                 175

Ile Pro Thr Phe His Met Ser Glu Ser His Trp Cys Tyr Ser His Asn
            180                 185                 190

Ile Ile Ala Ala Gly Cys Gln Asp Ala Ser Ala Ser Ser Met Tyr Ile
        195                 200                 205

Ser Met Gly Val Leu His Val Ser Ser Ser Gly Thr Pro Ile Phe Leu
    210                 215                 220

Thr Thr Ala Ser Glu Leu Ile Asp Asp Gly Val Asn Arg Lys Ser Cys
225                 230                 235                 240

Ser Ile Val Ala Thr Gln Phe Gly Cys Asp Ile Leu Cys Ser Ile Val
                245                 250                 255

Thr Glu Lys Glu Gly Asp Asp Tyr Trp Ser Asp Thr Pro Thr Pro Met
            260                 265                 270

Arg His Gly Arg Phe Ser Phe Asn Gly Ser Phe Val Glu Ala Glu Leu
        275                 280                 285

Pro Val Ser Ser Met Phe Ser Ser Phe Ser Ala Asn Tyr Pro Ala Val
    290                 295                 300

Gly Ser Gly Glu Ile Val Lys Asp Arg Ile Leu Phe Pro Ile Tyr Gly
305                 310                 315                 320

Gly Ile Lys Gln Thr Ser Pro Glu Phe Thr Glu Leu Val Lys Tyr Gly
                325                 330                 335

Leu Phe Val Ser Thr Pro Thr Thr Val Cys Gln Ser Ser Trp Thr Tyr
            340                 345                 350

Asp Gln Val Lys Ala Ala Tyr Arg Pro Asp Tyr Ile Ser Gly Arg Phe
        355                 360                 365

Trp Ala Gln Val Ile Leu Ser Cys Ala Leu Asp Ala Val Asp Leu Ser
    370                 375                 380

Ser Cys Ile Val Lys Ile Met Asn Ser Ser Thr Val Met Met Ala Ala
385                 390                 395                 400

Glu Gly Arg Ile Met Lys Ile Gly Ile Asp Tyr Phe Tyr Tyr Gln Arg
                405                 410                 415

Ser Ser Ser Trp Trp Pro Leu Ala Phe Val Thr Lys Leu Asp Pro Gln
            420                 425                 430

Glu Leu Ala Asp Thr Asn Ser Ile Trp Leu Thr Asn Ser Ile Pro Ile
        435                 440                 445

Pro Gln Ser Lys Phe Pro Arg Pro Ser Tyr Ser Glu Asn Tyr Cys Thr
    450                 455                 460

Lys Pro Ala Val Cys Pro Ala Thr Cys Val Thr Gly Val Tyr Ser Asp
465                 470                 475                 480

Ile Trp Pro Leu Thr Ser Ser Ser Ser Leu Pro Ser Ile Ile Trp Ile
                485                 490                 495

Gly Gln Tyr Leu Asp Ala Pro Val Gly Arg Thr Tyr Pro Arg Phe Gly
            500                 505                 510

Ile Ala Asn Gln Ser His Trp Tyr Leu Gln Glu Asp Ile Leu Pro Thr
```

-continued

```
       515                 520                 525

Ser Thr Ala Ser Ala Tyr Ser Thr Thr Thr Cys Phe Lys Asn Thr Ala
    530                 535                 540

Arg Asn Arg Val Phe Cys Val Thr Ile Ala Glu Phe Ala Asp Gly Leu
545                 550                 555                 560

Phe Gly Glu Tyr Arg Ile Thr Pro Gln Leu Tyr Glu Leu Val Arg Asn
                565                 570                 575

Asn


<210> SEQ ID NO 12
<211> LENGTH: 6741
<212> TYPE: DNA
<213> ORGANISM: artificial sequence
<220> FEATURE:
<223> OTHER INFORMATION: APMV8 L gene

<400> SEQUENCE: 12

atggagggcg acctctacac aaacatggat ataaaacaag ttgacctgat aatacaaccc     60

gaggttcatc tcgattcacc catcatattg aataaactgg cactattatg gcgcttgagt    120

ggtttaccca tgcctgcaga cctacgacaa aaatccgtag tgatgcacat cccggaccac    180

atcttagaaa aatcagaata tcggatcaag caccgtctag ggaaaatcaa gagtgacata    240

acacattact gtcagtattt taatattaat ttggcaaata ttgatccgat aacccacccc    300

aaaagtttgt attggttatc cagactaaca atagctagtg ctggaacttt taggcatatg    360

aaagatagaa tcttgtgtac agttggctct gaatttggac acaaaattca agatttattt    420

tcactgctga gccataaact agtaggtaac ggggatttat ttaatcaaag tctctcaggt    480

acacgtttga ctgcaagtcc gttatcccct ttatgcaatc aatttgtctc tgacatcaag    540

tctgcagtca cgacaccctg gtcagaagct cgttggtctt ggcttcatat caaacaaaca    600

atgagatatc tgataaaaca atcacgcact acaaattcgg ctcatttaac agaaatcata    660

aaagaagaat ggggtttagt aggtattact ccagatcttg tcattctttt tgacagagtc    720

aataatagtc tgactgcatt aacatttgag atggttctaa tgtattcaga tgtattagaa    780

tcccgtgaca atattgtgtt agtggggcga ctatctacct ttctacagcc agtagttagt    840

agactggagg tgttgtttga tctagtagat tcattggcaa aaatcttagg tgacacaata    900

tatgagatta ttgcagtgtt agagagcttg tcttatgggt cagttcaact acatgatgca    960

agtcactctc atgcagggtc tttttttca tttaacatga atgaacttga taacacacta   1020

tcaaagaggg tagatccgaa acacaagaac actataatga gcattataag acaatgcttt   1080

tctaatctag atgttgatca agctgcagag atgctatgcc tgatgagatt attcggacac   1140

ccaatgttaa ctgcaccgga tgcagcagcc aaagtgagga aagcaatgtg tgctccaaaa   1200

cttgttgaac acgacaccat cttgcagaca ttatctttct tcaaggggat aattataaat   1260

gggtacagaa gatcacactc tggcctgtgg cccaatgtag agccgtcttc aatttatgat   1320

gatgatctca gacagctgta cttagagtca gcagagattt cccatcattt tatgcttaaa   1380

aactacaaga gtttaagcat gatagaattc aagaagagca tagactacga tcttcatgat   1440

gacctaagta ctttcttaaa ggatagagca atttgccggc cgaaatccca gtgggatgtc   1500

atatttcgta agtctttacg cagatctcat acgcagtccc agtatctgga cgaaattaag   1560

agcaaccgat tgctaattga ttttcttgat tctgctgaat ttgaccctgg aaaagaattt   1620

gcatatgtaa ccacaatgga ttatttgcac gataatgaat tttgtgcttc atattctcta   1680

aaggaaaagg agatcaaaac tactgggagg atatttgcaa aaatgacacg caatatgaga   1740
```

agttgccaag taatacttga atctttgtta tcaaagcata tatgcaagtt cttcaaagag 1800
aatggcgttt cgatggagca attgtcattg accaagagtc tacttgcaat gtctcaactc 1860
tcaccaaaag tctcgacttt gcaggacact gcatcacgtc atgtaggtaa ctcaaaatct 1920
cagattgcaa ccagcaaccc atctcggcat cactcgacac ccaatcagat gtcactctca 1980
aatcgaaaaa cggttgtagc aactttctta acaactgact tggaaaaata ctgcctgcag 2040
tggcgatatt caactattaa attgtttgca caagctctaa atcaactctt tgggattgat 2100
cacggatttg aatggataca tttaagactt atgaacagca ccttatttgt tggcgatcct 2160
tactcgcctc ctgaagatcc aacactagaa gatatagata aagcaccaaa tgatgatatc 2220
ttcatagttt ctccaagggg aggcatagag ggtttatgtc agaaaatgtg gaccatgata 2280
tcaattagtg ctatacactg tgtagcagag aaaattggtg cacgagtggc agcaatggtg 2340
cagggtgata atcaagtaat agctatcacc aaagaattat tcagaggaga gaaagcttgt 2400
gatgtcagag atgagttaga cgagcttggt caagtgtttt ttgatgagtt caagagacac 2460
aattatgcaa ttggacacaa tcttaagcta aatgagacaa tacaaagcca atcctttttt 2520
gtatattcca aacgaatatt ctttgaaggg cgattgctta gtcaagtcct caaaaatgct 2580
gccaagttat gtatggttgc tgaccatcta ggtgaaaaca ctgtatcttc ctgtagcaac 2640
ctgagctcga caattgcccg cttagtggaa aatgggtttg agaaggacac tgcttttgtg 2700
ttgaacctag tctacatcat gactcagatt ctttttgatg agcattactc gattgtatgc 2760
gatcaccata gtgtcaaaag cttgattgga tcaaaaaacc atcggaattt attgtattca 2820
tctctaatac caggtcagct cggcggtttc aacttcctca atataagtcg gttgttcact 2880
aggaatatag gtgacccagt aacatgtagt ctgtctgatc tcaaatgctt catagccgca 2940
ggtctccttc caccctatgt cctaaaaaat gtggttctgc gtgagcctgg tcctgggaca 3000
tggttgacgt tgtgctctga tccttacacc cttaacatac catacacaca gcttccaacc 3060
acatatctca aaaagcacac ccagcgatca ttgctttcac gtgcagtaaa tcctttatta 3120
gccggtgtac aagtgccaaa tcagcatgag gaagaagaga tgttggctcg ctttctcctt 3180
gatcgtgaat atgtgatgcc ccgcgttgct catgtaatac tagaatcatc agtccttggc 3240
aaacggaaac aaatccaagg cttaattgat acaactccaa ccatcattag aacatctcta 3300
gttaatctgc cagtgtctag aaagaaatgc gaaaaaataa tcaattactc tctcaattat 3360
attgctgagt gtcatgactc cttacttagc caggtctgct tcagtgataa taaggaatac 3420
ttgtggtcaa cctccttaat atcagttgag acctgtagtg tgacaattgc ggactatctg 3480
agagctgtca gctggtctaa tatattaggg ggaagaaaca tatccggggt gactacacct 3540
gatactattg aattaattca aggttgttta ataggtgaaa attctagttg tactctttgt 3600
gaatcgcatg atgacgcatt cacgtggatg cacttgcctg gcccacttta catccctgaa 3660
ccatcagtta ctaactctaa aatgcgtgtg ccatatctgg gttcaaaaac agaggagcgg 3720
aaaacagcct caatggcagc aataaaagga atgtcacatc acctgcgtgc agtcttaaga 3780
ggcacatccg tatttatttg ggcatttggg gatacagata tcaattggga taatgcattg 3840
cagattgccc aatcacggtg taacatcaca ttggatcaaa tgagattact tacaccaatt 3900
cctagcagtt caaatattca acatagactc gatgacggaa tcagcacgca gaaatttact 3960
cctgcaagcc ttgctcgaat cacatccttc gttcacatct gtaatgacag ccagaggtta 4020
gagaaggatg gctcatctgt cgactcaaac ttgatttacc agcaaattat gttacttgga 4080
ctcagcatct ttgaaacaat gtactcaatg gaccaaaagt gggtattcaa taaccatacc 4140

-continued

```
ttgcatttgc acactggaca ctcctgttgt ccaagggaac tagacataag tttggtgaac   4200
ccgccgagac atcagacccc ggagctgact agcacaacaa ccaacccgtt cctatatgat   4260
cagctcccat taaatcaaga aaacttgaca acacttgaga ttaagacatt taaattcaat   4320
gagctcaaca ttgatggttt agattttggt gaaggaatac aattattgag tcgttgtact   4380
gcaagattaa tggcagaatg tattctagag gagggaatag gctcgtcagt taaaaatgaa   4440
gcaattgtca attttgataa ttcagtcaat tggatttcag agtgcctaat gtgtgatatt   4500
cgctcacttt gtgttaattt aggtcaagag atactatgta gcctggcata ccaaatgtat   4560
tacttgcgaa tcaggggtag acgggccatt cttaattact tggacacaac tttgcaaagg   4620
atccctgtga tacaattagc caacattgca ctcaccattt cgcaccctga gatatttcgc   4680
agaattgtca acaccgggat ccataaccag attaagggcc catatgtggc aacaacggat   4740
ttcatagctg caagtagaga tatcatatta tcaggtgcaa gggagtatct atcttattta   4800
agcagtgggc aggaagactg ttacacattc ttcaactgtc aagatgggga tcttactcca   4860
aaaatggaac agtatcttgc aaggagggca tgccttttaa cattattgta taatactggg   4920
caccagatcc ccgttatccg atcactgacg ccaatagaga agtgcaaggt gctcacagaa   4980
tacaatcaac aaattgagta cgcagatcaa gagtttagct ctgtactaaa agtggtcaat   5040
gcactactac aaaatcctaa gatagatgca ttagtttcaa atctctactt caccaccaga   5100
cgtgttctat caaacctcag atcatgtgat aaggctagat catatattga atatttgtac   5160
actgaggact tcggagagaa agaggataca gtacaatatg acatcatgac aacaaacgat   5220
atcatactta ctcatggtct attcacacag atcgaaatat cttatcaagg gaatagtctc   5280
cataagttcc ttactccgga taacgcgcct ggatctttga tcccattctc tatttcacca   5340
aattcacttg catgtgaccc tcttcatcac ttgctcaagt cggtcggtac atcaagcaca   5400
agttggtaca agtatgcaat cgcctatgca gtgtctgaaa agaggtcagc tcgattagga   5460
gggagcttgt acattggtga agggagcgga agtgtgatga ctttactcga gtatcttgag   5520
ccatctgttg acatatttta caattcactc ttctcaaatg gtatgaaccc accacaacga   5580
aattatgggc ttatgccact acaatttgtg aattcggtgg tttataagaa cttaacggct   5640
aaatcagaat gtaagctagg gtttgtccag caatttaaac cgttgtggag agacatagac   5700
attgagacta atgttacaga tccatcattt atcaattttg cattgaatga aatcccaatg   5760
caatcattaa aacgagtaaa ttgtgatgtg gaatttgacc gtggtatgcc gattgaacgg   5820
gttattcagg gttacaccca tatcttactt gttgccactt acggattaca gcaagattca   5880
atactgtggg tgaaggtata taggacatct gaaaaagtat ttcaattctt actgagtgcc   5940
atgatcatga tctttggtta tgtaaaaatc cacaggaatg gttatatgtc gacaaaggat   6000
gaagagtaca tattgatgtc tgactgcaag gaacctgtaa actatacagc tgtccctaac   6060
attcttacac gtgtaagtga tttagtgtcg aagaatctga gtcttatcca tccagaagac   6120
ctcagaaaag taaggtgtga aacagattcc ctgaatttga agtgcaatca tatttatgag   6180
aaaataattg ccagaaaaat tccattacag gtatcatcaa ctgactcttt gctcctccaa   6240
ttaggcggtg ttatcaactc ggtgggctca actgatccta gagaggttgc aacattatct   6300
tctattgagt gtatggacta tgttgtctca tcaattgatt tggctatatt ggaggcaaat   6360
attgtaatct cagagagtgc tggtcttgac ctcgctttaa tgttaggccc attcaactta   6420
aataagctta agaaaattga cacaatcctt aagtcaagca cctatcagct aatcccgtac   6480
tggttgcgct atgagtactc tattaatccg agatctttgt catttctaat cactaaatta   6540
```

```
caacaatgcc gaatttcatg gtcagatatg atcacgattt ctgaatttcg taagaaatcc   6600

aagcggccta tatttatcaa acgagtaata gggaatcaac agctaaaatc attctttaat   6660

gaaagctcaa gtattgtttt gactcgggct gaagttaaag tctgtataaa gttcctcggt   6720

gcaatcatca agttgaaata a                                              6741


<210> SEQ ID NO 13
<211> LENGTH: 2246
<212> TYPE: PRT
<213> ORGANISM: artificial sequence
<220> FEATURE:
<223> OTHER INFORMATION: APMV8 L protein1

<400> SEQUENCE: 13

Met Glu Gly Asp Leu Tyr Thr Asn Met Asp Ile Lys Gln Val Asp Leu
1               5                   10                  15

Ile Ile Gln Pro Glu Val His Leu Asp Ser Pro Ile Ile Leu Asn Lys
            20                  25                  30

Leu Ala Leu Leu Trp Arg Leu Ser Gly Leu Pro Met Pro Ala Asp Leu
        35                  40                  45

Arg Gln Lys Ser Val Val Met His Ile Pro Asp His Ile Leu Glu Lys
    50                  55                  60

Ser Glu Tyr Arg Ile Lys His Arg Leu Gly Lys Ile Lys Ser Asp Ile
65                  70                  75                  80

Thr His Tyr Cys Gln Tyr Phe Asn Ile Asn Leu Ala Asn Ile Asp Pro
                85                  90                  95

Ile Thr His Pro Lys Ser Leu Tyr Trp Leu Ser Arg Leu Thr Ile Ala
            100                 105                 110

Ser Ala Gly Thr Phe Arg His Met Lys Asp Arg Ile Leu Cys Thr Val
        115                 120                 125

Gly Ser Glu Phe Gly His Lys Ile Gln Asp Leu Phe Ser Leu Leu Ser
    130                 135                 140

His Lys Leu Val Gly Asn Gly Asp Leu Phe Asn Gln Ser Leu Ser Gly
145                 150                 155                 160

Thr Arg Leu Thr Ala Ser Pro Leu Ser Pro Leu Cys Asn Gln Phe Val
                165                 170                 175

Ser Asp Ile Lys Ser Ala Val Thr Thr Pro Trp Ser Glu Ala Arg Trp
            180                 185                 190

Ser Trp Leu His Ile Lys Gln Thr Met Arg Tyr Leu Ile Lys Gln Ser
        195                 200                 205

Arg Thr Thr Asn Ser Ala His Leu Thr Glu Ile Ile Lys Glu Glu Trp
    210                 215                 220

Gly Leu Val Gly Ile Thr Pro Asp Leu Val Ile Leu Phe Asp Arg Val
225                 230                 235                 240

Asn Asn Ser Leu Thr Ala Leu Thr Phe Glu Met Val Leu Met Tyr Ser
                245                 250                 255

Asp Val Leu Glu Ser Arg Asp Asn Ile Val Leu Val Gly Arg Leu Ser
            260                 265                 270

Thr Phe Leu Gln Pro Val Val Ser Arg Leu Glu Val Leu Phe Asp Leu
        275                 280                 285

Val Asp Ser Leu Ala Lys Ile Leu Gly Asp Thr Ile Tyr Glu Ile Ile
    290                 295                 300

Ala Val Leu Glu Ser Leu Ser Tyr Gly Ser Val Gln Leu His Asp Ala
305                 310                 315                 320

Ser His Ser His Ala Gly Ser Phe Phe Ser Phe Asn Met Asn Glu Leu
```

```
                325                 330                 335

Asp Asn Thr Leu Ser Lys Arg Val Asp Pro Lys His Lys Asn Thr Ile
            340                 345                 350

Met Ser Ile Ile Arg Gln Cys Phe Ser Asn Leu Asp Val Asp Gln Ala
        355                 360                 365

Ala Glu Met Leu Cys Leu Met Arg Leu Phe Gly His Pro Met Leu Thr
    370                 375                 380

Ala Pro Asp Ala Ala Ala Lys Val Arg Lys Ala Met Cys Ala Pro Lys
385                 390                 395                 400

Leu Val Glu His Asp Thr Ile Leu Gln Thr Leu Ser Phe Phe Lys Gly
                405                 410                 415

Ile Ile Ile Asn Gly Tyr Arg Arg Ser His Ser Gly Leu Trp Pro Asn
            420                 425                 430

Val Glu Pro Ser Ser Ile Tyr Asp Asp Asp Leu Arg Gln Leu Tyr Leu
        435                 440                 445

Glu Ser Ala Glu Ile Ser His His Phe Met Leu Lys Asn Tyr Lys Ser
    450                 455                 460

Leu Ser Met Ile Glu Phe Lys Lys Ser Ile Asp Tyr Asp Leu His Asp
465                 470                 475                 480

Asp Leu Ser Thr Phe Leu Lys Asp Arg Ala Ile Cys Arg Pro Lys Ser
                485                 490                 495

Gln Trp Asp Val Ile Phe Arg Lys Ser Leu Arg Arg Ser His Thr Gln
            500                 505                 510

Ser Gln Tyr Leu Asp Glu Ile Lys Ser Asn Arg Leu Leu Ile Asp Phe
        515                 520                 525

Leu Asp Ser Ala Glu Phe Asp Pro Gly Lys Glu Phe Ala Tyr Val Thr
    530                 535                 540

Thr Met Asp Tyr Leu His Asp Asn Glu Phe Cys Ala Ser Tyr Ser Leu
545                 550                 555                 560

Lys Glu Lys Glu Ile Lys Thr Thr Gly Arg Ile Phe Ala Lys Met Thr
                565                 570                 575

Arg Asn Met Arg Ser Cys Gln Val Ile Leu Glu Ser Leu Leu Ser Lys
            580                 585                 590

His Ile Cys Lys Phe Phe Lys Glu Asn Gly Val Ser Met Glu Gln Leu
        595                 600                 605

Ser Leu Thr Lys Ser Leu Leu Ala Met Ser Gln Leu Ser Pro Lys Val
    610                 615                 620

Ser Thr Leu Gln Asp Thr Ala Ser Arg His Val Gly Asn Ser Lys Ser
625                 630                 635                 640

Gln Ile Ala Thr Ser Asn Pro Ser Arg His His Ser Thr Pro Asn Gln
                645                 650                 655

Met Ser Leu Ser Asn Arg Lys Thr Val Val Ala Thr Phe Leu Thr Thr
            660                 665                 670

Asp Leu Glu Lys Tyr Cys Leu Gln Trp Arg Tyr Ser Thr Ile Lys Leu
        675                 680                 685

Phe Ala Gln Ala Leu Asn Gln Leu Phe Gly Ile Asp His Gly Phe Glu
    690                 695                 700

Trp Ile His Leu Arg Leu Met Asn Ser Thr Leu Phe Val Gly Asp Pro
705                 710                 715                 720

Tyr Ser Pro Pro Glu Asp Pro Thr Leu Glu Asp Ile Asp Lys Ala Pro
                725                 730                 735

Asn Asp Asp Ile Phe Ile Val Ser Pro Arg Gly Gly Ile Glu Gly Leu
            740                 745                 750
```

```
Cys Gln Lys Met Trp Thr Met Ile Ser Ile Ser Ala Ile His Cys Val
        755                 760                 765

Ala Glu Lys Ile Gly Ala Arg Val Ala Ala Met Val Gln Gly Asp Asn
    770                 775                 780

Gln Val Ile Ala Ile Thr Lys Glu Leu Phe Arg Gly Glu Lys Ala Cys
785                 790                 795                 800

Asp Val Arg Asp Glu Leu Asp Glu Leu Gly Gln Val Phe Phe Asp Glu
                805                 810                 815

Phe Lys Arg His Asn Tyr Ala Ile Gly His Asn Leu Lys Leu Asn Glu
            820                 825                 830

Thr Ile Gln Ser Gln Ser Phe Phe Val Tyr Ser Lys Arg Ile Phe Phe
        835                 840                 845

Glu Gly Arg Leu Leu Ser Gln Val Leu Lys Asn Ala Ala Lys Leu Cys
    850                 855                 860

Met Val Ala Asp His Leu Gly Glu Asn Thr Val Ser Ser Cys Ser Asn
865                 870                 875                 880

Leu Ser Ser Thr Ile Ala Arg Leu Val Glu Asn Gly Phe Glu Lys Asp
                885                 890                 895

Thr Ala Phe Val Leu Asn Leu Val Tyr Ile Met Thr Gln Ile Leu Phe
            900                 905                 910

Asp Glu His Tyr Ser Ile Val Cys Asp His His Ser Val Lys Ser Leu
        915                 920                 925

Ile Gly Ser Lys Asn His Arg Asn Leu Leu Tyr Ser Ser Leu Ile Pro
    930                 935                 940

Gly Gln Leu Gly Gly Phe Asn Phe Leu Asn Ile Ser Arg Leu Phe Thr
945                 950                 955                 960

Arg Asn Ile Gly Asp Pro Val Thr Cys Ser Leu Ser Asp Leu Lys Cys
                965                 970                 975

Phe Ile Ala Ala Gly Leu Leu Pro Pro Tyr Val Leu Lys Asn Val Val
            980                 985                 990

Leu Arg Glu Pro Gly Pro Gly Thr  Trp Leu Thr Leu Cys  Ser Asp Pro
        995                 1000                1005

Tyr Thr  Leu Asn Ile Pro Tyr  Thr Gln Leu Pro Thr  Thr Tyr Leu
    1010                1015                1020

Lys Lys  His Thr Gln Arg Ser  Leu Leu Ser Arg Ala  Val Asn Pro
    1025                1030                1035

Leu Leu  Ala Gly Val Gln Val  Pro Asn Gln His Glu  Glu Glu Glu
    1040                1045                1050

Met Leu  Ala Arg Phe Leu Leu  Asp Arg Glu Tyr Val  Met Pro Arg
    1055                1060                1065

Val Ala  His Val Ile Leu Glu  Ser Ser Val Leu Gly  Lys Arg Lys
    1070                1075                1080

Gln Ile  Gln Gly Leu Ile Asp  Thr Thr Pro Thr Ile  Ile Arg Thr
    1085                1090                1095

Ser Leu  Val Asn Leu Pro Val  Ser Arg Lys Lys Cys  Glu Lys Ile
    1100                1105                1110

Ile Asn  Tyr Ser Leu Asn Tyr  Ile Ala Glu Cys His  Asp Ser Leu
    1115                1120                1125

Leu Ser  Gln Val Cys Phe Ser  Asp Asn Lys Glu Tyr  Leu Trp Ser
    1130                1135                1140

Thr Ser  Leu Ile Ser Val Glu  Thr Cys Ser Val Thr  Ile Ala Asp
    1145                1150                1155

Tyr Leu  Arg Ala Val Ser Trp  Ser Asn Ile Leu Gly  Gly Arg Asn
    1160                1165                1170
```

```
Ile Ser  Gly Val Thr Thr Pro  Asp Thr Ile Glu Leu  Ile Gln Gly
    1175                 1180                 1185

Cys Leu  Ile Gly Glu Asn Ser  Ser Cys Thr Leu Cys  Glu Ser His
    1190                 1195                 1200

Asp Asp  Ala Phe Thr Trp Met  His Leu Pro Gly Pro  Leu Tyr Ile
    1205                 1210                 1215

Pro Glu  Pro Ser Val Thr Asn  Ser Lys Met Arg Val  Pro Tyr Leu
    1220                 1225                 1230

Gly Ser  Lys Thr Glu Glu Arg  Lys Thr Ala Ser Met  Ala Ala Ile
    1235                 1240                 1245

Lys Gly  Met Ser His His Leu  Arg Ala Val Leu Arg  Gly Thr Ser
    1250                 1255                 1260

Val Phe  Ile Trp Ala Phe Gly  Asp Thr Asp Ile Asn  Trp Asp Asn
    1265                 1270                 1275

Ala Leu  Gln Ile Ala Gln Ser  Arg Cys Asn Ile Thr  Leu Asp Gln
    1280                 1285                 1290

Met Arg  Leu Leu Thr Pro Ile  Pro Ser Ser Ser Asn  Ile Gln His
    1295                 1300                 1305

Arg Leu  Asp Asp Gly Ile Ser  Thr Gln Lys Phe Thr  Pro Ala Ser
    1310                 1315                 1320

Leu Ala  Arg Ile Thr Ser Phe  Val His Ile Cys Asn  Asp Ser Gln
    1325                 1330                 1335

Arg Leu  Glu Lys Asp Gly Ser  Ser Val Asp Ser Asn  Leu Ile Tyr
    1340                 1345                 1350

Gln Gln  Ile Met Leu Leu Gly  Leu Ser Ile Phe Glu  Thr Met Tyr
    1355                 1360                 1365

Ser Met  Asp Gln Lys Trp Val  Phe Asn Asn His Thr  Leu His Leu
    1370                 1375                 1380

His Thr  Gly His Ser Cys Cys  Pro Arg Glu Leu Asp  Ile Ser Leu
    1385                 1390                 1395

Val Asn  Pro Pro Arg His Gln  Thr Pro Glu Leu Thr  Ser Thr Thr
    1400                 1405                 1410

Thr Asn  Pro Phe Leu Tyr Asp  Gln Leu Pro Leu Asn  Gln Glu Asn
    1415                 1420                 1425

Leu Thr  Thr Leu Glu Ile Lys  Thr Phe Lys Phe Asn  Glu Leu Asn
    1430                 1435                 1440

Ile Asp  Gly Leu Asp Phe Gly  Glu Gly Ile Gln Leu  Leu Ser Arg
    1445                 1450                 1455

Cys Thr  Ala Arg Leu Met Ala  Glu Cys Ile Leu Glu  Glu Gly Ile
    1460                 1465                 1470

Gly Ser  Ser Val Lys Asn Glu  Ala Ile Val Asn Phe  Asp Asn Ser
    1475                 1480                 1485

Val Asn  Trp Ile Ser Glu Cys  Leu Met Cys Asp Ile  Arg Ser Leu
    1490                 1495                 1500

Cys Val  Asn Leu Gly Gln Glu  Ile Leu Cys Ser Leu  Ala Tyr Gln
    1505                 1510                 1515

Met Tyr  Tyr Leu Arg Ile Arg  Gly Arg Arg Ala Ile  Leu Asn Tyr
    1520                 1525                 1530

Leu Asp  Thr Thr Leu Gln Arg  Ile Pro Val Ile Gln  Leu Ala Asn
    1535                 1540                 1545

Ile Ala  Leu Thr Ile Ser His  Pro Glu Ile Phe Arg  Arg Ile Val
    1550                 1555                 1560

Asn Thr  Gly Ile His Asn Gln  Ile Lys Gly Pro Tyr  Val Ala Thr
```

```
    1565                1570                1575

Thr Asp  Phe Ile Ala Ala Ser  Arg Asp Ile Ile Leu  Ser Gly Ala
    1580                1585                1590

Arg Glu  Tyr Leu Ser Tyr Leu  Ser Ser Gly Gln Glu  Asp Cys Tyr
    1595                1600                1605

Thr Phe  Phe Asn Cys Gln Asp  Gly Asp Leu Thr Pro  Lys Met Glu
    1610                1615                1620

Gln Tyr  Leu Ala Arg Arg Ala  Cys Leu Leu Thr Leu  Leu Tyr Asn
    1625                1630                1635

Thr Gly  His Gln Ile Pro Val  Ile Arg Ser Leu Thr  Pro Ile Glu
    1640                1645                1650

Lys Cys  Lys Val Leu Thr Glu  Tyr Asn Gln Gln Ile  Glu Tyr Ala
    1655                1660                1665

Asp Gln  Glu Phe Ser Ser Val  Leu Lys Val Val Asn  Ala Leu Leu
    1670                1675                1680

Gln Asn  Pro Lys Ile Asp Ala  Leu Val Ser Asn Leu  Tyr Phe Thr
    1685                1690                1695

Thr Arg  Arg Val Leu Ser Asn  Leu Arg Ser Cys Asp  Lys Ala Arg
    1700                1705                1710

Ser Tyr  Ile Glu Tyr Leu Tyr  Thr Glu Asp Phe Gly  Glu Lys Glu
    1715                1720                1725

Asp Thr  Val Gln Tyr Asp Ile  Met Thr Thr Asn Asp  Ile Ile Leu
    1730                1735                1740

Thr His  Gly Leu Phe Thr Gln  Ile Glu Ile Ser Tyr  Gln Gly Asn
    1745                1750                1755

Ser Leu  His Lys Phe Leu Thr  Pro Asp Asn Ala Pro  Gly Ser Leu
    1760                1765                1770

Ile Pro  Phe Ser Ile Ser Pro  Asn Ser Leu Ala Cys  Asp Pro Leu
    1775                1780                1785

His His  Leu Leu Lys Ser Val  Gly Thr Ser Ser Thr  Ser Trp Tyr
    1790                1795                1800

Lys Tyr  Ala Ile Ala Tyr Ala  Val Ser Glu Lys Arg  Ser Ala Arg
    1805                1810                1815

Leu Gly  Gly Ser Leu Tyr Ile  Gly Glu Gly Ser Gly  Ser Val Met
    1820                1825                1830

Thr Leu  Leu Glu Tyr Leu Glu  Pro Ser Val Asp Ile  Phe Tyr Asn
    1835                1840                1845

Ser Leu  Phe Ser Asn Gly Met  Asn Pro Pro Gln Arg  Asn Tyr Gly
    1850                1855                1860

Leu Met  Pro Leu Gln Phe Val  Asn Ser Val Val Tyr  Lys Asn Leu
    1865                1870                1875

Thr Ala  Lys Ser Glu Cys Lys  Leu Gly Phe Val Gln  Gln Phe Lys
    1880                1885                1890

Pro Leu  Trp Arg Asp Ile Asp  Ile Glu Thr Asn Val  Thr Asp Pro
    1895                1900                1905

Ser Phe  Ile Asn Phe Ala Leu  Asn Glu Ile Pro Met  Gln Ser Leu
    1910                1915                1920

Lys Arg  Val Asn Cys Asp Val  Glu Phe Asp Arg Gly  Met Pro Ile
    1925                1930                1935

Glu Arg  Val Ile Gln Gly Tyr  Thr His Ile Leu Leu  Val Ala Thr
    1940                1945                1950

Tyr Gly  Leu Gln Gln Asp Ser  Ile Leu Trp Val Lys  Val Tyr Arg
    1955                1960                1965
```

Thr Ser Glu Lys Val Phe Gln Phe Leu Leu Ser Ala Met Ile Met
1970 1975 1980

Ile Phe Gly Tyr Val Lys Ile His Arg Asn Gly Tyr Met Ser Thr
1985 1990 1995

Lys Asp Glu Glu Tyr Ile Leu Met Ser Asp Cys Lys Glu Pro Val
2000 2005 2010

Asn Tyr Thr Ala Val Pro Asn Ile Leu Thr Arg Val Ser Asp Leu
2015 2020 2025

Val Ser Lys Asn Leu Ser Leu Ile His Pro Glu Asp Leu Arg Lys
2030 2035 2040

Val Arg Cys Glu Thr Asp Ser Leu Asn Leu Lys Cys Asn His Ile
2045 2050 2055

Tyr Glu Lys Ile Ile Ala Arg Lys Ile Pro Leu Gln Val Ser Ser
2060 2065 2070

Thr Asp Ser Leu Leu Leu Gln Leu Gly Gly Val Ile Asn Ser Val
2075 2080 2085

Gly Ser Thr Asp Pro Arg Glu Val Ala Thr Leu Ser Ser Ile Glu
2090 2095 2100

Cys Met Asp Tyr Val Val Ser Ser Ile Asp Leu Ala Ile Leu Glu
2105 2110 2115

Ala Asn Ile Val Ile Ser Glu Ser Ala Gly Leu Asp Leu Ala Leu
2120 2125 2130

Met Leu Gly Pro Phe Asn Leu Asn Lys Leu Lys Lys Ile Asp Thr
2135 2140 2145

Ile Leu Lys Ser Ser Thr Tyr Gln Leu Ile Pro Tyr Trp Leu Arg
2150 2155 2160

Tyr Glu Tyr Ser Ile Asn Pro Arg Ser Leu Ser Phe Leu Ile Thr
2165 2170 2175

Lys Leu Gln Gln Cys Arg Ile Ser Trp Ser Asp Met Ile Thr Ile
2180 2185 2190

Ser Glu Phe Arg Lys Lys Ser Lys Arg Pro Ile Phe Ile Lys Arg
2195 2200 2205

Val Ile Gly Asn Gln Gln Leu Lys Ser Phe Phe Asn Glu Ser Ser
2210 2215 2220

Ser Ile Val Leu Thr Arg Ala Glu Val Lys Val Cys Ile Lys Phe
2225 2230 2235

Leu Gly Ala Ile Ile Lys Leu Lys
2240 2245

<210> SEQ ID NO 14
<211> LENGTH: 2238
<212> TYPE: PRT
<213> ORGANISM: artificial sequence
<220> FEATURE:
<223> OTHER INFORMATION: APMV8 L protein2

<400> SEQUENCE: 14

Met Asp Ile Lys Gln Val Asp Leu Ile Ile Gln Pro Glu Val His Leu
1 5 10 15

Asp Ser Pro Ile Ile Leu Asn Lys Leu Ala Leu Leu Trp Arg Leu Ser
20 25 30

Gly Leu Pro Met Pro Ala Asp Leu Arg Gln Lys Ser Val Val Met His
35 40 45

Ile Pro Asp His Ile Leu Glu Lys Ser Glu Tyr Arg Ile Lys His Arg
50 55 60

Leu Gly Lys Ile Lys Ser Asp Ile Thr His Tyr Cys Gln Tyr Phe Asn

-continued

```
65                  70                  75                  80

Ile Asn Leu Ala Asn Ile Asp Pro Ile Thr His Pro Lys Ser Leu Tyr
                85                  90                  95

Trp Leu Ser Arg Leu Thr Ile Ala Ser Ala Gly Thr Phe Arg His Met
            100                 105                 110

Lys Asp Arg Ile Leu Cys Thr Val Gly Ser Glu Phe Gly His Lys Ile
        115                 120                 125

Gln Asp Leu Phe Ser Leu Leu Ser His Lys Leu Val Gly Asn Gly Asp
    130                 135                 140

Leu Phe Asn Gln Ser Leu Ser Gly Thr Arg Leu Thr Ala Ser Pro Leu
145                 150                 155                 160

Ser Pro Leu Cys Asn Gln Phe Val Ser Asp Ile Lys Ser Ala Val Thr
                165                 170                 175

Thr Pro Trp Ser Glu Ala Arg Trp Ser Trp Leu His Ile Lys Gln Thr
            180                 185                 190

Met Arg Tyr Leu Ile Lys Gln Ser Arg Thr Thr Asn Ser Ala His Leu
        195                 200                 205

Thr Glu Ile Ile Lys Glu Glu Trp Gly Leu Val Gly Ile Thr Pro Asp
    210                 215                 220

Leu Val Ile Leu Phe Asp Arg Val Asn Asn Ser Leu Thr Ala Leu Thr
225                 230                 235                 240

Phe Glu Met Val Leu Met Tyr Ser Asp Val Leu Glu Ser Arg Asp Asn
                245                 250                 255

Ile Val Leu Val Gly Arg Leu Ser Thr Phe Leu Gln Pro Val Val Ser
            260                 265                 270

Arg Leu Glu Val Leu Phe Asp Leu Val Asp Ser Leu Ala Lys Ile Leu
        275                 280                 285

Gly Asp Thr Ile Tyr Glu Ile Ile Ala Val Leu Glu Ser Leu Ser Tyr
    290                 295                 300

Gly Ser Val Gln Leu His Asp Ala Ser His Ser His Ala Gly Ser Phe
305                 310                 315                 320

Phe Ser Phe Asn Met Asn Glu Leu Asp Asn Thr Leu Ser Lys Arg Val
                325                 330                 335

Asp Pro Lys His Lys Asn Thr Ile Met Ser Ile Ile Arg Gln Cys Phe
            340                 345                 350

Ser Asn Leu Asp Val Asp Gln Ala Ala Glu Met Leu Cys Leu Met Arg
        355                 360                 365

Leu Phe Gly His Pro Met Leu Thr Ala Pro Asp Ala Ala Ala Lys Val
    370                 375                 380

Arg Lys Ala Met Cys Ala Pro Lys Leu Val Glu His Asp Thr Ile Leu
385                 390                 395                 400

Gln Thr Leu Ser Phe Phe Lys Gly Ile Ile Ile Asn Gly Tyr Arg Arg
                405                 410                 415

Ser His Ser Gly Leu Trp Pro Asn Val Glu Pro Ser Ser Ile Tyr Asp
            420                 425                 430

Asp Asp Leu Arg Gln Leu Tyr Leu Glu Ser Ala Glu Ile Ser His His
        435                 440                 445

Phe Met Leu Lys Asn Tyr Lys Ser Leu Ser Met Ile Glu Phe Lys Lys
    450                 455                 460

Ser Ile Asp Tyr Asp Leu His Asp Asp Leu Ser Thr Phe Leu Lys Asp
465                 470                 475                 480

Arg Ala Ile Cys Arg Pro Lys Ser Gln Trp Asp Val Ile Phe Arg Lys
                485                 490                 495
```

```
Ser Leu Arg Arg Ser His Thr Gln Ser Gln Tyr Leu Asp Glu Ile Lys
            500                 505                 510

Ser Asn Arg Leu Leu Ile Asp Phe Leu Asp Ser Ala Glu Phe Asp Pro
        515                 520                 525

Gly Lys Glu Phe Ala Tyr Val Thr Thr Met Asp Tyr Leu His Asp Asn
    530                 535                 540

Glu Phe Cys Ala Ser Tyr Ser Leu Lys Glu Lys Glu Ile Lys Thr Thr
545                 550                 555                 560

Gly Arg Ile Phe Ala Lys Met Thr Arg Asn Met Arg Ser Cys Gln Val
                565                 570                 575

Ile Leu Glu Ser Leu Leu Ser Lys His Ile Cys Lys Phe Phe Lys Glu
            580                 585                 590

Asn Gly Val Ser Met Glu Gln Leu Ser Leu Thr Lys Ser Leu Leu Ala
        595                 600                 605

Met Ser Gln Leu Ser Pro Lys Val Ser Thr Leu Gln Asp Thr Ala Ser
    610                 615                 620

Arg His Val Gly Asn Ser Lys Ser Gln Ile Ala Thr Ser Asn Pro Ser
625                 630                 635                 640

Arg His His Ser Thr Pro Asn Gln Met Ser Leu Ser Asn Arg Lys Thr
                645                 650                 655

Val Val Ala Thr Phe Leu Thr Thr Asp Leu Glu Lys Tyr Cys Leu Gln
            660                 665                 670

Trp Arg Tyr Ser Thr Ile Lys Leu Phe Ala Gln Ala Leu Asn Gln Leu
        675                 680                 685

Phe Gly Ile Asp His Gly Phe Glu Trp Ile His Leu Arg Leu Met Asn
    690                 695                 700

Ser Thr Leu Phe Val Gly Asp Pro Tyr Ser Pro Pro Glu Asp Pro Thr
705                 710                 715                 720

Leu Glu Asp Ile Asp Lys Ala Pro Asn Asp Asp Ile Phe Ile Val Ser
                725                 730                 735

Pro Arg Gly Gly Ile Glu Gly Leu Cys Gln Lys Met Trp Thr Met Ile
            740                 745                 750

Ser Ile Ser Ala Ile His Cys Val Ala Glu Lys Ile Gly Ala Arg Val
        755                 760                 765

Ala Ala Met Val Gln Gly Asp Asn Gln Val Ile Ala Ile Thr Lys Glu
    770                 775                 780

Leu Phe Arg Gly Glu Lys Ala Cys Asp Val Arg Asp Glu Leu Asp Glu
785                 790                 795                 800

Leu Gly Gln Val Phe Phe Asp Glu Phe Lys Arg His Asn Tyr Ala Ile
                805                 810                 815

Gly His Asn Leu Lys Leu Asn Glu Thr Ile Gln Ser Gln Ser Phe Phe
            820                 825                 830

Val Tyr Ser Lys Arg Ile Phe Phe Glu Gly Arg Leu Leu Ser Gln Val
        835                 840                 845

Leu Lys Asn Ala Ala Lys Leu Cys Met Val Ala Asp His Leu Gly Glu
    850                 855                 860

Asn Thr Val Ser Ser Cys Ser Asn Leu Ser Ser Thr Ile Ala Arg Leu
865                 870                 875                 880

Val Glu Asn Gly Phe Glu Lys Asp Thr Ala Phe Val Leu Asn Leu Val
                885                 890                 895

Tyr Ile Met Thr Gln Ile Leu Phe Asp Glu His Tyr Ser Ile Val Cys
            900                 905                 910

Asp His His Ser Val Lys Ser Leu Ile Gly Ser Lys Asn His Arg Asn
        915                 920                 925
```

```
Leu Leu Tyr Ser Ser Leu Ile Pro Gly Gln Leu Gly Gly Phe Asn Phe
    930                 935                 940

Leu Asn Ile Ser Arg Leu Phe Thr Arg Asn Ile Gly Asp Pro Val Thr
945                 950                 955                 960

Cys Ser Leu Ser Asp Leu Lys Cys Phe Ile Ala Ala Gly Leu Leu Pro
                965                 970                 975

Pro Tyr Val Leu Lys Asn Val Val Leu Arg Glu Pro Gly Pro Gly Thr
            980                 985                 990

Trp Leu Thr Leu Cys Ser Asp Pro  Tyr Thr Leu Asn Ile  Pro Tyr Thr
        995                 1000                1005

Gln Leu  Pro Thr Thr Tyr Leu  Lys Lys His Thr Gln  Arg Ser Leu
    1010                 1015                 1020

Leu Ser  Arg Ala Val Asn Pro  Leu Leu Ala Gly Val  Gln Val Pro
    1025                 1030                 1035

Asn Gln  His Glu Glu Glu Glu  Met Leu Ala Arg Phe  Leu Leu Asp
    1040                 1045                 1050

Arg Glu  Tyr Val Met Pro Arg  Val Ala His Val Ile  Leu Glu Ser
    1055                 1060                 1065

Ser Val  Leu Gly Lys Arg Lys  Gln Ile Gln Gly Leu  Ile Asp Thr
    1070                 1075                 1080

Thr Pro  Thr Ile Ile Arg Thr  Ser Leu Val Asn Leu  Pro Val Ser
    1085                 1090                 1095

Arg Lys  Lys Cys Glu Lys Ile  Ile Asn Tyr Ser Leu  Asn Tyr Ile
    1100                 1105                 1110

Ala Glu  Cys His Asp Ser Leu  Leu Ser Gln Val Cys  Phe Ser Asp
    1115                 1120                 1125

Asn Lys  Glu Tyr Leu Trp Ser  Thr Ser Leu Ile Ser  Val Glu Thr
    1130                 1135                 1140

Cys Ser  Val Thr Ile Ala Asp  Tyr Leu Arg Ala Val  Ser Trp Ser
    1145                 1150                 1155

Asn Ile  Leu Gly Gly Arg Asn  Ile Ser Gly Val Thr  Thr Pro Asp
    1160                 1165                 1170

Thr Ile  Glu Leu Ile Gln Gly  Cys Leu Ile Gly Glu  Asn Ser Ser
    1175                 1180                 1185

Cys Thr  Leu Cys Glu Ser His  Asp Asp Ala Phe Thr  Trp Met His
    1190                 1195                 1200

Leu Pro  Gly Pro Leu Tyr Ile  Pro Glu Pro Ser Val  Thr Asn Ser
    1205                 1210                 1215

Lys Met  Arg Val Pro Tyr Leu  Gly Ser Lys Thr Glu  Glu Arg Lys
    1220                 1225                 1230

Thr Ala  Ser Met Ala Ala Ile  Lys Gly Met Ser His  His Leu Arg
    1235                 1240                 1245

Ala Val  Leu Arg Gly Thr Ser  Val Phe Ile Trp Ala  Phe Gly Asp
    1250                 1255                 1260

Thr Asp  Ile Asn Trp Asp Asn  Ala Leu Gln Ile Ala  Gln Ser Arg
    1265                 1270                 1275

Cys Asn  Ile Thr Leu Asp Gln  Met Arg Leu Leu Thr  Pro Ile Pro
    1280                 1285                 1290

Ser Ser  Ser Asn Ile Gln His  Arg Leu Asp Asp Gly  Ile Ser Thr
    1295                 1300                 1305

Gln Lys  Phe Thr Pro Ala Ser  Leu Ala Arg Ile Thr  Ser Phe Val
    1310                 1315                 1320

His Ile  Cys Asn Asp Ser Gln  Arg Leu Glu Lys Asp  Gly Ser Ser
```

```
    1325                1330                1335

Val Asp  Ser Asn Leu Ile Tyr  Gln Gln Ile Met Leu  Leu Gly Leu
    1340                1345                1350

Ser Ile  Phe Glu Thr Met Tyr  Ser Met Asp Gln Lys  Trp Val Phe
    1355                1360                1365

Asn Asn  His Thr Leu His Leu  His Thr Gly His Ser  Cys Cys Pro
    1370                1375                1380

Arg Glu  Leu Asp Ile Ser Leu  Val Asn Pro Pro Arg  His Gln Thr
    1385                1390                1395

Pro Glu  Leu Thr Ser Thr Thr  Thr Asn Pro Phe Leu  Tyr Asp Gln
    1400                1405                1410

Leu Pro  Leu Asn Gln Glu Asn  Leu Thr Thr Leu Glu  Ile Lys Thr
    1415                1420                1425

Phe Lys  Phe Asn Glu Leu Asn  Ile Asp Gly Leu Asp  Phe Gly Glu
    1430                1435                1440

Gly Ile  Gln Leu Leu Ser Arg  Cys Thr Ala Arg Leu  Met Ala Glu
    1445                1450                1455

Cys Ile  Leu Glu Glu Gly Ile  Gly Ser Ser Val Lys  Asn Glu Ala
    1460                1465                1470

Ile Val  Asn Phe Asp Asn Ser  Val Asn Trp Ile Ser  Glu Cys Leu
    1475                1480                1485

Met Cys  Asp Ile Arg Ser Leu  Cys Val Asn Leu Gly  Gln Glu Ile
    1490                1495                1500

Leu Cys  Ser Leu Ala Tyr Gln  Met Tyr Tyr Leu Arg  Ile Arg Gly
    1505                1510                1515

Arg Arg  Ala Ile Leu Asn Tyr  Leu Asp Thr Thr Leu  Gln Arg Ile
    1520                1525                1530

Pro Val  Ile Gln Leu Ala Asn  Ile Ala Leu Thr Ile  Ser His Pro
    1535                1540                1545

Glu Ile  Phe Arg Arg Ile Val  Asn Thr Gly Ile His  Asn Gln Ile
    1550                1555                1560

Lys Gly  Pro Tyr Val Ala Thr  Thr Asp Phe Ile Ala  Ala Ser Arg
    1565                1570                1575

Asp Ile  Ile Leu Ser Gly Ala  Arg Glu Tyr Leu Ser  Tyr Leu Ser
    1580                1585                1590

Ser Gly  Gln Glu Asp Cys Tyr  Thr Phe Phe Asn Cys  Gln Asp Gly
    1595                1600                1605

Asp Leu  Thr Pro Lys Met Glu  Gln Tyr Leu Ala Arg  Arg Ala Cys
    1610                1615                1620

Leu Leu  Thr Leu Leu Tyr Asn  Thr Gly His Gln Ile  Pro Val Ile
    1625                1630                1635

Arg Ser  Leu Thr Pro Ile Glu  Lys Cys Lys Val Leu  Thr Glu Tyr
    1640                1645                1650

Asn Gln  Gln Ile Glu Tyr Ala  Asp Gln Glu Phe Ser  Ser Val Leu
    1655                1660                1665

Lys Val  Val Asn Ala Leu Leu  Gln Asn Pro Lys Ile  Asp Ala Leu
    1670                1675                1680

Val Ser  Asn Leu Tyr Phe Thr  Thr Arg Arg Val Leu  Ser Asn Leu
    1685                1690                1695

Arg Ser  Cys Asp Lys Ala Arg  Ser Tyr Ile Glu Tyr  Leu Tyr Thr
    1700                1705                1710

Glu Asp  Phe Gly Glu Lys Glu  Asp Thr Val Gln Tyr  Asp Ile Met
    1715                1720                1725
```

-continued

```
Thr Thr Asn Asp Ile Ile Leu Thr His Gly Leu Phe Thr Gln Ile
    1730                1735                1740

Glu Ile Ser Tyr Gln Gly Asn Ser Leu His Lys Phe Leu Thr Pro
    1745                1750                1755

Asp Asn Ala Pro Gly Ser Leu Ile Pro Phe Ser Ile Ser Pro Asn
    1760                1765                1770

Ser Leu Ala Cys Asp Pro Leu His His Leu Leu Lys Ser Val Gly
    1775                1780                1785

Thr Ser Ser Thr Ser Trp Tyr Lys Tyr Ala Ile Ala Tyr Ala Val
    1790                1795                1800

Ser Glu Lys Arg Ser Ala Arg Leu Gly Gly Ser Leu Tyr Ile Gly
    1805                1810                1815

Glu Gly Ser Gly Ser Val Met Thr Leu Leu Glu Tyr Leu Glu Pro
    1820                1825                1830

Ser Val Asp Ile Phe Tyr Asn Ser Leu Phe Ser Asn Gly Met Asn
    1835                1840                1845

Pro Pro Gln Arg Asn Tyr Gly Leu Met Pro Leu Gln Phe Val Asn
    1850                1855                1860

Ser Val Val Tyr Lys Asn Leu Thr Ala Lys Ser Glu Cys Lys Leu
    1865                1870                1875

Gly Phe Val Gln Gln Phe Lys Pro Leu Trp Arg Asp Ile Asp Ile
    1880                1885                1890

Glu Thr Asn Val Thr Asp Pro Ser Phe Ile Asn Phe Ala Leu Asn
    1895                1900                1905

Glu Ile Pro Met Gln Ser Leu Lys Arg Val Asn Cys Asp Val Glu
    1910                1915                1920

Phe Asp Arg Gly Met Pro Ile Glu Arg Val Ile Gln Gly Tyr Thr
    1925                1930                1935

His Ile Leu Leu Val Ala Thr Tyr Gly Leu Gln Gln Asp Ser Ile
    1940                1945                1950

Leu Trp Val Lys Val Tyr Arg Thr Ser Glu Lys Val Phe Gln Phe
    1955                1960                1965

Leu Leu Ser Ala Met Ile Met Ile Phe Gly Tyr Val Lys Ile His
    1970                1975                1980

Arg Asn Gly Tyr Met Ser Thr Lys Asp Glu Glu Tyr Ile Leu Met
    1985                1990                1995

Ser Asp Cys Lys Glu Pro Val Asn Tyr Thr Ala Val Pro Asn Ile
    2000                2005                2010

Leu Thr Arg Val Ser Asp Leu Val Ser Lys Asn Leu Ser Leu Ile
    2015                2020                2025

His Pro Glu Asp Leu Arg Lys Val Arg Cys Glu Thr Asp Ser Leu
    2030                2035                2040

Asn Leu Lys Cys Asn His Ile Tyr Glu Lys Ile Ile Ala Arg Lys
    2045                2050                2055

Ile Pro Leu Gln Val Ser Ser Thr Asp Ser Leu Leu Leu Gln Leu
    2060                2065                2070

Gly Gly Val Ile Asn Ser Val Gly Ser Thr Asp Pro Arg Glu Val
    2075                2080                2085

Ala Thr Leu Ser Ser Ile Glu Cys Met Asp Tyr Val Val Ser Ser
    2090                2095                2100

Ile Asp Leu Ala Ile Leu Glu Ala Asn Ile Val Ile Ser Glu Ser
    2105                2110                2115

Ala Gly Leu Asp Leu Ala Leu Met Leu Gly Pro Phe Asn Leu Asn
    2120                2125                2130
```

Lys Leu Lys Lys Ile Asp Thr Ile Leu Lys Ser Ser Thr Tyr Gln
2135 2140 2145

Leu Ile Pro Tyr Trp Leu Arg Tyr Glu Tyr Ser Ile Asn Pro Arg
2150 2155 2160

Ser Leu Ser Phe Leu Ile Thr Lys Leu Gln Gln Cys Arg Ile Ser
2165 2170 2175

Trp Ser Asp Met Ile Thr Ile Ser Glu Phe Arg Lys Lys Ser Lys
2180 2185 2190

Arg Pro Ile Phe Ile Lys Arg Val Ile Gly Asn Gln Gln Leu Lys
2195 2200 2205

Ser Phe Phe Asn Glu Ser Ser Ser Ile Val Leu Thr Arg Ala Glu
2210 2215 2220

Val Lys Val Cys Ile Lys Phe Leu Gly Ala Ile Ile Lys Leu Lys
2225 2230 2235

<210> SEQ ID NO 15
<211> LENGTH: 15186
<212> TYPE: DNA
<213> ORGANISM: artificial sequence
<220> FEATURE:
<223> OTHER INFORMATION: APMV1 genome sequence

<400> SEQUENCE: 15
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccat tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc agaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260
cgagctaaag ctaaccccag cagcaatgaa gggcctggca gctgctgccc aacgggtctc 1320
cgacgatacc agcagcatat acatgcctac tcaacaagtc ggagtcctca ctgggcttag 1380
cgaggggggg tcccaagctc tacaaggcgg atcgaataga tcgcaagggc aaccagaagc 1440

-continued

```
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccccctc tttcctccct ccccctgctg tacaactccg cacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ttcaggaccg   2220
gagcaagcaa ctctctgctg ttgatgcttg acaagctcag caataaatcg tccaatgcta   2280
aaaagggccc atggtcgagc ccccaagagg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aataccccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctccaag cggcaatcct   3180
ctctcgcttc ctcagcccca ctgaatggtc gcgtaaccgt aattaatcta gctacattta   3240
agattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caaggcacag gagatgggaa gaagcaaatc gccccgcaat ataggatcca   3420
gcgccttgac ttgtggactg atagtaagga ggactcagta ttcatcacca cctatggatt   3480
catctttcaa gttgggaatg aagaagccac tgtcggcatg atcgatgata aacccaagcg   3540
cgagttactt tccgctgcga tgctctgcct aggaagcgtc ccaaataccg gagaccttat   3600
tgagctggca agggcctgtc tcactatgat agtcacatgc aagaagagtg caactaatac   3660
tgagagaatg gttttctcag tagtgcaggc accccaagtg ctgcaaagct gtagggttgt   3720
ggcaaacaaa tactcatcag tgaatgcagt caagcacgtg aaagcgccag agaagattcc   3780
cgggagtgga accctagaat acaaggtgaa ctttgtctcc ttgactgtgg taccgaagaa   3840
```

-continued ggatgtctac aagatcccag ctgcagtatt gaaggtttct ggctcgagtc tgtacaatct 3900
tgcgctcaat gtcactatta atgtggaggt agacccgagg agtcctttgg ttaaatcttt 3960
gtctaagtct gacagcggat actatgctaa cctcttcttg catattggac ttatgaccac 4020
cgtagatagg aaggggaaga aagtgacatt tgacaagctg gaaaagaaaa taaggagcct 4080
tgatctatct gtcgggctca gtgatgtgct cgggccttcc gtgttggtaa aagcaagagg 4140
tgcacggact aagcttttgg cacctttctt ctctagcagt gggacagcct gctatcccat 4200
agcaaatgct tctcctcagg tggccaagat actctggagt caaaccgcgt gcctgcggag 4260
cgttaaaatc attatccaag caggtaccca acgcgctgtc gcagtgaccg ccgaccacga 4320
ggttacctct actaagctgg agaaggggca cacccttgcc aaatacaatc cttttaagaa 4380
ataagctgcg tctctgagat tgcgctccgc ccactcaccc agatcatcat gacacaaaaa 4440
actaatctgt cttgattatt tacagttagt ttacctgtct atcaagttag aaaaaacacg 4500
ggtagaagat tctggatccc ggttggcgcc ctccaggtgc aagatgggct ccagaccttc 4560
taccaagaac ccagcaccta tgatgctgac tatccgggtt gcgctggtac tgagttgcat 4620
ctgtccggca aactccattg atggcaggcc tcttgcagct gcaggaattg tggttacagg 4680
agacaaagcc gtcaacatat acacctcatc ccagacagga tcaatcatag ttaagctcct 4740
cccgaatctg cccaaggata aggaggcatg tgcgaaagcc cccttggatg catacaacag 4800
gacattgacc actttgctca cccccctggg tgactctatc cgtaggatac aagagtctgt 4860
gactacatct ggagggggga gacaggggcg ccttataggc gccattattg gcggtgtggc 4920
tcttggggtt gcaactgccg cacaaataac agcggccgca gctctgatac aagccaaaca 4980
aaatgctgcc aacatcctcc gacttaaaga gagcattgcc gcaaccaatg aggctgtgca 5040
tgaggtcact gacggattat cgcaactagc agtggcagtt gggaagatgc agcagtttgt 5100
taatgaccaa tttaataaaa cagctcagga attagactgc atcaaaattg cacagcaagt 5160
tggtgtagag ctcaacctgt acctaaccga attgactaca gtattcggac cacaaatcac 5220
ttcacctgct ttaaacaagc tgactattca ggcactttac aatctagctg gtggaaatat 5280
ggattactta ttgactaagt taggtgtagg gaacaatcaa ctcagctcat taatcggtag 5340
cggcttaatc accggtaacc ctattctata cgactcacag actcaactct tgggtataca 5400
ggtaactcta ccttcagtcg ggaacctaaa taatatgcgt gccacctact tggaaacctt 5460
atccgtaagc acaaccaggg gatttgcctc ggcacttgtc cccaaagtgg tgacacaggt 5520
cggttctgtg atagaagaac ttgacacctc atactgtata gaaactgact tagatttata 5580
ttgtacaaga atagtaacgt tccctatgtc ccctggtatt tattcctgct tgagcggcaa 5640
tacgtcggcc tgtatgtact caaagaccga aggcgcactt actacaccat acatgactat 5700
caaaggttca gtcatcgcca actgcaagat gacaacatgt agatgtgtaa accccccggg 5760
tatcatatcg caaaactatg gagaagccgt gtctctaata gataaacaat catgcaatgt 5820
tttatcctta ggcgggataa ctttaaggct cagtggggaa ttcgatgtaa cttatcagaa 5880
gaatatctca atacaagatt ctcaagtaat aataacaggc aatcttgata tctcaactga 5940
gcttgggaat gtcaacaact cgatcagtaa tgctttgaat aagttagagg aaagcaacag 6000
aaaactagac aaagtcaatg tcaaactgac tagcacatct gctctcatta cctatatcgt 6060
tttgactatc atatctcttg tttttggtat acttagcctg attctagcat gctacctaat 6120
gtacaagcaa aaggcgcaac aaaagacctt attatggctt gggaataata ctctagatca 6180
gatgagagcc actacaaaaa tgtgaacaca gatgaggaac gaaggtttcc ctaatagtaa 6240

-continued

```
tttgtgtgaa agttctggta gtctgtcagt tcagagagtt aagaaaaaac taccggttgt   6300
agatgaccaa aggacgatat acgggtagaa cggtaagaga ggccgcccct caattgcgag   6360
ccaggcttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
tccagggcag aagaaaagat tacatctaca cttggttcca atcaagatgt agtagatagg   6660
atatataagc aagtggccct tgagtctccg ttggcattgt taaatactga gaccacaatt   6720
atgaacgcaa taacatctct ctcttatcag attaatggag ctgcaaacaa cagtgggtgg   6780
ggggcaccta tccatgaccc agattatata ggggggatag gcaaagaact cattgtagat   6840
gatgctagtg atgtcacatc attctatccc tctgcatttc aagaacatct gaattttatc   6900
ccggcgccta ctacaggatc aggttgcact cgaataccct catttgacat gagtgctacc   6960
cattactgct acacccataa tgtaatattg tctggatgca gagatcactc acattcatat   7020
cagtatttag cacttggtgt gctccggaca tctgcaacag ggagggtatt cttttctact   7080
ctgcgttcca tcaacctgga cgacacccaa aatcggaagt cttgcagtgt gagtgcaact   7140
cccctgggtt gtgatatgct gtgctcgaaa gtcacggaga cagaggaaga agattataac   7200
tcagctgtcc ctacgcggat ggtacatggg aggttagggt tcgacggcca gtaccacgaa   7260
aaggacctag atgtcacaac attattcggg gactgggtgg ccaactaccc aggagtaggg   7320
ggtggatctt ttattgacag ccgcgtatgg ttctcagtct acggagggtt aaaacccaat   7380
tcacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aggtgtcaac atccttaggc   7560
gaagacccgg tactgactgt accgcccaac acagtcacac tcatgggggc cgaaggcaga   7620
attctcacag tagggacatc tcatttcttg tatcaacgag ggtcatcata cttctctccc   7680
gcgttattat atcctatgac agtcagcaac aaaacagcca ctcttcatag tccttataca   7740
ttcaatgcct tcactcggcc aggtagtatc ccttgccagg cttcagcaag atgccccaac   7800
tcgtgtgtta ctggagtcta tacagatcca tatcccctaa tcttctatag aaaccacacc   7860
ttgcgagggg tattcgggac aatgcttgat ggtgtacaag caagacttaa ccctgcgtct   7920
gcagtattcg atagcacatc ccgcagtcgc attactcgag tgagttcaag cagtaccaaa   7980
gcagcataca caacatcaac ttgttttaaa gtggtcaaga ctaataagac ctattgtctc   8040
agcattgctg aaatatctaa tactctcttc ggagaattca gaatcgtccc gttactagtt   8100
gagatcctca aagatgacgg ggttagagaa gccaggtctg gctagttgag tcaattataa   8160
aggagttgga aagatggcat tgtatcacct atcttctgcg acatcaagaa tcaaaccgaa   8220
tgccggcgcg tgctcgaatt ccatgttgcc agttgaccac aatcagccag tgctcatgcg   8280
atcagattaa gccttgtcat taatctcttg attaagaaaa aatgtaagtg gcaatgagat   8340
acaaggcaaa acagctcatg gtaaataata cgggtaggac atggcgagct ccggtcctga   8400
aagggcagag catcagatta tcctaccaga gccacacctg tcttcaccat tggtcaagca   8460
caaactactc tattactgga aattaactgg gctaccgctt cctgatgaat gtgacttcga   8520
ccacctcatt ctcagccgac aatggaaaaa aatacttgaa tcggcctctc ctgatactga   8580
gagaatgata aaactcggaa gggcagtaca ccaaactctt aaccacaatt ccagaataac   8640
```

-continued

```
cggagtgctc caccccaggt gtttagaaca actggctaat attgaggtcc cagattcaac   8700
caacaaattt cggaagattg agaagaagat ccaaattcac aacacgagat atggagaact   8760
gttcacaagg ctgtgtacgc atatagagaa gaaactgctg gggtcatctt ggtctaacaa   8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
ggtggcagct aagacaaggt ctgcggccaa caaattggtg atgctaaccc ataaggtagg   9000
ccaagtcttt gtcactcctg aacttgtcgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
aggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgtctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacgggt acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atatgaccct gtcaccaacc tgagcatgtt   9780
cctaaaagac aaggcaatcg cacaccccaa cgataattgg cttgcctcgt ttaggcggaa   9840
ccttctctcc gaagaccaga agaaacatgt aaaagaagca acttcgacta atcgcctctt   9900
gatagagttt ttagagtcaa atgattttga tccatataaa gagatggaat atctgacgac   9960
ccttgagtac cttagagatg acaatgtggc agtatcatac tcgctcaagg agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacaa tcaaattgtt cgctcatgcc atcaatcagt tgatgggcct  10380
acctcacttc ttcgaatgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag acgactctcc  10680
ggagatggtg ttgacacagt tgcatcaagc cagtgataat ttcttcaagg aattaattca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
```

-continued

```
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggatta ctgagtccta acattatgac taatatctta actaggccgc ctgggaatgg  11280
agattgggcc agtctgtgca acgacccata ctctttcaat tttgagactg ttgcaagccc  11340
aaatattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacaccgtaa ttaagattgc  11580
gcttactagg aggccattag gcatcaagag gctgatgcgg atagtcaatt attctagcat  11640
gcatgcaatg ctgtttagag acgatgtttt ttcctccagt agatccaacc accccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcaaa  12000
aatagctcat atgtcgccac atgtaaaggc tgccctaagg gcatcatccg tgttgatctg  12060
ggcttatggg gataatgaag taaattggac tgctgctctt acgattgcaa aatctcggtg  12120
taatgtaaac ttagagtatc ttcggttact gtccccttta cccacggctg ggaatcttca  12180
acatagacta gatgatggta taactcagat gacattcacc cctgcatctc tctacaggtg  12240
tcaccttaca ttcacatatc caatgattct caaaggctgt tcactgaaga aggagtcaaa  12300
gaggggaatg tggtttacca acagagtcat gctcttgggt ttatctctaa tcgaatcgat  12360
ctttccaatg acaacaacca ggacatatga tgagatcaca ctgcacctac atagtaaatt  12420
tagttgctgt atcagagaag cacctgttgc ggttcctttc gagctacttg gggtggtacc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgac gccataatag tgtatgacaa  12720
tacccgaaat tggatcagtg aagctcagaa ttcagatgtg gtccgcctat ttgaatatgc  12780
agcacttgaa gtgctcctcg actgttctta ccaactctat tacctgagag taagaggcct  12840
agacaatatt gtcttatata tgggtgattt atacaagaat atgccaggaa ttctactttc  12900
caacattgca gctacaatat ctcatcccgt cattcattca aggttacatg cagtgggcct  12960
ggtcaaccat gacggatcac accaacttgc agatacggat tttatcgaaa tgtctgcaaa  13020
actattagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
```

gcaagatatt ggtgctcgag tgaaagatcc attcacccga caacctgcgg catttttgca 13500
agagttagat ttgagtgctc cagcaaggta tgacgcattc acacttagtc agattcatcc 13560
tgaactcaca tctccaaatc cggaggaaga ctacttagta cgatacttgt tcagagggat 13620
agggactgca tcttcctctt ggtataaggc atctcatctc ctttctgtac ccgaggtaag 13680
atgtgcaaga cacgggaact ccttatactt agctgaaggg agcggagcca tcatgagtct 13740
tctcgaactg catgtaccac atgaaactat ctattacaat acgctctttt caaatgagat 13800
gaaccccccg caacgacatt tcgggccgac cccaactcag tttttgaatt cggttgttta 13860
taggaatcta caggcggagg taacatgcaa agatggattt gtccaagagt tccgtccatt 13920
atggagagaa aatacagagg aaagtgacct gacctcagat aaagcagtgg ggtatattac 13980
atctgcagtg ccctacagat ctgtatcatt gctgcattgt gacattgaaa ttcctccagg 14040
gtccaatcaa agcttactag atcaactagc tatcaattta tctctgattg ccatgcattc 14100
tgtaagggag ggcggggtag taatcatcaa agtgttgtat gcaatgggat actactttca 14160
tctactcatg aacttgtttg ctccgtgttc cacaaaagga tatattctct ctaatggtta 14220
tgcatgtcga ggagatatgg agtgttacct ggtatttgtc atgggttacc tgggcgggcc 14280
tacatttgta catgaggtgg tgaggatggc aaaaactctg gtgcagcggc acggtacgct 14340
cttgtctaaa tcagatgaga tcacactgac caggttattc acctcacagc ggcagcgtgt 14400
gacagacatc ctatccagtc ctttaccaag attaataaag tacttgagga agaatattga 14460
cactgcgctg attgaagccg ggggacagcc cgtccgtcca ttctgtgcgg agagtctggt 14520
gagcacgcta gcgaacataa ctcagataac ccagattatc gctagtcaca ttgacacagt 14580
tatccggtct gtgatatata tggaagctga gggtgatctc gctgacacag tatttctatt 14640
taccccttac aatctctcta ctgacgggaa aaagaggaca tcacttatac agtgcacgag 14700
acagatccta gaggttacaa tactaggtct tagagtcgaa aatctcaata aaataggcga 14760
tataatcagc ctagtgctta aaggcatgat ctccatggag gaccttatcc cactaaggac 14820
atacttgaag catagtacct gccctaaata tttgaaggct gtcctaggta ttaccaaact 14880
caaagaaatg tttacagaca cttctgtatt gtacttgact cgtgctcaac aaaaattcta 14940
catgaaaact ataggcaatg cagtcaaagg atattacagt aactgtgact cttaacgaaa 15000
atcacatatt aataggctcc ttttttggcc aattgtattc ttgttgattt aatcatatta 15060
tgttagaaaa aagttgaacc ctgactcctt aggactcgaa ttcgaactca aataaatgtc 15120
ttaaaaaaag gttgcgcaca attattcttg agtgtagtct cgtcattcac caaatctttg 15180
tttggt 15186

<210> SEQ ID NO 16
<211> LENGTH: 14904
<212> TYPE: DNA
<213> ORGANISM: artificial sequence
<220> FEATURE:
<223> OTHER INFORMATION: APMV8 genome sequence
<400> SEQUENCE: 16
accaaacaag gaataggtaa gcaacgtaaa tcttagataa aaccatagaa tccgtggggg 60
cgacatcgcc tgaagccgat ctcgagatcg ataactccgg ttaattggtc tcagcgtgag 120
gagcttatct gtctgtggca atgtcttctg tgttttcaga ataccaggct cttcaggacc 180
aactggtcaa gcctgccact cgaagggctg atgtggcatc gactggattg ttgagagcgg 240
agataccagt ttgtgtaacc ttgtctcagg acccaactga tagatggaac ctcgcatgtc 300

-continued

```
tcaatctgcg atggctgata agtgagtcct ctactactcc catgagacaa ggggcgatcc    360
tgtcactgct gagcttgcac tctgacaaca tgcgagctca cgcaaccctt gcagcgagat    420
ccgctgatgc tgccatcact gtgcttgagg ttgacgccat agacatggcg gatggcacaa    480
tcacttttaa tgccagaagt ggagtatccg agaggcgcag cacacagctc atggcaatcg    540
caaaagatct gccccgctct tgttccaatg actcaccatt caaagatgac actatcgagg    600
atcgcgaccc ccttgacctg tccgagacta tcgatagact gcaggggatt gctgcccaaa    660
tctggatagc ggccatcaag agcatgactg ccccggatac tgctgcggag tcagaaggca    720
agaggcttgc aaagtaccaa caacaaggcc gcttggtgcg acaggtgtta gtgcatgatg    780
cggtgcgtgc ggaattccta cgtgtcatca gaggcagcct ggtcttacgg caattcatgg    840
tatcagaatg taagagggca gcatccatgg gtagcgagac atctaggtac tatgccatgg    900
tgggtgacat cagcctctac atcaagaatg caggacttac cgccttcttc ttgacactca    960
gatttggtat tgggacacac taccccactc ttgccatgag tgtgttctct ggagaactga   1020
agaagatgtc gtccttgatc aggctgtata agtcaaaagg ggaaaatgct gcatacatgg   1080
cattcctgga ggatgcggac atgggaaact ttgcgcctgc taactttagt actctctact   1140
cctatgcaat gggggtaggt acagtgctgg aagcatcagt tgcgaaatac cagttcgctc   1200
gagagttcac cagtgagaca tacttcaggc ttggggttga gaccgcacag aaccaacagt   1260
gcgctctaga tgaaaagacc gccaaggaga tggggcttac tgatgaagcc agaaagcagg   1320
tgcaagcatt ggctagcaac atcgagcagg ggcaacattc aatgcccatg caacaacagc   1380
ccacattcat gagtcagccc taccaggatg acgatcgtga ccagccaagc accagcagac   1440
cagagccaag accatcgcaa ttgacaagcc aatcagcagc acaggacaat gatgcggcct   1500
cattagattg gtgaccgcaa tcagctcagc caagccattg ttggacgcag gacattcaaa   1560
tcatacattg ccctaagagt attaaagtga tttaagaaaa aaggaccctg gggcgaagt    1620
tgtcccaatc caggcaggcg ctgaaaccga atccctccaa cctccgagcc ccaggcgacc   1680
atggagttca ccgatgatgc cgaaattgct gagctgttgg acctcgggac ctcagtgatc   1740
caagagctgc agcgagccga agtcaagggc ccgcaaacaa ccggaaagcc caaagttccc   1800
ccggggaaca ctaagagcct ggctactctc tgggagcatg agactagcac ccaagggagt   1860
gcattgggca cacccgagaa caacacccag gcacccgatg acaacaacgc aggtgcagat   1920
acgccagcga ctaccgacgt ccatcgcact ctggatacca tagacaccga cacaccaccg   1980
gaagggagca agcccagctc cactaactcc caacccggtg atgaccttga caaggctctt   2040
tcgaagctag aggcgcgcgc caagctcgga ccagataggg ccagacaggt taaaaagggg   2100
aaggagatcg ggtcgagcac agggacgagg gaggcagcca gtcaccacat ggaagggagc   2160
cgacagtcgg agccaggagc gggcagccga gcacagccac aaggccatgg cgaccgggac   2220
acaggaggga gtactcattc atctctcgag atgggagact ggaagtcaca agctggtgca   2280
acccagtctg ctctcccatt agaagcgagc ccaggagaga aaagtgcaca tgtggaactt   2340
gcccagaatc ctgcatttta tgcaggcaac ccaactgatg caattatggg gttgacaaag   2400
aaagtcaatg atctagagac aaaattggct gaggtattgc gtctgttagg aatactcccc   2460
ggaataaaga atgagattag tcagctgaaa gcaaccgtgg ctctgatgtc aaatcagatt   2520
gcctccattc agattcttga tcctgggaat gccggagtca aatcccttaa tgagatgaaa   2580
gccctgtcaa aagcagccag catagttgtg gcaggtccag gagtccttcc tcctgaggtc   2640
acagaaggag gactgatcgc gaaagatgag ctagcaaggc ccatccccat ccaaccgcaa   2700
```

-continued

```
cgagactcca aacccaaaga cgacccgcac acatcaccaa atgatgtcct tgctgtacgc   2760
gctatgatcg acacccttgt ggatgatgag aagaagagaa agagattaaa ccaggccctt   2820
gacaaggcaa agaccaagga tgacgtctta agggtcaagc ggcagatata caatgcctag   2880
gagtccattt gtctaaagaa cctccaatca tatcaccagt ttcgtgccac atgcttccct   2940
gccgagaatc tagccgacac aaaaactaaa tcatagttta acaaaaaaga agtttggggg   3000
cgaagtctca catcatagag caccccttgca ttctaaaatg gctcaaacaa ccgtcaggct   3060
gtatatcgat gaagctagtc ccgacattga actgttgtct tacccactga taatgaaaga   3120
cacaggacat gggaccaaag agttgcagca gcaaatcaga gttgcagaga tcggtgcatt   3180
gcagggaggg aagaatgaat cagttttcat caatgcatat ggctttgttc agcaatgcaa   3240
agttaaaccg gggggcaaccc aattcttcca ggtagatgca gctacaaagc cagaagtggt   3300
cactgcaggg atgattataa tcggtgcagt caagggggtg gcaggcatca ctaagctggc   3360
agaagaggtg ttcgagctgg acatctccat caagaagtcc gcatcattcc atgagaaggt   3420
tgcggtgtcc tttaatactg tgccactatc actcatgaat tcgaccgcat gcagaaatct   3480
gggttatgtc acaaacgctg aggaggcgat caaatgcccg agcaaaatac aagcgggtgt   3540
gacgtacaaa tttaagataa tgtttgtctc cttgacacga ctgcataacg ggaaattgta   3600
ccgtgtcccc aaggcagtgt atgctgtaga ggcatcagct ctatataaag tgcaactgga   3660
agtcgggttc aagcttgacg tggccaagga tcacccacac gttaagatgt tgaagaaagt   3720
ggaacggaat ggtgagactc tgtatcttgg ttatgcatgg ttccacctgt gcaacttcaa   3780
gaagacaaat gccaagggtg agtcccggac aatctccaac ctagaaggga aagtcagagc   3840
tatggggatc aaggtttcct tgtacgactt atgggggcct actttggtgg tgcaaatcac   3900
aggtaagacc agcaagtatg cacaaggttt cttttcaacc acaggtacct gctgcctccc   3960
agtgtcgaag gctgcccctg agctggccaa acttatgtgg tcctgcaatg caacaatcgt   4020
tgaagctgca gtgattatcc aagggagtga taggagggca gtcgtgacct cagaggactt   4080
ggaagtatac ggggcagttg caaaagagaa gcaggctgca aaaggatttc acccgttccg   4140
caagtgacac gtggggccgc acacctcatt accccagaag cccgggcaac tgcaaattca   4200
cgcttatata atccaattac catgatctag aactgcaatc gatactaatc gctcattgat   4260
cgtattaaga aaaaacttaa ctacataact tcaacattgg gggcgacagc tccagactaa   4320
gtgggtggct aagctctgac tgataaggaa tcatgaatca agcactcgtg attttgttgg   4380
tatctttcca gctcggcgtt gccttagata actcagtgtt ggctccaata ggagtagcta   4440
gcgcacagga gtggcaactg gcggcatata caacgaccct cacagggacc atcgcagtga   4500
gatttatccc ggtcctgcct gggaacctat caacatgtgc acaggagacg ctgcaggaat   4560
ataatagaac tgtgactaat atcttaggcc cgttgagaga gaacttggat gctctcctat   4620
ctgacttcga taaacctgca tcgaggttcg tgggcgccat cattgggtcg gtggccttgg   4680
gggtagcaac agctgcacaa atcacagccg ccgtggctct caatcaagca caagagaatg   4740
cccggaatat atggcgtctc aaggaatcga taaagaaaac caatgcggct gtgttggaat   4800
tgaaggatgg acttgcaacg actgctatag ctttggacaa agtgcaaaag tttatcaatg   4860
atgatattat accacagatt aaggacattg actgccaggt agttgcaaat aaattaggcg   4920
tctacctctc cttatactta acagagctta caactgtatt tggttctcag atcactaatc   4980
ctgcattatc aacgctctct taccaggcgc tgtacagctt atgtggaggg gatatgggaa   5040
agctaactga gctgatcggt gtcaatgcaa aggatgtggg atccctctac gaggctaacc   5100
```

-continued tcataaccgg ccaaatcgtt ggatatgacc ctgaactaca gataatcctc atacaagtat 5160
cttacccaag tgtgtctgaa gtgacaggag tccgggctac tgagttagtc actgtcagtg 5220
tcactacacc aaaaggagaa gggcaggcaa ttgttccgag atatgtggca cagagtagag 5280
tgctgacaga ggagttggat gtctcgactt gtaggtttag caaaacaact ctttattgta 5340
ggtcgattct cacacggccc ctaccaactt tgatcgccag ctgcctgtca gggaagtacg 5400
acgattgtca gtacacaaca gagataggag cgctatcttc gagattcatc acagtcaatg 5460
gtggagtcct tgcaaactgc agagcaattg tgtgtaagtg tgtctcaccc ccgcatataa 5520
taccacaaaa cgacattggc tccgtaacag ttattgactc aagtatatgc aaggaagttg 5580
tcttagagag tgtgcagctt aggttagaag gaaagctgtc atcccaatac ttctccaacg 5640
tgacaattga cctttcccaa atcacaacgt cagggtcgct ggatataagc agtgaaattg 5700
gtagcattaa caacacagtt aatcgggtcg acgagttaat caaggaatcc aacgagtggc 5760
tgaacgctgt gaacccccgc cttgtgaaca atacgagcat catagtcctc tgtgtccttg 5820
ccgccctgat tattgtctgg ctaatagcgc tgacagtatg cttctgttac tccgcaagat 5880
actcagctaa gtcaaaacag atgaggggcg ctatgacagg gatcgataat ccatatgtaa 5940
tacagagtgc aactaagatg tagagaggtt gaataagcct aaacatgata tgatttaaga 6000
aaaaattgga aggtgggggc gacagcccat tcaatgaagg gtgtacactc caacttgatc 6060
ttgtgacttg atcatcatac tcgaggcacc atggatttcc catctaggga gaacctggca 6120
gcaggtgaca tatcggggcg gaagacttgg agattactgt tccggatcct cacattgagc 6180
ataggtgtgg tctgtcttgc catcaatatt gccacaattg caaaattgga tcacctggat 6240
aacatggctt cgaacacatg gacaacaact gaggctgacc gtgtgatatc tagcatcacg 6300
actccgctca aagtccctgt caaccagatt aatgacatgt ttcggattgt agcgcttgac 6360
ctacctctgc agatgacatc attacagaaa gaaataacat cccaagtcgg gttcttggct 6420
gaaagtatca acaatgtttt atccaagaat ggatctgcag gcctggttct tgttaatgac 6480
cctgaatatg caggggggat cgctgtcagc ttgtaccaag gagatgcatc tgcaggccta 6540
aatttccagc ccatttcttt aatagaacat ccaagttttg tccctggtcc tactactgct 6600
aagggctgta taaggatccc gaccttccat atgggccctt cacattggtg ttactcacat 6660
aacatcattg catcaggttg ccaggatgcg agccactcca gtatgtatat ctctctgggg 6720
gtgctgaaag catcgcagac cgggtcgcct atcttcttga caacggccag ccatctcgtg 6780
gatgacaaca tcaaccggaa gtcatgcagc atcgtagcct caaaatacgg ttgtgatatc 6840
ctatgcagta ttgtgattga aacagagaat gaggattata ggtctgatcc ggctactagc 6900
atgattatag gtaggctgtt cttcaacggg tcatacacag agagcaagat taacacaggg 6960
tccatcttca gtctattctc tgctaactac cctgcggtgg ggtcgggtat tgtagtcggg 7020
gatgaagccg cattcccaat atatggtggg gtcaagcaga acacatggtt gttcaaccag 7080
ctcaaggatt ttggttactt cacccataat gatgtgtaca agtgcaatcg gactgatata 7140
cagcaaacta tcctggatgc atacaggcca cctaaaatct caggaaggtt atgggtacaa 7200
ggcatcctat tgtgcccagt ttcactgaga cctgatcctg gctgtcgctt aaaggtgttc 7260
aataccagca atgtgatgat gggggcagaa gcgaggttga tccaagtagg ctcaaccgtg 7320
tatctatacc aacgctcatc ctcatggtgg gtggtaggac tgacttacaa attagatgtg 7380
tcagaaataa cttcacagac aggtaacaca ctcaaccatg tagaccccat tgcccataca 7440
aagttcccaa gaccatcttt caggcgagat gcgtgtgcga ggccaaacat atgccctgct 7500

-continued

```
gtctgtgtct ccggagttta tcaggacatt tggccgatca gtacagccac caataacagc   7560
aacattgtgt gggttggaca gtacttagaa gcattctatt ccaggaaaga cccaagaata   7620
gggatagcaa cccagtatga gtggaaagtc accaaccagc tgttcaattc gaatactgag   7680
ggagggtact caaccacaac atgcttccgg aacaccaaac gggacaaggc atattgtgta   7740
gtgatatcag agtacgctga tggggtgttc ggatcataca ggatcgttcc tcagcttata   7800
gagattagaa caaccaccgg taaatctgag tgatgcatca atcctaaatt ggaatgacca   7860
atcaaaagct acgtagtgtc taacagcatt gcgaagcctg gtttaagaaa aaacttgggg   7920
gcgaatgccc atcaaccatg gatcaaactc aagctgacac tataatacaa cctgaagtcc   7980
atctgaattc accacttgtt cgcgcaaaat tggttcttct atggaaattg actgggttac   8040
ctttgccgtc tgatttgaga tcatttgtac taactacaca tgcagctgat gaccaaatcg   8100
caaaaaatga gactaggatc aaggccaaaa ttaattccct aatcgataac ttaatcaaac   8160
actgcaaggc aaggcaagtg gcactttcag ggttgacacc tgtcgtacat ccaacaactc   8220
tacagtggtt gctatccatc acatgtgaac gagcagacca ccttgcaaaa gtacgcgaga   8280
aatcagttaa gcaagcaatg tcagagaagc aacacgggtt tagacatctc ttttcggcag   8340
taagtcatca gttagttgga aacgccacac tgttctgtgc acaagactct agcaccgtga   8400
atgtcgactc tccttgctca tcaggttgtg agaggctgat aatagactct attggagcct   8460
tacaaacacg atggacaaga tgtaggtggg cttggcttca cattaaacag gtaatgagat   8520
accaggtgct tcagagtcgc ctacacgctc atgccaattc tgttagcaca tggtctgagg   8580
cgtgggggtt cattgggatc acaccagata tagtccttat tgtagactat aagagcaaaa   8640
tgtttactat cctgaccttc gaaatgatgc tgatgtattc agatgtcata gagggtcgtg   8700
ataatgtggt agctgtagga agtatgtcac caaacctaca gcctgtggtg gagaggattg   8760
aggtgctgtt tgatgtagtg gacaccttgg cgaggaggat tcatgatcct atttatgatc   8820
tggttgctgc cttagaaagc atggcatacg ctgccgtcca attgcacgat gctagtgaga   8880
cacacgcagg ggaattcttt tcgttcaatt tgacagaaat agagtccact cttgccccct   8940
tgctggatcc tggccaagtc ctatcggtga tgaggactat cagttattgt tacagtgggc   9000
tatcgcctga ccaagctgca gagttgctct gtgtgatgcg cttatttgga caccctctgc   9060
tctccgcaca acaagcagcc aaaaaagtcc gggagtctat gtgtgcccct aaactgttag   9120
agcatgatgc aatactgcaa actctatctt tcttcaaggg aatcataatc aatggctaca   9180
ggaaaagtca ttctggagta tggcctgcaa ttgacccaga ttctatagtg gacgatgacc   9240
ttagacagct gtattacgag tcggcagaaa tttcacatgc tttcatgctt aagaaatatc   9300
ggtaccttag tatgattgag ttccgcaaga gcatagagtt tgacttaaat gatgacctga   9360
gcacattcct taaagacaaa gcaatctgca ggccaaaaga tcaatgggca cgcatcttcc   9420
ggaaatcatt gttcccttgc aaaacgaacc ttggcactag tatagatgtt aaaagtaatc   9480
gactgttgat agatttttg gagtcacatg acttcaatcc tgaggaagaa atgaagtatg   9540
tgactacgct agcatacctg gcagataatc aattctcagc atcatattca ctgaaggaga   9600
aagagatcaa gactactggc cggatcttcg ccaaaatgac caggaaaatg aggagctgtc   9660
aagtaatatt ggaatcacta ttgtccagtc acgtctgcaa attctttaag gagaacggtg   9720
tgtcaatgga acaactgtct ttgacaaaga gcttgcttgc aatgtcacag ttagcaccca   9780
ggatatcttc agttcgccag gcgacagcac gtagacagga cccaggactc agccactcta   9840
atggttgtaa tcacattgta ggagacttag gcccacacca gcaggacaga ccggcccgga   9900
```

```
agagtgtagt cgcaaccttc cttacaacag atcttcaaaa atattgcttg aattggcgat   9960
atgggagtat caagcttttc gcccaagcct taaaccagct attcggaatc gagcatgggt  10020
ttgaatggat acacctgaga ctgatgaata gcaccctgtt tgtcggggac ccattctcgc  10080
ctcctgaaag caaagtgctg agtgatcttg atgatgcgcc caattcagac atatttatcg  10140
tgtccgccag aggggggatt gaagggttat gccagaagct gtggaccatg atttcaataa  10200
gcataatcca ttgcgtggct gagaagatag gagcaagggt tgcggcgatg gttcagggag  10260
ataatcaggt aattgcaatc acgagagagc tgtataaggg agagacttac acgcagattc  10320
agccggagtt agatcgatta ggcaatgcat tttttgctga attcaaaaga cacaactatg  10380
caatgggaca taatctgaag cccaaagaga caatccaaag tcaatcattc tttgtgtatt  10440
cgaaacggat tttctgggaa gggagaattc ttagtcaagc actgaagaat gctaccaaac  10500
tatgcttcat tgcagatcac ctcggggata atactgtctc atcatgcagc aatctagcct  10560
ctacgataac ccgcttggtt gagaatgggt atgaaaagga cacagcattc attctgaata  10620
tcatctcagc aatgactcag ttgctgattg atgagcaata ttccctacaa ggagactact  10680
cagctgtgag aaaactgatt gggtcatcaa attaccgtaa tctcttagtg gcgtcgctca  10740
tgcctggtca ggttggcggc tataatttct tgaatatcag tcgcctattc acacgcaata  10800
ttggtgatcc agtaacatgc gccatagcag atctgaagtg gttcattagg agcgggttaa  10860
tcccagagtt catcctgaag aatatattac tacgagatcc cggagacgat atgtggagta  10920
ctctatgtgc tgacccttac gcattaaata tcccctacac tcagctaccc acaacatacc  10980
tgaagaagca tactcagagg gcattactat ccgattctaa taatccgctt cttgcagggg  11040
tgcaattgga caatcaatac attgaagagg aggagtttgc acgattcctt ttggatcggg  11100
aatccgtgat gcctcgagtg gcacacacaa tcatggagtc aagtatacta gggaagagaa  11160
agaacatcca gggtttaatc gacactaccc ctacaatcat taagactgca ctcatgaggc  11220
agcccatatc tcgtagaaag tgtgataaaa tagttaatta ctcgattaac tacctgactg  11280
agtgccacga ttcattattg tcctgtagga cattcgagcc aaggaaggaa ataatatggg  11340
agtcagctat gatctcagta gaaacttgca gtgtcacaat tgcggagttc ctgcgcgcca  11400
ccagctggtc caacatcctg aacggtagga ctatttcggg tgtaacatct ccagacacta  11460
tagagctgct caaggggtca ttaattggag agaatgccca ttgtattctt tgtgagcagg  11520
gagacgagac attcacgtgg atgcacttag ccgggcccat ctatatacca gacccggggg  11580
tgaccgcatc caagatgaga gtgccgtatc ttgggtcaaa gacagaggaa aggcgtacgg  11640
catccatggc caccattaag ggcatgtctc accacctaaa ggccgctttg cgaggagcct  11700
ctgtgatggt gtgggccttt ggtgatactg aagaaagttg ggaacatgcc tgccttgtgg  11760
ccaatacaag gtgcaagatt aatcttccgc agctacgcct gctgaccccg acaccaagca  11820
gctctaacat ccaacatcga ctaaatgatg gtatcagcgt gcaaaaattt acacctgcta  11880
gcttatcccg agtggcgtca tttgttcaca tttgcaacga tttccaaaag ctagagagag  11940
atggatcttc cgtagactct aacttgatat atcagcaaat catgctgact ggtctaagta  12000
ttatggagac acttcatcct atgcacgtct catgggtata caacaatcag acaattcact  12060
tacataccgg aacatcgtgt tgtcctaggg aaatagagac aagcattgtt aatcccgcta  12120
ggggagaatt cccaacaata actctcacaa ctaacaatca gtttctgttt gattgtaatc  12180
ccatacatga tgaggcactt acaaaactgt cagtaagtga gttcaagttc caggagctta  12240
atatagactc aatgcagggt tacagtgctg tgaacctgct gagcagatgt gtggctaagc  12300
```

-continued

```
tgatagggga atgcattctg gaagacggta tcggatcgtc aatcaagaat gaagcaatga  12360
tatcatttga taactctatc aactggattt ctgaagcact caatagtgac ctgcgtttgg  12420
tattcctcca gctggggcaa gaactacttt gtgacctggc gtaccaaatg tactatctga  12480
gggtcatcgg ctatcattcc atcgtggcat atctgcagaa tactctagaa agaattcctg  12540
ttatccaact cgcaaacatg gcactcacca tatcccaccc agaagtatgg aggagagtga  12600
cagtgagcgg attcaaccaa ggttaccgga gtccctatct ggccactgtc gactttatcg  12660
ccgcatgtcg tgatatcatt gtgcaaggtg cccagcatta tatggctgat ttgttgtcag  12720
gagtagagtg ccaatataca ttctttaatg ttcaagacgg cgatctgaca ccgaagatgg  12780
aacaattttt agcccggcgc atgtgcttgt ttgtattgtt aactgggacg atccgaccac  12840
tcccaatcat acgatccctt aatgcgattg agaaatgtgc aattctcact cagttcttgt  12900
attacctacc gtcagtcgac atggcagtag cagacaaggc tcgtgtgtta tatcaactgt  12960
caataaatcc gaaaatagat gctttagtct ccaacctttta tttcaccaca aggaggttgc  13020
tttcaaatat caggggagat tcttcttcac gagcgcaaat tgcattcctc tacgaggagg  13080
aagtaatcgt tgatgtgcct gcatctaatc aatttgatca gtaccatcgt gaccccatcc  13140
taagaggagg tctatttttc tctctctcct taaaaatgga aaggatgtct ctgaaccgat  13200
ttgcagtaca gaccctgcca acccaggggt ctaactcgca gggttcacga cagaccttgt  13260
ggcgtgcctc accgttagca cactgcctta aatcagtagg gcaggtaagt accagctggt  13320
acaagtatgc tgtagtgggg gcgtctgtag agaaagtcca accaacaaga tcaacaagcc  13380
tctacatcgg ggagggcagt gggagtgtca tgacattatt agagtatctg gaccctgcta  13440
caattatctt ctacaactcg ctattcagca atagcatgaa ccctccacaa aggaatttcg  13500
gactgatgcc cacacagttt caggactcag tcgtgtataa aaacatatca gcaggagttg  13560
actgcaagta cgggtttaag caagtctttc aaccattatg gcgtgatgta gatcaagaaa  13620
caaatgtggt agagacggcg ttcctaaact atgtgatgga agtagtgcca gtccactctt  13680
cgaagcgtgt cgtatgtgaa gttgagtttg acagggggat gcctgacgag atagtaataa  13740
cagggtacat acacgtgctg atggtgaccg catacagtct gcatcgagga gggcgtctaa  13800
taatcaaggt ctatcgtcac tccgaggctg tattccaatt cgtactctct gcgatagtca  13860
tgatgtttgg ggggcttgat atacaccgga actcgtacat gtcaactaac aaagaggagt  13920
acatcatcat agctgcggcg ccggaggcat taaactattc ctctgtacca gcaatattgc  13980
agagggtgaa gtctgttatt gaccagcagc ttacattaat ctctcctata gatctagaaa  14040
gattgcgcca tgagactgag tctctccgtg agaaggagaa taatctagta atatctctga  14100
cgagagggaa gtatcaactc cggccgacac agactgatat gcttctatca tacctaggtg  14160
ggagattcat caccctattc ggacagtctg ctagggattt gatggccact gatgttgctg  14220
accttgatgc taggaagatt gcattagttg atctactgat ggtggaatcc aacattattt  14280
taagtgagag cacagacttg gaccttgcac tgttgctgag cccgtttaac ttagacaaag  14340
ggcggaagat agttacccta gcaaaggcta ctacccgcca attgctgccc gtgtatatcg  14400
catcagagat aatgtgcaat cggcaggcat tcacacacct gacatcaatt atacagcgtg  14460
gtgtcataag aatagaaaac atgcttgcta caacggaatt tgtccgacag tcagttcgcc  14520
cccagttcat aaaggaggtg ataactatag cccaagtcaa ccaccttttt tcagatctat  14580
ccaaactcgt gctttctcga tctgaagtca agcaagcact taaatttgtc ggttgctgta  14640
tgaagttcag aaatgcaagc aattaaacag gattgttatt gtcaaatcac cggttactat  14700
```

agtcaaatta atatgtaaag ttccctcttt caagagtgat taagaaaaaa cgcgtcaaag 14760
gtggcggttt cactgatttg ctcttggaag ttgggcatcc tccagccaat atatcggtgc 14820
cgaaatcgaa agtctgacag ctgatttgga atataagcac tgcataatca ctgagttacg 14880
ttgctttgct attccatgtc tggt 14904

<210> SEQ ID NO 17
<211> LENGTH: 16272
<212> TYPE: DNA
<213> ORGANISM: artificial sequence
<220> FEATURE:
<223> OTHER INFORMATION: APMV3 genome sequence

<400> SEQUENCE: 17
actaaacaga aaattaatac ttgttagtag tcgccgatta atccgctaat atattaggag 60
cggaagtcct acactccgcc tccgaccacg aattgaaatc atcatggctg gaatttttaa 120
tacttatgag ctctttgtta aggatcagac atgtatgcac aagagggctg caagcctaat 180
atcgggaggt cagcttaaaa gcaatatacc agtcttcatc accacaaaag atgatccagc 240
tgtccgatgg gaccttgtat gttttaatct ccgacttgtt gttagtgaat catctacctc 300
ggtgatccgg cagggggctc ttatatcatt gctttccatt actgctagca atatgagggc 360
tcttgcagca attgctgggc agactgatga atcgatgatt aatattatag aagttgtgga 420
ctttgatgga cttgagcccc agtgtgacac tcgcagtggc ttagacgctc agaagcagga 480
gatgtttaag gatattgccc gtgatatgcc gagggcacta tccagcggga ccccgttcca 540
gcacggaaat gcggaagcga atgggcctga agacacacac atgttcctcc gatccgcaat 600
tagcgttctg acacagatct ggatcctggt tgcaaaagcc atgactaaca ttgatggcag 660
caacgaggca agcgatcgcc gccttgccaa gtatattcaa cagaatagaa ttgacaggcg 720
attcatgctt gctcaagcta ccaggactgt atgtcagcag gtcataaagg attctttgac 780
cttgagaagg ttccttgtaa ctgagcttcg aaagtcgcgg ggggcattgc atagcgggtc 840
atcttactat gctatgattg gagacatgca ggcatacata tttaatgcag gccttacacc 900
attcctcact accctcaggt acgggatcgg gactaaatac catgcccttg caattagctc 960
acttgcaggt gacctgaata agattaaggg gttactgact ctatacaaag agaaagggag 1020
tgatgcgggc tatatggcac ttctagagga tgctgactgc atgcaatttg cgccaggtaa 1080
ttactcacta ttatattcat atgcgatggg agtagcaagt gtacatgatg aaggcatgag 1140
gaattaccaa tacgcccggc gcttcctcca taaggggatg taccaatttg gacgtgatat 1200
cgcaacacaa cagcaacatg cacttgatga atccctcgcc caggagatga gaatcacaga 1260
ggctgacagg gcaaatctca aggtaatgat ggcaaacatt ggggaagcat caagcttcag 1320
tgatatgcct aatccaggag ctagcggcat tcctgccttc aatgaccgcc ctgatgagat 1380
cttctctgag ccaggctatc gcaagccccc tcaagatcag ccgctgataa agctcccaga 1440
tctcgaggaa gaagagcagg acgaattcga catgtagaga gccgcccacc acccagagcc 1500
agcgacaaac ccaggcaaaa caacccacca tctccgaccc ggaacacaac gcaacatcga 1560
ggaccccggg cagccgacac cgcagccgca agacctccgc atcatgaacg accagcatcc 1620
aaacatctgt cctccctatt ctatcagttt aataaaaaag gctttcgtgc acagacagag 1680
atcctgacat aattcagccg gggggattca acttaggagc ggaagtatcc ctcctaacct 1740
gcacctgcat ttcaatatgg atcttgagtt tagtagtgag gaagcagtcg cagccctctt 1800
ggatgtgagt tcctcaacca taaccgaggt tctgagcaag caaagtattc ctgaccctag 1860

-continued

```
ctttctcacg tccacggagg catccggtga gcaagttcca gattcgaagg tcgccaatca   1920
caaagccagt gtcgataaga ccccagatca aggccaacca tcggcaacgc cttcggctcc   1980
tcctgagact gccgaaaaca tcaatacacc atcttgcgag gacggtttac cccctaactt   2040
cttcatccca agggtagaga gttaccacac taaccttttt aaagggggcc cccaattgga   2100
ctcaacggag cggccgcctg gtcaccaaat agtttgcgga gatcaagacg cggacctctc   2160
ccgagccggg atagcgagaa agaagaagaa gcagaagcat tgcaaagcgc tcaacttttc   2220
ggaatcccca ctcacagaca atcaggccat agaagggagt attcaatctc atggagccct   2280
ggatcaggaa ccttccagac agagacctgg tgcaacccag cctgctctcc agtcaccgcc   2340
ttcccaaaac aatacaagtg tgcatgcaga cagtgcccaa gattctgcga tctctgtttc   2400
aatcccgctg actatggtgg aatcattgat ctctcaagtg tcaaagttgt cggaccaagt   2460
ctcgcagata cagaagttgg tgagtaccct tcctcaaatt aagactgata ttgcttcgat   2520
tcggaacatg caagcagctt tggaaggaca gctcagtatg attcgtatat tggatccagg   2580
aaactgttcg gaatcatcac tcaatgcgct gagagggttc agtggtaagg cacctgttat   2640
tgtgagtggt ccaggaaatc ccaatcaatg catcagccaa ggctcatcca ccacaatttg   2700
cctggatgag ttagcccggc ctgtgccaaa tcctatacag gtgaaacttc aagatgatca   2760
gaaggaccta tctgcacagc gacatgctgt cattgcatta ctcgaaacca gaatcccccc   2820
gggaccaaaa cgtgacaaat tactgtcatt ggttgcaatt gcaaagactg caagtgattt   2880
aatcaagatt aagagaatgg cagtcctcgg ccagtgatat caccctatgg caaccaggct   2940
acaaatgtaa gcagtttccg atatgtaccg aatcaataac acgacccctt ccgcaaaagc   3000
aagcgcgagc atgacacact cagcttcagc caattctagc ttcactaagc aggtgatctg   3060
accatctggc tttacttccg ctttataaaa aactcctaga tctaacatgg aggcagaccg   3120
agctaatgcg gagggagtac acaaggggaa tcaaaggagc ggaaggtact aagtcactcc   3180
accgcctgcc ctcgcccatc cgcagcctcc cccaacccgc ggcccaggct ccattcaaaa   3240
accatggccg ctgctctcgg gaacatgcac ccgtcatcgt cgattactct tatgcatgat   3300
gacccgtcca tccagacgca gttgctagcc ttccctctga taagtgagaa gacagagaca   3360
gggacgacaa agctgcagcc tcaagtgaga atgcaatctt tcctatcaac cgatagccag   3420
aagtatcatc tggtctttat caacacatat ggtttcattg cggaggattt taattgtagt   3480
ccagcaaacg gatttgtgcc tgcactattt caacccaagt ctaaagtctt atcgtcagcg   3540
atggttacac ttggggctgt ccctgctgac actgttctcc aggacctaca acgggactta   3600
atcgcaatga gatttaaagt ccgaaagagt gcgtcacgaa tggagctaat attattctcc   3660
acagacaatg tccctgcaac attaacaggg tcatcagtct ggaagaataa aggagtaata   3720
gctgatacag caactgcagt taaagcgccc ggtcgcatct catgcgatgc ggtatgcagt   3780
tattgcatta cattcatctc tttttgcttc ttccactcat ctgctctttt taaggtgccc   3840
aagcctctgc tgaatttcga gacggccata gcatattccc ttgtactcca ggtcgagctt   3900
gagttcccaa atatcaaaga taccttacac gagaagtatc tcaaagttaa agactcgaag   3960
tggtattgta caattgacat ccatattggg aatcttttaa agagaaccgc caagcaacga   4020
aggaggacac cttcagagat aatgcagaaa gtccgtaaga tgggtttcag gattgggtta   4080
tacgatttgt ggggtccaac aattgtggtt gaattaactg ggtcctcaag taagtcccta   4140
cacggattct tctcgagtga gcggctggcc tgccacccgg tatcacagta taatcctcat   4200
gttggacagc ttatctgggc acacgatgta tccatcacgg ggtgccacat gattatatct   4260
```

-continued gaacttgaga aaaagaaggc acttgcaatg gctgacctga ccgtgagtga tgcagtagct 4320
gtcaacacga gcatcaagag cttatcgcct ttcagactgt tcaaaaaata taagggcaag 4380
acaactccaa gggtgtgtgc ttataatttg catattctag attataatca ttaaccgcgt 4440
ccaaatgatc agaccgcata attaacagct cagccaggac tcgcaaatcc tgcataggct 4500
caaataacaa gacgacatat atactcacac aacaaggtgt aatatctaga aggaatcaga 4560
attgagacaa tatctaggtt atcagcgcta ctgccctgca actcactatg tatgcttggc 4620
attaataaaa aacattgtga gaatgcaatt taaggacgaa agtaggagcg gaacacgctc 4680
aactgaaccc aagcgcacac cagccccccg gcaccgcacc ggaaggacgc acaacagccg 4740
accgccccca ccagggcaga ggccatgcaa ccaggctcgg cactccacct cccgcacctg 4800
tacataataa ttgccttagt cagcgatggc actttaggcc aaacagctaa aattgatagg 4860
ctgatacagg cagggattgt cttgggtagt ggaaaggagc tccatatctc acaagattca 4920
gggacactgg atttattcgt gaggttgtta ccagtactcc cttcgaattt gtcccattgc 4980
cagcttgaag caataacaca gtataataag acggtgacta ggttattggc cccaataggg 5040
aagaacctag aacaggtact acaagcgaga ccgcgtggga ggctgttcgg tccaataata 5100
gggtccatcg cgcttggtgt tgccacatca gcacagatta ccgctgctat tgcactcgtc 5160
cgtgcacagc aaaatgctaa tgatatatta gcacttaaaa acgctctcca atccagcaat 5220
gaggcaatcc gtcaactcac gtatggccag gacaaacagt tacttgcaat ttctaaaata 5280
caaaaagctg tgaatgagca gatcctccct gcactcgatc agctggactg tgctgtcctt 5340
ggaaccaaac tagctgtgca gcttaatctg tatctcattg agatgactac cattttcggc 5400
gagcaaatca ataatccagt cttggcgacc atcccattaa gttacatttt acgcctgacc 5460
ggtgcggagt tgaacaacgt cctcatgaag caagcccgat cgtccttaag ccttgtacag 5520
ttagtttcaa aaggcttact tagtggacaa gtaattggct atgacccatc tgttcaaggt 5580
ctgataataa gggtgaatct gatgcgaacg cagaagatcg atagagcact agtttatcag 5640
ccgtatgtat taccaatcac tcttaactct aacatagtaa caccaatagc cccagaatgc 5700
gtaattcaga aagggacgat catagagggt atgtcacgga aggattgtac agagttggag 5760
caagacataa tttgtaggac agttacgaca tacacgcttg ccagagacac cagattgtgt 5820
ttacaaggca atatctcttc ttgtaggtat caacagtcag gcacccaact acacacccca 5880
tttattacgt acaacggggc agttatcgca aactgtgatt tagtctcttg tcggtgtctc 5940
cgtcctccta tgattatcac ccaagtaaaa gggtaccctc ttaccataat cacaaggtcc 6000
gtatgtcaag aattatccgt tgacaactta gtcctgaata ttgagacaca ccataatttc 6060
tcccttaatc caacaattat cgaccctcta acaagagtaa tagccactac accgttagag 6120
atagattcct taatccaaga ggcacaagat catgcgaatg cagcgctagc taaagtggaa 6180
gagagtgata aatatctcag ggcagttact ggcggtaatt attcgaattg gtatatcgtt 6240
cttgtcatcg tcttactatt tgggaatttg ggctggtcgc tgttgttaac agtacttcta 6300
tgtaggtcac ggaaacaaca gcgacgttat caacaagatg attccgtcgg gtcagaaaga 6360
ggtgttgggg ttgggaccat ccagtatatg tcataagtgg tgtcagacat cacaatccaa 6420
gtcactcagt tatctactcc gctggctcgg agccatcgac aacggggggg agccctcatc 6480
cggggacaat ccacaacctg atactaccag acagtggctc cgcacgatgg cagcagccca 6540
caacgtcctg catgtaaata tcattgcgtt actttaatta aaaaacctca aggtgaccca 6600
tcctggccca tccgattgga ggagcggaag gttttaaggt aatcaggcaa attgtttcca 6660

```
acatggaatc ccctccttct ggcaaggatg cgccagcctt ccgcgagcct aagcgaactt    6720

gcagactctg ttacagggcg acgactctct cccttaatct caccatcgtt gtattatcaa    6780

ttataagcat ttatgtatca actcaaactg gggcaaacaa ctcttgtgtc aatcccacaa    6840

tcgtaactcc tgattattta actggcagca cgacaggctc agttgaagat cttgctgact    6900

tagagagtca actccgggag atacgtagag acacagggat taatctccca gttcagatcg    6960

ataatacaga aaatctaata ctgacaactc tggcgagtat caactcgaat ttacgctttc    7020

tgcaaaatgc aacaactgag agccagacct gcctatctcc tgtcaatgac cctcgctttg    7080

tagctggcat aaataggatc ccagcagggt cgatggcata taatgacttc agcaacctca    7140

ttgagcacgt aaatttcata ccgtcgccga caacgttgtc aggctgcacc aggataccat    7200

cattttcact ctctaagacg cactggtgtt atacccacaa tgttatatca aacgggtgcc    7260

ttgaccatgc tgcaagttca caatacatct caatagggat cgttgatacc ggcctaaata    7320

atgagcccta ttttagaaca atgtcttcaa agtcactgaa tgacggatta aatagaaaga    7380

gttgctctgt gaccgcagcc gctaatgcat gttggttact ctgtagcgta gtaacagaat    7440

acgaagctgc ggactatcga tcacgaactc ctactgctat ggttctgggg cgattcgatt    7500

ttaatggtga atacacagaa atagctgtcc cctcctcact attcgatggc cggtttgcat    7560

ctaactatcc aggtgtggga tcgggaactc aagtcaatgg aacattatat ttccctttat    7620

atggaggggt ccttaatggg tcagatatag aaacggcaaa caaggggaaa tccttcaggc    7680

ctcagaatcc taagaatagg tgtccagact cggaggcgat ccaaagcttt agagcgcaag    7740

atagctatta cccgacgaga tttgggaagg tgctgatcca acaggcaatc attgcatgta    7800

ggatcagtaa caaaagttgt actgatttct atctcctgta cttcgacaac aacagagtga    7860

tgatgggtgc agaggcacgg ctatattatc ttaataacca attatatcta tatcaacgct    7920

cgtcgagctg gtggccgcat cctttgttct atagcatctc attaccgtca tgtcaagccc    7980

ttgctgtctg tcaaattaca gaggcccatc tgacactgac ttacgccacg tcgaggccag    8040

gaatgtctat ctgtacagga gcatcaaggt gtccaaataa ttgcgtagac ggtgtatata    8100

ctgatgtatg gccattgaca aagaacgatg ctcaggaccc caatctcttc tacactgtat    8160

acttaaataa ttcaactcgg cggattagcc caaccataag tctatacact tatgaccgca    8220

ggatcaaatc taagctggca gtgggtagtg atataggagc agcttatacc acgagtacct    8280

gtttcggccg atcagataca ggggcggttt attgcttaac tataatggag accgttaaca    8340

caatatttgg tcagtaccgg atcgtgccaa tattacttag agtgacaagc cggtaatgga    8400

ttgttcctag tgaagtgggg cctatggtta ctccgtaacg gagatgacct gatttatgct    8460

atgtaactaa ttttgctcaa tcgggagggt gatcggccgg gtatgtccac aatgacaatg    8520

actcctattc ccttgctaga gctagcttcc tctttaatcc aatacaatcc ctacctgtag    8580

tttaataaaa aaatcctcta tataagatcc agacgaaggc tatataagct aatagcttag    8640

gatggaaacg acaggagcgg aacatatccc tcctaccatg tcttctcata atattatcct    8700

ccctgaccac cacttaaatt cccctattgt actaaataaa ttgatgtact attgtaaact    8760

ccttaatata ttgcctgacc ctaagtcgcc atggtacgag aagattaagt cttggactaa    8820

ttgctgcatc cgtgtgtcag acagcaatcg catgactttg tcacgcgcct ccaagctacg    8880

agaactattg gcaacgtacg gcgtatattc gaagaaccac cagcaatgtt ataccaccat    8940

aatccatccc caatccctat cacccatcat gcagactgtc tctcaactgg gacgctcaat    9000

cccgacctgg gccaggatcc gaaaggagat cacacacagt atcatagccc aaacgaataa    9060
```

-continued

```
atttgaatcc ttattccaca acatctcaaa ggacctgaca gggaaaacca acttgtttgg   9120
cggattctgt gatttacatg ggagcataag cactgctgca aagcgcttaa tgaatcaacc   9180
gggtctctac ttggattcac ctgatgccca tgcatgtcaa tttttgttcc agcttaaaac   9240
ctgtcaacgg gaattgattc tacttatgag gcagaatgcc acaacagagc tgattagggt   9300
ttttgactat cctgagctac gggttcttgt gacacctgaa tattcggtct gggtttttac   9360
acggaccaaa caagttacat tactaacatt cgattgcttg ttaatgtact gcgatctttc   9420
agacggccgg cacaacatcc tattcacttg taagcttttg tctcacttaa accacctcgg   9480
gtgtcggata agggacctgc tggtgctaat tgattcactt gccgagaaac accccttaat   9540
agtttatgat gtagttgcaa gtctggagtc gttatcatat ggtgctatac agctacatga   9600
caaggtagct ggttatgctg gaacattttt ctcatttatc cttgcagaaa tacaggattc   9660
cttagaaaca gtgttggatc aaggtaatag tgaatctatc atatcccaaa taaggaacat   9720
atactcaggt ctcacagtaa acgaggctgc agaattgcta tgtgttatga ggctttgggg   9780
ccaccctgcc ctaaacagtg tagacgctgc aagcaaggtg agacagagta tgtgcgctgg   9840
caagctgctt aaatttgata cgatccagtt agtccttgca ttcttcaata cactaataat   9900
taatggatat aggagaaagc accatgggcg atggccgaat gtttgtagtg actctataat   9960
tgggaatgaa ctcaagcgga tgtattttga tcaatgtgag atcccccacg acttcacatt  10020
aaagaactac cgggaattaa gtcttcttga attcgagtgc acatttccca tagaattatc  10080
agataaactg aacatatttt taaaagataa ggcaatagca ttcccgaagt ccaggtggac  10140
atctcctttc aaagcagata tcacaccgcg ccatttgctg caagcgcctg agtttaaaac  10200
ccgtgccaac agactactgc tatcattctt acaactcgag gaattctcca tcgaatcaga  10260
actagaatat gtgactaccc tggcttacct ggatgatgat gagttcaacg tatcttactc  10320
cctcaaagag aaggaggtaa agacagatgg tcgaatcttc gctaagctca caaggaaaat  10380
gcggagctgt caggtgatat tcgaagaatt gctagcagag catgtctctc cattatttaa  10440
agacaacggc gttactatgg ccgaattgtc acttactaag agcctactcg ctattagcaa  10500
cctaagctcc accttatttg agacgcaaac aaggcaaggc gatcggaatg caagattcac  10560
gcatgcgcac ttcataacaa ctgacctgca aaagtactgt ttaaactgga ggtaccagag  10620
tgtaaaactg ttcgcacgtc aattgaaccg gttatttggt ctgcagcatg ggtttgaatg  10680
gatccattgc atactaatga agtccactat gtatgtcgca gacccctta accctccaca   10740
tagcaatgca cgtgaggcac tcgatgacaa cttaaatagc gacatattca ttgtatcacc  10800
tagggggggcc atcgagggac tatgccaaaa aatgtggaca atcatctcaa tctcggcgat  10860
ccatgcatcc gctgctgtgg ctgggctacg ggtggcatct atggtccaag gtgataacca  10920
agttattggg gtaacacgcg agttcctagc tgggcatgat caaacttttg tagacgatca  10980
attgacggtt tcacttgaga acttcactca gatattcaag gaagtcaact acgggctagg  11040
tcataatctc aagctgaggg aaacaatcaa gtcgagccac atgttcatct actcaaagag  11100
gatcttctac gacggccgag tgcttccaca acttctaaag aacattcgta agttaaccct  11160
atcagctaca actacagggg agaactgttt aacgagttgc ggggacctat catcatgcat  11220
cacacgatgt atagagaatg ggttccctaa agatgcagca ttcgttttga atcaattagt  11280
gattaggatc cagatacttg ccgatcactt ttattccatc cttggaggat gtttctctgg  11340
gttgaaccag gcggatatcc gtctccttct atatgagggt gcaattttac cggcacaatt  11400
aggagggttc aacaacctca acatgtcacg gctattctgt cggaatattg gtgacccatt  11460
```

-continued

```
agtcgcgtcc atcgcagaca ccaagagatt tgtgaagtgc caactgctcg ttcctcacat  11520
tttagactct gtcgttgcta ttaccgatag gaaggggtct tttacgacac tgatgatgga  11580
tccatattca ataaacttgg attatatcca gcaaccagag acacgattga agcgacatgt  11640
gcaaaaggtt ttactacaag agtcagtgaa tccgctactc caaggggtct tcctagagtc  11700
tcaacaagag gaagaggaac aacttgcagc gttcttgctg gaccgagaag tcgtaatgcc  11760
aagggttgcg cacgctatat ttgagtgtac cagcttaggt aggcgccgac atatccaggg  11820
cctcatcgac acgacaaaga ccattattgc acttgcgttg gatacacagc agttaagtta  11880
tactaaacgt gaacagattg tgacgtacaa tgcaacttat atgaggtcct tagcaagcat  11940
gctcagttca agccataatc agacacgtcg gtctgtgatt ggtcacgcat ccttcaatat  12000
caccgactgc tcggtcatcc tggctcaaca agtgagacgt gcaagctggg cgcccttgct  12060
gaattggcgg tcattagaag gcttagaagt acccgaccct attgagtcag tagccggcta  12120
cctgggtttg gattctaaca actgtttctt atgctgccac gagcagaaca gctattcctg  12180
gtttttcctt ccccgaatgt gccattttga tgattcgaga caatctaact ccatacaaag  12240
ggtaccttac attggttcta agactgacga gcgccagatg tctacgataa atctacttga  12300
gaaaactacc tgtcatgcta gagcagctac gaggcttgca tcattataca tttgggcctt  12360
tggggactca gacgatagtt gggatgcagt cgagactcta tctaacagtc gatgccagat  12420
cacccgagag cacttgcaag ctctgtgccc tatgccctct tcagtgaatc tccaccatcg  12480
attgaacgac ggaataacac aagtgaagtt tatgccatcg accaatagca gggtctctcg  12540
atttgttcat atttccaatg accggcagaa ttacgtattg gatgactccg ttactgacag  12600
taatctgatt taccaacaag tcatgttgct aggacttagt atacttgaaa catatttcag  12660
agaacctaca gcgacgaact tatcaagctt ggtgctgcac cttcacactg atgtatcttg  12720
ttgcttacga gaatgcccga tgacacaata tgcgcccccc ctgcgagaca tcccagagtt  12780
aactataact gcgtcaaatc ctttcttatt tgatcaagaa cctattagcg aagcagacct  12840
gtgtagactc tcaaagatag cattccgtag agcaggagac aactacgatg catacgacca  12900
gtttcaacta agagcaacac tggccgcaac tacaggtaag gatgtggcag caacaatctt  12960
tggtcctcta gctgcagtat cagcaaaaaa tgatgcaata gtcacaaatg actatagcgg  13020
gaattggatt tccgagttta ggtatagtga tctctatctt ttgagtgtta gcctgggcta  13080
cgagatcctt ttgattttcg cgtatcaact ttactaccta cggatacggt accggcaaaa  13140
tattgtatgc tatatggaat ctgtattccg acgttgtcat tctttatgct tgggcgactt  13200
aatccagact atttcgcact ctgaaatact ggttgggtta aatgcagcgg gctttaatct  13260
taccttggat cgaagtgatt tgaaggagaa tcaactctcg cggcttgctg tgaaatacct  13320
cacattgtgt gtccagactg caataagtaa tttggaggta ggatcagaac ccctttgtat  13380
tattggaggt caattagatg atgacatatc attccaagtt gcccacttcc tctgtcgacg  13440
actgtgcatc atcagcttgg tccactcaaa tgtacagaac ttacccccga ttagggataa  13500
tgaagttgat gtaaaatcca agttgatcta cgaccatctt aagctagttg ctaccacact  13560
caataatagg gaccagtcgt atctgctaac actactgaat aagcctaaca tcgagcttca  13620
tactccacag gtttacttca ttatgaggaa gtgtctggga ttattaaaag tctatggacc  13680
tgtacctcaa aagcaaccac ttccaacctc cccagtagta tcactaccaa ataagtgcaa  13740
atcgaaatgg aagcttgagg aggtaattga cagcattgag tcacctaagt cttttaactg  13800
ggttcctgat acgacgattc cattggatgc tgagcaaaat cccccaaatc ctaacagggt  13860
```

-continued

```
catcgataag ataaacattc taagatctct gagcccgcgt cactcagtct ggtaccgtaa  13920
ccggcaatac cggtacgtgt tgagccagtt agggcatgac cagctaggtg gtgcaaccct  13980
atatcttggt gaagggagcg gctccacaat cttgaacata gagccaaaag tcaggagtga  14040
taagatatat tatcatacct atttctctgc agacaaaagc cctgcacagc gcaatttcat  14100
cccccagcca actacttttc tgcgatctaa cttttatcac tacgaattag agccgtctgg  14160
atgtgagttc atcaattgtt ggtccgagga tgtaaatgca acgaatctta cggaactgcg  14220
ttgcataaat cacatattaa ctgtgattcc agtcggatct ctaacacgta ttatttgtga  14280
cgtggaattg gcaaatgaca cgtcaataca atcagtggcc accgcataca tgaacttaag  14340
cattcttgca catgctctcc tcaaccaggg aggcgtytgc atctgtaggt gccacctgtt  14400
agacacgtcc catcttgcga ttgtttcgtt tgtacttaaa acattatcaa gccagctggc  14460
gatttcgttt tcaggatatt gtggaaccaa tgacccatct tgtgtcatag gagtcacgaa  14520
agagtgctcc attagcctgg atgtcttaag ttcgattgca gctgcattta taaatgaatt  14580
gccctcaaat gagctgccgg tccctcaatc attattaacg ctactagggt gttatcaaga  14640
ccagttagag agccttagtg cactcattga aaaaacatgg atccaggaga tccgggaggc  14700
ctcatttaat gcatgtgaga tggagtggat aggacttttg ggaacagatg cgctgggcga  14760
tgtcgacaca tttatcagtt atcgcaatga ttcgtgtaat tccatccctg atctactgac  14820
gccagctgtg agtgccctct tatttgaatt aatcagcctg acacctgagc ttcctggtac  14880
ggaggaccag ccgagtaggc gtgtaatcag cattggccaa gcttttaacc tgactatttc  14940
gggaaaagtt aatacgatga tcagatcatg ctgtgagcag tgcattaagt tattagctgc  15000
caatgtctcc atccttagtg atgtagattt gtcgtatttt gtgaggggga ttagagatgg  15060
ttcttttgct ttggggttgt taatcaccca gcgtcaaata ctcaaggcat cgagagcacc  15120
aaagtacctc aaaacgcatc aggtccagaa ctggattgcg ttgttactgg aggtcaaact  15180
agaggaaatc ttctctcgcc actaccggaa agtgctattg agaactctac ggctgttatc  15240
cctctacggg ctcctgcagc agaaggaaag ttgatcatga tagatgtctc tctgatttcg  15300
cctcagccct atatacagat acctgctact gctgttgtaa ctatgcaaat ataggctaac  15360
ctcggtccgg agtattgagg taatggggag actcgtaatt ggagaaagaa gaagaacggg  15420
gcagatacca gaccccggga tacactacta taagctactt gggtgactca ggacgtcact  15480
aataagagta cactggtttt aacaataaca ctgatagtgt aacactgaat attgtaaaca  15540
gtctcaggga ttatttaatt aaaaagacat tgcggatcat catgtcaggc ctgaaccaat  15600
cagaaaccca tcctacaggc atgagtcgat taatccagtt taatttagtc caagatgatt  15660
agtactctta gatgttacta agtatcagga tttagcgtac tagattaaac gtctttgaaa  15720
gtcattttac cctgcaaggt gcataagcat atgcagggga atacccacca ctggttcgtt  15780
agtctaattt attcaaagat gccaccaact gagtgcactg ggagtctgat tgagctgaat  15840
caacctaaag ctcaagcttt cctgtgatgt agcatgcagt gtgctactgc tgcatagagc  15900
caatcagggg cgtcttgaag gcctccacct tcctcaggca acgataaagc agctcactgc  15960
tacacccacc atgcaaatac aaggatatgt aggtccatca ccctgcttgc taatgtggtc  16020
ggctccagga ccatggccat agcgctatcc gtctaattca atccgcctca tcatatgcgt  16080
atacaatcct ccactgagaa atgcacctgc tcaatccaat gacaaactac aacaacacga  16140
gatcattatg ggtcgattc ccttgaatca gaaaggtaaa aacggcagcg gagatggaga  16200
ataccagacc taatcggcaa agaacaaaag gttgaagact gatttaaaaa tcattataac  16260
```

tttttgttta gt 16272

<210> SEQ ID NO 18
<211> LENGTH: 15054
<212> TYPE: DNA
<213> ORGANISM: artificial sequence
<220> FEATURE:
<223> OTHER INFORMATION: APMV4 genome sequence

<400> SEQUENCE: 18
acgaaaaaga agaataaaag gcagaagcct tttaaaagga accctgggct gtcgtaggtg 60
tgggaaggtt gtattccgag tgcgcctccg aggcatctac tctacaccta tcacaatggc 120
tggtgtcttc tcccagtatg agaggtttgt ggacaatcaa tcccaagtgt caaggaagga 180
tcatcggtcc ttagcaggag gatgccttaa agttaacatc cctatgcttg tcactgcatc 240
tgaagacccc accactcgtt ggcaactagc atgcttatct ctaaggctcc tgatctccaa 300
ctcatcaacc agtgctatcc gtcagggggc aatactgact ctcatgtcat taccatcaca 360
aaacatgaga gcaacagcag ctattgctgg ttccacaaat gcagctgtta tcaacaccat 420
ggaagtctta agtgtcaacg actggacccc atccttcgac cctaggagcg gtctttctga 480
ggaagatgct caagttttca gagacatggc aagagatctg ccccctcagt tcacctctgg 540
atcacccttc acatcagcat tggcggaggg gttcactcct gaagatactc atgacctgat 600
ggaggccttg accagtgtgc tgatacagat ctggatcctg gtggctaagg ccatgaccaa 660
cattgacggc tctggggagg ccaatgaaag acgtcttgca aagtacatcc aaaaaggaca 720
gcttaatcgt cagtttgcaa ttggtaatcc tgcccgtctg ataatccaac agacaatcaa 780
aagctcctta actgtccgta ggttcttggt ctctgagctt cgtgcgtcac gaggtgcagt 840
aaaagaagga tccccttact atgcagctgt tggggatatc cacgcttaca tctttaatgc 900
gggattgaca ccattcttga ccaccttaag atacgggata ggcaccaagt acgccgctgt 960
tgcactcagt gtgttcgctg cagatattgc aaagttgaag agcctactta ccctgtacca 1020
ggacaagggt gtagaagctg gatacatggc actccttgag gatccagact ccatgcactt 1080
tgcacctgga aacttcccac acatgtactc ctatgcaatg gggtagctt cttaccatga 1140 tcctagcatg cgccaatacc aatacgccag gaggttcctc agccgtcctt tctacttact 1200
aggaagggac atggccgcca agaacacagg cacgctggat gagcaactgg cgaaggaact 1260
gcaagtatca gagagagatc gcgccgcatt atccgctgcg attcaatcag cgatggaggg 1320
gggagagtcc gacgacttcc cactgtcggg atccatgccg gctctctctg agaatgcgca 1380
accagttacc cccagacctc aacagtccca gctctctccc ccccaatcat caaacatgcc 1440
ccaatcagca cccaggaccc cagactatca acccgacttt gaactgtagg cttcatcacc 1500
gcaccaacaa cagcccaaga agaccacccc tccccccaca catctcaccc agccacccat 1560
aaagactcag tcccacgccc cagcatctcc ttcatttaat taaaaaccga ccaacagggt 1620
ggggaaggag agtcattggc tactgccaat tgtgtgcagc aatggatttt actgacattg 1680
atgctgtcaa ctcattgatc gaatcatcat cggcaatcat agactccata cagcatggag 1740
ggctgcaacc agcgggcacc gtcggcctat cgcagatccc aaaagggata accagcgcat 1800
taaccaaggc ctgggaggct gaggcggcaa ctgccggtaa tggggacacc caacacaaat 1860
ctgacagtcc ggaggatcat caggccaacg acacagattc ccctgaagac acaggtactg 1920
accagaccac ccaggaggcc aacatcgttg agacacccca ccccgaggtg ctgtcagcag 1980
ccaaagccag actcaagagg cccaaagcag ggagggacac ccgcgacaac tcccctgcgc 2040

-continued

```
aacccgatca tcttttaaag gggggcctcc tgagcccaca accagcagca tcatgggtgc   2100
aaaatccacc cagtcatgga ggtcccggca ccgccgatcc ccgcccatca caaactcagg   2160
atcattcccc caccggagag aaatggcgat tgtcaccgac aaagcaaccg gagacattga   2220
actggtggag tggtgcaacc cggggtgcac agcagtccga attgaaccca ccagactcga   2280
ctgtgtatgc ggacactgcc ccaccatctg tagcctctgc atgtatgacg actgatcagg   2340
tacaactact aatgaaggag gttgctgaca taaaatcact ccttcaggcg ttagtgagga   2400
acctcgctgt cttgccccaa ttgaggaatg aggttgcagc aatcagaaca tcacaggcca   2460
tgatagaggg gacactcaat tcgatcaaga ttcttgaccc tgggaattat caggaatcat   2520
cactaaacag ttggttcaaa cctcgccaag atcacactgt tgttgtgtct ggaccaggga   2580
atccattggc catgccaacc ccagtccaag acaacaccat attcctggac gagctagcca   2640
gacctcatcc tagtgtggtc aatccttccc cacccatcac caacaccaat gttgaccttg   2700
gcccacagaa gcaggctgca atagcctata tctccgctaa atgcaaggat ccggggaaac   2760
gagatcagct atcaaggctc attgagcgag caaccacccc aagtgagatc aacaaagtta   2820
aaagacaagc ccttgggctc tagatcactc gatcacccct catggtgatc acaacaataa   2880
tcagaaccct tccgaaccac atgaccaacc cagcccaccg cccacaccgt ccatcgacat   2940
cccttgccaa acatcctgcc gtagctgatt tattcaaaag agctcatttg atatgacctg   3000
gtaatcataa aatagggtgg ggaaggtgct ttgcctgtaa gggggctccc tcatcttcag   3060
acacgtgccc gccatctcac caacagtgca atggcagaca tggacacggt gtatatcaat   3120
ctgatggcag atgacccaac ccaccaaaaa gaactgctgt cctttcctct catccctgtg   3180
accggtcctg acgggaagaa ggaactccaa caccagatcc ggacccaatc cttgctcgcc   3240
tcagacaaac aaactgaacg gttcatcttc ctcaacactt acggattcat ctatgacacc   3300
acaccggaca agacaacttt ttccacccca gagcatatta atcagcctaa gaggacgacg   3360
gtgagtgccg cgatgatgac cattggcctg gttcccgcca atatacccct gaacgaacta   3420
acggctactg tgttcagcct taaagtaaga gtgaggaaaa gtgcgaggta tcgggaagtg   3480
gtctggtatc aatgcaatcc agtaccggcc ctgcttgcag ccaccaggtt tggtcgccaa   3540
ggaggtctcg agtcgagcac tggagtcagt gtaaaggctc ccgagaagat agattgtgag   3600
aaggattata cctactaccc ttatttctta tctgtgtgct acatcgccac ctccaacctg   3660
ttcaaggtac cgaggatggt tgctaatgca accaacagtc aattatacca ccttaccatg   3720
caggtcacat ttgcctttcc aaaaaaacatc cctccagcca accagaaact cctgacacag   3780
gtggatgagg gattcgaggg cactgtggat tgccattttg ggaacatgct gaaaaaggat   3840
cggaaaggga acatgaggac actgtcccag gcggcagata aggtcagacg aatgaatatt   3900
cttgttggta tctttgactt gcatgggcca acgctcttcc tggagtatac cgggaaactg   3960
acaaaggctc tgctagggtt catgtccacc agccgaacag caatcatccc catatctcag   4020
ctcaatccca tgctgagtca actcatgtgg agcagtgatg cccagatagt aaagttaagg   4080
gttgtcataa ctacatccaa acgcggcccg tgcgggggtg agcaggagta tgtgctggat   4140
cccaaattca cagttaagaa agaaaaggct cgactcaacc ctttcgagaa ggcagcctaa   4200
tgatttaatc cgcaagatcc cagaaatcag accactctat actatccact gatcactgga   4260
aatgtaattg tacagttgat gaatctgtga agaatcaatt aaaaaaccgg atccttatta   4320
gggtggggaa gtagttgatt gggtgtctaa acaaaagcat ttcttcacac ctccccgcca   4380
cgaaacaacc acaatgaggc tatcaaacac aatcttgacc ttgattctca tcatacttac   4440
```

-continued cggctatttg ataggtgtcc actccaccga tgtgaatgag aaaccaaagt ccgaagggat 4500
taggggtgat cttacaccag gtgcgggtat tttcgtaact caagtccgac agctccagat 4560
ctaccaacag tctgggtacc atgatcttgt catcagattg ttacctcttc taccaacaga 4620
gcttaatgat tgtcaaaggg aagttgtcac agagtacaat aacactgtat cacagctgtt 4680
gcagcctatc aaaaccaacc tggatacttt gttggcagat ggtagcacaa gggatgttga 4740
tatacagccg cgattcattg gggcaataat agccacaggt gccctggctg tagcaacggt 4800
agctgaggta actgcagctc aagcactatc tcagtcaaaa acgaatgctc aaaatattct 4860
caagttgaga gatagtattc aggccaccaa ccaagcagtt tttgaaattt cacagggact 4920
cgaagcaact gcaaccgtgc tatcaaaact gcaaactgag ctcaatgaga atatcatccc 4980
aagtctgaac aacttgtcct gtgctgccat ggggaatcgc cttggtgtat cactctcact 5040
ctatttgacc ttaatgacca ctctatttgg ggaccagatc acaaacccag tgctgacgcc 5100
aatctcttac agcaccctat cggcaatggc gggtggtcac attggtccag tgatgagtaa 5160
gatattagcc ggatctgtca caagtcagtt gggggcagaa caactgattg ctagtggctt 5220
aatacagtca caggtagtag gttatgattc ccagtatcag ctgttggtta tcagggtcaa 5280
ccttgtacgg attcaggaag tccagaatac tagggttgta tcactaagaa cactagcagt 5340
caatagggat ggtggacttt acagagccca ggtgccaccc gaggtagttg agcgatctgg 5400
cattgcagag cggttttatg cagatgattg tgttctaact acaactgatt acatctgctc 5460
atcgatccga tcttctcggc ttaatccaga gttagtcaag tgtctcagtg gggcacttga 5520
ttcatgcaca tttgagaggg aaagtgcatt actgtcaact cccttctttg tatacaacaa 5580
ggcagtcgtc gcaaattgta aagcagcgac atgtagatgt aataaaccgc catctatcat 5640
tgcccaatac tctgcatcag ctctagtaac catcaccacc gacacttgtg ctgaccttga 5700
aattgagggt tatcgtttca acatacagac tgaatccaac tcatgggttg caccaaactt 5760
cacggtctca acctcacaaa tagtatcggt tgatccaata gacatatcct ctgacattgc 5820
caaaattaac aattctatcg aggctgcgcg agagcagctg gaactgagca accagatcct 5880
ttcccgaatc aacccacgga ttgtgaacga cgaatcacta atagctatta tcgtgacaat 5940
tgttgtgctt agtctccttg taattggtct tattattgtt ctcggtgtga tgtacaagaa 6000
tcttaagaaa gtccaacgag ctcaagctgc tatgatgatg cagcaaatga gctcatcaca 6060
gcctgtgacc accaaattgg ggacaccctt ctaggtgaat aatcatatca atccattcaa 6120
taatgagcgg gacataccaa tcaccaacga ctgtgtcaca aggccggtta ggaatgcacc 6180
ggatctctct ccttcctttt taattaaaaa cggttgaact gagggtgagg ggggggggtgt 6240
gcatggtagg gtggggaagg tagccaattc ctgcccattg ggccgaccgt accaagagaa 6300
gtcaacagaa gtatagatgc agggcgacat ggagggtagc cgtgataacc tcacagtaga 6360
tgatgaatta aagacaacat ggaggttagc ttatagagtt gtatccctcc tattgatggt 6420
gagtgccttg ataatctcta tagtaatcct gacgagagat aacagccaaa gcataatcac 6480
ggcgatcaac cagtcgtatg acgcagactc aaagtggcaa acagggatag aagggaaaat 6540
cacctcaatc atgactgata cgctcgatac caggaatgca gctcttctcc acattccact 6600
ccagctcaat acacttgagg caaacctgtt gtccgccctc ggaggttaca cgggaattgg 6660
ccccggagat ctagagcact gtcgttatcc ggttcatgac tccgcttacc tgcatggagt 6720
caatcgatta ctcatcaatc aaacagctga ctacacagca gaaggccccc tggatcatgt 6780
gaacttcatt ccggcaccag ttacgactac tggatgcaca aggatcccat ccttttctgt 6840

-continued

```
atcatcatcc atttggtgct atacacacaa tgtgattgaa acaggttgca atgaccactc   6900
aggtagtaat caatatatca gtatgggggt gattaagagg gctggcaacg gcttacctta   6960
cttctcaaca gtcgtgagta agtatctgac cgatgggttg aatagaaaaa gctgttccgt   7020
agctgcggga tccgggcatt gttacctcct ttgtagccta gtgtcagagc ccgaacctga   7080
tgactatgtg tcaccagatc ccacaccgat gaggttaggg gtgctaacaa gggatgggtc   7140
ttacactgaa caggtggtac ccgaaagaat atttaagaac atatggagcg caaactaccc   7200
tggggtaggg tcaggtgcta tagcaggaaa taaggtgtta ttcccatttt acggcggagt   7260
gaagaatgga tcaacccctg aggtgatgaa taggggaaga tattactaca tccaggatcc   7320
aaatgactat tgccctgacc cgctgcaaga tcagatctta agggcagaac aatcgtatta   7380
tcctactcga tttggtagga ggatggtaat gcagggagtc ctaacatgtc cagtatccaa   7440
caattcaaca atagccagcc aatgccaatc ttactatttc aacaactcat taggattcat   7500
cggggcggaa tctaggatct attacctcaa tggtaacatt tacctttatc aaagaagctc   7560
gagctggtgg cctcaccccc aaatttacct acttgattcc aggattgcaa gtccgggtac   7620
gcagaacatt gactcaggcg ttaacctcaa gatgttaaat gttactgtca ttacacgacc   7680
atcatctggc ttttgtaata gtcagtcaag atgccctaat gactgcttat tcggggttta   7740
ttcagatgtc tggcctctta gccttacctc agacagcata tttgcattta caatgtactt   7800
acaagggaag acgacacgta ttgacccagc ttgggcgcta ttctccaatc atgtaattgg   7860
gcatgaggct cgtttgttca acaaggaggt tagtgctgct tattctacca ccacttgttt   7920
ttcggacacc atccaaaacc aggtgtattg tctgagtata cttgaagtca gaagtgagct   7980
cttgggggca ttcaagatag tgccattcct ctatcgtgtc ttataggcac ctgcttggtc   8040
aagaaccctg agcagccata aaattaacac ttgatcttcc ttaaaaacac ctatctaaat   8100
tactgtctga gatccctgat tagttaccct ttcaatcaat caattaattt ttaattaaaa   8160
acggaaaaat gggcctagtt ccaaggaaag gatgggaccc attagggtgg ggaaggatta   8220
ctttgttcct tgactcgcac ccacgtacac ccaatcccat tcctgtcaag aaggaaccct   8280
tcccaaactc accttgcaat gtccaatcag gcagctgaga ttatactacc caccttccat   8340
cttttatcac ccttgatcga gaataagtgc ttctactaca tgcaattact tggtctcgtg   8400
ttaccacatg atcactggag atggagggca ttcgtcaatt ttacagtgga tcaagcacac   8460
cttaaaaatc gtaatccccg cttaatggcc cacatcgatc acactaagga tagactaagg   8520
gctcatggtg tcttgggttt ccaccagact cagacaagtg agagccgttt ccgtgtcttg   8580
ctccatcctg aaactttacc ttggctatca gcaatgggag gatgcatcaa ccaggttccc   8640
aaggcatggc ggaacactct gaaatctatc gagcacagtg tgaagcagga ggcgactcaa   8700
ctgaagttac tcatggaaaa aacctcacta aagctaacag gagtatctta cttattctcc   8760
aattgcaatc ccgggaaaac tgcagcggga actatgcccg tactaagtga gatggcatca   8820
gaactcttgt caaatcccat ctcccaattc caatcaacat gggggtgtgc tgcttcaggg   8880
tggcaccatg tagtcagcat catgaggctc caacagtatc aaagaaggac aggtaaggaa   8940
gagaaagcaa tcactgaagt tcagtatggc tcggacacct gtctcattaa tgcagactac   9000
accgtcgttt tttccgcaca ggaccgtgtc atagcagtct tgcctttcga tgttgtcctc   9060
atgatgcaag acctgcttga atcccgacgg aatgtcttgt tctgtgcccg ctttatgtat   9120
cccagaagcc aactacatga gaggataagt acaatactgg cccttggaga ccaactcggg   9180
agaaaagcac cccaagtcct gtatgatttc gtagctaccc tcgaatcatt tgcatacgct   9240
```

-continued

```
gctgtccaac ttcatgacaa caaccctatc tacggtgggg ctttctttga gttcaatatc   9300
caagaactgg aagctatttt gtcccctgca cttaataagg atcaagtcaa cttctacata   9360
agtcaagttg tctcagcata cagtaacctt cccccatctg aatcagcaga attgctatgc   9420
ttactacgcc tgtggggtca tcccttgcta aacagtcttg atgcagcaaa gaaagtcaga   9480
gaatctatgt gtgctgggaa ggttcttgat tataatgcta ttcgactagt tttgtctttt   9540
tatcatacgt tattaatcaa tgggtatcgg aagaaacata agggtcgctg gccaaatgtg   9600
aatcaacatt cactactcaa cccgatagtg aagcagcttt actttgatca ggaggagatc   9660
ccacactctg ttgcccttga gcactattta gatatctcga tgatagaatt tgagaagact   9720
tttgaagtgg aactatctga tagtctaagc atctttctga aggataagtc gatagctttg   9780
gataaacaag aatggcacag tggttttgtc tcagaagtga ctccaaagca cctacgaatg   9840
tctcgtcatg atcgcaagtc taccaatagg ctattgttag cctttattaa ctcccctgaa   9900
ttcgatgtta aggaagagct taaatatttg actacaggtg agtatgccac tgacccaaat   9960
ttcaatgtct cttactcact gaaagagaag gaagttaaga aagaagggcg cattttcgca  10020
aagatgtcac agaaaatgag agcatgccag gttatttgtg aagagttact agcacatcat  10080
gtggctcctt tgtttaaaga gaatggtgtt acacaatcgg agctatccct gacaaagaat  10140
ttgttggcta ttagccaact gagttacaac tcgatggccg ctaaggtgcg attgctgagg  10200
ccaggggaca agttcaccgc tgcacactat atgaccacag acctaaaaaa gtactgcctt  10260
aactggcggc accagtcagt caaattgttc gccagaagcc tggatcgact atttgggtta  10320
gaccatgctt tttcttggat acacgtccgt ctcaccaata gcactatgta cgttgctgac  10380
ccattcaatc caccagactc agatgcatgc acaaatttag acgacaataa gaacactggg  10440
atttttatta taagtgctcg aggtggtata gaaggccttc aacagaaact atggactggc  10500
atatcaattg caatcgccca ggcggcagca gccctcgagg gcttacgaat tgctgccact  10560
ttgcaggggg ataaccaggt tttagcgatt acgaaagaat tcatgacccc agtctcggag  10620
gatgtaatcc acgagcagct atctgaagcg atgtcgcgat acaagaggac tttcacatac  10680
cttaattatt taatggggca ccaattgaag gataaagaaa ccatccaatc cagtgacttc  10740
ttcgtttact ccaaaaggat cttcttcaat gggtcaatcc taagtcaatg cctcaagaac  10800
ttcagtaaac tcactaccaa tgccactacc cttgctgaga acactgtagc cggctgcagt  10860
gacatctcct catgcatagc ccgttgtgtg gaaaacgggt tgcctaagga tgctgcatat  10920
gttcagaata taatcatgac tcggcttcaa ctgttgctag atcactacta ttctatgcat  10980
ggtggcataa actcagagtt agagcagcca actctaagta tccctgtccg aaacgcaacc  11040
tatttaccat ctcaattagg cggttacaat catttgaata tgacccgact attctgtcgc  11100
aatatcggtg acccgcttac tagttcttgg gcagagtcaa aaagactaat ggatgttggc  11160
cttctcagtc gtaagttctt agaggggata ttatggagac cccgggaagg tgggacattt  11220
tcaacactca tgcttgatcc gttcgcactt aacattgatt acttaaggcc accagagaca  11280
ataatccgaa aacacaccca aaaagtcttg ttgcaggatt gtcctaatcc tctattagca  11340
ggtgtagttg acccgaacta caaccaggaa ttagaattat tagctcagtt cctgcttgat  11400
cgggaaaccg ttattcccag ggctgcccat gccatctttg aactgtctgt cttgggaagg  11460
aaaaaacata tacaaggatt ggttgatact acaaaaacaa ttattcagtg ctcattagaa  11520
agacagccac tgtcctggag gaaagttgag aacattgtaa cctacaatgc gcagtatttc  11580
ctcggggcca cccagcaggt tgacaccaat atctcagaaa ggcagtgggt gatgccaggt  11640
```

-continued aatttcaaga agcttgtatc tcttgacgat tgctcagtca cgttgtccac tgtgtcacgg 11700
cgcatttctt gggccaatct acttaactgg agggctatag atggtttgga aactccagat 11760
gtgatagaga gtattgatgg ccgccttgtg caatcatcca atcaatgcgg cctatgtaat 11820
caaggattgg gctcctactc ctggttcttc ttgccctccg ggtgtgtgtt cgaccgtcca 11880
caagattctc gagtggttcc aaagatgcca tacgtgggat ccaaaacgga tgagagacag 11940
actgcgtcag tgcaggctat acagggatcc acatgtcacc ttagagcagc attgagactt 12000
gtatcactct acctttgggc ctatggagat tctgacatat catggctaga agccgcgaca 12060
ttggctcaaa cacggtgcaa tatttctctt gatgacctgc ggatcctgag ccctcttcct 12120
tcctcggcaa atttacacca cagattgaat gacggggtaa cacaagtgaa attcatgccc 12180
gccacatcga gccgggtgtc aaagttcgtc caaatttgca atgacaacca gaatcttatc 12240
cgtgatgatg ggagtgttga ttccaatatg atttatcagc aggttatgat attagggctt 12300
ggagagattg aatgtttgtt agctgaccca atcgatacaa acccagaaca actgattctt 12360
cacctacact ctgataattc ttgctgtctc cgggagatgc caacgaccgg ttttgtacct 12420
gctttaggat tgaccccatg cttaactgtc ccaaagcaca atccgtatat ttatgatgat 12480
agcccaatac ccggtgattt ggatcagagg ctcattcaaa ccaaattctt tatgggttct 12540
gacaatctag ataatcttga tatctaccag cagcgagctt tactgagtcg gtgtgtggct 12600
tatgacatta tccaatcagt attcgcttgc gatgcaccag tatctcagaa gaatgatgca 12660
atccttcaca ctgactacca tgaaaattgg atctcagagt tccgatgggg tgaccctcgc 12720
ataatccaag taacagcagg ttacgagtta attctgttcc ttgcatacca gctttattat 12780
ctcagagtga ggggtgaccg tgcaatcctg tgttatattg ataggatact caacaggatg 12840
gtatcttcca atctaggcag tctcatccag acgctctctc atccggagat taggaggaga 12900
ttttcattga gtgatcaagg gttccttgtc gaaagggagc tagagccagg taagccactg 12960
gtaaaacaag cggttatgtt cctaagggac tcagtccgct gcgctttagc aactatcaag 13020
gcaggaattg agcctgagat ctcccgaggt ggctgtaccc aggatgagct gagctttacc 13080
cttaagcact tactatgtcg gcgtctctgt ataattgctc tcatgcattc ggaagcaaag 13140
aacttggtca aagttagaaa ccttccagta gaggaaaaaa ccgccttact ataccagatg 13200
ttgatcactg aggccaatgc caggagatca gggtctgcta gtatcatcat aagcttagtt 13260
tcagcacccc agtgggacat tcatacacca gcgttgtatt ttgtatcaaa gaaaatgctg 13320
gggatgctca aaaggtcaac cacacccttg gatataagtg acctttctga gagccagaac 13380
ctcacaccaa cagaattgaa tgatgttcct ggtcacatgg cagaggaatt tccctgtttg 13440
tttagcagtt ataacgctac atatgaagac acaattactt acaatccaat gactgaaaaa 13500
ctcgcagtgc acttggacaa tggttccacc ccttccagag cgcttggtcg tcactacatc 13560
ctgcgacccc ttgggcttta ctcgtctgca tggtaccggt ctgcagcact attagcgtca 13620
ggggccctca gtgggttgcc tgaggggtca agcctgtact tgggagaggg gtatgggacc 13680
accatgactc tacttgagcc cgttgtcaag tcctcaactg tttactacca tacattgttt 13740
gacccaaccc ggaatccttc acagcggaac tacaaaccag aaccgcgggt attcactgat 13800
tccatttggt acaaggatga tttcacacga ccacctggtg gcattgtaaa tctatggggt 13860
gaagacgtac gtcagagtga tattacacag aaagacacgg ttaatttcat attatctcgg 13920
gtcccgccaa aatcactcaa attgatacac gttgatattg agttctcccc agactctgat 13980
gtacggacgc tactatctgg ctattcccat tgtgcactat tggcctactg gctactgcaa 14040
cctggagggc gatttgcggt tagagttttc ttaagtgacc atatcatagt caacttggtc 14100
actgccattc tgtccgcttt tgactctaat ctggtgtgca ttgcgtcagg attgacacac 14160
aaggatgatg gggcaggtta tatttgtgca aagaagcttg caaatgttga ggcttcaaga 14220
attgagtatt acttgaggat ggtccacggc tgtgttgact cattaaaaat tcctcatcaa 14280
ttaggaatca ttaaatgggc tgagggtgaa gtgtcccgac ttaccaaaaa ggcggatgat 14340
gaaataaact ggcggttagg tgatccagtt accagatcat ttgatccggt ttctgagcta 14400
ataattgcgc gaacaggggg atcagtatta atggaatacg ggacttttac taacctcagg 14460
tgtgcgaact tggcagatac atataaactt ttggcttcaa ttgtagagac caccttaatg 14520
gaaataaggg ttgagcaaga tcagttggaa gatgattcga ggagacaaat ccaggtagtc 14580
cctgctttta atacaagatc cgggggaagg atccgtacat tgattgagtg tgctcagctg 14640
caggtcatag atgttatctg tgtgaacata gatcacctct ttcccaaaca ccgacatgct 14700
cttgtcacac aacttactta ccagtcagtg tgccttgggg acttgattga aggcccccaa 14760
attaagacat atctaagggc caggaagtgg atccaacgta ggggactcaa tgagacaatt 14820
aaccatatca tcactggaca agtgtcgcgg aataaggcaa gggatttttt caagaggcgc 14880
ctgaagttgg ttggcttttc gctctgtggc ggttggggct acctctcact ttagctgctt 14940
agattgttga ttattatgaa taatcggagt cgaaatcgta aatagaaaga cataaaattg 15000
caaataagca atgatcgtat taatatttaa taaaaaatat gtcttttatt tcgt 15054

<210> SEQ ID NO 19
<211> LENGTH: 16236
<212> TYPE: DNA
<213> ORGANISM: artificial sequence
<220> FEATURE:
<223> OTHER INFORMATION: APMV6 genome sequence

<400> SEQUENCE: 19
accaaacaag gaaaccatat gcttggggaa tttacgagaa cgcttataaa atcgtgaggg 60
ggaagctggt ggactccggg tccggagtcg gtggacctga gtctagtagc ttccctgctg 120
tgccaagatg tcgtcggtgt tcactgacta cgctaagctg caagatgccc ttgtggcccc 180
ttcaaaaagg aaggtggata gtgcaccaag cggattgtta agggttggga tccctgtgtg 240
tgtcctactc tccgaggatc ctgaagaacg atggagcttt gtttgctttt gcatgaggtg 300
ggtggtgagc gattcagcca cagaggcaat gcgtgttggt gcaatgctat ctatcctcag 360
cgcacacgcc agcaacatgc ggagccatgt cgcacttgca gcaagatgtg gcgacgccga 420
catcaacata cttgaggttg aggcaattga ccaccaaaac cagaccattc gtttcactgg 480
gcgcagcaat gtgactgacg ggagagcacg ccagatgtat gcgattgccc aagatctgcc 540
tccctcctat aacaatggta gcccttttgt aaatagagac attgaggaca attatccgac 600
cgacatgtct gagctgctca acatggttta cagtgttgca actcaaatct gggtggcagc 660
tatgaagagc atgactgctc cagacacatc ctcagagtct gaagggaggc ggttggccaa 720
atacatccag caaaacagag tgatccggag tacgatttta gctcctgcaa ctcgcggtga 780
atgcacccgg ataatacgga gctccctagt catccgccac tttctaataa ctgagatcaa 840
gcgtgccaca tcaatgggtt ccaacacgac gagatattat gccacagttg ggatgctgc 900 agcttacttc aagaacgcgg gtatggctgc attcttctta actctgcggt ttggaattgg 960
gaccaagtac tccacacttg cagtttcagc gctgtccgcc gacatgaaga aactccagag 1020
cttgatccga gtataccaga gcaaaggtga ggatggaccc tatatggcat ttctggaaga 1080

-continued

```
ctccgacctt atgagcttcg cccctggaaa ctatccactc atgtattcat atgcaatggg   1140
agtagggtcc attcttgagg caagtattgc tcgatatcag tttgctcgat cattcatgaa   1200
tgacacgttc tatcgattgg gtgttgaaac tgcacaacga aaccaaggtt cacttgatga   1260
gaatctagcg aaggagctgc aactatctgg ggccgaacgg agggcagtgc aggaacttgt   1320
gaccagcctg gacctagctg gagaggcccc agtgccccag cgtcaaccaa cattcctcaa   1380
tgaccaggag tatgaggatg atcccccgc caggagacag agaattgagg atactccaga   1440
cgatgacgga gccagtcaag ctccacccac accaggagca ggtctcaccc catactctga   1500
taatgccagt ggcctggaca tctaaacgac cagtacttag tataacaatt gatcaaggtt   1560
aatccaaagt atgcaaatcc aatactccaa tcgataacaa gatcacatgt agactttaag   1620
aaaaaacaag ggtgaggggg aagttcctgg tacgcgggct gggcccatag tgactcagct   1680
agcaccatgg acttctccaa tgaccaggag attgcagaat tactcgagct gagttcggat   1740
gtgataaaga gcatccaaca tgccgagacc cagccagcac acactgtcgg caaatctgcc   1800
attcggaaag gaaatacatc cgagctgcga gcagcctggg aagccgagac acaaccaacc   1860
caaacagaaa acaagtctga ggaacaccca gagcaaactg cccgggatcc cgacagcaag   1920
ggcaacacag gaaattcgca accacgatcc aacgcagagg agacacccca atcagaaagt   1980
cacgacaggc aagtcgctgc tccaccccca gacaccacaa taggggttaa cgggaccaat   2040
gggcttgaag ctgctctaaa aaagctagaa aaacaaggga aaggtcccgg gaaaggccaa   2100
gtggatcgca acacccctca gagagatcca accactgcct cgggttcaaa aaaggggaaa   2160
gggggcgagc caaggagcaa tgccctccat cagggttacc cacaggggac caacttgatc   2220
ctgcccactc agaggccctc tcatgccaga ctggcgcagc aagcatcaca ggagataact   2280
cgccatgcgc tgcaacccca ggactccggc ggcatagaag ggaattctcc atttcttgga   2340
gacacggcca gtgcatcctg gccgagtggt gcaacccagt ctgtgcacct gtcacacctg   2400
aacccagagc attcaaatgc atttgcggga gatgccctcg agtatgcatc aactgtcgca   2460
acgatagtgg agactctgaa atttgtagtt agcaggttag aagcacttga aaatagggtg   2520
gcggagctca ccaaatttgt ctctcccatt cagcaaatca aagcagacat gcagattgta   2580
aagacatcct gcgctgtcat tgagggccaa cttgccacag tgcaaatatt ggagccgggc   2640
cactcatcga ttcgctcact tgaggagatg aagcaataca ccaagccagg aattgtcgtc   2700
caaacaggga tgactcaaga cataagcgcc gtcatgaggg acggcacgat cgtaaaagat   2760
gctcttgctc gcccagttaa tccggacaag tggtcagcaa caatcaatgc tcaatcaaca   2820
acaatgaagg taacccaaga agatataaag acggtgtata cactattgga caattttggc   2880
atcactggcc caaaaagagc gaaaattgag gcggaattgg ctaatgtcag tgaccgggac   2940
gcactagtaa ggattaagaa acgtgttatg aatgcataag cagccaaaaa atcacaacaa   3000
ttagtacaga tggcctccca atgtcacatc atgattctat tgtcaaatca cagcattctt   3060
tcttcctgat cacacccaac aatttgcttt ggacaccctt gacactgatt aataaaaaag   3120
tgagggggaa ctggtggtgt ccggactggg caacccaggg tcacccggtc cgaaccaaac   3180
acccgccagt tcctccaccg gcacagcgca ccactgactg caccgacccc aaccatggcc   3240
acgtcagaac tcaacctcta tatcgacaag gactcacccc aggtgagatt gctagcattc   3300
cccatcatca tgaaacccaa agaaaatggg gttagagagc tgcaaccgca actgaggact   3360
cagtacctcg gtgacatcac cggaggaaag aaaagcgcga tatttgtgaa ttgctatggg   3420
ttcgttgaag atcacggggg gcgagacagc ggattctcac ccatcagtga agaatccaaa   3480
```

-continued

```
ggatcgacag tcactgcagc ctgcatcact cttggcagca tcgagtatga tagtgacatc   3540
aaggaagtgg caaaggcctg ctataatctt caggtgtcag ttaggatgtc cgctgattca   3600
actcagaagg ttgtttacac aatcaatgct aaacctgcac tgttgttctc ctcccgtgtt   3660
gtcagagctg gggttgtgt ggttgcagca gagggtgcaa tcaagtgccc cgagaagatg   3720
acatccgatc gcctttacaa gttccgcgta atgtttgttt cattgacctt cttacatcgc   3780
agcagccttt tcaaagttag ccgtacggtg ctgtcaatga ggaattctgc tctaatagca   3840
gtacaggccg aagtgaagct gggattcgat ctgccactag accatccaat ggcaaaatat   3900
ctgagcaaag aggatggaca gctctttgcg actgtgtggg tacatttgtg caacttcaag   3960
cgcacagaca gacggggagt agaccgatcg gtggagaaca tcagaaacaa agtacgggcc   4020
atggggctga agctcacctt gtgtgatctg tggggtccca cacttgtttg tgaagctaca   4080
gggaagatga gcaagtacgc gctaggtttc ttctcggaga ccaaggttgg ctgtcatcca   4140
atctggaaat gcaactcgac tgtcgcgaag atcatgtggt catgcacaac ctggatcgca   4200
tcagcaaagg ccatcataca ggcctcctct gctcgtgccc tgttgacatc agaggacata   4260
gaagccaagg gagccatctc cactgacaaa aagaaaacag atgggtttaa tcccttcatc   4320
aagacagcaa agtagtcatc tgaatctcat cagtgaaccc actggcatat gttcagctgt   4380
gccttccttg ataatcacta aatcaatacg cagagtgctc tttgattaag atctcgattg   4440
ttccaataag tggatcattt atactttgaa gattgaactt cctaactatt ccttccttag   4500
aagtccagtc atattaatca aaaaaatcag tttgctggta aagtcgtata ctgcaggatc   4560
caatacctct caccaatgag tagctgaggg ggaaggcatg ggagcccgac tggggccctt   4620
aacaatggca cccggccggt atgtgatcat tttcaatctc atccttctcc atagggccgt   4680
ctcactagac aattcaaggt tactgcagca ggggatcatg agtgcgaccg agagagaaat   4740
taaagtgtac acgaactcca taaccggaag tattgctgtg agattaattc ccaacttacc   4800
tcaagaagtg cttaagtgct ccgctgggca gatcaaatcg tacaatgaca cccttaaccg   4860
aatttttaca cctattaagg cgaaccttga gaggttactg gccacaccaa gtatgcttga   4920
agacaaccag aaccctgctc cagaacctcg tctgattgga gcaattatag gcacagcagc   4980
actggggttg gcaacagcag ctcaggttac agctgccctt gcccttaacc aggcccagga   5040
taatgccaag gccatcttga acctcaaaga gtccataaca aagacaaacg aggctgtgct   5100
tgagcttaaa gatgcaacag ggcaaattgc aatagcgcta gataagactc aaagattcat   5160
aaatgacaat atcttaccgg cgattaataa tctgacatgt gaagtagcag gtgctaaagt   5220
aggtgtggaa ctgtcattat acttgaccga gttaagcact gtgtttggat cgcagataac   5280
caatccagca ctctcaactt tatccattca agccctcatg tcactctgtg gtaatgattt   5340
taattacctc ctgaatctaa tgggggccaa acactctgat ctgggtgcac tttatgaggc   5400
aaacttaatc aatggcagaa tcattcagta tgaccaagca agccaaatca tggttattca   5460
ggtctccgtg cccagcatat catcaatttc ggggttgcga ctgacagagt tgttcactct   5520
gagcattgaa acaccggtcg gcgagggcaa ggcagtagta ccccagtttg ttgtggaatc   5580
tggccagctt cttgaagaga ttgacaccca ggcatgcaca ctcactgaca ccactgctta   5640
ttgtactata gttagaacaa aaccattacc ggaactagtc gcacaatgcc tccgagggga   5700
tgagtctaga tgccaatata cgactggaat aggtatgctt gaatctcgat ttggggtgtt   5760
tgatggactt gttattgcta attgtaaggc caccatctgc cgatgtctag cccctgagat   5820
gataataact caaaacaagg gactccctct cacagtcata tcacaagaga cttgcaagag   5880
```

-continued

```
aatcctgata gatggagtta ctctacagat cgaagctcaa gttagtgggt cgtattccag   5940
gaatataaca gtcgggaaca gccaaattgc cccatccgga cccettgaca tctcaagcga   6000
actcgggaag gtcaaccaaa gtctatctaa tgtcgaagat ctcattgacc agagcaatca   6060
gctcttaaat agggtgaatc caaacatagt aaacaacacc gcaatcatag tcacaatagt   6120
actgctagtc ctcttggtat tatggtgttt ggccctaacg attagtatcc tgtatgtatc   6180
aaaacacgct gtgcggatga taaagacagt tccgaatccg tatgtaatgc aagcaaagtc   6240
gccgggaagt gccacacagt tctaacaata tagctggtcc tgatgattaa accatatacc   6300
tgattacatg ataaaaatat gtcgagggat gacattgatg agacccctta ttctctctca   6360
aactaagaca gtaatccatc tagaatgcaa tgatcctact tcctttactt taatcaaaaa   6420
atgcagaata atctaacagc ccaaccaaac tacccagaaa gaaacgcctg agggggggaag  6480
gaggttgact gcaacctcaa ttgatcagag gttgtagtat taattctcca taaccctcaa   6540
gatgagacca caagtggcgg tttgggcttt gcgcttattg gccaccggcc tagctatgat   6600
ctccttagtg ttctgcctga accaggtaat tatgcaggtg ctaattaggg acattgggga   6660
cttgttgaca tcctcagaaa taaagactac acgtgagaca ctgcgtgagc atctctcatc   6720
tattactctt ttcatgtcgt ttgcgctgac ttgctcaata agtgggtgcg ttcttagcct   6780
ggttgcatta tatccaagca agaacattaa tggcactaac actcagccac aagtagagga   6840
ggccagatcg gagaacctgt ctcactcttc catgcacaca atcaataggc cagcgacccc   6900
tcccccaccg tattatgtag caatacaact cagcgctgag atgcaacctg ggtaccatcc   6960
aggtgattga tcctcctagc atgttggcag agtctacccc accaagatct gttcttgtac   7020
cactttttttg atttaagaaa aaattgtgat ttatataaaa acataatggc tgagggggaa  7080
gcctggtgtc accgctggtg accatttccc agccggtggc aatggcttcc tcaagcgata   7140
tgaggcagag tcaggcaact ttatatgagg gtgaccctaa tagcaaaagg acatggagga   7200
ccgtgtaccg ggttatcacc atattgttgg atataaccgt cctttgtgtc ggcatagtgg   7260
cagtagtcag gatgtcaacc attacgacaa aggatattga taacagtatt tcatcgtcca   7320
ttacttccct gagtgccgat taccagccaa tatggtcaga tacccatcag aaagtcaaca   7380
gtattttcaa ggaagtcgga atcactatcc ccgtcacact cgacaagatg caagtggaaa   7440
tgggaacagc agttaacata atcactgatg ctgtaaggca actacaagga gtcaatgggt   7500
cagcaggatt tagcattacc aattcaccag aatatagtgg agggatagac acactgatat   7560
accctcttaa ctcacttaat gggaaggctt tagccgtatc agacctactg gaacatccga   7620
gcttcatacc agcgcctacc acctctcatg gttgcacccg cattcctaca ttccacctag   7680
gataccgtca ttggtgttat agtcacaaca caatagaatc tggttgtcac gatgcagaag   7740
aaagcattat gtacgtatct atgggtgcgg taggggtcgg ccatcgtggg agacccgtgt   7800
ttacgacaag tgcagcaaca atcctagatg atggaaggaa caggaaaagt tgtagcatca   7860
tagcaaaccc taatgggtgt gatgtcttgt gcagcttggt taagcaaaca gagaacgagg   7920
actacgctga ccctacaccg accccaatga tccacggtag gctccacttc aatggcacgt   7980
acaccgagtc tgaactcaac cctggcctat ttaataatca ttgggtcgct caatatccag   8040
cagttggcag cggtgtcgtc agccacggga aactattctt tccgctttac ggagggatat   8100
caccgaagtc aaaactgttc aacgagctta agtcatttgc ttacttcacc cataatgccg   8160
aattgaaatg tgagaacctg acagagagac aaaaagaaga tctatataac gcatataggc   8220
ctgggaaaat agcaggatct ctctgggctc aaggggttgt aacatgtaat ctgaccaatc   8280
```

-continued

```
tagctgattg taaagttgca attgcgaaca cgagcaccat gatgatggct gccgagggga   8340
ggttacaact tgtgcaagat aggattgtct tctaccaaag atcctcatca tggtggccag   8400
tcctaatata ttatgatatc cctattagtg accttatcag tgccgatcat ttagggatag   8460
taaactggac tccatatcca caatctaaat ttccgaggcc cacctggaca aagggcgtat   8520
gcgagaaacc ggcaatatgt cccgctgtgt gtgtaacggg tgtttaccag gatatttggg   8580
tagtcagtat agggtcccag agcaatgaga ctgttgtggt tggcggatac ttagatgctg   8640
cagcagcccg tcaggatcca tggattgcag cagccaacca gtataactgg ctggttaggc   8700
gtcgcctttt tacatctcag actgaagcag catactcatc aaccacttgc ttcagaaaca   8760
cgaagcagga tagagtgttc tgcctgacta taatggaagt tacagacaac ctactcggag   8820
actggaggat cgccccgctg ttatatgagg ttactgtggc tgataagcaa cagggtaatc   8880
gcaattacgc gccaatgaga aggatgggga cggataagtt ccaatattat acaccaggtg   8940
ataaatatac tcctcagcat tgatgactca ctgcagcttg tacataacaa ttctcttgct   9000
tcctctattt gcagagtaaa tcagaagaat gacggtcggt gattgaccga acttaattag   9060
atggtgacat acagcccgca ttcatcttga tttaataaaa aactggggag ctgttataac   9120
atggcagact gacggggcaa gacccgcgga gacaaagaat gcagtgaggg ggaaggcagg   9180
ctgggatcac gtcccagctg tagccttccc cgattcaatc tacttagtat cgacaagtca   9240
attctgctca cagaggtcat ctgaaagggt tgttgtgatg gatccacaag tccaaataca   9300
ccacatcatc aagccagagt gccatctcaa ctcacctgtg gtggagaaga aactgacgct   9360
attatggaag ctcacaggtt taccgttgcc acctgacctt aatagttgcg ttacacacaa   9420
ggatgtgacg tgggatgaag tgctccggtt ggaggctaat ttgacaaagg aattacggca   9480
attggtgcga ggcctgacca atagaatgca tgaaagaggg gagtttattg actcatataa   9540
acctttatgc catccacgta cgttaagttg gttgactaat atcagcttga ttaagagtga   9600
caacattcta gcaggccata agaaaatgct agtccggatt ggcggtatgt tgcatgaaca   9660
aacagaccaa ttgtttgtca ctcttggcag gaaattagca ggtgaccctt gcttgttcca   9720
tcaactaggc cacctagctg gatgtccacc caattccaga tttgaggaac aggtaggagg   9780
ctgcagtttg tggtcaccca taagcgatcc agccctggtc acaggtggtg aatatgccaa   9840
ctgtgtgtat gcgtggtact taatacgtca aaccatgcgg tacatggccc tccagagaaa   9900
gcaaacaaga gtgcaatcac agcagaatgt cctaattgga tcagatacaa tcgtgggaat   9960
tcatccagaa ctagtgataa ttactggaat tagagacagg acattcacct gtttgacttt  10020
tgatatggtg ctaatgtacg cagatgtggt ggaaggccgt gccatgacaa agttggtcgc  10080
actcaccgag ccgacaatgg tagaagtcat tcagagagtc gaaaaattgt ggttcctagt  10140
tgacagcatc tttgaggaaa tcggtggtgc aggttacaat attgttgcat ctctggagag  10200
cttggcatat ggtgctgttc aactgtggga taaatcactg gaacatgctg gtgagttttt  10260
ctcattcaat cttactgaga taaggagtga gctagagaac catttagatc ctggtatggc  10320
atttagagta gttgagcagg tgcggttgct atatactgga ctgagtgtga accaagcagg  10380
tgaaatgtta tgcattttac gtcactgggg gcatcccttg ctgtgcgctg tgaaggcggc  10440
aaagaaagtc agagaatcga tgtgtgcacc gaaattaacc tctctagata ccacactcaa  10500
agtgttagca ttctttattg cagatattat caatggacat agacggtcac attcagggtt  10560
atggccaagt gtcagacaag agtcacttgt gtccccattg ctccagaacc tctatagaga  10620
atccgccgag cttcagtacg cgattgtgct taagcactat agagaagtat cccttattga  10680
```

-continued

```
attccaaaaa agtattgatt ttgacttagt tgaagatctg agcgtgttcc ttaaggataa  10740
agccatctgt cgaccaaaga gtaactggtt agctgtattc aggaagtccc tactccccgg  10800
acatttgaaa gataagctgc aatctgaggg cccttctaac cggcttctgc ttgatttttt  10860
gcaatcaagc gaatttgacc cggctaagga gttcgagtac gtgacatcac tggagtatct  10920
tcaggaccca gagttctgcg catcttattc cttaaaggaa agggaagtca agactgatgg  10980
gcgcatattt gcaaaaatga ctagaaaaat gaggaactgt caagtcttgc tagagagttt  11040
gctcgcatgc cacatatgcg attatttcaa agagaacgga gtagtacaag agcaaatcag  11100
cttaacgaaa tcactgcttg cgatgtcgca acttgctcct cgtgtgtctg agtatcaagg  11160
gagagttctc cgttcaactg ataggtgcag tagagctaca gctacacctg ggcaggacac  11220
aagcccaggc gagggggtca ggcgacggaa aacgattata gcatcattct tgactactga  11280
cctacagaaa tattgtctca attggaggta cactgtagta aaacctttttg cacagaggct  11340
taaccagtta tttgggatac cccacggctt tgagtggatt cacctccgct tgatgaatac  11400
gaccatgttt gtaggagacc cacataatgt ccctcagttt tcatcaacac atgacttaga  11460
atcccaagaa aatgatggaa tatttattgt atcacctcgg ggtggtatag aagggctatg  11520
ccaaaaaatg tggaccatga tctccattgc ggcaattcat ctagcagcca cagaatcagg  11580
ttgtcgggtt gcatctatgg tccaagggga caatcaagca attgcaatca ccacagagat  11640
cgaagagggt gaggacgcat ccgtagcatc aataaggtta aaagaaatat ctgagaggtt  11700
ttttagagtg ttcagagaga taaacagagg tatagggcac aacttaaaag tccaagaaac  11760
aattcatagt gagtcattct tcgtgtactc gaaacggatc ttctttgagg ggaagatcct  11820
cagtcaacta ctaaaaaatg caagtaggtt agtgttggta tccgagaccg tgggtgagaa  11880
ttgtgtcggc aattgctcaa atatcagttc cacagttgct aggctcattg aaaatggatt  11940
ggataagaga gtcgcatggg ggctcaatat catgatgatc gtaaaacaaa ttctttttga  12000
cattgatttc tccttggagc ctgaaccatc tcaaggcttg attcatgcta ttcgccaaga  12060
tccaaacaac ataaaaaaca tctctatcac tcctgctcaa ttgggtggat taaattttct  12120
agccctatct cggctattta caaggaacat aggagacccc gtctcgtcag ccatggcaga  12180
tatgaagttc tacatacagg tcggattatt atcccctcat ctgctaagga atgcaatttt  12240
tagggaaccc ggagatggaa cgtggacaac actgtgcgcc gacccgtact cattaaacca  12300
accatatgtg caattgccaa cgtcgtactt aaaaaagcac acacaacgca tgctgctcac  12360
tgcctcaaca aatcctttat tgcaaggcac ccgagtagag aatcagtaca ttgaggaaga  12420
aagactagca aagttccttc tggatcgaga actggttatg ccacgtgtgg cgcatacagt  12480
ctttgagacc actgttgccg ggagacgaaa gcatctgcaa ggattgattg acaccacacc  12540
gaccattatt aaatatgccc ttcatcacca ccctatttct ttcaagaaaa gcatgctgat  12600
atcatcttac tcagctgact acattatgtc gttcatcgat actatcgcaa cagtggaata  12660
cccaaagcgt gacaccatga agctctggaa cagaggacta ataggtgtcg acacctgcgc  12720
ggtcacactt gcggattacg caagaacata ttcgtggtgg gagatcctaa agggaaggtc  12780
gataaaggga gttaccacac ctgatacatt agaactttgc tctgggagct taatagagca  12840
aggccatccg tgtgctcagt gcacaatggg tgatgaatcc ttttcatggt tcttcctccc  12900
aggaaatatt gatattgaaa ggccagactt ttctagggtg gcccagagaa tcgcttatgt  12960
cggctcaaag acggaagaaa ggcgggcagc ttcactgaca acaatcaaag ggatgtcaac  13020
tcaccttagg gcggcattaa gaggagcgag tgtttacatc tgggcgtatg gagacagtga  13080
```

-continued

```
caagaattgg gacgatgcta ccaagctcgc taacacaaga tgtgtaatat ctgaagacca  13140
tctacgtgcc ctttgtccaa tcccaagttc agcaaacata cagcatagac tgatggatgg  13200
aataagtgta acgaagttca ctcccgcgtc tctagcaagg gtgtcatcat atattcatat  13260
ttcaaatgac cggcatcaga gtagaattga cggtcaagtg atcgaatcaa atgtgatttt  13320
ccaacaggtt atgcttctcg gtctcggcat ttttgagaca tttcaccctt tgtctcacag  13380
gtttgtgact aaccccatga cactccactt acacacaggg tactcatgtt gcataagaga  13440
agctgataat ggtgatttct tagaatcccc ggctagtgta ccagacatga ctatcacgac  13500
tggcaataag tttctttttg accccatgcc catccaggat gacgatgctg caaaactaca  13560
ggtatcttca ttcaagtact gtgagatggg ccttgaagtg cttgacccac caggacttgt  13620
aaccttacta tccctagtga ctgcacgcat ctctattgat acatccatag gggagagcgc  13680
gtacaactcg atacacaatg atgctattgt atcattcgac aattccatca actggatatc  13740
tgagtacacg tactgcgatc ttagactact ggcagtagca atggctcggg agttttgcga  13800
caatctctct tatcagcttt actatctgag agttaaaggg cgacgggcaa tccgggatta  13860
tatccgtcaa gccctctcga ggataccagg gttacagctc gctaatatag ccttgactat  13920
atctcatccg ggaatttggg caagactgag gctaatcggg gcagtaagtg ctgggaatag  13980
ccccattagt gcaaccgtaa attatcctgc tgctgtgtgt gagctcatac tatggggtta  14040
tgaccaatat actgcacaac tactagatgg ttatgaatta gaaatcatag tcccaaatta  14100
taaggatgat gacttgaaca ggaaagttga acatatatta gcaagacggg cttgtctgct  14160
gagtctactg tgtgagtatc caggaaaata cccgaacatc aaagaccttg aacctattga  14220
gaaatgcact gccctgtctg acctgaataa attgtggatg gcgacagatc acagaactcg  14280
ggaatgtttt tcagggatat ctcagatatt tgattcaccc aagttaaatc cattcatcac  14340
taatctttac ttcttgagta ggaagctgct caatgcaatt agaagcagca cggactgtag  14400
ggcctacgtt gaaaaccttt atgaagatat tgacattgaa ctaacatctc tcactgaggt  14460
tgtaccctta ggagaggatg atcaaatgat cactgggcct ctgcgctttg accttgaact  14520
aaaagaactc accccagatt ttactatcac ttggtgttgc tttgactcca cggcagcact  14580
gatgtcacgg tgcattaatc atgccacaga aggtgcagag cgctacatcc gaagaacggt  14640
cgggacagct tcaacatctt ggtacaaagc agcaggaata ttaactacac ctggcttcct  14700
caacctccct aaaggcaatg gattgtatct cgctgagtca tcaggggcca ttatgactgt  14760
gatggagcat cttgtctgct ctaataaaat ctggtataac accttgttta gcaatgagct  14820
caacccacct cagaggaatt tcggtcctaa cccaattcag tttgaagaaa gtattgtggg  14880
gaaacacatt gcagctggga ttccttgcaa ggcaggacac gtgcaagagt tcgaggtact  14940
ctggagagag gtagatgaag agacagatct gacatccatg agatgtgtga attttatcat  15000
gtcgaaagtt gaacagcact cgtgtcatat tgtatgctgt gatttagaat tggctatggg  15060
aactcccctg gaagtggccc aatctgcata tacacacatc ataaccctcg ccttacattg  15120
cctaatgatt agcggaaaat tagtactgaa gttgtatttc tcacaaaatg ccttattaca  15180
ccatgttctc tccttgttac ttgtattacc atttcatgta acaatccaca ctaatgggta  15240
ttgctctcac cgaggctctg aagggtatat catcgccacg aggacagggg ttgctctggg  15300
ttcaaatgtg tcccaggtac taggcagtgt gactgagatg gtacggaaag gtcagaccct  15360
tgtccccgta aaggtactta cagcgatctc caatggattt aaaactgtat caagctcttt  15420
aggcaggctt aggggtgagc tctattcgcc atcgtgtagc attccgcagt cggctacaga  15480
```

-continued catgttcctc attcaacttg gagggaaggt gcagtcagat tggaatacaa actctcgagg 15540
ctatagagtg ggtgataccg aactcgtatt acaggacatt atatcaatat tgagcacact 15600
actaaaagaa ataatacatg taagggaatc cagggagtca gtggacaggg tgctgttgct 15660
tggggcatac aacctgcaag tatccggaaa agtaagaaca atggctgcgg ctgcaacaag 15720
aaacatattg catctccata tagttagact tattggggac tcaatgtcca atataaggag 15780
actagtacct ctgctagata agggctttat agtaatatca gacatgtata gtgtgaaaga 15840
tttcttgaga aaaactgagt cccctaagta cttcttgaac aagcttggca agagcgagat 15900
tgcacagata tttgaggtag agtccaagat tattctgagc agggcagaga tcaagaatat 15960
tttgaaaatg atagggattg tagcaaaaca gcactcagag taatctcttc aactttgcgc 16020
cgcttgaatc ctgaactgtg gacgcgcacg cttaagcgca ccagcctgac gtgacgattg 16080
atataatcct tggtatgaat caccaatcat ctggaactca cttacttccc gaaatcaccc 16140
atagaccggt atcggtatcg gagattatta tttaataaaa aacctggaaa gtcaacaagg 16200
atcatagtca aaaagcttat gatttccttg tttggt 16236

<210> SEQ ID NO 20
<211> LENGTH: 15480
<212> TYPE: DNA
<213> ORGANISM: artificial sequence
<220> FEATURE:
<223> OTHER INFORMATION: APMV7 genome sequence

<400> SEQUENCE: 20
accaaacaag gactgcataa gcagtgtaaa acttttaata aaaaataact ttcgtgaggg 60
tgaatcgatc atcgctcgaa gccgatatcg actcacccaa attagctgct tgtataagga 120
tccgaatatc aattggaatc atgtcatcga tttttactga ttataccaat ttgcaagagc 180
aattagtcag accggtaggc cggaaggttg ataatgcttc aagtggcttg ttgaaagttg 240
agataccagt ctgcgtcctg aattcacagg acccagttga gagacaccag ttcgcagtat 300
tatgtacaag gtggatctca agttcaattg ccacaactcc tgtcaagcaa ggtgccctgc 360
tttctcttct cagtttgcac acagaaaaca tgcgagcgca tgttctatta gcagcccggt 420
caggagatgc taatataaca attctagaag ttgatcatgt agatgttgaa aagggagaat 480
tacaatttaa tgcaaggagt ggtgtctcat ctgataaagc tgatcggctg ctggctgtcg 540
caatgaatct tattgcaggt tgtcagaata actcaccatt tgtcgaccca tcgattgagg 600
gtgatgaacc aactgatatg actgaatttt tagagctggc ttatgggtta gcggttcaag 660
catgggtagc tgcaataaag agtatgacgg caccagatac tgctgcggag agtgaggggc 720
ggcgattagc aaaataccag cagcaaggtc gtttaacacg acgtgctgct cttcaagcaa 780
ccgtgagggg ggagttgcag cggataatca ggggttctct ggtagttcga cacttcctta 840
taggagaaat cagaagagca ggaagtatgg gagaacagac aacagcctat tatgccatgg 900
tgggagatgt cagccaatac ataaagaatt caggaatgac tgcattcttc ctgacattac 960
gatttggggt gggtaccaag tatcctcccc ttgcaatggc tgcattttca ggagatctca 1020
ctaaactcca gagcctgatc agactatatc gaaataaagg tgacataggg ccttatatgg 1080
ccctactcga agatcctgac atgggcaact ttgctcctgc aaattacacc ttgctctatt 1140
catatgcaat gggcattggt tctgtattgg aggctagtat cggtagatac cagtatgcga 1200
gaacattcct gaatgaatca ttctttaggt tgggggcctc aactgctcaa cagcaacaag 1260
gagcactgga tgagaaattg gctaacgaga tggggctatc agaccaggca agggcagcag 1320

-continued

```
tttccagatt agttaatgag atggatatgg atcagcaagt agcccccaca ccagttaatc   1380
cagtctttgc aggagatcaa gcagccccac aggcaaatcc tccagcccaa ccaagacaga   1440
atgacacacc acagcagcct gctcctcttc agcagccaat tcgaattgcc atgcctcaaa   1500
attatgatga tatgccagac ttagagatgt agacagaacc ccaatcaagc aacaattggc   1560
attaagatct aagctgaatg tatgagcaca cgagtaccca agtatatttg ttagcagttg   1620
catgaaatca ttatccatat tattgatttg caatatagaa aattactgat aaacaattaa   1680
gaatcattta ataaaaaaat tccacaaaaa ttaaaaaaat tgtgaggggg aacacctttc   1740
agtcggtcaa ctgctgctaa taacctgcaa ttatcacgtg gattgaatat ggaattcagt   1800
aatgatgccg aggttgccgc gctcctggat cttggagata gcatcattca gggcattcag   1860
catgcaacaa tggctgatcc gggaacacta gggaagtcag ctattcctgc aggtaatacc   1920
aaacgcttag agaaattatg ggagaaagaa tctgttccta atcatgataa tatgattcac   1980
tcttccatga gtgcagaacc tataagcggg gaactacctg aggaaaacgc taaaactgaa   2040
ccaacaggga ctcaagaaat gccagaacaa attcaaaaga atgacaatct ccaacctgca   2100
tccatcgata acatattgag cagcattaat gcattagagt caaaacaggt taaaaaaggg   2160
ttagtgctat cgccccaatc actgaaaggt gtgtccccct taatcaagaa ccaggatctg   2220
aagaacacca tgcaggacct ggaaaccaaa cccaaggctg taacgactgt aaatccatta   2280
gcaaaccgac aagtgtcacc tggaagcctg gtcatagacg agagtattcc tttgcttgga   2340
gtgcaggaac aaacaaattt attgtctcct cgtggtgtaa cccaacttgc gccccaatca   2400
gaccctatcc tacagtcgaa cgatgcaggt gcgggaattg cccaaaattc tgccctggat   2460
gtcaatcagc tctgggatgt aatcaatcag caacacaaga tgctgataaa cctacaaaat   2520
caagtaacaa agatcactga gctggttgct ttaattccaa ttcttcgaag tgatattcag   2580
gctgtaaagg gaagttgcgc attattagaa gcacagctag catctataag aatactagat   2640
cctgggaaca tcggggtatc ttcattagat gatcttaaaa cagcagggaa acaaagtgta   2700
gttattaatc aagggagcta tactgatgca aaggatctga tggttggggg aggattgatt   2760
cttgatgaac ttgctagacc tactaaatta gtcaatccaa agccacaaca atcttccaaa   2820
atattggatc aggcagaaat tgaaagtgtc aaggccctaa tccataccta cactcacgat   2880
gataagaagc ggaacaaatt cttaactgca cttgacaagg tgacaaccca ggatcagcta   2940
actcgcatca agcagcaagt attaaatcaa tagatagaca attagcattc attcaagcta   3000
tactcattta agtgctttga ttgtgttgcg gaaactatat tgagataatt tagtcttaca   3060
tgcaaaataa cattaaaaat taattatgag caatcttgat ttttctaact cataatcaac   3120
ctccttctct ataaaggcat acttagtatt gcaaaaagag aaaattaaga aaaaaagaaa   3180
aagaaaattg agggagaccg cttgatagat ctgtgatcgg tctcataacc tcaaattaaa   3240
atggaatcta tatctctggg gttatatgtt gatgaaagtg atccagcatg ctcattactt   3300
gcattcccca taatcatgca gactacaagt gaaggaaaga aggtcttaca accgcaagtc   3360
agaataaacc gtctagggag tatatcgata gaaggagttc gggcaatgtt cataaataca   3420
tatggcttca ttgaggagag gcctacggaa aggacaggtt tctttcagcc aggcgaaaaa   3480
aatcagcagc aagttgtgac agctggtatg ctgacattgg gccaaataag gaccaatata   3540
gacccggacg aaattggaga ggcatgcttg agactcaaag tgaatgctaa aaaatcagca   3600
gcaagtgagg agaagatagt atttagcatt cttgaaaagc ctcccgccct gatgactgca   3660
cctgtagtac aagatggggg cttaattgct aaagcagaag gatcaatcaa atgcccaggt   3720
```

-continued

```
aagatgatga gtgaaattca ctactcattt agagtaatgt ttgtgagtat cacaatgctg   3780
gataatcaga gcctatacag agtaccaaca gccatcagct cgttcaaaaa taaagctcta   3840
tattctattc agttagaggt attgctggaa gttgatgtga agcctgagag cccccagtgt   3900
aaatttctag cagaccagaa agggaagaaa gttgcttctg tatggttcca tctctgcaat   3960
tctaaaaaga cgaatgccag cgggaaaccg agatcattag aggatatgag aaagaaggtc   4020
cgagatatgg gaatcaaagt gtctctggcc gacctttggg gccctacgat catcgtcagg   4080
gccacaggga agatgagtaa atatatgcta ggatttttct ctacctcagg gacttcatgt   4140
catccagtaa caaagagttc accagatttg gcaaaaatat tatggtcatg ctcaagcaca   4200
atcatcaaag caaatgccat tgttcaaggg tcagtcaaag tcgatgtcct gaccctcgaa   4260
gatatccaag tttccagtgc tgcaaaaatc aacaaatcag gaatagggaa gtttaatcca   4320
tttaagaaat aaagtcatat gcagattaaa atttgatcaa gattggtctt agcaaattaa   4380
ctgaatgtaa ttataaaata cctcagtaaa atgctaatga atcagtggat gatattgaat   4440
tagcagattg aaaattaaag aaaaccttat gagggcgaat gagcttagat gatttaataa   4500
aggagactaa tccaacattt ccctcaaatt aacaaaatca gaaagtaaaa agaaagggag   4560
caatgagagt acgaccttta ataataatcc tggtgctttt agtgttgctg tggttaaata   4620
ttctacccgt aattggctta gacaattcaa agattgcaca agcaggtatt atcagtgcac   4680
aagaatatgc agttaatgtg tattcacaga gtaatgaggc ttacattgca ctgcgcactg   4740
tgccatatat acctccacac aatctctctt gtttccagga tttaatcaac acatacaata   4800
caacgattca aaacatattc tcaccaattc aggatcaaat cacatctata acatcggcgt   4860
caacgctccc ctcatcaaga tttgcaggat tagtagtcgg tgcaatcgct ctcggagtag   4920
cgacatctgc acaaataact gcagccgtgg cactcacaaa ggcacagcag aacgctcaag   4980
aaataatacg attacgtgat tctatccaaa atactatcaa tgctgtgaat gacataacag   5040
tagggttaag ttcaatagga gtagcactaa gcaaggtcca aaactacttg aatgatgtga   5100
taaaccctgc tctgcagaac ctgagctgcc aggtttctgc attaaactta gggatccaat   5160
taaatcttta tttaaccgaa attacaacta tctttggacc gcaaattaca aatccatcat   5220
tgaccccatt gtcaattcag gcattataca ccctagcagg agataacctg atgcaatttc   5280
ttaccaggta tggctatgga gagacaagtg ttagcagtat tctcgagtca ggactaatat   5340
cagcacaaat tgtatctttt gataaacaga caggcattgc aatattgtat gtcacattac   5400
catcaattgc gactctttcc ggttctagag ttaccaaatt gatgtcagtt agtgtccaaa   5460
ctggagttgg agagggttct gctattgtac catcatacgt tattcagcag ggaacagtaa   5520
tagaagaatt tattcctgac agttgcatct tcacaagatc agatgtttat tgtactcaat   5580
tgtacagtaa attattgcct gatagcatat tgcaatgcct ccagggatca atggcagatt   5640
gccaatttac tcgctcattg ggttcatttg caaacagatt catgaccgtt gcaggtgggg   5700
tgatagcaaa ttgtcagaca gtcctgtgcc gatgctataa tccagttatg attattcccc   5760
agaacaatgg aattgctgtc actctgatag atggtagttt atgtaaagaa cttgaattgg   5820
aggggataag actaacaatg gcagacccag tatttgcttc atactctcgt gatctgatta   5880
taaatgggaa tcaatttgct ccgtctgatg ctttagacat tagtagcgaa ttaggtcaac   5940
tgaataactc aattagctca gcaactgata atttacagaa ggcacaggaa tcattgaata   6000
agagtatcat tccagctgcg acttccagct ggttaattat attactattt gtattagtat   6060
caatctcatt agtgatagga tgtatctcca tttattttat atataaacat tcaaccacaa   6120
```

-continued atagatcacg aaatctctca agtgacatca tcagtaatcc ttatatacag aaagctaatt 6180
gatgaattaa tttctaaaaa ataatttgat gttctaatag gagaatgcaa tatcaatatg 6240
tccattataa tatacttgat tgattgaaag atctgataat aatagtttat aagacactaa 6300
gtaagagtta aatgctaaag caagttgatt cctaaatttc tgcacaatag gaccatacta 6360
tatcatatta gataattaat aaaaaacgcc ctatcctgag ggcgaaaggc cgatcattag 6420
tgactttaac cgttgctctc ccaatttaaa atatatttca catggagtca atcgggaaag 6480
gaacctggag aactgtgtat agagtcctta cgattctatt agatgtagtg atcattattc 6540
tctctgtgat tgctctgatt tcattgggtc tgaagccagg tgagaggatc atcaatgaag 6600
tcaatggatc tatccataat caacttgttc ccttatcggg gattacttcc gatattcagg 6660
caaaagtcag cagcatatat cggagcaact tgctaagtat cccactacaa cttgatcaaa 6720
tcaaccaggc aatatcatca tctgctaggc aaattgctga tacaatcaac tcgtttctcg 6780
ctctgaatgg cagtggaact tttatttata caaattcacc tgagtttgca aatggtttca 6840
atagagcaat gttcccaacc ctaaatcaaa gcttaaatat gctaacacct ggtaatctaa 6900
ttgaatttac taattttatt ccaactccaa caacaaaatc aggatgtatc agaataccat 6960
cattttcaat gtcatcaagt cactggtgtt atacccataa tatcattgct agtggatgtc 7020
aggatcattc aaccagtagt gaatacatat cgatgggggt tgttgaagtg actgatcagg 7080
cttacccgaa ctttcggaca actctttcta ttacattagc tgataatcta aacagaaagt 7140
catgtagcat tgcagcaact gggttcgggt gtgatatatt atgtagtgtt gtcactgaga 7200
cagaaaatga tgattatcaa tcaccagaac cgactcagat gatctatgga agattatttt 7260
ttaatggcac atattcagag atgtcattga atgtgaacca aatgttcgca gattgggttg 7320
caaattatcc agcagttgga tcaggagtag agttagcaga ttttgtcatt ttcccactct 7380
atggaggtgt taaaatcact tcaaccctag gagcatcttt aagccagtat tactatattc 7440
ccaaggtgcc cacagtcaat tgctctgaga cagatgcaca acaaatagag aaggcaaaag 7500
catcctattc accacctaaa gtggctccaa atatctgggc tcaggcagtc gttaggtgca 7560
ataaatctgt taatcttgca aattcatgtg aaattctgac atttaacact agcactatga 7620
tgatgggtgc tgagggaaga ctcttgatga taggaaagaa tgtatacttt tatcaacgat 7680
ctagttcgta ttggccagtg ggaattatat ataaattaga tctacaagaa ttgacaacat 7740
tttcatcaaa tcaattgctg tcaacaatac caattccatt tgagaaattc cctagacctg 7800
catctactgc tggtgtatgt tcaaaaccaa atgtgtgtcc tgcagtatgc cagactggtg 7860
tttatcaaga tctctgggta ctatatgatc ttggcaaatt agaaaatacc acagcagtag 7920
gattgtatct aaactcagca gtaggccgaa tgaacccttt tattgggatt gcaaatacgc 7980
tatcttggta taatacaact agattattcg cacagggtac tccagcatca tattcaacaa 8040
cgacctgctt caaaaatact aagattgaca cggcatactg cttatcaata ttagaattaa 8100
gtgattcttt gttaggatca tggagaatta caccattatt gtacaatatc actttaagta 8160
ttatgagcta gatcctgttt taacattgaa tcgtatgaac ttataagact gaaggatgtc 8220
tgttggtatt aagcatcata aaacacggtt gtttttgatt tgacacctaa tcgtactcaa 8280
tactctccat agatttaatc taacagattt agatactatt gatcatatag gcatagatgg 8340
tatatgggca attagattga actgagttaa atccgattga tacttatcaa attaagatct 8400
agattattta ataaaaaatc taagttagaa aatgaggggg acctcattat ggagttcaga 8460
caatctgatc aaataataca tcctgaagtg catctagatt cacctattat tgggaataaa 8520

-continued

```
atactctatt tatggcgaat tacaggctta cctactccgc ctgttcttga gcttaactct   8580
actatatcgc ctgaagtctg gacaaacttg aaagccaatg atcctagagt agcctttaaa   8640
tgggacaaac taagaccacg gttgctaaca tgggcagcac atcaagggat atcactatcg   8700
gatctgatcc ctattacaca tcctgagtca ttgcagtggt taacaacaat atcctgtcct   8760
aaaattgatg aaaattttgc gttaattaag aagtgccttc ttagaacaag ggactataca   8820
gcatcaggat ttaagaattt attccaaatg atctcacaga aattgacgtc gacgaatatt   8880
ctattttgcg cagaaaatcc gacaactccc cccatctccg acgaagcatc ctgggcatta   8940
aagaatcctg agcactggtt taatacacct tggtcatctt gttgtatgtt ttggttacat   9000
gtgaaacaga ctatgaggaa cttaattaga atacaacgat ctcaaccaga atcacaaagc   9060
atatacagta tcacggttga taacttgttt gttggattga ctcctgactt gtgtgtcata   9120
gctgattctc aaagacaatc aattacagta ctgtcatttg agtgtgtatt gatgtattgt   9180
gacttaattg aaggtcgtaa caatgtttat gacctctgtc aattgtctcc tgtgctaagt   9240
cctcttcaag atagaatttt acttttactg agattaattg attctttagc atatgacatc   9300
ggagcgccaa tttttgatgt aattgcttct cttgaatctt tagcatatgg agctattcag   9360
ctatatgatt acgacacaga ggcagccggt gattttttct catttaattt aagagaaatt   9420
tcccaggtca tagaagagag caaatgtagg aatcaaaccc atactataat cagtgcaatt   9480
agtaagattt acacagggat caatcctgat caagcagctg aaatgctgtg tatcatgaga   9540
ctgtggggtc acccattgct ttatgcatcc aaggctgcat ctaaggttcg cgagtcaatg   9600
tgtgcaccta aagttatcca atttgatgca atgctgcttg tattagcatt ctttaagaga   9660
agcatcataa atggatatag acgaaagcat ggtgggctat ggccgaacat catagttgag   9720
tcacttcttt ctgcagaact tgtcgcggca catcatgatg cagttgaatt gacagacact   9780
tttgttatta aacactatag agaagtagcc atgattgact tcaaaaaatc attcgactac   9840
gatatagggg atgacttaag tttatacctc aaggataaag caatttgtcg acagaaatca   9900
gagtggctta atatcttcaa gggtcaattg cttgagcccg ctgtacgatc gaagcgaatt   9960
cgtggaatag gtgaaaaccg attactgtta catttcttga attcagtcga ttttgatcct  10020
gaacaagaat tcaaatacgt cactgatatg gagtacctct acgatgaaac attctgtgca  10080
tcctattcac tgaaggaaaa agaagtgaaa agagatggaa gaatattcgc aaaaatgaca  10140
ccaaaaatga gaagctgtca agttttatta gaggcattgt tagcaaaaca tgtaagcgaa  10200
cttttcaagg agaatggagt ctcaatggag cagatatccc tcacaaagtc attggtagcc  10260
atgtcacaat tagctccccg agtgaatatg agaggtggga gagcagctag atcaacagac  10320
gttaaaatca atcaacgaag ggtcaagtca atcaaagagc atgttaaatc gagaaatgat  10380
tcgaatcaag agaaaattgt aattgcaggt tatctgacta ctgatttaca aaaatactgc  10440
ctcaattgga gatatgaatc aataaaatta tttgcaagag cacttaacca attatttgga  10500
ataccccatg gatttgaatg gatacactta aggctcataa gaagtacaat gtttgttggg  10560
gatccttaca atcctcctgc atcaatccaa tctttggatc tcgatgaaca gcctaatgat  10620
gatattttta ttgtctcgcc acgtggtggg attgaaggat tatgtcagaa gatgtggaca  10680
ctcatctcaa ttgcattaat tcaagctgca gctgcaaaaa taggatgtcg ggttacaagt  10740
atggtacagg gagataatca ggttattgct atcaccagag aagtgcgagt gggggaacct  10800
gtgagggagg cgtcacgaga actcagatta ttgtgtgatg agttcttcac tgaattcaaa  10860
caattaaact acggaatagg gcacaatctt aaagcaaaag aaactatcaa gagtcaatcg  10920
```

-continued

```
tttttgtat atagcaagag agttttcttt gagggaagag tgttaagtca gatattgaag  10980
aatgcctcaa aattgaatct aatttctgac tgtctggctg aaaatacagt tgcttcatgt  11040
agcaatattt cttctactgt agcaaggcta atagagaatg gccttgggaa agacgtagcc  11100
ttcattttaa actttcagac tattataagg caactgattt ttgatgaagt atatacgatt  11160
tcattgaact atagtacagc aagacggcag gtgggaagcg agaatcctca cgcattggct  11220
atagccgctt tgattcctgg tcaacttggg ggattcaatt tcctaaacgt tgctaggtta  11280
tttacacgga atatcgggga tccaatcact tgctcattga gtgatatcaa atggtttgca  11340
aaagttggat tgatgcctga gtacatcctt aaaaacattg ttttgagggc accaggttca  11400
ggaacatgga caactttagt cgctgatccc tactccttaa acattacgta cacaaaattg  11460
cctacgtcgt acctaaagaa acatacacag aggacattag ttgctgattc ccctaatccg  11520
ttgcttcagg gggtgtttct attaaatcag cagcaggagg atgaagcatt atgtaaattt  11580
cttcttgacc gagaacaagt gatgccacga gctgcccatg taatctatga tcagtcagtt  11640
ctcggccgga ggaaatattt acaagggctt gttgatacta cacagacaat cataaggtat  11700
gcactccaaa aaatgccggt atcatacaaa aagagtgaaa aaatccaaaa ttacaatctc  11760
ctctacatac aatcactttt tgatgaggtc ttgacacaga atgtcattca tagtggattg  11820
gatactatat ggaaaagaga tctaattagc attgagacct gttctgtcac acttgccaat  11880
tttacgagga cttgctcgtg gtctaatatt ctacagggca ggcaaattgt tggagttaca  11940
actccagaca cgatagaatt gtgtaccggt tctttgattt cttgcaacag tgcatgtgag  12000
ttttgtagaa ttggagataa aagctactct tggtttcata caccaggggg tatctcattt  12060
gatacaatga gccctggcaa tctgattcaa agagtgccgt acctaggatc aaagactgat  12120
gaacagcgag ctgcctctct aacaaccatc aaggggatgg attaccatct gagacaagct  12180
cttcgaggag catcattgta tgtgtgggca tatggagaga ctgatcagaa ttggttagat  12240
gcgctgaagt tagcaaacac ccggtgcaat gtaacattac aagctttgac tgcactctgc  12300
ccaataccga gtaccgcaaa tctacaacac cggcttgcgg atggaataag tacagttaaa  12360
ttcacacctg caagtttgtc acgaatagca gcttatattc acatttgtaa tgaccaacaa  12420
aagcatgata acctagggaa tagttttgaa tcaaatctga tttaccagca aataatgctt  12480
cttggaacag gaatatttga aacaattttc ccactatcag ttcaatatat ccacgaggaa  12540
caaacacttc acttgcacac tggattttcc tgttgtgtca gggaagctga cacaatgatt  12600
atagatgaga gcagaactgg attcccagga ttgacagtga ctaagagtaa taagttttta  12660
ttcaaccctg accctattcc tgcagtgtgg gcagataaaa tattcacgac tgaatttaga  12720
ttcttcgagt acaatataga gaatcaagga acttatgaac taataaaatt tctttcttct  12780
tgctgcgcga aagttgttac agaatcgcta gttcaggata ctttccatag ttctgtcaaa  12840
aatgatgcaa taattgcgta tgacaattca attaattaca tcagtgagct acaacaatgt  12900
gacattgttc tgtttagcag tgaacttgga aaggaattac ttctagattt agcttaccag  12960
ctgtactacc ttcgaattag atcgaaacga ggtataatta gttacttgaa ggtactgctg  13020
actcggcttc caattattca gtttgcaccg cttgcgttga caatatcaca tcctgtaatc  13080
tacgagcgat tacgccaacg gaggttggtt atggaaccgt tgcaacctta tttggcttcg  13140
atagattatg tcaaagccgc aagagagctt gttttgattg gtgcttcttc ttacctctca  13200
atgcttgaga caggtttaga taccacttac aacatataca gtcatttaga cggggattca  13260
gagggcaaga ttgatcaggc gatggcaagg agactgtgcc taatcacatt attagtgaat  13320
```

cctggatatg cattacctgt gatcaaagga ctaactgcaa ttgagaaatg tagactatta 13380
acagattttt tacaatcaga tatcatttct gtttctttat ctgagcagat tgcaacactt 13440
attctaacac caaagattga agtgcacccg acaaatttat actatatgat gcggaagacc 13500
ttgaatctaa tccggtcacg agatgataca gttgtgatca tggcagaatt gtataatata 13560
gatcaagagt ctgcgataat gagggttgaa tcagaagagg acggccctgt agacaaaatg 13620
aatcttgcac ccatactaag gcttgtgcca atcacattca aatcaatgga cttgcatgcc 13680
ttaactgggc taggtagaaa agaggtggaa ctgatgggta gcccagtttg caaaatcact 13740
cagagattag ataagtacat ctatcgcaca attggcacca tatctactgc atggtataaa 13800
gcaagtagtt taatcgccag tgacatactt aagggggccc cattggggga cagcttatat 13860
ttatgtgagg gaagtggtag tagtatgaca tgtttggaat attgtttccc ttcgaaaaca 13920
atctggtata attcattctt ctcaaatgag ctaaatccac ctcaacggaa catcggccca 13980
ttaccaacac aattttgttc aagcattgtc tatcacaatt tgaatgctga agtcccgtgc 14040
tctgcagggt ttatccaaga tttcaaagta ctctgggccg acaaatcagt ggagactgat 14100
atttctacaa ctgaatgtgt gaatttcatc ctaagcaaag ttgaacttga aacatgcaaa 14160
ttgatacatg cagaccttga tctacctatt gagaccccaa gatctgtctg gatggcttgt 14220
gtcacaaata cattcatttt gggaaatgcc ttattgaagt caggagggaa attggtcatg 14280
aaattatatg cagtagatga gctcctcttt tcatcttgct taggattcgc atggtgcctt 14340
atggacgata taaatatcct ccgaaatggc tacttcaatg acaaatcaaa ggaatgctac 14400
ctcattggga caaaaaaggt gacaatcccg caccagaaaa tccaggatat ccagcagcaa 14460
ataaataaga ttgctagtca agggttaagt gtcatacctg aagctgtaat tcatgacatt 14520
tacaaccagc ttgaggacag tattagatgt gagaaaaaat tcaaaaatga taatgcaccg 14580
acttggtcca atgggatcct caattcgaca gatctattac taataagact tggagggaaa 14640
ccaattgggg aatcactatt agagttaaca tccatacaag gcatggatta tgatgattta 14700
acaggggata taattcaagt aatagacaca gcgctaaatg agattattca cctcaagtct 14760
gatacttcga gcttagatct tgtactgcta atgtctcctt acaatctggc acttggaggg 14820
aaaataagca caattctgaa atctgttgtt caccagactc taatactcag gattatccaa 14880
tctaggcaga ataaggatat accattaaaa ggatggttgt ctctgttgaa tcaaggagtc 14940
atctcactat cttcattgat cccgttgcat gattatctga ggaagagtaa gttgagaaaa 15000
tttatagttc aaaaattagg ccaacaggaa ttacaagcat tttggcagag caggtctcaa 15060
caaatgctga gtagaagtga gaccaagttg ctaataaaag tgctgagtgc tgcttggaag 15120
ggattgttgt aaaattgtaa atatacactg catgtatata aattggttgc tacccttatc 15180
agctaaccac aggtgtaaat tttcatatgg aatgcatatc aataaagata ggcatttaaa 15240
ttatacaatg ataacatatt ttaggttgac aacaatcatt gatataatca ccaatagtag 15300
ctctattact tatttgttaa taataaatgg tacactttga atttaagaaa aaattagaat 15360
tgctatattt tatcgctata gtgggcctgt cggctgcgtt agcggtaaga caaagaggac 15420
ttgtctttta aaaatttatt aaaaaatcat taattgatca tattgctttc cttgtttggt 15480

<210> SEQ ID NO 21
<211> LENGTH: 31
<212> TYPE: DNA
<213> ORGANISM: artificial sequence
<220> FEATURE:
<223> OTHER INFORMATION: APMV-polyT oligo

<400> SEQUENCE: 21
tttttttttt tttttttac caaacarrga a 31

<210> SEQ ID NO 22
<211> LENGTH: 24
<212> TYPE: DNA
<213> ORGANISM: artificial sequence
<220> FEATURE:
<223> OTHER INFORMATION: 8NPf1 oligo

<400> SEQUENCE: 22
caggagacct gatgttgcct caac 24

<210> SEQ ID NO 23
<211> LENGTH: 25
<212> TYPE: DNA
<213> ORGANISM: artificial sequence
<220> FEATURE:
<223> OTHER INFORMATION: 8NPr oligo

<400> SEQUENCE: 23
gcaggcgatc tatagtctct gatag 25

<210> SEQ ID NO 24
<211> LENGTH: 15
<212> TYPE: DNA
<213> ORGANISM: artificial sequence
<220> FEATURE:
<223> OTHER INFORMATION: NP gene start sequence

<400> SEQUENCE: 24
cccccgcuuc uguca 15

<210> SEQ ID NO 25
<211> LENGTH: 15
<212> TYPE: RNA
<213> ORGANISM: artificial sequence
<220> FEATURE:
<223> OTHER INFORMATION: P gene start sequence

<400> SEQUENCE: 25
cccccgcugg aguua 15

<210> SEQ ID NO 26
<211> LENGTH: 15
<212> TYPE: DNA
<213> ORGANISM: artificial sequence
<220> FEATURE:
<223> OTHER INFORMATION: M gene start sequence

<400> SEQUENCE: 26
cccccgcuuc ugugc 15

<210> SEQ ID NO 27
<211> LENGTH: 15
<212> TYPE: DNA
<213> ORGANISM: artificial sequence
<220> FEATURE:
<223> OTHER INFORMATION: F gene start sequence

<400> SEQUENCE: 27
cccccgcuuu agaac 15

<210> SEQ ID NO 28
<211> LENGTH: 15
<212> TYPE: DNA

-continued

```
<213> ORGANISM: artificial sequence
<220> FEATURE:
<223> OTHER INFORMATION: HN gene start sequence

<400> SEQUENCE: 28

cccccgcugg guaaa                                                      15

<210> SEQ ID NO 29
<211> LENGTH: 15
<212> TYPE: DNA
<213> ORGANISM: artificial sequence
<220> FEATURE:
<223> OTHER INFORMATION: L gene start sequence

<400> SEQUENCE: 29

cucccgcugg agaug                                                      15

<210> SEQ ID NO 30
<211> LENGTH: 16
<212> TYPE: DNA
<213> ORGANISM: artificial sequence
<220> FEATURE:
<223> OTHER INFORMATION: NP gene end sequence

<400> SEQUENCE: 30

aacuaaauuc uuuuuu                                                     16

<210> SEQ ID NO 31
<211> LENGTH: 16
<212> TYPE: DNA
<213> ORGANISM: artificial sequence
<220> FEATURE:
<223> OTHER INFORMATION: P gene end sequence

<400> SEQUENCE: 31

uaacuaauuc uuuuuu                                                     16

<210> SEQ ID NO 32
<211> LENGTH: 16
<212> TYPE: DNA
<213> ORGANISM: artificial sequence
<220> FEATURE:
<223> OTHER INFORMATION: M gene end sequence

<400> SEQUENCE: 32

aggauuaaua uuuuuu                                                     16

<210> SEQ ID NO 33
<211> LENGTH: 16
<212> TYPE: DNA
<213> ORGANISM: artificial sequence
<220> FEATURE:
<223> OTHER INFORMATION: F gene end sequence

<400> SEQUENCE: 33

cuauaaauua uuuuuu                                                     16

<210> SEQ ID NO 34
<211> LENGTH: 16
<212> TYPE: DNA
<213> ORGANISM: artificial sequence
<220> FEATURE:
<223> OTHER INFORMATION: HN gene end sequence

<400> SEQUENCE: 34

uacuuaauuc uuuuuu                                                     16
```

<210> SEQ ID NO 35
<211> LENGTH: 16
<212> TYPE: DNA
<213> ORGANISM: artificial sequence
<220> FEATURE:
<223> OTHER INFORMATION: L gene (1) end sequence

<400> SEQUENCE: 35
acuaaaauuc uuuuuu 16

<210> SEQ ID NO 36
<211> LENGTH: 16
<212> TYPE: DNA
<213> ORGANISM: artificial sequence
<220> FEATURE:
<223> OTHER INFORMATION: L gene(2) end sequence

<400> SEQUENCE: 36
uuauugauuu uuuuuu 16

<210> SEQ ID NO 37
<211> LENGTH: 15342
<212> TYPE: DNA
<213> ORGANISM: artificial sequence
<220> FEATURE:
<223> OTHER INFORMATION: AMPV8 genome FJ215863

<400> SEQUENCE: 37
accaaacaag gaatgcaaga ccaacgggaa ctttaaataa aacaatcgaa ttattggggg 60
cgaagcaagt ggatctcgag ctcgaggccg aaaccctgaa tttcactgga ggttttgaat 120
aggtcgctat aggactcaat atgtcatctg tattcaatga gtatcaggcg cttcaagaac 180
aacttgtaaa gccggctgtc aggagacctg atgttgcctc aacgggttta ctcagagcgg 240
aaatacctgt ctgtgtcaca ttatctcaag accccggtga gagatggagc cttgcttgct 300
tgaatatcag atggcttgtg agtgattcat caaccacacc aatgaagcaa ggagcaatat 360
tgtcactgct gagtctacat tcagacaata tgcgagctca cgcaacatta gcagcaaggt 420
ctgcagatgc ttcactcacc atacttgagg tagatgaagt agatattggc aactcactaa 480
tcaaattcaa cgccagaagt ggtgtatctg ataaacgctc aaatcaattg cttgcaattg 540
cggatgacat ccccaaaagt tgcagtaatg ggcatccatt tcttgacaca gacattgaga 600
ccagagaccc gctcgatcta tcagagacta tagaccgcct gcagggtatt gcagctcaga 660
tatgggtgtc agccataaag agcatgacag cgcctgacac cgcatcagag tcagaaagta 720
agaggctggc caaatatcaa caacaaggcc gactggttaa gcaagtactc ttgcattctg 780
tagtcaggac agaatttatg agagttattc ggggcagctt ggtactgcgc cagtttatgg 840
ttagcgagtg caagagggct tcagccatgg gcggagacac atctaggtac tatgctatgg 900
tgggcgacat cagtctgtac atcaagaatg caggattgac tgcatttttc ctcaccctga 960
agttcggagt tggtacccag tatccaacct tagcaatgag tgttttctcc agtgacctta 1020
aaaggcttgc tgcactaatc aggctataca aaaccaaggg agacaatgca ccatacatgg 1080
cattcctgga ggactccgat atgggaaatt ttgctccagc aaattatagc acaatgtact 1140
cttatgccat gggcattggg acaattctgg aagcatctgt atctcgatac cagtatgcca 1200
gagactttac cagtgagaat tatttccgtc ttggagttga gacagcccaa agccagcagg 1260
gagcatttga cgagagaaca gcccgagaaa tgggcttgac tgaggaatca aaacagcagg 1320
ttagatcact gctaatgtca gtagacatgg gtcccagttc agttcatgag ccatctcgcc 1380

-continued

```
ctgcatttat cagtcaagaa gaaaataggc agcctgccca gaactcgtca gatactcagg   1440
gtcagaccaa gccagtcccg aagcagcccg caccaagggc cgactcagat gacattgatc   1500
catacgagaa cgggctagaa tggtaattca accaccccga cacatccacc tatacaccaa   1560
ttctgtgaca tattaaccca atcaaacatt tcataaacta tagtagtcat tgatttaaga   1620
aaaaattggg ggcgacctca attgtgaaac ataccagatc cgtccacaac accactcaac   1680
aacccacaca caatggattt cgccaatgat gaagaaattg cagaactttt gaatctcagc   1740
accaatgtaa tcaaggagat tcagaaatcc gaactcaagc ctccccaaac caccggacga   1800
ccacctgtca gtcaagggaa cacaagaaat ctaactgatc tatgggaaaa agagactgca   1860
agtcagacca agacaccggc ccaatctcca caaaccacac aagttcagtc tgatgaaaat   1920
gaggagggag aaatcaagtc cgagtcaatt gatggccaca tcagaggaac tgttaatcaa   1980
tcagagcaag tcccagaaca aaaccagagc agatcttcac caggtgatga tctcgacaga   2040
gctctcaaca agcttgaagg gagaatcaat tcaatcagct caatggacaa agaaattaaa   2100
aagggccctc gcatccagaa tctccctggg tcccaggcgg caactcaaca ggcgacccac   2160
ccattggcag gggacacccc gaacatgcaa gcacagacaa aagccctggc gaagccacat   2220
caagaggcaa tcaatcctgg caaccaggac acaggagaga gtattcattt accaccttcc   2280
atggcaccac cagagtcatt agttggtgca atccgcaatg caccccaatt cgtgccagac   2340
caatctatga cgaatgtaga tgcggggagt gtccaactac atgcatcatg tgcagagatg   2400
ataagtagaa tgtttgtaga agttatatcc aagcttgata aactcgagtc gagactgaat   2460
gatatagcaa aagttgtgaa caccaccccc cttattagga atgatattaa ccaacttaag   2520
gccacaaccg cactgatgtc caaccaaatt gcttccatac aaattcttga cccagggaat   2580
gcaggggtga ggtccctctc tgaaatgaaa tctgtgacga agaaagctgc tgttgtaatt   2640
gcagggtttg gagacgaccc aactcaaatt attgaagaag gcattatggc caaagatgct   2700
cttggaaaac ctgtgcctcc aacatctgtt atctcagcta aagctcagac ttcttccggt   2760
gtgagtaagg gtgaaataga aggattgatt gcattggtgg aaacattagt tgacaatgac   2820
aagaaggcag caaaaactgat taaaatgatt gatcaagtta aatcccacgc cgattacgcc  2880
cgagtcaagc aggcaatata taatgcgtaa tactgtaact atacaaacaa tcaatactgc   2940
tgtcggttgc acccacctca gcaaatcaat aatcttttag aatttattga ttaagaaaaa   3000
attgactact ataaggaaag aacaccaagt tgggggcgaa gacacgattg accacagtcg   3060
ctatctgtaa ggctcctcac caaaaatggc atatacaaca ttgaaactgt gggtggatga   3120
gggtgacatg tcgtcttcgc tcctatcatt cccgttggta ctaaaagaga cagacagagg   3180
cacaaaggag cttcaaccac aggtaagggt agattcaatt ggcgatgtgc agaacgccaa   3240
agagtcctcg atattcgtga ctctatatgg tttcatccaa gcaattaagg agagtacaga   3300
tcgatcgaaa ttcttccatc caaaagatga cttcaaacct gagacagtca ctgcaggact   3360
ggtagtggta ggtgcgatcc gaatgatggc tgatgttaat accatctcta atgacgcact   3420
agcgctggag atcactgtta agaaatctgc aacttctcaa gagaaaatga cggtgatgtt   3480
ccacaatagc ccccccttcat tgagaactgc aataactatc cgagcaggag gtttcatctc  3540
gaatgcagac gagaatataa aatgtgccag caagttgact gcaggagtgc agtacatatt   3600
ccgcccaatg tttgtttcaa tcactaaatt acacaatggc aaactatata gggtgcccaa   3660
aagcatccac agcatctcgt ccactctact gtatagtgtg atgttggagg taggattcaa   3720
agtggatatt gggaaggatc atccccaggc aaagatgctg aagaaggtca caatcggcga   3780
```

-continued tgcagacaca tactgggggt ttgcatggtt ccacctgtgc aatttcaaaa agacatcctc 3840
taagggaaag ccaagaacgc tagacgaact aaagacaaaa gtcaaaaaca tggggttgaa 3900
attggagtta catgacttgt ggggtccgac tattgtggtc caaatcactg gcaagagcag 3960
caaatatgct caaggatttt tttcctccaa tggtacttgt tgcctcccaa tcagcagatc 4020
tgcaccaggg cttgggaagc ttctgtggtc ctgttcagca actatcggtg acgcaacagt 4080
tgttatccag tcaagcgaga aaggggaact cctaaggtct gatgacctcg agatacgagg 4140
tgctgtggcc tccaagaaag gtagactgag ctcatttcac cccttcaaga aatgatgcag 4200
gacatagtac agagaattag agagccatta gatgtgcgca aaaaacataa cctgcgatga 4260
actgcccaga ctccacttta acctaggttg cagggaaata gtacacgaca tgcacaatac 4320
tatcacggtc accagcaatc aataaagttg atcaatcact atattaggaa tcaaatagga 4380
taacaattat taatccaatt tcctaattat aaaaaattgc tttaaaggtt attgacgagt 4440
cgggggcgaa atcttgccac ttagtctgca gtcaatctta gaatctacat attgaactat 4500
gggtcaaata tcagtatatc taattaatag cgtgctatta ttgctggtat atcctgtgaa 4560
ttcgattgac aatacactca ttgccccaat cggagttgcc agcgcaaatg aatggcagct 4620
tgctgcatat acaacatcac tttcagggac aattgccgtg cgattcctac ctgtgctccc 4680
ggataatatg actacctgtc ttagagaaac aatcactaca tataataata ctgtcaacaa 4740
catcttaggc ccactcaaat ccaatctgga tgcactgctc tcatctgaga cttatcccca 4800
gacaagatta attggggcag ttataggttc aattgctctc ggtgttgcaa catcggctca 4860
aatcactgct gcagttgctc tcaagcaagc gcaagacaat gcaaggaaca tactagcact 4920
caaagaagca ctgtccaaaa ccaatgaggc ggtcaaggag cttagtagtg ggttacaaca 4980
aacagctatt gcacttggta agatacagag ttttgtgaat gaggaaattc tgccatctat 5040
caaccaactg agctgcgagg tgacagccaa taaacttggg gtgtatttat ctctgtatct 5100
cacagaactg accaccatat tcggtgcaca gctgactaac cctgcattga cttcattatc 5160
atatcaagcg ctgtacaacc tgtgtggtgg caacatggca atgcttactc agaagattgg 5220
aattaaacaa caagacgtta attcgctata tgaagccgga ctaatcacag gacaagtcat 5280
tggttatgac tctcagtacc agctgctggt catccaggtc aattatccaa gcatttctga 5340
ggtcactggt gtacgtgcaa cagaattagt cactgttagt gtaacaacag acaagggtga 5400
agggaaagca attgtacccc aatttgtagc tgaaagtcgg gtgactattg aagagcttga 5460
tgtagcatct tgtaaattca gcagcacgac cctatattgc aggcaggtca acacaagggc 5520
acttcccccg ctagtagcta gctgtcttcg aggtaactat gatgattgtc aatataccac 5580
agagattgga gcattatcat cccggtatat aacactagat ggggggtct tagttaattg 5640
taagtcaatt gtttgtaggt gccttaatcc aagtaagatc atctctcaaa atacaaacgc 5700
tgcagtaaca tatgttgatg ccacaatctg caaaacaatt caattggatg atatacaact 5760
ccagctggaa gggtcactat catcagttta tgcaagaaac atctcaattg agatcagtca 5820
ggtgaccacc tccgggtctt tagatatcag cagtgagata ggaaacatca ataatacggt 5880
gaatcgtgtg gaggatttaa ttcaccaatc agaggaatgg ctggcaaagg ttaacccaca 5940
cattgttaat aatacaacac taatcgtact ctgtgtgtta agtgcgcttg ctgtgatctg 6000
gctggcagta ttaacggcta ttataatata cttgagaaca aagttgaaga ctatatcggc 6060
attagctgta accaatacaa tacagtctaa cccctatgtt aaccaaacga aacgtgaatc 6120
taagttttga tcattcaagc caaaacagag gatctaggct cgggttaata atagttcaat 6180

-continued

```
caatgtttga tttattaggt ttttcccact aattattaat atattcgtga ttagatgata   6240
acgttaaaag tcttaaatat ttaataaaaa atgtaacctg ggggcgaccc atttataggt   6300
tagtatatat taggaagtcc ttatattgca ctgtaatttc aaacaattat attacctcat   6360
atctaccttg tctaaagaca tcatgagtaa cattgcatcc agtttagaaa acattgtaga   6420
gcaggatagt cgaaaaacaa cttggagagc catctttaga tggtccgttc ttcttatcac   6480
aacaggatgc ttagccttat ccattattag catagttcaa attggaaatt tgaaaattcc   6540
ttctgtaggg gatctggctg atgaagtggt gacacccttg aaaaccactc tgtctgatac   6600
actcaggaat ccaattaacc agataaatga catatttagg attgttgccc ttgatattcc   6660
attgcaagtg accaatatcc aaaaagacct tgcaagtcaa tttaacatgt tgatagatag   6720
tttaaatgct atcaaattag gcaacgggac caaccttatc atacctacat cagacaagga   6780
gtatgcagga ggaattggaa accctgtatt tactgtcgat gctggaggtt ctataggatt   6840
caaacagttt agcttaatag aacatccgag ctttattgct ggacctacaa cgacccgagg   6900
ctgtacaaga atacccactt ttcacatgtc agaaagtcat tggtgctact cacacaacat   6960
catcgctgct ggctgtcaag atgccagtgc atccagtatg tatatctcaa tgggagttct   7020
ccatgtgtcc tcatctggca ctcccatttt tcttactact gcaagtgagc tgatagacga   7080
tggagttaac cgtaagtcat gcagcattgt agcaacccga tttggctgtg acattttgtg   7140
cagtattgtc acagagaagg agggagatga ttactggtct gatactccga ctccaatgcg   7200
ccacggccgt tttcattca atggtagttt tgtagaagcc gaactaccag tgtccagtat   7260
gttctcgtca ttctctgcca actaccctgc tgtgggatca ggcgaaattg taaaagatag   7320
aatattattc ccaatttacg gaggtataaa gcagacttca ccagagttta ccgaattagt   7380
gaaatacgga ctctttgtat caacacctac aactgtgtgc cagagtagct ggacttatga   7440
ccaggtaaaa gcagcgtata ggccagatta catatcaggc cggttctggg cacaagtgat   7500
actcagctgc gctcttgatg cagtcgactt atcaagttgt attgtaaaga ttatgaatag   7560
cagcacagtg atgatggcag cggaaggaag gataatgaag atagggattg attactttta   7620
ctatcagcgg tcatcttctt ggtggccatt ggcatttgtt acaaaactag acccgcaaga   7680
attggcagac acaaactcaa tatggctgac caattccata ccaatcccgc aatcaaagtt   7740
ccctcggcct tcatattcag aaaattattg cacaaagcca gcagtttgcc ctgctacttg   7800
tgtcactggt gtgtactctg atatttggcc cctgacctca tcttcatcac tcccgagcat   7860
aatttggatc ggccagtacc ttgatgctcc tgttagaagg acttatccca gatttggaat   7920
tgcaaatcag tcacactggt acctccaaga agatattcta cccacttcca ccgcaagtgc   7980
gtattcaacc actacatgtt ttaagaatac tgccaggaat agagtgttct gcgtcaccat   8040
tgccgaattt gcagatgggt tgtttggaga gtacaggata acacctcagt tgtacgaatt   8100
agtgagaaat aattgaataa cgataatttt gagactcatt ttgtcgcaaa gtgaaattgt   8160
catctttaaa aataatcaat tctatgattt ttattgaaca tgattaagca atcatgtggg   8220
aaatttatta tctcataaat tctaatagtt gtaaatgacg aattaagaaa aaatggaggg   8280
cgacctctac acaaacatgg atataaaaca agttgacctg ataatacaac ccgaggttca   8340
tctcgattca cccatcatat tgaataaact ggcactatta tggcgcttga gtggtttacc   8400
catgcctgca gacctacgac aaaaatccgt agtgatgcac atcccggacc acatcttaga   8460
aaaatcagaa tatcggatca agcaccgtct agggaaaatc aagagtgaca taacacatta   8520
ctgccagtat tttaatatta atttggcaaa tcttgatccg ataacccacc ccaaaagttt   8580
```

-continued

```
gtattggtta tccagactaa caatagctag tgctggaacc tttagacata tgaaagatag   8640
aatcttgtgt acagttggct ctgaattcgg acacaaaatt caagatttat tttcactgtt   8700
gagccataaa ctagtaggta acggtgattt atttaatcaa agtctctcag gtacacgttt   8760
gactgcgagt ccgttatccc ctttatgcga tcaatttgtc tctgacatca agtctgcagt   8820
cacgacaccc tggtcagaag ctcgttggtc ttggcttcat atcaaacaaa caatgagata   8880
tctaataaaa caatcatgca ctacaaattc ggctcattta acagaaatca taaaagagga   8940
atggggttta gtaggtatta ctccagatct tgtcattctt tttgacagag tcaataatag   9000
tctgactgca ttaacatttg agatggttct aatgtattca gatgtattag aatcccgtga   9060
caatattgtg ttagtggggc gactatctac ctttctacag ccagtagtta gtagactgga   9120
ggtgttgttt gatctagtag attcattggc aaaaatctta ggtgacacaa tatatgagat   9180
tattgcagtg ttagagagct tgtcttatgg gtcagttcaa ctacatgatg caagtcactc   9240
tcatgcaggg tctttttttt catttaacat gaatgaactt gataacacac tatcaaagag   9300
ggtagatccg aaacacaaga acaccataat gagcattata agacaatgct tttctaatct   9360
agatgttgat caagctgcag agatgctatg cctgatgaga ttattcggac acccaatgtt   9420
aactgcaccg gatgcagcag ccaaagtgag gaaagcaatg tgtgctccaa aacttgttga   9480
acacgacacc atcttgcaga cattatcttt cttcaagggg ataattataa atgggtacag   9540
aagatcacac tctggcctgt ggcccaatgt agagccgtct tcaatttatg atgatgatct   9600
cagacagctg tacttagagt cagcagagat ttcccatcat ttcatgctta aaaactacaa   9660
gagtttgagc atgatagaat tcaagaagag catagactac gatcttcatg atgacttaag   9720
tactttctta aaggatagag caatttgccg gccgaaatcc cagtgggatg tcatatttcg   9780
taaatcttta cgcagatctc atacgcagtc ccagtatcta gacgaaatta agagcaaccg   9840
gttgctaatt gattttcttg attctgctga atttgaccct gaaaaagaat ttgcatatgt   9900
aaccacaatg gattatttgc acgataatga attttgtgct tcatattctc taaaggaaaa   9960
ggagatcaaa actactggga ggatatttgc aaaaatgaca cgcaatatga gaagttgcca  10020
agtaatactt gaatctttgt tatcaaagca tatatgcaag ttcttcaaag agaatggcgt  10080
ttcgatggag caattgtcat tgaccaagag tctacttgca atgtctcaac tctcaccaaa  10140
agtctcgact ttgcaggaca ctgcatcacg tcatgtaggc aactcaaaat ctcagattgc  10200
aaccagcaac ccatctcggc atcactcgac agccaatcag atgtcactct caaatcgaaa  10260
aacggttgta gcaactttct taacaactga cttggaaaaa tactgcctgc agtggcgata  10320
ctcaactatt aaattgtttg cacaagctct aaatcaactc tttgggattg atcacggatt  10380
tgaatggata catttaagac ttatgaacag caccttattt gttggcgatc cttactcgcc  10440
tcctgaagat ccaacactag aagatataga taaagcacca aatgatgata tcttcatagt  10500
ttctccaagg ggaggcatag agggtttatg tcagaaaatg tggaccatga tatcaattag  10560
tgctatacac tgtgtagcag agaaaattgg tgcacgagtg gcagcaatgg tgcagggtga  10620
taatcaagta atagctatca ccaaagaact attcagagga gaaaaagctt gtgatgtcag  10680
agatgagtta gacgagcttg gtcaagtgtt ttttgatgag ttcaagagac acaattatgc  10740
aattggacac aatcttaagc taaatgagac aatacaaagc caatcctttt ttgtatattc  10800
caaacgaata ttctttgaag ggcgattgct tagtcaagtc ctcaaaaatg ctgccaagtt  10860
atgtatggtt gctgaccatc taggtgaaaa cactgtatct tcctgtagca acctgagctc  10920
gacaattgcc cgcttggtgg aaaatgggtt tgagaaggac actgcttttg tgttgaacct  10980
```

-continued

```
agtctacatc atgactcaga ttctttttga tgagcattac tcgattgtat gcgatcacca  11040
tagtgtcaaa agtttgattg gatcaaaaaa ccatcggaat ttattgtact catctctaat  11100
accaggtcag ctcggcggtt tcaacttcct caatataagt cggttgttca ctaggaatat  11160
aggtgaccca gtaacatgta gtctgtctga tctcaaatgc ttcatagccg caggtctcct  11220
tccaccctat gtcctaaaaa atgtggttct gcgtgagcct ggtcctggga catggttgac  11280
gttgtgctct gatccttaca cccttaacat accatacaca cagcttccaa ccacatatct  11340
caaaaagcac acccagcgat cattgctttc acgtgcagta aatcctttat tagccggtgt  11400
acaagtgcca aatcagcatg aggaagaaga ggtgttggct cgctttctcc ttgatcgtga  11460
atatgtgatg ccccgcgttg ctcatgtaat actagaaaca tcggtccttg gcaaacggaa  11520
acaaatccaa ggcttaattg atacaactcc aaccatcatt agaacatctc tagttaatct  11580
gccagtgtct agaaagaaat gcgaaaaaat aatcaattac tctctcaatt atattgctga  11640
gtgtcatgac tccttactta gccaggtctg cttcagtgat aataaggaat acttgtggtc  11700
aacctcctta atatcagttg agacatgtag tgtgacaatc gcggactatc tgagagctgt  11760
cagctggtct aatatattag ggggaagaaa catatccggg gtgactacac ctgatactat  11820
tgaattaatt caaggttgtt taataggtga aaattctagt tgtactcttt gtgaatcgca  11880
tgatgacgca ttcacgtgga tgcacttgcc tggcccactt tacatccctg aaccatcagt  11940
tactaactct aaaatgcgtg tgccatatct gggttcgaaa acagaggagc gtaaaacagc  12000
ctcaatggca gcaataaaag gaatgtcaca tcacctgcgt gcagtcttaa gaggcacatc  12060
cgtatttatt tgggcatttg ggatacaga tattaattgg gataatgcat tgcagattgc  12120
ccaatcacgg tgtaacatca cattggatca aatgagatta cttacaccaa ttcctagcag  12180
ttcaaatatt caacatagac tcgatgacgg aatcagcacg cagaaattta ctcctgcaag  12240
ccttgctcga atcacatcct tcgttcacat ctgtaatgac agccagaggt tagagaagga  12300
tggctcatct gttgactcaa acttgattta ccagcaaatt atgttacttg gactcagcat  12360
ctttgaaaca atgtactcaa tggaccaaaa gtgggtattc aataaccata ccttgcattt  12420
gcacactgga cactcctgtt gtccaaggga actagacata agtttggtga acccgccgag  12480
acatcagacc ccggagctga ctagcacaac aaccaacccg ttcctatatg atcagctccc  12540
attaaatcaa gaaaacttga caacacttga gattaagaca tttaaattca atgagctcaa  12600
cattgatggt ttagattttg gtgaaggaat acaattattg agtcgttgta ctgcaagatt  12660
gatggcagaa tgtattctag aggagggaat aggctcgtca gttaaaaatg aagcaattgt  12720
caattttgat aattcagtca attggatttc agagtgccta atgtgtgata ttcgctcact  12780
ttgtgttaat ttaggtcaag agatactatg tagcctggca taccaaatgt attacttgcg  12840
aatcaggggt agacgggcca ttcttaatta cttggacaca actttgcaaa ggatccctgt  12900
gatacaatta gccaacattg cactcaccat ttcgcaccct gagatatttc gcagaattgt  12960
caacaccggg atccataacc agattaaggg cccatatgtc gcaacaacgg atttcatagc  13020
tgcaagtaga gatatcatat tatcaggtgc aagggagtat ctatcttatt taagcagtgg  13080
gcaggaagac tgttacacat tcttcaactg tcaagatggg gatcttactc caaaaatgga  13140
acagtatctt gcaaggaggg catgcctttt aacattattg tataatactg ggcaccagat  13200
ccccgttatc cgatcactga caccaataga gaagtgcaag gtgctcacag aatacaatca  13260
acaaattgag tatgcagatc aagagtttag ctctgtatta aaagtggtca atgcactact  13320
acaaaatcct aagatagatg cattagtttc aaatctctac ttcaccacca gacgtgttct  13380
```

-continued

```
atcaaacctc agatcatgtg ataaggctag atcatatatt gaatatttgt acactgagga  13440
cttcggagag aaagaggata cagtacaata tgacatcatg acaacaaacg atatcatact  13500
tactcatggt ctattcacac agatcgaaat atcttatcaa gggaatagtc tccataagtt  13560
ccttactccg gataacgcgc ctggatcttt gatcccattc tctatttcac caaattcact  13620
tgcatgtgat cctcttcatc acttgctcaa gtcggtcggt acatcaagca caagttggta  13680
caagtatgca atcgcctatg cagtgtctga aaagaggtca gctcgattag gagggagctt  13740
gtacattggt gaagggagcg gaagtgtgat gactttactc gagtatcttg agccatctgt  13800
tgacatattt tacaattcac tcttctcaaa tggtatgaac ccaccacaac gaaattatgg  13860
gcttatgcca ctacaatttg tgaattcggt ggtttataag aacttaacgg ctaaatcaga  13920
atgtaagcta gggtttgtcc agcaatttaa accgttgtgg agagacatag acattgagac  13980
taatgttaca gatccatcat ttgtcaattt tgcattgaat gaaatcccaa tgcaatcatt  14040
aaaacgagta aattgtgatg tggaatttga ccgtggtatg ccgattgaac gggttattca  14100
gggttatacc catatcttac ttgttgctac ttacggatta cagcaagatt caatactgtg  14160
ggtgaaggta tataggacat ctgaaaaagt atttcaattc ttactgagtg ccatgatcat  14220
gatctttggt tatgtcaaaa tccacaggaa tggttatatg tcgacaaagg atgaagagta  14280
catattgatg tctgactgca aggaacctgt aaactataca gctgtcccta acattcttac  14340
acgtgtaagt gatttagtgt cgaagaatct gagtcttatc catccagaag acctcagaaa  14400
agtaaggtgt gaaacagatt ccctgaattt gaagtgcaat catatttatg agaaaataat  14460
tgccagaaaa attccattac aggtatcatc aactgattct ttgctcctcc aattaggcgg  14520
tgttatcaac tcggtgggct caactgatcc tagagaggtt gcaacattat cttctattga  14580
gtgtatggac tatgttgtct catcaattga tttggctata ttggaggcaa atattgtaat  14640
ctcagagagt gctggtcttg acctcgcttt aatgttaggc ccattcaact tgaataagct  14700
taagaaaatt gatacaatcc ttaagtcaag cacctatcag ctaatcccgt actggttgcg  14760
ctatgagtac tctattaatc cgagatcttt gtcatttcta atcactaaat tacaacaatg  14820
ccgaatttca tggtcagata tgatcacgat ttctgaattt cgtaagaaat ccaagcggcc  14880
tatatttatc aaacgagtaa tagggaatca acagctaaaa tcattcttta atgaaagctc  14940
aagtattgtt ttgactcggg ctgaagttaa agtctgtata aagttcctcg gtgcaatcat  15000
caagttgaaa taatttctgc gattttaaag gggtgtaatg ttctaatttg cacttggagt  15060
aatatagctt gtaatcattc gataggggat aggataattt ctctaacctc tgaatctata  15120
tccctagagt ataacaaata tatacataat aaaaatgatt ttaagaaaaa atccgacact  15180
caaagaaaat tggtgcctgt aatattcttc ttgccagatg attgtggagt gtctagccta  15240
acttaaaaca atcgtattcg atagggaaga atggtatata aaataactaa taaaaaaatg  15300
tattagtaaa aattaccgta tttcctgtat tccatttctg gt                     15342
```

<210> SEQ ID NO 38
<211> LENGTH: 15342
<212> TYPE: DNA
<213> ORGANISM: artificial sequence
<220> FEATURE:
<223> OTHER INFORMATION: APMV8 genome FJ215864

<400> SEQUENCE: 38

```
accaaacaag gaatgcaaga ccaacgggaa ctttaaataa aacaatcgaa tcattggggg     60
cgaagcaagt ggatctcggg ctcgaggccg aaacactgga tttcgctgga ggttttgaat    120
```

-continued

```
aggtcgctat aagactcaat atgtcatctg tattcaatga atatcaggca cttcaagaac    180
aacttgtaaa gccggctgtc aggagacctg atgttgcctc aacaggttta ctcagggcgg    240
aaatacctgt ctgtgttaca ttgtctcaag accccggtga gagatggagc cttgcttgcc    300
ttaatatccg atggcttgtg agtgattcat caaccacacc aatgaagcag ggagcaatat    360
tgtcactgct gagtctacat tcagacaata tgcgagctca cgcaacatta gcagcaaggt    420
ctgcagatgc ttcactcacc atacttgagg tagatgaagt agatattggc aactccctaa    480
tcaaattcaa cgctagaagt ggtgtatctg ataaacgatc aaatcaattg cttgcaattg    540
cggatgacat ccccaaaagt tgcagtaatg ggcatccatt tcttgacaca gacattgaga    600
ccagagaccc gctcgatcta tcagagacca tagaccgcct gcagggtatt gcagctcaga    660
tatgggtgtc agccataaag agcatgacag cgcctgacac cgcatcagag tcagaaagta    720
agaggctggc caaataccaa caacaaggcc gactggttaa gcaagtactt ttgcattctg    780
tagtcaggac agaatttatg agagttattc ggggcagctt ggtactgcgc cagtttatgg    840
ttagcgagtg caagagggct tcagccatgg gcggagacac atctaggtac tatgctatgg    900
tgggtgacat cagtctgtac atcaagaatg caggattgac tgcatttttc ctcaccctga    960
agttcggggt tggtacccag tatccaacct tagcaatgag tgttttctcc agtgacctta   1020
aaagacttgc tgcactcatc aggctgtaca aaaccaaggg agacaatgca ccatacatgg   1080
cattcctgga ggactccgat atgggaaatt ttgctccagc aaattatagc acaatgtact   1140
cttatgccat gggcattggg acgattctgg aagcatctgt atctcgatac cagtatgcta   1200
gagactttac cagtgagaat tatttccgtc ttggagttga gacagcccaa agccagcagg   1260
gagcgtttga cgagagaaca gcccgagaga tgggcttgac tgaggaatcc aaacagcagg   1320
ttagatcact gctaatgtca gtagacatgg gtcccagttc agttcgcgag ccatcccgcc   1380
ctgcattcat cagtcaagaa gaaaatagc agcctgccca gaattcttca gatactcagg   1440
gtcagaccaa gccagtcccg aatcaacccg caccaagggc cgacccagat gacattgatc   1500
catacgagaa cgggctagaa tggtaattca atcacctcga cacatccacc tatacaccaa   1560
ttctgtgaca tattaaccta atcaaacatt tcataaacta tagtagtcat tgatttaaga   1620
aaaaattggg ggcgacctca actgtgaaac acgccagatc tgtccacaac accactcaac   1680
aacccacaca agatggactt cgccaatgat gaagaaattg cagaacttct gaacctcagc   1740
accactgtaa tcaaggagat tcagaaatct gaactcaagc ctccccaaac cactgggcga   1800
ccacctgtca gtcaagggaa cacaagaaat ctaactgatc tatgggaaaa ggagactgca   1860
agtcagaaca agacatcggc tcaatctcca caaaccacac aagttcagtc tgatggaaat   1920
gaggaggaag aaatcaaatc agagtcaatt gatggccaca tcagtggaac tgttaatcaa   1980
ttagagcaag tcccagaaca aaaccagagc agatcttcac caggtgatga tctcgacaga   2040
gctctcaaca agcttgaagg gagaatcaac tcaatcagct caatggataa agaaattaaa   2100
aagggccctc gcatccagaa tctccctggg tcccaagcag caactcaaca ggcgacccac   2160
ccattggcag gggacacccc gaacatgcaa gcacggacaa aacccctgac caagccacat   2220
caagaggcaa tcaatcctgg caaccaggac acaggagaga atattcattt accaccttcc   2280
atggcaccac cagagtcatt agttggtgca atccgcaatg taccccaatt cgtgccagac   2340
caatctatga cgaatgtaga tgcggggagt gtccaactac atgcatcatg tgcagagatg   2400
ataagtagaa tgtttgtaga agttatatct aagcttgata aactcgagtc gagactgaat   2460
gatatagcaa aagttgtaaa caccaccccc cttatcagga atgatattaa ccaacttaag   2520
```

-continued

```
gccacaactg cactgatgtc caaccaaatt gcttccatac aaattcttga cccagggaat   2580
gcaggggtga ggtccctctc tgaaatgaga tctgtgacga agaaagctgc tgttgtaatt   2640
gcaggatttg gagacgaccc aactcaaatt attgaagaag gtatcatggc caaagatgct   2700
cttggaaaac ctgtgcctcc aacatctgtt atcgcagcca aagctcagac ttcttccggt   2760
gtgagtaagg gtgaaataga aggattgatt gcattggtgg aaacattagt tgacaatgac   2820
aagaaggcag cgaaactgat taaaatgatt gatcaagtta aatcccacgc cgattacgcc   2880
cgagtcaagc aggcaatata taatgcataa tattgtaatt atacaaacaa tcaatactgc   2940
tgtcggttgc acccacctta gcaaatcaat aatcttttaa aattgattga ttaagaaaaa   3000
attgactaca ataaggaaag aacaccaagt tgggggcgaa gtcacgattg accacagtcg   3060
ctatctgtaa ggctcctcac caaaaatggc atatacaaca ctaaaactgt gggtggatga   3120
gggtgacatg tcgtcttcgc ttctatcatt cccgttggta ctaaaagaga cagacagagg   3180
cacaaagaag cttcaaccac aggtaagggt agattcaatt ggcgatgtgc agaatgccaa   3240
agagtcctcg atattcgtga ctctatatgg tttcatccaa gcaattaagg agaattcaga   3300
tcgatcgaaa ttcttccatc caaaagatga cttcaaacct gagacagtca ctgcaggact   3360
ggtagtagtg ggtgcaatcc gaatgatggc tgatgtcaat accatctcta atgatgcact   3420
agcgctggag atcactgtta agaaatctgc aacttctcaa gagaaaatga cggtgatgtt   3480
ccacaatagc ccccccttcat tgagaactgc aataactatc cgagcaggag gtttcatctc   3540
gaatgcagac gaaaatataa aatgtgccag caagttgact gcaggagtgc agtacatatt   3600
ccgtccaatg tttgtttcaa tcactaaatt acacaatggc aaactatata gggtgcccaa   3660
aagtatccac agcatctcgt ctaccctact gtatagtgtg atgttggagg taggattcaa   3720
agtggacatc gggaaggatc atccccaggc aaaaatgctg aagagggtca caattggcga   3780
tgcagacaca tactggggat ttgcatggtt ccacctgtgc aatttcaaaa agacatcctc   3840
taagggaaag ccgagaacgc tagacgaact gaagacaaaa gtcaaaaata tggggttgaa   3900
attggagtta catgacctat ggggtccgac tattgtggtc caaatcactg gcaagagcag   3960
caaatatgct caaggatttt tttcttccaa tggtacttgt tgcctcccaa tcagcagatc   4020
tgcaccagag cttgggaagc ttctgtggtc ctgctcagca actattggtg acgcaacagt   4080
tgttatccaa tcaagcgaga agggggaact cctaaggtct gatgatctcg agatacgagg   4140
tgctgtggcc tccaagaaag gtagactgag ctcatttcac cccttcaaaa aatgatgcag   4200
gacatagtac agagaatgaa agggccatca gatgtgcgaa aaaaactaaa tctgaaaaaa   4260
actgcccaga ctccacatta atctaggttg cagggaaata atacccgaca tgcacaatac   4320
tatcacggtc accagcaatc agcaaagttg atcaatcact atataaggaa tcaagtggga   4380
taacaattat taatccaatt tcataattat aaaaaattgc tttaaaggtt actgacgagt   4440
cgggggcgaa accttgccac ttaagctgca gtcaatttta gaatctacat attgaattat   4500
gggtaaaata tcaatatatc taattaatag cgtgctatta ttgctggtat atcctgtgaa   4560
ttcgattgac aatacactcg ttgccccaat cggagtcgcc agcgcaaatg aatggcagct   4620
tgctgcatat acaacatcac tttcagggac aattgccgtg cgattcctac ctgtgctccc   4680
ggataatatg actacctgtc ttagagaaac aataactaca tataataata ctgtcaacaa   4740
catcttaggc ccactcaaat ccaatctgga tgcactgctc tcatctgaga cttatcccca   4800
gacaagatta attggggcag ttataggttc aattgctctt ggtgttgcaa catcggctca   4860
aatcactgct gcagtcgctc tcaagcaagc acaagataat gcaagaaaca tactggcact   4920
```

-continued

```
caaagaggca ctgtccaaaa ctaatgaggc ggtcaaggag cttagcagtg gattgcaaca   4980
aacagctatt gcacttggta agatacagag ctttgtgaat gaggaaattc tgccatctat   5040
caaccaactg agctgcgagg tgacagccaa taaacttggg gtgtatttat ctctgtatct   5100
cacagaactg accactatat tcggtgcaca gttgactaac cctgcattga cttcattatc   5160
atatcaagcg ctgtacaacc tgtgtggtgg caacatggca atgcttactc agaagattgg   5220
aattaaacag caagacgtta attcgctata tgaagccgga ctaatcacag gacaagtcat   5280
tggttatgac tctcagtacc agctgctggt catccaggtc aattatccaa gcatttctga   5340
ggtaactggt gtgcgtgcga cagaattagt cactgttagt gtaacaacag acaagggtga   5400
agggaaagca attgtacccc aatttgtagc tgaaagtcgg gtgactattg aggagcttga   5460
tgtagcatct tgtaaattca gcagcacaac cctatactgc aggcaggtca acacaagggc   5520
acttcccccg ctagtggcta gctgtctccg aggtaactat gatgattgtc aatataccac   5580
agagattgga gcattatcat cccggtatat aacactagat ggaggggtct tagtcaattg   5640
taagtcaatt gtttgtaggt gccttaatcc aagtaagatc atctctcaaa atacaaatgc   5700
tgcagtaaca tatgttgatg ctacaatatg caaaacaatt caattggatg acatacaact   5760
ccagttggaa gggtcactat catcagttta tgcaaggaac atctcaattg agatcagtca   5820
ggtgactacc tccggttctt tggatatcag cagtgagata gggaacatca ataatacggt   5880
gaatcgtgtg gaggatttaa tccaccaatc ggaggaatgg ctggcaaaag ttaacccaca   5940
cattgttaat aatactacac taattgtact ctgtgtgtta agtgcgcttg ctgtgatctg   6000
gctggcagta ttaacggcta ttataatata cttgagaaca aagttgaaga ctatatcggc   6060
attggctgta accaatacaa tacagtctaa tccctatgtt aaccaaacga aacgtgaatc   6120
taagttttga tcattcaggc caaaacagag ggtctaggct cgggttaata aaagttcaat   6180
caatgtttga tttattaggc tttccctact aattattaat gtatttgtga ttatatgata   6240
acgttaaaag tcttaaatat ttaataaaaa atgtaacctg ggggcgacct atttacaggc   6300
tagtatatat taggaagtcc tcatattgca ctataatctc aaacaattat attacctcgt   6360
atccaccttg tctaaagaca tcatgagtaa cattgcatcc agtttagaaa atattgtgga   6420
gcaggatagt cgaaaaacaa cttggagggc catctttaga tggtccgttc ttcttattac   6480
aacaggatgc ttagccttat ccattgttag catagttcaa attgggaatt tgaaaattcc   6540
ttctgtaggg gatctggcgg acgaggtggt aacacctttg aaaaccactc tgtctgatac   6600
actcaggaat ccaattaacc agataaatga catattcagg attgttgccc ttgatattcc   6660
attgcaagta actagtatcc aaaaagacct cgcaagtcaa tttagcatgt tgatagatag   6720
tttaaatgct atcaaattgg gcaacgggac caaccttatc atacctacat cagataagga   6780
gtatgcagga ggaattggaa accctgtatt tactgtcgat gctggaggtt ctataggatt   6840
caagcaattt agcttaatag aacatccgag ctttattgct ggacctacaa cgacccgagg   6900
ctgtacaaga atacccactt ttcacatgtc agaaagtcat tggtgctact cacacaacat   6960
catcgctgct ggctgtcaag atgccagtgc atctagtatg tatatctcaa tgggggttct   7020
ccatgtgtct tcatctggca ctcctatctt tcttactact gcaagtgaac tgatagacga   7080
tggagttaat cgtaagtcat gcagtattgt agcaacccaa ttcggctgtg acattttgtg   7140
cagtattgtc atagagaagg agggagatga ttattggtct gatactccga ctccaatgcg   7200
ccacggccgt tttcattca atgggagttt tgtagaaacc gaactacccg tgtccagtat   7260
gttctcgtca ttctctgcca actaccctgc tgtgggatca ggcgaaattg taaaagatag   7320
```

-continued

```
aatattattc ccaatttacg gaggtataaa gcagacttca ccagagttta ccgaattagt   7380
gaaatatgga ctctttgtgt caacacctac aactgtatgt cagagtagct ggacttatga   7440
ccaggtaaaa gcagcgtata ggccagatta catatcaggc cggttctggg cacaagtgat   7500
actcagctgc gctcttgatg cagtcgactt atcaagttgt attgtaaaga ttatgaatag   7560
cagcacagtg atgatggcag cagaaggaag gataataaag atagggattg attactttta   7620
ctatcagcgg tcatcttctt ggtggccatt ggcatttgtt acaaaactag acccgcaaga   7680
gttagcagac acaaactcga tatggctgac caattccata ccaatcccac aatcaaagtt   7740
ccctcggcct tcatattcag aaaattattg cacaaagcca gcagtttgcc ctgctacttg   7800
tgtcactggt gtatactctg atatttggcc cttgacctca tcttcatcac tcccgagcat   7860
aatttggatc ggccagtacc ttgatgcccc tgttggaagg acttatccca gatttggaat   7920
tgcaaatcaa tcacactggt accttcaaga agatattcta cccacctcca ctgcaagtgc   7980
gtattcaacc actacatgtt ttaagaatac tgccaggaat agagtgttct gcgtcaccat   8040
tgctgaattt gcagatgggt tgtttggaga gtacaggata acacctcagt tgtatgaatt   8100
agtgagaaat aattgaatca cgataatttt gggactcatt taattgcaga gtgaaattgt   8160
catcttagga aataatcaat tccatgattt ttattgaaca tgatcaagca atcatgtggg   8220
aaatttatta tcacataact tctaatagtt ttaaatgacg aattaagaaa aaatggaggg   8280
cgacctctac acaaacatgg atgtaaaaca agttgaccta ataatacaac ccgaggttca   8340
tctcgattca cccatcatat tgaataaact ggcactatta tggcgcttga gtggtttacc   8400
catgcctgca gacttacgac aaaaatccgt agtgatgcac atcccagacc acatcttaga   8460
aaaatcagaa tatcggatca agcaccgtct agggaaaatc aagagtgaca tagcacatta   8520
ctgtcagtat tttaatatta atttggcaaa tcttgatccg ataacccacc ccaaaagttt   8580
gtattggtta tccagactaa caatagctag tgctggaacc tttagacata tgaaagatag   8640
aatcttatgt acagttggct ccgaattcgg acacaaaatt caagatttat tttcactgct   8700
gagccataaa ttagtaggta acggtgattt atttaatcaa agtctctcag gtacacgttt   8760
gactgcgagt ccgttatccc ctttatgcaa tcaatttgtc tctgacatca agtctgcagt   8820
cacgacaccc tggtcagaag ctcgttggtc ttggcttcat atcaaacaaa caatgagata   8880
cctgataaaa caatcacgca ctacaaattc agctcattta acagaaatta taaaagagga   8940
atggggttta gtaggtatta ctccagatct tgtcattctt tttgacagag tcaataatag   9000
tctaactgca ttaacatttg agatggttct aatgtattca gatgtattag aatcccgtga   9060
caatattgtg ctagtggggc gattatctac ttttctgcag ccagtagtta gtagactgga   9120
ggtgttgttt gatctagtag attcattggc aaaaacctta ggtgacacaa tatacgaaat   9180
tattgcggtg ttagagagct tgtcttatgg gtccgttcaa ctacatgatg caagtcactc   9240
tcatgcaggg tctttctttt catttaacat gaatgaactt gataacacac tatcaaagag   9300
ggtggatccg aaacacaaga acaccataat gagcattata agacaatgct tttctaatct   9360
agatgttgat caagctgcag agatgctatg cctgatgaga ttatttggac acccaatgtt   9420
aactgcaccg gatgcagcag ccaaagtaag gaaagcaatg tgtgctccaa aacttgttga   9480
acatgacacc atcttgcaga cattatcctt cttcaaggga ataattataa atgggtacag   9540
aagatcacac tctggcctgt ggcccaatgt agagccgtct tcaatctatg atgatgatct   9600
cagacagctg tacttagagt cagcagagat ttcccatcat ttcatgctta aaaactacaa   9660
gagtttgagc atgatagaat tcaagaagag catagactac gatcttcacg acgacttaag   9720
```

-continued

```
tactttctta aaggatagag caatttgccg gccaaaatcc cagtgggatg ttatattccg   9780
taagtcttta cgcagatccc acacgcggtc ccagtatatg gacgaaatta agagcaaccg   9840
attgctaatt gattttcttg attctgctga ttttgaccct gaaaaggaat ttgcatatgt   9900
aaccacaatg gattatttgc acgataatga attttgtgct tcatattctc taaaggaaaa   9960
ggagatcaaa actaccggga ggatatttgc aaaaatgaca cgcaatatga gaagttgcca  10020
agtgatactt gaatctctgt tatcaaaaca tatatgcaag ttcttcaaag agaacggcgt  10080
ttcgatggag caattgtcat tgaccaagag tctacttgca atgtctcaac tctcaccaaa  10140
agtctcgact ctgcaggaca ctgcatcacg tcatgtaggc aactcaaaat ctcagatcgc  10200
aaccagcaac ccatctcggc atcactcaac aaccaatcag atgtcactct caaatcggaa  10260
aacggttgta gcaactttct taacaactga tttggaaaaa tactgcctgc agtggcgata  10320
ctcgactatt aagttgtttg cacaagctct aaatcaactc tttgggattg atcacggatt  10380
tgaatggata catttaagac tcatgaacag caccttattt gtcggtgatc cttactcgcc  10440
tcctgaagat ccaacactag aggatataga taaagcacca aatgacgata tcttcatagt  10500
ttctccaagg ggaggcatag agggtttatg tcagaagatg tggaccatga tatcaattag  10560
tgcgatacac tgtgtagcag agaaaattgg tgcacgagtg gcagcaatgg tgcagggtga  10620
taatcaagta atagctatca ccaaagaact attcagagga gagaaagcct gtgatgtcag  10680
agatgagtta gacgagctcg gtcaggtgtt ttttgatgag ttcaagaggc acaattatgc  10740
aattggacac aaccttaagc taaatgagac aatacaaagc caatcctttt ttgtatattc  10800
caaacgaata ttctttgaag ggcgattgct tagtcaagtc ctcaaaaatg ctgccaagtt  10860
atgtatggtt gctgaccatc taggtgaaaa cacagtatct tcctgtagca acctgagctc  10920
tacaattgcc cggttggtgg aaaatgggtt tgagaaggac actgcttttg tgttgaacct  10980
agtctacatc atgactcaaa ttctttttga tgagcattac tcgattgtat gcgatcacaa  11040
tagtgtcaaa agcttgatcg gatcaaaaaa ctatcggaat ctattgtact catctctaat  11100
accaggtcag ctcggtggtt tcaacttcct caatataagt cggttgttca ctaggaatat  11160
aggtgaccca gtaacatgta gtctgtctga tctcaaatgc ttcatagccg caggtctcct  11220
tccaccctat gtacttaaaa atgtggttct gcgtgagcct ggtcctggga catggttgac  11280
gttgtgctct gatccttaca cccttaacat accatacaca cagctaccaa ccacatatct  11340
caaaaagcac acccagcgat cgttgctttc acgtgcagta aatcctttat tagcaggtgt  11400
acaagtgcca aatcagcatg aggaagaaga gatgttggct cgctttctcc ttgatcgtga  11460
atatgtgatg ccccgcgttg ctcatgtaat actagaaaca tcggtccttg gcaaacggaa  11520
acaaatccaa ggcttaattg atacaactcc aactatcatt agaacatctc tagttaatct  11580
accagtgtct aggaagaaat gcgaaaaaat aatcaattat tctctcaatt atattgctga  11640
gtgtcatgac tccttactta gtcagatctg cttcagtgat aataaggaat acttgtggtc  11700
cacctcctta atatcagttg agacctgtag tgtgacaatt gcggactatt tgagagctgt  11760
cagctggtct aatatattag gggaagaaaa catatccggg gtgactacac ctgatactat  11820
tgaattaatt caaggttgtt taataggtga aaattccagt tgtactcttt gtgaatcgca  11880
tgacgacgca ttcacatgga tgcacttgcc tggcccactt tacatccctg aaccatcagt  11940
tactaactct aaaatgcgtg tgccatatct gggttcaaaa acagaggagc gtaaaacagc  12000
ttcaatggca gcaataaaag gaatgtcaca tcacctgcgt gcagtcttaa gaggtacatc  12060
cgtatttatt tgggcatttg gggacacaga tattaattgg gataatgcat tgcagattgc  12120
```

-continued ccaatcacgg tgtaacatca cattggatca aatgagatta cttacaccaa ttcctagcag 12180
ttcaaatatc caacatagac tcgatgacgg aatcagcacg cagaaattta ctcctgcaag 12240
ccttgctcga atcacatcct ttgttcacat ctgtaatgac agccaaaggt tagagaagga 12300
tggctcctct gtcgactcaa acttgattta ccagcaaatt atgttacttg gactcagcat 12360
ctttgaaaca atgtactcaa tggaccaaaa gtgggtattc aataaccata ccttacattt 12420
gcacactgga cactcctgtt gtccaaggga actagacata agtttagtga acccgccaag 12480
acatcagacc ccggagctga ctagcacaac aaccaacccg ttcctatatg atcagctccc 12540
actaaatcag gataatctga caacacttga gattaagaca ttcaaattta atgagctcaa 12600
cattgatggt ttagattttg gtgaaggaat acaattattg agtcgttgta ctgcaagatt 12660
aatggcagaa tgtattctag aggagggaat aggctcgtca gttaaaaatg aagcaattgt 12720
caattttgat aattcagtca attggatttc agagtgccta atgtgtgata ttcgctcact 12780
ttgtgttaat ttaggtcaag agatactatg tagcctggca taccaaatgt attacttgcg 12840
aatcaggggt agaagggcca ttcttaatta cttggacaca actttgcaaa ggatccctgt 12900
gatacaatta gccaacattg cactcaccat ttcacaccct gagatatttc gcagaattgt 12960
caacaccggg atccataacc agattaaggg cccatatgtg gcaacaacag atttcatagc 13020
tgcaagtaga gatatcatat tatcaggtgc aagggagtat ctatcttatc taagcagtgg 13080
acaggaagac tgttacacat tcttcaactg tcaagatggg gatcttactc caaaaatgga 13140
acagtatctt gcaaggaggg catgcctttt aacattactg tataatactg ggcaccagat 13200
ccccattatc cgatcactga caccaataga gaagtgcaag gtgctcacag aatacaatca 13260
acaaattgag tatgcagatc aagagtttag ctctgtattg aaagtggtca atgcactact 13320
acaaaatcct aatatagatg cattggtttc aaatctctac ttcaccacca gacgtgtttt 13380
atcaaacctc agatcatgtg ataaggctat atcatatatt gaatatttgt acactgagga 13440
cttcggagaa aaagaagata cagtacaata tgacatcatg acaacaaacg atatcatact 13500
tactcatggt ctattcacac agatcgaaat atcttaccaa gggagtagtc tccataaatt 13560
cctaactccg gataacgcgc ctggatcatt gatcccattc tctatttcac caaattcgct 13620
tgcatgtgat cctcttcacc acttactcaa gtcggtcggt acatcaagca caagctggta 13680
caagtatgca atcgcctatg cagtgtctga aaagaggtcg gctcgattag gagggagctt 13740
gtacattggt gaagggagcg gaagtgtgat gactttgcta gagtatcttg agccatctgt 13800
tgacatattt tacaattcac tcttctcaaa tggtatgaac ccaccacaac gaaattatgg 13860
gcttatgcca ctacaatttg tgaattcggt ggtttataag aacttaacgg ctaaatcaga 13920
atgtaagcta ggatttgtcc agcaatttaa accgttgtgg agagacatag acattgagac 13980
taatgttaca gatccatcat ttgtcaattt tgcattgaat gaaatcccaa tgcaatcatt 14040
aaaacgagta aattgtgatg tggaatttga ccgtggtatg ccgattgaac gggttattca 14100
gggttacact catatcttac ttgttgctac ttacggattg cagcaagatt caatactgtg 14160
ggtgaaagta tataggacat ctgaaaaagt atttcagttc ttactgagtg ccatgatcat 14220
gatctttggt tatgtcaaaa tccacaggaa tggttatatg tcggcaaagg atgaggagta 14280
catattgatg tctgactgca aggaacctgt aaactataca gctgtcccta acattcttac 14340
acgtgtaagt gatttagtgt cgaagaatct gagtcttatc catccagaag acctcagaaa 14400
ggtaaggtgt gaaacagatt ccctgaattt gaagtgcaat catatttatg agaaaataat 14460
tgctagaaaa attccattac aggtatcatc aactgattct ttgctcctcc agttaggcgg 14520

```
tgtcatcaac tcggtgggct caactgatcc tagagaggtt gcaacattat cttccattga  14580

gtgtatggac tatgttgtct catcaattga tttggctata ttagaggcaa atattgtgat  14640

ctcagagagt gctggtcttg acctcgcttt aatgttaggc ccattcaact tgaataagct  14700

taagaaaatt gacacaatcc ttaagtcaag cacctatcag ctaatcccgt attggttgcg  14760

ctatgagtac tctattaatc cgagatcttt gtcatttcta atcactaaat tacaacaatg  14820

ccgaatttca tggtcagata tgataacaat ctctgaattt tgcaagaaat ccaagcggcc  14880

tatatttatt aaacgagtaa tagggaatca acagctgaaa tcattcttta atgaaagctc  14940

aagtattgtt ttgacccggg ctgaagtcaa agtctgtata aagttcctcg gtgcaatcat  15000

caagttgaaa taatttctgt gtttttaag gggtataata ttctaagttg cacttgaagt  15060

aatatagctt gtaatcattc gctaggggat agaataattc ctataatctc tgaatatata  15120

tctctaggtt ataacaaata tatacataat aaaaatgatt ttaagaaaaa atccgactct  15180

caaagaagat tggtgcctgt aatattcttc ttgccagatg attatggagt gtctagccta  15240

acttaaaaca atcgtattcg atagggaaga atgacatata aagtaactaa taaaaaattg  15300

tattagtgaa aattaccgta tttcctgtat tccatttctg gt                    15342


<210> SEQ ID NO 39
<211> LENGTH: 15342
<212> TYPE: DNA
<213> ORGANISM: artificial sequence
<220> FEATURE:
<223> OTHER INFORMATION: APMV8 genome FJ619036

<400> SEQUENCE: 39

accaaacaag gaatgcaaga ccaacgggaa ctttaaataa aacaatcgaa tcattggggg     60

cgaagcaagt ggatctcggg ctcgaggccg aaacactgga tttcgctgga ggttttgaat    120

aggtcgctat aagactcaat atgtcatctg tattcaatga atatcaggca cttcaagaac    180

aacttgtaaa gccggctgtc aggagacctg atgttgcctc aacaggttta ctcagggcgg    240

aaatacctgt ctgtgttaca ttgtctcaag accccggtga gagatggagc cttgcttgcc    300

ttaatatccg atggcttgtg agtgattcat caaccacacc aatgaagcag ggagcaatat    360

tgtcactgct gagtctacat tcagacaata tgcgagctca cgcaacatta gcagcaaggt    420

ctgcagatgc ttcactcacc atacttgagg tagatgaagt agatattggc aactccctaa    480

tcaaattcaa cgctagaagt ggtgtatctg ataaacgatc aaatcaattg cttgcaattg    540

cggatgacat ccccaaaagt tgcagtaatg ggcatccatt tcttgacaca gacattgaga    600

ccagagaccc gctcgatcta tcagagacca tagaccgcct gcagggtatt gcagctcaga    660

tatgggtgtc agccataaag agcatgacag cgcctgacac cgcatcagag tcagaaagta    720

agaggctggc caaataccaa caacaaggcc gactggttaa gcaagtactt ttgcattctg    780

tagtcaggac agaatttatg agagttattc ggggcagctt ggtactgcgc cagtttatgg    840

ttagcgagtg caagagggct tcagccatgg gcggagacac atctaggtac tatgctatgg    900

tgggtgacat cagtctgtac atcaagaatg caggattgac tgcatttttc ctcaccctga    960

agttcggggt tggtacccag tatccaacct tagcaatgag tgttttctcc agtgacctta   1020

aaagacttgc tgcactcatc aggctgtaca aaaccaaggg agacaatgca ccatacatgg   1080

cattcctgga ggactccgat atgggaaatt ttgctccagc aaattatagc acaatgtact   1140

cttatgccat gggcattggg acgattctgg aagcatctgt atctcgatac cagtatgcta   1200

gagactttac cagtgagaat tatttccgtc ttggagttga gacagcccaa agccagcagg   1260
```

-continued

```
gagcgtttga cgagagaaca gcccgagaga tgggcttgac tgaggaatcc aaacagcagg   1320
ttagatcact gctaatgtca gtagacatgg gtcccagttc agttcgcgag ccatcccgcc   1380
ctgcattcat cagtcaagaa gaaaataggc agcctgccca gaattcttca gatactcagg   1440
gtcagaccaa gccagtcccg aatcaacccg caccaagggc cgacccagat gacattgatc   1500
catacgagaa cgggctagaa tggtaattca atcacctcga cacatccacc tatacaccaa   1560
ttctgtgaca tattaaccta atcaaacatt tcataaacta tagtagtcat tgatttaaga   1620
aaaaattggg ggcgacctca actgtgaaac acgccagatc tgtccacaac accactcaac   1680
aacccacaca agatggactt cgccaatgat gaagaaattg cagaacttct gaacctcagc   1740
accactgtaa tcaaggagat tcagaaatct gaactcaagc ctccccaaac cactgggcga   1800
ccacctgtca gtcaagggaa cacaagaaat ctaactgatc tatgggaaaa ggagactgca   1860
agtcagaaca agacatcggc tcaatctcca caaaccacac aagttcagtc tgatggaaat   1920
gaggaggaag aaatcaaatc agagtcaatt gatggccaca tcagtggaac tgttaatcaa   1980
ttagagcaag tcccagaaca aaaccagagc agatcttcac caggtgatga tctcgacaga   2040
gctctcaaca agcttgaagg gagaatcaac tcaatcagct caatggataa agaaattaaa   2100
aagggccctc gcatccagaa tctccctggg tcccaagcag caactcaaca ggcgacccac   2160
ccattggcag gggacacccc gaacatgcag gcacggacaa aacccctgac caagccacat   2220
caagaggcaa tcaatcctgg caaccaggac acaggagaga atattcattt accaccttcc   2280
atggcaccac cagagtcatt agttggtgca atccgcaatg taccccaatt cgtgccagac   2340
caatctatga cgaatgtaga tgcggggagt gtccaactac atgcatcatg tgcagagatg   2400
ataagtagaa tgcttgtaga agttatatct aagcttgata aactcgagtc gagactgaat   2460
gatatagcaa aagttgtaaa caccaccccc cttatcagga atgatattaa ccaacttaag   2520
gccacaactg cactgatgtc caaccaaatt gcttccatac aaattcttga cccagggaat   2580
gcaggggtga ggtccctctc tgaaatgaga tctgtgacga agaaagctgc tgttgtaatt   2640
gcaggatttg gagacgaccc aactcaaatt attgaagaag gtatcatggc caaagatgct   2700
cttggaaaac ctgtgcctcc aacatctgtt atcgcagcca aagctcagac ttcttccggt   2760
gtgagtaagg gtgaaataga aggattgatt gcattggtgg aaacattagt tgacaatgac   2820
aagaaggcag cgaaactgat taaaatgatt gatcaagtta aatcccacgc cgattacgcc   2880
cgagtcaagc aggcaatata taatgcataa tattgtaatt atacaaacaa tcaatactgc   2940
tgtcggttgc acccacctta gcaaatcaat aatcttttaa aattgattga ttaagaaaaa   3000
attgactaca ataaggaaag aacaccaagt tgggggcgaa gtcacgattg accacagtcg   3060
ctatctgtaa ggctcctcac caaaaatggc atatacaaca ctaaaactgt gggtggatga   3120
gggtgacatg tcgtcttcgc ttctatcatt cccgttggta ctaaaagaga cagacagagg   3180
cacaaagaag cttcaaccac aggtaagggt agattcaatt ggcgatgtgc agaatgccaa   3240
agagtcctcg atattcgtga ctctatatgg tttcatccaa gcaattaagg agaattcaga   3300
tcgatcgaaa ttcttccatc caaaagatga cttcaaacct gagacagtca ctgcaggact   3360
ggtagtagtg ggtgcaatcc gaatgatggc tgatgtcaat accatctcta atgatgcact   3420
agcgctggag atcactgtta agaaatctgc aacttctcaa gagaaaatga cggtgatgtt   3480
ccacaatagc ccccccttcat tgagaactgc aataactatc cgagcaggag gtttcatctc   3540
gaatgcagac gaaaatataa aatgtgccag caagttgact gcaggagtgc agtacatatt   3600
ccgtccaatg tttgtttcaa tcactaaatt acacaatggc aaactatata gggtgcccaa   3660
```

-continued

```
aagtatccac agcatctcgt ctaccctact gtatagtgtg atgttggagg taggattcaa   3720
agtggacatc gggaaggatc atccccaggc aaaaatgctg aagagggtca caattggcga   3780
tgcagacaca tactggggat ttgcatggtt ccacctgtgc aatttcaaaa agacatcctc   3840
taagggaaag ccgagaacgc tagacgaact gaggacaaaa gtcaaaaata tggggttgaa   3900
attggagtta catgacctat ggggtccgac tattgtggtc caaatcactg gcaagagcag   3960
caaatatgct caaggatttt tttcttccaa tggtacttgt tgcctcccaa tcagcagatc   4020
tgcaccagag cttgggaagc ttctgtggtc ctgctcagca actattggtg acgcaacagt   4080
tgttatccaa tcaagcgaga agggggaact cctaaggtct gatgatctcg agatacgagg   4140
tgctgtggcc tccaagaaag gtagactgag ctcatttcac cccttcaaaa aatgatgcag   4200
gacatagtac agagaatgaa agggccatca gacgtgcgaa aaaaactaaa tctgaaaaaa   4260
actgcccaga ctccacatta atctaggttg cagggaaata atacccgaca tgcacaatac   4320
tatcacggtc accagcaatc agcaaagttg atcaatcact atataaggaa tcaagtggga   4380
taacaattat taatccaatt tcataattat aaaaaattgc tttaaaggtt actgacgagt   4440
cgggggcgaa accttgccac ttaagctgca gtcaatttta gaatctacat attgaattat   4500
gggtaaaata tcaatatatc taattaatag cgtgctatta ttgctggtat atcctgtgaa   4560
ttcgattgac aatacactcg ttgccccaat cggagtcgcc agcgcaaatg aatggcagct   4620
tgctgcatat acaacatcac tttcagggac aattgccgtg cgattcctac ctgtgctccc   4680
ggataatatg actacctgtc ttagagaaac aataactaca tataataata ctgtcaacaa   4740
catcttaggc ccactcaaat ccaatctgga tgcactgctc tcatctgaga cttatcccca   4800
gacaagatta attggggcag ttataggttc aattgctctt ggtgttgcaa catcggctca   4860
aatcactgct gcagtcgctc tcaagcaagc acaagataat gcaagaaaca tactggcact   4920
caaagaggca ctgtccaaaa ctaatgaggc ggtcaaggag cttagcagtg gattgcaaca   4980
aacagctatt gcacttggta agatacagag ctttgtgaat gaggaaattc tgccatctat   5040
caaccaactg agctgcgagg tgacagccaa taaacttggg gtgtatttat ctctgtatct   5100
cacagaactg accactatat tcggtgcaca gttgactaac cctgcattga cttcattatc   5160
atatcaagcg ctgtacaacc tgtgtggtgg caacatggca atgcttactc agaagattgg   5220
aattaaacag caagacgtta attcgctata tgaagccgga ctaatcacag gacaagtcat   5280
tggttatgac tctcagtacc agctgctggt catccaggtc aattatccaa gcatttctga   5340
ggtaactggt gtgcgtgcga cagaattagt cactgttagt gtaacaacag acaagggtga   5400
agggaaagca attgtacccc aatttgtagc tgaaagtcgg gtgactattg aggagcttga   5460
tgtagcatct tgtaaattca gcagcacaac cctatactgc aggcaggtca acacaagggc   5520
acttcccccg ctagtggcta gctgtctccg aggtaactat gatgattgtc aatataccac   5580
agagattgga gcattatcat cccggtatat aacactagat ggaggggtct tagtcaattg   5640
taagtcaatt gtttgtaggt gccttaatcc aagtaagatc atctctcaaa atacaaatgc   5700
tgcagtaaca tatgttgatg ctacaatatg caaaacaatt caattggatg acatacaact   5760
ccagttggaa gggtcactat catcagttta tgcaaggaac atctcaattg agatcagtca   5820
ggtgactacc tccggttctt tggatatcag cagtgagata gggaacatca ataatacggt   5880
gaatcgtgtg gaggatttaa tccaccaatc ggaggaatgg ctggcaaaag ttaacccaca   5940
cattgttaat aatactacac taattgtact ctgtgtgtta agtgcgcttg ctgtgatctg   6000
gctggcagta ttaacggcta ttataatata cttgagaaca aagttgaaga ctatatcggc   6060
```

-continued

```
attggctgta accaatacaa tacagtctaa tccctatgtt aaccaaacga aacgtgaatc   6120
taagttttga tcattcaggc caaaacagag ggtctaggct cgggttaata aaagttcaat   6180
caatgtttga tttattaggc tttccctact aattattaat gtatttgtga ttatatgata   6240
acgttaaaag tcttaaatat ttaataaaaa atgtaacctg ggggcgacct atttacaggc   6300
tagtatatat taggaagtcc tcatattgca ctataatctc aaacaattat attacctcgt   6360
atccaccttg tctaaagaca tcatgagtaa cattgcatcc agtttagaaa atattgtgga   6420
gcaggatagt cgaaaaacaa cttggagggc catctttaga tggtccgttc ttcttattac   6480
aacaggatgc ttagccttat ccattgttag catagttcaa attgggaatt tgaaaattcc   6540
ttctgtaggg gatctggcgg acgaggtggt aacacctttg aaaaccactc tgtctgatac   6600
actcaggaat ccaattaacc agataaatga catattcagg attgttgccc ttgatattcc   6660
attgcaagta actagtatcc aaaaagacct cgcaagtcaa tttagcatgt tgatagatag   6720
tttaaatgct atcaaattgg gcaacgggac caaccttatc atacctacat cagataagga   6780
gtatgcagga ggaattggaa accctgtctt tactgtcgat gctggaggtt ctataggatt   6840
caagcaattt agcttaatag aacatccgag ctttattgct ggacctacaa cgacccgagg   6900
ctgtacaaga atacccactt ttcacatgtc agaaagtcat tggtgctact cacacaacat   6960
catcgctgct ggctgtcaag atgccagtgc atctagtatg tatatctcaa tgggggttct   7020
ccatgtgtct tcatctggca ctcctatctt tcttactact gcaagtgaac tgatagacga   7080
tggagttaat cgtaagtcat gcagtattgt agcaacccaa ttcggctgtg acattttgtg   7140
cagtattgtc atagagaagg agggagatga ttattggtct gatactccga ctccaatgcg   7200
ccacggccgt tttcattca atgggagttt tgtagaaacc gaactacccg tgtccagtat   7260
gttctcgtca ttctctgcca actaccctgc tgtgggatca ggcgaaattg taaaagatag   7320
aatattattc ccaatttacg gaggtataaa gcagacttca ccagagttta ccgaattagt   7380
gaaatatgga ctctttgtgt caacacctac aactgtatgt cagagtagct ggacttatga   7440
ccaggtaaaa gcagcgtata ggccagatta catatcaggc cggttctggg cacaagtgat   7500
actcagctgc gctcttgatg cagtcgactt atcaagttgt attgtaaaga ttatgaatag   7560
cagcacagtg atgatggcag cagaaggaag gataataaag atagggattg attactttta   7620
ctatcagcgg tcatcttctt ggtggccatt ggcatttgtt acaaaactag acccgcaaga   7680
gttagcagac acaaactcga tatggctgac caattccata ccaatcccac aatcaaagtt   7740
ccctcggcct tcatattcag aaaattattg cacaaagcca gcagtttgcc ctgctacttg   7800
tgtcactggt gtatactctg atatttggcc cttgacctca tcttcatcac tcccgagcat   7860
aatttggatc ggccagtacc ttgatgcccc tgttggaagg acttatccca gatttggaat   7920
tgcaaatcaa tcacactggt accttcaaga agatattcta cccacctcca ctgcaagtgc   7980
gtattcaacc actacatgtt ttaagaatac tgccaggaat agagtgttct gcgtcaccat   8040
tgctgaattt gcagatgggt tgtttggaga gtacaggata acacctcagt tgtatgaatt   8100
agtgagaaat aattgaatca cgataatttt gggactcatt taattgcaga gtgaaattgt   8160
catcttagga aataatcaat tccatgattt ttattgaaca tgatcaagca atcatgtggg   8220
aaatttatta tcacataact tctaatagtt ttaaatgacg aattaagaaa aaatggaggg   8280
cgacctctac acaaacatgg atgtaaaaca agttgaccta ataatacaac ccgaggttca   8340
tctcgattca cccatcatat tgaataaact ggcactatta tggcgcttga gtggtttacc   8400
catgcctgca gacttacgac aaaaatccgt agtgatgcac atcccagacc acatcttaga   8460
```

-continued

```
aaaatcagaa tatcggatca agcaccgtct agggaaaatc aagagtgaca tagcacatta   8520
ctgtcagtat tttaatatta atttggcaaa tcttgatccg ataacccacc ccaaaagttt   8580
gtattggtta tccagactaa caatagctag tgctggaacc tttagacata tgaaagatag   8640
aatcttatgt acagttggct ccgaattcgg acacaaaatt caagatttat tttcactgct   8700
gagccataaa ttagtaggta acggtgattt atttaatcaa agtctctcag gtacacgttt   8760
gactgcgagt ccgttatccc ctttatgcaa tcaatttgtc tctgacatca agtctgcagt   8820
cacgacaccc tggtcagaag ctcgttggtc ttggcttcat atcaaacaaa caatgagata   8880
cctgataaaa caatcacgca ctacaaattc agctcattta acagaaatta taaaagagga   8940
atggggttta gtaggtatta ctccagatct tgtcattctt tttgacagag tcaataatag   9000
tctaactgca ttaacatttg agatggttct aatgtattca gatgtattag aatcccgtga   9060
caatattgtg ctagtggggc gattatctac ttttctgcag ccagtagtta gtagactgga   9120
ggtgttgttt gatctagtag attcattggc aaaaacctta ggtgacacaa tatacgaaat   9180
tattgcggtg ttagagagct tgtcttatgg gtccgttcaa ctacatgatg caagtcactc   9240
tcatgcaggg tctttctttt catttaacat gaatgaactt gataacacac tatcaaagag   9300
ggtggatccg aaacacaaga acaccataat gagcattata agacaatgct tttctaatct   9360
agatgttgat caagctgcag agatgctatg cctgatgaga ttatttggac acccaatgtt   9420
aactgcaccg gatgcagcag ccaaagtaag gaaagcaatg tgtgctccaa aacttgttga   9480
acatgacacc atcttgcaga cattatcctt cttcaaggga ataattataa atgggtacag   9540
aagatcacac tctggcctgt ggcccaatgt agagccgtct tcaatctatg atgatgatct   9600
cagacagctg tacttagagt cagcagagat ttcccatcat ttcatgctta aaaactacaa   9660
gagtttgagc atgatagaat tcaagaagag catagactac gatcttcacg acgacttaag   9720
tactttctta aaggatagag caatttgccg gccaaaatcc cagtgggatg ttatattccg   9780
taagtcttta cgcagatccc acacgcggtc ccagtatatg gacgaaatta agagcaaccg   9840
attgctaatt gattttcttg attctgctga ttttgaccct gaaaaggaat ttgcatatgt   9900
aaccacaatg gattatttgc acgataatga attttgtgct tcatattctc taaaggaaaa   9960
ggagatcaaa actaccggga ggatatttgc aaaaatgaca cgcaatatga gaagttgcca  10020
agtgatactt gaatctctgt tatcaaaaca tatatgcaag ttcttcaaag agaacggcgt  10080
ttcgatggag caattgtcat tgaccaagag tctacttgca atgtctcaac tctcaccaaa  10140
agtctcgact ctgcaggaca ctgcatcacg tcatgtaggc aactcaaaat ctcagatcgc  10200
aaccagcaac ccatctcggc atcactcaac aaccaatcag atgtcactct caaatcggaa  10260
aacggttgta gcaactttct taacaactga tttggaaaaa tactgcctgc agtggcgata  10320
ctcgactatt aagttgtttg cacaagctct aaatcaactc tttgggattg atcacggatt  10380
tgaatggata catttaagac tcatgaacag caccttattt gtcggtgatc cttactcgcc  10440
tcctgaagat ccaacactag aggatataga taaagcacca aatgacgata tcttcatagt  10500
ttctccaagg ggaggcatag agggtttatg tcagaagatg tggaccatga tatcaattag  10560
tgcgatacac tgtgtagcag agaaaattgg tgcacgagtg gcagcaatgg tgcagggtga  10620
taatcaagta atagctatca ccaaagaact attcagagga gagaaagcct gtgatgtcag  10680
agatgagtta gacgagctcg gtcaggtgtt ttttgatgag ttcaagaggc acaattatgc  10740
aattggacac aaccttaagc taaatgagac aatacaaagc caatcctttt ttgtatattc  10800
caaacgaata ttctttgaag ggcgattgct tagtcaagtc ctcaaaaatg ctgccaagtt  10860
```

-continued atgtatggtt gctgaccatc taggtgaaaa cacagtatct tcctgtagca acctgagctc 10920
tacaattgcc cggttggtgg aaaatgggtt tgagaaggac actgcttttg tgttgaacct 10980
agtctacatc atgactcaaa ttctttttga tgagcattac tcgattgtat gcgatcacaa 11040
tagtgtcaaa agcttgatcg gatcaaaaaa ctatcggaat ctattgtact catctctaat 11100
accaggtcag ctcggtggtt tcaacttcct caatataagt cggttgttca ctaggaatat 11160
aggtgaccca gtaacatgta gtctgtctga tctcaaatgc ttcatagccg caggtctcct 11220
tccaccctat gtacttaaaa atgtggttct gcgtgagcct ggtcctggga catggttgac 11280
gttgtgctct gatccttaca cccttaacat accatacaca cagctaccaa ccacatatct 11340
caaaaagcac acccagcgat cgttgctttc acgtgcagta aatcctttat tagcaggtgt 11400
acaagtgcca aatcagcatg aggaagaaga gatgttggct cgctttctcc ttgatcgtga 11460
atatgtgatg ccccgcgttg ctcatgtaac actagaaaca tcggtccttg gcaaacggaa 11520
acaaatccaa ggcttaattg atacaactcc aactatcatt agaacatctc tagtcaatct 11580
accagtgtct aggaagaaat gcgaaaaaat aatcaattat tctctcaatt atattgctga 11640
gtgtcatgac tccttactta gtcagatctg cttcagtgat aataaggaat acttgtggtc 11700
cacctcctta atatcagttg agacctgtag tgtgacaatt gcggactatt tgagagctgt 11760
cagctggtct aatatattag gggaagaag catatccggg gtgactacac ctgatactat 11820
tgaattaatt caaggttgtt taataggtga aaattccagt tgtactcttt gtgaatcgca 11880
tgacgacgca ttcacatgga tgcacttgcc tggcccactt tacatccctg aaccatcagt 11940
tactaactct aaaatgcgtg tgccatatct gggttcaaaa acagaggagc gtaaaacagc 12000
ttcaatggca gcaataaaag gaatgtcaca tcacctgcgt gcagtcttaa gaggtacatc 12060
cgtatttatt tgggcatctg gggacacaga tattaattgg gataatgcat tgcagattgc 12120
ccaatcacgg tgtaacatca cattggatca aatgagatta cttacaccaa ttcctagcag 12180
ttcaaatatc caacgtagac tcgatgacgg aatcagcacg cagaaattta ctcctgcaag 12240
ccttgctcga atcacatcct ctgttcacat ctgtaatgac agccaaaggt tagagaagga 12300
tggctcctct gtcgactcaa acttgattta ccagcaaatt atgttacttg gactcagcat 12360
ctttgaaaca atgtactcaa tggaccaaaa gtgggtattc aataaccata ccttacattt 12420
gcacactgga cactcctgtt gtccaaggga actagacata agtttagtga acccgccaag 12480
acatcagacc ccggagctga ctagcacaac aaccaacccg ttcctatatg atcagctccc 12540
actaaatcag gataatctga caacacttga gattaagaca ttcaaattta atgagctcaa 12600
cattgatggt ttagattttg gtgaaggaat acaattattg agtcgttgta ctgcaagatt 12660
aatggcagaa tgtattctag aggagggaat aggctcgtca gttaaaaatg aagcaattgt 12720
caattttgat aattcagtca attggatttc agagtgccta atgtgtgata ttcgctcact 12780
ttgtgttaat ttaggtcaag agatactatg tagcctggca taccaaatgt attacttgcg 12840
aatcaggggt agaagggcca ttcttaatta cttggacaca actttgcaaa ggatccctgt 12900
gatacagtta gccaacattg cactcaccat ttcacaccct gagatatttc gcagaattgt 12960
caacaccggg atccataacc agattaaggg cccatatgtg gcaacaacag atttcatagc 13020
tgcaagtaga gatatcatat tatcaggtgc aagggagtat ctatcttatc taagcagtgg 13080
acaggaagac tgttacacat tcttcaactg tcaagatggg gatcttactc caaaaatgga 13140
acagtatctt gcaaggaggg catgcctttt aacattactg tataatactg ggcaccagat 13200
ccccattatc cgatcactga caccaataga gaagtgcaag gtgctcacag aatacaatca 13260
acaaattgag tatgcagatc aagagtttag ctctgtattg aaagtggtca atgcactact 13320
acaaaatcct aatatagatg cattggtttc aaatctctac ttcaccacca gacgtgtttt 13380
atcaaacctc agatcatgtg ataaggctat atcatatatt gaatatttgt acactgagga 13440
cttcggagaa aaagaagata cagtacaata tgacatcatg acaacaaacg atatcatact 13500
tactcatggt ctattcacac agatcgaaat atcttaccaa gggagtagtc tccataaatt 13560
cctaactccg gataacgcgc ctggatcatt gatcccattc tctatttcac caaattcgct 13620
tgcatgtgat cctcttcacc acttactcaa gtcggtcggt acatcaagca caagctggta 13680
caagtatgca atcgcctatg cagtgtctga aaagaggtcg gctcgattag gagggagctt 13740
gtacattggt gaagggagcg gaagtgtgat gactttgcta gagtatcttg agccatctgt 13800
tgacatattt tacaattcac tcttctcaaa tggtatgaac ccaccacaac gaaattatgg 13860
gcttatgcca ctacaatttg tgaattcggt ggtttataag aacttaacgg ctaaatcaga 13920
atgtaagcta ggatttgtcc agcaatttaa accgttgtgg agagacatag acattgagac 13980
taatgttaca gatccatcat ttgtcaattt tgcattgaat gaaatcccaa tgcaatcatt 14040
aaaacgagta aattgtgatg tggaatttga ccgtggtatg ccgattgaac gggttattca 14100
gggttacact catatcttac ttgttgctac ttacggattg cagcaagatt caatactgtg 14160
ggtgaaagta tataggacat ctgaaaaagt atttcagttc ttactgagtg ccatgatcat 14220
gatctttggt tatgtcaaaa tccacaggaa tggttatatg tcggcaaagg atgaggagta 14280
catattgatg tctgactgca aggaacctgt aaactataca gctgtcccta acattcttac 14340
acgtgtaagt gatttagtgt cgaagaatct gagtcttatc catccagaag acctcagaaa 14400
ggtaaggtgt gaaacagatt ccctgaattt gaagtgcaat catatttatg agaaaataat 14460
tgctagaaaa attccattac aggtgtcatc aactgattct ttgctcctcc agttaggcgg 14520
tgtcatcaac tcggtgggct caactgatcc tagagaggtt gcaacgttat cttccattga 14580
gtgtatggac tatgttgtct catcaattga tttggctata ttagaggcaa atattgtgat 14640
ctcagagagt gctgatcttg acctcgcttt aatgttaggc ccattcaact tgaataagct 14700
taagaaaatt gacacaatcc ttaagtcaag cacctatcag ctaatcccgt attggttgcg 14760
ctatgagtac tctattaatc cgagatcttt gtcatttcta atcactaaat tacaacaatg 14820
ccgaatttca tggtcagata tgataacaat ctctgaattt tgcaagaaat ccaagcggcc 14880
tatatttatt aaacgagtaa tagggaatca acggctgaaa tcattcttta atgaaagctc 14940
aagtattgtt ttgacccggg ctgaagtcaa agtctgtata aagttcctcg gtgcgatcat 15000
caagttgaaa taatttctgt gttttttaag gggtatagta ttctaagttg cacttgaagt 15060
aatatagctt gtaatcattc gctaggggat agaataattc ctataatctc tgaatatata 15120
tctctaggtt ataacaaata tatacataat aaaattgatt ttaagaaaaa atccgacttt 15180
caaagaagat tggtgcctgt aatattcttc ttgccagatg attatggagg gtctagccta 15240
acttaaaaca atcgtattcg atagggaaga atgacatata aagtaactaa taaaaaattg 15300
tattagtgaa aattaccgta tttcctgtat tccatttctg gt 15342

<210> SEQ ID NO 40
<211> LENGTH: 15438
<212> TYPE: DNA
<213> ORGANISM: artificial sequence
<220> FEATURE:
<223> OTHER INFORMATION: APMV9 genome EU910942

<400> SEQUENCE: 40

-continued

```
accaaacaaa gaaattgtaa gatacgttaa agaccgaagt agcaactgac ttcgtacggg     60
tagaaggatt gaatctcgag tgcgaacacg acgctgtgat tcgaaggtcc gtactaccat    120
catgtcctct atattcaatg agtatgagag tctgcttgaa agtcaactca aaccgacggg    180
ctcgaacgtc ttaggagaga aaggtgacac tccaaaagtc gagatccctg tatttgtgct    240
caacagtgac aaccctgaag atcgctggaa ctttactacc ttctgtctca gagtcgctgt    300
gagcgaggat gctaataggc ctttgcgtca gggggcactc atctctctac tttgcgctca    360
ttctcaggtg atgaagaatc atgtggccat agcaggaaag caggatgagg ctctgattgt    420
agttctagag attgatacta ttaatgatgg tgttccagcc ttcaacaata ggagcggtgt    480
cacagaggaa cgagctcagc gtttcgctat gatagctcaa gcattacccc gtgcttgtgc    540
aaatgggaca ccgttcaccg tccaagatgc agaagatgat ccagtcgaag acataacaga    600
cgccccttgat cgcatattgt caatccaggc gcaagtatgg gtgaccgtcg caaaatccat    660
gacagcgtac gagactgcag atgaatcaga acagaagcga ttgaccaagt atgttcagca    720
aggtcgagtg cagaagaaat gcatgatcta ccctgtatgt cggagcatgc tgcagcagat    780
cataaggcaa tctttagcag tccgacggtt cattgtcagt gagctgaaac gagctcggaa    840
tacagcagga ggaacatcca cgtattataa cttcgttgct gatgtagatt cctacattag    900
gaatgctggg ttaactgcat tcttcttgac ccttaagtat ggtgtgaata caaagacttc    960
tgtccttgcc cttagcagct tggcaggcga tcttcaaact gtcaaacagt tgatgcggct   1020
gtataaagcc aaaggagatg atgcaccata catgactata ctgggagacg gagaccagat   1080
gagatttgca cctgctgaat acgcacagct atactcatac gctatgggaa tggcatcagt   1140
catagacaaa gggacctcaa ggtatcagta cgctcgtgac ttcctaaacc ccagcttctg   1200
gaggctggga gtggagtatg cccagactca aggaagcaac atcaacgaag agatggcatc   1260
agaactgaaa ctcagcccaa tagctagaag gatgctgacc actgccgtca caaaagtagc   1320
aaccggagcg tctgattatt cggtacctca gcatacagca ggagtcctaa ctggcttgaa   1380
ttcaacagac ggcaaccttg ggtctcagaa gctgcccacc tcaattcagc aggatcagaa   1440
tgatgatact gccatgttga acttcatgag ggccgtagca caaggaatga aggagacacc   1500
aattcaggct cctcccaccc ctggattcgg atctcaacag gccgcagacg acgatgactc   1560
gcgggatcaa gcagactcct gggggctcta atgaaatacg gaggttgact ccagcccaaa   1620
cgaacctcta gcaactccta atccctcatc cacctacaaa ctccacatct acatgaccaa   1680
tccgctcaca caacacggcg gaagacacca tccatcccca actgtcccaa cccgaagaac   1740
atcctcaact tagcccgcta atttcacgaa ccattacaaa aaacttatca acagaaaaaa   1800
ctacgggtag aactgtctgc cactgcgaga aagcaaacgc atcaacgcag tcagcactca   1860
tcgcagctct ccatcacacc aattctagct caggcacacg cctccagaga gaaccatggc   1920
atccttcaca gacgacgaga tatcagatct gatggaacaa agtggtcttg taatagatga   1980
gatcatgaca tcccaaggga tgcctaaaga gaccctaggg cgaagtgcaa tcccaccagg   2040
gaaaactcag gccctaactg atgcctggga gaaacacaac aagtcacaga gatccaatgc   2100
ggatcacagc accggatcaa ataacaaaac tgatgtcaac acaccccaca atgctgagcc   2160
gccacaatcc accggcgatc cctccgcatc tccagaaatg gacggcgaca caaccccact   2220
cccaaagcag gaaaccgccg aaaagcaccc ctgcaaagaa ggggccactg gagggctgct   2280
ggatatgctt gaccggattg ctgccaagca ggatagagct aaaaaagggc tcaatccgag   2340
atcacaagac acgggcaccc tgcactcagg ccaattccct acgcagacgc aagacccgac   2400
```

-continued

```
atcccgccga tcaaccaact catcgggaca cagcatggag tccagaacgc ccgcccagct   2460
gccaatcccg aggagagacg acagcccgca tcaggtaaga agagaggagg agggcatcgc   2520
agagaacaca gcatggtctg gaatgcaaac gggattgtca ccatcagctg gtgcaaccca   2580
gtttgctctc cagtcaccta cgaaccaaga gaattcacat gttcatgcgg gagctgccct   2640
acagaatgcc gactttgtgc aggctctcat agggatatta gaaagcattc agcagagagt   2700
gagtaaaatg gaatatcaga tggatttagt cctgcgtcac ctgtctagta tgccagccat   2760
tcgaaatgac attcaacaag ttaagaccgc tatggcagtg cttgaggcca acattgggat   2820
gatgaaaatc cttgaccctg gatcagcaca tatttcttcg ctcaatgatc ttcgagcagt   2880
tgcaaggtat catccagtcc ttgtagcagg ccccggtgac cccaataaaa caattgctga   2940
tgataaaacc atcactgtca atcggctctc ccagccggta actgatcagc gcagcttggt   3000
aagagaactc acaccccctt ccggtgattt cgaggcagaa aaatgcgcaa tcaaggcgtt   3060
attagctgcg agaccactac atccatcggc tgcaaaacga atgtctgata ggttagatgc   3120
agccaagaca tgtgaagaat tgaggaaggt gaagagacag attctgaata actgacccaa   3180
atagtgtggt ttccgccaat gatcaagcgt gatccgcctt ggacaacttt tttgccgatc   3240
ttaaggagag acaaatcaat ttacaccgat ctaaaatatc atcagacacc ctcaaatcaa   3300
gaaaacatag atgacagtct gcttgactca tctcttgcat ctgatgctat caattgccct   3360
aaaataccac ctgacataaa taccagatta tctctagacc tccttggttg ttaagaaaaa   3420
aaagtaagta cgggtagaaa caggactcaa ccgacctacc accatggatg cttctaggat   3480
gatcagtcta tatgtagacc ccactagcag ttctagttca atactcgcat tcccaatagt   3540
catggaagcc acaggagacg gacgaaagca aatttcaccc caatatcgca ttcagagatt   3600
agatcactgg tcagacagca gtcgagatgc agtattcatc accacatatg ggtttatatt   3660
tggataccct aaatcacgtg ctgatcgagg ccagcttaat gaagaaatta ggcctgtgct   3720
gctctctgct gcaacgctat gtctgggcag tgtggcgaat actggagatc aggttgcaat   3780
tgctcgggca tgcttgtcac tacaaatatc ttgcaaaaag agtgctacta gtgaggagaa   3840
aatgatattt gcaatcaccc aagctccgca gattttacaa tcatgtcgtg ctgtttcgca   3900
aaaattcgtc tccgttggat caaataaatg tgtgaaagca cctgaaagaa tcgagggagg   3960
ccagcagtat gactataagg tcaacttcgt gtctctcact atagtaccaa aagatgacgt   4020
atatagggtc ccaaaacctg tcctatcagt cagcagtccc actctattcc gccttgccct   4080
gagtgttaac atcgcaatcg acatcaatgc cgacaatcct ttgtctaaga cgcttattaa   4140
gaccgaaagc ggctttgaag caaatttgtt cctgcatgtg ggtattctct caaacattga   4200
caagcgggga aagaaggtga cgttcgagaa gttagagaag aaaatccggc ggatggaact   4260
gactgcagga ttaagtgata tgtttggtcc gtccatcatc ctgaaggcca aagggccgag   4320
gacaaagttg atgtcagcat tcttttctaa tacgggaaca gcgtgttatc cgatcgcaca   4380
agcatctcct ccagtatcga agatcttgtg gagccaaagc ggacacctcc aggaggttaa   4440
gatacttgta caatcgggaa cctcgaaaat gattgcatta acagccgatc aagaaatcac   4500
aacaacaaag ctcgatcagc acgccaagat tcaatcattt aacccattca aaaagtaagt   4560
tgcatggctc acgaatagct caggtcttct tgccttaaaa tcagccaatg aatatgtgat   4620
aggatattca gtgtctcgaa tcattaccga tcaaaaaacc ccattaaatc atacacctga   4680
tcattagaca agaggtaatc caaatagcat taaaaaaaat ccccaaaaga attaaaacta   4740
aaacacagca cgggtagaaa gtgagctgta tatcactcaa tccacaatct accatagtga   4800
```

-continued

```
cacaatgggg tacttccacc tattacttat actaacagcg attgccatat ctgcgcacct   4860
ctgctatacc acgacattgg atggtagaaa actgcttggt gcaggcatag tgataacaga   4920
agagaagcaa gttagggtgt acacagctgc gcaatcagga acaattgtct taaggtcttt   4980
ccgtgtggtc tccttagaca gatactcgtg catggaatcc actattgagt catataacaa   5040
gactgtatat aacatacttg cacctctggg cgatgcaatc cgccgaatac aggcaagtgg   5100
tgtatcggtt gagcgtatcc gagagggccg catatttggt gccatccttg gggagttgc    5160
cttaggtgta gccaccgcag cacagataac agctgcaatt gctttgattc aggctaacga   5220
gaacgcaaaa aacatcctgc gtattaaaga cagtataact aagaccaacg aggcagtgag   5280
agatgtaact aatggcgtgt cgcagttaac tatcgctgta ggtaaattac aggacttcgt   5340
caataaggaa ttcaataaga caactgaggc cattaattgt gtacaggcag ctcaacaatt   5400
aggtgtggag ctaagcctct atctgaccga gatcactaca gtcttcggac ctcagataac   5460
ctctcctgct ttaagcaaat tgactatcca agcgctgtat aatttggcgg gcgtaagctt   5520
ggatgtacta ctgggaaggc tcggagcaga caattcacag ttatcatctt tggttagtag   5580
tggtcttatt accggacagc ccattctcta cgactcggaa tctcaaatat tggcactgca   5640
agtgtcacta ccctccatta gtgacttaag ggagtgaga gcgacatact tagacacgtt    5700
ggctgtcaac actgcagcag gacttgcatc tgctatgatt ccaaaggtag taatccaatc   5760
taataatata gttgaagaat tagatactac agcatgtata gcagcagaag ctgacttata   5820
ctgtacgagg attactacat tccccattgc gtcggctgta tcagcctgca ttcttgggga   5880
tgtatcgcaa tgcctttatt caaagactaa tggcgtctta accactccat atgtagcagt   5940
aaaggggaaa attgtagcca attgtaagca tgtcacatgt aggtgtgtag atcctacatc   6000
catcatatct caaaattacg gtgaagcagc gactcttatc gatgatcagc tatgcaaggt   6060
aatcaactta gatggtgtgt ccatacagct gagcggcaca tttgaatcga cttatgtgcg   6120
caacgtctcg ataagtgcaa acaaggtcat tgtctcaagc agtatagata tatctaatga   6180
gctggagaat gttaacagct ctttaagttc ggctctggaa aaactggatg aaagtgacgc   6240
tgcgctaagc aaagtaaatg ttcacttaac tagcacctca gctatggcca catacattgt   6300
tctaactgta attgctctta tcttggggtt tgtcggccta ggattgggtt gctttgctat   6360
gataaaagta aagtctcaag caaagacact actatggctt ggtgcacatg ctgaccgatc   6420
atatatactc cagagtaagc cggctcaatc gtccacataa tacaacaaca atcaatcctg   6480
actatcatat aatacatgaa tcatttcttc ttccgattat aaaaaaataa gaaacctaat   6540
taggccaata cgggtagaac aggcttccac cccgtatttc ttcggctgtg atcctgtacc   6600
tgagttcttc ccaccaacac caggacctct cctaaattgc atcaccatgg aatcaggaat   6660
cagccaggca tctcttgtca atgacaacat agaattaagg aatacgtggc gcacggcctt   6720
ccgtgtggtc tccttattac tcggcttcac cagcttggtg ctcactgctt gcgctttaca   6780
cttcgctttg aatgccgcta cccctgcgga tctctctagt atcccagtcg ctgttgacca   6840
aagtcatcat gaaattctac aaaccttgag tctgatgagc gacattggca ataagattta   6900
caagcaggta gcactagata gtccagtggc gctgctcaac actgaatcaa ccttaatgag   6960
cgcaattaca tcactatctt atcagattaa caatgcagcg aataactcag gttgtggcgc   7020
ccctgtgcat gataaggatt ttatcaatgg agtggcaaag gaattatttg tagggtctca   7080
atacaatgcc tcgaactatc gaccctccag gttccttgag catctaaatt tcatccccgc   7140
ccctactacg ggaaaaggtt gcaccagaat tccgtccttt gatctagctg caacacattg   7200
```

-continued

```
gtgttatact cacaatgtga ttcttaatgg ttgtaatgat catgctcaat cttatcaata   7260
catatccctc gggatactca aggtgtcagc cacgggaaac gtgttcttat ctactctcag   7320
atctatcaac ctggatgatg atgaaaaccg gaaatcatgt agcatatcag caacgccact   7380
agggtgtgac ttactttgtg ctaaagtcac tgagagagaa gaggcagatt acaattcaga   7440
tgcagcgacg agattagttc atggcaggtt aggttttgat ggggtatacc atgagcaggc   7500
cctgcctgta gaatcattgt tcagtgactg ggttgcaaac tatccgtcag tcggcggagg   7560
cagttacttt gataataggg tatggtttgg cgtgtatggg ggatcagac ctggctctca   7620
gactgatctg ctccagtctg agaagtacgc gatatatcgt aggtacaata atacctgccc   7680
tgataataat cccacccaga ttgagcgggc caaatcatct tatcgtccgc agcggtttgg   7740
ccagcggctt gtacaacaag caattctatc aattagagtg gagccatctt tgggtaatga   7800
tcctaaacta tctgtgttag ataatacagt cgtgttgatg ggggcggaag caaggataat   7860
gacatttggc cacgtggcat taatgtatca aagagggtca tcatattttc cttctgcact   7920
attataccct ctcagtttaa caaatggtag tgcagcagca tccaagcctt tcatattcga   7980
gcaatataca aggccaggta gcccaccttg tcaggccact gcaagatgtc caaattcatg   8040
tgttactggt gtctacacag acgcataccc gttattttgg tctgaagatc ataaagtgaa   8100
tggtgtatat ggtatgatgt tagatgacat cacatcacgg ttaaacccgg tagcagctat   8160
atttgatagg tatggtagga gtagagtgac tagggttagc agtagcagca cgaaggcagc   8220
ttacactaca aatacatgct ttaaggttgt caaaacaaag agagtatact gcttgagcat   8280
tgccgagata gagaatacac tgtttggaga attcagaata acccctttac tctccgagat   8340
aatatttgac ccaaaccttg aaccctcaga cacgagccgt aactgaggaa aatccgttct   8400
ggcagacagt ggttggatag accttgcgtc gatagccctc actgttggca ctgcgtcgtc   8460
cctatattca aacaccacat tagcggagta tacagatagt cggccatgat gaatcaaatg   8520
tcatgcgatt tgagcataac cgaagcagaa tcaggatata cccggctcta ccatatcagg   8580
gagaacagct ggtaagctgt aatcctcaat aatcctaaaa actgcaggta atacaaaagg   8640
atcagcctat agggagcttc aacaatcgtt agaaaaaaac gggtagaaca tggataatcc   8700
aggacaatct cgccctgatc atcaagtgat tctacccgaa gcgcatcttt cctcaccgat   8760
cgtaaggcat aagttatatt atttctggag actaacagga gtaccactac cccactcagc   8820
agaatttgat acgctagtcc tatccagacc atggaacaaa atattgcaga gcaactcgcc   8880
agaagtactg aggatgaagc ggctaggtgc gaacgtccac gcgactctag atcactctcg   8940
accaataaag gctttgatcc acccggagac tttagcatgg ctaactgatc tgtctatagg   9000
ggtatctatc tctagattta gaggaataga aaagaaagta tctcgcctgc tccatgacaa   9060
tagagagaaa ttttgtacac ttgtttctca gattcatgaa ggattgttcg gtggtgtagg   9120
aggggttcgg aataatctgt caccagagtt tgaaagtttg ctcaatggaa ctaacttctg   9180
gtttggcggg aaatattcaa acacaaaatt cacttggctt cacattaaac aattgcagag   9240
acatcttata ctcacagcgc gtatgagatc tgggcagcaa ctttacatcc aattaaagca   9300
tacaaggggt tatgtccata taactccaga gttaactatg attacatgca acggaaaaaa   9360
ccttgttaca gcacttacac ctgagatggt cttaatgtat agtgacatgc tagaaggaag   9420
agatatggtc ataagtgttg cacagcttgt gaatggcctg aatgtcctag cagataggat   9480
tgagtgtctt cttgacttga ttgaccaatt ggcgtgcttg ataaaggatg ctatatatga   9540
aataattggg attttggagg gtttagctta tgcagcagtc cagctgctgg agccgtccgg   9600
```

-continued

```
aaaattcgca ggggatttct ttgaattcaa tctcagagag atagctgcca tattgcgaga   9660
acacatagac cctgtgttag ctaacagggt acttgagtct attacctgga tttacagtgg   9720
tctgacagac aaccaagcag cagagatgct ctgtatcctc cgcttgtggg gccaccctac   9780
attagagtcc agaacagctg cagctgcagt gcgaaagcaa atgtgcgcgc caaaactcat   9840
tgacttcgac atgatccaac aagtattggc tttctttaaa gggacaatca tcaatggata   9900
tagaagacaa aactcaggag tctggccaag agttaaaaag gatactatct atggatcaac   9960
actccaacag ttgcatgctg actatgcaga gatatcacac gaattaatgc tgaaagaata  10020
caagcgtcta gcaatgcttg agtttgagaa gtgtattgac atagacccag tatccaattt  10080
aagcatgttc ttgaaggaca aggctatagc acacacgcga ccaaattggc tggcatcttt  10140
taaaagaact ttgttatccg atagacagca gctcttagca aaggatgcaa cttcgaccaa  10200
tcgtctgctg atagaattcc tagaatctag caactttgac ccatatcagg agatgaccta  10260
tttgacaagt cttgaatttc ttagagataa tgacgtggca gtatcatatt cgttaaagga  10320
gaaagaagtt aagcccaatg gtagaatctt cgcaaagctt accaaacgac tcagaaattg  10380
tcaggtgatg gcagagaata tcctagcaga cgaaattgca cctttttttcc aagggaatgg  10440
agtcattcaa agcagcatct ctctgacgaa aagtatgtta gcaatgagtc aactgtcatt  10500
taattgcaac agattctcga tcggaaaccg cagagaaggg atcaaagaga ataggacacg  10560
acaccgtgaa cgaaagcgaa gaaggcgagt agctacatat atcacaactg acctgcagaa  10620
gtactgtctc aattggaggt atcagaccat caagcctttt gcccatgcga ttaatcagct  10680
gacagggctt gatttgtttt ttgagtggat ccaccttcgt ctaatggata ccactatgtt  10740
cgttggagat ccatacaacc caccctctga tccaacaatt gaaaacctgg atgatgcacc  10800
caatgatgat atctttattg taagcggaag aggagggatc gagggattat gtcaaaagct  10860
ttggactacc atatcaatat ccgcaataca attagcagcc acccggtcaa agtgtagggt  10920
agcctgtatg gtgcaaggtg acaatcaggt gatcgcagtg acccgagaag taaatccaga  10980
tgactcagaa gatgcggtct tagatgaatt acataaggcc agcgacagat tctttgagga  11040
actcactcac gtgaatcatc tgatcggaca taacctgaaa gatagagaga ccatacgctc  11100
agatacttgt tttatctata gcaagcgagt attcaaggat ggtaagatac tttctcaggc  11160
cctcaagaat gctgcaaagc tcgtcttaat atctggggag attggggaga acactcctat  11220
gtcatgcggg aatattgctt ctacagtgtc tcgtctgtgt gaaaatgggc tgcccaaaga  11280
tgcctgctat atgatcaatt atatattaac ctgtatacaa tttttctttg acaatgagtt  11340
ttccattgtc cccgcttctc agcgtggatc cacagttgaa tgggtggata acctttcatt  11400
tgtacacgcg tatgcactgt ggccaggcca atttggagga ttgaacaact tacaatattc  11460
tagattgttt actcgcaata tcggggaccc atgcactact gcacttgcag agattaagag  11520
attagagaga gctcaactaa taccagggaa gctaatcaag aacttgcttg ctaggaagcc  11580
aagcaatgga acatgggcgt ctctttgtaa tgatccttat tcactcaata ttgaaacagc  11640
accaagccca aatctcatcc tcaagaaaca tactcagaga gtactatttg aatcctgcac  11700
caatcccccta ttacaagggg tttatagtga agaaaatgat acggaagaag cagaattagc  11760
agaattcttg ctcaatcaag aagctataca tccgcgcgtg gcacacgtta taatggaggc  11820
cagcgcagtc ggtagaaaga agcaaattca gggactaatc gatacaacta acaccatcat  11880
aaagattgca cttgggcggc gtcctcttgg tgcaaggagg ttaaggaaga taaacagtta  11940
ttcttctatg cacatgttga tcttcctgga tgatatattc ctacctaacc atcctccatc  12000
```

-continued

```
tcccttcgtc tcctcagtga tgtgttctgt tgccctagcg gattacctac gtcagattac  12060
ctggttgcct ctgacaaatg gtaggaagat attaggtgta aataatccag atacccttga  12120
gttagtatca ggatcgatgc tgaatctaaa cggatattgt gacttatgta atagtggaga  12180
taaccaattt acgtggttcc atctcccagc agatatagag ctagcggaca gttcatcatc  12240
caaccctcca atgcgtatac cttatgtggg atccaagacc caggaaagga gaaatgcatc  12300
aatggccaag attagcaaca tgtcccctca tatgaaggca gcattgagat tggcgtctgt  12360
gaaggtaagg gcttacggtg ataatgagca taattggcaa gttgcatggc agctagcaaa  12420
tactcgatgt gcgatatccc ttgaacatct aaaacttcta gcccctctac caactgcagg  12480
gaaccttcag catcgattgg atgatagcat aacccagatg acctttactc ccgcttctct  12540
ctatcgggtg gcaccttata tccacatctc caatgactca caaagaatgt tttctgatga  12600
gggggttaag gagagcaaca tcatctatca gcagataatg ttattgggtc tatcagctat  12660
cgaatcattg ttccccttga ccactaatca tgtatatgaa gaagtgacac tacaccttca  12720
tactcaattc agctgctgcc tgagagaggc ggcccttgcg gtcccatttg agctccaggg  12780
caaagtacct aggattcgtg ctgctgaggg gaaccaattc gtgtatgact catccccact  12840
tttggaacct gaggctcttc aactcgatgt ggctactttc aagaactatg agttggactt  12900
agaccattat tcaacgatag acttgatgca tgtacttgag gttacgtgtg gaaagctaat  12960
aggtcagtcg gtgatttcat acaatgagga cacttctata aagaatgatg caattattgt  13020
atacgataat acccggaatt ggatcagtga ggcccaaaat tgtgacctgg tgaagttatt  13080
tgagtatgct gcactagaaa tcttgctgga ctgcgcattc caaatgtatt atctaagggt  13140
tcgcggatac aagaacatcc taatatacat ggcagaccta attcgtaata tgcccggtat  13200
attgctctct aatattgctg ccacaatctc ccatcccatt atccatacta gactatacaa  13260
tgcagggttg ctggatcatg ggagtgcgca ccaacttgca agcattgatt ttattgaatt  13320
atcagctaat ttattggtaa catgtatagc tcgtgtatgt actacacttc tatccggtga  13380
aaccctgatg cttgcatttc catccgttct agacgagaat ttgacggaga aaatgtttct  13440
tctaatcgct cgatactgct ctttgttagc gttgttgtac tcatctaagg ttcctatacc  13500
aaatattagg ggcctgactg ccgaagataa gtgccggatg ctcacaaatc atctcatgaa  13560
ccttccatct gaatttcggc tgaccgaaaa tcaggtacga aatgtactgc aaccagcact  13620
gacaactttc ccagcaaacc tctattatat gtcaagaaag agtcttaata tcatcagaga  13680
gagggagata aagatgctat tattcaaatg ttgttccctg ccggggatga agctacaagc  13740
acggtggcag ttaatttggg atacgaaagt aaatgacccc attgttaagt ggcgacgcat  13800
tgaattctta tgcgagctcg atctctctgg tcaggcaagg tttggagtca tactggatga  13860
atgcatctct gatgttgata aaaacggaca gggcatcctc gactttgtcc caatgactcg  13920
atacctattc aggggtgtag gccaggcatc ctcatcatgg tataaagctg ccaatttatt  13980
gtcacttcct gaagtgcgcc aggcacgttt cggtaactca ttgtacttag cagaaggtag  14040
cggtgcaata atgagtctgt tagagctcca cgtaccacat gagaagattt actacaatac  14100
tctcttttat aacgagatga accccccgca aagacatttc ggcccaacgc caactcaatt  14160
ccttgcatcg gtcgtttaca agaaccttca ggcaggtata gtctgcaaag atgggtatgt  14220
tcaggagttc tgccctttat ggagagacgt tgccgatgaa agtgatcttg cttcagatag  14280
gtgtgtctca ttcattacat cagaggtgcc tggaggcact gtatctctac tccattgtga  14340
catagaaaca accctggaac caagctgggc ttacttggag caattagcca ctaatatctc  14400
```

-continued

```
tctaatcggg atgcacgtcc tgcgagagaa tggagtgttc atcatcaaag tactatacac    14460

ccagagtttc ttttttcatc tattgctggc aatcttagct ccttgtagta aaaggatacg    14520

gatcatatcc aatggatact cagtacgggg agattttgag tgctacctag tcgcgacaat    14580

cagttataca gggggcatg tcttcatgca agaggtgatc cgctctgcca aggcgttagt    14640

tagagggggc ggtagtatca tgacaaaaca agatgaacaa caattgaatc ttgctttcca    14700

gaggcagctc aacaggattc gtgggatact gggacagagg atatcgataa tgatacgcta    14760

cttgcagcat actattgata tggcattgat tgaagcggga ggccaacctg taagaccgag    14820

caatgttgga atcaacaagg cactcgactt aggagatgag acatatgagg aaatcatgat    14880

acagcatatt gacacaacac ttaagacagc aatcttccta gaacaagaag aagaactggc    14940

agacacagtc tttgtgttaa caccttataa cctaacggca agaggaaaat gtaatacagt    15000

acttattgca tgcactaaac atctatttga aacaactata ttacagacta cacgagacga    15060

catggataag atagagaaat tgttgtccct tatcttacaa ggtcatatct cgcttcagga    15120

tctcctgcca ctcaagtcat atcttaaacg tagcaattgt cccaagtacc tcctcgattc    15180

actaggacgt atcaggctaa aagaggtatt tgaacactca tcccgcatgg tactaaccag    15240

accgatgcaa aagatgtatc tcaaatgtct cggaaatgct attaagggat accttgcagt    15300

ggatgcatct cattgcaatt gaatcatgac gcaatctctt ttatacatca tactcgtaat    15360

caatcatagt taccatcatt tttaagaaaa acagtaacga tttatggtgt cacgtatgtt    15420

gccaaatctt tgtttggt                                                  15438

<210> SEQ ID NO 41
<211> LENGTH: 36
<212> TYPE: DNA
<213> ORGANISM: artificial sequence
<220> FEATURE:
<223> OTHER INFORMATION: NP-FP-pc3 primer

<400> SEQUENCE: 41

ccgaattcat gtcatctgtg ttcaatgagt atcagg                              36

<210> SEQ ID NO 42
<211> LENGTH: 36
<212> TYPE: DNA
<213> ORGANISM: artificial sequence
<220> FEATURE:
<223> OTHER INFORMATION: NP-RP-pc3 primer

<400> SEQUENCE: 42

ccgcggccgc ttaccattct agcccgttct cgtatg                              36

<210> SEQ ID NO 43
<211> LENGTH: 30
<212> TYPE: DNA
<213> ORGANISM: artificial sequence
<220> FEATURE:
<223> OTHER INFORMATION: P-FP-pc3 primer

<400> SEQUENCE: 43

ccgaattcat ggatttcgcc aatgatgaag                                     30

<210> SEQ ID NO 44
<211> LENGTH: 40
<212> TYPE: DNA
<213> ORGANISM: artificial sequence
<220> FEATURE:
<223> OTHER INFORMATION: P-RP-pc3 primer
```

<400> SEQUENCE: 44
ccgcggccgc ttacgcatta tatattgcct gcttgactcg                        40

<210> SEQ ID NO 45
<211> LENGTH: 40
<212> TYPE: DNA
<213> ORGANISM: artificial sequence
<220> FEATURE:
<223> OTHER INFORMATION: L-FP-pc3 primer

<400> SEQUENCE: 45
ccgcggccgc ttacgcatta tatattgcct gcttgactcg                        40

<210> SEQ ID NO 46
<211> LENGTH: 32
<212> TYPE: DNA
<213> ORGANISM: artificial sequence
<220> FEATURE:
<223> OTHER INFORMATION: L-RP-pc3 primer

<400> SEQUENCE: 46
ccggtaccat ggatataaaa caagttgacc tg                                32

<210> SEQ ID NO 47
<211> LENGTH: 6231
<212> TYPE: DNA
<213> ORGANISM: artificial sequence
<220> FEATURE:
<223> OTHER INFORMATION: 5'-FLG APMV8 genome

<400> SEQUENCE: 47
gggcggccgc gttgacattg attattgact agttattaat agtaatcaat tacggggtca 60
ttagttcata gcccatatat ggagttccgc gttacataac ttacggtaaa tggcccgcct 120
ggctgaccgc ccaacgaccc ccgcccattg acgtcaataa tgacgtatgt tcccatagta 180
acgccaatag ggactttcca ttgacgtcaa tgggtggagt atttacggta aactgcccac 240
ttggcagtac atcaagtgta tcatatgcca agtacgcccc ctattgacgt caatgacggt 300
aaatggcccg cctggcatta tgcccagtac atgaccttat gggactttcc tacttggcag 360
tacatctacg tattagtcat cgctattacc atggtgatgc ggttttggca gtacatcaat 420
gggcgtggat agcggtttga ctcacgggga tttccaagtc tccaccccat tgacgtcaat 480
gggagtttgt tttggcacca aaatcaacgg gactttccaa aatgtcgtaa caactccgcc 540
ccattgacgc aaatgggcgg taggcgtgta cggtgggagg tctatataag cagagctccc 600
gggtgttaag cgtctgatga gtccgtgagg acgaaactat aggaaaggaa ttcctatagt 660
caccaaacaa ggaatgcaag accaacggga actttaaata aaacaatcga attattgggg 720
gcgaagcaag tggatctcga gctcgaggcc gaaaccctga atttcactgg aggttttgaa 780
taggtcgcta taggactcaa tatgtcatct gtgttcaatg agtatcaggc gcttcaagaa 840
caacttgtga agccggctgt caggagacct gatgttgcct caacgggttt actcagagcg 900
gaaatacctg tctgtgttac attatctcaa gaccccggtg agagatggag ccttgcttgc 960
ttgaatatta gatggcttgc gagtgattca tcaaccacac caatgaagca aggagcaata 1020
ttgtcactgc tgagtctaca ttcagacaat atgcgagctc acgcaacatt agcagcaagg 1080
tctgcagatg cttcactcac catacttgag gtagatgaag tagatattag caactcacta 1140
atcaaattca acgccagaag tggtgtatct gacaaacgct caaatcaatt gcttgcaatt 1200
gcggatgaca tccccaaaag ttgcagtaat gggcatccat ttcttgacac agacattgag 1260

-continued

```
accagagacc cgctcgatct atcagagact atagatcgcc tgcagggtat tgcagctcag   1320
atatgggtgt cagccataaa gagcatgaca gcgcctgaca ccgcatcaga gtcagaaagt   1380
aagaggctgg ccaaatatca acaacaaggc cgactggtta agcaagtact cttgcattct   1440
gtagtcagga cagaatttat gagagttatt cggggcagct tggtactgcg ccagtttatg   1500
gttagcgagt gcaagagggc ttcagccatg ggcggagaca catctaggta ctatgctatg   1560
gtgggtgaca tcagtcttta catcaagaat gcaggattga ctgcattttt cctcaccctg   1620
aagttcggag ttggtaccca gtatccaacc ttagcaatga gtgttttctc cagtgacctt   1680
aaaaggcttg ctgcactcat caggctatac aaaaccaagg gagacaatgc accatacatg   1740
gcattcctgg aggactccga tatgggaaat tttgctccag caaattatag cacaatgtac   1800
tcttatgcca tgggcattgg gacaattctg gaagcatctg tatctcgata ccagtatgcc   1860
agagacttta ccagtgagaa ttatttccgt cttggagttg agacagccca aagccagcag   1920
ggagcatttg acgagagaac agcccgagaa atgggcttga ctgaggaatc aaaacagcag   1980
gttagatcac tgctaatgtc agtagacatg ggtcccagtt caattcatga gccatctcgc   2040
cctgcattta tcagtcaaga agaaaatagg cagcctgccc agaacttgtc agatactcag   2100
ggtcagacca agccagtccc gaagcagccc gcaccaaggg ccgactcaga tgacattgat   2160
ccatacgaga acgggctaga atggtaattc aaccaccccg acacatccac ctatacacca   2220
attccgtgac atattaaccc aatcaaacat ttcataaact atagtagtca ttgatttaag   2280
aaaaaattgg gggcgacctc aattgtgaaa cataccagat ccgtccacaa caccactcaa   2340
caacccacac acaatggatt tcgccaatga tgaagaaatt gcagaacttt tgaatctcag   2400
caccaatgta atcaaggaga ttcagaaatc cgaactcaag cctccccaaa ccaccggacg   2460
accacctgtc agtcaaggga acacaagaaa tctaactgat ctatgggaaa aggagactgc   2520
aagtcagacc aagacaccgg cccaatctac acaaaccaca caagttcagt ctgatgaaaa   2580
tgaggaggga gaaatcaagt ccgagtcaac tgatggccac atcagaggaa ctgttaatca   2640
atcagagcaa gtcccagaac aaaaccagag cagatcttca ccaggtgatg atctcgacag   2700
agctctcaac aagcttgaag ggagaatcaa tttaatcagc tcaatggaca aagaaattaa   2760
aaagggccct cgcatccaga atctccctgg gtcccaggcg gcaactcaac aggcgaccca   2820
cccattggca ggggacaccc cgaacatgca agcacagaca aaagccctgg cgaagccaca   2880
tcaagaggca atcaatcctg gcaaccagga cacaggagag agtattcatt taccaccttc   2940
catggcacca ccagagtcat tagttggtgc aatccgcaat gcaccccaat tcgtgccaga   3000
ccaatctatg acgaatgtag atgcggggag tgtccaacta catgcatcat gtgcagagat   3060
gataagtaga atgtttgtag aagttatatc caagcttgat aaactcgagt cgagactgaa   3120
tgatatagca aaagttgtga acactacccc ccttattagg aatgatatta accaacttaa   3180
ggccacaacc gcactgatgt ctaaccaaat tgcctccata caaattcttg acccagggaa   3240
tgcagggggtg aggtccctct ctgaaatgaa atctgtgacg aagaaagctg ctgttgtaat   3300
tgcagggttt ggagacgacc caactcaaat tattgaagaa ggcattatgg ccaaagatgc   3360
tcttggaaaa cctgtgcctc caacatctgt tatctcagcc aaagctcaga cttcttccgg   3420
tgtgagtaag ggtgaaatag aaggattgat tgcattggtg gaaacattag ttgacaatga   3480
caagaaggca gcaaaactga ttaaaatgat tgatcaagtt aaatcccatg ccgattacgc   3540
ccgagtcaag caggcaatat ataatgcgta atactgtaac tacacaaaca atcaatactg   3600
ctgtcggttg cacccacctc agcaaatcaa taatctttta gaatttattg attaagaaaa   3660
```

aattgactac tataagaaaa gaacaccaag ttgggggcga agacacgatt gaccacagtc 3720
gctatctgta aggctcctca ccaaaaatgg catatacaac attgaaactg tgggtggatg 3780
agggtgacat gtcgtcttcg ctcctatcat tcccgttggt actaaaagag acagacagag 3840
gcacaaagga gcttcaacca caggtaaggg tagattcaat tggcgatgtg cagaacgcca 3900
aagagtcctc gatattcgtg actctatatg gtttcatcca agcaattaag gagagttcag 3960
atcgatcgaa attcttccat ccaaaagatg acttcaaacc tgagacagtc actgcaggac 4020
tggtagtggt aggtgcgatc cgaatgatgg ctgatgttaa taccatctct aatgacgcac 4080
tagcgctgga gatcactgtt aagaaatctg caacttctca agagaaaatg acggtgatgt 4140
tccacaatag ccccccttca ttgagaactg caataactat ccgagcagga ggtttcatct 4200
cgaatgcaga cgagaatata aaatgtgcca gcaaattgac tgcaggagtg cagtacatat 4260
tccgcccaat gtttgtttca atcactaaat tacacaatgg caaactatat agggtgccca 4320
aaagcatcca cagcatctca tccactctac tgtatagtgt gatgttggag gtaggattca 4380
aagtggatat tgggaaggat catccccagg caaagatgct gaagaaggtc acaatcggcg 4440
atgcagacac atactggggg tttgcatggt tccacctgtg caatttcaaa aagacatcct 4500
ctaagggaaa gccaagaacg ctagacgaac taaagacaaa agtcaaaaat atggggttga 4560
aattggagtt acatgacctg tggggtccga ctattgtggt ccaaatcact ggcaagagca 4620
gcaaatatgc tcaaggattt ttttcctcca atggtacttg ttgtctccca atcagcagat 4680
ctgcaccaga gcttgggaag cttctgtggt cttgttcagc aactataggt gacgcaacag 4740
ttgttatcca atcaagcgag aaaggggaac tcctaaggtc tgatgacctc gagatacgag 4800
gtgctgtggc ctccaagaaa ggtagactgg gctcatttca ccccttcaaa aaatgatgca 4860
ggacatagta cagagaatta gagagccatt agatgtgcgc aaaaaacata atctgcgatg 4920
aactgcccag actccacttt aatctaggtt gcagggaaat agtacacgac atgcgaaata 4980
ctatcacggt caccagcaat caataaagct gatcaatcac tatattagga atcaaatagg 5040
ataacaatta ttaatccaat ttcctaatta taaaaaattg ctttaaaggt tattgacgag 5100
tcgggggcga aatcttgcca cttagtctgc agtcaatctt agaatctaca tattgaacta 5160
tgggtcaaat atcagtatat ctaattaata gcgtgctatt attgctggta tatcctgtga 5220
attcgattga caatacactc attgccccaa tcggagttgc cagcgcaaat gaatggcagc 5280
ttgctgcata tacaacatca ctttcaggga caattgccgt gcgattccta cctgtgctcc 5340
cggataatat gactacctgt cttaaagaaa caatcactac atacaataat actgtcaaca 5400
acatcttagg cccactcaaa tccaatctgg atgcactgct ctcatctgag acttatcccc 5460
agacaagatt aattggggca gttataggtt caattgctct cggtgttgca acatcggctc 5520
aaatcactgc tgcagttgct ctcaagcaag cgcaagacaa tgcaaggaac atactagcac 5580
tcaaagaagc actgtccaaa accaatgagg cggtcaagga gcttagtagt gggttacaac 5640
aaacagctat tgcacttggt aagatacaga gttttgtgaa tgaggaaatt ctgccatcta 5700
tcaaccaact gagctgcgag gtgacagcca ataaacttgg ggtgtattta tctctgtatc 5760
tcacagaact gaccaccata ttcggtgcac agctgaccaa ccctgcattg acttcattat 5820
catatcaagc actgtacaac ctgtgtggtg gcaacatggc aatgcttact cagaagattg 5880
gaattaaaca gcaagacgtt aattcgctat atgaagccgg actaatcaca ggacaagtca 5940
ttggttatga ctctcattac cagctgctgg tcatccaggt caattatcca agcatttctg 6000
aggtcactgg tgtacgtgcg acagaattag tcactgttag tgtaacaaca gacaagggtg 6060

-continued aagggaaagc aattgtaccc caatttgtag ctgaaagtcg ggtgactatt gaagagcttg 6120
atgtcgcatc ttgtaaattc agcagcacga ccctatattg caggcaggtc aacacaaggg 6180
cacttccccc gctagtagct agctgtcttc gaggtaacta tgatgccgcg g 6231

<210> SEQ ID NO 48
<211> LENGTH: 10189
<212> TYPE: DNA
<213> ORGANISM: artificial sequence
<220> FEATURE:
<223> OTHER INFORMATION: 3'-FLG APMV8 genome

<400> SEQUENCE: 48
gcggccgcca ggtcaacaca agggcacttc ccccgctagt agctagctgt cttcgaggta 60
actatgatga ttgtcaatat accacagaga ttggagcatt atcatcccgg tatataacac 120
tagatggggg ggtcttagtt aattgcaagt caattgtttg taggtgcctt aatccaagta 180
agatcatctc tcaaaataca aacgctgcag taacatatgt tgatgccaca atctgcaaaa 240
caattcaatt ggatgatata caactccagc tggaagggtc actatcatca gtttatgcaa 300
gaaacatctc aattgagatc agtcaggtga ccacatccgg gtctttagat atcagcagtg 360
agataggaaa catcaataat acggtgaatc gtgtggagga tttaattcac caatcagagg 420
aatggctggc aaaggttaac ccacacattg ttaataatac aacactaatt gtactctgtg 480
tgttaagtgc gcttgctgtg atctggctgg cagtattaac ggctattata atatacttga 540
gaacaaagtt gaagactata tcggcattag ctgtaaccaa tacaatacag tctaacccct 600
atgttaacca aacgaaacat gaatctaagt tttgatcatt caagccaaaa cagaggatct 660
aggctcaggt taataatagt tcaatcaata tttgatttat taggtttttt tcactaatta 720
ttaatatact cgtgattaga tgataacgtt aaaagtctta gatatttaat aaaaaatgta 780
acctgggggc gacccattta taggtgagta tatattagga agtccttata ttgcactgtg 840
atttcaaaca attatattac ctcatatcta ccttgtctaa agacatcatg agtaacattg 900
catccagttt agaaaacatt gtagagcagg atagtcgaaa aacaacttgg agggccatct 960
ttagatggtc cgttcttctt attacaacag gatgcttagc cttatccatt gttagcatag 1020
ttcaaattgg aaatttgaaa attccttctg taggggatct ggctgatgaa gtggtgacac 1080
ccttgaaaac cactctgtca gatacactca ggaatccaat taaccagata aatgatatat 1140
ttaggattgt tgcccttgat attccattgc aagtgaccag tatccaaaaa gaccttgcaa 1200
gtcaatttaa catgttgata gatagtttaa atgctatcaa attaggcaac gggaccaacc 1260
ttatcatacc tacatcagac aaggagtatg caggaggaat tggaaaccct gtatttactg 1320
tcgatgctgg aggttctata ggattcaaac agtttagctt aatagaacat ccgagcttta 1380
ttgctggacc tacaacgacc cgaggctgta caagaatacc cacttttcac atgtcagaaa 1440
gtcattggtg ctactcacac aacatcatcg ctgctggctg tcaagatgcc agtgcatcca 1500
gtatgtatat ctcaatggga gttctccatg tgtcctcatc tggcactccc atttttctta 1560
ctactgcaag tgagctgata gacgatggag ttaaccgtaa gtcatgcagc attgtagcaa 1620
cccaatttgg ctgtgacatt ttgtgcagta ttgtcacaga gaaggaggga gatgattact 1680
ggtctgatac tccgactcca atgcgccacg gccgtttttc attcaatggt agttttgtag 1740
aagccgaact accagtgtcc agtatgttct catcattctc tgccaactac cctgctgtgg 1800
gatcaggcga aattgtaaaa gatagaatat tattcccaat ttacggaggt ataaagcaga 1860
cttcaccaga gtttaccgaa ttagtgaaat acggactctt tgtatcaaca cctacaactg 1920

-continued

```
tgtgccagag tagctggact tatgaccagg taaaagctgc gtataggcca gattacatat   1980
caggccggtt ctgggcacaa gtgatactca gctgcgctct tgatgcagtc gacttatcaa   2040
gttgtattgt aaagattatg aatagcagca cagtgatgat ggcagcggaa ggaaggataa   2100
tgaagatagg gattgattac ttttactatc agcggtcatc ttcttggtgg ccattggcat   2160
ttgtcacaaa actagacccg caagagttgg cagacacaaa ctcaatatgg ctgaccaatt   2220
ccataccaat cccgcaatca aagttccctc ggccttcata ttcagaaaat tattgcacaa   2280
agccagcagt ttgccctgct acttgtgtca ctggtgtgta ctctgatatt tggcccctga   2340
cctcatcttc atcactcccg agcataattt ggatcggcca gtaccttgat gctcctgttg   2400
gaaggactta tcctagattt ggaattgcaa atcagtcaca ctggtacctc caagaagata   2460
ttctacccac ttccaccgca agtgcgtatt caaccactac atgttttaag aatactgcca   2520
ggaatagagt gttctgcgtc accattgccg aatttgcaga tgggttgttt ggagagtaca   2580
ggataacacc tcagttgtac gaattagtga gaaataattg aataacaata attttgggac   2640
tcattttgtc gcaaagtgaa attgtcatct ttaaaaataa tcaattcgat gatttttatt   2700
gaacatgatt aagcaatcat gtgggaaatt tattatctca taaattctaa tagttgtaaa   2760
tgatgaatta agaaaaaatg gagggcgacc tctacacaaa catggatata aaacaagttg   2820
acctgataat acaacccgag gttcatctcg attcacccat catattgaat aaactggcac   2880
tattatggcg cttgagtggt ttacccatgc ctgcagacct acgacaaaaa tccgtagtga   2940
tgcacatccc ggaccacatc ttagaaaaat cagaatatcg gatcaagcac cgtctaggga   3000
aaatcaagag tgacataaca cattactgtc agtattttaa tattaatttg gcaaatattg   3060
atccgataac ccaccccaaa agtttgtatt ggttatccag actaacaata gctagtgctg   3120
gaacttttag gcatatgaaa gatagaatct tgtgtacagt tggctctgaa tttggacaca   3180
aaattcaaga tttatttca ctgctgagcc ataaactagt aggtaacggg gatttattta   3240
atcaaagtct ctcaggtaca cgtttgactg caagtccgtt atccccttta tgcaatcaat   3300
ttgtctctga catcaagtct gcagtcacga caccctggtc agaagctcgt tggtcttggc   3360
ttcatatcaa acaaacaatg agatatctga taaaacaatc acgcactaca aattcggctc   3420
atttaacaga aatcataaaa gaagaatggg gtttagtagg tattactcca gatcttgtca   3480
ttctttttga cagagtcaat aatagtctga ctgcattaac atttgagatg gttctaatgt   3540
attcagatgt attagaatcc cgtgacaata ttgtgttagt ggggcgacta tctacctttc   3600
tacagccagt agttagtaga ctggaggtgt tgtttgatct agtagattca ttggcaaaaa   3660
tcttaggtga cacaatatat gagattattg cagtgttaga gagcttgtct tatgggtcag   3720
ttcaactaca tgatgcaagt cactctcatg cagggtcttt tttttcattt aacatgaatg   3780
aacttgataa cacactatca aagagggtag atccgaaaca caagaacact ataatgagca   3840
ttataagaca atgcttttct aatctagatg ttgatcaagc tgcagagatg ctatgcctga   3900
tgagattatt cggacaccca atgttaactg caccggatgc agcagccaaa gtgaggaaag   3960
caatgtgtgc tccaaaactt gttgaacacg acaccatctt gcagacatta tctttcttca   4020
aggggataat tataaatggg tacagaagat cacactctgg cctgtggccc aatgtagagc   4080
cgtcttcaat ttatgatgat gatctcagac agctgtactt agagtcagca gagatttccc   4140
atcattttat gcttaaaaac tacaagagtt taagcatgat agaattcaag aagagcatag   4200
actacgatct tcatgatgac ctaagtactt tcttaaagga tagagcaatt tgccggccga   4260
aatcccagtg ggatgtcata tttcgtaagt ctttacgcag atctcatacg cagtcccagt   4320
```

-continued

```
atctggacga aattaagagc aaccgattgc taattgattt tcttgattct gctgaatttg   4380
accctggaaa agaatttgca tatgtaacca caatggatta tttgcacgat aatgaatttt   4440
gtgcttcata ttctctaaag gaaaaggaga tcaaaactac tgggaggata tttgcaaaaa   4500
tgacacgcaa tatgagaagt tgccaagtaa tacttgaatc tttgttatca aagcatatat   4560
gcaagttctt caaagagaat ggcgtttcga tggagcaatt gtcattgacc aagagtctac   4620
ttgcaatgtc tcaactctca ccaaaagtct cgactttgca ggacactgca tcacgtcatg   4680
taggtaactc aaaatctcag attgcaacca gcaacccatc tcggcatcac tcgacaccca   4740
atcagatgtc actctcaaat cgaaaaacgg ttgtagcaac tttcttaaca actgacttgg   4800
aaaaatactg cctgcagtgg cgatattcaa ctattaaatt gtttgcacaa gctctaaatc   4860
aactctttgg gattgatcac ggatttgaat ggatacattt aagacttatg aacagcacct   4920
tatttgttgg cgatccttac tcgcctcctg aagatccaac actagaagat atagataaag   4980
caccaaatga tgatatcttc atagtttctc caaggggagg catagagggt ttatgtcaga   5040
aaatgtggac catgatatca attagtgcta tacactgtgt agcagagaaa attggtgcac   5100
gagtggcagc aatggtgcag ggtgataatc aagtaatagc tatcaccaaa gaattattca   5160
gaggagagaa agcttgtgat gtcagagatg agttagacga gcttggtcaa gtgtttttttg   5220
atgagttcaa gagacacaat tatgcaattg gacacaatct taagctaaat gagacaatac   5280
aaagccaatc ctttttttgta tattccaaac gaatattctt tgaagggcga ttgcttagtc   5340
aagtcctcaa aaatgctgcc aagttatgta tggttgctga ccatctaggt gaaaacactg   5400
tatcttcctg tagcaacctg agctcgacaa ttgcccgctt agtggaaaat gggtttgaga   5460
aggacactgc ttttgtgttg aacctagtct acatcatgac tcagattctt tttgatgagc   5520
attactcgat tgtatgcgat caccatagtg tcaaaagctt gattggatca aaaaaccatc   5580
ggaatttatt gtattcatct ctaataccag gtcagctcgg cggtttcaac ttcctcaata   5640
taagtcggtt gttcactagg aatataggtg acccagtaac atgtagtctg tctgatctca   5700
aatgcttcat agccgcaggt ctccttccac cctatgtcct aaaaaatgtg gttctgcgtg   5760
agcctggtcc tgggacatgg ttgacgttgt gctctgatcc ttacaccctt aacataccat   5820
acacacagct tccaaccaca tatctcaaaa agcacaccca gcgatcattg ctttcacgtg   5880
cagtaaatcc tttattagcc ggtgtacaag tgccaaatca gcatgaggaa gaagagatgt   5940
tggctcgctt tctccttgat cgtgaatatg tgatgccccg cgttgctcat gtaatactag   6000
aatcatcagt ccttggcaaa cggaaacaaa tccaaggctt aattgataca actccaacca   6060
tcattagaac atctctagtt aatctgccag tgtctagaaa gaaatgcgaa aaaataatca   6120
attactctct caattatatt gctgagtgtc atgactcctt acttagccag gtctgcttca   6180
gtgataataa ggaatacttg tggtcaacct ccttaatatc agttgagacc tgtagtgtga   6240
caattgcgga ctatctgaga gctgtcagct ggtctaatat attaggggga agaaacatat   6300
ccggggtgac tacacctgat actattgaat taattcaagg ttgtttaata ggtgaaaatt   6360
ctagttgtac tctttgtgaa tcgcatgatg acgcattcac gtggatgcac ttgcctggcc   6420
cactttacat ccctgaacca tcagttacta actctaaaat gcgtgtgcca tatctgggtt   6480
caaaaacaga ggagcggaaa acagcctcaa tggcagcaat aaaaggaatg tcacatcacc   6540
tgcgtgcagt cttaagaggc acatccgtat ttatttgggc atttggggat acagatatca   6600
attgggataa tgcattgcag attgcccaat cacggtgtaa catcacattg gatcaaatga   6660
gattacttac accaattcct agcagttcaa atattcaaca tagactcgat gacggaatca   6720
```

-continued

```
gcacgcagaa atttactcct gcaagccttg ctcgaatcac atccttcgtt cacatctgta   6780
atgacagcca gaggttagag aaggatggct catctgtcga ctcaaacttg atttaccagc   6840
aaattatgtt acttggactc agcatctttg aaacaatgta ctcaatggac caaaagtggg   6900
tattcaataa ccataccttg catttgcaca ctggacactc ctgttgtcca agggaactag   6960
acataagttt ggtgaacccg ccgagacatc agaccccgga gctgactagc acaacaacca   7020
acccgttcct atatgatcag ctcccattaa atcaagaaaa cttgacaaca cttgagatta   7080
agacatttaa attcaatgag ctcaacattg atggtttaga ttttggtgaa ggaatacaat   7140
tattgagtcg ttgtactgca agattaatgg cagaatgtat tctagaggag ggaataggct   7200
cgtcagttaa aaatgaagca attgtcaatt ttgataattc agtcaattgg atttcagagt   7260
gcctaatgtg tgatattcgc tcactttgtg ttaatttagg tcaagagata ctatgtagcc   7320
tggcatacca aatgtattac ttgcgaatca ggggtagacg ggccattctt aattacttgg   7380
acacaacttt gcaaaggatc cctgtgatac aattagccaa cattgcactc accatttcgc   7440
accctgagat atttcgcaga attgtcaaca ccgggatcca taaccagatt aagggcccat   7500
atgtggcaac aacggatttc atagctgcaa gtagagatat catattatca ggtgcaaggg   7560
agtatctatc ttatttaagc agtgggcagg aagactgtta cacattcttc aactgtcaag   7620
atggggatct tactccaaaa atggaacagt atcttgcaag gagggcatgc cttttaacat   7680
tattgtataa tactgggcac cagatccccg ttatccgatc actgacgcca atagagaagt   7740
gcaaggtgct cacagaatac aatcaacaaa ttgagtacgc agatcaagag tttagctctg   7800
tactaaaagt ggtcaatgca ctactacaaa atcctaagat agatgcatta gtttcaaatc   7860
tctacttcac caccagacgt gttctatcaa acctcagatc atgtgataag gctagatcat   7920
atattgaata tttgtacact gaggacttcg gagagaaaga ggatacagta caatatgaca   7980
tcatgacaac aaacgatatc atacttactc atggtctatt cacacagatc gaaatatctt   8040
atcaagggaa tagtctccat aagttcctta ctccggataa cgcgcctgga tctttgatcc   8100
cattctctat ttcaccaaat tcacttgcat gtgaccctct tcatcacttg ctcaagtcgg   8160
tcggtacatc aagcacaagt tggtacaagt atgcaatcgc ctatgcagtg tctgaaaaga   8220
ggtcagctcg attaggaggg agcttgtaca ttggtgaagg gagcggaagt gtgatgactt   8280
tactcgagta tcttgagcca tctgttgaca tattttacaa ttcactcttc tcaaatggta   8340
tgaacccacc acaacgaaat tatgggctta tgccactaca atttgtgaat tcggtggttt   8400
ataagaactt aacggctaaa tcagaatgta agctagggtt tgtccagcaa tttaaaccgt   8460
tgtggagaga catagacatt gagactaatg ttacagatcc atcatttatc aattttgcat   8520
tgaatgaaat cccaatgcaa tcattaaaac gagtaaattg tgatgtggaa tttgaccgtg   8580
gtatgccgat tgaacgggtt attcagggtt acacccatat cttacttgtt gccacttacg   8640
gattacagca agattcaata ctgtgggtga aggtatatag gacatctgaa aaagtatttc   8700
aattcttact gagtgccatg atcatgatct ttggttatgt aaaaaatccac aggaatggtt   8760
atatgtcgac aaaggatgaa gagtacatat tgatgtctga ctgcaaggaa cctgtaaact   8820
atacagctgt ccctaacatt cttacacgtg taagtgattt agtgtcgaag aatctgagtc   8880
ttatccatcc agaagacctc agaaaagtaa ggtgtgaaac agattccctg aatttgaagt   8940
gcaatcatat ttatgagaaa ataattgcca gaaaaattcc attacaggta tcatcaactg   9000
actctttgct cctccaatta ggcggtgtta tcaactcggt gggctcaact gatcctagag   9060
aggttgcaac attatcttct attgagtgta tggactatgt tgtctcatca attgatttgg   9120
```

-continued

```
ctatattgga ggcaaatatt gtaatctcag agagtgctgg tcttgacctc gctttaatgt   9180

taggcccatt caacttaaat aagcttaaga aaattgacac aatccttaag tcaagcacct   9240

atcagctaat cccgtactgg ttgcgctatg agtactctat taatccgaga tctttgtcat   9300

ttctaatcac taaattacaa caatgccgaa tttcatggtc agatatgatc acgatttctg   9360

aatttcgtaa gaaatccaag cggcctatat ttatcaaacg agtaataggg aatcaacagc   9420

taaaatcatt ctttaatgaa agctcaagta ttgttttgac tcgggctgaa gttaaagtct   9480

gtataaagtt cctcggtgca atcatcaagt tgaaataatt tctgcgattt taaaggggtg   9540

taatgttcta atttgcactt gaagtaatat agcttgtaat cattcgctag ggataggat   9600

aatttctcta acctctgaat ctatattcct agagtataac aaatatatac ataataaaaa   9660

tgattttaag aaaaaatccg acactcaaag aaaattggtg cctgtaatat tcttcttgcc   9720

aaatgattgt gaagtgtcta gcctaactta aaacaatcgt attcgatagg gaagaatgat   9780

atataaaata actaataaaa aattgtatta gtaaaaatta ccgtatttcc tgtattccat   9840

ttctggtggg tcggcatggc atctccacct cctcgcggtc cgacctgggc atccgaagga   9900

ggacgcacgt ccactcggat ggctaaggga gggcgctaga gctcgctgat cagcctcgac   9960

tgtgccttct agttgccagc catctgttgt ttgcccctcc cccgtgcctt ccttgaccct  10020

ggaaggtgcc actcccactg tcctttccta ataaaatgag gaaattgcat cgcattgtct  10080

gagtaggtgt cattctattc tggggggtgg ggtggggcag gacagcaagg gggaggattg  10140

ggaagacaat agcaggcatg ctggggatgc ggtgggctct atgccgcgg              10189
```

<210> SEQ ID NO 49
<211> LENGTH: 2652
<212> TYPE: DNA
<213> ORGANISM: artificial sequence
<220> FEATURE:
<223> OTHER INFORMATION: T7 polymerase condon-optimized

<400> SEQUENCE: 49

```
atgaatacaa ttaacatcgc caaaaacgac ttcagcgata tcgaactggc cgccatccca     60

ttcaatacac tggccgatca ctatggcgag cgcctggcca gagagcagct ggccctggag    120

cacgagtcct acgagatggg cgaggcccgc ttccggaaga tgttcgagcg gcagctgaag    180

gccggcgaag tggccgacaa cgccgccgcc aagcccctga tcaccaccct gctgcccaaa    240

atgatcgccc gcattaatga ctggttcgaa gaggtgaaag ccaaaagggg gaaacgcccc    300

accgccttcc agttcctgca ggagatcaaa cccgaggccg tggcctatat caccattaag    360

acaacactgg cctgtctgac aagcgccgat aacacaacag tgcaggccgc cgcctctgcc    420

atcggccggg ccatcgagga cgaggccaga ttcggccgca ttcgggacct ggaggccaaa    480

cacttcaaaa agaacgtgga agagcagctg aacaagcggg tgggacacgt gtacaagaaa    540

gccttcatgc aggtggtgga ggccgatatg ctgtctaaag ggctgctggg aggcgaggcc    600

tggagctcct ggcacaagga agatagcatc cacgtgggag tgagatgcat cgagatgctg    660

atcgagtcta ccgggatggt gtccctgcac agacagaacg ccggggtggt gggccaggat    720

agcgagacaa ttgagctggc ccccgagtat gccgaagcca ttgccacacg ggccggcgcc    780

ctggccggaa tctccccaat gttccagcca tgtgtggtgc tgcctaagcc ctggacagga    840

atcacaggcg gggggatactg ggccaatggc aggaggccac tggccctggt gaggacacac    900

tccaagaagg ccctgatgag atatgaagac gtgtatatgc ctgaggtgta taaggccatc    960

aatatcgccc agaacaccgc ctggaaaatt aataagaagg tgctggccgt ggccaatgtg   1020
```

-continued atcacaaagt ggaagcactg cccagtggag aatatcccag ccattgagcg cgaagagctg 1080
cccatgaagc cagagaacat tgatatgaac ccagaggccc tgatcgcctg gaagagagcc 1140
gccgccgccg tgtatcgcaa ggataaagcc aggaagtccc gccggatcag cctggagttc 1200
atgctggagc aggccaataa gtttgccaac cacaaggcca tttggtttcc ttataatatg 1260
gactggcgcg ggagagtgta cgccgtgtct atgttcaatc cacagggaaa cgatatgacc 1320
aagggactgc tgaccctggc caagggcaag cctattggga aagagggcta ctattggctg 1380
aagatccacg gggccaactg cgccggagtg gataaggtgc cttttcccga gcgcatcaag 1440
ttcatcgagg aaaaccacga aaacatcatt gcctgcgcca agagccccct ggaaaacaca 1500
tggtgggccg agcaggacag ccccttttgc tttctggcct tttgctttga gtacgccggc 1560
gtgcagcacc acggcctgtc ctacaactgc tccctgcccc tggccttcga tggatcttgt 1620
tctggcatcc agcacttttc cgccatgctg cgcgacgagg tgggggggcag ggccgtgaat 1680 ctgctgccta gcgagaccgt gcaggatatc tacggcatcg tggccaagaa ggtgaacgag 1740
attctgcagg ccgatgccat taacggaaca gacaacgagg tggtgaccgt gaccgatgaa 1800
aatacaggcg agatttccga gaaagtgaag ctgggcacca aggccctggc cggacagtgg 1860
ctggcctata gcgtgacccg gtccgtgacc aagcgctctg tgatgacact ggcctacggg 1920
tctaaggaat ttggatttcg gcagcaggtg ctggaagaca ccattcagcc cgccatcgac 1980
tccggaaagg gcctgatgtt tacccagcca aatcaggccg ccgggtacat ggccaagctg 2040
atctgggaaa gcgtgtccgt gacagtggtg gccgccgtgg aagccatgaa ctggctgaag 2100
tctgccgcca agctgctggc cgccgaagtg aaggacaaga aaaccgggga aattctgcgg 2160
aaaagatgtg ccgtgcactg ggtgaccccca gacggattcc cagtgtggca ggagtacaag 2220
aagccaattc agacaaggct gaacctgatg ttcctggggc agtttcgcct gcagccaaca 2280
atcaacacaa ataaggatag cgagatcgac gcccacaagc aggaatccgg cattgcccct 2340
aatttcgtgc acagccagga cggctctcac ctgcgcaaga cagtggtgtg ggcccacgag 2400
aagtacggca ttgaatcttt tgccctgatc cacgactctt tcggcaccat cccagccgat 2460
gccgccaacc tgttcaaggc cgtgagagag accatggtgg acacctacga gagctgcgat 2520
gtgctggccg acttttacga ccagttcgcc gatcagctgc acgaaagcca gctggataag 2580
atgcctgccc tgcccgccaa ggggaacctg aacctgagag acatcctgga gtccgatttc 2640
gccttcgcct ga 2652

<210> SEQ ID NO 50
<211> LENGTH: 32
<212> TYPE: DNA
<213> ORGANISM: artificial sequence
<220> FEATURE:
<223> OTHER INFORMATION: EGFP-FP primer

<400> SEQUENCE: 50
ccggatccat ggtgagcaag ggcgaggagc tg 32

<210> SEQ ID NO 51
<211> LENGTH: 35
<212> TYPE: DNA
<213> ORGANISM: artificial sequence
<220> FEATURE:
<223> OTHER INFORMATION: EGFP-RP primer

<400> SEQUENCE: 51
ccgcggccgc ttacttgtac agctcgtcca tgccg 35

<210> SEQ ID NO 52
<211> LENGTH: 1419
<212> TYPE: DNA
<213> ORGANISM: artificial sequence
<220> FEATURE:
<223> OTHER INFORMATION: APMV8 minigenome

<400> SEQUENCE: 52
gaattctaat acgactcact atagggacca gaaatggaat acaggaaata cggtaatttt 60
tactaataca attttttatt agttatttta tatatcattc ttccctatcg aatacgattg 120
ttttaagtta ggctagacac ttcacaatca tttggcaaga agaatattac aggcaccaat 180
tttctttgag tgtcggattt tttcttaaaa tcatttttat tatgtatata tttgttatac 240
tctaggaata tagattcaga ggttagagaa attatcctat cccctagcga atgattacaa 300
gctatattac ttcaagtgca aattagaaca ttacacccct ttaaaatcgc agaaattaca 360
agctatatta cttcaagtgc aaattagaac attacacccc tttaaaatcg cagaaattac 420
ttgtacagct cgtccatgcc gagagtgatc ccggcggcgg tcacgaactc cagcaggacc 480
atgtgatcgc gcttctcgtt ggggtctttg ctcagggcgg actgggtgct caggtagtgg 540
ttgtcgggca gcagcacggg gccgtcgccg atgggggtgt tctgctggta gtggtcggcg 600
agctgcacgc tgccgtcctc gatgttgtgg cggatcttga agttcacctt gatgccgttc 660
ttctgcttgt cggccatgat atagacgttg tggctgttgt agttgtactc cagcttgtgc 720
cccaggatgt tgccgtcctc cttgaagtcg atgcccttca gctcgatgcg gttcaccagg 780
gtgtcgccct cgaacttcac ctcggcgcgg gtcttgtagt tgccgtcgtc cttgaagaag 840
atggtgcgct cctggacgta gccttcgggc atggcggact tgaagaagtc gtgctgcttc 900
atgtggtcgg ggtagcggct gaagcactgc acgccgtagg tcagggtggt cacgagggtg 960
ggccagggca cgggcagctt gccggtggtg cagatgaact tcagggtcag cttgccgtag 1020
gtggcatcgc cctcgccctc gccggacacg ctgaacttgt ggccgtttac gtcgccgtcc 1080
agctcgacca ggatgggcac caccccggtg aacagctcct cgcccttgct caccatattg 1140
agtcctatag cgacctattc aaaacctcca gtgaaattca gggtttcggc ctcgagctcg 1200
agatccactt gcttcgcccc caataattcg attgttttat ttaaagttcc cgttggtctt 1260
gcattccttg tttggtgggt cggcatggca tctccacctc ctcgcggtcc gacctgggca 1320
tccgaaggag gacgcacgtc cactcggatg gctaagggag ggcgtagcat aacccccttgg 1380 ggcctctaaa cgggtcttga ggggtttttt ggcggccgc 1419

<210> SEQ ID NO 53
<211> LENGTH: 1386
<212> TYPE: DNA
<213> ORGANISM: artificial sequence
<220> FEATURE:
<223> OTHER INFORMATION: NP gene of FJ215863

<400> SEQUENCE: 53
atgtcatctg tattcaatga gtatcaggcg cttcaagaac aacttgtaaa gccggctgtc 60
aggagacctg atgttgcctc aacgggttta ctcagagcgg aaatacctgt ctgtgtcaca 120
ttatctcaag accccggtga gagatggagc cttgcttgct tgaatatcag atggcttgtg 180
agtgattcat caaccacacc aatgaagcaa ggagcaatat tgtcactgct gagtctacat 240
tcagacaata tgcgagctca cgcaacatta gcagcaaggt ctgcagatgc ttcactcacc 300
atacttgagg tagatgaagt agatattggc aactcactaa tcaaattcaa cgccagaagt 360

```
ggtgtatctg ataaacgctc aaatcaattg cttgcaattg cggatgacat ccccaaaagt    420

tgcagtaatg ggcatccatt tcttgacaca gacattgaga ccagagaccc gctcgatcta    480

tcagagacta tagaccgcct gcagggtatt gcagctcaga tatgggtgtc agccataaag    540

agcatgacag cgcctgacac cgcatcagag tcagaaagta agaggctggc caaatatcaa    600

caacaaggcc gactggttaa gcaagtactc ttgcattctg tagtcaggac agaatttatg    660

agagttattc ggggcagctt ggtactgcgc cagtttatgg ttagcgagtg caagagggct    720

tcagccatgg gcggagacac atctaggtac tatgctatgg tgggcgacat cagtctgtac    780

atcaagaatg caggattgac tgcatttttc ctcaccctga agttcggagt tggtacccag    840

tatccaacct tagcaatgag tgttttctcc agtgacctta aaaggcttgc tgcactaatc    900

aggctataca aaaccaaggg agacaatgca ccatacatgg cattcctgga ggactccgat    960

atgggaaatt ttgctccagc aaattatagc acaatgtact cttatgccat gggcattggg   1020

acaattctgg aagcatctgt atctcgatac cagtatgcca gagactttac cagtgagaat   1080

tatttccgtc ttggagttga gacagcccaa agccagcagg gagcatttga cgagagaaca   1140

gcccgagaaa tgggcttgac tgaggaatca aaacagcagg ttagatcact gctaatgtca   1200

gtagacatgg gtcccagttc agttcatgag ccatctcgcc ctgcatttat cagtcaagaa   1260

gaaaataggc agcctgccca gaactcgtca gatactcagg gtcagaccaa gccagtcccg   1320

aagcagcccg caccaagggc cgactcagat gacattgatc catacgagaa cgggctagaa   1380

tggtaa                                                              1386
```

<210> SEQ ID NO 54
<211> LENGTH: 461
<212> TYPE: PRT
<213> ORGANISM: artificial sequence
<220> FEATURE:
<223> OTHER INFORMATION: NP protein ACO48297

<400> SEQUENCE: 54

```
Met Ser Ser Val Phe Asn Glu Tyr Gln Ala Leu Gln Glu Gln Leu Val
1               5                   10                  15

Lys Pro Ala Val Arg Arg Pro Asp Val Ala Ser Thr Gly Leu Leu Arg
            20                  25                  30

Ala Glu Ile Pro Val Cys Val Thr Leu Ser Gln Asp Pro Gly Glu Arg
        35                  40                  45

Trp Ser Leu Ala Cys Leu Asn Ile Arg Trp Leu Val Ser Asp Ser Ser
    50                  55                  60

Thr Thr Pro Met Lys Gln Gly Ala Ile Leu Ser Leu Leu Ser Leu His
65                  70                  75                  80

Ser Asp Asn Met Arg Ala His Ala Thr Leu Ala Ala Arg Ser Ala Asp
                85                  90                  95

Ala Ser Leu Thr Ile Leu Glu Val Asp Glu Val Asp Ile Gly Asn Ser
            100                 105                 110

Leu Ile Lys Phe Asn Ala Arg Ser Gly Val Ser Asp Lys Arg Ser Asn
        115                 120                 125

Gln Leu Leu Ala Ile Ala Asp Asp Ile Pro Lys Ser Cys Ser Asn Gly
    130                 135                 140

His Pro Phe Leu Asp Thr Asp Ile Glu Thr Arg Asp Pro Leu Asp Leu
145                 150                 155                 160

Ser Glu Thr Ile Asp Arg Leu Gln Gly Ile Ala Ala Gln Ile Trp Val
                165                 170                 175

Ser Ala Ile Lys Ser Met Thr Ala Pro Asp Thr Ala Ser Glu Ser Glu
```

180 185 190

Ser Lys Arg Leu Ala Lys Tyr Gln Gln Gln Gly Arg Leu Val Lys Gln
195 200 205

Val Leu Leu His Ser Val Val Arg Thr Glu Phe Met Arg Val Ile Arg
210 215 220

Gly Ser Leu Val Leu Arg Gln Phe Met Val Ser Glu Cys Lys Arg Ala
225 230 235 240

Ser Ala Met Gly Gly Asp Thr Ser Arg Tyr Tyr Ala Met Val Gly Asp
245 250 255

Ile Ser Leu Tyr Ile Lys Asn Ala Gly Leu Thr Ala Phe Phe Leu Thr
260 265 270

Leu Lys Phe Gly Val Gly Thr Gln Tyr Pro Thr Leu Ala Met Ser Val
275 280 285

Phe Ser Ser Asp Leu Lys Arg Leu Ala Ala Leu Ile Arg Leu Tyr Lys
290 295 300

Thr Lys Gly Asp Asn Ala Pro Tyr Met Ala Phe Leu Glu Asp Ser Asp
305 310 315 320

Met Gly Asn Phe Ala Pro Ala Asn Tyr Ser Thr Met Tyr Ser Tyr Ala
325 330 335

Met Gly Ile Gly Thr Ile Leu Glu Ala Ser Val Ser Arg Tyr Gln Tyr
340 345 350

Ala Arg Asp Phe Thr Ser Glu Asn Tyr Phe Arg Leu Gly Val Glu Thr
355 360 365

Ala Gln Ser Gln Gln Gly Ala Phe Asp Glu Arg Thr Ala Arg Glu Met
370 375 380

Gly Leu Thr Glu Glu Ser Lys Gln Gln Val Arg Ser Leu Leu Met Ser
385 390 395 400

Val Asp Met Gly Pro Ser Ser Val His Glu Pro Ser Arg Pro Ala Phe
405 410 415

Ile Ser Gln Glu Glu Asn Arg Gln Pro Ala Gln Asn Ser Ser Asp Thr
420 425 430

Gln Gly Gln Thr Lys Pro Val Pro Lys Gln Pro Ala Pro Arg Ala Asp
435 440 445

Ser Asp Asp Ile Asp Pro Tyr Glu Asn Gly Leu Glu Trp
450 455 460

<210> SEQ ID NO 55
<211> LENGTH: 1218
<212> TYPE: DNA
<213> ORGANISM: artificial sequence
<220> FEATURE:
<223> OTHER INFORMATION: P gene of FJ215863

<400> SEQUENCE: 55
atggatttcg ccaatgatga agaaattgca gaacttttga atctcagcac caatgtaatc 60
aaggagattc agaaatccga actcaagcct ccccaaacca ccggacgacc acctgtcagt 120
caagggaaca caagaaatct aactgatcta tgggaaaaag agactgcaag tcagaccaag 180
acaccggccc aatctccaca aaccacacaa gttcagtctg atgaaaatga ggagggagaa 240
atcaagtccg agtcaattga tggccacatc agaggaactg ttaatcaatc agagcaagtc 300
ccagaacaaa accagagcag atcttcacca ggtgatgatc tcgacagagc tctcaacaag 360
cttgaaggga gaatcaattc aatcagctca atggacaaag aaattaaaaa gggccctcgc 420
atccagaatc tccctgggtc ccaggcggca actcaacagg cgacccaccc attggcaggg 480
gacaccccga acatgcaagc acagacaaaa gccctggcga agccacatca agaggcaatc 540

```
aatcctggca accaggacac aggagagagt attcatttac caccttccat ggcaccacca    600

gagtcattag ttggtgcaat ccgcaatgca ccccaattcg tgccagacca atctatgacg    660

aatgtagatg cggggagtgt ccaactacat gcatcatgtg cagagatgat aagtagaatg    720

tttgtagaag ttatatccaa gcttgataaa ctcgagtcga gactgaatga tatagcaaaa    780

gttgtgaaca ccaccccccct tattaggaat gatattaacc aacttaaggc cacaaccgca    840

ctgatgtcca accaaattgc ttccatacaa attcttgacc cagggaatgc aggggtgagg    900

tccctctctg aaatgaaatc tgtgacgaag aaagctgctg ttgtaattgc agggtttgga    960

gacgacccaa ctcaaattat tgaagaaggc attatggcca aagatgctct tggaaaacct   1020

gtgcctccaa catctgttat ctcagctaaa gctcagactt cttccggtgt gagtaagggt   1080

gaaatagaag gattgattgc attggtggaa acattagttg acaatgacaa gaaggcagca   1140

aaactgatta aaatgattga tcaagttaaa tcccacgccg attacgcccg agtcaagcag   1200

gcaatatata atgcgtaa                                                 1218
```

<210> SEQ ID NO 56
<211> LENGTH: 405
<212> TYPE: PRT
<213> ORGANISM: artificial sequence
<220> FEATURE:
<223> OTHER INFORMATION: P protein ACO48298

<400> SEQUENCE: 56

```
Met Asp Phe Ala Asn Asp Glu Glu Ile Ala Glu Leu Leu Asn Leu Ser
1               5                   10                  15

Thr Asn Val Ile Lys Glu Ile Gln Lys Ser Glu Leu Lys Pro Pro Gln
            20                  25                  30

Thr Thr Gly Arg Pro Pro Val Ser Gln Gly Asn Thr Arg Asn Leu Thr
        35                  40                  45

Asp Leu Trp Glu Lys Glu Thr Ala Ser Gln Thr Lys Thr Pro Ala Gln
    50                  55                  60

Ser Pro Gln Thr Thr Gln Val Gln Ser Asp Glu Asn Glu Glu Gly Glu
65                  70                  75                  80

Ile Lys Ser Glu Ser Ile Asp Gly His Ile Arg Gly Thr Val Asn Gln
                85                  90                  95

Ser Glu Gln Val Pro Glu Gln Asn Gln Ser Arg Ser Ser Pro Gly Asp
            100                 105                 110

Asp Leu Asp Arg Ala Leu Asn Lys Leu Glu Gly Arg Ile Asn Ser Ile
        115                 120                 125

Ser Ser Met Asp Lys Glu Ile Lys Lys Gly Pro Arg Ile Gln Asn Leu
    130                 135                 140

Pro Gly Ser Gln Ala Ala Thr Gln Gln Ala Thr His Pro Leu Ala Gly
145                 150                 155                 160

Asp Thr Pro Asn Met Gln Ala Gln Thr Lys Ala Leu Ala Lys Pro His
                165                 170                 175

Gln Glu Ala Ile Asn Pro Gly Asn Gln Asp Thr Gly Glu Ser Ile His
            180                 185                 190

Leu Pro Pro Ser Met Ala Pro Pro Glu Ser Leu Val Gly Ala Ile Arg
        195                 200                 205

Asn Ala Pro Gln Phe Val Pro Asp Gln Ser Met Thr Asn Val Asp Ala
    210                 215                 220

Gly Ser Val Gln Leu His Ala Ser Cys Ala Glu Met Ile Ser Arg Met
225                 230                 235                 240
```

```
Phe Val Glu Val Ile Ser Lys Leu Asp Lys Leu Glu Ser Arg Leu Asn
                245                 250                 255

Asp Ile Ala Lys Val Val Asn Thr Thr Pro Leu Ile Arg Asn Asp Ile
            260                 265                 270

Asn Gln Leu Lys Ala Thr Thr Ala Leu Met Ser Asn Gln Ile Ala Ser
        275                 280                 285

Ile Gln Ile Leu Asp Pro Gly Asn Ala Gly Val Arg Ser Leu Ser Glu
    290                 295                 300

Met Lys Ser Val Thr Lys Lys Ala Ala Val Val Ile Ala Gly Phe Gly
305                 310                 315                 320

Asp Asp Pro Thr Gln Ile Ile Glu Glu Gly Ile Met Ala Lys Asp Ala
                325                 330                 335

Leu Gly Lys Pro Val Pro Pro Thr Ser Val Ile Ser Ala Lys Ala Gln
            340                 345                 350

Thr Ser Ser Gly Val Ser Lys Gly Glu Ile Glu Gly Leu Ile Ala Leu
        355                 360                 365

Val Glu Thr Leu Val Asp Asn Asp Lys Lys Ala Ala Lys Leu Ile Lys
    370                 375                 380

Met Ile Asp Gln Val Lys Ser His Ala Asp Tyr Ala Arg Val Lys Gln
385                 390                 395                 400

Ala Ile Tyr Asn Ala
                405
```

<210> SEQ ID NO 57
<211> LENGTH: 1110
<212> TYPE: DNA
<213> ORGANISM: artificial sequence
<220> FEATURE:
<223> OTHER INFORMATION: M gene of FJ215863

<400> SEQUENCE: 57

```
atggcatata caacattgaa actgtgggtg gatgagggtg acatgtcgtc ttcgctccta     60

tcattcccgt tggtactaaa agagacagac agaggcacaa aggagcttca accacaggta    120

agggtagatt caattggcga tgtgcagaac gccaaagagt cctcgatatt cgtgactcta    180

tatggtttca tccaagcaat taaggagagt acagatcgat cgaaattctt ccatccaaaa    240

gatgacttca aacctgagac agtcactgca ggactggtag tggtaggtgc gatccgaatg    300

atggctgatg ttaataccat ctctaatgac gcactagcgc tggagatcac tgttaagaaa    360

tctgcaactt ctcaagagaa aatgacggtg atgttccaca atagcccccc ttcattgaga    420

actgcaataa ctatccgagc aggaggtttc atctcgaatg cagacgagaa tataaaatgt    480

gccagcaagt tgactgcagg agtgcagtac atattccgcc caatgtttgt ttcaatcact    540

aaattacaca atggcaaact atatagggtg cccaaaagca tccacagcat ctcgtccact    600

ctactgtata gtgtgatgtt ggaggtagga ttcaaagtgg atattgggaa ggatcatccc    660

caggcaaaga tgctgaagaa ggtcacaatc ggcgatgcag acacatactg ggggtttgca    720

tggttccacc tgtgcaattt caaaaagaca tcctctaagg gaaagccaag aacgctagac    780

gaactaaaga caaaagtcaa aaacatgggg ttgaaattgg agttacatga cttgtggggt    840

ccgactattg tggtccaaat cactggcaag agcagcaaat atgctcaagg atttttttcc    900

tccaatggta cttgttgcct cccaatcagc agatctgcac cagggcttgg gaagcttctg    960

tggtcctgtt cagcaactat cggtgacgca acagttgtta tccagtcaag cgagaaaggg   1020

gaactcctaa ggtctgatga cctcgagata cgaggtgctg tggcctccaa gaaaggtaga   1080

ctgagctcat ttcacccctt caagaaatga                                    1110
```

<210> SEQ ID NO 58
<211> LENGTH: 369
<212> TYPE: PRT
<213> ORGANISM: artificial sequence
<220> FEATURE:
<223> OTHER INFORMATION: M protein of AC048299

<400> SEQUENCE: 58

```
Met Ala Tyr Thr Thr Leu Lys Leu Trp Val Asp Glu Gly Asp Met Ser
1               5                   10                  15

Ser Ser Leu Leu Ser Phe Pro Leu Val Leu Lys Glu Thr Asp Arg Gly
            20                  25                  30

Thr Lys Glu Leu Gln Pro Gln Val Arg Val Asp Ser Ile Gly Asp Val
        35                  40                  45

Gln Asn Ala Lys Glu Ser Ser Ile Phe Val Thr Leu Tyr Gly Phe Ile
    50                  55                  60

Gln Ala Ile Lys Glu Ser Thr Asp Arg Ser Lys Phe Phe His Pro Lys
65                  70                  75                  80

Asp Asp Phe Lys Pro Glu Thr Val Thr Ala Gly Leu Val Val Val Gly
                85                  90                  95

Ala Ile Arg Met Met Ala Asp Val Asn Thr Ile Ser Asn Asp Ala Leu
            100                 105                 110

Ala Leu Glu Ile Thr Val Lys Lys Ser Ala Thr Ser Gln Glu Lys Met
        115                 120                 125

Thr Val Met Phe His Asn Ser Pro Pro Ser Leu Arg Thr Ala Ile Thr
    130                 135                 140

Ile Arg Ala Gly Gly Phe Ile Ser Asn Ala Asp Glu Asn Ile Lys Cys
145                 150                 155                 160

Ala Ser Lys Leu Thr Ala Gly Val Gln Tyr Ile Phe Arg Pro Met Phe
                165                 170                 175

Val Ser Ile Thr Lys Leu His Asn Gly Lys Leu Tyr Arg Val Pro Lys
            180                 185                 190

Ser Ile His Ser Ile Ser Ser Thr Leu Leu Tyr Ser Val Met Leu Glu
        195                 200                 205

Val Gly Phe Lys Val Asp Ile Gly Lys Asp His Pro Gln Ala Lys Met
    210                 215                 220

Leu Lys Lys Val Thr Ile Gly Asp Ala Asp Thr Tyr Trp Gly Phe Ala
225                 230                 235                 240

Trp Phe His Leu Cys Asn Phe Lys Lys Thr Ser Ser Lys Gly Lys Pro
                245                 250                 255

Arg Thr Leu Asp Glu Leu Lys Thr Lys Val Lys Asn Met Gly Leu Lys
            260                 265                 270

Leu Glu Leu His Asp Leu Trp Gly Pro Thr Ile Val Val Gln Ile Thr
        275                 280                 285

Gly Lys Ser Ser Lys Tyr Ala Gln Gly Phe Phe Ser Ser Asn Gly Thr
    290                 295                 300

Cys Cys Leu Pro Ile Ser Arg Ser Ala Pro Gly Leu Gly Lys Leu Leu
305                 310                 315                 320

Trp Ser Cys Ser Ala Thr Ile Gly Asp Ala Thr Val Val Ile Gln Ser
                325                 330                 335

Ser Glu Lys Gly Glu Leu Leu Arg Ser Asp Asp Leu Glu Ile Arg Gly
            340                 345                 350

Ala Val Ala Ser Lys Lys Gly Arg Leu Ser Ser Phe His Pro Phe Lys
        355                 360                 365
```

Lys

<210> SEQ ID NO 59
<211> LENGTH: 1632
<212> TYPE: DNA
<213> ORGANISM: artificial sequence
<220> FEATURE:
<223> OTHER INFORMATION: F gene of FJ215863

<400> SEQUENCE: 59
atgggtcaaa tatcagtata tctaattaat agcgtgctat tattgctggt atatcctgtg 60
aattcgattg acaatacact cattgcccca atcggagttg ccagcgcaaa tgaatggcag 120
cttgctgcat atacaacatc actttcaggg acaattgccg tgcgattcct acctgtgctc 180
ccggataata tgactacctg tcttagagaa acaatcacta catataataa tactgtcaac 240
aacatcttag gcccactcaa atccaatctg gatgcactgc tctcatctga gacttatccc 300
cagacaagat taattggggc agttataggt tcaattgctc tcggtgttgc aacatcggct 360
caaatcactg ctgcagttgc tctcaagcaa gcgcaagaca atgcaaggaa catactagca 420
ctcaaagaag cactgtccaa aaccaatgag gcggtcaagg agcttagtag tgggttacaa 480
caaacagcta ttgcacttgg taagatacag agttttgtga atgaggaaat tctgccatct 540
atcaaccaac tgagctgcga ggtgacagcc aataaacttg ggtgtatttt atctctgtat 600
ctcacagaac tgaccaccat attcggtgca cagctgacta accctgcatt gacttcatta 660
tcatatcaag cgctgtacaa cctgtgtggt ggcaacatgg caatgcttac tcagaagatt 720
ggaattaaac aacaagacgt taattcgcta tatgaagccg gactaatcac aggacaagtc 780
attggttatg actctcagta ccagctgctg gtcatccagg tcaattatcc aagcatttct 840
gaggtcactg gtgtacgtgc aacagaatta gtcactgtta gtgtaacaac agacaagggt 900
gaagggaaag caattgtacc ccaatttgta gctgaaagtc gggtgactat tgaagagctt 960
gatgtagcat cttgtaaatt cagcagcacg accctatatt gcaggcaggt caacacaagg 1020
gcacttcccc cgctagtagc tagctgtctt cgaggtaact atgatgattg tcaatatacc 1080
acagagattg gagcattatc atcccggtat ataacactag atggggggt cttagttaat 1140 tgtaagtcaa ttgtttgtag gtgccttaat ccaagtaaga tcatctctca aaatacaaac 1200
gctgcagtaa catatgttga tgccacaatc tgcaaaacaa ttcaattgga tgatatacaa 1260
ctccagctgg aagggtcact atcatcagtt tatgcaagaa acatctcaat tgagatcagt 1320
caggtgacca cctccgggtc tttagatatc agcagtgaga taggaaacat caataatacg 1380
gtgaatcgtg tggaggattt aattcaccaa tcagaggaat ggctggcaaa ggttaaccca 1440
cacattgtta ataatacaac actaatcgta ctctgtgtgt taagtgcgct tgctgtgatc 1500
tggctggcag tattaacggc tattataata tacttgagaa caaagttgaa gactatatcg 1560
gcattagctg taaccaatac aatacagtct aacccctatg ttaaccaaac gaaacgtgaa 1620
tctaagtttt ga 1632

<210> SEQ ID NO 60
<211> LENGTH: 543
<212> TYPE: PRT
<213> ORGANISM: artificial sequence
<220> FEATURE:
<223> OTHER INFORMATION: F protein of ACO48300

<400> SEQUENCE: 60

Met Gly Gln Ile Ser Val Tyr Leu Ile Asn Ser Val Leu Leu Leu Leu
1 5 10 15

```
Val Tyr Pro Val Asn Ser Ile Asp Asn Thr Leu Ile Ala Pro Ile Gly
            20                  25                  30

Val Ala Ser Ala Asn Glu Trp Gln Leu Ala Ala Tyr Thr Thr Ser Leu
        35                  40                  45

Ser Gly Thr Ile Ala Val Arg Phe Leu Pro Val Leu Pro Asp Asn Met
    50                  55                  60

Thr Thr Cys Leu Arg Glu Thr Ile Thr Thr Tyr Asn Asn Thr Val Asn
65                  70                  75                  80

Asn Ile Leu Gly Pro Leu Lys Ser Asn Leu Asp Ala Leu Leu Ser Ser
                85                  90                  95

Glu Thr Tyr Pro Gln Thr Arg Leu Ile Gly Ala Val Ile Gly Ser Ile
            100                 105                 110

Ala Leu Gly Val Ala Thr Ser Ala Gln Ile Thr Ala Ala Val Ala Leu
        115                 120                 125

Lys Gln Ala Gln Asp Asn Ala Arg Asn Ile Leu Ala Leu Lys Glu Ala
    130                 135                 140

Leu Ser Lys Thr Asn Glu Ala Val Lys Glu Leu Ser Ser Gly Leu Gln
145                 150                 155                 160

Gln Thr Ala Ile Ala Leu Gly Lys Ile Gln Ser Phe Val Asn Glu Glu
                165                 170                 175

Ile Leu Pro Ser Ile Asn Gln Leu Ser Cys Glu Val Thr Ala Asn Lys
            180                 185                 190

Leu Gly Val Tyr Leu Ser Leu Tyr Leu Thr Glu Leu Thr Thr Ile Phe
        195                 200                 205

Gly Ala Gln Leu Thr Asn Pro Ala Leu Thr Ser Leu Ser Tyr Gln Ala
    210                 215                 220

Leu Tyr Asn Leu Cys Gly Gly Asn Met Ala Met Leu Thr Gln Lys Ile
225                 230                 235                 240

Gly Ile Lys Gln Gln Asp Val Asn Ser Leu Tyr Glu Ala Gly Leu Ile
                245                 250                 255

Thr Gly Gln Val Ile Gly Tyr Asp Ser Gln Tyr Gln Leu Leu Val Ile
            260                 265                 270

Gln Val Asn Tyr Pro Ser Ile Ser Glu Val Thr Gly Val Arg Ala Thr
        275                 280                 285

Glu Leu Val Thr Val Ser Val Thr Thr Asp Lys Gly Glu Gly Lys Ala
    290                 295                 300

Ile Val Pro Gln Phe Val Ala Glu Ser Arg Val Thr Ile Glu Glu Leu
305                 310                 315                 320

Asp Val Ala Ser Cys Lys Phe Ser Ser Thr Thr Leu Tyr Cys Arg Gln
                325                 330                 335

Val Asn Thr Arg Ala Leu Pro Pro Leu Val Ala Ser Cys Leu Arg Gly
            340                 345                 350

Asn Tyr Asp Asp Cys Gln Tyr Thr Thr Glu Ile Gly Ala Leu Ser Ser
        355                 360                 365

Arg Tyr Ile Thr Leu Asp Gly Gly Val Leu Val Asn Cys Lys Ser Ile
    370                 375                 380

Val Cys Arg Cys Leu Asn Pro Ser Lys Ile Ile Ser Gln Asn Thr Asn
385                 390                 395                 400

Ala Ala Val Thr Tyr Val Asp Ala Thr Ile Cys Lys Thr Ile Gln Leu
                405                 410                 415

Asp Asp Ile Gln Leu Gln Leu Glu Gly Ser Leu Ser Ser Val Tyr Ala
            420                 425                 430

Arg Asn Ile Ser Ile Glu Ile Ser Gln Val Thr Thr Ser Gly Ser Leu
```

```
        435                 440                 445

Asp Ile Ser Ser Glu Ile Gly Asn Ile Asn Asn Thr Val Asn Arg Val
    450                 455                 460

Glu Asp Leu Ile His Gln Ser Glu Glu Trp Leu Ala Lys Val Asn Pro
465                 470                 475                 480

His Ile Val Asn Asn Thr Thr Leu Ile Val Leu Cys Val Leu Ser Ala
                485                 490                 495

Leu Ala Val Ile Trp Leu Ala Val Leu Thr Ala Ile Ile Ile Tyr Leu
            500                 505                 510

Arg Thr Lys Leu Lys Thr Ile Ser Ala Leu Ala Val Thr Asn Thr Ile
        515                 520                 525

Gln Ser Asn Pro Tyr Val Asn Gln Thr Lys Arg Glu Ser Lys Phe
    530                 535                 540


<210> SEQ ID NO 61
<211> LENGTH: 1734
<212> TYPE: DNA
<213> ORGANISM: artificial sequence
<220> FEATURE:
<223> OTHER INFORMATION: HN gene of FJ215863

<400> SEQUENCE: 61

atgagtaaca ttgcatccag tttagaaaac attgtagagc aggatagtcg aaaaacaact     60

tggagagcca tctttagatg gtccgttctt cttatcacaa caggatgctt agccttatcc    120

attattagca tagttcaaat tggaaatttg aaaattcctt ctgtagggga tctggctgat    180

gaagtggtga caccccttgaa aaccactctg tctgatacac tcaggaatcc aattaaccag    240

ataaatgaca tatttaggat tgttgccctt gatattccat tgcaagtgac caatatccaa    300

aaagaccttg caagtcaatt taacatgttg atagatagtt taaatgctat caaattaggc    360

aacgggacca accttatcat acctacatca gacaaggagt atgcaggagg aattggaaac    420

cctgtattta ctgtcgatgc tggaggttct ataggattca aacagtttag cttaatagaa    480

catccgagct ttattgctgg acctacaacg acccgaggct gtacaagaat acccactttt    540

cacatgtcag aaagtcattg gtgctactca cacaacatca tcgctgctgg ctgtcaagat    600

gccagtgcat ccagtatgta tatctcaatg ggagttctcc atgtgtcctc atctggcact    660

cccatttttc ttactactgc aagtgagctg atagacgatg gagttaaccg taagtcatgc    720

agcattgtag caacccgatt tggctgtgac attttgtgca gtattgtcac agagaaggag    780

ggagatgatt actggtctga tactccgact ccaatgcgcc acggccgttt ttcattcaat    840

ggtagttttg tagaagccga actaccagtg tccagtatgt tctcgtcatt ctctgccaac    900

taccctgctg tgggatcagg cgaaattgta aaagatagaa tattattccc aatttacgga    960

ggtataaagc agacttcacc agagtttacc gaattagtga aatacggact ctttgtatca   1020

acacctacaa ctgtgtgcca gagtagctgg acttatgacc aggtaaaagc agcgtatagg   1080

ccagattaca tatcaggccg gttctgggca caagtgatac tcagctgcgc tcttgatgca   1140

gtcgacttat caagttgtat tgtaaagatt atgaatagca gcacagtgat gatggcagcg   1200

gaaggaagga taatgaagat agggattgat tacttttact atcagcggtc atcttcttgg   1260

tggccattgg catttgttac aaaactagac ccgcaagaat tggcagacac aaactcaata   1320

tggctgacca attccatacc aatcccgcaa tcaaagttcc ctcggccttc atattcagaa   1380

aattattgca caaagccagc agtttgccct gctacttgtg tcactggtgt gtactctgat   1440

atttggcccc tgacctcatc ttcatcactc ccgagcataa tttggatcgg ccagtacctt   1500
```

-continued

```
gatgctcctg ttagaaggac ttatcccaga tttggaattg caaatcagtc acactggtac   1560

ctccaagaag atattctacc cacttccacc gcaagtgcgt attcaaccac tacatgtttt   1620

aagaatactg ccaggaatag agtgttctgc gtcaccattg ccgaatttgc agatgggttg   1680

tttggagagt acaggataac acctcagttg tacgaattag tgagaaataa ttga         1734


<210> SEQ ID NO 62
<211> LENGTH: 577
<212> TYPE: PRT
<213> ORGANISM: artificial sequence
<220> FEATURE:
<223> OTHER INFORMATION: HN protein of AC048301

<400> SEQUENCE: 62

Met Ser Asn Ile Ala Ser Ser Leu Glu Asn Ile Val Glu Gln Asp Ser
1               5                   10                  15

Arg Lys Thr Thr Trp Arg Ala Ile Phe Arg Trp Ser Val Leu Leu Ile
            20                  25                  30

Thr Thr Gly Cys Leu Ala Leu Ser Ile Ile Ser Ile Val Gln Ile Gly
        35                  40                  45

Asn Leu Lys Ile Pro Ser Val Gly Asp Leu Ala Asp Glu Val Val Thr
    50                  55                  60

Pro Leu Lys Thr Thr Leu Ser Asp Thr Leu Arg Asn Pro Ile Asn Gln
65                  70                  75                  80

Ile Asn Asp Ile Phe Arg Ile Val Ala Leu Asp Ile Pro Leu Gln Val
                85                  90                  95

Thr Asn Ile Gln Lys Asp Leu Ala Ser Gln Phe Asn Met Leu Ile Asp
            100                 105                 110

Ser Leu Asn Ala Ile Lys Leu Gly Asn Gly Thr Asn Leu Ile Ile Pro
        115                 120                 125

Thr Ser Asp Lys Glu Tyr Ala Gly Gly Ile Gly Asn Pro Val Phe Thr
    130                 135                 140

Val Asp Ala Gly Gly Ser Ile Gly Phe Lys Gln Phe Ser Leu Ile Glu
145                 150                 155                 160

His Pro Ser Phe Ile Ala Gly Pro Thr Thr Thr Arg Gly Cys Thr Arg
                165                 170                 175

Ile Pro Thr Phe His Met Ser Glu Ser His Trp Cys Tyr Ser His Asn
            180                 185                 190

Ile Ile Ala Ala Gly Cys Gln Asp Ala Ser Ala Ser Ser Met Tyr Ile
        195                 200                 205

Ser Met Gly Val Leu His Val Ser Ser Ser Gly Thr Pro Ile Phe Leu
    210                 215                 220

Thr Thr Ala Ser Glu Leu Ile Asp Asp Gly Val Asn Arg Lys Ser Cys
225                 230                 235                 240

Ser Ile Val Ala Thr Arg Phe Gly Cys Asp Ile Leu Cys Ser Ile Val
                245                 250                 255

Thr Glu Lys Glu Gly Asp Asp Tyr Trp Ser Asp Thr Pro Thr Pro Met
            260                 265                 270

Arg His Gly Arg Phe Ser Phe Asn Gly Ser Phe Val Glu Ala Glu Leu
        275                 280                 285

Pro Val Ser Ser Met Phe Ser Ser Phe Ser Ala Asn Tyr Pro Ala Val
    290                 295                 300

Gly Ser Gly Glu Ile Val Lys Asp Arg Ile Leu Phe Pro Ile Tyr Gly
305                 310                 315                 320

Gly Ile Lys Gln Thr Ser Pro Glu Phe Thr Glu Leu Val Lys Tyr Gly
                325                 330                 335
```

```
Leu Phe Val Ser Thr Pro Thr Thr Val Cys Gln Ser Ser Trp Thr Tyr
            340                 345                 350

Asp Gln Val Lys Ala Ala Tyr Arg Pro Asp Tyr Ile Ser Gly Arg Phe
        355                 360                 365

Trp Ala Gln Val Ile Leu Ser Cys Ala Leu Asp Ala Val Asp Leu Ser
    370                 375                 380

Ser Cys Ile Val Lys Ile Met Asn Ser Ser Thr Val Met Met Ala Ala
385                 390                 395                 400

Glu Gly Arg Ile Met Lys Ile Gly Ile Asp Tyr Phe Tyr Tyr Gln Arg
                405                 410                 415

Ser Ser Ser Trp Trp Pro Leu Ala Phe Val Thr Lys Leu Asp Pro Gln
            420                 425                 430

Glu Leu Ala Asp Thr Asn Ser Ile Trp Leu Thr Asn Ser Ile Pro Ile
        435                 440                 445

Pro Gln Ser Lys Phe Pro Arg Pro Ser Tyr Ser Glu Asn Tyr Cys Thr
    450                 455                 460

Lys Pro Ala Val Cys Pro Ala Thr Cys Val Thr Gly Val Tyr Ser Asp
465                 470                 475                 480

Ile Trp Pro Leu Thr Ser Ser Ser Ser Leu Pro Ser Ile Ile Trp Ile
                485                 490                 495

Gly Gln Tyr Leu Asp Ala Pro Val Arg Arg Thr Tyr Pro Arg Phe Gly
            500                 505                 510

Ile Ala Asn Gln Ser His Trp Tyr Leu Gln Glu Asp Ile Leu Pro Thr
        515                 520                 525

Ser Thr Ala Ser Ala Tyr Ser Thr Thr Thr Cys Phe Lys Asn Thr Ala
    530                 535                 540

Arg Asn Arg Val Phe Cys Val Thr Ile Ala Glu Phe Ala Asp Gly Leu
545                 550                 555                 560

Phe Gly Glu Tyr Arg Ile Thr Pro Gln Leu Tyr Glu Leu Val Arg Asn
                565                 570                 575

Asn
```

<210> SEQ ID NO 63
<211> LENGTH: 6717
<212> TYPE: DNA
<213> ORGANISM: artificial sequence
<220> FEATURE:
<223> OTHER INFORMATION: L gene of FJ215863

<400> SEQUENCE: 63

```
atggatataa aacaagttga cctgataata caacccgagg ttcatctcga ttcacccatc      60

atattgaata aactggcact attatggcgc ttgagtggtt tacccatgcc tgcagaccta     120

cgacaaaaat ccgtagtgat gcacatcccg gaccacatct tagaaaaatc agaatatcgg     180

atcaagcacc gtctagggaa aatcaagagt gacataacac attactgcca gtattttaat     240

attaatttgg caaatcttga tccgataacc caccccaaaa gtttgtattg gttatccaga     300

ctaacaatag ctagtgctgg aacctttaga catatgaaag atagaatctt gtgtacagtt     360

ggctctgaat tcggacacaa aattcaagat ttattttcac tgttgagcca taaactagta     420

ggtaacggtg atttatttaa tcaaagtctc tcaggtacac gtttgactgc gagtccgtta     480

tcccctttat gcgatcaatt tgtctctgac atcaagtctg cagtcacgac accctggtca     540

gaagctcgtt ggtcttggct tcatatcaaa caaacaatga gatatctaat aaaacaatca     600

tgcactacaa attcggctca tttaacagaa atcataaaag aggaatgggg tttagtaggt     660
```

-continued

```
attactccag atcttgtcat tctttttgac agagtcaata atagtctgac tgcattaaca    720
tttgagatgg ttctaatgta ttcagatgta ttagaatccc gtgacaatat tgtgttagtg    780
gggcgactat ctacctttct acagccagta gttagtagac tggaggtgtt gtttgatcta    840
gtagattcat tggcaaaaat cttaggtgac acaatatatg agattattgc agtgttagag    900
agcttgtctt atgggtcagt tcaactacat gatgcaagtc actctcatgc agggtctttt    960
ttttcattta acatgaatga acttgataac acactatcaa agagggtaga tccgaaacac   1020
aagaacacca taatgagcat tataagacaa tgcttttcta atctagatgt tgatcaagct   1080
gcagagatgc tatgcctgat gagattattc ggacacccaa tgttaactgc accggatgca   1140
gcagccaaag tgaggaaagc aatgtgtgct ccaaaacttg ttgaacacga caccatcttg   1200
cagacattat ctttcttcaa ggggataatt ataaatgggt acagaagatc acactctggc   1260
ctgtggccca atgtagagcc gtcttcaatt tatgatgatg atctcagaca gctgtactta   1320
gagtcagcag agatttccca tcatttcatg cttaaaaact acaagagttt gagcatgata   1380
gaattcaaga agagcataga ctacgatctt catgatgact taagtacttt cttaaaggat   1440
agagcaattt gccggccgaa atcccagtgg gatgtcatat ttcgtaaatc tttacgcaga   1500
tctcatacgc agtcccagta tctagacgaa attaagagca accggttgct aattgatttt   1560
cttgattctg ctgaatttga ccctgaaaaa gaatttgcat atgtaaccac aatggattat   1620
ttgcacgata atgaattttg tgcttcatat tctctaaagg aaaaggagat caaaactact   1680
gggaggatat ttgcaaaaat gacacgcaat atgagaagtt gccaagtaat acttgaatct   1740
ttgttatcaa agcatatatg caagttcttc aaagagaatg gcgtttcgat ggagcaattg   1800
tcattgacca agagtctact tgcaatgtct caactctcac caaaagtctc gactttgcag   1860
gacactgcat cacgtcatgt aggcaactca aaatctcaga ttgcaaccag caacccatct   1920
cggcatcact cgacagccaa tcagatgtca ctctcaaatc gaaaaacggt tgtagcaact   1980
ttcttaacaa ctgacttgga aaaatactgc ctgcagtggc gatactcaac tattaaattg   2040
tttgcacaag ctctaaatca actctttggg attgatcacg gatttgaatg gatacattta   2100
agacttatga acagcacctt atttgttggc gatccttact cgcctcctga agatccaaca   2160
ctagaagata tagataaagc accaaatgat gatatcttca tagtttctcc aaggggaggc   2220
atagagggtt tatgtcagaa aatgtggacc atgatatcaa ttagtgctat acactgtgta   2280
gcagagaaaa ttggtgcacg agtggcagca atggtgcagg gtgataatca agtaatagct   2340
atcaccaaag aactattcag aggagaaaaa gcttgtgatg tcagagatga gttagacgag   2400
cttggtcaag tgtttttga tgagttcaag agacacaatt atgcaattgg acacaatctt   2460
aagctaaatg agacaataca aagccaatcc ttttttgtat attccaaacg aatattcttt   2520
gaagggcgat tgcttagtca agtcctcaaa aatgctgcca agttatgtat ggttgctgac   2580
catctaggtg aaaacactgt atcttcctgt agcaacctga gctcgacaat tgcccgcttg   2640
gtggaaaatg ggtttgagaa ggacactgct tttgtgttga acctagtcta catcatgact   2700
cagattcttt ttgatgagca ttactcgatt gtatgcgatc accatagtgt caaaagtttg   2760
attggatcaa aaaaccatcg gaatttattg tactcatctc taataccagg tcagctcggc   2820
ggtttcaact tcctcaatat aagtcggttg ttcactagga atataggtga cccagtaaca   2880
tgtagtctgt ctgatctcaa atgcttcata gccgcaggtc tccttccacc ctatgtccta   2940
aaaaatgtgg ttctgcgtga gcctggtcct gggacatggt tgacgttgtg ctctgatcct   3000
tacaccctta acataccata cacacagctt ccaaccacat atctcaaaaa gcacacccag   3060
```

-continued

```
cgatcattgc tttcacgtgc agtaaatcct ttattagccg gtgtacaagt gccaaatcag   3120
catgaggaag aagaggtgtt ggctcgcttt ctccttgatc gtgaatatgt gatgccccgc   3180
gttgctcatg taatactaga aacatcggtc cttggcaaac ggaaacaaat ccaaggctta   3240
attgatacaa ctccaaccat cattagaaca tctctagtta atctgccagt gtctagaaag   3300
aaatgcgaaa aaataatcaa ttactctctc aattatattg ctgagtgtca tgactcctta   3360
cttagccagg tctgcttcag tgataataag gaatacttgt ggtcaacctc cttaatatca   3420
gttgagacat gtagtgtgac aatcgcggac tatctgagag ctgtcagctg gtctaatata   3480
ttagggggaa gaaacatatc cggggtgact acacctgata ctattgaatt aattcaaggt   3540
tgtttaatag gtgaaaattc tagttgtact ctttgtgaat cgcatgatga cgcattcacg   3600
tggatgcact tgcctggccc actttacatc cctgaaccat cagttactaa ctctaaaatg   3660
cgtgtgccat atctgggttc gaaaacagag gagcgtaaaa cagcctcaat ggcagcaata   3720
aaaggaatgt cacatcacct gcgtgcagtc ttaagaggca catccgtatt tatttgggca   3780
tttggggata cagatattaa ttgggataat gcattgcaga ttgcccaatc acggtgtaac   3840
atcacattgg atcaaatgag attacttaca ccaattccta gcagttcaaa tattcaacat   3900
agactcgatg acggaatcag cacgcagaaa tttactcctg caagccttgc tcgaatcaca   3960
tccttcgttc acatctgtaa tgacagccag aggttagaga aggatggctc atctgttgac   4020
tcaaacttga tttaccagca aattatgtta cttggactca gcatctttga aacaatgtac   4080
tcaatggacc aaaagtgggt attcaataac cataccttgc atttgcacac tggacactcc   4140
tgttgtccaa gggaactaga cataagtttg gtgaacccgc cgagacatca gaccccggag   4200
ctgactagca caacaaccaa cccgttccta tatgatcagc tcccattaaa tcaagaaaac   4260
ttgacaacac ttgagattaa gacatttaaa ttcaatgagc tcaacattga tggtttagat   4320
tttggtgaag gaatacaatt attgagtcgt tgtactgcaa gattgatggc agaatgtatt   4380
ctagaggagg gaataggctc gtcagttaaa aatgaagcaa ttgtcaattt tgataattca   4440
gtcaattgga tttcagagtg cctaatgtgt gatattcgct cactttgtgt taatttaggt   4500
caagagatac tatgtagcct ggcataccaa atgtattact tgcgaatcag gggtagacgg   4560
gccattctta attacttgga cacaactttg caaaggatcc ctgtgataca attagccaac   4620
attgcactca ccatttcgca ccctgagata tttcgcagaa ttgtcaacac cgggatccat   4680
aaccagatta agggcccata tgtcgcaaca acggatttca tagctgcaag tagagatatc   4740
atattatcag gtgcaaggga gtatctatct tatttaagca gtgggcagga agactgttac   4800
acattcttca actgtcaaga tggggatctt actccaaaaa tggaacagta tcttgcaagg   4860
agggcatgcc ttttaacatt attgtataat actgggcacc agatccccgt tatccgatca   4920
ctgacaccaa tagagaagtg caaggtgctc acagaataca atcaacaaat tgagtatgca   4980
gatcaagagt ttagctctgt attaaaagtg gtcaatgcac tactacaaaa tcctaagata   5040
gatgcattag tttcaaatct ctacttcacc accagacgtg ttctatcaaa cctcagatca   5100
tgtgataagg ctagatcata tattgaatat ttgtacactg aggacttcgg agagaaagag   5160
gatacagtac aatatgacat catgacaaca aacgatatca tacttactca tggtctattc   5220
acacagatcg aaatatctta tcaagggaat agtctccata agttccttac tccggataac   5280
gcgcctggat ctttgatccc attctctatt tcaccaaatt cacttgcatg tgatcctctt   5340
catcacttgc tcaagtcggt cggtacatca agcacaagtt ggtacaagta tgcaatcgcc   5400
tatgcagtgt ctgaaaagag gtcagctcga ttaggaggga gcttgtacat tggtgaaggg   5460
```

```
agcggaagtg tgatgacttt actcgagtat cttgagccat ctgttgacat attttacaat   5520

tcactcttct caaatggtat gaacccacca caacgaaatt atgggcttat gccactacaa   5580

tttgtgaatt cggtggttta taagaactta acggctaaat cagaatgtaa gctagggttt   5640

gtccagcaat ttaaaccgtt gtggagagac atagacattg agactaatgt tacagatcca   5700

tcatttgtca attttgcatt gaatgaaatc ccaatgcaat cattaaaacg agtaaattgt   5760

gatgtggaat ttgaccgtgg tatgccgatt gaacgggtta ttcagggtta tacccatatc   5820

ttacttgttg ctacttacgg attacagcaa gattcaatac tgtgggtgaa ggtatatagg   5880

acatctgaaa aagtatttca attcttactg agtgccatga tcatgatctt tggttatgtc   5940

aaaatccaca ggaatggtta tatgtcgaca aaggatgaag agtacatatt gatgtctgac   6000

tgcaaggaac ctgtaaacta tacagctgtc cctaacattc ttacacgtgt aagtgattta   6060

gtgtcgaaga atctgagtct tatccatcca gaagacctca gaaaagtaag gtgtgaaaca   6120

gattccctga atttgaagtg caatcatatt tatgagaaaa taattgccag aaaaattcca   6180

ttacaggtat catcaactga ttctttgctc ctccaattag gcggtgttat caactcggtg   6240

ggctcaactg atcctagaga ggttgcaaca ttatcttcta ttgagtgtat ggactatgtt   6300

gtctcatcaa ttgatttggc tatattggag gcaaatattg taatctcaga gagtgctggt   6360

cttgacctcg ctttaatgtt aggcccattc aacttgaata agcttaagaa aattgataca   6420

atccttaagt caagcaccta tcagctaatc ccgtactggt tgcgctatga gtactctatt   6480

aatccgagat ctttgtcatt tctaatcact aaattacaac aatgccgaat ttcatggtca   6540

gatatgatca cgatttctga atttcgtaag aaatccaagc ggcctatatt tatcaaacga   6600

gtaataggga atcaacagct aaaatcattc tttaatgaaa gctcaagtat tgttttgact   6660

cgggctgaag ttaaagtctg tataaagttc ctcggtgcaa tcatcaagtt gaaataa      6717
```

```
<210> SEQ ID NO 64
<211> LENGTH: 2238
<212> TYPE: PRT
<213> ORGANISM: artificial sequence
<220> FEATURE:
<223> OTHER INFORMATION: L protein of AC048302

<400> SEQUENCE: 64

Met Asp Ile Lys Gln Val Asp Leu Ile Ile Gln Pro Glu Val His Leu
1               5                   10                  15

Asp Ser Pro Ile Ile Leu Asn Lys Leu Ala Leu Leu Trp Arg Leu Ser
            20                  25                  30

Gly Leu Pro Met Pro Ala Asp Leu Arg Gln Lys Ser Val Val Met His
        35                  40                  45

Ile Pro Asp His Ile Leu Glu Lys Ser Glu Tyr Arg Ile Lys His Arg
    50                  55                  60

Leu Gly Lys Ile Lys Ser Asp Ile Thr His Tyr Cys Gln Tyr Phe Asn
65                  70                  75                  80

Ile Asn Leu Ala Asn Leu Asp Pro Ile Thr His Pro Lys Ser Leu Tyr
                85                  90                  95

Trp Leu Ser Arg Leu Thr Ile Ala Ser Ala Gly Thr Phe Arg His Met
            100                 105                 110

Lys Asp Arg Ile Leu Cys Thr Val Gly Ser Glu Phe Gly His Lys Ile
        115                 120                 125

Gln Asp Leu Phe Ser Leu Leu Ser His Lys Leu Val Gly Asn Gly Asp
    130                 135                 140

Leu Phe Asn Gln Ser Leu Ser Gly Thr Arg Leu Thr Ala Ser Pro Leu
```

```
145                 150                 155                 160

Ser Pro Leu Cys Asp Gln Phe Val Ser Asp Ile Lys Ser Ala Val Thr
                165                 170                 175

Thr Pro Trp Ser Glu Ala Arg Trp Ser Trp Leu His Ile Lys Gln Thr
            180                 185                 190

Met Arg Tyr Leu Ile Lys Gln Ser Cys Thr Thr Asn Ser Ala His Leu
        195                 200                 205

Thr Glu Ile Ile Lys Glu Glu Trp Gly Leu Val Gly Ile Thr Pro Asp
    210                 215                 220

Leu Val Ile Leu Phe Asp Arg Val Asn Asn Ser Leu Thr Ala Leu Thr
225                 230                 235                 240

Phe Glu Met Val Leu Met Tyr Ser Asp Val Leu Glu Ser Arg Asp Asn
                245                 250                 255

Ile Val Leu Val Gly Arg Leu Ser Thr Phe Leu Gln Pro Val Val Ser
            260                 265                 270

Arg Leu Glu Val Leu Phe Asp Leu Val Asp Ser Leu Ala Lys Ile Leu
        275                 280                 285

Gly Asp Thr Ile Tyr Glu Ile Ile Ala Val Leu Glu Ser Leu Ser Tyr
    290                 295                 300

Gly Ser Val Gln Leu His Asp Ala Ser His Ser His Ala Gly Ser Phe
305                 310                 315                 320

Phe Ser Phe Asn Met Asn Glu Leu Asp Asn Thr Leu Ser Lys Arg Val
                325                 330                 335

Asp Pro Lys His Lys Asn Thr Ile Met Ser Ile Ile Arg Gln Cys Phe
            340                 345                 350

Ser Asn Leu Asp Val Asp Gln Ala Ala Glu Met Leu Cys Leu Met Arg
        355                 360                 365

Leu Phe Gly His Pro Met Leu Thr Ala Pro Asp Ala Ala Ala Lys Val
    370                 375                 380

Arg Lys Ala Met Cys Ala Pro Lys Leu Val Glu His Asp Thr Ile Leu
385                 390                 395                 400

Gln Thr Leu Ser Phe Phe Lys Gly Ile Ile Ile Asn Gly Tyr Arg Arg
                405                 410                 415

Ser His Ser Gly Leu Trp Pro Asn Val Glu Pro Ser Ser Ile Tyr Asp
            420                 425                 430

Asp Asp Leu Arg Gln Leu Tyr Leu Glu Ser Ala Glu Ile Ser His His
        435                 440                 445

Phe Met Leu Lys Asn Tyr Lys Ser Leu Ser Met Ile Glu Phe Lys Lys
    450                 455                 460

Ser Ile Asp Tyr Asp Leu His Asp Asp Leu Ser Thr Phe Leu Lys Asp
465                 470                 475                 480

Arg Ala Ile Cys Arg Pro Lys Ser Gln Trp Asp Val Ile Phe Arg Lys
                485                 490                 495

Ser Leu Arg Arg Ser His Thr Gln Ser Gln Tyr Leu Asp Glu Ile Lys
            500                 505                 510

Ser Asn Arg Leu Leu Ile Asp Phe Leu Asp Ser Ala Glu Phe Asp Pro
        515                 520                 525

Glu Lys Glu Phe Ala Tyr Val Thr Thr Met Asp Tyr Leu His Asp Asn
    530                 535                 540

Glu Phe Cys Ala Ser Tyr Ser Leu Lys Glu Lys Glu Ile Lys Thr Thr
545                 550                 555                 560

Gly Arg Ile Phe Ala Lys Met Thr Arg Asn Met Arg Ser Cys Gln Val
                565                 570                 575
```

```
Ile Leu Glu Ser Leu Leu Ser Lys His Ile Cys Lys Phe Phe Lys Glu
            580                 585                 590

Asn Gly Val Ser Met Glu Gln Leu Ser Leu Thr Lys Ser Leu Leu Ala
        595                 600                 605

Met Ser Gln Leu Ser Pro Lys Val Ser Thr Leu Gln Asp Thr Ala Ser
    610                 615                 620

Arg His Val Gly Asn Ser Lys Ser Gln Ile Ala Thr Ser Asn Pro Ser
625                 630                 635                 640

Arg His His Ser Thr Ala Asn Gln Met Ser Leu Ser Asn Arg Lys Thr
                645                 650                 655

Val Val Ala Thr Phe Leu Thr Thr Asp Leu Glu Lys Tyr Cys Leu Gln
            660                 665                 670

Trp Arg Tyr Ser Thr Ile Lys Leu Phe Ala Gln Ala Leu Asn Gln Leu
        675                 680                 685

Phe Gly Ile Asp His Gly Phe Glu Trp Ile His Leu Arg Leu Met Asn
    690                 695                 700

Ser Thr Leu Phe Val Gly Asp Pro Tyr Ser Pro Pro Glu Asp Pro Thr
705                 710                 715                 720

Leu Glu Asp Ile Asp Lys Ala Pro Asn Asp Asp Ile Phe Ile Val Ser
                725                 730                 735

Pro Arg Gly Gly Ile Glu Gly Leu Cys Gln Lys Met Trp Thr Met Ile
            740                 745                 750

Ser Ile Ser Ala Ile His Cys Val Ala Glu Lys Ile Gly Ala Arg Val
        755                 760                 765

Ala Ala Met Val Gln Gly Asp Asn Gln Val Ile Ala Ile Thr Lys Glu
    770                 775                 780

Leu Phe Arg Gly Glu Lys Ala Cys Asp Val Arg Asp Glu Leu Asp Glu
785                 790                 795                 800

Leu Gly Gln Val Phe Phe Asp Glu Phe Lys Arg His Asn Tyr Ala Ile
                805                 810                 815

Gly His Asn Leu Lys Leu Asn Glu Thr Ile Gln Ser Gln Ser Phe Phe
            820                 825                 830

Val Tyr Ser Lys Arg Ile Phe Phe Glu Gly Arg Leu Leu Ser Gln Val
        835                 840                 845

Leu Lys Asn Ala Ala Lys Leu Cys Met Val Ala Asp His Leu Gly Glu
    850                 855                 860

Asn Thr Val Ser Ser Cys Ser Asn Leu Ser Ser Thr Ile Ala Arg Leu
865                 870                 875                 880

Val Glu Asn Gly Phe Glu Lys Asp Thr Ala Phe Val Leu Asn Leu Val
                885                 890                 895

Tyr Ile Met Thr Gln Ile Leu Phe Asp Glu His Tyr Ser Ile Val Cys
            900                 905                 910

Asp His His Ser Val Lys Ser Leu Ile Gly Ser Lys Asn His Arg Asn
        915                 920                 925

Leu Leu Tyr Ser Ser Leu Ile Pro Gly Gln Leu Gly Gly Phe Asn Phe
    930                 935                 940

Leu Asn Ile Ser Arg Leu Phe Thr Arg Asn Ile Gly Asp Pro Val Thr
945                 950                 955                 960

Cys Ser Leu Ser Asp Leu Lys Cys Phe Ile Ala Ala Gly Leu Leu Pro
                965                 970                 975

Pro Tyr Val Leu Lys Asn Val Val Leu Arg Glu Pro Gly Pro Gly Thr
            980                 985                 990

Trp Leu Thr Leu Cys Ser Asp Pro  Tyr Thr Leu Asn Ile  Pro Tyr Thr
        995                 1000                1005
```

-continued

Gln Leu Pro Thr Thr Tyr Leu Lys Lys His Thr Gln Arg Ser Leu
1010 1015 1020

Leu Ser Arg Ala Val Asn Pro Leu Leu Ala Gly Val Gln Val Pro
1025 1030 1035

Asn Gln His Glu Glu Glu Glu Val Leu Ala Arg Phe Leu Leu Asp
1040 1045 1050

Arg Glu Tyr Val Met Pro Arg Val Ala His Val Ile Leu Glu Thr
1055 1060 1065

Ser Val Leu Gly Lys Arg Lys Gln Ile Gln Gly Leu Ile Asp Thr
1070 1075 1080

Thr Pro Thr Ile Ile Arg Thr Ser Leu Val Asn Leu Pro Val Ser
1085 1090 1095

Arg Lys Lys Cys Glu Lys Ile Ile Asn Tyr Ser Leu Asn Tyr Ile
1100 1105 1110

Ala Glu Cys His Asp Ser Leu Leu Ser Gln Val Cys Phe Ser Asp
1115 1120 1125

Asn Lys Glu Tyr Leu Trp Ser Thr Ser Leu Ile Ser Val Glu Thr
1130 1135 1140

Cys Ser Val Thr Ile Ala Asp Tyr Leu Arg Ala Val Ser Trp Ser
1145 1150 1155

Asn Ile Leu Gly Gly Arg Asn Ile Ser Gly Val Thr Thr Pro Asp
1160 1165 1170

Thr Ile Glu Leu Ile Gln Gly Cys Leu Ile Gly Glu Asn Ser Ser
1175 1180 1185

Cys Thr Leu Cys Glu Ser His Asp Asp Ala Phe Thr Trp Met His
1190 1195 1200

Leu Pro Gly Pro Leu Tyr Ile Pro Glu Pro Ser Val Thr Asn Ser
1205 1210 1215

Lys Met Arg Val Pro Tyr Leu Gly Ser Lys Thr Glu Glu Arg Lys
1220 1225 1230

Thr Ala Ser Met Ala Ala Ile Lys Gly Met Ser His His Leu Arg
1235 1240 1245

Ala Val Leu Arg Gly Thr Ser Val Phe Ile Trp Ala Phe Gly Asp
1250 1255 1260

Thr Asp Ile Asn Trp Asp Asn Ala Leu Gln Ile Ala Gln Ser Arg
1265 1270 1275

Cys Asn Ile Thr Leu Asp Gln Met Arg Leu Leu Thr Pro Ile Pro
1280 1285 1290

Ser Ser Ser Asn Ile Gln His Arg Leu Asp Asp Gly Ile Ser Thr
1295 1300 1305

Gln Lys Phe Thr Pro Ala Ser Leu Ala Arg Ile Thr Ser Phe Val
1310 1315 1320

His Ile Cys Asn Asp Ser Gln Arg Leu Glu Lys Asp Gly Ser Ser
1325 1330 1335

Val Asp Ser Asn Leu Ile Tyr Gln Gln Ile Met Leu Leu Gly Leu
1340 1345 1350

Ser Ile Phe Glu Thr Met Tyr Ser Met Asp Gln Lys Trp Val Phe
1355 1360 1365

Asn Asn His Thr Leu His Leu His Thr Gly His Ser Cys Cys Pro
1370 1375 1380

Arg Glu Leu Asp Ile Ser Leu Val Asn Pro Pro Arg His Gln Thr
1385 1390 1395

Pro Glu Leu Thr Ser Thr Thr Thr Asn Pro Phe Leu Tyr Asp Gln

```
    1400                1405                1410

Leu Pro  Leu Asn Gln Glu Asn  Leu Thr Thr Leu Glu  Ile Lys Thr
    1415                1420                1425

Phe Lys  Phe Asn Glu Leu Asn  Ile Asp Gly Leu Asp  Phe Gly Glu
    1430                1435                1440

Gly Ile  Gln Leu Leu Ser Arg  Cys Thr Ala Arg Leu  Met Ala Glu
    1445                1450                1455

Cys Ile  Leu Glu Glu Gly Ile  Gly Ser Ser Val Lys  Asn Glu Ala
    1460                1465                1470

Ile Val  Asn Phe Asp Asn Ser  Val Asn Trp Ile Ser  Glu Cys Leu
    1475                1480                1485

Met Cys  Asp Ile Arg Ser Leu  Cys Val Asn Leu Gly  Gln Glu Ile
    1490                1495                1500

Leu Cys  Ser Leu Ala Tyr Gln  Met Tyr Tyr Leu Arg  Ile Arg Gly
    1505                1510                1515

Arg Arg  Ala Ile Leu Asn Tyr  Leu Asp Thr Thr Leu  Gln Arg Ile
    1520                1525                1530

Pro Val  Ile Gln Leu Ala Asn  Ile Ala Leu Thr Ile  Ser His Pro
    1535                1540                1545

Glu Ile  Phe Arg Arg Ile Val  Asn Thr Gly Ile His  Asn Gln Ile
    1550                1555                1560

Lys Gly  Pro Tyr Val Ala Thr  Thr Asp Phe Ile Ala  Ala Ser Arg
    1565                1570                1575

Asp Ile  Ile Leu Ser Gly Ala  Arg Glu Tyr Leu Ser  Tyr Leu Ser
    1580                1585                1590

Ser Gly  Gln Glu Asp Cys Tyr  Thr Phe Phe Asn Cys  Gln Asp Gly
    1595                1600                1605

Asp Leu  Thr Pro Lys Met Glu  Gln Tyr Leu Ala Arg  Arg Ala Cys
    1610                1615                1620

Leu Leu  Thr Leu Leu Tyr Asn  Thr Gly His Gln Ile  Pro Val Ile
    1625                1630                1635

Arg Ser  Leu Thr Pro Ile Glu  Lys Cys Lys Val Leu  Thr Glu Tyr
    1640                1645                1650

Asn Gln  Gln Ile Glu Tyr Ala  Asp Gln Glu Phe Ser  Ser Val Leu
    1655                1660                1665

Lys Val  Val Asn Ala Leu Leu  Gln Asn Pro Lys Ile  Asp Ala Leu
    1670                1675                1680

Val Ser  Asn Leu Tyr Phe Thr  Thr Arg Arg Val Leu  Ser Asn Leu
    1685                1690                1695

Arg Ser  Cys Asp Lys Ala Arg  Ser Tyr Ile Glu Tyr  Leu Tyr Thr
    1700                1705                1710

Glu Asp  Phe Gly Glu Lys Glu  Asp Thr Val Gln Tyr  Asp Ile Met
    1715                1720                1725

Thr Thr  Asn Asp Ile Ile Leu  Thr His Gly Leu Phe  Thr Gln Ile
    1730                1735                1740

Glu Ile  Ser Tyr Gln Gly Asn  Ser Leu His Lys Phe  Leu Thr Pro
    1745                1750                1755

Asp Asn  Ala Pro Gly Ser Leu  Ile Pro Phe Ser Ile  Ser Pro Asn
    1760                1765                1770

Ser Leu  Ala Cys Asp Pro Leu  His His Leu Leu Lys  Ser Val Gly
    1775                1780                1785

Thr Ser  Ser Thr Ser Trp Tyr  Lys Tyr Ala Ile Ala  Tyr Ala Val
    1790                1795                1800
```

```
Ser Glu  Lys Arg Ser Ala Arg  Leu Gly Gly Ser Leu  Tyr Ile Gly
    1805                 1810                 1815

Glu Gly  Ser Gly Ser Val Met  Thr Leu Leu Glu Tyr  Leu Glu Pro
    1820                 1825                 1830

Ser Val  Asp Ile Phe Tyr Asn  Ser Leu Phe Ser Asn  Gly Met Asn
    1835                 1840                 1845

Pro Pro  Gln Arg Asn Tyr Gly  Leu Met Pro Leu Gln  Phe Val Asn
    1850                 1855                 1860

Ser Val  Val Tyr Lys Asn Leu  Thr Ala Lys Ser Glu  Cys Lys Leu
    1865                 1870                 1875

Gly Phe  Val Gln Gln Phe Lys  Pro Leu Trp Arg Asp  Ile Asp Ile
    1880                 1885                 1890

Glu Thr  Asn Val Thr Asp Pro  Ser Phe Val Asn Phe  Ala Leu Asn
    1895                 1900                 1905

Glu Ile  Pro Met Gln Ser Leu  Lys Arg Val Asn Cys  Asp Val Glu
    1910                 1915                 1920

Phe Asp  Arg Gly Met Pro Ile  Glu Arg Val Ile Gln  Gly Tyr Thr
    1925                 1930                 1935

His Ile  Leu Leu Val Ala Thr  Tyr Gly Leu Gln Gln  Asp Ser Ile
    1940                 1945                 1950

Leu Trp  Val Lys Val Tyr Arg  Thr Ser Glu Lys Val  Phe Gln Phe
    1955                 1960                 1965

Leu Leu  Ser Ala Met Ile Met  Ile Phe Gly Tyr Val  Lys Ile His
    1970                 1975                 1980

Arg Asn  Gly Tyr Met Ser Thr  Lys Asp Glu Glu Tyr  Ile Leu Met
    1985                 1990                 1995

Ser Asp  Cys Lys Glu Pro Val  Asn Tyr Thr Ala Val  Pro Asn Ile
    2000                 2005                 2010

Leu Thr  Arg Val Ser Asp Leu  Val Ser Lys Asn Leu  Ser Leu Ile
    2015                 2020                 2025

His Pro  Glu Asp Leu Arg Lys  Val Arg Cys Glu Thr  Asp Ser Leu
    2030                 2035                 2040

Asn Leu  Lys Cys Asn His Ile  Tyr Glu Lys Ile Ile  Ala Arg Lys
    2045                 2050                 2055

Ile Pro  Leu Gln Val Ser Ser  Thr Asp Ser Leu Leu  Leu Gln Leu
    2060                 2065                 2070

Gly Gly  Val Ile Asn Ser Val  Gly Ser Thr Asp Pro  Arg Glu Val
    2075                 2080                 2085

Ala Thr  Leu Ser Ser Ile Glu  Cys Met Asp Tyr Val  Val Ser Ser
    2090                 2095                 2100

Ile Asp  Leu Ala Ile Leu Glu  Ala Asn Ile Val Ile  Ser Glu Ser
    2105                 2110                 2115

Ala Gly  Leu Asp Leu Ala Leu  Met Leu Gly Pro Phe  Asn Leu Asn
    2120                 2125                 2130

Lys Leu  Lys Lys Ile Asp Thr  Ile Leu Lys Ser Ser  Thr Tyr Gln
    2135                 2140                 2145

Leu Ile  Pro Tyr Trp Leu Arg  Tyr Glu Tyr Ser Ile  Asn Pro Arg
    2150                 2155                 2160

Ser Leu  Ser Phe Leu Ile Thr  Lys Leu Gln Gln Cys  Arg Ile Ser
    2165                 2170                 2175

Trp Ser  Asp Met Ile Thr Ile  Ser Glu Phe Arg Lys  Lys Ser Lys
    2180                 2185                 2190

Arg Pro  Ile Phe Ile Lys Arg  Val Ile Gly Asn Gln  Gln Leu Lys
    2195                 2200                 2205
```

```
Ser Phe Phe Asn Glu Ser Ser Ser Ile Val Leu Thr Arg Ala Glu
    2210                2215                2220

Val Lys Val Cys Ile Lys Phe Leu Gly Ala Ile Ile Lys Leu Lys
    2225                2230                2235
```

<210> SEQ ID NO 65
<211> LENGTH: 1386
<212> TYPE: DNA
<213> ORGANISM: artificial sequence
<220> FEATURE:
<223> OTHER INFORMATION: NP gene of FJ215864

<400> SEQUENCE: 65

```
atgtcatctg tattcaatga atatcaggca cttcaagaac aacttgtaaa gccggctgtc     60

aggagacctg atgttgcctc aacaggttta ctcagggcgg aaatacctgt ctgtgttaca    120

ttgtctcaag accccggtga gagatggagc cttgcttgcc ttaatatccg atggcttgtg    180

agtgattcat caaccacacc aatgaagcag ggagcaatat tgtcactgct gagtctacat    240

tcagacaata tgcgagctca cgcaacatta gcagcaaggt ctgcagatgc ttcactcacc    300

atacttgagg tagatgaagt agatattggc aactccctaa tcaaattcaa cgctagaagt    360

ggtgtatctg ataaacgatc aaatcaattg cttgcaattg cggatgacat ccccaaaagt    420

tgcagtaatg ggcatccatt tcttgacaca gacattgaga ccagagaccc gctcgatcta    480

tcagagacca tagaccgcct gcagggtatt gcagctcaga tatgggtgtc agccataaag    540

agcatgacag cgcctgacac cgcatcagag tcagaaagta agaggctggc caaataccaa    600

caacaaggcc gactggttaa gcaagtactt ttgcattctg tagtcaggac agaatttatg    660

agagttattc ggggcagctt ggtactgcgc cagtttatgg ttagcgagtg caagagggct    720

tcagccatgg gcggagacac atctaggtac tatgctatgg tgggtgacat cagtctgtac    780

atcaagaatg caggattgac tgcatttttc ctcaccctga agttcggggt tggtacccag    840

tatccaacct tagcaatgag tgttttctcc agtgacctta aaagacttgc tgcactcatc    900

aggctgtaca aaaccaaggg agacaatgca ccatacatgg cattcctgga ggactccgat    960

atgggaaatt ttgctccagc aaattatagc acaatgtact cttatgccat gggcattggg   1020

acgattctgg aagcatctgt atctcgatac cagtatgcta gagactttac cagtgagaat   1080

tatttccgtc ttggagttga gacagcccaa agccagcagg gagcgtttga cgagagaaca   1140

gcccgagaga tgggcttgac tgaggaatcc aaacagcagg ttagatcact gctaatgtca   1200

gtagacatgg gtcccagttc agttcgcgag ccatcccgcc ctgcattcat cagtcaagaa   1260

gaaaataggc agcctgccca gaattcttca gatactcagg gtcagaccaa gccagtcccg   1320

aatcaacccg caccaagggc cgacccagat gacattgatc catacgagaa cgggctagaa   1380

tggtaa                                                              1386
```

<210> SEQ ID NO 66
<211> LENGTH: 461
<212> TYPE: PRT
<213> ORGANISM: artificial sequence
<220> FEATURE:
<223> OTHER INFORMATION: NP protein of ACO48303

<400> SEQUENCE: 66

```
Met Ser Ser Val Phe Asn Glu Tyr Gln Ala Leu Gln Glu Gln Leu Val
1               5                   10                  15

Lys Pro Ala Val Arg Arg Pro Asp Val Ala Ser Thr Gly Leu Leu Arg
            20                  25                  30
```

```
Ala Glu Ile Pro Val Cys Val Thr Leu Ser Gln Asp Pro Gly Glu Arg
        35                  40                  45

Trp Ser Leu Ala Cys Leu Asn Ile Arg Trp Leu Val Ser Asp Ser Ser
    50                  55                  60

Thr Thr Pro Met Lys Gln Gly Ala Ile Leu Ser Leu Leu Ser Leu His
65                  70                  75                  80

Ser Asp Asn Met Arg Ala His Ala Thr Leu Ala Ala Arg Ser Ala Asp
                85                  90                  95

Ala Ser Leu Thr Ile Leu Glu Val Asp Glu Val Asp Ile Gly Asn Ser
            100                 105                 110

Leu Ile Lys Phe Asn Ala Arg Ser Gly Val Ser Asp Lys Arg Ser Asn
        115                 120                 125

Gln Leu Leu Ala Ile Ala Asp Asp Ile Pro Lys Ser Cys Ser Asn Gly
    130                 135                 140

His Pro Phe Leu Asp Thr Asp Ile Glu Thr Arg Asp Pro Leu Asp Leu
145                 150                 155                 160

Ser Glu Thr Ile Asp Arg Leu Gln Gly Ile Ala Ala Gln Ile Trp Val
                165                 170                 175

Ser Ala Ile Lys Ser Met Thr Ala Pro Asp Thr Ala Ser Glu Ser Glu
            180                 185                 190

Ser Lys Arg Leu Ala Lys Tyr Gln Gln Gln Gly Arg Leu Val Lys Gln
        195                 200                 205

Val Leu Leu His Ser Val Val Arg Thr Glu Phe Met Arg Val Ile Arg
    210                 215                 220

Gly Ser Leu Val Leu Arg Gln Phe Met Val Ser Glu Cys Lys Arg Ala
225                 230                 235                 240

Ser Ala Met Gly Gly Asp Thr Ser Arg Tyr Tyr Ala Met Val Gly Asp
                245                 250                 255

Ile Ser Leu Tyr Ile Lys Asn Ala Gly Leu Thr Ala Phe Phe Leu Thr
            260                 265                 270

Leu Lys Phe Gly Val Gly Thr Gln Tyr Pro Thr Leu Ala Met Ser Val
        275                 280                 285

Phe Ser Ser Asp Leu Lys Arg Leu Ala Ala Leu Ile Arg Leu Tyr Lys
    290                 295                 300

Thr Lys Gly Asp Asn Ala Pro Tyr Met Ala Phe Leu Glu Asp Ser Asp
305                 310                 315                 320

Met Gly Asn Phe Ala Pro Ala Asn Tyr Ser Thr Met Tyr Ser Tyr Ala
                325                 330                 335

Met Gly Ile Gly Thr Ile Leu Glu Ala Ser Val Ser Arg Tyr Gln Tyr
            340                 345                 350

Ala Arg Asp Phe Thr Ser Glu Asn Tyr Phe Arg Leu Gly Val Glu Thr
        355                 360                 365

Ala Gln Ser Gln Gln Gly Ala Phe Asp Glu Arg Thr Ala Arg Glu Met
    370                 375                 380

Gly Leu Thr Glu Glu Ser Lys Gln Gln Val Arg Ser Leu Leu Met Ser
385                 390                 395                 400

Val Asp Met Gly Pro Ser Ser Val Arg Glu Pro Ser Arg Pro Ala Phe
                405                 410                 415

Ile Ser Gln Glu Glu Asn Arg Gln Pro Ala Gln Asn Ser Ser Asp Thr
            420                 425                 430

Gln Gly Gln Thr Lys Pro Val Pro Asn Gln Pro Ala Pro Arg Ala Asp
        435                 440                 445

Pro Asp Asp Ile Asp Pro Tyr Glu Asn Gly Leu Glu Trp
```

450 455 460

<210> SEQ ID NO 67
<211> LENGTH: 1218
<212> TYPE: DNA
<213> ORGANISM: artificial sequence
<220> FEATURE:
<223> OTHER INFORMATION: P gene of FJ215864

<400> SEQUENCE: 67
atggacttcg ccaatgatga agaaattgca gaacttctga acctcagcac cactgtaatc 60
aaggagattc agaaatctga actcaagcct ccccaaacca ctgggcgacc acctgtcagt 120
caagggaaca caagaaatct aactgatcta tgggaaaagg agactgcaag tcagaacaag 180
acatcggctc aatctccaca aaccacacaa gttcagtctg atggaaatga ggaggaagaa 240
atcaaatcag agtcaattga tggccacatc agtggaactg ttaatcaatt agagcaagtc 300
ccagaacaaa accagagcag atcttcacca ggtgatgatc tcgacagagc tctcaacaag 360
cttgaaggga gaatcaactc aatcagctca atggataaag aaattaaaaa gggccctcgc 420
atccagaatc tccctgggtc ccaagcagca actcaacagg cgacccaccc attggcaggg 480
gacaccccga acatgcaagc acggacaaaa cccctgacca agccacatca agaggcaatc 540
aatcctggca accaggacac aggagagaat attcatttac caccttccat ggcaccacca 600
gagtcattag ttggtgcaat ccgcaatgta ccccaattcg tgccagacca atctatgacg 660
aatgtagatg cggggagtgt ccaactacat gcatcatgtg cagagatgat aagtagaatg 720
tttgtagaag ttatatctaa gcttgataaa ctcgagtcga gactgaatga tatagcaaaa 780
gttgtaaaca ccaccccct tatcaggaat gatattaacc aacttaaggc cacaactgca 840
ctgatgtcca accaaattgc ttccatacaa attcttgacc cagggaatgc aggggtgagg 900
tccctctctg aaatgagatc tgtgacgaag aaagctgctg ttgtaattgc aggatttgga 960
gacgacccaa ctcaaattat tgaagaaggt atcatggcca aagatgctct tggaaaacct 1020
gtgcctccaa catctgttat cgcagccaaa gctcagactt cttccggtgt gagtaagggt 1080
gaaatagaag gattgattgc attggtggaa acattagttg acaatgacaa gaaggcagcg 1140
aaactgatta aaatgattga tcaagttaaa tcccacgccg attacgcccg agtcaagcag 1200
gcaatatata atgcataa 1218

<210> SEQ ID NO 68
<211> LENGTH: 405
<212> TYPE: PRT
<213> ORGANISM: artificial sequence
<220> FEATURE:
<223> OTHER INFORMATION: P protein of ACO48304

<400> SEQUENCE: 68

Met Asp Phe Ala Asn Asp Glu Glu Ile Ala Glu Leu Leu Asn Leu Ser
1 5 10 15

Thr Thr Val Ile Lys Glu Ile Gln Lys Ser Glu Leu Lys Pro Pro Gln
20 25 30

Thr Thr Gly Arg Pro Pro Val Ser Gln Gly Asn Thr Arg Asn Leu Thr
35 40 45

Asp Leu Trp Glu Lys Glu Thr Ala Ser Gln Asn Lys Thr Ser Ala Gln
50 55 60

Ser Pro Gln Thr Thr Gln Val Gln Ser Asp Gly Asn Glu Glu Glu Glu
65 70 75 80

Ile Lys Ser Glu Ser Ile Asp Gly His Ile Ser Gly Thr Val Asn Gln

```
                85                  90                  95

Leu Glu Gln Val Pro Glu Gln Asn Gln Ser Arg Ser Ser Pro Gly Asp
            100                 105                 110

Asp Leu Asp Arg Ala Leu Asn Lys Leu Glu Gly Arg Ile Asn Ser Ile
        115                 120                 125

Ser Ser Met Asp Lys Glu Ile Lys Lys Gly Pro Arg Ile Gln Asn Leu
    130                 135                 140

Pro Gly Ser Gln Ala Ala Thr Gln Gln Ala Thr His Pro Leu Ala Gly
145                 150                 155                 160

Asp Thr Pro Asn Met Gln Ala Arg Thr Lys Pro Leu Thr Lys Pro His
                165                 170                 175

Gln Glu Ala Ile Asn Pro Gly Asn Gln Asp Thr Gly Glu Asn Ile His
            180                 185                 190

Leu Pro Pro Ser Met Ala Pro Pro Glu Ser Leu Val Gly Ala Ile Arg
        195                 200                 205

Asn Val Pro Gln Phe Val Pro Asp Gln Ser Met Thr Asn Val Asp Ala
    210                 215                 220

Gly Ser Val Gln Leu His Ala Ser Cys Ala Glu Met Ile Ser Arg Met
225                 230                 235                 240

Phe Val Glu Val Ile Ser Lys Leu Asp Lys Leu Glu Ser Arg Leu Asn
                245                 250                 255

Asp Ile Ala Lys Val Val Asn Thr Thr Pro Leu Ile Arg Asn Asp Ile
            260                 265                 270

Asn Gln Leu Lys Ala Thr Thr Ala Leu Met Ser Asn Gln Ile Ala Ser
        275                 280                 285

Ile Gln Ile Leu Asp Pro Gly Asn Ala Gly Val Arg Ser Leu Ser Glu
    290                 295                 300

Met Arg Ser Val Thr Lys Lys Ala Ala Val Val Ile Ala Gly Phe Gly
305                 310                 315                 320

Asp Asp Pro Thr Gln Ile Ile Glu Glu Gly Ile Met Ala Lys Asp Ala
                325                 330                 335

Leu Gly Lys Pro Val Pro Pro Thr Ser Val Ile Ala Ala Lys Ala Gln
            340                 345                 350

Thr Ser Ser Gly Val Ser Lys Gly Glu Ile Glu Gly Leu Ile Ala Leu
        355                 360                 365

Val Glu Thr Leu Val Asp Asn Asp Lys Lys Ala Ala Lys Leu Ile Lys
    370                 375                 380

Met Ile Asp Gln Val Lys Ser His Ala Asp Tyr Ala Arg Val Lys Gln
385                 390                 395                 400

Ala Ile Tyr Asn Ala
                405
```

<210> SEQ ID NO 69
<211> LENGTH: 1110
<212> TYPE: DNA
<213> ORGANISM: artificial sequence
<220> FEATURE:
<223> OTHER INFORMATION: M gene of FJ215864

<400> SEQUENCE: 69

```
atggcatata caacactaaa actgtgggtg gatgagggtg acatgtcgtc ttcgcttcta      60

tcattcccgt tggtactaaa agagacagac agaggcacaa agaagcttca accacaggta     120

agggtagatt caattggcga tgtgcagaat gccaaagagt cctcgatatt cgtgactcta     180

tatggtttca tccaagcaat taaggagaat tcagatcgat cgaaattctt ccatccaaaa     240
```

```
gatgacttca aacctgagac agtcactgca ggactggtag tagtgggtgc aatccgaatg    300

atggctgatg tcaataccat ctctaatgat gcactagcgc tggagatcac tgttaagaaa    360

tctgcaactt ctcaagagaa aatgacggtg atgttccaca atagcccccc ttcattgaga    420

actgcaataa ctatccgagc aggaggtttc atctcgaatg cagacgaaaa tataaaatgt    480

gccagcaagt tgactgcagg agtgcagtac atattccgtc caatgtttgt ttcaatcact    540

aaattacaca atggcaaact atatagggtg cccaaaagta tccacagcat ctcgtctacc    600

ctactgtata gtgtgatgtt ggaggtagga ttcaaagtgg acatcgggaa ggatcatccc    660

caggcaaaaa tgctgaagag ggtcacaatt ggcgatgcag acacatactg gggatttgca    720

tggttccacc tgtgcaattt caaaaagaca tcctctaagg gaaagccgag aacgctagac    780

gaactgaaga caaaagtcaa aaatatgggg ttgaaattgg agttacatga cctatggggt    840

ccgactattg tggtccaaat cactggcaag agcagcaaat atgctcaagg atttttttct    900

tccaatggta cttgttgcct cccaatcagc agatctgcac cagagcttgg gaagcttctg    960

tggtcctgct cagcaactat tggtgacgca acagttgtta tccaatcaag cgagaagggg   1020

gaactcctaa ggtctgatga tctcgagata cgaggtgctg tggcctccaa gaaaggtaga   1080

ctgagctcat ttcacccctt caaaaaatga                                    1110
```

<210> SEQ ID NO 70
<211> LENGTH: 369
<212> TYPE: PRT
<213> ORGANISM: artificial sequence
<220> FEATURE:
<223> OTHER INFORMATION: M protein of AC048305

<400> SEQUENCE: 70

```
Met Ala Tyr Thr Thr Leu Lys Leu Trp Val Asp Glu Gly Asp Met Ser
1               5                   10                  15

Ser Ser Leu Leu Ser Phe Pro Leu Val Leu Lys Glu Thr Asp Arg Gly
            20                  25                  30

Thr Lys Lys Leu Gln Pro Gln Val Arg Val Asp Ser Ile Gly Asp Val
        35                  40                  45

Gln Asn Ala Lys Glu Ser Ser Ile Phe Val Thr Leu Tyr Gly Phe Ile
    50                  55                  60

Gln Ala Ile Lys Glu Asn Ser Asp Arg Ser Lys Phe Phe His Pro Lys
65                  70                  75                  80

Asp Asp Phe Lys Pro Glu Thr Val Thr Ala Gly Leu Val Val Val Gly
                85                  90                  95

Ala Ile Arg Met Met Ala Asp Val Asn Thr Ile Ser Asn Asp Ala Leu
            100                 105                 110

Ala Leu Glu Ile Thr Val Lys Lys Ser Ala Thr Ser Gln Glu Lys Met
        115                 120                 125

Thr Val Met Phe His Asn Ser Pro Pro Ser Leu Arg Thr Ala Ile Thr
    130                 135                 140

Ile Arg Ala Gly Gly Phe Ile Ser Asn Ala Asp Glu Asn Ile Lys Cys
145                 150                 155                 160

Ala Ser Lys Leu Thr Ala Gly Val Gln Tyr Ile Phe Arg Pro Met Phe
                165                 170                 175

Val Ser Ile Thr Lys Leu His Asn Gly Lys Leu Tyr Arg Val Pro Lys
            180                 185                 190

Ser Ile His Ser Ile Ser Ser Thr Leu Leu Tyr Ser Val Met Leu Glu
        195                 200                 205

Val Gly Phe Lys Val Asp Ile Gly Lys Asp His Pro Gln Ala Lys Met
```

```
    210                 215                 220

Leu Lys Arg Val Thr Ile Gly Asp Ala Asp Thr Tyr Trp Gly Phe Ala
225                 230                 235                 240

Trp Phe His Leu Cys Asn Phe Lys Lys Thr Ser Ser Lys Gly Lys Pro
                245                 250                 255

Arg Thr Leu Asp Glu Leu Lys Thr Lys Val Lys Asn Met Gly Leu Lys
            260                 265                 270

Leu Glu Leu His Asp Leu Trp Gly Pro Thr Ile Val Val Gln Ile Thr
        275                 280                 285

Gly Lys Ser Ser Lys Tyr Ala Gln Gly Phe Phe Ser Ser Asn Gly Thr
    290                 295                 300

Cys Cys Leu Pro Ile Ser Arg Ser Ala Pro Glu Leu Gly Lys Leu Leu
305                 310                 315                 320

Trp Ser Cys Ser Ala Thr Ile Gly Asp Ala Thr Val Val Ile Gln Ser
                325                 330                 335

Ser Glu Lys Gly Glu Leu Leu Arg Ser Asp Asp Leu Glu Ile Arg Gly
            340                 345                 350

Ala Val Ala Ser Lys Lys Gly Arg Leu Ser Ser Phe His Pro Phe Lys
        355                 360                 365

Lys


<210> SEQ ID NO 71
<211> LENGTH: 1632
<212> TYPE: DNA
<213> ORGANISM: artificial sequence
<220> FEATURE:
<223> OTHER INFORMATION: F gene of FJ215864

<400> SEQUENCE: 71

atgggtaaaa tatcaatata tctaattaat agcgtgctat tattgctggt atatcctgtg     60

aattcgattg acaatacact cgttgcccca atcggagtcg ccagcgcaaa tgaatggcag    120

cttgctgcat atacaacatc actttcaggg acaattgccg tgcgattcct acctgtgctc    180

ccggataata tgactacctg tcttagagaa acaataacta catataataa tactgtcaac    240

aacatcttag gcccactcaa atccaatctg gatgcactgc tctcatctga gacttatccc    300

cagacaagat taattggggc agttataggt tcaattgctc ttggtgttgc aacatcggct    360

caaatcactg ctgcagtcgc tctcaagcaa gcacaagata atgcaagaaa catactggca    420

ctcaaagagg cactgtccaa aactaatgag gcggtcaagg agcttagcag tggattgcaa    480

caaacagcta ttgcacttgg taagatacag agctttgtga atgaggaaat tctgccatct    540

atcaaccaac tgagctgcga ggtgacagcc aataaacttg ggtgtattt atctctgtat     600

ctcacagaac tgaccactat attcggtgca cagttgacta accctgcatt gacttcatta    660

tcatatcaag cgctgtacaa cctgtgtggt ggcaacatgg caatgcttac tcagaagatt    720

ggaattaaac agcaagacgt taattcgcta tatgaagccg gactaatcac aggacaagtc    780

attggttatg actctcagta ccagctgctg gtcatccagg tcaattatcc aagcatttct    840

gaggtaactg gtgtgcgtgc gacagaatta gtcactgtta gtgtaacaac agacaagggt    900

gaagggaaag caattgtacc ccaatttgta gctgaaagtc gggtgactat tgaggagctt    960

gatgtagcat cttgtaaatt cagcagcaca accctatact gcaggcaggt caacacaagg   1020

gcacttcccc cgctagtggc tagctgtctc cgaggtaact atgatgattg tcaatatacc   1080

acagagattg gagcattatc atcccggtat ataacactag atggaggggt cttagtcaat   1140

tgtaagtcaa ttgtttgtag gtgccttaat ccaagtaaga tcatctctca aaatacaaat   1200
```

```
gctgcagtaa catatgttga tgctacaata tgcaaaacaa ttcaattgga tgacatacaa   1260

ctccagttgg aagggtcact atcatcagtt tatgcaagga acatctcaat tgagatcagt   1320

caggtgacta cctccggttc tttggatatc agcagtgaga tagggaacat caataatacg   1380

gtgaatcgtg tggaggattt aatccaccaa tcggaggaat ggctggcaaa agttaaccca   1440

cacattgtta ataatactac actaattgta ctctgtgtgt taagtgcgct tgctgtgatc   1500

tggctggcag tattaacggc tattataata tacttgagaa caaagttgaa gactatatcg   1560

gcattggctg taaccaatac aatacagtct aatccctatg ttaaccaaac gaaacgtgaa   1620

tctaagtttt ga                                                       1632
```

<210> SEQ ID NO 72
<211> LENGTH: 543
<212> TYPE: PRT
<213> ORGANISM: artificial sequence
<220> FEATURE:
<223> OTHER INFORMATION: F protein of AC048306

<400> SEQUENCE: 72

```
Met Gly Lys Ile Ser Ile Tyr Leu Ile Asn Ser Val Leu Leu Leu Leu
1               5                   10                  15

Val Tyr Pro Val Asn Ser Ile Asp Asn Thr Leu Val Ala Pro Ile Gly
            20                  25                  30

Val Ala Ser Ala Asn Glu Trp Gln Leu Ala Ala Tyr Thr Thr Ser Leu
        35                  40                  45

Ser Gly Thr Ile Ala Val Arg Phe Leu Pro Val Leu Pro Asp Asn Met
    50                  55                  60

Thr Thr Cys Leu Arg Glu Thr Ile Thr Thr Tyr Asn Asn Thr Val Asn
65                  70                  75                  80

Asn Ile Leu Gly Pro Leu Lys Ser Asn Leu Asp Ala Leu Leu Ser Ser
                85                  90                  95

Glu Thr Tyr Pro Gln Thr Arg Leu Ile Gly Ala Val Ile Gly Ser Ile
            100                 105                 110

Ala Leu Gly Val Ala Thr Ser Ala Gln Ile Thr Ala Ala Val Ala Leu
        115                 120                 125

Lys Gln Ala Gln Asp Asn Ala Arg Asn Ile Leu Ala Leu Lys Glu Ala
    130                 135                 140

Leu Ser Lys Thr Asn Glu Ala Val Lys Glu Leu Ser Ser Gly Leu Gln
145                 150                 155                 160

Gln Thr Ala Ile Ala Leu Gly Lys Ile Gln Ser Phe Val Asn Glu Glu
                165                 170                 175

Ile Leu Pro Ser Ile Asn Gln Leu Ser Cys Glu Val Thr Ala Asn Lys
            180                 185                 190

Leu Gly Val Tyr Leu Ser Leu Tyr Leu Thr Glu Leu Thr Thr Ile Phe
        195                 200                 205

Gly Ala Gln Leu Thr Asn Pro Ala Leu Thr Ser Leu Ser Tyr Gln Ala
    210                 215                 220

Leu Tyr Asn Leu Cys Gly Gly Asn Met Ala Met Leu Thr Gln Lys Ile
225                 230                 235                 240

Gly Ile Lys Gln Gln Asp Val Asn Ser Leu Tyr Glu Ala Gly Leu Ile
                245                 250                 255

Thr Gly Gln Val Ile Gly Tyr Asp Ser Gln Tyr Gln Leu Leu Val Ile
            260                 265                 270

Gln Val Asn Tyr Pro Ser Ile Ser Glu Val Thr Gly Val Arg Ala Thr
        275                 280                 285
```

```
Glu Leu Val Thr Val Ser Val Thr Thr Asp Lys Gly Glu Gly Lys Ala
    290                 295                 300

Ile Val Pro Gln Phe Val Ala Glu Ser Arg Val Thr Ile Glu Glu Leu
305                 310                 315                 320

Asp Val Ala Ser Cys Lys Phe Ser Ser Thr Thr Leu Tyr Cys Arg Gln
                325                 330                 335

Val Asn Thr Arg Ala Leu Pro Pro Leu Val Ala Ser Cys Leu Arg Gly
            340                 345                 350

Asn Tyr Asp Asp Cys Gln Tyr Thr Thr Glu Ile Gly Ala Leu Ser Ser
        355                 360                 365

Arg Tyr Ile Thr Leu Asp Gly Gly Val Leu Val Asn Cys Lys Ser Ile
    370                 375                 380

Val Cys Arg Cys Leu Asn Pro Ser Lys Ile Ile Ser Gln Asn Thr Asn
385                 390                 395                 400

Ala Ala Val Thr Tyr Val Asp Ala Thr Ile Cys Lys Thr Ile Gln Leu
                405                 410                 415

Asp Asp Ile Gln Leu Gln Leu Glu Gly Ser Leu Ser Ser Val Tyr Ala
            420                 425                 430

Arg Asn Ile Ser Ile Glu Ile Ser Gln Val Thr Thr Ser Gly Ser Leu
        435                 440                 445

Asp Ile Ser Ser Glu Ile Gly Asn Ile Asn Asn Thr Val Asn Arg Val
    450                 455                 460

Glu Asp Leu Ile His Gln Ser Glu Glu Trp Leu Ala Lys Val Asn Pro
465                 470                 475                 480

His Ile Val Asn Asn Thr Thr Leu Ile Val Leu Cys Val Leu Ser Ala
                485                 490                 495

Leu Ala Val Ile Trp Leu Ala Val Leu Thr Ala Ile Ile Ile Tyr Leu
            500                 505                 510

Arg Thr Lys Leu Lys Thr Ile Ser Ala Leu Ala Val Thr Asn Thr Ile
        515                 520                 525

Gln Ser Asn Pro Tyr Val Asn Gln Thr Lys Arg Glu Ser Lys Phe
    530                 535                 540
```

<210> SEQ ID NO 73
<211> LENGTH: 1734
<212> TYPE: DNA
<213> ORGANISM: artificial sequence
<220> FEATURE:
<223> OTHER INFORMATION: HN gene of FJ215864

<400> SEQUENCE: 73

```
atgagtaaca ttgcatccag tttagaaaat attgtggagc aggatagtcg aaaaacaact      60

tggagggcca tctttagatg gtccgttctt cttattacaa caggatgctt agccttatcc     120

attgttagca tagttcaaat tgggaatttg aaaattcctt ctgtagggga tctggcggac     180

gaggtggtaa cacctttgaa aaccactctg tctgatacac tcaggaatcc aattaaccag     240

ataaatgaca tattcaggat tgttgccctt gatattccat tgcaagtaac tagtatccaa     300

aaagacctcg caagtcaatt tagcatgttg atagatagtt taaatgctat caaattgggc     360

aacgggacca accttatcat acctacatca gataaggagt atgcaggagg aattggaaac     420

cctgtattta ctgtcgatgc tggaggttct ataggattca agcaatttag cttaatagaa     480

catccgagct ttattgctgg acctacaacg acccgaggct gtacaagaat acccactttt     540

cacatgtcag aaagtcattg gtgctactca cacaacatca tcgctgctgg ctgtcaagat     600

gccagtgcat ctagtatgta tatctcaatg gggttctcc atgtgtcttc atctggcact     660
```

```
cctatctttc ttactactgc aagtgaactg atagacgatg gagttaatcg taagtcatgc    720
agtattgtag caacccaatt cggctgtgac attttgtgca gtattgtcat agagaaggag    780
ggagatgatt attggtctga tactccgact ccaatgcgcc acggccgttt ttcattcaat    840
gggagttttg tagaaaccga actacccgtg tccagtatgt tctcgtcatt ctctgccaac    900
taccctgctg tgggatcagg cgaaattgta aaagatagaa tattattccc aatttacgga    960
ggtataaagc agacttcacc agagtttacc gaattagtga aatatggact ctttgtgtca   1020
acacctacaa ctgtatgtca gagtagctgg acttatgacc aggtaaaagc agcgtatagg   1080
ccagattaca tatcaggccg gttctgggca caagtgatac tcagctgcgc tcttgatgca   1140
gtcgacttat caagttgtat tgtaaagatt atgaatagca gcacagtgat gatggcagca   1200
gaaggaagga taataaagat agggattgat tacttttact atcagcggtc atcttcttgg   1260
tggccattgg catttgttac aaaactagac ccgcaagagt tagcagacac aaactcgata   1320
tggctgacca attccatacc aatcccacaa tcaaagttcc ctcggccttc atattcagaa   1380
aattattgca caaagccagc agtttgccct gctacttgtg tcactggtgt atactctgat   1440
atttggccct tgacctcatc ttcatcactc ccgagcataa tttggatcgg ccagtacctt   1500
gatgcccctg ttggaaggac ttatcccaga tttggaattg caaatcaatc acactggtac   1560
cttcaagaag atattctacc cacctccact gcaagtgcgt attcaaccac tacatgtttt   1620
aagaatactg ccaggaatag agtgttctgc gtcaccattg ctgaatttgc agatgggttg   1680
tttggagagt acaggataac acctcagttg tatgaattag tgagaaataa ttga         1734
```

<210> SEQ ID NO 74
<211> LENGTH: 577
<212> TYPE: PRT
<213> ORGANISM: artificial sequence
<220> FEATURE:
<223> OTHER INFORMATION: HN protein of AC048307

<400> SEQUENCE: 74

```
Met Ser Asn Ile Ala Ser Ser Leu Glu Asn Ile Val Glu Gln Asp Ser
1               5                   10                  15

Arg Lys Thr Thr Trp Arg Ala Ile Phe Arg Trp Ser Val Leu Leu Ile
            20                  25                  30

Thr Thr Gly Cys Leu Ala Leu Ser Ile Val Ser Ile Val Gln Ile Gly
        35                  40                  45

Asn Leu Lys Ile Pro Ser Val Gly Asp Leu Ala Asp Glu Val Val Thr
    50                  55                  60

Pro Leu Lys Thr Thr Leu Ser Asp Thr Leu Arg Asn Pro Ile Asn Gln
65                  70                  75                  80

Ile Asn Asp Ile Phe Arg Ile Val Ala Leu Asp Ile Pro Leu Gln Val
                85                  90                  95

Thr Ser Ile Gln Lys Asp Leu Ala Ser Gln Phe Ser Met Leu Ile Asp
            100                 105                 110

Ser Leu Asn Ala Ile Lys Leu Gly Asn Gly Thr Asn Leu Ile Ile Pro
        115                 120                 125

Thr Ser Asp Lys Glu Tyr Ala Gly Gly Ile Gly Asn Pro Val Phe Thr
    130                 135                 140

Val Asp Ala Gly Gly Ser Ile Gly Phe Lys Gln Phe Ser Leu Ile Glu
145                 150                 155                 160

His Pro Ser Phe Ile Ala Gly Pro Thr Thr Thr Arg Gly Cys Thr Arg
                165                 170                 175
```

```
Ile Pro Thr Phe His Met Ser Glu Ser His Trp Cys Tyr Ser His Asn
            180                 185                 190

Ile Ile Ala Ala Gly Cys Gln Asp Ala Ser Ala Ser Ser Met Tyr Ile
        195                 200                 205

Ser Met Gly Val Leu His Val Ser Ser Ser Gly Thr Pro Ile Phe Leu
    210                 215                 220

Thr Thr Ala Ser Glu Leu Ile Asp Asp Gly Val Asn Arg Lys Ser Cys
225                 230                 235                 240

Ser Ile Val Ala Thr Gln Phe Gly Cys Asp Ile Leu Cys Ser Ile Val
                245                 250                 255

Ile Glu Lys Glu Gly Asp Asp Tyr Trp Ser Asp Thr Pro Thr Pro Met
            260                 265                 270

Arg His Gly Arg Phe Ser Phe Asn Gly Ser Phe Val Glu Thr Glu Leu
        275                 280                 285

Pro Val Ser Ser Met Phe Ser Ser Phe Ser Ala Asn Tyr Pro Ala Val
    290                 295                 300

Gly Ser Gly Glu Ile Val Lys Asp Arg Ile Leu Phe Pro Ile Tyr Gly
305                 310                 315                 320

Gly Ile Lys Gln Thr Ser Pro Glu Phe Thr Glu Leu Val Lys Tyr Gly
                325                 330                 335

Leu Phe Val Ser Thr Pro Thr Thr Val Cys Gln Ser Ser Trp Thr Tyr
            340                 345                 350

Asp Gln Val Lys Ala Ala Tyr Arg Pro Asp Tyr Ile Ser Gly Arg Phe
        355                 360                 365

Trp Ala Gln Val Ile Leu Ser Cys Ala Leu Asp Ala Val Asp Leu Ser
    370                 375                 380

Ser Cys Ile Val Lys Ile Met Asn Ser Ser Thr Val Met Met Ala Ala
385                 390                 395                 400

Glu Gly Arg Ile Ile Lys Ile Gly Ile Asp Tyr Phe Tyr Tyr Gln Arg
                405                 410                 415

Ser Ser Ser Trp Trp Pro Leu Ala Phe Val Thr Lys Leu Asp Pro Gln
            420                 425                 430

Glu Leu Ala Asp Thr Asn Ser Ile Trp Leu Thr Asn Ser Ile Pro Ile
        435                 440                 445

Pro Gln Ser Lys Phe Pro Arg Pro Ser Tyr Ser Glu Asn Tyr Cys Thr
    450                 455                 460

Lys Pro Ala Val Cys Pro Ala Thr Cys Val Thr Gly Val Tyr Ser Asp
465                 470                 475                 480

Ile Trp Pro Leu Thr Ser Ser Ser Ser Leu Pro Ser Ile Ile Trp Ile
                485                 490                 495

Gly Gln Tyr Leu Asp Ala Pro Val Gly Arg Thr Tyr Pro Arg Phe Gly
            500                 505                 510

Ile Ala Asn Gln Ser His Trp Tyr Leu Gln Glu Asp Ile Leu Pro Thr
        515                 520                 525

Ser Thr Ala Ser Ala Tyr Ser Thr Thr Thr Cys Phe Lys Asn Thr Ala
    530                 535                 540

Arg Asn Arg Val Phe Cys Val Thr Ile Ala Glu Phe Ala Asp Gly Leu
545                 550                 555                 560

Phe Gly Glu Tyr Arg Ile Thr Pro Gln Leu Tyr Glu Leu Val Arg Asn
                565                 570                 575

Asn

<210> SEQ ID NO 75
<211> LENGTH: 6717
```

-continued

<212> TYPE: DNA
<213> ORGANISM: artificial sequence
<220> FEATURE:
<223> OTHER INFORMATION: L gene of FJ215864

<400> SEQUENCE: 75

```
atggatgtaa aacaagttga cctaataata caacccgagg ttcatctcga ttcacccatc     60
atattgaata aactggcact attatggcgc ttgagtggtt tacccatgcc tgcagactta    120
cgacaaaaat ccgtagtgat gcacatccca gaccacatct tagaaaaatc agaatatcgg    180
atcaagcacc gtctagggaa aatcaagagt gacatagcac attactgtca gtattttaat    240
attaatttgg caaatcttga tccgataacc caccccaaaa gtttgtattg gttatccaga    300
ctaacaatag ctagtgctgg aacctttaga catatgaaag atagaatctt atgtacagtt    360
ggctccgaat tcggacacaa aattcaagat ttattttcac tgctgagcca taaattagta    420
ggtaacggtg atttatttaa tcaaagtctc tcaggtacac gtttgactgc gagtccgtta    480
tcccctttat gcaatcaatt tgtctctgac atcaagtctg cagtcacgac accctggtca    540
gaagctcgtt ggtcttggct tcatatcaaa caaacaatga gatacctgat aaaacaatca    600
cgcactacaa attcagctca tttaacagaa attataaaag aggaatgggg tttagtaggt    660
attactccag atcttgtcat tctttttgac agagtcaata atagtctaac tgcattaaca    720
tttgagatgg ttctaatgta ttcagatgta ttagaatccc gtgacaatat tgtgctagtg    780
gggcgattat ctacttttct gcagccagta gttagtagac tggaggtgtt gtttgatcta    840
gtagattcat tggcaaaaac cttaggtgac acaatatacg aaattattgc ggtgttagag    900
agcttgtctt atgggtccgt tcaactacat gatgcaagtc actctcatgc agggtctttc    960
ttttcattta acatgaatga acttgataac acactatcaa agagggtgga tccgaaacac   1020
aagaacacca taatgagcat tataagacaa tgcttttcta atctagatgt tgatcaagct   1080
gcagagatgc tatgcctgat gagattattt ggacacccaa tgttaactgc accggatgca   1140
gcagccaaag taaggaaagc aatgtgtgct ccaaaacttg ttgaacatga caccatcttg   1200
cagacattat ccttcttcaa gggaataatt ataaatgggt acagaagatc acactctggc   1260
ctgtggccca atgtagagcc gtcttcaatc tatgatgatg atctcagaca gctgtactta   1320
gagtcagcag agatttccca tcatttcatg cttaaaaact acaagagttt gagcatgata   1380
gaattcaaga agagcataga ctacgatctt cacgacgact taagtacttt cttaaaggat   1440
agagcaattt gccggccaaa atcccagtgg gatgttatat tccgtaagtc tttacgcaga   1500
tcccacacgc ggtcccagta tatggacgaa attaagagca accgattgct aattgatttt   1560
cttgattctg ctgattttga ccctgaaaag gaatttgcat atgtaaccac aatggattat   1620
ttgcacgata atgaattttg tgcttcatat tctctaaagg aaaaggagat caaaactacc   1680
gggaggatat ttgcaaaaat gacacgcaat atgagaagtt gccaagtgat acttgaatct   1740
ctgttatcaa aacatatatg caagttcttc aaagagaacg gcgtttcgat ggagcaattg   1800
tcattgacca agagtctact tgcaatgtct caactctcac caaaagtctc gactctgcag   1860
gacactgcat cacgtcatgt aggcaactca aaatctcaga tcgcaaccag caacccatct   1920
cggcatcact caacaaccaa tcagatgtca ctctcaaatc ggaaaacggt tgtagcaact   1980
ttcttaacaa ctgatttgga aaaatactgc ctgcagtggc gatactcgac tattaagttg   2040
tttgcacaag ctctaaatca actctttggg attgatcacg gatttgaatg gatacattta   2100
agactcatga acagcacctt atttgtcggt gatccttact cgcctcctga agatccaaca   2160
ctagaggata tagataaagc accaaatgac gatatcttca tagtttctcc aaggggaggc   2220
```

atagagggtt tatgtcagaa gatgtggacc atgatatcaa ttagtgcgat acactgtgta 2280
gcagagaaaa ttggtgcacg agtggcagca atggtgcagg gtgataatca agtaatagct 2340
atcaccaaag aactattcag aggagagaaa gcctgtgatg tcagagatga gttagacgag 2400
ctcggtcagg tgtttttga tgagttcaag aggcacaatt atgcaattgg acacaacctt 2460
aagctaaatg agacaataca aagccaatcc tttttgtat attccaaacg aatattcttt 2520
gaagggcgat tgcttagtca agtcctcaaa aatgctgcca agttatgtat ggttgctgac 2580
catctaggtg aaaacacagt atcttcctgt agcaacctga gctctacaat tgcccggttg 2640
gtggaaaatg ggtttgagaa ggacactgct tttgtgttga acctagtcta catcatgact 2700
caaattcttt ttgatgagca ttactcgatt gtatgcgatc acaatagtgt caaaagcttg 2760
atcggatcaa aaaactatcg gaatctattg tactcatctc taataccagg tcagctcggt 2820
ggtttcaact tcctcaatat aagtcggttg ttcactagga atataggtga cccagtaaca 2880
tgtagtctgt ctgatctcaa atgcttcata gccgcaggtc tccttccacc ctatgtactt 2940
aaaaatgtgg ttctgcgtga gcctggtcct gggacatggt tgacgttgtg ctctgatcct 3000
tacaccctta acataccata cacacagcta ccaaccacat atctcaaaaa gcacacccag 3060
cgatcgttgc tttcacgtgc agtaaatcct ttattagcag gtgtacaagt gccaaatcag 3120
catgaggaag aagagatgtt ggctcgcttt ctccttgatc gtgaatatgt gatgccccgc 3180
gttgctcatg taatactaga aacatcggtc cttggcaaac ggaaacaaat ccaaggctta 3240
attgatacaa ctccaactat cattagaaca tctctagtta atctaccagt gtctaggaag 3300
aaatgcgaaa aaataatcaa ttattctctc aattatattg ctgagtgtca tgactcctta 3360
cttagtcaga tctgcttcag tgataataag gaatacttgt ggtccacctc cttaatatca 3420
gttgagacct gtagtgtgac aattgcggac tatttgagag ctgtcagctg gtctaatata 3480
ttagggggaa gaaacatatc cggggtgact acacctgata ctattgaatt aattcaaggt 3540
tgtttaatag gtgaaaattc cagttgtact ctttgtgaat cgcatgacga cgcattcaca 3600
tggatgcact tgcctggccc actttacatc cctgaaccat cagttactaa ctctaaaatg 3660
cgtgtgccat atctgggttc aaaaacagag gagcgtaaaa cagcttcaat ggcagcaata 3720
aaaggaatgt cacatcacct gcgtgcagtc ttaagaggta catccgtatt tatttgggca 3780
tttggggaca cagatattaa ttgggataat gcattgcaga ttgcccaatc acggtgtaac 3840
atcacattgg atcaaatgag attacttaca ccaattccta gcagttcaaa tatccaacat 3900
agactcgatg acggaatcag cacgcagaaa tttactcctg caagccttgc tcgaatcaca 3960
tcctttgttc acatctgtaa tgacagccaa aggttagaga aggatggctc ctctgtcgac 4020
tcaaacttga tttaccagca aattatgtta cttggactca gcatctttga aacaatgtac 4080
tcaatggacc aaaagtgggt attcaataac catacccttac atttgcacac tggacactcc 4140
tgttgtccaa gggaactaga cataagttta gtgaacccgc caagacatca gaccccggag 4200
ctgactagca caacaaccaa cccgttccta tatgatcagc tcccactaaa tcaggataat 4260
ctgacaacac ttgagattaa gacattcaaa tttaatgagc tcaacattga tggtttagat 4320
tttggtgaag gaatacaatt attgagtcgt tgtactgcaa gattaatggc agaatgtatt 4380
ctagaggagg gaataggctc gtcagttaaa aatgaagcaa ttgtcaattt tgataattca 4440
gtcaattgga tttcagagtg cctaatgtgt gatattcgct cactttgtgt taatttaggt 4500
caagagatac tatgtagcct ggcataccaa atgtattact tgcgaatcag ggtagaaagg 4560
gccattctta attacttgga cacaactttg caaaggatcc ctgtgataca attagccaac 4620

-continued attgcactca ccatttcaca ccctgagata tttcgcagaa ttgtcaacac cgggatccat 4680
aaccagatta agggcccata tgtggcaaca acagatttca tagctgcaag tagagatatc 4740
atattatcag gtgcaaggga gtatctatct tatctaagca gtggacagga agactgttac 4800
acattcttca actgtcaaga tggggatctt actccaaaaa tggaacagta tcttgcaagg 4860
agggcatgcc ttttaacatt actgtataat actgggcacc agatccccat tatccgatca 4920
ctgacaccaa tagagaagtg caaggtgctc acagaataca atcaacaaat tgagtatgca 4980
gatcaagagt ttagctctgt attgaaagtg gtcaatgcac tactacaaaa tcctaatata 5040
gatgcattgg tttcaaatct ctacttcacc accagacgtg ttttatcaaa cctcagatca 5100
tgtgataagg ctatatcata tattgaatat ttgtacactg aggacttcgg agaaaaagaa 5160
gatacagtac aatatgacat catgacaaca aacgatatca tacttactca tggtctattc 5220
acacagatcg aaatatctta ccaagggagt agtctccata aattcctaac tccggataac 5280
gcgcctggat cattgatccc attctctatt tcaccaaatt cgcttgcatg tgatcctctt 5340
caccacttac tcaagtcggt cggtacatca agcacaagct ggtacaagta tgcaatcgcc 5400
tatgcagtgt ctgaaaagag gtcggctcga ttaggaggga gcttgtacat tggtgaaggg 5460
agcggaagtg tgatgacttt gctagagtat cttgagccat ctgttgacat attttacaat 5520
tcactcttct caaatggtat gaacccacca caacgaaatt atgggcttat gccactacaa 5580
tttgtgaatt cggtggttta taagaactta acggctaaat cagaatgtaa gctaggattt 5640
gtccagcaat ttaaaccgtt gtggagagac atagacattg agactaatgt tacagatcca 5700
tcatttgtca attttgcatt gaatgaaatc ccaatgcaat cattaaaacg agtaaattgt 5760
gatgtggaat ttgaccgtgg tatgccgatt gaacgggtta ttcagggtta cactcatatc 5820
ttacttgttg ctacttacgg attgcagcaa gattcaatac tgtgggtgaa agtatatagg 5880
acatctgaaa aagtatttca gttcttactg agtgccatga tcatgatctt tggttatgtc 5940
aaaatccaca ggaatggtta tatgtcggca aaggatgagg agtacatatt gatgtctgac 6000
tgcaaggaac ctgtaaacta tacagctgtc cctaacattc ttacacgtgt aagtgattta 6060
gtgtcgaaga atctgagtct tatccatcca gaagacctca gaaaggtaag gtgtgaaaca 6120
gattccctga atttgaagtg caatcatatt tatgagaaaa taattgctag aaaaattcca 6180
ttacaggtat catcaactga ttctttgctc ctccagttag gcggtgtcat caactcggtg 6240
ggctcaactg atcctagaga ggttgcaaca ttatcttcca ttgagtgtat ggactatgtt 6300
gtctcatcaa ttgatttggc tatattagag gcaaatattg tgatctcaga gagtgctggt 6360
cttgacctcg ctttaatgtt aggcccattc aacttgaata agcttaagaa aattgacaca 6420
atccttaagt caagcaccta tcagctaatc ccgtattggt tgcgctatga gtactctatt 6480
aatccgagat ctttgtcatt tctaatcact aaattacaac aatgccgaat ttcatggtca 6540
gatatgataa caatctctga attttgcaag aaatccaagc ggcctatatt tattaaacga 6600
gtaataggga atcaacagct gaaatcattc tttaatgaaa gctcaagtat tgttttgacc 6660
cgggctgaag tcaaagtctg tataaagttc ctcggtgcaa tcatcaagtt gaaataa 6717

<210> SEQ ID NO 76
<211> LENGTH: 2238
<212> TYPE: PRT
<213> ORGANISM: artificial sequence
<220> FEATURE:
<223> OTHER INFORMATION: L protein of AC048308

<400> SEQUENCE: 76

```
Met Asp Val Lys Gln Val Asp Leu Ile Ile Gln Pro Glu Val His Leu
1               5                   10                  15

Asp Ser Pro Ile Ile Leu Asn Lys Leu Ala Leu Leu Trp Arg Leu Ser
            20                  25                  30

Gly Leu Pro Met Pro Ala Asp Leu Arg Gln Lys Ser Val Val Met His
        35                  40                  45

Ile Pro Asp His Ile Leu Glu Lys Ser Glu Tyr Arg Ile Lys His Arg
    50                  55                  60

Leu Gly Lys Ile Lys Ser Asp Ile Ala His Tyr Cys Gln Tyr Phe Asn
65                  70                  75                  80

Ile Asn Leu Ala Asn Leu Asp Pro Ile Thr His Pro Lys Ser Leu Tyr
                85                  90                  95

Trp Leu Ser Arg Leu Thr Ile Ala Ser Ala Gly Thr Phe Arg His Met
            100                 105                 110

Lys Asp Arg Ile Leu Cys Thr Val Gly Ser Glu Phe Gly His Lys Ile
        115                 120                 125

Gln Asp Leu Phe Ser Leu Leu Ser His Lys Leu Val Gly Asn Gly Asp
    130                 135                 140

Leu Phe Asn Gln Ser Leu Ser Gly Thr Arg Leu Thr Ala Ser Pro Leu
145                 150                 155                 160

Ser Pro Leu Cys Asn Gln Phe Val Ser Asp Ile Lys Ser Ala Val Thr
                165                 170                 175

Thr Pro Trp Ser Glu Ala Arg Trp Ser Trp Leu His Ile Lys Gln Thr
            180                 185                 190

Met Arg Tyr Leu Ile Lys Gln Ser Arg Thr Thr Asn Ser Ala His Leu
        195                 200                 205

Thr Glu Ile Ile Lys Glu Glu Trp Gly Leu Val Gly Ile Thr Pro Asp
    210                 215                 220

Leu Val Ile Leu Phe Asp Arg Val Asn Asn Ser Leu Thr Ala Leu Thr
225                 230                 235                 240

Phe Glu Met Val Leu Met Tyr Ser Asp Val Leu Glu Ser Arg Asp Asn
                245                 250                 255

Ile Val Leu Val Gly Arg Leu Ser Thr Phe Leu Gln Pro Val Val Ser
            260                 265                 270

Arg Leu Glu Val Leu Phe Asp Leu Val Asp Ser Leu Ala Lys Thr Leu
        275                 280                 285

Gly Asp Thr Ile Tyr Glu Ile Ile Ala Val Leu Glu Ser Leu Ser Tyr
    290                 295                 300

Gly Ser Val Gln Leu His Asp Ala Ser His Ser His Ala Gly Ser Phe
305                 310                 315                 320

Phe Ser Phe Asn Met Asn Glu Leu Asp Asn Thr Leu Ser Lys Arg Val
                325                 330                 335

Asp Pro Lys His Lys Asn Thr Ile Met Ser Ile Ile Arg Gln Cys Phe
            340                 345                 350

Ser Asn Leu Asp Val Asp Gln Ala Ala Glu Met Leu Cys Leu Met Arg
        355                 360                 365

Leu Phe Gly His Pro Met Leu Thr Ala Pro Asp Ala Ala Ala Lys Val
    370                 375                 380

Arg Lys Ala Met Cys Ala Pro Lys Leu Val Glu His Asp Thr Ile Leu
385                 390                 395                 400

Gln Thr Leu Ser Phe Phe Lys Gly Ile Ile Ile Asn Gly Tyr Arg Arg
                405                 410                 415

Ser His Ser Gly Leu Trp Pro Asn Val Glu Pro Ser Ser Ile Tyr Asp
```

```
            420                 425                 430

Asp Asp Leu Arg Gln Leu Tyr Leu Glu Ser Ala Glu Ile Ser His His
        435                 440                 445

Phe Met Leu Lys Asn Tyr Lys Ser Leu Ser Met Ile Glu Phe Lys Lys
    450                 455                 460

Ser Ile Asp Tyr Asp Leu His Asp Asp Leu Ser Thr Phe Leu Lys Asp
465                 470                 475                 480

Arg Ala Ile Cys Arg Pro Lys Ser Gln Trp Asp Val Ile Phe Arg Lys
                485                 490                 495

Ser Leu Arg Arg Ser His Thr Arg Ser Gln Tyr Met Asp Glu Ile Lys
            500                 505                 510

Ser Asn Arg Leu Leu Ile Asp Phe Leu Asp Ser Ala Asp Phe Asp Pro
        515                 520                 525

Glu Lys Glu Phe Ala Tyr Val Thr Thr Met Asp Tyr Leu His Asp Asn
    530                 535                 540

Glu Phe Cys Ala Ser Tyr Ser Leu Lys Glu Lys Glu Ile Lys Thr Thr
545                 550                 555                 560

Gly Arg Ile Phe Ala Lys Met Thr Arg Asn Met Arg Ser Cys Gln Val
                565                 570                 575

Ile Leu Glu Ser Leu Leu Ser Lys His Ile Cys Lys Phe Phe Lys Glu
            580                 585                 590

Asn Gly Val Ser Met Glu Gln Leu Ser Leu Thr Lys Ser Leu Leu Ala
        595                 600                 605

Met Ser Gln Leu Ser Pro Lys Val Ser Thr Leu Gln Asp Thr Ala Ser
    610                 615                 620

Arg His Val Gly Asn Ser Lys Ser Gln Ile Ala Thr Ser Asn Pro Ser
625                 630                 635                 640

Arg His His Ser Thr Thr Asn Gln Met Ser Leu Ser Asn Arg Lys Thr
                645                 650                 655

Val Val Ala Thr Phe Leu Thr Thr Asp Leu Glu Lys Tyr Cys Leu Gln
            660                 665                 670

Trp Arg Tyr Ser Thr Ile Lys Leu Phe Ala Gln Ala Leu Asn Gln Leu
        675                 680                 685

Phe Gly Ile Asp His Gly Phe Glu Trp Ile His Leu Arg Leu Met Asn
    690                 695                 700

Ser Thr Leu Phe Val Gly Asp Pro Tyr Ser Pro Pro Glu Asp Pro Thr
705                 710                 715                 720

Leu Glu Asp Ile Asp Lys Ala Pro Asn Asp Asp Ile Phe Ile Val Ser
                725                 730                 735

Pro Arg Gly Gly Ile Glu Gly Leu Cys Gln Lys Met Trp Thr Met Ile
            740                 745                 750

Ser Ile Ser Ala Ile His Cys Val Ala Glu Lys Ile Gly Ala Arg Val
        755                 760                 765

Ala Ala Met Val Gln Gly Asp Asn Gln Val Ile Ala Ile Thr Lys Glu
    770                 775                 780

Leu Phe Arg Gly Glu Lys Ala Cys Asp Val Arg Asp Glu Leu Asp Glu
785                 790                 795                 800

Leu Gly Gln Val Phe Phe Asp Glu Phe Lys Arg His Asn Tyr Ala Ile
                805                 810                 815

Gly His Asn Leu Lys Leu Asn Glu Thr Ile Gln Ser Gln Ser Phe Phe
            820                 825                 830

Val Tyr Ser Lys Arg Ile Phe Phe Glu Gly Arg Leu Leu Ser Gln Val
        835                 840                 845
```

-continued

```
Leu Lys Asn Ala Ala Lys Leu Cys Met Val Ala Asp His Leu Gly Glu
    850                 855                 860

Asn Thr Val Ser Ser Cys Ser Asn Leu Ser Ser Thr Ile Ala Arg Leu
865                 870                 875                 880

Val Glu Asn Gly Phe Glu Lys Asp Thr Ala Phe Val Leu Asn Leu Val
                885                 890                 895

Tyr Ile Met Thr Gln Ile Leu Phe Asp Glu His Tyr Ser Ile Val Cys
            900                 905                 910

Asp His Asn Ser Val Lys Ser Leu Ile Gly Ser Lys Asn Tyr Arg Asn
        915                 920                 925

Leu Leu Tyr Ser Ser Leu Ile Pro Gly Gln Leu Gly Gly Phe Asn Phe
    930                 935                 940

Leu Asn Ile Ser Arg Leu Phe Thr Arg Asn Ile Gly Asp Pro Val Thr
945                 950                 955                 960

Cys Ser Leu Ser Asp Leu Lys Cys Phe Ile Ala Ala Gly Leu Leu Pro
                965                 970                 975

Pro Tyr Val Leu Lys Asn Val Val Leu Arg Glu Pro Gly Pro Gly Thr
            980                 985                 990

Trp Leu Thr Leu Cys Ser Asp Pro  Tyr Thr Leu Asn Ile  Pro Tyr Thr
        995                 1000                1005

Gln Leu  Pro Thr Thr Tyr Leu  Lys Lys His Thr Gln  Arg Ser Leu
    1010                1015                1020

Leu Ser  Arg Ala Val Asn Pro  Leu Leu Ala Gly Val  Gln Val Pro
    1025                1030                1035

Asn Gln  His Glu Glu Glu Glu  Met Leu Ala Arg Phe  Leu Leu Asp
    1040                1045                1050

Arg Glu  Tyr Val Met Pro Arg  Val Ala His Val Ile  Leu Glu Thr
    1055                1060                1065

Ser Val  Leu Gly Lys Arg Lys  Gln Ile Gln Gly Leu  Ile Asp Thr
    1070                1075                1080

Thr Pro  Thr Ile Ile Arg Thr  Ser Leu Val Asn Leu  Pro Val Ser
    1085                1090                1095

Arg Lys  Lys Cys Glu Lys Ile  Ile Asn Tyr Ser Leu  Asn Tyr Ile
    1100                1105                1110

Ala Glu  Cys His Asp Ser Leu  Leu Ser Gln Ile Cys  Phe Ser Asp
    1115                1120                1125

Asn Lys  Glu Tyr Leu Trp Ser  Thr Ser Leu Ile Ser  Val Glu Thr
    1130                1135                1140

Cys Ser  Val Thr Ile Ala Asp  Tyr Leu Arg Ala Val  Ser Trp Ser
    1145                1150                1155

Asn Ile  Leu Gly Gly Arg Asn  Ile Ser Gly Val Thr  Thr Pro Asp
    1160                1165                1170

Thr Ile  Glu Leu Ile Gln Gly  Cys Leu Ile Gly Glu  Asn Ser Ser
    1175                1180                1185

Cys Thr  Leu Cys Glu Ser His  Asp Asp Ala Phe Thr  Trp Met His
    1190                1195                1200

Leu Pro  Gly Pro Leu Tyr Ile  Pro Glu Pro Ser Val  Thr Asn Ser
    1205                1210                1215

Lys Met  Arg Val Pro Tyr Leu  Gly Ser Lys Thr Glu  Glu Arg Lys
    1220                1225                1230

Thr Ala  Ser Met Ala Ala Ile  Lys Gly Met Ser His  His Leu Arg
    1235                1240                1245

Ala Val  Leu Arg Gly Thr Ser  Val Phe Ile Trp Ala  Phe Gly Asp
    1250                1255                1260
```

```
Thr Asp  Ile Asn Trp Asp Asn  Ala Leu Gln Ile Ala  Gln Ser Arg
    1265                 1270                 1275

Cys Asn  Ile Thr Leu Asp Gln  Met Arg Leu Leu Thr  Pro Ile Pro
    1280                 1285                 1290

Ser Ser  Ser Asn Ile Gln His  Arg Leu Asp Asp Gly  Ile Ser Thr
    1295                 1300                 1305

Gln Lys  Phe Thr Pro Ala Ser  Leu Ala Arg Ile Thr  Ser Phe Val
    1310                 1315                 1320

His Ile  Cys Asn Asp Ser Gln  Arg Leu Glu Lys Asp  Gly Ser Ser
    1325                 1330                 1335

Val Asp  Ser Asn Leu Ile Tyr  Gln Gln Ile Met Leu  Leu Gly Leu
    1340                 1345                 1350

Ser Ile  Phe Glu Thr Met Tyr  Ser Met Asp Gln Lys  Trp Val Phe
    1355                 1360                 1365

Asn Asn  His Thr Leu His Leu  His Thr Gly His Ser  Cys Cys Pro
    1370                 1375                 1380

Arg Glu  Leu Asp Ile Ser Leu  Val Asn Pro Pro Arg  His Gln Thr
    1385                 1390                 1395

Pro Glu  Leu Thr Ser Thr Thr  Thr Asn Pro Phe Leu  Tyr Asp Gln
    1400                 1405                 1410

Leu Pro  Leu Asn Gln Asp Asn  Leu Thr Thr Leu Glu  Ile Lys Thr
    1415                 1420                 1425

Phe Lys  Phe Asn Glu Leu Asn  Ile Asp Gly Leu Asp  Phe Gly Glu
    1430                 1435                 1440

Gly Ile  Gln Leu Leu Ser Arg  Cys Thr Ala Arg Leu  Met Ala Glu
    1445                 1450                 1455

Cys Ile  Leu Glu Glu Gly Ile  Gly Ser Ser Val Lys  Asn Glu Ala
    1460                 1465                 1470

Ile Val  Asn Phe Asp Asn Ser  Val Asn Trp Ile Ser  Glu Cys Leu
    1475                 1480                 1485

Met Cys  Asp Ile Arg Ser Leu  Cys Val Asn Leu Gly  Gln Glu Ile
    1490                 1495                 1500

Leu Cys  Ser Leu Ala Tyr Gln  Met Tyr Tyr Leu Arg  Ile Arg Gly
    1505                 1510                 1515

Arg Arg  Ala Ile Leu Asn Tyr  Leu Asp Thr Thr Leu  Gln Arg Ile
    1520                 1525                 1530

Pro Val  Ile Gln Leu Ala Asn  Ile Ala Leu Thr Ile  Ser His Pro
    1535                 1540                 1545

Glu Ile  Phe Arg Arg Ile Val  Asn Thr Gly Ile His  Asn Gln Ile
    1550                 1555                 1560

Lys Gly  Pro Tyr Val Ala Thr  Thr Asp Phe Ile Ala  Ala Ser Arg
    1565                 1570                 1575

Asp Ile  Ile Leu Ser Gly Ala  Arg Glu Tyr Leu Ser  Tyr Leu Ser
    1580                 1585                 1590

Ser Gly  Gln Glu Asp Cys Tyr  Thr Phe Phe Asn Cys  Gln Asp Gly
    1595                 1600                 1605

Asp Leu  Thr Pro Lys Met Glu  Gln Tyr Leu Ala Arg  Arg Ala Cys
    1610                 1615                 1620

Leu Leu  Thr Leu Leu Tyr Asn  Thr Gly His Gln Ile  Pro Ile Ile
    1625                 1630                 1635

Arg Ser  Leu Thr Pro Ile Glu  Lys Cys Lys Val Leu  Thr Glu Tyr
    1640                 1645                 1650

Asn Gln  Gln Ile Glu Tyr Ala  Asp Gln Glu Phe Ser  Ser Val Leu
```

```
    1655                1660                1665

Lys Val  Val Asn Ala Leu Leu  Gln Asn Pro Asn Ile  Asp Ala Leu
    1670                1675                1680

Val Ser  Asn Leu Tyr Phe Thr  Thr Arg Arg Val Leu  Ser Asn Leu
    1685                1690                1695

Arg Ser  Cys Asp Lys Ala Ile  Ser Tyr Ile Glu Tyr  Leu Tyr Thr
    1700                1705                1710

Glu Asp  Phe Gly Glu Lys Glu  Asp Thr Val Gln Tyr  Asp Ile Met
    1715                1720                1725

Thr Thr  Asn Asp Ile Ile Leu  Thr His Gly Leu Phe  Thr Gln Ile
    1730                1735                1740

Glu Ile  Ser Tyr Gln Gly Ser  Ser Leu His Lys Phe  Leu Thr Pro
    1745                1750                1755

Asp Asn  Ala Pro Gly Ser Leu  Ile Pro Phe Ser Ile  Ser Pro Asn
    1760                1765                1770

Ser Leu  Ala Cys Asp Pro Leu  His His Leu Leu Lys  Ser Val Gly
    1775                1780                1785

Thr Ser  Ser Thr Ser Trp Tyr  Lys Tyr Ala Ile Ala  Tyr Ala Val
    1790                1795                1800

Ser Glu  Lys Arg Ser Ala Arg  Leu Gly Gly Ser Leu  Tyr Ile Gly
    1805                1810                1815

Glu Gly  Ser Gly Ser Val Met  Thr Leu Leu Glu Tyr  Leu Glu Pro
    1820                1825                1830

Ser Val  Asp Ile Phe Tyr Asn  Ser Leu Phe Ser Asn  Gly Met Asn
    1835                1840                1845

Pro Pro  Gln Arg Asn Tyr Gly  Leu Met Pro Leu Gln  Phe Val Asn
    1850                1855                1860

Ser Val  Val Tyr Lys Asn Leu  Thr Ala Lys Ser Glu  Cys Lys Leu
    1865                1870                1875

Gly Phe  Val Gln Gln Phe Lys  Pro Leu Trp Arg Asp  Ile Asp Ile
    1880                1885                1890

Glu Thr  Asn Val Thr Asp Pro  Ser Phe Val Asn Phe  Ala Leu Asn
    1895                1900                1905

Glu Ile  Pro Met Gln Ser Leu  Lys Arg Val Asn Cys  Asp Val Glu
    1910                1915                1920

Phe Asp  Arg Gly Met Pro Ile  Glu Arg Val Ile Gln  Gly Tyr Thr
    1925                1930                1935

His Ile  Leu Leu Val Ala Thr  Tyr Gly Leu Gln Gln  Asp Ser Ile
    1940                1945                1950

Leu Trp  Val Lys Val Tyr Arg  Thr Ser Glu Lys Val  Phe Gln Phe
    1955                1960                1965

Leu Leu  Ser Ala Met Ile Met  Ile Phe Gly Tyr Val  Lys Ile His
    1970                1975                1980

Arg Asn  Gly Tyr Met Ser Ala  Lys Asp Glu Glu Tyr  Ile Leu Met
    1985                1990                1995

Ser Asp  Cys Lys Glu Pro Val  Asn Tyr Thr Ala Val  Pro Asn Ile
    2000                2005                2010

Leu Thr  Arg Val Ser Asp Leu  Val Ser Lys Asn Leu  Ser Leu Ile
    2015                2020                2025

His Pro  Glu Asp Leu Arg Lys  Val Arg Cys Glu Thr  Asp Ser Leu
    2030                2035                2040

Asn Leu  Lys Cys Asn His Ile  Tyr Glu Lys Ile Ile  Ala Arg Lys
    2045                2050                2055
```

```
Ile Pro  Leu Gln Val Ser Ser  Thr Asp Ser Leu Leu  Leu Gln Leu
    2060                 2065                 2070

Gly Gly  Val Ile Asn Ser Val  Gly Ser Thr Asp Pro  Arg Glu Val
    2075                 2080                 2085

Ala Thr  Leu Ser Ser Ile Glu  Cys Met Asp Tyr Val  Val Ser Ser
    2090                 2095                 2100

Ile Asp  Leu Ala Ile Leu Glu  Ala Asn Ile Val Ile  Ser Glu Ser
    2105                 2110                 2115

Ala Gly  Leu Asp Leu Ala Leu  Met Leu Gly Pro Phe  Asn Leu Asn
    2120                 2125                 2130

Lys Leu  Lys Lys Ile Asp Thr  Ile Leu Lys Ser Ser  Thr Tyr Gln
    2135                 2140                 2145

Leu Ile  Pro Tyr Trp Leu Arg  Tyr Glu Tyr Ser Ile  Asn Pro Arg
    2150                 2155                 2160

Ser Leu  Ser Phe Leu Ile Thr  Lys Leu Gln Gln Cys  Arg Ile Ser
    2165                 2170                 2175

Trp Ser  Asp Met Ile Thr Ile  Ser Glu Phe Cys Lys  Lys Ser Lys
    2180                 2185                 2190

Arg Pro  Ile Phe Ile Lys Arg  Val Ile Gly Asn Gln  Gln Leu Lys
    2195                 2200                 2205

Ser Phe  Phe Asn Glu Ser Ser  Ser Ile Val Leu Thr  Arg Ala Glu
    2210                 2215                 2220

Val Lys  Val Cys Ile Lys Phe  Leu Gly Ala Ile Ile  Lys Leu Lys
    2225                 2230                 2235
```

<210> SEQ ID NO 77
<211> LENGTH: 1570
<212> TYPE: DNA
<213> ORGANISM: artificial sequence
<220> FEATURE:
<223> OTHER INFORMATION: NP gene of FJ619036

<400> SEQUENCE: 77

```
gggggcgaag caagtggatc tcgggctcga ggccgaaaca ctggatttcg ctggaggttt     60

tgaataggtc gctataagac tcaatatgtc atctgtattc aatgaatatc aggcacttca    120

agaacaactt gtaaagccgg ctgtcaggag acctgatgtt gcctcaacag gtttactcag    180

ggcggaaata cctgtctgtg ttacattgtc tcaagacccc ggtgagagat ggagccttgc    240

ttgccttaat atccgatggc ttgtgagtga ttcatcaacc acaccaatga agcagggagc    300

aatattgtca ctgctgagtc tacattcaga caatatgcga gctcacgcaa cattagcagc    360

aaggtctgca gatgcttcac tcaccatact tgaggtagat gaagtagata ttggcaactc    420

cctaatcaaa ttcaacgcta gaagtggtgt atctgataaa cgatcaaatc aattgcttgc    480

aattgcggat gacatcccca aaagttgcag taatgggcat ccatttcttg acacagacat    540

tgagaccaga gacccgctcg atctatcaga gaccatagac cgcctgcagg gtattgcagc    600

tcagatatgg gtgtcagcca taaagagcat gacagcgcct gacaccgcat cagagtcaga    660

aagtaagagg ctggccaaat accaacaaca aggccgactg gttaagcaag tacttttgca    720

ttctgtagtc aggacagaat ttatgagagt tattcggggc agcttggtac tgcgccagtt    780

tatggttagc gagtgcaaga gggcttcagc catgggcgga gacacatcta ggtactatgc    840

tatggtgggt gacatcagtc tgtacatcaa gaatgcagga ttgactgcat tttcctcac     900

cctgaagttc ggggttggta cccagtatcc aaccttagca atgagtgttt tctccagtga    960

ccttaaaaga cttgctgcac tcatcaggct gtacaaaacc aagggagaca atgcaccata   1020
```

-continued

```
catggcattc ctggaggact ccgatatggg aaattttgct ccagcaaatt atagcacaat   1080

gtactcttat gccatgggca ttgggacgat tctggaagca tctgtatctc gataccagta   1140

tgctagagac tttaccagtg agaattattt ccgtcttgga gttgagacag cccaaagcca   1200

gcagggagcg tttgacgaga gaacagcccg agagatgggc ttgactgagg aatccaaaca   1260

gcaggttaga tcactgctaa tgtcagtaga catgggtccc agttcagttc gcgagccatc   1320

ccgccctgca ttcatcagtc aagaagaaaa taggcagcct gcccagaatt cttcagatac   1380

tcagggtcag accaagccag tcccgaatca acccgcacca agggccgacc cagatgacat   1440

tgatccatac gagaacgggc tagaatggta attcaatcac ctcgacacat ccacctatac   1500

accaattctg tgacatatta acctaatcaa acatttcata aactatagta gtcattgatt   1560

taagaaaaaa                                                          1570


<210> SEQ ID NO 78
<211> LENGTH: 461
<212> TYPE: PRT
<213> ORGANISM: artificial sequence
<220> FEATURE:
<223> OTHER INFORMATION: NP protein of ACN88139

<400> SEQUENCE: 78

Met Ser Ser Val Phe Asn Glu Tyr Gln Ala Leu Gln Glu Gln Leu Val
1               5                   10                  15

Lys Pro Ala Val Arg Arg Pro Asp Val Ala Ser Thr Gly Leu Leu Arg
            20                  25                  30

Ala Glu Ile Pro Val Cys Val Thr Leu Ser Gln Asp Pro Gly Glu Arg
        35                  40                  45

Trp Ser Leu Ala Cys Leu Asn Ile Arg Trp Leu Val Ser Asp Ser Ser
    50                  55                  60

Thr Thr Pro Met Lys Gln Gly Ala Ile Leu Ser Leu Leu Ser Leu His
65                  70                  75                  80

Ser Asp Asn Met Arg Ala His Ala Thr Leu Ala Ala Arg Ser Ala Asp
                85                  90                  95

Ala Ser Leu Thr Ile Leu Glu Val Asp Glu Val Asp Ile Gly Asn Ser
            100                 105                 110

Leu Ile Lys Phe Asn Ala Arg Ser Gly Val Ser Asp Lys Arg Ser Asn
        115                 120                 125

Gln Leu Leu Ala Ile Ala Asp Asp Ile Pro Lys Ser Cys Ser Asn Gly
    130                 135                 140

His Pro Phe Leu Asp Thr Asp Ile Glu Thr Arg Asp Pro Leu Asp Leu
145                 150                 155                 160

Ser Glu Thr Ile Asp Arg Leu Gln Gly Ile Ala Ala Gln Ile Trp Val
                165                 170                 175

Ser Ala Ile Lys Ser Met Thr Ala Pro Asp Thr Ala Ser Glu Ser Glu
            180                 185                 190

Ser Lys Arg Leu Ala Lys Tyr Gln Gln Gln Gly Arg Leu Val Lys Gln
        195                 200                 205

Val Leu Leu His Ser Val Val Arg Thr Glu Phe Met Arg Val Ile Arg
    210                 215                 220

Gly Ser Leu Val Leu Arg Gln Phe Met Val Ser Glu Cys Lys Arg Ala
225                 230                 235                 240

Ser Ala Met Gly Gly Asp Thr Ser Arg Tyr Tyr Ala Met Val Gly Asp
                245                 250                 255

Ile Ser Leu Tyr Ile Lys Asn Ala Gly Leu Thr Ala Phe Phe Leu Thr
            260                 265                 270
```

```
Leu Lys Phe Gly Val Gly Thr Gln Tyr Pro Thr Leu Ala Met Ser Val
        275                 280                 285

Phe Ser Ser Asp Leu Lys Arg Leu Ala Ala Leu Ile Arg Leu Tyr Lys
    290                 295                 300

Thr Lys Gly Asp Asn Ala Pro Tyr Met Ala Phe Leu Glu Asp Ser Asp
305                 310                 315                 320

Met Gly Asn Phe Ala Pro Ala Asn Tyr Ser Thr Met Tyr Ser Tyr Ala
                325                 330                 335

Met Gly Ile Gly Thr Ile Leu Glu Ala Ser Val Ser Arg Tyr Gln Tyr
            340                 345                 350

Ala Arg Asp Phe Thr Ser Glu Asn Tyr Phe Arg Leu Gly Val Glu Thr
        355                 360                 365

Ala Gln Ser Gln Gln Gly Ala Phe Asp Glu Arg Thr Ala Arg Glu Met
    370                 375                 380

Gly Leu Thr Glu Glu Ser Lys Gln Gln Val Arg Ser Leu Leu Met Ser
385                 390                 395                 400

Val Asp Met Gly Pro Ser Ser Val Arg Glu Pro Ser Arg Pro Ala Phe
                405                 410                 415

Ile Ser Gln Glu Glu Asn Arg Gln Pro Ala Gln Asn Ser Ser Asp Thr
            420                 425                 430

Gln Gly Gln Thr Lys Pro Val Pro Asn Gln Pro Ala Pro Arg Ala Asp
        435                 440                 445

Pro Asp Asp Ile Asp Pro Tyr Glu Asn Gly Leu Glu Trp
    450                 455                 460
```

<210> SEQ ID NO 79
<211> LENGTH: 1374
<212> TYPE: DNA
<213> ORGANISM: artificial sequence
<220> FEATURE:
<223> OTHER INFORMATION: P gene of FJ619036

<400> SEQUENCE: 79

```
gggggcgacc tcaactgtga aacacgccag atctgtccac aacaccactc aacaacccac      60

acaagatgga cttcgccaat gatgaagaaa ttgcagaact tctgaacctc agcaccactg     120

taatcaagga gattcagaaa tctgaactca agcctcccca aaccactggg cgaccacctg     180

tcagtcaagg gaacacaaga aatctaactg atctatggga aaaggagact gcaagtcaga     240

acaagacatc ggctcaatct ccacaaacca cacaagttca gtctgatgga aatgaggagg     300

aagaaatcaa atcagagtca attgatggcc acatcagtgg aactgttaat caattagagc     360

aagtcccaga acaaaaccag agcagatctt caccaggtga tgatctcgac agagctctca     420

acaagcttga agggagaatc aactcaatca gctcaatgga taaagaaatt aaaaagggcc     480

ctcgcatcca gaatctccct gggtcccaag cagcaactca acaggcgacc cacccattgg     540

caggggacac cccgaacatg caggcacgga caaaacccct gaccaagcca catcaagagg     600

caatcaatcc tggcaaccag gacacaggag agaatattca tttaccacct tccatggcac     660

caccagagtc attagttggt gcaatccgca atgtacccca attcgtgcca gaccaatcta     720

tgacgaatgt agatgcgggg agtgtccaac tacatgcatc atgtgcagag atgataagta     780

gaatgcttgt agaagttata tctaagcttg ataaactcga gtcgagactg aatgatatag     840

caaaagttgt aaacaccacc ccccttatca ggaatgatat taaccaactt aaggccacaa     900

ctgcactgat gtccaaccaa attgcttcca tacaaattct tgacccaggg aatgcagggg     960

tgaggtccct ctctgaaatg agatctgtga cgaagaaagc tgctgttgta attgcaggat    1020
```

```
ttggagacga cccaactcaa attattgaag aaggtatcat ggccaaagat gctcttggaa   1080

aacctgtgcc tccaacatct gttatcgcag ccaaagctca gacttcttcc ggtgtgagta   1140

agggtgaaat agaaggattg attgcattgg tggaaacatt agttgacaat gacaagaagg   1200

cagcgaaact gattaaaatg attgatcaag ttaaatccca cgccgattac gcccgagtca   1260

agcaggcaat atataatgca taatattgta attatacaaa caatcaatac tgctgtcggt   1320

tgcacccacc ttagcaaatc aataatcttt taaaattgat tgattaagaa aaaa         1374
```

<210> SEQ ID NO 80
<211> LENGTH: 405
<212> TYPE: PRT
<213> ORGANISM: artificial sequence
<220> FEATURE:
<223> OTHER INFORMATION: P protein of ACN88140

<400> SEQUENCE: 80

```
Met Asp Phe Ala Asn Asp Glu Glu Ile Ala Glu Leu Leu Asn Leu Ser
1               5                   10                  15

Thr Thr Val Ile Lys Glu Ile Gln Lys Ser Glu Leu Lys Pro Pro Gln
            20                  25                  30

Thr Thr Gly Arg Pro Pro Val Ser Gln Gly Asn Thr Arg Asn Leu Thr
        35                  40                  45

Asp Leu Trp Glu Lys Glu Thr Ala Ser Gln Asn Lys Thr Ser Ala Gln
    50                  55                  60

Ser Pro Gln Thr Thr Gln Val Gln Ser Asp Gly Asn Glu Glu Glu Glu
65                  70                  75                  80

Ile Lys Ser Glu Ser Ile Asp Gly His Ile Ser Gly Thr Val Asn Gln
                85                  90                  95

Leu Glu Gln Val Pro Glu Gln Asn Gln Ser Arg Ser Ser Pro Gly Asp
            100                 105                 110

Asp Leu Asp Arg Ala Leu Asn Lys Leu Glu Gly Arg Ile Asn Ser Ile
        115                 120                 125

Ser Ser Met Asp Lys Glu Ile Lys Lys Gly Pro Arg Ile Gln Asn Leu
    130                 135                 140

Pro Gly Ser Gln Ala Ala Thr Gln Gln Ala Thr His Pro Leu Ala Gly
145                 150                 155                 160

Asp Thr Pro Asn Met Gln Ala Arg Thr Lys Pro Leu Thr Lys Pro His
                165                 170                 175

Gln Glu Ala Ile Asn Pro Gly Asn Gln Asp Thr Gly Glu Asn Ile His
            180                 185                 190

Leu Pro Pro Ser Met Ala Pro Pro Glu Ser Leu Val Gly Ala Ile Arg
        195                 200                 205

Asn Val Pro Gln Phe Val Pro Asp Gln Ser Met Thr Asn Val Asp Ala
    210                 215                 220

Gly Ser Val Gln Leu His Ala Ser Cys Ala Glu Met Ile Ser Arg Met
225                 230                 235                 240

Leu Val Glu Val Ile Ser Lys Leu Asp Lys Leu Glu Ser Arg Leu Asn
                245                 250                 255

Asp Ile Ala Lys Val Val Asn Thr Thr Pro Leu Ile Arg Asn Asp Ile
            260                 265                 270

Asn Gln Leu Lys Ala Thr Thr Ala Leu Met Ser Asn Gln Ile Ala Ser
        275                 280                 285

Ile Gln Ile Leu Asp Pro Gly Asn Ala Gly Val Arg Ser Leu Ser Glu
    290                 295                 300
```

```
Met Arg Ser Val Thr Lys Lys Ala Ala Val Val Ile Ala Gly Phe Gly
305                 310                 315                 320

Asp Asp Pro Thr Gln Ile Ile Glu Glu Gly Ile Met Ala Lys Asp Ala
                325                 330                 335

Leu Gly Lys Pro Val Pro Pro Thr Ser Val Ile Ala Ala Lys Ala Gln
            340                 345                 350

Thr Ser Ser Gly Val Ser Lys Gly Glu Ile Glu Gly Leu Ile Ala Leu
        355                 360                 365

Val Glu Thr Leu Val Asp Asn Asp Lys Lys Ala Ala Lys Leu Ile Lys
    370                 375                 380

Met Ile Asp Gln Val Lys Ser His Ala Asp Tyr Ala Arg Val Lys Gln
385                 390                 395                 400

Ala Ile Tyr Asn Ala
                405
```

```
<210> SEQ ID NO 81
<211> LENGTH: 1110
<212> TYPE: DNA
<213> ORGANISM: artificial sequence
<220> FEATURE:
<223> OTHER INFORMATION: M gene of FJ619036

<400> SEQUENCE: 81

atggcatata caacactaaa actgtgggtg gatgagggtg acatgtcgtc ttcgcttcta     60

tcattcccgt tggtactaaa agagacagac agaggcacaa agaagcttca accacaggta    120

agggtagatt caattggcga tgtgcagaat gccaaagagt cctcgatatt cgtgactcta    180

tatggtttca tccaagcaat taaggagaat tcagatcgat cgaaattctt ccatccaaaa    240

gatgacttca aacctgagac agtcactgca ggactggtag tagtgggtgc aatccgaatg    300

atggctgatg tcaataccat ctctaatgat gcactagcgc tggagatcac tgttaagaaa    360

tctgcaactt ctcaagagaa aatgacggtg atgttccaca atagcccccc ttcattgaga    420

actgcaataa ctatccgagc aggaggtttc atctcgaatg cagacgaaaa tataaaatgt    480

gccagcaagt tgactgcagg agtgcagtac atattccgtc caatgtttgt ttcaatcact    540

aaattacaca atggcaaact atatagggtg cccaaaagta tccacagcat ctcgtctacc    600

ctactgtata gtgtgatgtt ggaggtagga ttcaaagtgg acatcgggaa ggatcatccc    660

caggcaaaaa tgctgaagag ggtcacaatt ggcgatgcag acacatactg gggatttgca    720

tggttccacc tgtgcaattt caaaaagaca tcctctaagg gaaagccgag aacgctagac    780

gaactgagga caaaagtcaa aaatatgggg ttgaaattgg agttacatga cctatggggt    840

ccgactattg tggtccaaat cactggcaag agcagcaaat atgctcaagg attttttttct    900

tccaatggta cttgttgcct cccaatcagc agatctgcac cagagcttgg gaagcttctg    960

tggtcctgct cagcaactat tggtgacgca acagttgtta tccaatcaag cgagaagggg   1020

gaactcctaa ggtctgatga tctcgagata cgaggtgctg tggcctccaa gaaaggtaga   1080

ctgagctcat ttcacccctt caaaaaatga                                    1110
```

```
<210> SEQ ID NO 82
<211> LENGTH: 369
<212> TYPE: PRT
<213> ORGANISM: artificial sequence
<220> FEATURE:
<223> OTHER INFORMATION: M protein of ACN88143

<400> SEQUENCE: 82

Met Ala Tyr Thr Thr Leu Lys Leu Trp Val Asp Glu Gly Asp Met Ser
```

```
1               5                   10                  15

Ser Ser Leu Leu Ser Phe Pro Leu Val Leu Lys Glu Thr Asp Arg Gly
            20                  25                  30

Thr Lys Lys Leu Gln Pro Gln Val Arg Val Asp Ser Ile Gly Asp Val
        35                  40                  45

Gln Asn Ala Lys Glu Ser Ser Ile Phe Val Thr Leu Tyr Gly Phe Ile
    50                  55                  60

Gln Ala Ile Lys Glu Asn Ser Asp Arg Ser Lys Phe Phe His Pro Lys
65                  70                  75                  80

Asp Asp Phe Lys Pro Glu Thr Val Thr Ala Gly Leu Val Val Val Gly
                85                  90                  95

Ala Ile Arg Met Met Ala Asp Val Asn Thr Ile Ser Asn Asp Ala Leu
            100                 105                 110

Ala Leu Glu Ile Thr Val Lys Lys Ser Ala Thr Ser Gln Glu Lys Met
        115                 120                 125

Thr Val Met Phe His Asn Ser Pro Pro Ser Leu Arg Thr Ala Ile Thr
    130                 135                 140

Ile Arg Ala Gly Gly Phe Ile Ser Asn Ala Asp Glu Asn Ile Lys Cys
145                 150                 155                 160

Ala Ser Lys Leu Thr Ala Gly Val Gln Tyr Ile Phe Arg Pro Met Phe
                165                 170                 175

Val Ser Ile Thr Lys Leu His Asn Gly Lys Leu Tyr Arg Val Pro Lys
            180                 185                 190

Ser Ile His Ser Ile Ser Ser Thr Leu Leu Tyr Ser Val Met Leu Glu
        195                 200                 205

Val Gly Phe Lys Val Asp Ile Gly Lys Asp His Pro Gln Ala Lys Met
    210                 215                 220

Leu Lys Arg Val Thr Ile Gly Asp Ala Asp Thr Tyr Trp Gly Phe Ala
225                 230                 235                 240

Trp Phe His Leu Cys Asn Phe Lys Lys Thr Ser Ser Lys Gly Lys Pro
                245                 250                 255

Arg Thr Leu Asp Glu Leu Arg Thr Lys Val Lys Asn Met Gly Leu Lys
            260                 265                 270

Leu Glu Leu His Asp Leu Trp Gly Pro Thr Ile Val Val Gln Ile Thr
        275                 280                 285

Gly Lys Ser Ser Lys Tyr Ala Gln Gly Phe Phe Ser Ser Asn Gly Thr
    290                 295                 300

Cys Cys Leu Pro Ile Ser Arg Ser Ala Pro Glu Leu Gly Lys Leu Leu
305                 310                 315                 320

Trp Ser Cys Ser Ala Thr Ile Gly Asp Ala Thr Val Val Ile Gln Ser
                325                 330                 335

Ser Glu Lys Gly Glu Leu Leu Arg Ser Asp Asp Leu Glu Ile Arg Gly
            340                 345                 350

Ala Val Ala Ser Lys Lys Gly Arg Leu Ser Ser Phe His Pro Phe Lys
        355                 360                 365

Lys
```

<210> SEQ ID NO 83
<211> LENGTH: 1632
<212> TYPE: DNA
<213> ORGANISM: artificial sequence
<220> FEATURE:
<223> OTHER INFORMATION: F gene of FJ619036

<400> SEQUENCE: 83

-continued

```
atgggtaaaa tatcaatata tctaattaat agcgtgctat tattgctggt atatcctgtg     60

aattcgattg acaatacact cgttgcccca atcggagtcg ccagcgcaaa tgaatggcag    120

cttgctgcat atacaacatc actttcaggg acaattgccg tgcgattcct acctgtgctc    180

ccggataata tgactacctg tcttagagaa acaataacta catataataa tactgtcaac    240

aacatcttag gcccactcaa atccaatctg gatgcactgc tctcatctga gacttatccc    300

cagacaagat taattggggc agttataggt tcaattgctc ttggtgttgc aacatcggct    360

caaatcactg ctgcagtcgc tctcaagcaa gcacaagata atgcaagaaa catactggca    420

ctcaaagagg cactgtccaa aactaatgag gcggtcaagg agcttagcag tggattgcaa    480

caaacagcta ttgcacttgg taagatacag agctttgtga atgaggaaat tctgccatct    540

atcaaccaac tgagctgcga ggtgacagcc aataaacttg ggtgtatttt atctctgtat    600

ctcacagaac tgaccactat attcggtgca cagttgacta accctgcatt gacttcatta    660

tcatatcaag cgctgtacaa cctgtgtggt ggcaacatgg caatgcttac tcagaagatt    720

ggaattaaac agcaagacgt taattcgcta tatgaagccg gactaatcac aggacaagtc    780

attggttatg actctcagta ccagctgctg gtcatccagg tcaattatcc aagcatttct    840

gaggtaactg gtgtgcgtgc gacagaatta gtcactgtta gtgtaacaac agacaagggt    900

gaagggaaag caattgtacc ccaatttgta gctgaaagtc gggtgactat tgaggagctt    960

gatgtagcat cttgtaaatt cagcagcaca accctatact gcaggcaggt caacacaagg   1020

gcacttcccc cgctagtggc tagctgtctc cgaggtaact atgatgattg tcaatatacc   1080

acagagattg gagcattatc atcccggtat ataacactag atggaggggt cttagtcaat   1140

tgtaagtcaa ttgtttgtag gtgccttaat ccaagtaaga tcatctctca aaatacaaat   1200

gctgcagtaa catatgttga tgctacaata tgcaaaacaa ttcaattgga tgacatacaa   1260

ctccagttgg aagggtcact atcatcagtt tatgcaagga acatctcaat tgagatcagt   1320

caggtgacta cctccggttc tttggatatc agcagtgaga tagggaacat caataatacg   1380

gtgaatcgtg tggaggattt aatccaccaa tcggaggaat ggctggcaaa agttaaccca   1440

cacattgtta ataatactac actaattgta ctctgtgtgt taagtgcgct tgctgtgatc   1500

tggctggcag tattaacggc tattataata tacttgagaa caaagttgaa gactatatcg   1560

gcattggctg taaccaatac aatacagtct aatccctatg ttaaccaaac gaaacgtgaa   1620

tctaagtttt ga                                                       1632
```

<210> SEQ ID NO 84
<211> LENGTH: 543
<212> TYPE: PRT
<213> ORGANISM: artificial sequence
<220> FEATURE:
<223> OTHER INFORMATION: F protein of ACN88144

<400> SEQUENCE: 84

```
Met Gly Lys Ile Ser Ile Tyr Leu Ile Asn Ser Val Leu Leu Leu Leu
1               5                   10                  15

Val Tyr Pro Val Asn Ser Ile Asp Asn Thr Leu Val Ala Pro Ile Gly
            20                  25                  30

Val Ala Ser Ala Asn Glu Trp Gln Leu Ala Ala Tyr Thr Thr Ser Leu
        35                  40                  45

Ser Gly Thr Ile Ala Val Arg Phe Leu Pro Val Leu Pro Asp Asn Met
    50                  55                  60

Thr Thr Cys Leu Arg Glu Thr Ile Thr Thr Tyr Asn Asn Thr Val Asn
65                  70                  75                  80
```

```
Asn Ile Leu Gly Pro Leu Lys Ser Asn Leu Asp Ala Leu Leu Ser Ser
                85                  90                  95

Glu Thr Tyr Pro Gln Thr Arg Leu Ile Gly Ala Val Ile Gly Ser Ile
            100                 105                 110

Ala Leu Gly Val Ala Thr Ser Ala Gln Ile Thr Ala Ala Val Ala Leu
        115                 120                 125

Lys Gln Ala Gln Asp Asn Ala Arg Asn Ile Leu Ala Leu Lys Glu Ala
    130                 135                 140

Leu Ser Lys Thr Asn Glu Ala Val Lys Glu Leu Ser Ser Gly Leu Gln
145                 150                 155                 160

Gln Thr Ala Ile Ala Leu Gly Lys Ile Gln Ser Phe Val Asn Glu Glu
                165                 170                 175

Ile Leu Pro Ser Ile Asn Gln Leu Ser Cys Glu Val Thr Ala Asn Lys
            180                 185                 190

Leu Gly Val Tyr Leu Ser Leu Tyr Leu Thr Glu Leu Thr Thr Ile Phe
        195                 200                 205

Gly Ala Gln Leu Thr Asn Pro Ala Leu Thr Ser Leu Ser Tyr Gln Ala
    210                 215                 220

Leu Tyr Asn Leu Cys Gly Gly Asn Met Ala Met Leu Thr Gln Lys Ile
225                 230                 235                 240

Gly Ile Lys Gln Gln Asp Val Asn Ser Leu Tyr Glu Ala Gly Leu Ile
                245                 250                 255

Thr Gly Gln Val Ile Gly Tyr Asp Ser Gln Tyr Gln Leu Leu Val Ile
            260                 265                 270

Gln Val Asn Tyr Pro Ser Ile Ser Glu Val Thr Gly Val Arg Ala Thr
        275                 280                 285

Glu Leu Val Thr Val Ser Val Thr Thr Asp Lys Gly Glu Gly Lys Ala
    290                 295                 300

Ile Val Pro Gln Phe Val Ala Glu Ser Arg Val Thr Ile Glu Glu Leu
305                 310                 315                 320

Asp Val Ala Ser Cys Lys Phe Ser Ser Thr Thr Leu Tyr Cys Arg Gln
                325                 330                 335

Val Asn Thr Arg Ala Leu Pro Pro Leu Val Ala Ser Cys Leu Arg Gly
            340                 345                 350

Asn Tyr Asp Asp Cys Gln Tyr Thr Thr Glu Ile Gly Ala Leu Ser Ser
        355                 360                 365

Arg Tyr Ile Thr Leu Asp Gly Gly Val Leu Val Asn Cys Lys Ser Ile
    370                 375                 380

Val Cys Arg Cys Leu Asn Pro Ser Lys Ile Ile Ser Gln Asn Thr Asn
385                 390                 395                 400

Ala Ala Val Thr Tyr Val Asp Ala Thr Ile Cys Lys Thr Ile Gln Leu
                405                 410                 415

Asp Asp Ile Gln Leu Gln Leu Glu Gly Ser Leu Ser Ser Val Tyr Ala
            420                 425                 430

Arg Asn Ile Ser Ile Glu Ile Ser Gln Val Thr Thr Ser Gly Ser Leu
        435                 440                 445

Asp Ile Ser Ser Glu Ile Gly Asn Ile Asn Asn Thr Val Asn Arg Val
    450                 455                 460

Glu Asp Leu Ile His Gln Ser Glu Glu Trp Leu Ala Lys Val Asn Pro
465                 470                 475                 480

His Ile Val Asn Asn Thr Thr Leu Ile Val Leu Cys Val Leu Ser Ala
                485                 490                 495

Leu Ala Val Ile Trp Leu Ala Val Leu Thr Ala Ile Ile Ile Tyr Leu
```

```
            500                 505                 510

Arg Thr Lys Leu Lys Thr Ile Ser Ala Leu Ala Val Thr Asn Thr Ile
        515                 520                 525

Gln Ser Asn Pro Tyr Val Asn Gln Thr Lys Arg Glu Ser Lys Phe
    530                 535                 540


<210> SEQ ID NO 85
<211> LENGTH: 1734
<212> TYPE: DNA
<213> ORGANISM: artificial sequence
<220> FEATURE:
<223> OTHER INFORMATION: HN gene of FJ619036

<400> SEQUENCE: 85

atgagtaaca ttgcatccag tttagaaaat attgtggagc aggatagtcg aaaaacaact      60

tggagggcca tctttagatg gtccgttctt cttattacaa caggatgctt agccttatcc     120

attgttagca tagttcaaat tgggaatttg aaaattcctt ctgtagggga tctggcggac     180

gaggtggtaa cacctttgaa aaccactctg tctgatacac tcaggaatcc aattaaccag     240

ataaatgaca tattcaggat tgttgccctt gatattccat tgcaagtaac tagtatccaa     300

aaagacctcg caagtcaatt tagcatgttg atagatagtt taaatgctat caaattgggc     360

aacgggacca accttatcat acctacatca gataaggagt atgcaggagg aattggaaac     420

cctgtcttta ctgtcgatgc tggaggttct ataggattca agcaatttag cttaatagaa     480

catccgagct ttattgctgg acctacaacg acccgaggct gtacaagaat acccactttt     540

cacatgtcag aaagtcattg gtgctactca cacaacatca tcgctgctgg ctgtcaagat     600

gccagtgcat ctagtatgta tatctcaatg gggttctcc atgtgtcttc atctggcact     660

cctatctttc ttactactgc aagtgaactg atagacgatg gagttaatcg taagtcatgc     720

agtattgtag caacccaatt cggctgtgac attttgtgca gtattgtcat agagaaggag     780

ggagatgatt attggtctga tactccgact ccaatgcgcc acggccgttt ttcattcaat     840

gggagttttg tagaaaccga actacccgtg tccagtatgt tctcgtcatt ctctgccaac     900

taccctgctg tgggatcagg cgaaattgta aaagatagaa tattattccc aatttacgga     960

ggtataaagc agacttcacc agagtttacc gaattagtga aatatggact ctttgtgtca    1020

acacctacaa ctgtatgtca gagtagctgg acttatgacc aggtaaaagc agcgtatagg    1080

ccagattaca tatcaggccg gttctgggca caagtgatac tcagctgcgc tcttgatgca    1140

gtcgacttat caagttgtat tgtaaagatt atgaatagca gcacagtgat gatggcagca    1200

gaaggaagga taataaagat agggattgat tacttttact atcagcggtc atcttcttgg    1260

tggccattgg catttgttac aaaactagac ccgcaagagt tagcagacac aaactcgata    1320

tggctgacca attccatacc aatcccacaa tcaaagttcc ctcggccttc atattcagaa    1380

aattattgca caaagccagc agtttgccct gctacttgtg tcactggtgt atactctgat    1440

atttggccct tgacctcatc ttcatcactc ccgagcataa tttggatcgg ccagtacctt    1500

gatgcccctg ttggaaggac ttatcccaga tttggaattg caaatcaatc acactggtac    1560

cttcaagaag atattctacc cacctccact gcaagtgcgt attcaaccac tacatgtttt    1620

aagaatactg ccaggaatag agtgttctgc gtcaccattg ctgaatttgc agatgggttg    1680

tttggagagt acaggataac acctcagttg tatgaattag tgagaaataa ttga          1734

<210> SEQ ID NO 86
<211> LENGTH: 577
<212> TYPE: PRT
```

<213> ORGANISM: artificial sequence
<220> FEATURE:
<223> OTHER INFORMATION: HN protein of ACN88145

<400> SEQUENCE: 86

```
Met Ser Asn Ile Ala Ser Ser Leu Glu Asn Ile Val Glu Gln Asp Ser
1               5                   10                  15

Arg Lys Thr Thr Trp Arg Ala Ile Phe Arg Trp Ser Val Leu Leu Ile
            20                  25                  30

Thr Thr Gly Cys Leu Ala Leu Ser Ile Val Ser Ile Val Gln Ile Gly
        35                  40                  45

Asn Leu Lys Ile Pro Ser Val Gly Asp Leu Ala Asp Glu Val Val Thr
    50                  55                  60

Pro Leu Lys Thr Thr Leu Ser Asp Thr Leu Arg Asn Pro Ile Asn Gln
65                  70                  75                  80

Ile Asn Asp Ile Phe Arg Ile Val Ala Leu Asp Ile Pro Leu Gln Val
                85                  90                  95

Thr Ser Ile Gln Lys Asp Leu Ala Ser Gln Phe Ser Met Leu Ile Asp
            100                 105                 110

Ser Leu Asn Ala Ile Lys Leu Gly Asn Gly Thr Asn Leu Ile Ile Pro
        115                 120                 125

Thr Ser Asp Lys Glu Tyr Ala Gly Gly Ile Gly Asn Pro Val Phe Thr
    130                 135                 140

Val Asp Ala Gly Gly Ser Ile Gly Phe Lys Gln Phe Ser Leu Ile Glu
145                 150                 155                 160

His Pro Ser Phe Ile Ala Gly Pro Thr Thr Thr Arg Gly Cys Thr Arg
                165                 170                 175

Ile Pro Thr Phe His Met Ser Glu Ser His Trp Cys Tyr Ser His Asn
            180                 185                 190

Ile Ile Ala Ala Gly Cys Gln Asp Ala Ser Ala Ser Ser Met Tyr Ile
        195                 200                 205

Ser Met Gly Val Leu His Val Ser Ser Ser Gly Thr Pro Ile Phe Leu
    210                 215                 220

Thr Thr Ala Ser Glu Leu Ile Asp Asp Gly Val Asn Arg Lys Ser Cys
225                 230                 235                 240

Ser Ile Val Ala Thr Gln Phe Gly Cys Asp Ile Leu Cys Ser Ile Val
                245                 250                 255

Ile Glu Lys Glu Gly Asp Asp Tyr Trp Ser Asp Thr Pro Thr Pro Met
            260                 265                 270

Arg His Gly Arg Phe Ser Phe Asn Gly Ser Phe Val Glu Thr Glu Leu
        275                 280                 285

Pro Val Ser Ser Met Phe Ser Ser Phe Ser Ala Asn Tyr Pro Ala Val
    290                 295                 300

Gly Ser Gly Glu Ile Val Lys Asp Arg Ile Leu Phe Pro Ile Tyr Gly
305                 310                 315                 320

Gly Ile Lys Gln Thr Ser Pro Glu Phe Thr Glu Leu Val Lys Tyr Gly
                325                 330                 335

Leu Phe Val Ser Thr Pro Thr Thr Val Cys Gln Ser Ser Trp Thr Tyr
            340                 345                 350

Asp Gln Val Lys Ala Ala Tyr Arg Pro Asp Tyr Ile Ser Gly Arg Phe
        355                 360                 365

Trp Ala Gln Val Ile Leu Ser Cys Ala Leu Asp Ala Val Asp Leu Ser
    370                 375                 380

Ser Cys Ile Val Lys Ile Met Asn Ser Ser Thr Val Met Met Ala Ala
385                 390                 395                 400
```

```
Glu Gly Arg Ile Ile Lys Ile Gly Ile Asp Tyr Phe Tyr Tyr Gln Arg
                405                 410                 415

Ser Ser Ser Trp Trp Pro Leu Ala Phe Val Thr Lys Leu Asp Pro Gln
            420                 425                 430

Glu Leu Ala Asp Thr Asn Ser Ile Trp Leu Thr Asn Ser Ile Pro Ile
        435                 440                 445

Pro Gln Ser Lys Phe Pro Arg Pro Ser Tyr Ser Glu Asn Tyr Cys Thr
    450                 455                 460

Lys Pro Ala Val Cys Pro Ala Thr Cys Val Thr Gly Val Tyr Ser Asp
465                 470                 475                 480

Ile Trp Pro Leu Thr Ser Ser Ser Ser Leu Pro Ser Ile Ile Trp Ile
                485                 490                 495

Gly Gln Tyr Leu Asp Ala Pro Val Gly Arg Thr Tyr Pro Arg Phe Gly
            500                 505                 510

Ile Ala Asn Gln Ser His Trp Tyr Leu Gln Glu Asp Ile Leu Pro Thr
        515                 520                 525

Ser Thr Ala Ser Ala Tyr Ser Thr Thr Thr Cys Phe Lys Asn Thr Ala
    530                 535                 540

Arg Asn Arg Val Phe Cys Val Thr Ile Ala Glu Phe Ala Asp Gly Leu
545                 550                 555                 560

Phe Gly Glu Tyr Arg Ile Thr Pro Gln Leu Tyr Glu Leu Val Arg Asn
                565                 570                 575

Asn


<210> SEQ ID NO 87
<211> LENGTH: 6717
<212> TYPE: DNA
<213> ORGANISM: artificial sequence
<220> FEATURE:
<223> OTHER INFORMATION: L gene of FJ619036

<400> SEQUENCE: 87

atggatgtaa aacaagttga cctaataata caacccgagg ttcatctcga ttcacccatc     60

atattgaata aactggcact attatggcgc ttgagtggtt tacccatgcc tgcagactta    120

cgacaaaaat ccgtagtgat gcacatccca gaccacatct tagaaaaatc agaatatcgg    180

atcaagcacc gtctagggaa aatcaagagt gacatagcac attactgtca gtattttaat    240

attaatttgg caaatcttga tccgataacc caccccaaaa gtttgtattg gttatccaga    300

ctaacaatag ctagtgctgg aacctttaga catatgaaag atagaatctt atgtacagtt    360

ggctccgaat tcggacacaa aattcaagat ttattttcac tgctgagcca taaattagta    420

ggtaacggtg atttatttaa tcaaagtctc tcaggtacac gtttgactgc gagtccgtta    480

tcccctttat gcaatcaatt tgtctctgac atcaagtctg cagtcacgac accctggtca    540

gaagctcgtt ggtcttggct tcatatcaaa caaacaatga gatacctgat aaaacaatca    600

cgcactacaa attcagctca tttaacagaa attataaaag aggaatgggg tttagtaggt    660

attactccag atcttgtcat tctttttgac agagtcaata atagtctaac tgcattaaca    720

tttgagatgg ttctaatgta ttcagatgta ttagaatccc gtgacaatat tgtgctagtg    780

gggcgattat ctacttttct gcagccagta gttagtagac tggaggtgtt gtttgatcta    840

gtagattcat tggcaaaaac cttaggtgac acaatatacg aaattattgc ggtgttagag    900

agcttgtctt atgggtccgt tcaactacat gatgcaagtc actctcatgc agggtctttc    960

ttttcattta acatgaatga acttgataac acactatcaa agagggtgga tccgaaacac   1020
```

-continued

```
aagaacacca taatgagcat tataagacaa tgcttttcta atctagatgt tgatcaagct   1080
gcagagatgc tatgcctgat gagattattt ggacacccaa tgttaactgc accggatgca   1140
gcagccaaag taaggaaagc aatgtgtgct ccaaaacttg ttgaacatga caccatcttg   1200
cagacattat ccttcttcaa gggaataatt ataaatgggt acagaagatc acactctggc   1260
ctgtggccca atgtagagcc gtcttcaatc tatgatgatg atctcagaca gctgtactta   1320
gagtcagcag agatttccca tcatttcatg cttaaaaact acaagagttt gagcatgata   1380
gaattcaaga agagcataga ctacgatctt cacgacgact taagtacttt cttaaaggat   1440
agagcaattt gccggccaaa atcccagtgg gatgttatat tccgtaagtc tttacgcaga   1500
tcccacacgc ggtcccagta tatggacgaa attaagagca accgattgct aattgatttt   1560
cttgattctg ctgattttga ccctgaaaag gaatttgcat atgtaaccac aatggattat   1620
ttgcacgata atgaattttg tgcttcatat tctctaaagg aaaaggagat caaaactacc   1680
gggaggatat ttgcaaaaat gacacgcaat atgagaagtt gccaagtgat acttgaatct   1740
ctgttatcaa aacatatatg caagttcttc aaagagaacg gcgtttcgat ggagcaattg   1800
tcattgacca agagtctact tgcaatgtct caactctcac caaaagtctc gactctgcag   1860
gacactgcat cacgtcatgt aggcaactca aaatctcaga tcgcaaccag caacccatct   1920
cggcatcact caacaaccaa tcagatgtca ctctcaaatc ggaaaacggt tgtagcaact   1980
ttcttaacaa ctgatttgga aaaatactgc ctgcagtggc gatactcgac tattaagttg   2040
tttgcacaag ctctaaatca actctttggg attgatcacg gatttgaatg gatacattta   2100
agactcatga acagcacctt atttgtcggt gatccttact cgcctcctga agatccaaca   2160
ctagaggata tagataaagc accaaatgac gatatcttca tagtttctcc aaggggaggc   2220
atagagggtt tatgtcagaa gatgtggacc atgatatcaa ttagtgcgat acactgtgta   2280
gcagagaaaa ttggtgcacg agtggcagca atggtgcagg gtgataatca agtaatagct   2340
atcaccaaag aactattcag aggagagaaa gcctgtgatg tcagagatga gttagacgag   2400
ctcggtcagg tgtttttttga tgagttcaag aggcacaatt atgcaattgg acacaacctt   2460
aagctaaatg agacaataca aagccaatcc ttttttgtat attccaaacg aatattcttt   2520
gaagggcgat tgcttagtca agtcctcaaa aatgctgcca agttatgtat ggttgctgac   2580
catctaggtg aaaacacagt atcttcctgt agcaacctga gctctacaat tgcccggttg   2640
gtggaaaatg ggtttgagaa ggacactgct tttgtgttga acctagtcta catcatgact   2700
caaattcttt ttgatgagca ttactcgatt gtatgcgatc acaatagtgt caaaagcttg   2760
atcggatcaa aaaactatcg gaatctattg tactcatctc taataccagg tcagctcggt   2820
ggtttcaact tcctcaatat aagtcggttg ttcactagga atataggtga cccagtaaca   2880
tgtagtctgt ctgatctcaa atgcttcata gccgcaggtc tccttccacc ctatgtactt   2940
aaaaatgtgg ttctgcgtga gcctggtcct gggacatggt tgacgttgtg ctctgatcct   3000
tacaccctta acataccata cacacagcta ccaaccacat atctcaaaaa gcacacccag   3060
cgatcgttgc tttcacgtgc agtaaatcct ttattagcag gtgtacaagt gccaaatcag   3120
catgaggaag aagagatgtt ggctcgcttt ctccttgatc gtgaatatgt gatgccccgc   3180
gttgctcatg taacactaga aacatcggtc cttggcaaac ggaaacaaat ccaaggctta   3240
attgatacaa ctccaactat cattagaaca tctctagtca atctaccagt gtctaggaag   3300
aaatgcgaaa aaataatcaa ttattctctc aattatattg ctgagtgtca tgactcctta   3360
cttagtcaga tctgcttcag tgataataag gaatacttgt ggtccacctc cttaatatca   3420
```

-continued

```
gttgagacct gtagtgtgac aattgcggac tatttgagag ctgtcagctg gtctaatata   3480
ttagggggaa gaagcatatc cggggtgact acacctgata ctattgaatt aattcaaggt   3540
tgtttaatag gtgaaaattc cagttgtact ctttgtgaat cgcatgacga cgcattcaca   3600
tggatgcact tgcctggccc actttacatc cctgaaccat cagttactaa ctctaaaatg   3660
cgtgtgccat atctgggttc aaaaacagag gagcgtaaaa cagcttcaat ggcagcaata   3720
aaaggaatgt cacatcacct gcgtgcagtc ttaagaggta catccgtatt tatttgggca   3780
tctggggaca cagatattaa ttgggataat gcattgcaga ttgcccaatc acggtgtaac   3840
atcacattgg atcaaatgag attacttaca ccaattccta gcagttcaaa tatccaacgt   3900
agactcgatg acggaatcag cacgcagaaa tttactcctg caagccttgc tcgaatcaca   3960
tcctctgttc acatctgtaa tgacagccaa aggttagaga aggatggctc ctctgtcgac   4020
tcaaacttga tttaccagca aattatgtta cttggactca gcatctttga aacaatgtac   4080
tcaatggacc aaaagtgggt attcaataac cataccttac atttgcacac tggacactcc   4140
tgttgtccaa gggaactaga cataagttta gtgaacccgc caagacatca gaccccggag   4200
ctgactagca caacaaccaa cccgttccta tatgatcagc tcccactaaa tcaggataat   4260
ctgacaacac ttgagattaa gacattcaaa tttaatgagc tcaacattga tggtttagat   4320
tttggtgaag gaatacaatt attgagtcgt tgtactgcaa gattaatggc agaatgtatt   4380
ctagaggagg gaataggctc gtcagttaaa aatgaagcaa ttgtcaattt tgataattca   4440
gtcaattgga tttcagagtg cctaatgtgt gatattcgct cactttgtgt taatttaggt   4500
caagagatac tatgtagcct ggcataccaa atgtattact tgcgaatcag ggtagaaggg   4560
gccattctta attacttgga cacaactttg caaaggatcc ctgtgataca gttagccaac   4620
attgcactca ccatttcaca ccctgagata tttcgcagaa ttgtcaacac cgggatccat   4680
aaccagatta agggcccata tgtggcaaca acagatttca tagctgcaag tagagatatc   4740
atattatcag gtgcaaggga gtatctatct tatctaagca gtggacagga agactgttac   4800
acattcttca actgtcaaga tggggatctt actccaaaaa tggaacagta tcttgcaagg   4860
agggcatgcc ttttaacatt actgtataat actgggcacc agatccccat tatccgatca   4920
ctgacaccaa tagagaagtg caaggtgctc acagaataca atcaacaaat tgagtatgca   4980
gatcaagagt ttagctctgt attgaaagtg gtcaatgcac tactacaaaa tcctaatata   5040
gatgcattgg tttcaaatct ctacttcacc accagacgtg ttttatcaaa cctcagatca   5100
tgtgataagg ctatatcata tattgaatat ttgtacactg aggacttcgg agaaaaagaa   5160
gatacagtac aatatgacat catgacaaca aacgatatca tacttactca tggtctattc   5220
acacagatcg aaatatctta ccaagggagt agtctccata aattcctaac tccggataac   5280
gcgcctggat cattgatccc attctctatt tcaccaaatt cgcttgcatg tgatcctctt   5340
caccacttac tcaagtcggt cggtacatca agcacaagct ggtacaagta tgcaatcgcc   5400
tatgcagtgt ctgaaaagag gtcggctcga ttaggaggga gcttgtacat tggtgaaggg   5460
agcggaagtg tgatgacttt gctagagtat cttgagccat ctgttgacat attttacaat   5520
tcactcttct caaatggtat gaacccacca caacgaaatt atgggcttat gccactacaa   5580
tttgtgaatt cggtggttta taagaactta acggctaaat cagaatgtaa gctaggattt   5640
gtccagcaat ttaaaccgtt gtggagagac atagacattg agactaatgt tacagatcca   5700
tcatttgtca attttgcatt gaatgaaatc ccaatgcaat cattaaaacg agtaaattgt   5760
gatgtggaat ttgaccgtgg tatgccgatt gaacgggtta ttcagggtta cactcatatc   5820
```

```
ttacttgttg ctacttacgg attgcagcaa gattcaatac tgtgggtgaa agtatatagg   5880

acatctgaaa aagtatttca gttcttactg agtgccatga tcatgatctt tggttatgtc   5940

aaaatccaca ggaatggtta tatgtcggca aaggatgagg agtacatatt gatgtctgac   6000

tgcaaggaac ctgtaaacta tacagctgtc cctaacattc ttacacgtgt aagtgattta   6060

gtgtcgaaga atctgagtct tatccatcca gaagacctca gaaaggtaag gtgtgaaaca   6120

gattccctga atttgaagtg caatcatatt tatgagaaaa taattgctag aaaaattcca   6180

ttacaggtgt catcaactga ttctttgctc ctccagttag gcggtgtcat caactcggtg   6240

ggctcaactg atcctagaga ggttgcaacg ttatcttcca ttgagtgtat ggactatgtt   6300

gtctcatcaa ttgatttggc tatattagag gcaaatattg tgatctcaga gagtgctgat   6360

cttgacctcg ctttaatgtt aggcccattc aacttgaata agcttaagaa aattgacaca   6420

atccttaagt caagcaccta tcagctaatc ccgtattggt tgcgctatga gtactctatt   6480

aatccgagat ctttgtcatt tctaatcact aaattacaac aatgccgaat ttcatggtca   6540

gatatgataa caatctctga attttgcaag aaatccaagc ggcctatatt tattaaacga   6600

gtaataggga atcaacggct gaaatcattc tttaatgaaa gctcaagtat tgttttgacc   6660

cgggctgaag tcaaagtctg tataaagttc ctcggtgcga tcatcaagtt gaaataa      6717
```

<210> SEQ ID NO 88
<211> LENGTH: 2238
<212> TYPE: PRT
<213> ORGANISM: artificial sequence
<220> FEATURE:
<223> OTHER INFORMATION: L protein of ACN88146

<400> SEQUENCE: 88

```
Met Asp Val Lys Gln Val Asp Leu Ile Ile Gln Pro Glu Val His Leu
1               5                   10                  15

Asp Ser Pro Ile Ile Leu Asn Lys Leu Ala Leu Leu Trp Arg Leu Ser
            20                  25                  30

Gly Leu Pro Met Pro Ala Asp Leu Arg Gln Lys Ser Val Val Met His
        35                  40                  45

Ile Pro Asp His Ile Leu Glu Lys Ser Glu Tyr Arg Ile Lys His Arg
    50                  55                  60

Leu Gly Lys Ile Lys Ser Asp Ile Ala His Tyr Cys Gln Tyr Phe Asn
65                  70                  75                  80

Ile Asn Leu Ala Asn Leu Asp Pro Ile Thr His Pro Lys Ser Leu Tyr
                85                  90                  95

Trp Leu Ser Arg Leu Thr Ile Ala Ser Ala Gly Thr Phe Arg His Met
            100                 105                 110

Lys Asp Arg Ile Leu Cys Thr Val Gly Ser Glu Phe Gly His Lys Ile
        115                 120                 125

Gln Asp Leu Phe Ser Leu Leu Ser His Lys Leu Val Gly Asn Gly Asp
    130                 135                 140

Leu Phe Asn Gln Ser Leu Ser Gly Thr Arg Leu Thr Ala Ser Pro Leu
145                 150                 155                 160

Ser Pro Leu Cys Asn Gln Phe Val Ser Asp Ile Lys Ser Ala Val Thr
                165                 170                 175

Thr Pro Trp Ser Glu Ala Arg Trp Ser Trp Leu His Ile Lys Gln Thr
            180                 185                 190

Met Arg Tyr Leu Ile Lys Gln Ser Arg Thr Thr Asn Ser Ala His Leu
        195                 200                 205

Thr Glu Ile Ile Lys Glu Glu Trp Gly Leu Val Gly Ile Thr Pro Asp
```

-continued

```
    210                 215                 220

Leu Val Ile Leu Phe Asp Arg Val Asn Asn Ser Leu Thr Ala Leu Thr
225                 230                 235                 240

Phe Glu Met Val Leu Met Tyr Ser Asp Val Leu Glu Ser Arg Asp Asn
                245                 250                 255

Ile Val Leu Val Gly Arg Leu Ser Thr Phe Leu Gln Pro Val Val Ser
            260                 265                 270

Arg Leu Glu Val Leu Phe Asp Leu Val Asp Ser Leu Ala Lys Thr Leu
        275                 280                 285

Gly Asp Thr Ile Tyr Glu Ile Ile Ala Val Leu Glu Ser Leu Ser Tyr
    290                 295                 300

Gly Ser Val Gln Leu His Asp Ala Ser His Ser His Ala Gly Ser Phe
305                 310                 315                 320

Phe Ser Phe Asn Met Asn Glu Leu Asp Asn Thr Leu Ser Lys Arg Val
                325                 330                 335

Asp Pro Lys His Lys Asn Thr Ile Met Ser Ile Ile Arg Gln Cys Phe
            340                 345                 350

Ser Asn Leu Asp Val Asp Gln Ala Ala Glu Met Leu Cys Leu Met Arg
        355                 360                 365

Leu Phe Gly His Pro Met Leu Thr Ala Pro Asp Ala Ala Ala Lys Val
    370                 375                 380

Arg Lys Ala Met Cys Ala Pro Lys Leu Val Glu His Asp Thr Ile Leu
385                 390                 395                 400

Gln Thr Leu Ser Phe Phe Lys Gly Ile Ile Ile Asn Gly Tyr Arg Arg
                405                 410                 415

Ser His Ser Gly Leu Trp Pro Asn Val Glu Pro Ser Ser Ile Tyr Asp
            420                 425                 430

Asp Asp Leu Arg Gln Leu Tyr Leu Glu Ser Ala Glu Ile Ser His His
        435                 440                 445

Phe Met Leu Lys Asn Tyr Lys Ser Leu Ser Met Ile Glu Phe Lys Lys
    450                 455                 460

Ser Ile Asp Tyr Asp Leu His Asp Asp Leu Ser Thr Phe Leu Lys Asp
465                 470                 475                 480

Arg Ala Ile Cys Arg Pro Lys Ser Gln Trp Asp Val Ile Phe Arg Lys
                485                 490                 495

Ser Leu Arg Arg Ser His Thr Arg Ser Gln Tyr Met Asp Glu Ile Lys
            500                 505                 510

Ser Asn Arg Leu Leu Ile Asp Phe Leu Asp Ser Ala Asp Phe Asp Pro
        515                 520                 525

Glu Lys Glu Phe Ala Tyr Val Thr Thr Met Asp Tyr Leu His Asp Asn
    530                 535                 540

Glu Phe Cys Ala Ser Tyr Ser Leu Lys Glu Lys Glu Ile Lys Thr Thr
545                 550                 555                 560

Gly Arg Ile Phe Ala Lys Met Thr Arg Asn Met Arg Ser Cys Gln Val
                565                 570                 575

Ile Leu Glu Ser Leu Leu Ser Lys His Ile Cys Lys Phe Phe Lys Glu
            580                 585                 590

Asn Gly Val Ser Met Glu Gln Leu Ser Leu Thr Lys Ser Leu Leu Ala
        595                 600                 605

Met Ser Gln Leu Ser Pro Lys Val Ser Thr Leu Gln Asp Thr Ala Ser
    610                 615                 620

Arg His Val Gly Asn Ser Lys Ser Gln Ile Ala Thr Ser Asn Pro Ser
625                 630                 635                 640
```

```
Arg His His Ser Thr Thr Asn Gln Met Ser Leu Ser Asn Arg Lys Thr
                645                 650                 655

Val Val Ala Thr Phe Leu Thr Thr Asp Leu Glu Lys Tyr Cys Leu Gln
            660                 665                 670

Trp Arg Tyr Ser Thr Ile Lys Leu Phe Ala Gln Ala Leu Asn Gln Leu
        675                 680                 685

Phe Gly Ile Asp His Gly Phe Glu Trp Ile His Leu Arg Leu Met Asn
    690                 695                 700

Ser Thr Leu Phe Val Gly Asp Pro Tyr Ser Pro Pro Glu Asp Pro Thr
705                 710                 715                 720

Leu Glu Asp Ile Asp Lys Ala Pro Asn Asp Asp Ile Phe Ile Val Ser
                725                 730                 735

Pro Arg Gly Gly Ile Glu Gly Leu Cys Gln Lys Met Trp Thr Met Ile
            740                 745                 750

Ser Ile Ser Ala Ile His Cys Val Ala Glu Lys Ile Gly Ala Arg Val
        755                 760                 765

Ala Ala Met Val Gln Gly Asp Asn Gln Val Ile Ala Ile Thr Lys Glu
    770                 775                 780

Leu Phe Arg Gly Glu Lys Ala Cys Asp Val Arg Asp Glu Leu Asp Glu
785                 790                 795                 800

Leu Gly Gln Val Phe Phe Asp Glu Phe Lys Arg His Asn Tyr Ala Ile
                805                 810                 815

Gly His Asn Leu Lys Leu Asn Glu Thr Ile Gln Ser Gln Ser Phe Phe
            820                 825                 830

Val Tyr Ser Lys Arg Ile Phe Phe Glu Gly Arg Leu Leu Ser Gln Val
        835                 840                 845

Leu Lys Asn Ala Ala Lys Leu Cys Met Val Ala Asp His Leu Gly Glu
    850                 855                 860

Asn Thr Val Ser Ser Cys Ser Asn Leu Ser Ser Thr Ile Ala Arg Leu
865                 870                 875                 880

Val Glu Asn Gly Phe Glu Lys Asp Thr Ala Phe Val Leu Asn Leu Val
                885                 890                 895

Tyr Ile Met Thr Gln Ile Leu Phe Asp Glu His Tyr Ser Ile Val Cys
            900                 905                 910

Asp His Asn Ser Val Lys Ser Leu Ile Gly Ser Lys Asn Tyr Arg Asn
        915                 920                 925

Leu Leu Tyr Ser Ser Leu Ile Pro Gly Gln Leu Gly Gly Phe Asn Phe
    930                 935                 940

Leu Asn Ile Ser Arg Leu Phe Thr Arg Asn Ile Gly Asp Pro Val Thr
945                 950                 955                 960

Cys Ser Leu Ser Asp Leu Lys Cys Phe Ile Ala Ala Gly Leu Leu Pro
                965                 970                 975

Pro Tyr Val Leu Lys Asn Val Val Leu Arg Glu Pro Gly Pro Gly Thr
            980                 985                 990

Trp Leu Thr Leu Cys Ser Asp Pro  Tyr Thr Leu Asn Ile  Pro Tyr Thr
        995                 1000                 1005

Gln Leu  Pro Thr Thr Tyr Leu  Lys Lys His Thr Gln  Arg Ser Leu
    1010                 1015                 1020

Leu Ser  Arg Ala Val Asn Pro  Leu Leu Ala Gly Val  Gln Val Pro
    1025                 1030                 1035

Asn Gln  His Glu Glu Glu Glu  Met Leu Ala Arg Phe  Leu Leu Asp
    1040                 1045                 1050

Arg Glu  Tyr Val Met Pro Arg  Val Ala His Val Thr  Leu Glu Thr
    1055                 1060                 1065
```

Ser Val Leu Gly Lys Arg Lys Gln Ile Gln Gly Leu Ile Asp Thr
1070 1075 1080

Thr Pro Thr Ile Ile Arg Thr Ser Leu Val Asn Leu Pro Val Ser
1085 1090 1095

Arg Lys Lys Cys Glu Lys Ile Ile Asn Tyr Ser Leu Asn Tyr Ile
1100 1105 1110

Ala Glu Cys His Asp Ser Leu Leu Ser Gln Ile Cys Phe Ser Asp
1115 1120 1125

Asn Lys Glu Tyr Leu Trp Ser Thr Ser Leu Ile Ser Val Glu Thr
1130 1135 1140

Cys Ser Val Thr Ile Ala Asp Tyr Leu Arg Ala Val Ser Trp Ser
1145 1150 1155

Asn Ile Leu Gly Gly Arg Ser Ile Ser Gly Val Thr Thr Pro Asp
1160 1165 1170

Thr Ile Glu Leu Ile Gln Gly Cys Leu Ile Gly Glu Asn Ser Ser
1175 1180 1185

Cys Thr Leu Cys Glu Ser His Asp Asp Ala Phe Thr Trp Met His
1190 1195 1200

Leu Pro Gly Pro Leu Tyr Ile Pro Glu Pro Ser Val Thr Asn Ser
1205 1210 1215

Lys Met Arg Val Pro Tyr Leu Gly Ser Lys Thr Glu Glu Arg Lys
1220 1225 1230

Thr Ala Ser Met Ala Ala Ile Lys Gly Met Ser His His Leu Arg
1235 1240 1245

Ala Val Leu Arg Gly Thr Ser Val Phe Ile Trp Ala Ser Gly Asp
1250 1255 1260

Thr Asp Ile Asn Trp Asp Asn Ala Leu Gln Ile Ala Gln Ser Arg
1265 1270 1275

Cys Asn Ile Thr Leu Asp Gln Met Arg Leu Leu Thr Pro Ile Pro
1280 1285 1290

Ser Ser Ser Asn Ile Gln Arg Arg Leu Asp Asp Gly Ile Ser Thr
1295 1300 1305

Gln Lys Phe Thr Pro Ala Ser Leu Ala Arg Ile Thr Ser Ser Val
1310 1315 1320

His Ile Cys Asn Asp Ser Gln Arg Leu Glu Lys Asp Gly Ser Ser
1325 1330 1335

Val Asp Ser Asn Leu Ile Tyr Gln Gln Ile Met Leu Leu Gly Leu
1340 1345 1350

Ser Ile Phe Glu Thr Met Tyr Ser Met Asp Gln Lys Trp Val Phe
1355 1360 1365

Asn Asn His Thr Leu His Leu His Thr Gly His Ser Cys Cys Pro
1370 1375 1380

Arg Glu Leu Asp Ile Ser Leu Val Asn Pro Pro Arg His Gln Thr
1385 1390 1395

Pro Glu Leu Thr Ser Thr Thr Thr Asn Pro Phe Leu Tyr Asp Gln
1400 1405 1410

Leu Pro Leu Asn Gln Asp Asn Leu Thr Thr Leu Glu Ile Lys Thr
1415 1420 1425

Phe Lys Phe Asn Glu Leu Asn Ile Asp Gly Leu Asp Phe Gly Glu
1430 1435 1440

Gly Ile Gln Leu Leu Ser Arg Cys Thr Ala Arg Leu Met Ala Glu
1445 1450 1455

Cys Ile Leu Glu Glu Gly Ile Gly Ser Ser Val Lys Asn Glu Ala

-continued

```
    1460                1465                1470

Ile Val  Asn Phe Asp Asn Ser  Val Asn Trp Ile Ser  Glu Cys Leu
    1475                1480                1485

Met Cys  Asp Ile Arg Ser Leu  Cys Val Asn Leu Gly  Gln Glu Ile
    1490                1495                1500

Leu Cys  Ser Leu Ala Tyr Gln  Met Tyr Tyr Leu Arg  Ile Arg Gly
    1505                1510                1515

Arg Arg  Ala Ile Leu Asn Tyr  Leu Asp Thr Thr Leu  Gln Arg Ile
    1520                1525                1530

Pro Val  Ile Gln Leu Ala Asn  Ile Ala Leu Thr Ile  Ser His Pro
    1535                1540                1545

Glu Ile  Phe Arg Arg Ile Val  Asn Thr Gly Ile His  Asn Gln Ile
    1550                1555                1560

Lys Gly  Pro Tyr Val Ala Thr  Thr Asp Phe Ile Ala  Ala Ser Arg
    1565                1570                1575

Asp Ile  Ile Leu Ser Gly Ala  Arg Glu Tyr Leu Ser  Tyr Leu Ser
    1580                1585                1590

Ser Gly  Gln Glu Asp Cys Tyr  Thr Phe Phe Asn Cys  Gln Asp Gly
    1595                1600                1605

Asp Leu  Thr Pro Lys Met Glu  Gln Tyr Leu Ala Arg  Arg Ala Cys
    1610                1615                1620

Leu Leu  Thr Leu Leu Tyr Asn  Thr Gly His Gln Ile  Pro Ile Ile
    1625                1630                1635

Arg Ser  Leu Thr Pro Ile Glu  Lys Cys Lys Val Leu  Thr Glu Tyr
    1640                1645                1650

Asn Gln  Gln Ile Glu Tyr Ala  Asp Gln Glu Phe Ser  Ser Val Leu
    1655                1660                1665

Lys Val  Val Asn Ala Leu Leu  Gln Asn Pro Asn Ile  Asp Ala Leu
    1670                1675                1680

Val Ser  Asn Leu Tyr Phe Thr  Thr Arg Arg Val Leu  Ser Asn Leu
    1685                1690                1695

Arg Ser  Cys Asp Lys Ala Ile  Ser Tyr Ile Glu Tyr  Leu Tyr Thr
    1700                1705                1710

Glu Asp  Phe Gly Glu Lys Glu  Asp Thr Val Gln Tyr  Asp Ile Met
    1715                1720                1725

Thr Thr  Asn Asp Ile Ile Leu  Thr His Gly Leu Phe  Thr Gln Ile
    1730                1735                1740

Glu Ile  Ser Tyr Gln Gly Ser  Ser Leu His Lys Phe  Leu Thr Pro
    1745                1750                1755

Asp Asn  Ala Pro Gly Ser Leu  Ile Pro Phe Ser Ile  Ser Pro Asn
    1760                1765                1770

Ser Leu  Ala Cys Asp Pro Leu  His His Leu Leu Lys  Ser Val Gly
    1775                1780                1785

Thr Ser  Ser Thr Ser Trp Tyr  Lys Tyr Ala Ile Ala  Tyr Ala Val
    1790                1795                1800

Ser Glu  Lys Arg Ser Ala Arg  Leu Gly Gly Ser Leu  Tyr Ile Gly
    1805                1810                1815

Glu Gly  Ser Gly Ser Val Met  Thr Leu Leu Glu Tyr  Leu Glu Pro
    1820                1825                1830

Ser Val  Asp Ile Phe Tyr Asn  Ser Leu Phe Ser Asn  Gly Met Asn
    1835                1840                1845

Pro Pro  Gln Arg Asn Tyr Gly  Leu Met Pro Leu Gln  Phe Val Asn
    1850                1855                1860
```

-continued

```
Ser Val  Val Tyr Lys Asn Leu  Thr Ala Lys Ser Glu  Cys Lys Leu
    1865                1870                 1875

Gly Phe  Val Gln Gln Phe Lys  Pro Leu Trp Arg Asp  Ile Asp Ile
    1880                1885                 1890

Glu Thr  Asn Val Thr Asp Pro  Ser Phe Val Asn Phe  Ala Leu Asn
    1895                1900                 1905

Glu Ile  Pro Met Gln Ser Leu  Lys Arg Val Asn Cys  Asp Val Glu
    1910                1915                 1920

Phe Asp  Arg Gly Met Pro Ile  Glu Arg Val Ile Gln  Gly Tyr Thr
    1925                1930                 1935

His Ile  Leu Leu Val Ala Thr  Tyr Gly Leu Gln Gln  Asp Ser Ile
    1940                1945                 1950

Leu Trp  Val Lys Val Tyr Arg  Thr Ser Glu Lys Val  Phe Gln Phe
    1955                1960                 1965

Leu Leu  Ser Ala Met Ile Met  Ile Phe Gly Tyr Val  Lys Ile His
    1970                1975                 1980

Arg Asn  Gly Tyr Met Ser Ala  Lys Asp Glu Glu Tyr  Ile Leu Met
    1985                1990                 1995

Ser Asp  Cys Lys Glu Pro Val  Asn Tyr Thr Ala Val  Pro Asn Ile
    2000                2005                 2010

Leu Thr  Arg Val Ser Asp Leu  Val Ser Lys Asn Leu  Ser Leu Ile
    2015                2020                 2025

His Pro  Glu Asp Leu Arg Lys  Val Arg Cys Glu Thr  Asp Ser Leu
    2030                2035                 2040

Asn Leu  Lys Cys Asn His Ile  Tyr Glu Lys Ile Ile  Ala Arg Lys
    2045                2050                 2055

Ile Pro  Leu Gln Val Ser Ser  Thr Asp Ser Leu Leu  Leu Gln Leu
    2060                2065                 2070

Gly Gly  Val Ile Asn Ser Val  Gly Ser Thr Asp Pro  Arg Glu Val
    2075                2080                 2085

Ala Thr  Leu Ser Ser Ile Glu  Cys Met Asp Tyr Val  Val Ser Ser
    2090                2095                 2100

Ile Asp  Leu Ala Ile Leu Glu  Ala Asn Ile Val Ile  Ser Glu Ser
    2105                2110                 2115

Ala Asp  Leu Asp Leu Ala Leu  Met Leu Gly Pro Phe  Asn Leu Asn
    2120                2125                 2130

Lys Leu  Lys Lys Ile Asp Thr  Ile Leu Lys Ser Ser  Thr Tyr Gln
    2135                2140                 2145

Leu Ile  Pro Tyr Trp Leu Arg  Tyr Glu Tyr Ser Ile  Asn Pro Arg
    2150                2155                 2160

Ser Leu  Ser Phe Leu Ile Thr  Lys Leu Gln Gln Cys  Arg Ile Ser
    2165                2170                 2175

Trp Ser  Asp Met Ile Thr Ile  Ser Glu Phe Cys Lys  Lys Ser Lys
    2180                2185                 2190

Arg Pro  Ile Phe Ile Lys Arg  Val Ile Gly Asn Gln  Arg Leu Lys
    2195                2200                 2205

Ser Phe  Phe Asn Glu Ser Ser  Ser Ile Val Leu Thr  Arg Ala Glu
    2210                2215                 2220

Val Lys  Val Cys Ile Lys Phe  Leu Gly Ala Ile Ile  Lys Leu Lys
    2225                2230                 2235
```

RECOMBINANT AVIAN PARAMYXOVIRUS VACCINE AND METHOD FOR MAKING AND USING THEREOF

INCORPORATION BY REFERENCE

This application claims benefit of U.S. provisional application Ser. No. 61/235,912 filed Aug. 21, 2009.

FIELD OF THE INVENTION

The invention relates to avian paramyxoviruses (APMV) and APMV sequences. The invention relates to viral vectors for the insertion and expression of foreign genes for use as safe immunization vehicles to protect against a variety of pathogens. It relates to vector vaccine in a reverse genetics system for the production of live attenuated vaccines. It also relates to polynucleotides which can be used for the production of subunits in an in vitro expression vector or as sequences to be integrated into a viral or plasmid type in vivo expression vector.

The present invention relates to unmodified and modified APMV virus, to methods of making and using the same, and to certain DNA and protein sequences. More in particular, the invention relates to APMV virus in which the naturally occurring genome of the virus has been altered ("APMV mutants" or "recombinant APMV") and to methods of making and using such APMV mutants or recombinant APMV.

BACKGROUND OF THE INVENTION

Viral vector vaccines represent one of the most rapidly growing areas in vaccine development. Many vaccines in clinical development for major global infectious diseases, HIV, tuberculosis and malaria, are based on viral vectors. Viral vector vaccines for animals are already on the market, e.g. avipox vector vaccines for companion animals and poultry, avian herpes viruses vectored vaccines for poultry, and vaccinia virus vectored vaccines for wildlife. But other livestock vector vaccines are in development. The advantage of viral vector vaccines is that they can be administered safely due to the use of a vector backbone which is strongly attenuated and does not cause disease in the animal itself. The disadvantage of currently used viral vectors is the existence of maternally derived or antibodies acquired due to a past infection. These antibodies will neutralize the vector virus and thus diminish the success of the vector vaccine. One major impetus for the development of vector vaccines was the occurrence of highly pathogenic influenza virus H5N1 occurring first in Asia and later in Europe and Africa. Several vector vaccine candidates have been developed including fowl poxvirus (Taylor et al, 1988), vaccinia virus (Chambers et al., 1988), Rous sarcoma virus (Hunt et al, 1988), adenoviruses (Tang et al., 2002, Gao et al, 2006), Venezuelan equine encephalitis virus (Schultz-Cherry et al, 2000), Newcastle disease virus (U.S. Pat. No. 6,719,979, Veits et al., 2006, Swayne et al, 2002, Park et al, 2006), herpesvirus of infectious laryngotracheitis (Veits et al. 2003), herpesvirus of turkey (Darteil et al., 1995), and adenovirus based vector vaccines (Hoelscher et al, 2008, Toro et al, 2007). The efficacy of these vector vaccines have been tested in naive birds, but so far no reports have been published on the efficacy of these vector vaccines in birds with a preexisting immunity to the viral vector and/or to the protein coded by the insert.

The virus family Paramyxoviridae includes both human (measles, mumps, parainfluenza and respiratory syncytial virus) and animal pathogens (Newcastle disease virus and rinderpest virus) that cause significant impact on public health as well as the global economy (Lamb et al., 2007). Members of this virus family are defined by having a monopartite, negative sense, single-stranded RNA genome. The Paramyxoviridae family consists of two subfamilies namely Paramyxovirinae and Pneumovirinae. Owing to recent reclassification, the subfamily Paramyxovirinae includes five genera, i.e Morbillivirus, Henipavirus, Rubulavirus, Respirovirus and Avulavirus while Pneumovirinae includes Pneumovirus and Metapneumovirus (Mayo, 2002). Avian paramyxoviruses (APMV) are classified in the genus *Avulavirus* and comprise nine antigenically distinct serotypes that have been defined using hemagglutination inhibition (HI) tests (Alexander, 1988). Of the nine serotypes, isolates belonging to the APMV-1 subtype can cause a devastating disease in commercial poultry and are classified as velogenic Newcastle disease virus (NDV). Milder forms of NDV are designated as mesogenic and lentogenic isolates, wherein the latter form is mostly asymptomatic in domestic poultry. Isolates belonging to the APMV-2, 3, 6 and 7 have also been associated with disease in domestic poultry. Specifically, infections by isolates of APMV-2 and 3 can cause mild respiratory disease and problems in egg quality and quantity (Bankowski et al., 1981; Redmann et al., 1991; Tumova et al., 1979; Zhang et al., 2007). Isolates of APMV-6 and 7 have been known to infect turkeys, ducks and migratory birds and can induce respiratory disease that may be complicated by secondary infection (Saif et al., 1997; Shortridge et al., 1980). On the other hand, isolates of APMV-4, 5, 8 and 9 have been isolated from ducks, waterfowl and other wild birds but the birds rarely show clinical signs after viral infection (Alexander et al., 1983; Capua et al., 2004; Gough et al., 1984; Maldonado et al., 1995; Shortridge et al., 1980).

The complete genomic sequences of several NDV isolates have been established and used to elucidate the various determinants of NDV virulence (de Leeuw et al., 1999; Krishnamurthy et al., 1998; Zou et al., 2005). In the recent two years several APMV sequences other than APMV1 have been published, such as GenBank accession number EU338414 for APMV-2, EU403085 for APMV-3, FJ177514 for APMV-4, EU622637 for APMV-6, FJ231524 for APMV-7, FJ215863, FJ215864 and FJ619036 for APMV-8, EU910942 for APMV-9. Besides the sequence information, not much is known about virulence factors. Isolates of APMV 2-9 have been mostly isolated from migratory birds. Interestingly, there are very few reports of experimental infection of chickens with such isolates (Saif et al., 1997). Since these APMV circulate widely in wild birds and in certain cases have been isolated from commercial flocks (Zhang et al., 2007) that sometimes cause disease in them (Saif et al., 1997; Shihmanter et al., 1998; Shihmanter et al., 1998), knowledge about their virulence in poultry is needed.

Most of the APMV isolates cause a relatively mild disease that may be exacerbated in the presence of concomitant bacterial or viral infections which might lead to economic impact. In particular, APMV-2 was first isolated as a secondary pathogen in 1956 from chickens affected by acute laryngotracheitis in Southern California (Bankowski et al., 1960). Since then numerous strains of this serotype have been isolated from several avian species signifying that APMV-2 is widely disseminated worldwide (Andral et al., 1984; Bradshaw et al., 1979; Fleury et al., 1979; Goodman et al., 1988; Lang et al., 1975; Lipkind et al., 1982; Lipkind et al., 1979; Zhang et al., 2006). Bankowski et. al. reported that natural as well as artificial exposure of laying turkey hens to APMV-2 caused a pronounced decline in hatchability and poultry yield (Bankowski et al., 1981). Initial examples of APMV-4 isolation were from hunter-killed feral ducks on the Mississippi flyway in the United States (Webster et al., 1976) and from chickens, ducks and geese in Hong Kong during influenza surveillance programs of poultry (Alexander et al., 1979). Apart from an isolate from a ringed teal suffering from hemorrhagic enteritis (Gough et al., 1984), all other isolates were seemingly non-pathogenic in poultry and found to have wide distribution among waterfowl throughout the world (Stanislawek et al., 2002; Tumova et al., 1989; Yamane et al., 1982). Gough et al. reported that no clinical signs and very low HI titers (1:8 or less) were obtained after the intranasal inoculation of one-week old ducklings and two-week old chickens with the isolate from a ringed teal (Gough et al., 1984). Similarly, the first isolates of APMV-6 were also from domestic poultry in Hong Kong as a result of an influenza surveillance program and were reported to be non-pathogenic in chickens based on low HI titers from experimentally infected chickens (Shortridge et al., 1980). However, there have been reports of APMV-6 infection of turkeys leading to mild respiratory disease and egg production problems (Alexander, 2003).

APMV-8 (Goose/Delaware/1053/76) was first isolated in the USA from a hunter-killed Canada goose (*Branta canadensis*) (Rosenberger et al., 1974). A serological survey (from 1990 to 1992) of wildfowl in southern Spain showed a notable prevalence of APMV-8 antibodies in up to 43% of the tested sera (Maldonado et al., 1995). Another serological study to determine the status of live, healthy mallard ducks in New Zealand for APMV infection revealed the presence of APMV-8 antibodies in 56% of the tested sera (Stanislawek et al., 2002). Warke et al (2008) described that between 16% to 31% of investigated chicken sera might have had APMV-8 antibodies. But due to existing high titers against APMV 1 the probability of a false positive HI test is possible since the sera do not react very specifically in the HI assay. With the exception of a few waterfowl isolates of APMV-8 isolated while the populations were being surveyed for avian influenza viruses (Stallknecht et al., 1991), there has been a dearth of information about the prevalence and pathogenicity of this virus.

The development of reverse genetics systems for the negative stranded RNA genome of NDV has made it possible to insert foreign gene sequences into the genome, thus making it possible to create recombinant NDV vectors for vaccination and gene therapy (Krishnamurthy et al., 2000; Peeters et al., 1999; Roemer-Oberdoerfer et al., 1999). Recombinant NDV vectors expressing foreign viral proteins such as the HA protein of the HI subtype of influenza A virus (Nakaya et al., 2001), VP2 protein of infectious bursal disease virus (IBDV) (Huang et al., 2004), avian influenza virus hemagglutinin of subtype H5 (Veits et al., 2006; Ge et al., 2007) and subtype H7 (Park et al., 2006) have been reported. However the efficacy of most of such vaccines has been demonstrated only in SPF birds. NDV causes a devastating disease in poultry leading to serious economic losses in the poultry industry. Commercial chickens therefore are routinely vaccinated against NDV in most countries of the world. Due to this, chickens from immunized parent flocks have a high level of maternally derived antibodies. Conventional live NDV vaccines provide protection even in the presence of these antibodies. However recombinant NDV vaccines (with foreign gene insertions) are generally more attenuated as compared to live NDV vaccines and their efficacy may be impaired in presence of NDV maternal antibodies. Therefore, there is a need for a vector vaccine platform which can provide the basis for safe vaccines for the expression of heterologous antigens. Ideally, the recombinant vaccine can induce a strong humoral immune response, can be applicable by mass administration, and is inexpensive.

SUMMARY OF THE INVENTION

The present invention relates to a vaccine or composition comprising (i) a recombinant APMV and (ii) a pharmaceutically or veterinarily acceptable carrier. The present invention encompasses methods for modifying the genome of APMV to produce recombinant APMV virus or APMV rival vector; modified APMV prepared by such methods; DNA and protein sequences; and methods for infecting cells and host animals with such recombinant APMV to provoke the amplification of exogenous DNA and proteins encoded by the exogenous DNA, including antigenic proteins, by said cells and host animals.

One aspect of the invention relates to APMV virus, DNA and protein sequences involved in making modified or recombinant virus. One embodiment of the invention relates to the genomic and protein sequence of APMV-2, 4, 6, or 8.

Another aspect of the invention relates to a modified recombinant APMV virus, which viruses have enhanced safety, strong humoral immune response, and a method of making such recombinant viruses.

Another aspect of the invention relates to a recombinant APMV virus vaccine or composition having an increased level of safety compared to known APMV or other recombinant vaccines.

In another aspect, the present invention provides unmodified and modified APMV viral vector for expressing a gene product in a host.

Another aspect of the invention is directed to a recombinant APMV virus modified by the insertion therein of DNA from any source into the intergenic region or the nonessential region of the APMV genome. Synthetically modified APMV virus recombinants carrying heterologous genes coding for and expressing an antigen, are used according to the invention to create novel compositions or vaccines.

Another aspect of the invention relates to an APMV viral vector which provides a reverse genetics system, wherein the vector can be used as a backbone for recombinant vaccines or compositions in different host animals.

In one aspect, the present invention relates to a pharmaceutical composition or vaccine for inducing an immunological response in a host animal inoculated with the composition or vaccine, the composition or vaccine including a pharmaceutical acceptable carrier and a modified APMV recombinant virus or viral vector. In yet another aspect of the invention, the recombinant APMV virus or viral vector includes, within a non-essential region of the virus genome, a heterologous DNA which encodes an antigenic protein derived from a pathogen wherein the composition or vaccine when administered to a host, is capable of inducing an immunological response specific to the protein encoded by the pathogen.

Another aspect of the invention relates to a method for inducing an immunological response in an animal to an antigen, which method comprises inoculating the animal with a vaccine or a pharmaceutical composition containing modified recombinant APMV virus or viral vector which comprises and expresses the antigenic determinant of a pathogen for said animal. Yet another aspect of the invention relates to a method for inducing an immunological response in an animal to an antigen in a prime-boost regime.

Another aspect of the invention relates to a method of expressing a gene product in a cell culture in vitro by introducing into the cell a modified recombinant APMV virus, wherein the gene may be an antigenic protein derived from a pathogen.

BRIEF DESCRIPTION OF THE DRAWINGS

The following detailed description, given by way of example, and which is not intended to limit the invention to specific embodiments described, may be understood in conjunction with the accompanying figures, in which:

FIG. 1 is a table showing virus isolation from several organs of chickens after experimental infection with APMV-2, 4, 6 in embryonated chicken eggs.

FIG. 2 is a table showing the histology results of several organs of chickens after experimental infection with APMV-2, 4, 6.

FIG. 4 shows HI antibody titers in SPF chickens and ducks experimentally infected with APMV-8. Chickens and ducks were oro-nasal infected with a dose of $10^6$ $EID_{50}$ of APMV-8. Sera samples were collected at day 2, 4, 7, 14, and 28 p. i. and analyzed by the HI test with the APMV-8 antigen. The HI serum titers (in $log_2$) are shown on the left axis

FIG. 7 is a table showing virus isolation from chicken and ducks experimentally infected with APMV-8. The virus isolation from chicken tissue was performed in embryonated chicken eggs and the detection of viral RNA from duck tissue by RT-PCR.

FIG. 8 is a table showing the results of the histological examination of several organs after infection of chicken and Pekin ducks with APMV-8.

FIG. 11 is a table showing the SEQ ID NOs of the corresponding DNA and protein sequences.

FIG. 12 depicts the full length genome sequence of APMV-8 strain (APMV-8: SCWDS ID: MA-7, isolated from a mallard) and a genetic map of the full length APMV-8 genome.

FIG. 12F depicts the DNA sequence (SEQ ID NO:2) encoding APMV-8 Nucleoprotein (NP) and the NP protein sequence (SEQ ID NO:3).

FIG. 13 depicts the DNA sequence (SEQ ID NO:4) encoding APMV-8 Phospho Protein (P) and the P protein sequence (SEQ ID NO:5).

FIG. 14 depicts the DNA sequence (SEQ ID NO:6) encoding APMV-8 Matrixprotein (M) and the M protein sequence (SEQ ID NO:7).

FIG. 15 depicts the DNA sequence (SEQ ID NO:8) encoding APMV-8 Fusionprotein (F) and the F protein sequence (SEQ ID NO:9).

FIG. 16 depicts the DNA sequence (SEQ ID NO:10) encoding APMV-8 Hemagglutinin/neuraminidase (HN) and the FIN protein sequence (SEQ ID NO:11).

FIG. 17 depicts the DNA sequence (SEQ ID NO:12) encoding APMV-8 Polymerase (L) and the L protein sequence (SEQ ID NO:13). This APMV-8 L(1) protein is translated from the ATG codon located at positions 8273-8275 of SEQ ID NO:1.

FIG. 18 depicts the protein sequence (2) of APMV-8 Polymerase (L) (SEQ ID NO:14). This APMV-8 L(2) protein is translated from the ATG codon located at positions 8297-8299 of SEQ ID NO:1. SEQ ID NO:14 does not contain the first 8 amino acids of SEQ ID NO:13.

FIG. 25 depicts 5'-full length genome (5'-FLG) and 3'-full length genome (3'-FLG) sequences, including the franking sequences.

FIG. 27 depicts plasmid maps of pUC18-MG-APMV-8 and pCITE4A-EGFP.

FIG. 28 depicts plasmid map of pUC57-FL-APMV-8.

FIG. 29 depicts minigenome APMV-8 sequence.

FIG. 30 shows the NP protein sequence alignment and the sequence identity at the DNA and protein levels.

FIG. 31 shows the P protein sequence alignment and the sequence identity at the DNA and protein levels.

FIG. 32 shows the M protein sequence alignment and the sequence identity at the DNA and protein levels.

FIG. 33 shows the F protein sequence alignment and the sequence identity at the DNA and protein levels.

FIG. 34 shows the HN protein sequence alignment and the sequence identity at the DNA and protein levels.

FIG. 35 shows the L protein sequence alignment and the sequence identity at the DNA and protein levels.

DETAILED DESCRIPTION OF THE INVENTION

Figure 3:
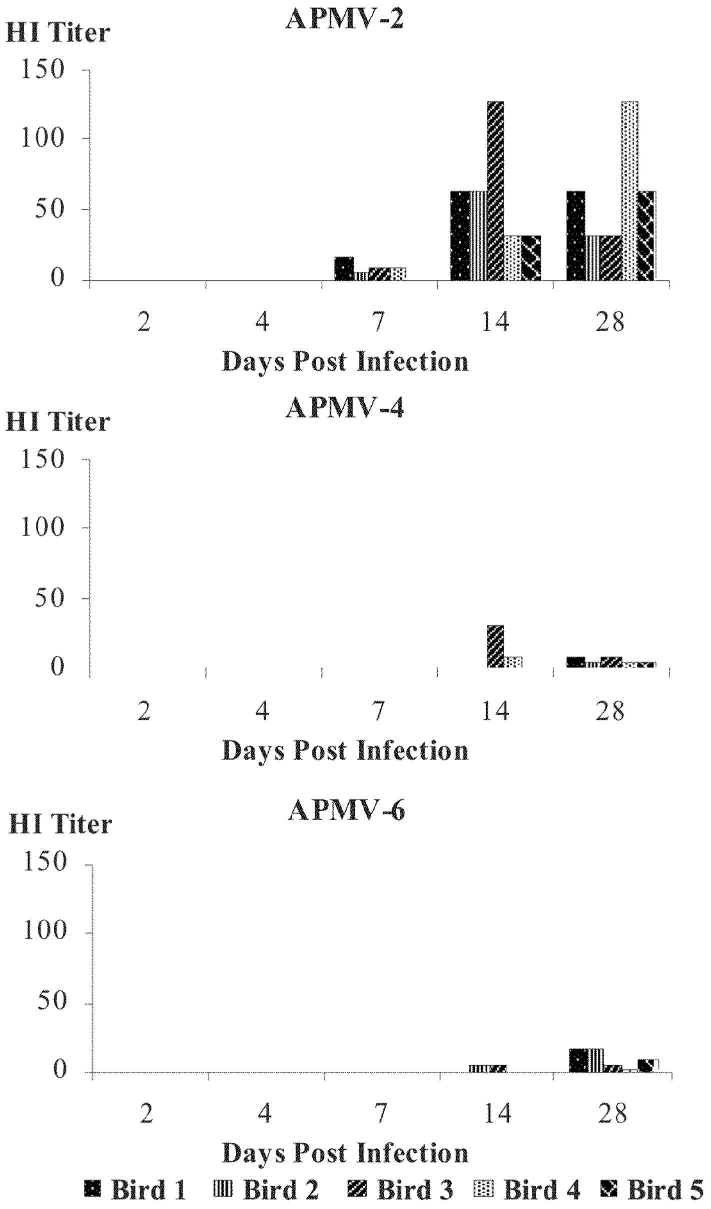
FIG. 3 depicts HI antibody titers in SPF chickens experimentally inoculated with APMV-2, 4 or 6. Chicken sera samples collected at day 2, 4, 7, 14 and 28 post infection were subject to the HI test to analyze the presence of HI antibodies.

It is noted that in this disclosure and particularly in the claims, terms such as “comprises”, “comprised”, “comprising” and the like can have the meaning attributed to it in U.S. patent law; e.g., they can mean “includes”, “included”, “including”, and the like; and that terms such as “consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

It is noted in this disclosure and the appended claims and/or paragraphs, the term "Avian Paramyxoviruses" or "APMV" is used interchangeably, and refers to and includes APMV-1, APMV-2, APMV-3, APMV-4, APMV-5, APMV-6, APMV-7, APMV-8, and APMV-9.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), porcine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The terms "nucleic acid", "nucleotide", and "polynucleotide" are used interchangeably and refer to RNA, DNA, cDNA (complementary DNA), or cRNA (complementary RNA) and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA). The term "genomic RA (nucleic acid)" as used herein includes RNA, mRNA, cRNA, DNA and cDNA.

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

One embodiment of the invention provides the genomic DNA sequence and encoded protein sequences of APMV-8. The complementary genomic DNA(cDNA) sequence of APMV-8 strain of the present invention has a polynucleotide sequence as set forth in SEQ ID NO:1. The APMV-8 genomic cDNA sequence (SEQ ID NO:1) has 48% sequence identity to APMV-1 genomic DNA (SEQ ID NO:15), 61% sequence identity to APMV-2 genomic DNA (SEQ ID NO:16), 47.2% sequence identity to APMV-3 genomic DNA (SEQ ID NO:17), 47.6% sequence identity to APMV-4 genomic DNA (SEQ ID NO:18), 52% sequence identity to APMV-6 genomic DNA (SEQ ID NO:19), 53% sequence identity to APMV-7 genomic DNA (SEQ ID NO:20), 99.1% sequence identity to APMV-8 genomic DNA (SEQ ID NO:37), 96.5% sequence identity to APMV-8 genomic DNA (SEQ ID NO:38), 96.4% sequence identity to APMV-8 genomic DNA (SEQ ID NO:39), 48% sequence identity to APMV-9 genomic DNA (SEQ ID NO:40). In another embodiment, the invention provides a polynucleotide having a sequence as set forth in SEQ ID NO:1, 2, 4, 6, 8, 10 or 12, and variant or fragment thereof. The invention further comprises a complementary strand to a polynucleotide described herein. In yet another embodiment, the invention provides a polypeptide having a sequence as set forth in SEQ ID NO:3, 5, 7, 9, 11, 13 or 14, and variant or fragment thereof.

Moreover, homologs of polynucleotides or polypeptides from APMV, for example APMV-8, APMV-2, APMV-4, APMV-6 strains are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by specification. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type APMV polypeptide can differ from the wild-type APMV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity with all or part of the polynucleotide or polypeptide sequences of APMV-8, and will exhibit a similar function.

In another aspect, the present invention provides a genomic cDNA of APMV-8 having the sequence as set forth in SEQ ID NO:1. In yet another embodiment, the polynucleotide is a reverse complementary strand of the polynucleotide having the sequence as set forth in SEQ ID NO:1. In yet another embodiment, the polynucleotide or a reverse complementary strand of a polynucleotide of the present invention has at least 70%, at least 75%, at least 80%, at least 85%, at least 90%, at least 95%, 96%, 97%, 98% or 99% sequence identity to a polypeptide having a sequence as set forth in SEQ ID NO:1.

In one embodiment, the present invention provides a fragment of polynucleotide encoding an AMPV-8 polypeptide, such as a polynucleotide encoding a polypeptide having a sequence as set forth in SEQ ID NO: 3, 5, 7, 9, 11, 13 or 14. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3, 5, 7, 9, 11, 13 or 14, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO:1, 2, 4, 6, 8, 10, or 12, or a variant thereof. In yet another embodiment, the polynucleotide is a reverse complementary strand of the polynucleotide having the sequence as set forth in SEQ ID NO:1. In yet another aspect, the present invention provides a polynucleotide or a reverse complementary strand of a polynucleotide having at least 70%, at least 75%, at least 80%, at least 85%, at least 90%, at least 95%, 96%, 97%, 98% or 99% sequence identity to one of a polynucleotide having a sequence as set forth in SEQ ID NO:1, 2, 4, 6, 8, 10, or 12, or a variant thereof.

In another aspect, the present invention provides a polypeptide having at least 70%, at least 75%, at least 80%, at least 85%, at least 90%, at least 95%, 96%, 97%, 98% or 99% sequence identity to a polypeptide having a sequence as set forth in SEQ ID NO:3, 5, 7, 9, 11, 13 or 14. In yet another aspect, the present invention provides fragments and variants of the APMV polypeptides identified above (SEQ ID NO: 3, 5, 7, 9, 11, 13 or 14) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 3, 5, 7, 9, 11, 13 or 14.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

In one aspect, the present invention relates to a pharmaceutical composition or vaccine for inducing an immunological response in a host animal inoculated with the vaccine or composition, the vaccine or composition including a pharmaceutical acceptable carrier and a modified APMV recombinant virus or viral vector. In yet another aspect of the invention, the recombinant APMV virus or viral vector includes, within a non-essential region of the virus genome, a heterologous DNA sequence which encodes an antigenic protein derived from a pathogen wherein the composition or vaccine when administered to a host, is capable of inducing an immunological response specific to the protein encoded by the pathogen.

A "vector" refers to a recombinant DNA or RNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes vectors for cloning as well as viral vectors.

The term "engineered" or "recombinant" means a polynucleotide of semisynthetic, or synthetic origin that either does not occur in nature or is linked to another polynucleotide in an arrangement not found in nature.

The term "nonessential region" refers to a region of a virus genome which is not essential for replication and propagation of the virus in tissue culture and whose deletion or inactivation may reduce virulence in a variety of animal systems. Any nonessential region or portion thereof can be deleted from the APMV genome or a foreign sequence can be inserted in it, and the viability and stability of the recombinant APMV resulting from the deletion or insertion can be used to ascertain whether a deleted region or portion thereof is indeed nonessential. In one embodiment, the nonessential region of the APMV genome is any region on the APMV-2, 4, 6, or 8 genome that does not encode Polymerase (L). In yet another embodiment, the nonessential region comprises an open reading frame encoding a nonessential protein. In this aspect, the open reading frame is selected from the group consisting of nucleoprotein (NP), phosphoprotein (P), matrixprotein (M), fusionprotein (F), and hemagglutinin/neuraminidase (HN). In one embodiment, the nonessential region is located upstream of the NP gene. In another embodiment, the nonessential region is located downstream of the L gene. In yet another embodiment, the nonessential region is a non-coding or intergenic region. In this aspect, the non-coding or intergenic region may be a region between NP and P genes, between P and M genes, between M and F genes, or between F and FIN genes on the APMV-2, 4, 6, or 8 genome. In yet another embodiment, the nonessential region may be in the region of nucleotide positions 1-140, 1526-1692, 2910-3085, 4195-4498, 6130-6382, 8116-8272, 8116-8289, or 15013-15342 of SEQ ID NO:1.

In another aspect, the invention includes APMV chimeras in which one part or the full gene or several parts or full genes of the APMV vector are replaced by similar genes from other viruses, in particular those belonging to the paramyxoviridae family.

In one embodiment of the invention, the vaccine or pharmaceutical composition comprises an antigen selected from the group of avian pathogens including, but not limited to, *Salmonella typhimurium, Salmonella enteritidis*, Infectious Bronchitis virus (IBV), Newcastle Disease virus (NDV), egg drop syndrome virus (EDS), or Infectious Bursal Disease virus (IBDV), Infectious Laryngotracheitis virus (ILTV), avian adenoviruses, Marek's disease virus (MDV), fowlpox virus, duck enteritis virus (DEV), duck parvoviruses, avian influenza virus, APMV, such as APMV-1, and the like, and combinations thereof.

In another embodiment, the vaccine or pharmaceutical composition comprises an antigen selected from a feline pathogen such as, but not limited to, feline herpesvirus (FHV), feline calicivirus (FCV), feline leukemia virus (FeLV), feline immunodeficiency virus (Fly), feline parvovirus (FPV), feline infectious peritonitis virus (FIPV), rabies virus, and the like, and combinations thereof.

In yet another embodiment, the vaccine or pharmaceutical composition of the present invention comprises an antigen selected from a canine pathogen including, but not limited to, rabies virus, canine herpesvirus (CHV), canine parvovirus (CPV), canine distemper virus (CDV), canine parainfluenza 2 (CPI2), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment, the vaccine or pharmaceutical composition comprises an antigen selected from an equine pathogen, such as equine herpesvirus (type 1 or type 4), equine influenza virus, tetanus, west nile virus, equine arterivirus and the like or combinations thereof.

In yet another embodiment, the vaccine or pharmaceutical composition comprises an antigen selected from a bovine, ovine or caprine pathogen, such as rabies virus, bovine rotavirus, bovine parainfluenza virus type 3 (bPIV-3), bovine coronavirus, bovine viral diarrhea virus (BVDV), foot and mouth disease virus (FMDV), Rinderpest virus (RPV), Peste des Petits Ruminants virus (PPRV), malignant catarrhal fever viruses, bovine respiratory syncytial virus (BRSV), Infectious Bovine Rhinotracheitis virus (IBR), *Escherichia coli, Pasteurella multocida, Pasteurella haemolytica* and the like, and combinations thereof.

In still another embodiment, the vaccine or pharmaceutical composition comprises an antigen selected from a porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *Mycoplasma hyopneumoniae, Erysipelothrix rhusiopathiae, Pasteurella multocida, Bordetella bronchiseptica, Escherichia coli* and the like, and combinations thereof.

Construction of recombinant virus is well known in the art as described in, e.g., U.S. Pat. Nos. 4,769,330, 4,722,848, 4,603,112, 5,174,993, and 5,756,103, 6,719,979. Specifically, a recombinant APMV virus may be constructed in two steps. First, the gene of interest to be inserted into the virus, such as an open reading frame of an antigen from an APMV-1 (NDV) or avian influenza virus or other organism, is placed into an *E. coli* plasmid construct into which the cDNA homologous to a section of cDNA of the APMV is inserted. Separately, the cDNA gene sequence to be inserted is preceded by a promoter region (gene start region) and followed by a gene end region which is specific for the APMV vector. The gene start/foreign antigen/gene end DNA fragment is flanked by cDNA fragment homologous of APMV-8 cDNA containing unique restriction enzyme cleavage sites. The resulting plasmid construct is then amplified by growing in *E. coli* bacteria and isolated. Next the recombinant plasmid is used in a restriction enzyme digest to cut out the gene start/foreign antigen/gene end DNA fragment that is flanked by cDNA homologous of APMV-8 cDNA and this fragment is ligated into the appropriately cleaved full length construct of APMV-8.

Figure 19A:
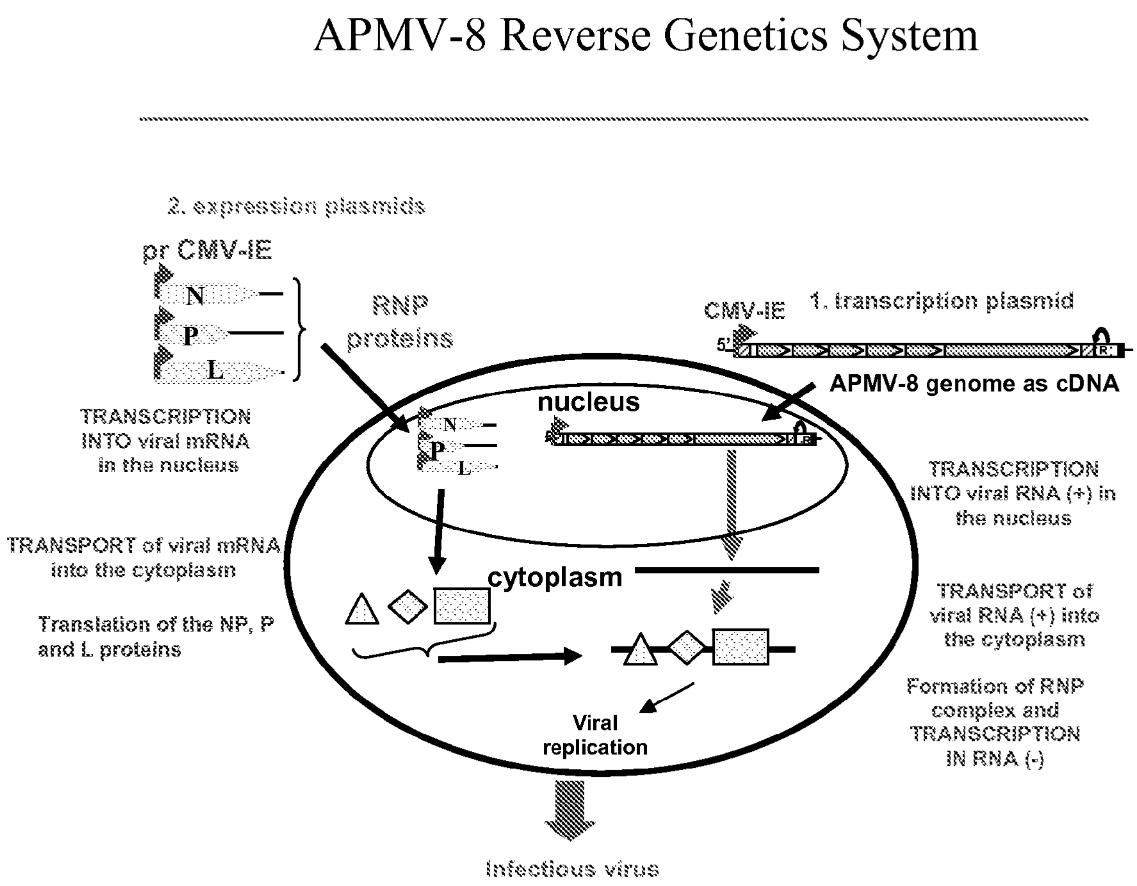
FIG. 19A is a flow diagram of the APMV-8 reverse genetics system.

The full length construct containing the gene of interest is transfected into cells along with plasmids containing polynucleotides for expression of the APMV nucleoprotein (NP), the APMV phosphoprotein (P) and the APMV RNA polymerase (L) as well as the T7 RNA polymerase. All APMV cDNA constructs are under the control of the T7 polymerase promoter. The rescue of infectious virus is performed as described in Römer-Oberdörfer et al., 1999 and as shown in FIG. 19A. The expression of the T7 RNA polymerase in transfected cells can be obtained by different means including transfection of plasmid DNA containing an expression cassette of the T7 RNA polymerase, recombinant virus (such as fowlpox or canarypox virus) expressing the T7 RNA polymerase or in cells that express the T7 RNA polymerase. In another aspect, the polynucleotides for expression of the APMV nucleoprotein (NP), the APMV phosphoprotein (P) and the APMV RNA polymerase (L) and the full length viral cRNA are under the control of the immediate early promoter of the human cytomegalovirus. The rescue of the virus is performed as described in Inoue K, et al., 2003.

Successful expression of the inserted cDNA of interest (foreign cDNA or heterologous cDNA) by the modified infectious virus requires two conditions. First, the insertion must be introduced into a region of the genome of the virus in order that the modified virus remains viable. The second condition for expression of inserted cDNA is the presence of a regulatory sequences allowing expression of the gene in the viral background (for instance: gene start, gene stop, promoter, enhancer, polyadenylation signals, intergenic and untranslated regions).

In general, it is advantageous to employ a strong promoter functional in eukaryotic cells. In one embodiment, the promoter used for the transcription of viral mRNA by the viral RNA polymerase is the "gene start sequence". The "gene start sequence" is the binding site for the L protein to bind and to transcribe the downstream located viral RNA into viral mRNA.

In one embodiment, the invention provides for the administration of a therapeutically effective amount of an APMV vaccine for the delivery and expression of an antigen, epitope or immunogen in a target cell. Determination of the therapeutically effective amount is routine experimentation for one of ordinary skill in the art. In one embodiment, the APMV vaccine formulation comprises an expression vector comprising a polynucleotide that encodes an antigen, epitope or immunogen and a pharmaceutically or veterinarily acceptable carrier, vehicle or excipient. In another embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection and/or improve preservation of the vector (or protein). Doses and dose volumes are herein discussed in the general description and can also be determined by the skilled artisan from this disclosure read in conjunction with the knowledge in the art, without any undue experimentation.

In another embodiment, pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, from 3 to 8 p/v %, the latter being in total or in part, or in a mixture either polyglycerol esters, said polyglycerol esters being polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (see, e.g., U.S. Pat. No. 6,358,500). Examples of other suitable emulsions are described in U.S. Pat. No. 7,371,395.

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

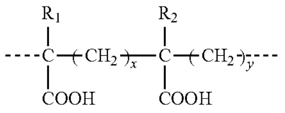

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between 0.01 and 1.5% w/v, between 0.05 and 1% w/v, and between 0.1 and 0.4% w/v.

Another aspect of the invention relates to a method for inducing an immunological response in an animal to an antigen, which method comprises inoculating the animal with a vaccine or a pharmaceutical composition including modified recombinant APMV virus which comprises and encodes the antigen of a pathogen for said animal. Yet another aspect of the invention relates to a method for inducing an immunological response in an animal to an antigen in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster. In one aspect of the prime-boost protocol of the invention, a composition or vaccine comprising the recombinant APMV virus (viral vector)

of the present invention is administered followed by the administration of an inactivated viral vaccine or composition comprising an antigen, or a vaccine or composition comprising a subunit (protein, antigen), or a DNA plasmid vaccine or composition that contains or expresses an antigen. Likewise, a prime-boost protocol may comprise the administration of an inactivated viral vaccine or composition comprising an antigen, or a vaccine or composition comprising a subunit (protein, antigen), or a DNA plasmid vaccine or composition that contains or expresses an antigen, followed by the administration of a composition or vaccine comprising the recombinant APMV virus (viral vector) of the present invention. It is further noted that both the primary and the secondary administrations may comprise the composition or vaccine comprising the recombinant APMV virus (viral vector) of the present invention.

The primary administration may comprise one or more administrations of the same viral vector-based immunological compositions of vaccines. Similarly, the booster administration may comprise one or more administrations of the same viral vector-based or immunological composition of vaccine. The administration route of the prime and the boost may be the same or different. Similarly, the origin of the protective gene present in the prime and the boost may be the same or different (e.g. different strain).

The various administrations are preferably carried out 1 to 6 weeks apart, and more particularly about 3 weeks apart. According to a preferred mode, an annual booster, preferably using the viral vector-based immunological composition of vaccine, is also envisaged. The animals are preferably at least one day old at the time of the first administration.

A variety of administration routes may be used such as subcutaneously or intramuscularly, intradermally, transdermally, spray, drinking water, eye drop, intranasal, oral, oral baits, in ovo or a combination (e.g. oculonasal, oronasal).

The invention will now be further described by way of the following non-limiting examples.

EXAMPLES

Example 1

APMV-2, APMV-4, and APMV-6

A. Viruses and Birds

One-day-old SPF (specific pathogen free) chickens (Merial, Gainesville, Ga.) were housed in positive pressure Horsfall-Baur isolation units. Feed and water were provided ad libitum and the birds were examined twice daily. The viruses (APMV-2, 4, and 6) used for experimental studies were isolated from wild birds and classified by the National Veterinary Service Laboratory (NVSL, Ames Iowa, USA). Viruses were propagated in 9-day-old embryonated SPF chicken eggs (SunRise Farms, Catskill, N.Y., USA) by inoculation via the allantoic route. The allantoic fluid was harvested at day 3 after inoculation, aliquoted, and stored at −80° C. The APMV subtype was confirmed by the HI test using standard sera (NVSL, Ames, Iowa, USA). The 50% egg infectious dose ($EID_{50}$) for each isolate was determined by inoculating 10-fold serial dilutions of allantoic fluid in embryonated SPF eggs. The titer was calculated following the method as described by Reed and Muench (Reed, L J et al., 1938, Am. J. Epidemiol. 27:493-497).

B. Experimental Infection

Twenty-five one-day-old SPF chickens per group were infected with $10^6$ $EID_{50}$ per chicken by the ocular-nasal route. Chickens of the control group were mock inoculated with PBS (phosphate buffered saline). At days 2, 4, 7, 14, and 28 p. i. (post infection) five birds from each group were bled via the wing vein to collect serum samples, euthanized with $CO_2$, and necropsied. Tissue specimens of the trachea, lung, pancreas and gut were collected. For each organ, a fresh pair of sterile scissors and forceps was used. Half of the tissue sample was placed in a Lysing Matrix D tube (MP Biomedicals, Solon, Ohio) containing viral transport medium (1× minimal essential medium, 7.5% sodium bicarbonate, 15 mM HEPES, 1% fetal bovine serum, 4,000 U/ml penicillin, 400 μg/ml gentamycin, 8 μg/ml amphotericin B, 4,000 μg/ml streptomycin, 1000 μg/mlkanamycin sulfate). The second half of the tissue sample was fixed in 10% buffered formalin and embedded in paraffin wax. Sections of the paraffin-embedded tissues were stained with Mayer's hematoxylin and eosin (H&E).

The results showed that mild diarrhea was observed at day four and seven p. i. in birds infected with APMV-2 or APMV 4. During necropsy, birds infected with APMV-2 showed slightly enlarged pancreas at day two and four after infection. No other gross lesions were observed in any group.

C. Serology

The hemagglutination (HA) and hemagglutination-inhibition (HI) tests were used to detect virus in allantoic fluid and analyze the presence of HI antibodies in collected serum samples, respectively. The tests were conducted by standard procedures using 0.8% chicken red blood cells resuspended in PBS. The HI test was performed by the diluted-serum constant-antigen method. Eight HA units of viral antigen was used for each serum dilution.

The HI antibody titers were investigated at day 2, 4, 7, 14, and 28 p.i. Positive HI titers (≧1:16) were observed in serum samples of APMV-2 infected birds at day 7 (1/5), day 14 (5/5), and day 28 p.i. (5/5). Interestingly, only one chicken infected with APMV-4 developed an HI titer which has been considered as positive during the course of the experiment at day 14 p.i. Similarly for APMV-6, two chickens out of five developed a HI titer of 1:16, only on day 28 p.i. Mock inoculated birds remained negative for HI antibodies to all three APMV used in this experiment. In addition, to exclude cross contamination all sera were tested for HI antibodies against the other two antigens and remained negative.

D. Virus Isolation

The tissue samples collected in the Lysing Matrix D tubes (MP Biomedicals, Solon, Ohio, USA) were homogenized twice using the Fastprep®-24 (MP Biomedicals, Solon, Ohio) at a setting of 4.0 M/S for 20 seconds. Following incubation for 15 min at room temperature, the homogenized samples were centrifuged for 20 min at 2000 g at 4° C. Sterility was tested after inoculation of 50 μl of the obtained supernatant in 2 ml tryptose phosphate broth (TPB) (DIFCO, Becton Dickenson, Sparks, Md., USA) supplemented with 10% hydrolactalbumin by incubation at 37° C. in an orbital shaker overnight. Non-sterile samples were filtered with 0.45 μm syringe filters (Whatman Inc., Florham Park, N.J., USA). Samples were stored at −80° C. Virus isolation was performed by inoculation of 0.1 ml into the allantoic cavity of 9-day-old embryonated SPF chicken eggs. After incubation for three days at 37.5° C., the allantoic fluid was harvested and tested for the presence of haemagglutinating activity by HA.

To analyze sites of virus replication, several organs (trachea, lung, gut, pancreas) were analyzed for infectious virus by virus isolation in embryonated eggs (FIG. 1). Overall, replicating virus was only detected in a few chickens. Briefly, APMV-4 was recovered on day 2 from trachea, lung and pancreas while APMV-6 was isolated from lung and pancreas. At day 4, APMV-2 was isolated from trachea and lung while APMV-6 was isolated from all tested organs except the gut. At day 7, APMV-2 was isolated from a single gut sample, APMV-4 was isolated from the pancreas while APMV-6 was isolated from lung and pancreas samples. Surprisingly, at day 14 p.i. no virus was isolated whereas at day 28 p.i. APMV-2, 4 and 6 could be isolated from the pancreas. No virus was isolated from mock inoculated birds. The identity of the back isolated virus was confirmed by HI test using standard sera as provided by NVSL.

To evaluate the pathological potential of the investigated viruses, microscopical lesions in the obtained organs were analyzed (FIG. 2). At day 2 p.i., a catarrhal tracheitis in addition to ciliary loss on the respiratory epithelium and mild enteritis was observed in all infected chickens. At day 4 p.i., APMV-2 infected chickens showed an increased number of hypertrophic mucous glands in the trachea and focal ulcerations of the respiratory epithelium. APMV-4 infected birds showed changes highly suggestive of a respiratory infection such as mild tracheitis, mild to moderate multifocal lymphocytic pancreatitis and also a focal BALT (Bronchus-Associated Lymphoid Tissue) hyperplasia at day 4 p.i. The investigation on organs of APMV-6 infected chickens revealed tracheal changes such as catarrhal and ulcerative tracheitis and a focal pancreatitis that are consistent with a viral stimulation. At day 7 p.i., APMV-2 infected chickens showed focal tracheal attenuation or replacement of respiratory epithelium as indicative of healing. Birds infected with APMV-4 showed mild BALT hyperplasia while APMV-6 infected birds showed cystic enteropathy, focal enteritis and lymphocytic infiltrates in the pancreas. In addition to mild lymphocytic enteritis and mild GALT hyperplasia, APMV-2 infected birds also showed healing changes such as tracheal attenuation at day 14 p.i. Organ samples from chicken infected with APMV-4 or 6 showed changes suggestive of viral infection such as mild interstitial pneumonia, catarrhal tracheitis and BALT or GALT hyperplasia at day 14 p.i. All investigated samples obtained from infected chicken showed lesions such as GALT hyperplasia, lymphocytic pancreatitis and lymphocytic bronchitis at day 28 p.i. At day 2, birds of the control group showed a mild catarrhal tracheitis which could be attributed to environmental factors.

FIG. 3 shows low HI titers (up to 1:32 at day 14) from SPF chickens infected with APMV-4 or APMV-6 indicating that only APMV-2 infection elicited an HI response that could be characterized as seropositive. Nevertheless, all three viruses were recovered from the infected birds' trachea, lungs, gut and pancreas up to day 7 p.i. and from the pancreas up to day 28 p.i. Infection with APMV-2, 4, or 6 showed characteristic histopathological lesions (summarized in FIG. 2) in all the infected birds, indicative of stimulation with a viral antigen. The viral isolation and histological profiles of the infected birds clearly depicted the tropism of the viruses in the infected birds (trachea and lungs from day 2 to day 7 and gut, lung and pancreas from day 7 onwards). All isolates were detected in the pancreas up to 28 days p.i. but virus isolation was not possible at day 14 p.i. This indicated that the investigated APMV can probably persist and later become reactivated. Thus virus carriers can be present in infected flocks. Only APMV-2 induced HI antibodies while HI antibodies of chickens infected with APMV-4 and 6 were not detected.

Example 2

APMV-8

A. Viruses and Birds

One-day-old SPF chickens (Merial, Gainesville, Ga., USA) and Pekin ducks (Metzer Farms, Gonzales, Calif., USA) were housed in positive pressure Horsfall Baur isolation units. Feed and water were provided ad libitum, and the birds were examined twice daily. The APMV-8 virus (APMV-8: SCWDS ID: MA-7) used for experimental studies was isolated from a mallard and classified by the National Veterinary Service Laboratory (NVSL, Ames Iowa, USA). The virus was propagated in 9-day-old embryonated SPF chicken eggs by inoculation via the allantoic route. Allantoic fluids were harvested at day 3 after inoculation, pooled, aliquoted and stored at −80° C. The APMV-8 subtype was confirmed by HI testing using standard sera as provided by the National Veterinary Service Laboratory (Ames, Iowa, USA). The $EID_{50}$ was determined by inoculating 10-fold serial dilutions of allantoic fluid in embryonated SPF eggs. The titer was calculated following the method as described by Reed and Muench (Reed & Muench, 1938).

B. Experimental Infection

Twenty five one-day-old SPF chickens or Pekin ducks per group were infected via the oculonasal route with $10^6$ $EID_{50}$ per bird diluted in PBS. Birds of the control chicken or duck group were mock inoculated with PBS. Five birds from each group were bled via the brachial vein to collect serum samples, humanely euthanized with $CO_2$, and necropsy was performed at two, four, seven, fourteen and twenty eight days post infection (d p.i). Tissue specimens of the trachea, lung, pancreas, and gut (duodenum) were collected. For each organ, a fresh pair of sterile scissors and forceps was used. Half of the tissue sample was placed in a Lysing Matrix D tube (MP Biomedicals, Solon, Ohio, USA) containing viral transport medium (VTM, 1× minimal essential medium, 7.5% sodium bicarbonate, 15 mM HEPES, 1% fetal bovine serum, 4,000 U/ml penicillin, 400 μg/ml gentamycin, 8 μg/ml amphotericin B, 4,000 μg/ml streptomycin, 1000 μg/ml kanamycin sulfate). The second half of the tissue sample was fixed in 10% buffered formalin and routinely processed, embedded, sectioned and stained with hematoxylin and eosin (H&E).

C. Virus Isolation

The tissue samples collected in the Lysing Matrix D tubes were homogenized twice using the FastPrep-24 (MP Biomedicals) at a setting of 4.0 M/S for 20 seconds. The homogenized samples were incubated for 15 min at room temperature and then centrifuged for 20 min at 2000×g at 4° C. 50 μl of the obtained supernatant was inoculated in 2 ml sterile TFB supplemented with 10% hydrolactalbumin followed by incubation at 37° C. in an orbital shaker overnight to test for sterility. Non-sterile samples were filtered with 0.45 μm syringe filters (Whatman Inc.). Samples were stored at −80° C. Virus isolation was performed by inoculation of 0.1 ml into the allantoic cavity of 9-day-old embryonated SPF chicken eggs. After incubation for three days at 37.5° C., the allantoic fluid was harvested and tested for the presence of hemagglutinating activity by HA.

D. Serology

The hemagglutination (HA) and hemagglutination-inhibition (HI) tests were used to detect virus in allantoic fluid and to analyze the presence of HI antibodies in collected serum samples, respectively. The tests were conducted by standard procedures using 0.8% chicken red blood cells resuspended in PBS. The HI test was performed by the diluted-serum constant-antigen method. Eight HA units of viral antigen were used for each serum dilution. The geometric mean titer was determined as described previously (Brugh, 1978).

FIG. 4 shows HI antibody titers in SPF chickens and ducks infected with APMV-8. Chickens and ducks were oro-nasal infected with a dose of $10^6$ $EID_{50}$ of APMV-8. Sera samples were collected at day 2, 4, 7, 14, and 28 p.i. and analyzed by the HI test with the APMV-8 antigen. The HI serum titers (in $\log_2$) are shown on the left axis.

E. Pathogenicity Indices of APMV-8 in Chicken

To assess the virulence of APMV-8, the intracerebral pathogenicity index (ICPI) was determined following the World Organization for Animal Health (OIE, 2008) procedures for Newcastle disease virus. The mean dead time (MDT) in chicken embryos was determined as described previously (Swayne et al., 1998) using a serial dilution of APMV-8 from $10^{-1}$ through $10^{-8}$.

The determination of the mean dead time (MDT) in embryonated eggs as well as the assessment of the intracerebral pathogenicity index (ICPI) is an important measurement for the pathogencity of the virus. With respect to the MDT in embryonated eggs, none of the embryos of the inoculated eggs died after the 7 day period and thus the APMV-8 isolate can be classified as lentogenic. The presence of virus was confirmed by HA test using the allantoic fluid of eggs inoculated with the $10^{-6}$ dilution. All the chickens intracerebrally inoculated showed no clinical signs over the observation time resulting in an ICPI value of zero which results in a lentogenic phenotype.

F. APMV-8 Booster Vaccination

Ten one-day-old SPF chickens per group were infected via the oculo-nasal route with $10^6$ $EID_{50}$ per bird. Birds of the control chicken group were mock inoculated with PBS. The birds were infected again with the same dose 14 days after the first infection. The presence of infectious virus was monitored at day 2, 4, 7 and 14 after the first infection and day 2 and 4 after the second infection by virus isolation from tracheal swabs using 9-day-old embryonated SPF eggs. Antibody response was monitored by HI titer of serum samples collected at 0, 7, and 14 days after each vaccination.

Figure 5:
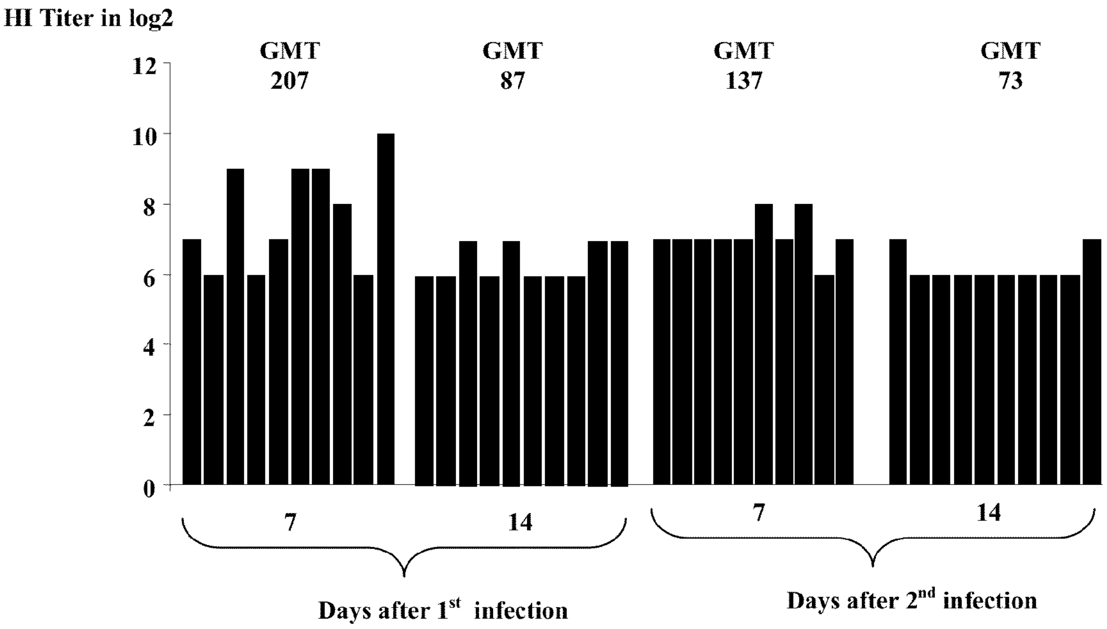
FIG. 5 shows the development of HI antibody titers in SPF chickens during a prime/boost vaccination scheme with APMV-8. One-day old SPF chickens were infected at day 1 (prime) and day 14 (boost) with a dose of $10^6$ $EID_{50}$ of APMV-8. Serum samples were obtained at day 7 and 14 p.i. after the first infection and day 7 and 14 p.i. after the second infection. The sera were subjected to the HI test. The HI serum titers (in log 2) are shown on the left axis.

In order to investigate if a second immunization would allow developing a more sustainable HI titer, a prime/boost scheme experiment was performed (FIG. 5). On day 7 after the first infection, all ten birds showed an HI ranging from 64 to 1024 (GMT 207). The titer declined at 14 d p.i. after the first infection (GMT 84) but increased after the boost infection at day 14 after the initial infection. On day 7 after the boost vaccination, the GMT increased to 137 and decreased again to a GMT of 73 at day 14 after the second infection. Infectious virus could be isolated from tracheal swabs at day 2 (5/10 birds) and day 4 (4/10) birds after the first infection. After the second infection no virus was isolated from the swabs taken at day 2 and 4 p.i.

G. Detection of Viral RNA by RT-PCR

Figure 6:
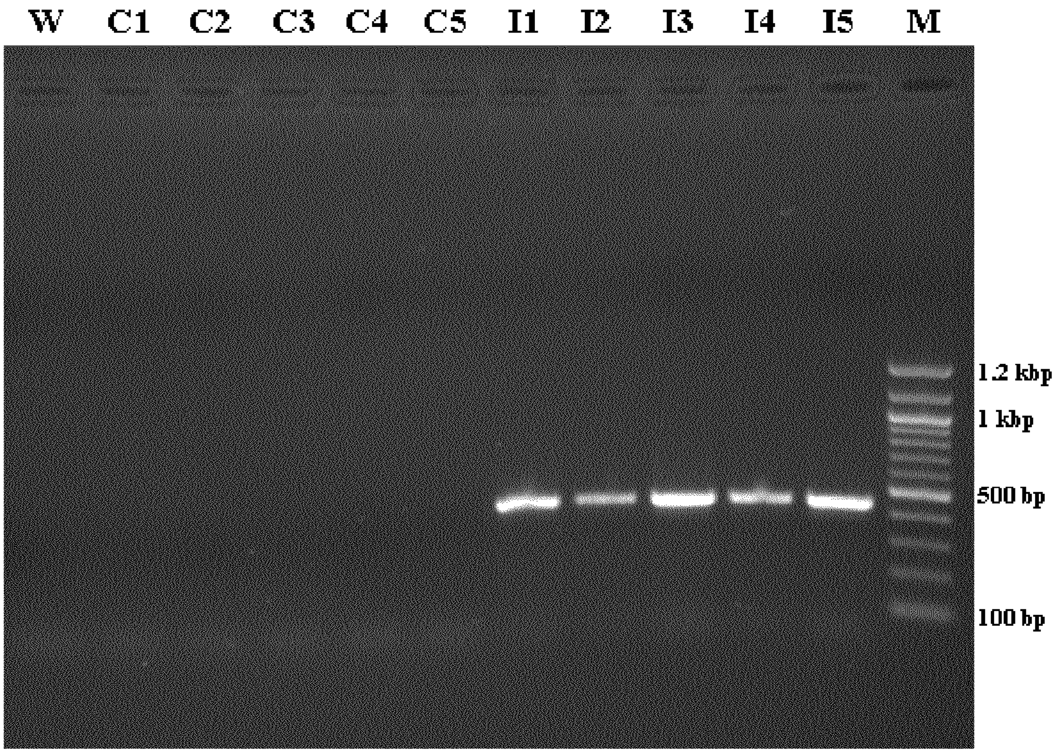
FIG. 6 shows the analysis of RT-PCR products by agarose gel electrophoresis. Tracheal tissues were taken at day 2 p.i. from non-infected ducks (C1-C5) and APMV-8 infected ducks (I1-I5). The tissues were homogenized and RNA was prepared for RT-PCR. A water control (W) was prepared in parallel. The reaction products were separated on a 1.5% agarose gel. The size of the fragment was controlled by using the 100 by ladder (New England Biolabs). The sizes of the DNA fragments are shown at the right.

The detection of viral RNA from tissue samples was performed after homogenization of tissue samples followed by isolation of RNA by using the High Pure RNA isolation kit (Roche, Mannheim, Germany). A primer pair (8NPfl, 8NPr, see table 1) was used in an RT-PCR using the Supercript III One Step RT-PCR kit with Platinum Taq (Invitrogen, Carlsbad, Calif., USA) following the instructions of the manufacturer. The obtained reaction products were analyzed on a 1% agarose gel (FIG. 6). Tracheal tissues were taken at day 2 p.i. from non-infected ducks (C1-C5) and APMV-8 infected ducks (I1-I5). The tissues were homogenized and RNA was prepared for RT-PCR. A water control (W) was prepared in parallel. The reaction products were separated on a 1.5% agarose gel. The size of the fragment was controlled by using the 100 bp ladder (New England Biolabs, Boston, Mass., USA). The sizes of the DNA fragments are shown at the right.

TABLE 1

Oligonucleotides used for RT-PCR for the detection of viral RNA in tissue samples

| Name | Sequence | orientation | Location[A] | SEQ ID NO |
|---|---|---|---|---|
| APMV-PolyT | TTTTTTTTTTTTTTTTTTACCAAACARRGAA | sense | 1-14 | 21 |
| 8NPf1 | CAGGAGACCTGATGTTGCCTCAAC | sense | 200-223 | 22 |
| 8NPr | GCAGGCGATCTATAGTCTCTGATAG | antisense | 618-642 | 23 |

H. Determination of the Minimal Infectious Dose in Chicken and Ducks

In order to determine which viral titer would be sufficient in chickens to detect a seroconversion, one-day-old SPF chickens were infected with different doses of APMV-8. The birds were housed as described above. Ten chickens per group were infected each with $10^1$, $10^2$, $10^3$, $10^4$, $10^5$, or $10^6$ $EID_{50}$. The virus was diluted in VTM. One group was inoculated with VTM and served as control. The birds were bled at day 7 and 14 after infection via the brachial vein. Based on the results obtained during the chicken experiment three-day-old Pekin ducks were infected with different amount of virus. The infection dose was chosen $10^3$, $10^4$, $10^5$, or $10^6$ $EID_{50}$ per duck. One group was mock-infected with VTM. The birds were bled at day 7 and 14 after infection via the leg vein. The serum sample was analyzed for the presence of virus specific antibodies by HI as described above.

I. Determination of the Pathogenicity in Ducks and Chickens

During the experiments, no clinical signs were observed in chickens and ducks. During necropsy, three infected chickens showed slightly enlarged pancreas and inflamed duodenum at day two and four p.i. No other gross lesions were observed in any group.

The serological response was examined at 2, 4, 7, 14, and 28 d p.i. by investigation of the HI titers in the serum (FIG. 4). Serum samples of APMV-8 infected chickens showed positive HI titers ($\geqq 16$) starting with 7 d p.i. (5/5, GMT: 111), 14 d p.i. (5/5, GMT: 48), and 28 d p.i. (5/5, GMT: 48). Serum samples of APMV-8 infected ducks also showed positive HI titers ($\geqq 16$) at 7 (5/5, GMT 21), 14 (5/5, GMT 28), and 28 (4/5, GMT 14) d.p.i. The HI titers ranged from 32 to 256 for chickens, while for ducks the range was from 16 to 64. Sham inoculated birds remained negative for HI antibodies to APMV-8 at all time points investigated in both species.

To determine the sites of virus replication in chickens and ducks, several organs (trachea, lung, duodenum, and pancreas) were analyzed for infectious virus by virus isolation in embryonated eggs (FIG. 7). In chickens, APMV-8 was recovered at 2 d p.i. from trachea, lung, and duodenum. At 4 d p.i., APMV-8 was isolated from all the analyzed organs; while at 7 d p.i., APMV-8 was isolated only from the pancreas. At 14 and 28 d p.i. no virus was isolated from any organ. No virus was isolated from sham inoculated birds. The identity of the back isolated virus was confirmed by HI test using standard sera as provided by NVSL. No virus was isolated from any of the collected duck tissues at any time point even after two subpassages in 9-day-old embryonated SPF chicken eggs. Therefore, RT-PCR primers were designed based on the APMV-8 sequence information available to detect the presence of viral RNA in the collected tissue samples (FIG. 7). At 2 d p.i viral RNA was detected in the trachea (FIG. 6), gut and pancreas while at 4 d p.i viral RNA was detected in all the organs analyzed. At 7, 14, and 28 d p.i, viral RNA was detected only in the trachea and lung. RT-PCR using RNA obtained from organs of mock inoculated birds did not result in the amplification of an RT-PCR fragment which indicates the absence of APMV-8 in these birds.

To evaluate the pathological potential of the investigated virus, the organs were analyzed for the presence of microscopic lesions (FIG. 8). At 2 d p.i., a mild multifocal proliferative tracheitis was observed in all infected chickens. The remaining organs showed no difference to the control group. APMV-8 infected chickens showed focal attenuation or regeneration of respiratory epithelium in the trachea at 4 d p.i. as indicative of healing. Additionally, the birds also showed mild multifocal lymphocytic pancreatitis which indicated a viral infection. Infected chicken showed changes in the lung at 7 d p.i. such as moderate to severe BALT, tracheal changes such as catarrhal tracheitis and multifocal lymphocytic pancreatitis. These findings are consistent with an antigenic stimulation. At 14 d p.i, tracheal changes consistent with healing and pancreatic changes such as lymphocytic pancreatitis suggestive of viral infection were observed in infected chickens. At 28 d p.i., only a mild catarrhal tracheitis and mild enteritis were observed in some of the infected chickens. In infected ducks, multifocal mild lymphocytic tracheitis, lung changes (interstitial pneumonia) and intestinal changes (lymphocytic enteritis) were observed at 2 d p.i while tracheal changes consistent with respiratory infection were seen at 4 d.p.i. At 7 d p.i., infected ducks showed lymphocytic tracheitis and pancreatitis consistent with viral infection whereas the observed catarrhal tracheitis was a suggestive of healing at 14 d p.i. In addition, infected ducks showed a lymphocytic pancreatitis at 14 d p.i. Later, at 28 d p.i., in the lung of infected ducks a BALT hyperplasia and also mild multifocal heterophilic tracheitis were noticed. Both pathological microscopic lesions were indicative of a viral infection. In the non infected controls no changes in the examined organs were observed.

J. Determination of the Minimal Dose Needed for Induction of an Immune Response

Figure 9:
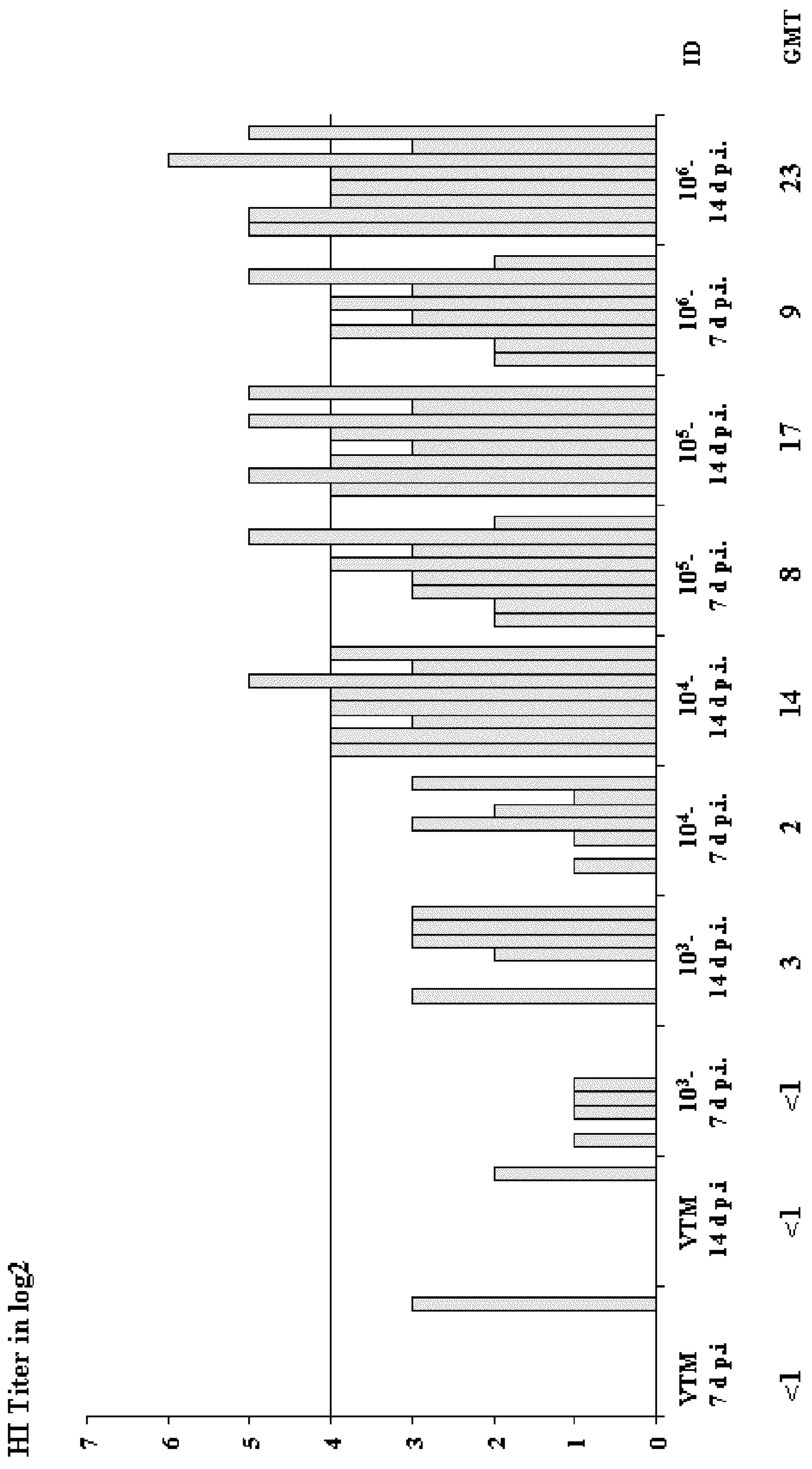
FIG. 9 shows the development of HI antibody titers in SPF chickens after infection with different doses of APMV-8. One-day old SPF chickens were infected at day 1 with different infectious doses (ID) of APMV-8 or mock-infected with virus transport medium (VTM). Blood was taken at day 7 and 14 p.i. and the obtained serum samples were analyzed by the HI test. The HI serum titers (in log 2) are shown on the left axis. The geometric mean titer (GMT) of the serum samples are shown in the lowest row.

In order to examine the minimal infectious dose which is necessary to induce a seroconversion in chicken, tenfold dilutions of APMV-8 were used to infect ten one-day-old SPF chickens (FIG. 9). For the HI test, 4 HA units were used which results in a threshold of 16 to be considered as positive. The serum samples taken at day 14 p.i. showed that an $EID_{50}$ of $10^3$ was sufficient to induce an immune response in 4/10 chickens which was considered as positive (GMT 11). At day 14 after infection with an $EID_{50}$ of $10^4$ nine of ten birds showed a titer≧16 (GMT 34). The infection with an $EID_{50}$ of $10^5$ and $10^6$ induced an HI titer of ≧16 at day 14 p.i. in all birds with a GMT of 73 and 137, respectively.

Figure 10:
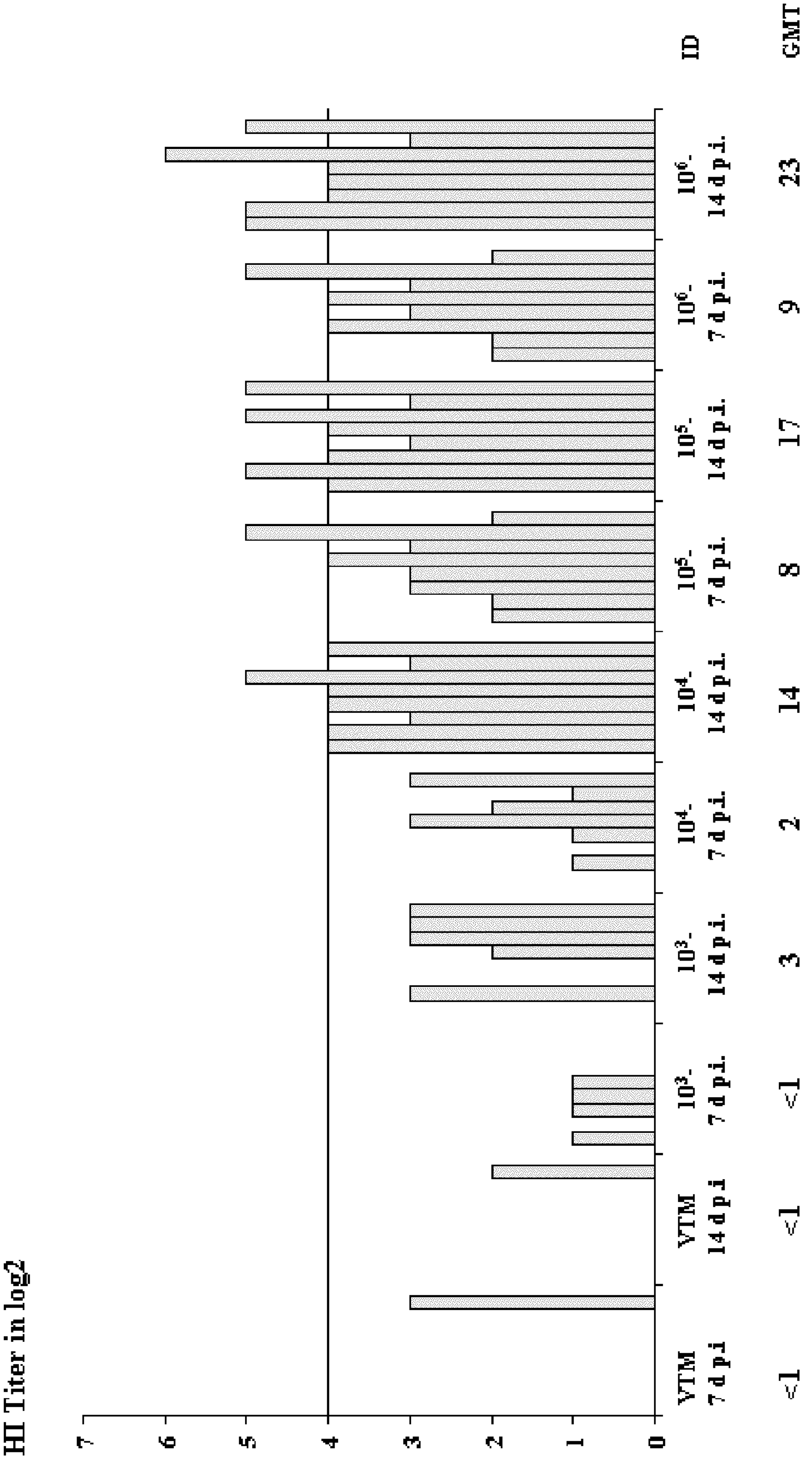
FIG. 10 shows the development of HI antibody titers in Pekin ducks after infection with different doses of APMV-8. One-day old SPF Pekin ducks were infected at day 1 with different infectious doses (ID) of APMV-8 or mock-infected with virus transport medium (VTM). Blood was taken at day 7 and 14 p.i. and the obtained serum samples were analyzed by the HI test. The HI serum titers (in log 2) are shown on the left axis. The geometric mean titer (GMT) of the serum samples are shown in the lowest row.

Based on this result, 8 ducks each were infected with APMV-8 starting with a dose $EID_{50}$ of $10^3$ per bird up to a dose of $EID_{50}$ of $10^6$ per bird (FIG. 10). Six out of eight ducks developed significant titers (≧16) 14 days after infection with a GMT of 14 after infection with an $EID_{50}$ of $10^4$/bird. At day 14 p.i. 6/8 ducks infected with an $EID_{50}$ of $10^5$/bird and 7/8 ducks infected with an $EID_{50}$ of $10^6$/birds developed significant titers (≧16) with a GMT of 17 and 23, respectively.

Example 3

Determination of the Full Length Sequence of APMV-8

For the determination of the full length sequence of APMV-8, viral RNA sequence information is initially needed. To this end, the 3'-end of the viral genome was cloned by using a primer (APMV-polyT, see table 1) which contained a degenerated sequence based on available 3'-sequences of APMV1 (Genbank accession No. AF077761), APMV-2 (Genbank accession No. EU338414), and APMV-6 (Genbank accession No. EF569970). Viral RNA was purified from allantoic fluid using the High Pure RNA isolation kit (Roche, Mannheim, Germany). The sequence was amplified using the 5' RACE System for Rapid Amplification of cDNA Ends Version 2.0 (Invitrogen) following the manufacturer's instructions. Several fragments were obtained, gel eluted and cloned into the Topo TA cloning vector (Invitrogen) and positive selected clones were sequenced. The obtained nucleotide sequences were analyzed in an nblast search against the NCBI database which resulted in no similarities. A tblastx search against the NCBI database showed similarities to the nucleoprotein of 83% similarity of an Avian paramyxovirus 2 (APMV-2/Chicken/California/Yucaipa/56, Genbank accession No. EU338414) and of 56% similarity of an Avian paramyxovirus 6 strain (APMV-6/Goose/FarEast/4440/2003, Genbank accession No. EF569970). Using this primer, the primer walking method was employed using the 5' RACE System for Rapid Amplification of cDNA Ends Version 2.0 (Invitrogen). The 5'-RACE produced an approximately 800 by fragment. Using this technique, new sequence information was obtained based on sequence information from the previous sequence which has been used for the delineation of new oligonucleotides. The 5'-end of the viral genome was also determined by the 5'-RACE method. The 3'-end of the viral genome was obtained after ligation of the RNA with T4 RNA ligasel (New England Biolabs). The ligation reaction was purified again with High Pure RNA isolation kit (Roche) and an RT-PCR was performed using Superscript III One Step RT-PCR kit with Platinum Taq (Invitrogen). The obtained cDNA fragment was cloned into the pCR2.1 vector (Invitrogen) and sequenced. Three plasmids from each cloned fragment were sequenced in both directions, thus resulting in sequence 6×-coverage of per nucleotide.

The full length genome sequence of the analyzed APMV-8 strain is 15342 nucleotides, this is in accordance to the rule of six (Calain, P. & Roux, L., 1993) for Paramyxovirinae. Six open reading frames (ORF) have been detected and are encoding for proteins. The order of the proteins was determined as 3'-NP-P-M-F-HN-L-5' (the genome sequence SEQ ID NO:1 is in the 5' to 3' orientation antigenomic) using similarities of the protein sequence to proteins of other avian paramyxoviruses. The putative start and stop codons of the ORF's and the theoretical molecular weight (Swiss Institute of Bioinformatics ExPASy website) of the proteins are shown in table 2.

TABLE 2

Parameter of the proteins encoded by the APMV-8 sequence

| Protein | Start codon | Stop codon | Theoretical MW (kD) |
|---|---|---|---|
| Nucleoprotein (NP) | 141-143 | 1524-1526 | 51.2 |
| Phospho protein (P) | 1693-1695 | 2908-2910 | 43.5 |
| Matrixprotein (M) | 3076-3078 | 4193-4195 | 40.6 |
| Fusioprotein (F) | 4499-4501 | 6128-6130 | 58.5 |
| Hemagglutinin/ neuraminidase (HN) | 6383-6385 | 8114-8116 | 63.5 |
| Polymerase (L) | 8273-8275 or 8297-8299 | 15011-15013 | 254.6 253.6 |

The putative genomic leader and trailer sequences were determined by determination of the putative gene start sequence of the NP gene (leader) and putative gene end sequence of the L protein (trailer). The leader sequence is located from nucleotide 1 to nucleotide 55. The putative gene start sequence (nt 56-63) of the NP gene ends the leader sequence. The trailer sequence is localized behind the last gene end sequence in the viral genome. Due to the presence of two putative gene end sequences for the RNA polymerase gene (nt 15161-15171 or 15288-15297) two putative trailer sequences have been identified (nt 15172-15342 or nt 15289-15342). The location of the putative gene start sequence (poly G containing sequences) and gene end sequences (signal sequence for a polyadenylation) and the intergenic sequences were summarized in table 3.

TABLE 3

Sequence and location of putative gene start, intergenic, and gene end sequence of APMV-8

| Gene | Gene start | Gene end | intergenic |
|---|---|---|---|
| Nucleoprotein | 56-63 | 1615-1625 | 1626-1627 |
| Phosphoprotein | 1628-1635 | 2991-3001 | 3002-3031 |
| Matrixprotein | 3032-3039 | 4404-4416 | 4417-4441 |
| Fusionprotein | 4442-4449 | 6260-6271 | 6272-6278 |
| Hemagglutinin/neuraminidase | 6279-6287 | 8261-8273 | 8274-8275 |
| RNA polymerase | 8275-8283 | 15161-15171 or 15288-15297 | |

TABLE 4

SEQ ID NO v. DNA and protein sequences.

| SEQ ID NO | Gene name | Type |
|---|---|---|
| 1 | APMV-8 genome sequence | DNA or RNA |
| 2 | APMV-8 Nucleoprotien (NP) | DNA or RNA |
| 3 | APMV-8 Nucleoprotien (NP) | Protein |
| 4 | APMV-8 phospho protein (P) | DNA or RNA |
| 5 | APMV-8 phospho protein (P) | Protein |
| 6 | APMV-8 Matrixprotein (M) | DNA or RNA |
| 7 | APMV-8 Matrixprotein (M) | Protein |
| 8 | APMV-8 Fusioprotein (F) | DNA or RNA |
| 9 | APMV-8 Fusioprotein (F) | Protein |
| 10 | APMV-8 Hemagglutinin/ neuraminidase (HN) | DNA or RNA |
| 11 | APMV-8 Hemagglutinin/ neuraminidase (HN) | Protein |
| 12 | APMV-8 Polymerase (L) DNA | DNA or RNA |
| 13 | APMV-8 Polymerase (L) protein 1 | Protein |
| 14 | APMV-8 Polymerase (L) protein 2 | Protein |

The putative gene start sequences for APMV-8 were conserved containing a poly $(C)_5$ sequence followed by a 3'-GCU-5' sequence. The only exception is the putative gene start sequence for the viral RNA polymerase (3'-CUC-CCGCU-5'). The putative gene end sequences were also conserved and contain a poly $(U)_6$ sequence at the genomic viral 5' sequence (Table 5).

TABLE 5

Gene Start and Gene End sequences of APMV-8

| Gene Name | Sequences (5-3' antigenomic orientation) | SEQ ID NO |
|---|---|---|
| | Gene start | |
| NP gene | **CCCCCGCU**UCUGUCA | 24 |
| P gene | **CCCCCGCU**GGAGUUA | 25 |
| M gene | **CCCCCGCU**UCUGUGC | 26 |
| F gene | **CCCCCGCU**UUAGAAC | 27 |
| HN gene | **CCCCCGCU**GGGUAAA | 28 |
| L | **CUCCCGCU**GGAGAUG | 29 |
| | Gene end | |
| NP gene | AACUAA**AUUCUUUUUU** | 30 |
| P gene | UAACUA**AUUCUUUUUU** | 31 |
| M gene | AGGAUU**AAUAUUUUUU** | 32 |
| F gene | CUAUAA**AUUAUUUUUU** | 33 |
| HN gene | UACUUA**AUUCUUUUUU** | 34 |
| L gene (1) | ACUAAA**AUUCUUUUUU** | 35 |
| L gene (2) | UUAUUG**AUUUUUUUUU** | 36 |

These sequences were predicted based on sequences which were described for other paramyxoviruses of the genus *Avulavirus* (Chang et al., 2001, Nayak et al, 2008, Jeon et al., 2008). There are two possible start codons for the ORF of the RNA polymerase. The first start codon (nt 8273-8275) is localized in the gene end—intergenic region—gene start region between the FIN ORF and the viral RNA polymerase ORF. This makes this start codon unlikely but not impossible. The second start codon (8297-8299) is down stream of the gene end—intergenic region—gene start region and may act as initiation codon for the start of the translation of the RNA polymerase of APMV-8.

The genome of APMV-8 is 15342 nt long. This is larger than APMV-1 (SQ ID NO:15, 15186 nt, de Leeuw & Peeters, 1999), APMV-2 (SEQ ID NO:16, 14,904 nt, Subbiah et al., 2008), and APMV-4 (SEQ ID NO:18, 15054 nt, Nayak et al., 2008), and smaller than APMV-3 (SEQ ID NO:17, 16,272 nt, Kumar et al., 2008) and APMV-9 (SEQ ID NO:20, 15,438 nt, Samuel et al., 2009). The length of 55 nt of the leader sequence seemed to be conserved between all APMV (Krishnamurthy & Samal, 1998, de Leeuw & Peeters, 1999, Subbiah et al., 2008, Nayak et al., 2008, Kumar et al., 2008, Samuel et al., 2009) whereas the trailer sequence seemed to be variable in length. The gene start and gene end sequences of the viral genes were also highly conserved for APMV-8 (as shown in Table 5). This has been also described for sequences of APMV-2 (Subbiah et al, 2008), APMV-3 (Kumar et al, 2008), APMV-4 (Jeon et al., 2008, Nayak et al, 2008), APMV-6 (Chang et al, 2001), and recently for APMV-9 (Samuel et al., 2009). The number of the nucleotides of the full length sequence is a multiple of six which is agreement with the role of six for the genomes of paramyxoviruses (Kolakofsky et al., 1998).

The sequence identity between APMV-1, 2, 3, 4, 6, 8, and 9 genome sequences are shown in Table 6.

TABLE 6

| sequence identity percentage between the genome of APMV-1, 2, 3, 4, 6, 7, 8, and 9 | | | | | | | | | | | | |
|---|---|---|---|---|---|---|---|---|---|---|---|---|
| | | APMV | | | | | | | | | | |
| | | 1 | 2 | 3 | 4 | 6 | 7 | 8 | 8 | 8 | 8 | 9 |
| | SEQ ID NO | 15 | 16 | 17 | 18 | 19 | 20 | 1 | 37 | 38 | 39 | 40 |
| 8 | 1 | 48 | 61 | 47.2 | 47.6 | 52 | 53 | 100 | 99.1 | 96.5 | 96.4 | 48 |

The percent sequence identity between two nucleic acid or polypeptide sequences is determined using Vector NTI 11.0 (PC) software package (Invitrogen, 1600 Faraday Ave., Carlsbad, Calif.). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. The percent identity was calculated based on the shorter sequence.

Example 4

Vaccination of One-Day-Old Broiler Chickens with APMV-8 Strain

Twenty one-day-old broiler chickens were separated into two groups according to table 7 shown below.

At day 1, the one-day-old chickens were bled to determine the antibody status directed against Newcastle disease virus (NDV) and APMV-8 using the hemagglutination inhibition assay (HI test). The test was performed using allantoic fluid from either NDV strain Lasota or APMV-8 infected SPF eggs. Four HA units of NDV strain Lasota or APMV-8 and 1% chicken red blood cells were used for the HI test. The resulting HI titers show that the serum of the chickens contained HI antibodies directed against NDV but no detectable antibodies against APMV-8 virus.

TABLE 7

Infection/vaccination of one-day-old broiler chickens

| Treatment | Group 1 (ten one-day-old chickens) | Group 2 (control) (ten one-day-old chickens) |
|---|---|---|
| Day 1: vaccination with APMV-8 strain | Yes | No |
| Day 14: HI test | Yes | Yes |
| Day 14: second vaccination with APMV-8 strain (boost) | 5 chickens (group 1-1): 2nd vaccination/ $1^{st}$ vaccination. 5 chickens (group 1-2): no $2^{nd}$ vaccination/ $1^{st}$ vaccination | 5 chickens (group 2-1): 2nd vaccination 5 chickens (group 2-2): not vaccinated |
| Day 28: HI test | Yes | Yes |

At day 1, group 1 of 10 chickens were infected with via the nasal route with $10^6$ $EID_{50}$ of APMV-8 strain, group 2 of 10 chickens were not infected serving as control.

Figure 20:
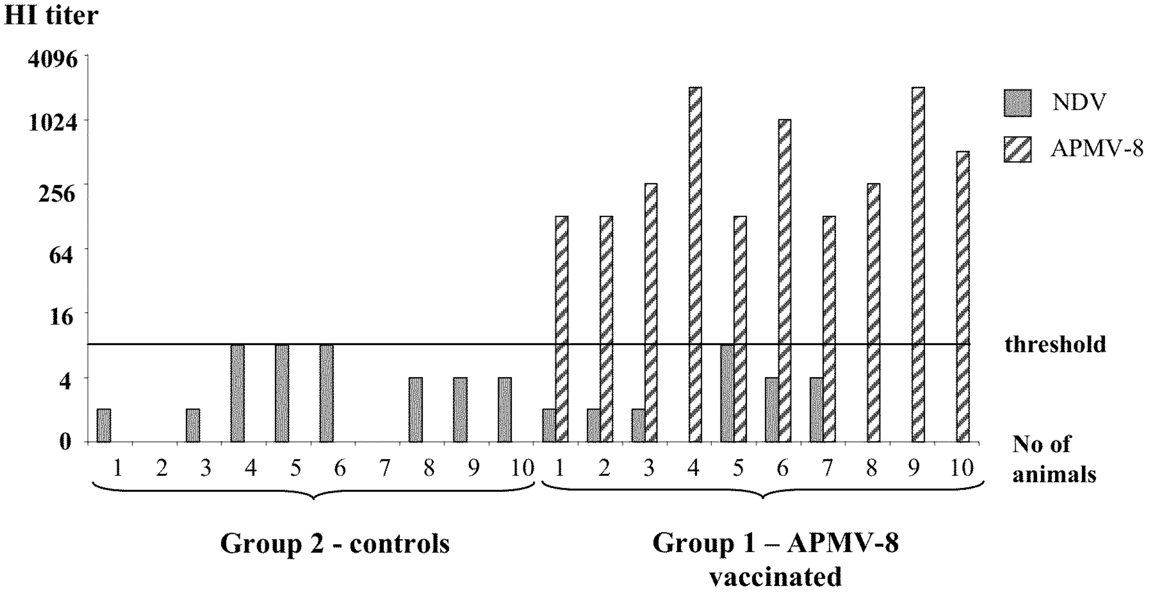
FIG. 20 depicts the HI test result of commercial broiler chickens 2 weeks after APMV-8 vaccination.

Fourteen days after infection (day 14), the chickens were bled and the obtained serum samples were analyzed again for the presence of HI antibodies directed against NDV and APMV-8 (FIG. 20). The result showed that the APMV-8 vaccinated chickens showed HI titers using APMV-8 as antigen. The APMV-8 specific HI titers were between 128 and 2048. The HI titers against NDV declined to a HI titer below 16, thus they are not considered as NDV positive. The result showed that chickens maternal derived antibodies directed against NDV did not omit the infection with APMV-8, thus interference of such antibodies with APMV-8 vaccination is unlikely.

Figure 21:
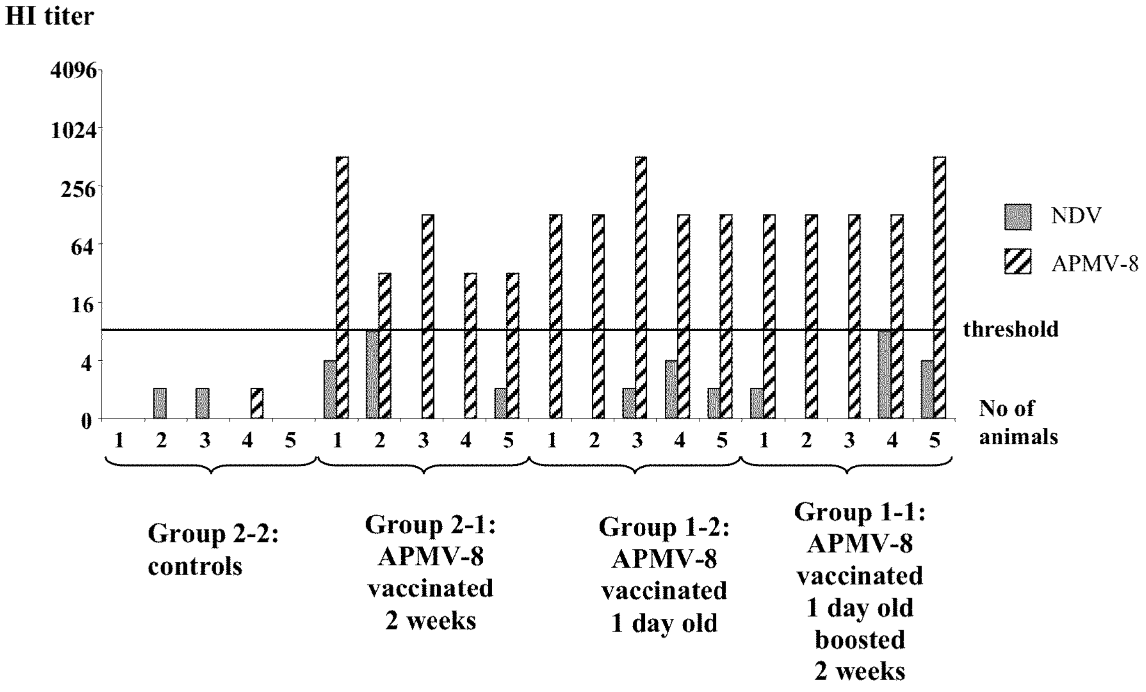
FIG. 21 depicts the HI test result of commercial broiler chickens 4 weeks after APMV-8 vaccination.

Fourteen days after infection (day 14), the chickens in group 1 and group 2 were split. Five chickens in each of group 1 (group 1-1) and group 2 (group 2-1) were again infected with $10^6$ $EID_{50}$ of APMV-8 strain (table 7), the remaining five chickens in each group (group 1-2 and group 2-2) were not infected. This experiment is designed to investigate where a later infection of chickens would have an effect on the infection and whether a second infection (boost vaccination) would increase the antibody titer. Fourteen days later (day 28), all chickens were bled again and the serum was investigated for the presence of APMV-8 and NDV antibodies. The serum titers (FIG. 21) showed that a first vaccination at day 14 (group 2-1) did induce APMV-8 specific antibody titers ranging from 32 to 512. In chickens vaccinated only at day 1 (group 1-2), the antibody titers declined to titers in a range from 128 to 512. In chickens which have been vaccinated at day 1 and day 14 (group 1-1), the APMV-8 specific antibody titer did not increase, suggesting that the virus used for the second infection was neutralized by APMV-8 specific antibodies induced by the first infection. The serum of the non-vaccinated controls (group 2-2) did not contain APMV-8 specific HI antibodies. At day 28, the NDV antibodies declined further, only 11 chickens out of the 20 chickens showed any HI titers with the NDV antigen whereas at day 14 fourteen chickens showed low antibody titers against NDV.

Example 5

In Ovo Vaccination of Embryonated SPF Eggs

This study was performed to test if an in ovo vaccination with APMV-8 would result in an antibody response in chickens and if in ovo vaccination would interfere with hatchability and livability.

Figure 22:
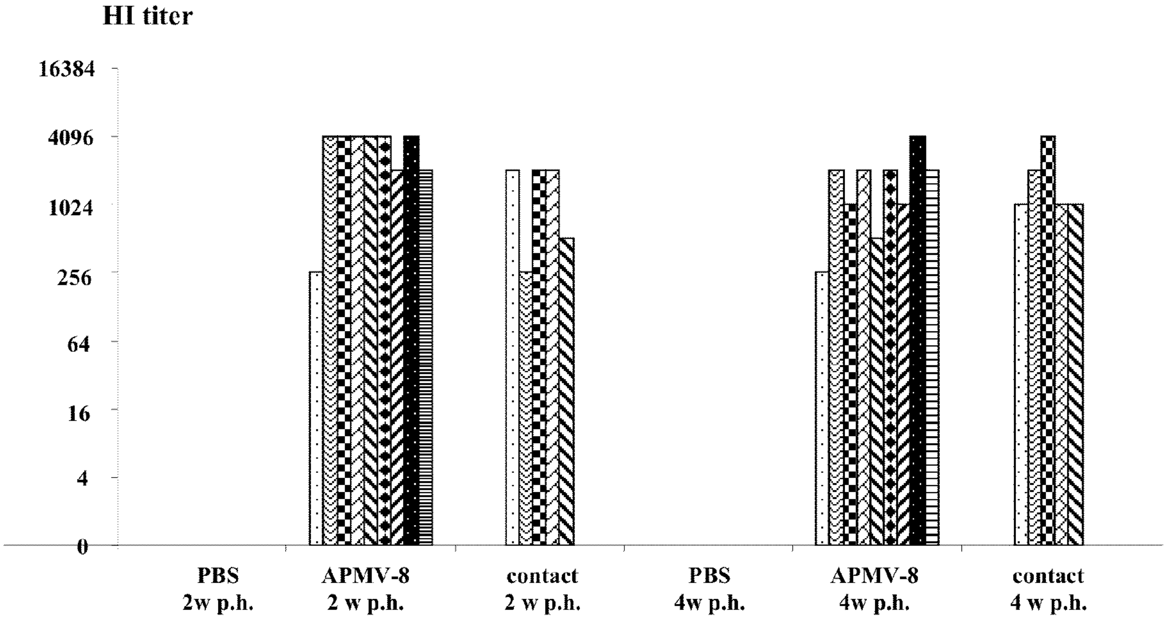
FIG. 22 shows the HI test results after the in ovo vaccination at day 18 (study 1).

In study 1, 108 SPF eggs were in ovo vaccinated with APMV-8 virus strain using the INOVOJECT (Pfizer Animal Health, NY, USA) at day 18 of incubation. The virus was diluted in 0.9% sterile NaCl saline. The back titration of the diluted virus revealed a titer of $10^{5.5}$ $EID_{50}/100$ µl. As control, 108 eggs were inoculated with 0.9% sterile NaCl saline. The volume for the inoculation was 100 µl per egg. Eighty chickens hatched from the control group and forty-five chickens hatched from the APMV-8 vaccinated group. Ten chickens from each group were transferred to one Horsefall-Bauer unit. In addition, the chickens of the APMV-8 vaccinated group and five chickens of the control group were co-mingled in a Horsefall-Bauer unit to test transmission of APMV-8 after vaccination. Water and feed were provided ad libitum. Fourteen and twenty-eight days after hatch, blood samples were taken and tested for the presence of HI antibodies directed against APMV-8 using 4 HA units and 1% of chicken red blood cells. The results (FIG. 22) showed that in ovo vaccination at day 18 of incubation resulted in an immune response as indicated by the presence of HI titers in the tested serum samples. Fourteen days after hatch, an HI titer from 256 to 4048 was observed in the in ovo vaccinated group. In the serum of the contact chickens, an HI titer from 256 to 2048 was observed 14 days after contact with chickens from the vaccinated group, indicating shedding of the virus used for vaccination. The control group did not show any HI titer specific for APMV-8. Fourteen days later, the chickens were bled again and showed titers from 256 to 4096 in the APMV-8 vaccinated group and 256 to 1024 in the APMV-8 contact group. The control group showed no presence of APMV-8 HI antibodies.

Figure 23:
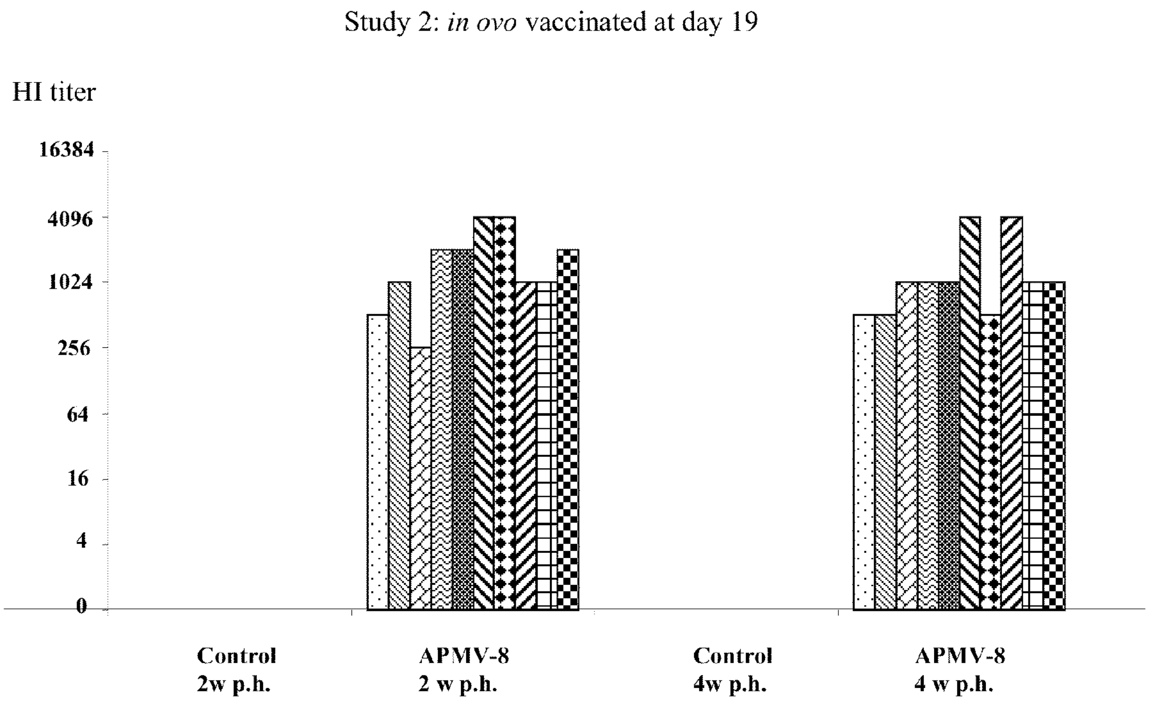
FIG. 23 depicts the HI test results after the in ovo vaccination at day 19 (study 2).

In study 2, 88 SPF (specific pathogen free) eggs were in ovo vaccinated using the INOVOJECT at day 19 of incubation. The APMV-8 virus strain was diluted in 0.9% sterile NaCl saline. The titer of the virus was $10^{5.75}$ $EID_{50}$/100 μl as observed after back titration of the diluted virus. As control, 88 SPF eggs were inoculated with 0.9% sterile NaCl saline. The volume for the inoculation was 100 μl per egg. Seventy-four chickens hatched from the control group (NaCl) and seventy-six chickens hatched from the APMV-8 vaccinated group. Ten chickens from each group were transferred to one Horsefall-Bauer unit. Water and feed were provided ad libitum. Fourteen days after hatch, blood samples were taken and tested for the presence of HI antibodies directed against APMV-8 using 4 HA units and 1% of chicken red blood cells. The results (FIG. 23) showed that in ovo vaccination at day 19 of incubation resulted in an immune response with HI titers specific for APMV-8. Fourteen days after hatch, an HI titer from 256 to 4048 was observed in the APMV-8 in ovo vaccinated group. The control group did not show any HI titer specific for APMV-8. The chickens were bled again at day 28 after hatch. The HI titers for the APMV-8 vaccinated group ranged from 512 to 4096 (FIG. 23) whereas the sera of the control chickens were still APMV-8 negative.

Figure 24:
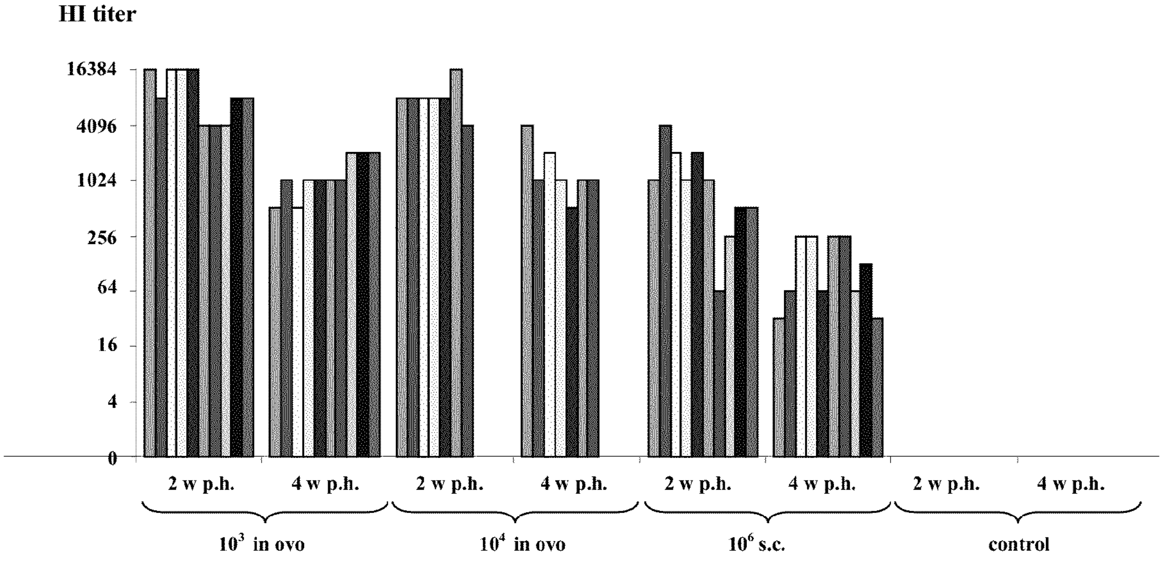
FIG. 24 shows the HI test results after the in ovo vaccination at day 18 (study 3).
Figure 26:
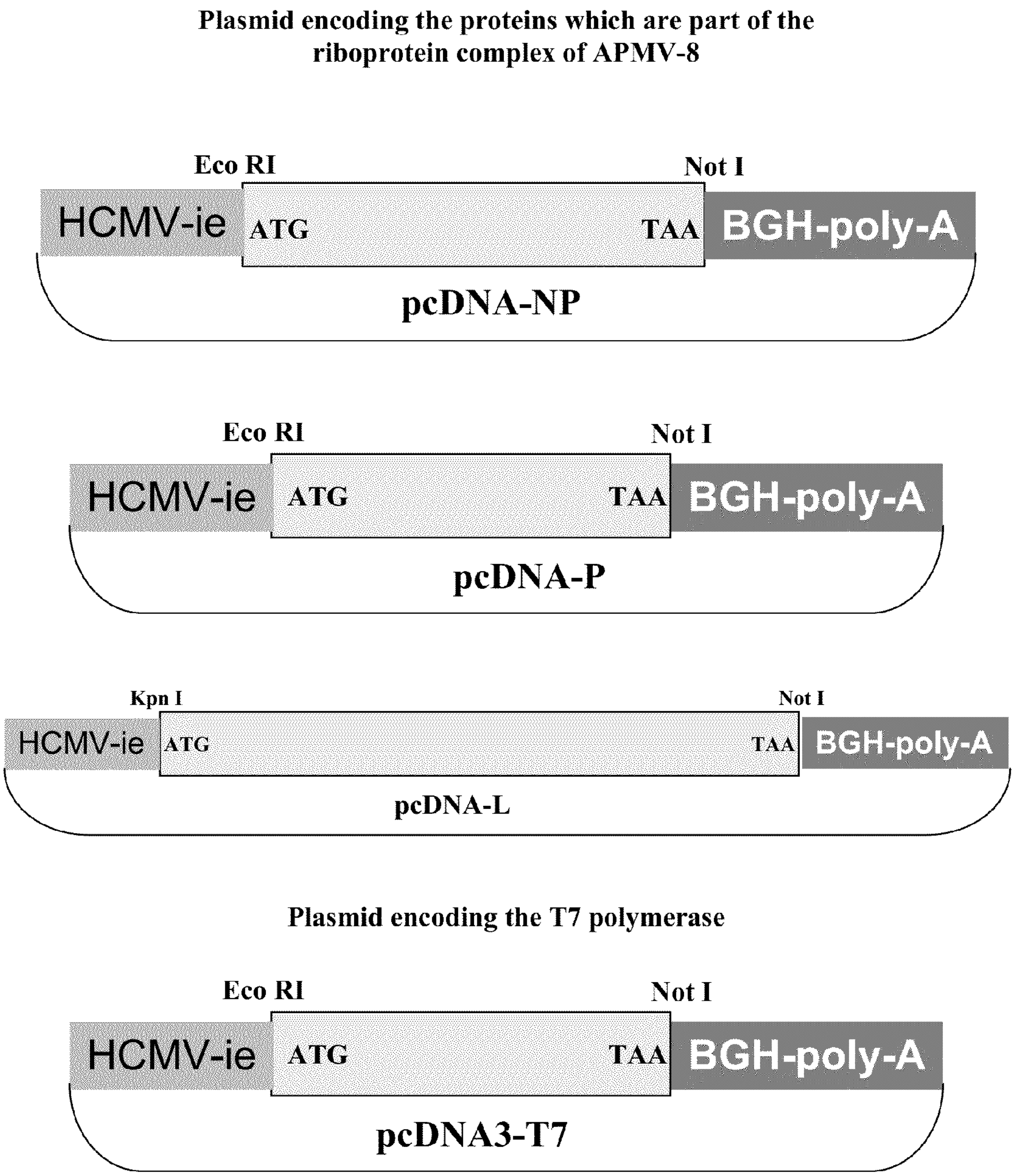
FIG. 26 depicts plasmid maps of pcNDA-NP, pcNDA-P, pcDNA-L, and pcDNA3-T7.

In a third study, 108 SPF eggs in group 1 and group 2 were in ovo vaccinated using the INOVOJECT at day 18 of incubation with $10^{3.5}$ $EID_{50}$ and $10^{4.5}$ $EID_{50}$, respectively. The APMV-8 virus strain was diluted in 0.9% sterile NaCl saline. In a third group 108 SPF eggs were inoculated with 0.9% sterile NaCl saline as control. Eighty-three chickens hatched from group 1, seventy-nine chickens hatched from group 2, and eighty-eight chickens hatched from group 3 (see table 8). After hatch, ten chickens from each group were transferred to one Horsefall-Bauer unit. Water and feed were provided ad libitum. After hatch, ten chickens from group 3 were vaccinated subcutaneously in the neck region with a volume of 100 μl $10^{6}$ $EID_{50}$ APMV-8 virus. Fourteen days after hatch, blood samples were taken and tested for the presence of HI antibodies directed against APMV-8 using 4 HA units and 1% of chicken red blood cells (CRBS). The results (FIG. 24) showed that in ovo vaccination at day 18 of incubation resulted in an immune response with HI titers specific for APMV-8. Fourteen days after hatch, an HI titer from 4096 to 16384 was observed in the APMV-8 in ovo vaccinated groups. The control group did not show any HI titer specific for APMV-8. The group subcutaneously vaccinated with APMV-8 showed a seroconversion with a titer ranging from 64 to 4096. The chickens were bled again at day 28 after hatch and tested for the presence of APMV-8 specific HI antibodies. The HI titer at four weeks after hatch decreased and ranged between 512 and 4096. The control group did not show any HI titer specific for APMV-8. The HI titer in the group which was subcutaneously vaccinated showed HI titers ranging between 32 and 256.

TABLE 8

| | Group 1 | Group 2 | Group 3 (control) |
|---|---|---|---|
| SPF eggs | 108 | 108 | 108 |
| Hatched chicken | 83 | 79 | 88 |
| Vaccination with APMV-8 at day 18 of incubation | $10^{3.5}$ $EID_{50}$ 100 μl per egg | $10^{4.5}$ $EID_{50}$ 100 μl per egg | 0.9% sterile NaCl saline |

Example 6

Development of Reverse Genetics of the APMV-8 Strain and Generation of APMV-8 Mutants Expressing Heterologous Genes Construction of the Expression Plasmids Containing the NP, P, and L Genes of APMV-8

For the establishment of a reverse genetics system for paramyxoviruses, the establishment of plasmids expressing the proteins involved in viral RNA replication is essential. The open reading frames (ORF) of three APMV-8 proteins (nucleoprotein NP, phosphoprotein P, RNA dependent RNA polymerase protein or protein L) were cloned into the eukaryotic expressions vector pcDNA3 (Invitrogen, California, USA). To this end, the RNA of allantoic fluid containing APMV-8 was purified using the High Pure RNA Isolation Kit (Roche, Basel, Switzerland). The purified RNA was used for reverse transcription polymerase chain reaction (RT-PCR) using the Titan One Tube RT-PCR Kit (Roche). The ORFs of the proteins were amplified using the appropriate primer pairs: [NP(NP-FP, NP-RP), P(P-FP, P-RP), L (L-FP, L-RP), see table 9]. The reactions products were separated on a 0.7% agarose gel and eluted from the gel using the QIAquick Gel Extraction Kit (Qiagen, Hilden, Germany) following the protocol provided by the manufacturer. The RT-PCR fragments were incubated with the appropriate restriction enzymes (NP and P with Eco RI/NotI; L with Kpn I/NotI), gel eluted again and ligated into the eukaryotic expression vector pcDNA3 cleaved with the appropriate restriction enzymes. The ligation reactions were transformed into Top10F cells (Invitrogen) and plasmid DNA harvested from the Top10F cells was digested with the appropriate restriction enzymes (see above). Plasmids containing DNA fragments (pcDNA-NP, pcDNA-P, pcDNA-L) with the appropriate size were sequenced.

TABLE 9

Primer for amplification of the genes for the proteins of the RNP complexes

| Primer name | Primer sequence[a] | Orientation[b] | Position[c] | SEQ ID NO: |
|---|---|---|---|---|
| NP-FP-pc3 | Eco RI<br>ccGAATTC *ATG*TCATCTGTGTTCAATGAGTATCAGG | sense | 141-168 | 41 |

TABLE 9-continued

Primer for amplification of the genes for the proteins of the RNP complexes

| Primer name | Primer sequence[a] | Orientation[b] | Position[c] | SEQ ID NO: |
|---|---|---|---|---|
| NP-RP-pc3 | Not I<br>ccGCGGCCGC*TTA*CCATTCTAGCCCGTTCTCGTATG | antisense | 1501-1526 | 42 |
| P-FP-pc3 | Eco RI<br>ccGAATTC*ATG*GATTTCGCCAATGATGAAG | sense | 1693-1714 | 43 |
| P-RP-pc3 | Not I<br>ccGCGGCCGC*TTA*CGCATTATATATTGCCTGCTTGACTCG | antisense | 2881-2910 | 44 |
| L-FP-pc3 | Kpn I<br>ccGGTACC*ATG*GATATAAAACAAGTTGACCTG | sense | 8292-8320 | 45 |
| L-RP-pc3 | Not I<br>ccGCGGCCGC*TTA*TTTCAACTTGATGATTGCACCG | antisense | 14989-15013 | 46 |

[a]The primer sequence contains the restriction enzyme cleavage sites used for cloning. The restriction sites are bold and identified. The start and stop codons are highlighted by italics. Virus specific sequences are underlined.

[b]The orientation of the primer sequence in accordance with the viral messenger RNA.

[c]The position are the virus specific sequences in the full length genome as shown.

Construction of a Plasmid Containing the Full Length Genome of APMV-8

For the generation of a plasmid containing the full length APMV-8 genome, the cDNA genome of the virus was synthesized (Genscript, New York, USA) based on the generated consensus sequence in two different parts (5'-FLG, 3'-FLG, see FIG. 25). The 5'-part (5'-FLG, SEQ ID NO:47) of the viral sequence was synthesized from nucleotide 1-5564. Preceding the APMV-8 sequence is a sequence cassette consisting of the CMV-IE promoter, followed by a restriction enzyme cleavage sequence for XmaI (for possible subsequent cloning procedures) and the hammerhead ribozyme sequence. At the 5'-end and the 3'-end of the sequence, restriction enzyme cleavage sites for Not I and SacII were added, respectively. The synthesized 3'-part (3'-FLG, SEQ ID NO:48) of the sequence (nucleotide 5503-15342) is followed by the hepatitis delta ribozyme sequence and poly-A signal sequence of the bovine growth hormone. For cloning purpose, the sequence for the Not I restriction enzyme was added at the 5'-end of 3'-FLG and the sequence for the Sac II restriction enzyme was added at the 3'-end of the sequence. Within the overlapping parts of 5'-FLG and 3'-FLG (nucleotide 5503-5564), the sequence for a unique restriction enzyme (Bmt I) was located which cleaves at nucleotide 5541 of the full length sequence. Both parts of the DNA (5'-FLG, 3'-FLG) were ligated separately into the plasmid pUC57 (Genscript) resulting in the plasmids pUC57/5'-FLG and pUC57/3'-FLG. To clone both fragments together, pUC57/5'-FLG was cleaved with BmtI and Sac II and the 5'-FLG-containing plasmid was gel eluted. In parallel, pUC57/3'-FLG was cleaved with the same enzymes and the fragment 3'-FLG was eluted. The 3'-FLG was subsequently ligated into 5'-FLG-containing plasmid to obtain a plasmid which contains the full length cDNA sequence of the APMV-8 genome under the control of the CMV-IE promoter (pUC57-FL-APMV-8).

Construction of the Plasmid Containing the Minigenome of APMV-8

The plasmid containing all functional elements of a minigenome for APMV-8 (pMG-APMV-8) was constructed using the method described by Conzelmann, et al. (J Virol. 68:713-719, 1994). Plasmid pMG-APMV-8 contains the trailer and leader region of the APMV-8 genome which is flanked by the T7 promoter and the antigenome hepatitis delta virus ribozyme sequence (Collins, et al., PNAS USA 88:9663-9667, 1991).The antigenome hepatitis delta virus ribozyme sequence is followed by a T7 transcription terminator sequence. Between the trailer and leader region the coding sequence of the enhanced green fluorescent protein in antisense orientation is located. Preceding the trailer sequence and immediate after the T7 promoter three additional G residues are located. The insert is flanked by the restriction enzyme cleavage sites Eco RI and Not I and was cloned blunt end into the plasmid pUC57. This construct was subcloned into the plasmid pUC18. To this end, plasmid pMG-APMV-8 then was cleaved with Eco RI and Hind III and the appropriate fragment was gel eluted and ligated into the appropriately cleaved plasmid pUC18 to obtained puC18-MG-APMV-8. The presence of the insert was confirmed by sequencing.

Generation of an Expression Plasmid Allowing the Expression of the T7 Polymerase For the generation of a plasmid encoding the T7 DNA dependent RNA polymerase (T7 polymerase) the coding sequence (GenBank accession number AY264778) was synthesized by Genscript. The T7 polymerase sequence (SEQ ID NO:49) was modified for optimization of the codon usage for expression in a eukaryotic system and to remove possible splice donor/acceptor sites in the sequence. The T7 polymerase encoding sequence was flanked by an EcoRI (5') and NotI (3') site. The synthesized fragment was cloned blunt end into the vector pUC57 (pCU57-T7). This plasmid was cleaved with EcoRI/NotI and the T7 polymerase-encoding fragment was gel eluted. The fragment was then cloned into the eukaryotic expressions vector pcDNA3 (Invitrogen) to obtain pcDNA3-T7. The presence of the fragment in the vector pcDNA3-T7 was verified by sequencing.

Generation of a Plasmid for the Expression of the Enhanced Green Fluorescent Protein with the Use of an Internal Ribosomal Entry Site Under the Control of a T7 Promoter.

To test the functionality of the T7 polymerase, the open reading frame of the enhanced green fluorescent protein (EGFP) was amplified by PCR using the plasmid pEGFP-N1 (Clontech, California, USA) and the primer pair:

```
                                      SEQ ID NO: 50
EGFP-FP (CCGGATCCATGGTGAGCAAGGGCGAGGAGCTG)
and
                                      SEQ ID NO: 51
EGFP-RP (CCGCGGCCGCTTACTTGTACAGCTCGTCCATGCCG)
```

The obtained PCR fragment was gel eluted and incubated with the restriction enzymes BamHI and NotI. The reaction product was gel eluted and ligated into the appropriately cleaved vector pCITE 4A (Novagen). The obtained plasmid (pCITE4A-EGFP) was used for subsequent experiments. Plasmids pCITE4A-EGFP and pcDNA3-T7 were transfected alone or in combination into the chicken cell line DF1 grown in 24-well-plates using Lipofectin 2000 (Invitrogen). Twenty four hours after transfection, the medium was removed and sterile phosphate buffered saline (PBS) was added. The cells were evaluated using the inverted fluorescence microscope Axiovert 40 CFL (Zeiss, Jena, Germany). Green fluorescence was only observed in wells of the tissue culture plate which was co-transfected with both plasmids. This result indicates that both plasmids, pCITE4A-EGFP and pcDNA3-T7, were functional.

Validation of the Functionality of the Expressed Viral Proteins NP, P, and L Using the Minigenome Plasmid DF1 cells were co-transfected with pcDNA3-T7, pUC18-MG-APMV-8, pcDNA-NP, pcDNA-P, and pcDNA-L to validate the functionality of the expressed NP, P and L proteins. Twenty four hours after transfection, the medium was removed and sterile phosphate buffered saline (PBS) was added. The cells were evaluated using the inverted fluorescence microscope Axiovert 40 CFL (Zeiss, Jena, Germany). Green fluorescence was only observed in wells of the tissue culture plate which was co-transfected with the 5 plasmids. This result indicates that the expressed viral proteins NP, P and L were functional to transcribe the APMV-8 minigenome into mRNA and express the EGFP protein encoded by pUC18-MG-APMV-8.

Rescue of AMPV8 Virus from Plasmid Containing the Full Length Sequence of APMV-8

DF1 cells were co-transfected with pUC57-FL-APMV-8, pcDNA-NP, pcDNA-P, and pcDNA-L. After 48 to 96 hours, the supernatants of the DF1 cells were inoculated in 10-day-old embryonated eggs to propagate the virus. After 3 to 5 days, the allantoic fluid was harvested and tested for hemagglutination activity (HA) using 1% chicken red blood cells. Allantoic fluid tested positive for HA activity was used for three procedures. 1) DF1 cells were infected with the allantoic fluid and tested 36 hours after infection with an APMV-8 specific antiserum for the presence of APMV-8 protein expression in an indirect immunofluorescence assay. 2) The allantoic fluid was tested for APMV-8 specificity using an APMV-8 specific chicken serum (provided by the National Central Veterinary Laboratory, Ames, Iowa, USA) by an hemagglutination inhibition assay. 3) The rescue virus was identified by RT-PCR using APMV-8 specific oligonucleotides. The absence of viral cDNA was verified by omitting the RT step during the reaction. Samples tested positive in all three assays were further propagated in embryonated SPF chicken eggs.

Propagation of APMV-8 in Cells Other than Chicken Origin

Cells from different species [hamster (Baby hamster kidney cells, BHK-21 cells), monkey (Vero cells, cell line with the origin of the kidney of an African green monkey), and canine (Madin-Darby canine kidney cells, MDCK), and quail (Quail muscle cell line QM7)] were grown in 24 well tissue culture plates and infected with a multiplicity of infection of 0.01. The cells were fixed with ice cold ethanol 24 hours after infection and analyzed for the presence of APMV-8 specific proteins by indirect immunofluorescence using an APMV-8 specific antiserum from an APMV-8 infected SPF chicken. The binding of the antibodies was visualized by using a goat anti-chicken IgY specific FITC conjugate. Non-infected cells were used as negative control. Only in the APMV-8 infected cells was green fluorescence observed. This indicated that APMV-8 was able to infect cells from species other than chicken.

Figure 19B:
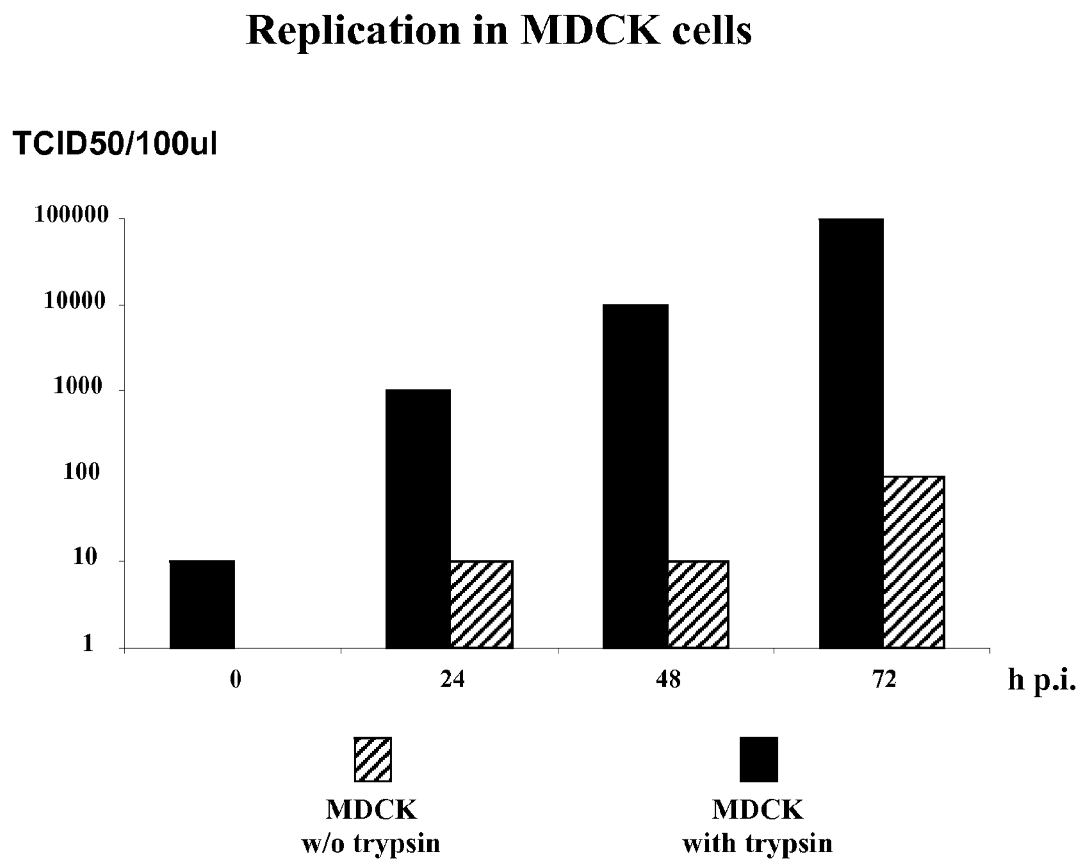
FIG. 19B depicts the result of replication of APMV-8 virus in MDCK cells.

The replication of APMV-8 was increased in presence of trypsin. MDCK cells were infected with APMV-8 as described above. After infection the cells were rinsed with serum-free medium and either overlaid with trypzin-containing serum-free medium in a concentration of 1 ug/ml or with serum-free medium only. Twenty four, forty eight, and ninety six hours after infection the cell supernatants were removed and the TCID50 was determined on DF1 cells using indirect immunofluorescence as described above. The obtained data indicated that in presence of trypsin APMV-8 replicated to a higher titer than in absence of this enzyme (FIG. 19B).

The results of this example showed that, like AMPV-1, APMV-8 is able to penetrate into cells of different species and to initiate its replication cycle. It is therefore a suitable vector for multiple species.

Production of Recombinant APMV-8 Virus Expressing Foreign Genes Using the Reverse Genetics System For the generation of a recombinant APMV-8 virus (viral vector) expressing the hemagglutinin (HA) gene of a highly pathogenic avian influenza (HPAI), the coding sequence for the HA gene of HPAI of the H5 or H7 subtype virus is inserted in the non-essential regions, for example, between the M and F genes or between the P and M genes of the APMV-8 genome in the plasmid containing the full length APMV-8 genome. To this end the coding sequence of the hemagglutinin open reading frame is flanked by all the necessary regulatory sequences of the F gene which includes the gene start sequence, the 5' non-coding sequence, the 3' non-coding sequence and the gene stop sequence. The construct is synthesized in a way that the restriction enzyme cleavage sites Bsu 36I and Nhe I are used for the ligation of the appropriate fragment into the existing plasmid containing full length APMV-8 genome due to their uniqueness in the plasmid construct. The resulting plasmid is designated transcription plasmid which contains the hemagglutinin gene in the nonessential region of the full length APMV-8 genome. Using this approach the coding sequences of a variety of viral and bacterial antigen can be cloned into the backbone of the APMV-8 sequence. Other possible antigens which could be inserted into the APMV-8 genome are the fusion protein of the Newcastle disease virus, the S protein of avian bronchitis virus, other hemagglutinin genes from non-H5 and non-H7 avian influenza virus, the chicken anemia virus structural protein gene VP1, glycoprotein genes from infectious laryngotracheitis virus.

Example 7

Vaccination of Animals

The animals are vaccinated with one, two administrations or a prime-boost regime of the composition or vaccine containing the recombinant APMV-8 virus (viral vector) as described in example 6. For chickens/avian, various administrations are performed, for example, in ovo administration at D18 or D19, subcutaneous (SC) at one-day-old, or mucosal administration (spray, drinking water, eye drop) at different ages. The dose is between 3 and 7 log 10 (preferably 4-6 log 10 EID50). For mammals, mucosal route (intra-nasal, intraocular, oral) or parenteral (IM, SC, needle-free, trans-dermal or intra-dermal) is used. The dose ranges from 5 to 9 log (preferably 6-8 log). Two administrations are usually performed at 3-4 weeks interval. Heterologous prime-boost (for instance, boost with proteins) would be also advantageous.

The protective efficacy induced by the composition or vaccine is evaluated against the specific pathogen challenge in the animals. The protective effect is evaluated by clinical observations and/or viral load of the specific pathogen in tissues, blood or mucosal swabs. The blood samples from the vaccinated animals are taken at various stages and tested for serology. The results show that the composition or vaccine of the present invention is immunogenic and provides protection in the vaccinated animals.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

REFERENCES

1. Alexander, 1988. Newcastle disease, p. x, 378 p. In D. J. Alexander (ed.), Developments in veterinary virology. Kluwer Academic, Boston.
2. Alexander, Characterization of viruses which represent further distinct serotypes (PMV-8 and PMV-9) of avian paramyxoviruses. Arch Virol 78:29-36.
3. Alexander, et al., 1979. Properties of a newly isolated, serologically distinct avian paramyxovirus. Arch Virol 60:105-13.
4. Alexander, 2003. Newcastle Disease, other Paramyxoviruses, and Pneumovirus Avian Paramyxoviruses 2-9, p. 63-99. In Y. M. Saif (ed.), Diseases of poultry, 11th ed. Iowa State Press, Ames, Iowa.
5. Andral, et al., 1984. Isolation of avian paramyxovirus 2 and 3 from turkeys in Brittany. Vet Rec 114:570-1.
6. Bankowski, et al., 1981, Effect of paramyxovirus yucaipa on fertility, hatchability, and poult yield of turkeys. Avian Dis 25:517-20.
7. Bankowski, et al., 1960. Isolation of an Unidentified Agent from the Respiratory Tract of Chickens. Science 132:292-293.
8. Bradshaw, et al., 1979. The Epidemiology of Yucaipa Virus in Relationship to the Acute Respiratory Disease Syndrome in Turkeys. Avian Diseases 23:539-542.
9. Capua, et al., 2004. Isolation of an avian paramyxovirus type 9 from migratory waterfowl in Italy. Vet Rec 155:156.
10. Chambers, et al., 1988. Protection of chickens from lethal influenza infection by vaccine expressed hemagglutinin. Virology 167:414-421.
11. Collins, P. L., et al., 1991. Rescue of synthetic analogs of respiratory syncytial virus genomic RNA and effect of truncations and mutations on the expression of a foreign reporter gene. Proc. Natl. Acad. Sci. USA 88:9663-9667
12. Conzelmann K K, and Schnell M., 1994. Rescue of synthetic genomic RNA analogs of rabies virus by plasmid-encoded proteins. J Virol. 68:713-719
13. Darteil, R., M. Bublot, E. Laplace, J. F. Bouquet, J. C. Audonnet and M. Riviere (1995). Herpesvirus of turkey recombinant viruses expressing infectious bursal disease virus (IBDV) VP2 immunogen induce protection against an IBDV virulent challenge in chickens. *Virology* 211, 481-490.
14. de Leeuw, et al., 1999. Complete nucleotide sequence of Newcastle disease virus: evidence for the existence of a new genus within the subfamily Paramyxovirinae. J Gen Virol 80:131-136.
15. Fleury, et al., 1979. Isolation of twenty-three Yucaipa-like viruses from 616 wild birds in Senegal, West Africa. Avian Dis 23:742-4.
16. Gao, et al., (2006). Protection of mice and poultry from lethal H5N1 avian influenza virus through adenovirus-based immunization. J Virol 80:1959-1964.
17. Ge, et al., (2007) Newcastle disease virus-based live attenuated vaccine completely protects chickens and mice from lethal challenge of homologous and heterologous H5N1 avian influenza viruses. Journal of Virology, 81(1), 150-158.
18. Goodman, et al., 1988. Isolation of avian paramyxovirus-2 from domestic and wild birds in Costa Rica. Avian Dis 32:713-7.
19. Gough, et al., 1984. Avian paramyxovirus type 4 isolated from a ringed teal (Calonetta leucophrys). Vet Rec 115: 653.
20. Hoelscher, et al., (2008). A broadly protective vaccine against globally dispersed Glade 1 and Glade 2 H5N1 influenza viruses. J Infect Dis. 197:1185-1188.
21. Huang, et al., (2004) A recombinant Newcastle Disease Virus (NDV) expressing VP2 protein of Infectious Bursal Disease Virus (IBDV) protects against NDV and IBDV. Journal of Virology, 78, 10054-10063.
22. Hunt, et al., (1988). Retrovirus-expressed hemagglutinin protects against lethal influenza virus infections. J Virol 62:3014-3019.
23. Inoue K, Shoji Y, Kurane I, Iijima T, Sakai T, Morimoto K. (2003). An improved method for recovering rabies virus from cloned cDNA. J Virol Methods. 107:229-236.
24. Krishnamurthy, et al., 1998. Nucleotide sequences of the trailer, nucleocapsid protein gene and intergenic regions of Newcastle disease virus strain Beaudette C and completion of the entire genome sequence. J Gen Virol 79:2419-2424.
25. Krishnamurthy, S., Huang, Z. & Samal, S. K. (2000) Recovery of a virulent strain of Newcastle disease virus from cloned cDNA: expression of a foreign gene results in growth retardation and attenuation. Virology, 278, 168-182.
26. Lamb, et al., 2007. Paramyxoviridae: The viruses and Their Replication, p. 1449-1496. In B. N. Fields, D. M. Knipe, and P. M. Howley (ed.), Fields' virology 5th ed. Wolters Kluwer Health/Lippincott Williams & Wilkins, Philadelphia.
27. Lang, G., A. Gagnon, and J. Howell. 1975. The occurrence of Paramyxovirus yucaipa in Canadian poultry. Can Vet J 16:233-7.
28. Lipkind, et al., 1982. Isolation of yucaipa-like avian paramyxovirus from a wild mallard duck (Anas platyrhinchos) wintering in Israel. Vet Rec 110:15-6.
29. Lipkind, et al., 1979. The isolation of yucaipa-like paramyxoviruses from epizootics of a respiratory disease in turkey poultry farms in Israel. Vet Rec 105:577-8.
30. Maldonado, et al., (1995) Serological survey for avian paramyxoviruses from wildfowl in aquatic habitats in Andalusia. Journal of Wildlife Diseases, 31(1), 66-69.
31. Mayo, et al., 2002. A summary of taxonomic changes recently approved by ICTV. Arch Virol 147:1655-63.

32. Nayak B, et al., (2008). Molecular characterization and complete genome sequence of avian paramyxovirus type 4 prototype strain duck/Hong Kong/D3/75. Virol J. 20; 5:124.
33. Park, et al., (2006) Engineered viral vaccine constructs with dual specificity: Avian influenza and Newcastle disease. Proceedings of the National Academy of Sciences, 103(21), 8203-8208.
34. Peeters, et al., (1999) Rescue of Newcastle disease virus from cloned cDNA: evidence that cleavability of the fusion protein is a major determinant for virulence. Journal of Virology, 73(6), 5001-5009.
35. Redmann, et al., 1991. [Isolation of a paramyxovirus-3 from turkeys with respiratory tract disease in Germany]. Dtsch Tierarztl Wochenschr 98:138-41.
36. Reed, et al., 1938. A SIMPLE METHOD OF ESTIMATING FIFTY PER CENT ENDPOINTS. Am. J. Epidemiol. 27:493-497.
37. Römer-Oberdörfer, et al., (1999) Generation of recombinant lentogenic Newcastle disease virus from cDNA. Journal of General Virology, 80, 2987-2995.
38. Rosenberger, et al., (1974) Isolation of Newcastle disease and type-A influenza viruses from migratory waterfowl in the Atlantic flyway. Avian Diseases, 18(4), 610-613.
39. Saif, et al., 1997. Natural and Experimental Infection of Turkeys with Avian Paramyxovirus-7. Avian Diseases 41:326-329.
40. Shihmanter, et al., 1998. Isolation of avian serotype 3 paramyxoviruses from imported caged birds in Israel. Avian Dis 42:829-31.
41. Shihmanter, et al., 1998. Avian paramyxoviruses serotype 3 isolated from captive birds in Israel: clinical signs, pathology, and antigenic characterization. Avian Dis 42:418-22.
42. Shortridge, et al., 1980. Isolation and properties of viruses from poultry in Hong Kong which represent a new (sixth) distinct group of avian paramyxoviruses. J Gen Virol 49:255-262.
43. Schultz-Cherry, et al., (2000). Influenza virus (A/HK/156/97) hemagglutinin expressed by an alphavirus replicon system protects chickens against lethal infection with Hong Kong-origin H5N1 viruses. Virology 278:55-59.
44. Stallknecht, et al., (1991) Avian paramyxoviruses from migrating and resident ducks in coastal Louisiana. Journal of Wildlive Diseases. 27:123-128.
45. Stanislawek, et al., (2002) Avian paramyxoviruses and influenza viruses isolated from mallard ducks (Anas platyrhynchos) in New Zealand. Archives of Virology, V147, 1287-1302.
46. Tang M, et al., 2002. Recombinant adenovirus encoding the HA gene from swine H3N2 influenza virus partially protects mice from challenge with heterologous virus: A/HK/I/68 (H3N2). Arch Virol 147:2125-2141.
47. Taylor, et al., (1998). Protective immunity against avian influenza induced by a fowlpox virus recombinant. Vaccine 6:504-508.
48. Toro, et al., (2007). Protective avian influenza in ovo vaccination with non-replicating human adenovirus vector. Vaccine 25:2886-2891.
49. Tumova, et al., 1979. A hitherto unreported paramyxovirus of turkeys. Res Vet Sci 27:135-40.
50. Tumova, et al., 1989. Further evidence of the circulation of PMV-4 and influenza viruses with N2-1957 enzyme in the migratory waterfowls. Acta Virol 33:573-6.
51. Veits, et al., (2003). Deletion of the non-essential UL0 gene of infectious laryngotracheitis (ILT) virus leads to attenuation in chickens, and UL0 mutants expressing influenza virus haemagglutinin (H7) protect against ILT and fowl plague. J Gen Virol 84:3343-3352.
52. Veits, et al., (2006) Newcastle disease virus expressing H5 hemagglutinin gene protects chickens against Newcastle disease and avian influenza. Proceedings of the National Academy of Sciences, 103(21), 8197-8202.
53. Webster, et al., 1976. Ortho- and paramyxoviruses from migrating feral ducks: characterization of a new group of influenza A viruses. J Gen Virol 32:217-25.
54. Yamane, et al., 1982. Characterization of avian paramyxoviruses isolated from feral ducks in northern Japan: the presence of three distinct viruses in nature. Microbiol. Immunol 26:557-68.
55. Zhang, et al., 2007. Serological survey on prevalence of antibodies to avian paramyxovirus serotype 2 in China. Avian Dis 51:137-9.
56. Zhang, et al., 2006. Isolation, identification, and comparison of four isolates of avian paramyxovirus serotype 2 in China. Avian Dis 50:386-90.
57. Zou, et al., 2005. Complete Genome Sequence and Biological Characterizations of A Novel Goose Paramyxovirus-SF02 Isolated in China. Virus Genes 30:13-21.

What we claim is:

1. An isolated APMV-8 virus comprising a polynucleotide selected from the group consisting of:

a) a polynucleotide having the sequence as set forth in SEQ ID NO:1 or a polynucleotide complementary to a polynucleotide having the sequence as set forth in SEQ ID NO:1;

b) a polynucleotide encoding a polypeptide having the sequence as set forth in SEQ ID NO:3, a polynucleotide having the sequence as set forth in SEQ ID NO:2, or a polynucleotide complementary to a polynucleotide having the sequence as set forth in SEQ ID NO:2;

c) a polynucleotide encoding a polypeptide having the sequence as set forth in SEQ ID NO:5, a polynucleotide having the sequence as set forth in SEQ ID NO:4, or a polynucleotide complementary to a polynucleotide having the sequence as set forth in SEQ ID NO:4;

d) a polynucleotide encoding a polypeptide having the sequence as set forth in SEQ ID NO:7, a polynucleotide having the sequence as set forth in SEQ ID NO:6, or a polynucleotide complementary to a polynucleotide having the sequence as set forth in SEQ ID NO:6;

e) a polynucleotide encoding a polypeptide having the sequence as set forth in SEQ ID NO:9, a polynucleotide having the sequence as set forth in SEQ ID NO:8, or a polynucleotide complementary to a polynucleotide having the sequence as set forth in SEQ ID NO:8;

f) a polynucleotide encoding a polypeptide having the sequence as set forth in SEQ ID NO:11, a polynucleotide having the sequence as set forth in SEQ ID NO:10, or a polynucleotide complementary to a polynucleotide having the sequence as set forth in SEQ ID NO:10; and g) a polynucleotide encoding a polypeptide having the sequence as set forth in SEQ ID NO:13, a polynucleotide encoding a polypeptide having the sequence as set forth in SEQ ID NO:14, a polynucleotide having the sequence as set forth in SEQ ID NO:12, or a polynucleotide complementary to a polynucleotide having the sequence as set forth in SEQ ID NO:12.

2. The isolated APMV-8 virus of claim 1, wherein the polynucleotide has at least 96% sequence identity to a polynucleotide having the sequence as set forth in SEQ ID NO:1 or is complementary to a polynucleotide having at least 96% sequence identity to a polynucleotide having the sequence as set forth in SEQ ID NO:1.

3. The isolated APMV-8 virus of claim 1, wherein the polynucleotide encodes a polypeptide having at least 98% sequence identity to a polypeptide having the sequence as set forth in SEQ ID NO:3, or has at least 97% sequence identity to a polynucleotide having the sequence as set forth in SEQ ID NO:2, or is complementary to a polynucleotide having at least 97% sequence identity to SEQ ID NO:2.

4. The isolated APMV-8 virus of claim 1, wherein the polynucleotide encodes a polypeptide having at least 95% sequence identity to a polypeptide having the sequence as set forth in SEQ ID NO:5, or has at least 96% sequence identity to a polynucleotide having the sequence as set forth in SEQ ID NO:4, or is complementary to a polynucleotide having at least 96% sequence identity to SEQ ID NO:4.

5. The isolated APMV-8 virus of claim 1, wherein the polynucleotide encodes a polypeptide having at least 98% sequence identity to a polypeptide having the sequence as set forth in SEQ ID NO:7, or has at least 97% sequence identity to a polynucleotide having the sequence as set forth in SEQ ID NO:6, or is complementary to a polynucleotide having at least 97% sequence identity to SEQ ID NO:6.

6. The isolated APMV-8 virus of claim 1, wherein the polynucleotide encodes a polypeptide having at least 98% sequence identity to a polypeptide having the sequence as set forth in SEQ ID NO:9, or has at least 97% sequence identity to a polynucleotide having the sequence as set forth in SEQ ID NO:8, or is complementary to a polynucleotide having at least 97% sequence identity to SEQ ID NO:8.

7. The isolated APMV-8virus of claim 1, wherein the polynucleotide encodes a polypeptide having at least 99% sequence identity to a polypeptide having the sequence as set forth in SEQ ID NO:11, or has at least 97% sequence identity to a polynucleotide having the sequence as set forth in SEQ ID NO:10, or is complementary to a polynucleotide having at least 97% sequence identity to SEQ ID NO:10.

8. The isolated APMV-8 virus of claim 1, wherein the polynucleotide encodes a polypeptide having at least 98% sequence identity to a polypeptide having the sequence as set forth in SEQ ID NO:14, or has at least 97% sequence identity to a polynucleotide having the sequence as set forth in SEQ ID NO:12, or is complementary to a polynucleotide having at least 97% sequence identity to SEQ ID NO:12.

9. The isolated APMV-8 virus of claim 1 further comprising an isolated polynucleotide inserted in a nonessential region of APMV-8 genome.

10. A composition or vaccine comprising the APMV-8 virus of any one of claims 1 and 3-8.

11. The composition or vaccine of claim 10, wherein the APMV-8 virus further comprises an isolated polynucleotide encoding an antigen, and wherein the polynucleotide is inserted in a nonessential region of the APMV-8 genome.

12. The composition or vaccine of claim 11, wherein the nonessential region is selected from the regions consisting of untranslated region located upstream of the NP open reading frame, intergenic regions between two open reading frames of the APMV-8 genome, and untranslated region located downstream of the L open reading frame.

13. The composition or vaccine of claim 10 further comprising a pharmaceutically or veterinarily acceptable carrier, vehicle, excipient or adjuvant.

14. The composition or vaccine of claim 11, wherein the antigen is from avian pathogens, feline pathogens, canine pathogens, equine pathogens, porcine pathogens, or bovine or ovine pathogens.

15. The composition or vaccine of claim 14, wherein the avian pathogens are selected from the group consisting of *Salmonella typhimurium, Salmonella enteritidis*, infectious bronchitis virus, Newcastle disease virus, egg drop syndrome virus , infectious bursal disease virus, infectious laryngotracheitis virus, avian adenoviruses, Marek's disease virus, fowlpox virus, duck enteritis virus, duck parvoviruses, avian influenza virus, APMV, and combinations thereof.

16. The composition or vaccine of claim 12, wherein the nonessential region is any region within the nucleotide positions 1-140, 1526-1692, 2910-3085, 4195-4498, 6130-6382, 8116-8272, 8116-8289, or 15013-15342 of SEQ ID NO:1.

17. A method for producing the APMV-8 virus of claim 9, wherein the method comprises the introduction into the APMV-8 genome an isolated polynucleotide in a nonessential region of the APMV-8 genome.

18. The method of claim 17, wherein the nonessential region is selected from the regions consisting of untranslated region located upstream of the NP open reading frame, intergenic regions between two open reading frames of the APMV-8 genome, and untranslated region located downstream of the L open reading frame.

19. The method of claim 17, wherein the method comprises the steps of:

a) preparing expression plasmids expressing NP, P and L genes;

b) preparing a transcription plasmid comprising an isolated polynucleotide in a nonessential region of the full length APMV-8 genome;

c) transfection of the expression plasmids and transcription plasmid into a host cell;

d) rescuing/recovering the infectious APMV-8 virus from the host cell.

20. The method of claim 17, wherein the method comprises the steps of:

a) preparing expression plasmids expressing NP, P and L genes;

b) preparing a transcription plasmid comprising an isolated polynucleotide in a nonessential region of the full length APMV-8 genome;

c) preparing an expression plasmid expressing T7 polymerase;

d) transfection of the expression plasmids and transcription plasmid into a host cell;

e) rescuing/recovering the infectious APMV-8 virus from the host cell.

21. A method for inducing an immunological response in an animal to an antigen comprising inoculating the animal with a composition or vaccine comprising the APMV-8 virus of claim 1, wherein the APMV-8 virus comprises and expresses the antigen of a pathogen for said animal.

22. The method of claim 21, wherein the immunological response in an animal to the antigen is induced in a prime-boost regime.

23. The method of claim 21, wherein the animal is avian, equine, canine, feline, porcine, bovine, ovine, or human.

24. The method of claim 18, wherein the nonessential region is any region within the nucleotide positions 1-140, 1526-1692, 2910-3085, 4195-4498, 6130-6382, 8116-8272, 8116-8289, or 15013-15342 of SEQ ID NO:1.

25. The method of claim 19, wherein the NP gene encodes a polypeptide having at least 98% sequence identity to SEQ ID NO:3, and wherein the P gene encodes a polypeptide having at least 95% sequence identity to SEQ ID NO:5, and wherein the L gene encodes a polypeptide having at least 98% sequence identity to SEQ ID NO:14.

26. The method of claim 19, wherein the NP gene has at least 97% sequence identity to SEQ ID NO:2, and wherein the P gene has at least 96% sequence identity to SEQ ID NO:4, and wherein the L gene has at least 97% sequence identity to SEQ ID NO:12.

27. The method of claim 20, wherein the NP gene encodes a polypeptide having at least 98% sequence identity to SEQ ID NO:3, and wherein the P gene encodes a polypeptide having at least 95% sequence identity to SEQ ID NO:5, and wherein the L gene encodes a polypeptide having at least 98% sequence identity to SEQ ID NO:14.

28. The method of claim 20, wherein the NP gene has at least 97% sequence identity to SEQ ID NO:2, and wherein the P gene has at least 96% sequence identity to SEQ ID NO:4, and wherein the L gene has at least 97% sequence identity to SEQ ID NO:12.

29. The method of claim 21, wherein the antigen is from avian pathogens, feline pathogens, canine pathogens, equine pathogens, porcine pathogens, or bovine or ovine pathogens.

30. The method of claim 29, wherein the avian pathogens are selected from the group consisting of *Salmonella typhimurium, Salmonella enteritidis*, infectious bronchitis virus, Newcastle disease virus, egg drop syndrome virus , infectious bursal disease virus, infectious laryngotracheitis virus, avian adenoviruses, Marek's disease virus, fowlpox virus, duck enteritis virus, duck parvoviruses, avian influenza virus, APMV, and combinations thereof.

31. The method of claim 21, wherein the immunological response in an animal to the antigen is induced by a single administration of the composition or vaccine of claim 10.

32. An isolated polynucleotide selected from the group consisting of:

a) a polynucleotide having the sequence as set forth in SEQ ID NO:1 or a polynucleotide complementary to a polynucleotide having the sequence as set forth in SEQ ID NO:1;

b) a polynucleotide encoding a polypeptide having the sequence as set forth in SEQ ID NO:3, a polynucleotide having the sequence as set forth in SEQ ID NO:2, or a polynucleotide complementary to a polynucleotide having the sequence as set forth in SEQ ID NO:2;

c) a polynucleotide encoding a polypeptide having the sequence as set forth in SEQ ID NO:5, a polynucleotide having the sequence as set forth in SEQ ID NO:4, or a polynucleotide complementary to a polynucleotide having the sequence as set forth in SEQ ID NO:4;

d) a polynucleotide encoding a polypeptide having the sequence as set forth in SEQ ID NO:7, a polynucleotide having the sequence as set forth in SEQ ID NO:6, or a polynucleotide complementary to a polynucleotide having the sequence as set forth in SEQ ID NO:6;

e) a polynucleotide encoding a polypeptide having the sequence as set forth in SEQ ID NO:9, a polynucleotide having the sequence as set forth in SEQ ID NO:8, or a polynucleotide complementary to a polynucleotide having the sequence as set forth in SEQ ID NO:8;

f) a polynucleotide encoding a polypeptide having the sequence as set forth in SEQ ID NO:11, a polynucleotide having the sequence as set forth in SEQ ID NO:10, or a polynucleotide complementary to a polynucleotide having the sequence as set forth in SEQ ID NO:10; and g) a polynucleotide encoding a polypeptide having the sequence as set forth in SEQ ID NO:13, a polynucleotide encoding a polypeptide having the sequence as set forth in SEQ ID NO:14, a polynucleotide having the sequence as set forth in SEQ ID NO:12, or a polynucleotide complementary to a polynucleotide having the sequence as set forth in SEQ ID NO:12.

* * * * *